US008133995B2

(12) United States Patent
Dixon et al.

(10) Patent No.: US 8,133,995 B2
(45) Date of Patent: Mar. 13, 2012

(54) SUBSTITUTED 4-AMINO-PYRROLOTRIAZINE DERIVATIVES USEFUL FOR TREATING HYPER-PROLIFERATIVE DISORDERS AND DISEASES ASSOCIATED WITH ANGIOGENESIS

(75) Inventors: Julie Dixon, Bethany, CT (US); Steven Magnuson, Wallingford, CT (US); Barton Phillips, New Haven, CT (US); Yamin Wang, Sandy Hook, CT (US); Tandy Li, West Haven, CT (US); Kyle Parcella, Wallingford, CT (US); Jason Newcom, Northford, CT (US); Harold Kluender, Hartland, WI (US); Zhenqiu Hong, Milford, CT (US); Brent Chandler, Princeton, NJ (US); Zhonghua Zhang, Derby, CT (US); Kristen Allegue, Rocky Hill, CT (US); Zheng Liu, Beacon Falls, CT (US)

(73) Assignee: Bayer HealthCare LLC, Tarrytown, NY (US)

( * ) Notice: Subject to any disclaimer, the term of this patent is extended or adjusted under 35 U.S.C. 154(b) by 62 days.

(21) Appl. No.: 12/085,879

(22) PCT Filed: Nov. 30, 2006

(86) PCT No.: PCT/US2006/045996
§ 371 (c)(1),
(2), (4) Date: May 30, 2008

(87) PCT Pub. No.: WO2007/064883
PCT Pub. Date: Jun. 7, 2007

(65) Prior Publication Data
US 2009/0281079 A1  Nov. 12, 2009

Related U.S. Application Data

(60) Provisional application No. 60/742,151, filed on Dec. 2, 2005.

(51) Int. Cl.
*C07D 487/04* (2006.01)
*C07D 417/02* (2006.01)
*C07D 413/02* (2006.01)
*A61K 31/53* (2006.01)
*A61P 35/00* (2006.01)

(52) U.S. Cl. .................. 544/183; 514/243
(58) Field of Classification Search .............. 544/183; 514/243
See application file for complete search history.

(56) References Cited

U.S. PATENT DOCUMENTS

| 7,563,791 B2 * | 7/2009 | Dixon et al. ............. 514/243 |
| 2005/0153966 A1 | 7/2005 | Gangloff et al. |
| 2007/0004733 A1 | 1/2007 | Chen et al. |
| 2010/0063038 A1 | 3/2010 | Dixon et al. |
| 2010/0075958 A1 | 3/2010 | Dixon et al. |
| 2010/0179125 A1 | 7/2010 | Dixon et al. |
| 2010/0273800 A1 | 10/2010 | Magnuson et al. |

FOREIGN PATENT DOCUMENTS

| WO | WO-00/71129 A1 | 11/2000 |
| WO | WO-03/042172 A2 | 5/2003 |
| WO | WO-2004/009601 A1 | 1/2004 |
| WO | WO-2005/121147 A1 | 12/2005 |
| WO | WO-2007/056170 A2 | 5/2007 |
| WO | WO-2007/061882 A2 | 5/2007 |

OTHER PUBLICATIONS

Cecil Textbook of Medicine, edited by Bennet, J.C., and Plum F., 20th edition, vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Powell et al., British Journal of Dermatology, 141: 802-810, 1999.*
Cohen et al., Current Opinion in Chemical Biology, 3,459-465, 1999.*
Golub et al., Science, 286, 531-537, 1999.*
Mass, R. D., Int. J. Radiation Oncology Bio. Phys.vol. 58(3): 932-940, 2004.*
Fabbro et al. Pharmacology & Therapeutics 93, 79-98, 2002.*
Simone, Oncology: Introduction, Cecil Textbook of Medicine, edited by Bennet, J.C., and Plum F., 20th edition, vol. 1, 1004-1010, 1996.
Freshney et al. "Culture of Animal Cells, A Manual of Basic Technique," Alan R. Liss, Inc, 1983, New York, p. 4.
Cohen et al., Current Opinion in Chemical Biology, 3, 456-465, 1999.
Mass, R.D., International Journal of Radiation Oncology Bio Phys. vol. 58(3): 932-940, 2004.
Fabbro et al., Pharmacology & Therapeutics 93, 79-98, 2002.
West—Solid State Chemistry 1987.
Vippagunta et al., Advanced Drug Delivery Reviews 48; 3-26, 2001.
Gautschi et al., Clin. Cancer Research, 14(6), 1639-1648, 2008.
Mountzios et al., Cancer Treatments Reviews, 34, 175-182, 2008.
Ferrara, N., Oncology, 69 suppl. 3, 11-16, 2005.
Jain et al., Nature Clinical Practice Oncology, 3(1) 24-40, 2006.

* cited by examiner

*Primary Examiner* — Venkataraman Balasubramanian
(74) *Attorney, Agent, or Firm* — Edwards Wildman Palmer LLP; Barry Kramer; Nicholas J. DiCeglie, Jr.

(57) ABSTRACT

This invention relates to novel pyrrozolotriazine compounds, pharmaceutical compositions containing such compounds and the use of those compounds and compositions for the prevention and/or treatment of hyper-proliferative disorders and diseases associated with angiogenesis.

13 Claims, No Drawings

SUBSTITUTED 4-AMINO-PYRROLOTRIAZINE DERIVATIVES USEFUL FOR TREATING HYPER-PROLIFERATIVE DISORDERS AND DISEASES ASSOCIATED WITH ANGIOGENESIS

FIELD OF THE INVENTION

This invention relates to novel pyrrozolotriazine compounds, pharmaceutical compositions containing such compounds and the use of those compounds or compositions for treating hyper-proliferative and/or angiogenesis disorders, as a sole agent or in combination with other active ingredients.

BACKGROUND OF THE INVENTION

Cancer is a disease resulting from an abnormal growth of tissue. Certain cancers have the potential to invade into local tissues and also metastasize to distant organs. This disease can develop in a wide variety of different organs, tissues and cell types. Therefore, the term "cancer" refers to a collection of over a thousand different diseases.

Over 4.4 million people worldwide were diagnosed with breast, colon, ovarian, lung, or prostate cancer in 2002 and over 2.5 million people died of these devastating diseases (Globocan 2002 Report). In the United States alone, over 1.25 million new cases and over 500,000 deaths from cancer were predicted in 2005. The majority of these new cases were expected to be cancers of the colon (~100,000), lung (~170,000), breast (~210,000) and prostate (~230,000). Both the incidence and prevalence of cancer is predicted to increase by approximately 15% over the next ten years, reflecting an average growth rate of 1.4% (American Cancer Society, Cancer Facts and Figures 2005).

Cancer treatments are of two major types, either curative or palliative. The main curative therapies for cancer are surgery and radiation. These options are generally successful only if the cancer is found at an early localized stage (Gibbs J B, 2000). Once the disease has progressed to locally advanced cancer or metastatic cancer, these therapies are less effective and the goal of therapy aims at symptom palliation and maintaining good quality of life. The most prevalent treatment protocols in either treatment mode involve a combination of surgery, radiation therapy and/or chemotherapy.

Cytotoxic drugs (also known as cytoreductive agents) are used in the treatment of cancer, either as a curative treatment or with the aim of prolonging life or palliating symptoms. Cytotoxics may be combined with radiotherapy and/or surgery, as neo-adjuvant treatment (initial chemotherapy aimed at shrinking the tumor, thereby rendering local therapy such as surgery and radiation more effective) or as adjuvant chemotherapy (used in conjunction or after surgery and/or localized therapy). Combinations of different drugs are frequently more effective than single drugs: they may provide an advantage in certain tumors of enhanced response, reduced development of drug resistance and/or increased survival. It is for these reasons that the use of combined cytotoxic regimens in the treatment of many cancers is very common.

Cytotoxic agents in current use employ different mechanisms to block proliferation and induce cell death. They can be generally categorized into the following groups based on their mechanism of action: the microtubule modulators that interfere with the polymerization or depolymerization of microtubules (e.g. docetaxel, paclitaxel, vinblastine, vinorelbine); anti-metabolites including nucleoside analogs and other inhibitors of key cellular metabolic pathways (e.g. capecitabine, gemcitabine, methotrexate); agents that interact directly with DNA (e.g. carboplatin, cyclophosphamide); anthracycline DNA interchalators that interfere with DNA polymerase and Topoisomerase II (e.g. doxorubicin, epirubicin); and the non-anthracycline inhibitors of Topoisomerase II and I enzymatic activity (e.g. topotecan, irinotecan, and etoposide). Even though different cytotoxic drugs act via different mechanisms of action, each generally leads to at least transient shrinkage of tumors.

Cytotoxic agents continue to represent an important component in an oncologist's arsenal of weapons for use in fighting cancer. The majority of drugs currently undergoing late Phase II and Phase III clinical trials are focusing on known mechanisms of action (tubulin binding agents, anti-metabolites, DNA processing), and on incremental improvements in known drug classes (for example the taxanes or the camptothecins). A small number of cytotoxic drugs based on novel mechanisms have recently emerged. Modes of action for these cytotoxics include inhibition of enzymes involved in DNA modification [e.g. histone deacetylase (HDAC)], inhibition of proteins involved in microtubule movement and cell cycle progression (e.g. kinesins, aurora kinase), and novel inducers of the apoptotic pathway (e.g. bcl-2 inhibitors).

The link between activity in tumor cell proliferation assays in vitro and anti-tumor activity in the clinical setting has been well established in the art. For example, the therapeutic utility of taxol (Silvestrini et al. *Stem Cells* 1993, 11 (6), 528-35), taxotere (Bissery et al. *Anti Cancer Drugs* 1995, 6 (3), 339), and topoisomerase inhibitors (Edelman et al. *Cancer Chemother.*

Cells protect their DNA by adopting a higher-order complex termed chromatin. Chromatin condensation is evident during mitosis and cell death induced by apoptosis while chromatin decondensation is necessary for replication, repair, recombination and transcription. Histones are among some of the DNA-binding proteins that are involved in the regulation of DNA condensation; and post-translational modifications of histone tails serve a critical role in the dynamic condensation/decondensation that occurs during the cell cycle. Phoshorylation of the tails of histone H3 is involved in both transcription and cell division (Prigent et al. *J. Cell Science* 2003, 116, 3677). A number of protein kinases have been reported to phosphorylate histone H3 and these kinases function both as signal transduction and mitotic kinases.

Even though cytotoxic agents remain in the forefront of approaches to treat patients with advanced solid tumors, their limited efficacy and narrow therapeutic indices result in significant side effects. Moreover, basic research into cancer has led to the investigation of less toxic therapies based on the specific mechanisms central to tumor progression. Such studies could lead to effective therapy with improvement of the quality of life for cancer patients. Thus, a new class of therapeutic agents has emerged, referred to as cytostatics. Cytostatics direct their action on tumor stabilization and are generally associated with a more limited and less aggravating side effect profile. Their development has resulted from the identification of specific genetic changes involved in cancer progression and an understanding of the proteins activated in cancer such as tyrosine kinases and serine/threonine kinases.

In addition to direct inhibition of tumor cell targets, cytostatic drugs are being developed to block the process of tumor angiogenesis. This process supplies the tumor with existing and new blood vessels to support continued nourishment and therefore help promote tumor growth. Key tyrosine kinase receptors including Vascular Endothelial Growth Factor Receptor 2 (VEGFR2), Fibroblast Growth Factor 1 (FGFR1)

and Tie2 have been shown to regulate angiogenesis and have emerged as highly attractive drug targets.

To support progressive tumor growth beyond the size of 1-2 mm$^3$, it is recognized that tumor cells require a functional stroma, a support structure consisting of fibroblast, smooth muscle cells, endothelial cells, extracellular matrix proteins, and soluble factors (Folkman, J., *Semin Oncol,* 2002. 29 (6 Suppl 16), 15-8). Tumors induce the formation of stromal tissues through the secretion of soluble growth factors such as PDGF and transforming growth factor-beta (TGF-beta), which in turn stimulate the secretion of complimentary factors by host cells such as fibroblast growth factor (FGF), epidermal growth factor (EGF), and vascular endothelial growth factor (VEGF). These stimulatory factors induce the formation of new blood vessels, or angiogenesis, which brings oxygen and nutrients to the tumor and allows it to grow and provides a route for metastasis. It is believed some therapies directed at inhibiting stroma formation will inhibit the growth of epithelial tumors from a wide variety of histological types. (George, D. *Semin Oncol,* 2001. 28 (5 Suppl 17), 27-33; Shaheen, R. M., et al., *Cancer Res,* 2001. 61 (4), 1464-8; Shaheen, R. M., et al. *Cancer Res,* 1999. 59 (21), 5412-6). However, because of the complex nature and the multiple growth factors involved in angiogenesis process and tumor progression, an agent targeting a single pathway may have limited efficacy. It is desirable to provide treatment against a number of key signaling pathways utilized by tumors to induce angiogenesis in the host stroma. These include PDGF, a potent stimulator of stroma formation (Ostman, A. and C. H. Heldin, *Adv Cancer Res,* 2001, 80, 1-38), FGF, a chemo-attractant and mitogen for fibroblasts and endothelial cells, and VEGF, a potent regulator of vascularization.

A major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are reported to be highly specific for vascular endothelial cells (for reviews, see: Farrara et al. *Endocr. Rev.* 1992, 13, 18; Neufield et al. *FASEB J.* 1999, 13, 9).

VEGF expression is reported to be induced by hypoxia (Shweiki et al. *Nature* 1992, 359, 843), as well as by a variety of cytokines and growth factors, such as interleukin-1, interleukin-6, epidermal growth factor and transforming growth factor. To date, VEGF and the VEGF family members have been reported to bind to one or more of three transmembrane receptor tyrosine kinases (Mustonen et al. *J. Cell Biol.,* 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependant tyrosine phosphorylation in intact cells, whereas flt-1 displays a weak response. Thus, binding to KDR is believed to be a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. It is believed regulation of the VEGF-mediated signal transduction cascade by some agents can provide a useful mode for control of abnormal angiogenesis and/or hyperpermeability processes.

The vascular endothelial growth factors (VEGF, VEGF-C, VEGF-D) and their receptors (VEGFR2, VEGFR3) are not only key regulators of tumor angiogenesis, but also lymphangiogenesis. VEGF, VEGF-C and VEGF-D are expressed in most tumors, primarily during periods of tumor growth and, often at substantially increased levels. VEGF expression is stimulated by hypoxia, cytokines, oncogenes such as ras, or by inactivation of tumor suppressor genes (McMahon, G. *Oncologist* 2000, 5 (Suppl. 1), 3-10; McDonald, N. Q.; Hendrickson, W. A. *Cell* 1993, 73, 421-424).

The biological activities of the VEGFs are mediated through binding to their receptors. VEGFR3 (also called Flt-4) is predominantly expressed on lymphatic endothelium in normal adult tissues. VEGFR3 function is needed for new lymphatic vessel formation, but not for maintenance of the pre-existing lymphatics. VEGFR3 is also upregulated on blood vessel endothelium in tumors. Recently VEGF-C and VEGF-D, ligands for VEGFR3, have been identified as regulators of lymphangiogenesis in mammals. Lymphangiogenesis induced by tumor-associated lymphangiogenic factors could promote the growth of new vessels into the tumor, providing tumor cells access to systemic circulation. Cells that invade the lymphatics could find their way into the bloodstream via the thoracic duct. Tumor expression studies have allowed a direct comparison of VEGF-C, VEGF-D and VEGFR3 expression with clinicopathological factors that relate directly to the ability of primary tumors to spread (e.g., lymph node involvement, lymphatic invasion, secondary metastases, and disease-free survival). In many instances, these studies demonstrate a statistical correlation between the expression of lymphangiogenic factors and the ability of a primary solid tumor to metastasize (Skobe, M. et al. *Nature Med.* 2001, 7 (2), 192-198; Stacker, S. A. et al. *Nature Med.* 2001, 7 (2), 186-191; Makinen, T. et al. *Nature Med.* 2001, 7 (2), 199-205; Mandriota, S. J. et al. *EMBO J.* 2001, 20 (4), 672-82; Karpanen, T. et al. *Cancer Res.* 2001, 61 (5), 1786-90; Kubo, H. et al. *Blood* 2000, 96 (2), 546-53).

Hypoxia appears to be an important stimulus for VEGF production in malignant cells. Activation of p38 MAP kinase is required for VEGF induction by tumor cells in response to hypoxia (Blaschke, F. et al. *Biochem. Biophys. Res. Commun.* 2002, 296, 890-896; Shemirani, B. et al. *Oral Oncology* 2002, 38, 251-257). In addition to its involvement in angiogenesis through regulation of VEGF secretion, p38 MAP kinase promotes malignant cell invasion, and migration of different tumor types through regulation of collagenase activity and urokinase plasminogen activator expression (Laferriere, J. et al. *J. Biol. Chem.* 2001, 276, 33762-33772; Westermarck, J. et al. *Cancer Res.* 2000, 60, 7156-7162; Huang, S. et al. *J. Biol. Chem.* 2000, 275, 12266-12272; Simon, C. et al. *Exp. Cell Res.* 2001, 271, 344-355). Moreover, VEGF activates the extracellular signal-regulated protein kinase (ERK) in human umbilical vein endothelial cells (HUVEC) (Yu, Y.; Sato, D. *J. Cell Physiol* 1999, 178, 235-246).

The VEGF-VEGFR2 signaling pathway has been extensively characterized as an important regulator of angiogenesis. Mice lacking VEGFR2 (Flk-1) are almost completely lacking in vasculature and have very few endothelial cells (Shalaby et al., *Nature,* 1995, 376, 62-66). VEGF is a potent mitogen for endothelial cells, promotes angiogenic sprouting, and increases vascular permeability (reviewed in Yancopoulos et al. *Nature* 2000, 407, 242). Administration of soluble VEGFR2 inhibits the growth of wide variety of tumors (Shirakawa et al. *Int J Cancer,* 2002, 99, 244, Bruns et al. *Cancer,* 2000, 89, 495, Millauer et al., *Nature* 1994, 367, 576). Similarly, neutralizing antibodies to VEGF (Kim et al., *Nature,* 1993, 262, 841) or VEGFR2 (Prewett et al., *Cancer Res* 1999, 59, 5209), as well as VEGF antisense (Saleh et al. *Cancer Res* 1996, 56, 393) suppress tumor growth in vivo. Furthermore, small molecule inhibitors of VEGFR2 have been shown to inhibit tumor growth in preclinical xenograft models (reviewed in Shepherd and Sridhar, *Lung Cancer,* 2003, 41, S63) and are being tested in clinical trials. A monoclonal antibody to VEGF (Avastin™) was recently approved for use in combination with other anticancer drugs for treatment of advanced colon cancer.

The Ang-Tie2 signal transduction pathway also plays a key role in vascular formation, particularly with respect to remodeling and stabilization of vessels. The major ligands for Tie2, Angiopoietin-1 and Angiopoietin-2 (Ang1 and Ang2), have distinct activities. While Ang1 is a Tie2 agonist, promoting vessel maturation and stability, Ang2 is partial Tie2 agonist/antagonist having varied activities that are dependent on the tissue and growth factor context (Yancopoulos et al. *Nature,* 2000, 407, 242). When the local concentration of VEGF is low, Ang2 promotes vessel regression, whereas in areas where VEGF concentrations are high, Ang2 induces vessel destabilization and branching (Holash et al. *Ocogene,* 1999, 18, 5356). This latter situation is likely the case during active tumor angiogenesis. Ang1 has been shown to regulate endothelial cell survival (Kwak et al. *FEBS,* 1999, 448, 249, Bussolati et al. *FEBS,* 2003, 9, 1159) and migration (Witzenbichler et al. *J. Biol Chem,* 1998, 373, 18514). The role of Ang-Tie2 signaling in tumor angiogenesis is supported by numerous xenograft tumor studies involving the administration of soluble Tie2. Significant inhibition of tumor growth by soluble Tie2 was observed in the WIBC-9 and MC-5 human breast tumors (Shirakawa et al. *Int J Cancer,* 2002, 99, 344), C26 colon and TS/A breast tumors, R3230AC breast tumor (Lin et al. *J Clin Invest,* 1997, 100, 2072), A375v melanoma (Siemeister et al. *Cancer Res,* 1999, 59, 3185), as well as 4T1 murine mammary and B16F10.9 murine melanoma tumors.

The central role of the FGF-FGFR1 signal transduction pathway in angiogenesis is well established. The FGF family includes 22 members expressed from different genes and having distinct activities (Ornitz and Itoh, *Genome Biology,* 2001, 2, reviews 3005). During mammalian development, FGF1 and FGF2 regulate branching morphogenesis in tissues undergoing vascularization. Administration of FGFs can promote neovascularization in ischemic tissues (Yanagisawa-Miwa et al., *Science,* 1992, 257, 1401, Tabata et al *Cardiovasc Res,* 1997, 35, 470). FGFR1 binds FGF1 and FGF2 with similar affinity (Dionne et al., *EMBO J,* 1990, 9, 2685). The FGF-FGFR1 pathway has also been associated with angiogenesis in a variety of tumor types. FGF2 is a key regulator of angiogenesis in prostate cancer (Doll et al. *Prostate,* 2001, 49, 293) and melanomas (Straume and Akslen *Am J Pathol,* 2002, 160, 1009). In addition, antisense targeting of FGFR1 (Wang and Becker *Nat Med,* 1997, 3, 887) or anti-FGF2 antibodies (Rofstad and Halsor *Cancer Res,* 2000, 60, 4932) inhibit tumor growth and angiogenesis in human melanomas. Similarly, expression of soluble FGFR decreases the growth of spontaneous pancreatic tumors in mice (Compagni et al. *Cancer Res,* 2000, 60, 7163), as well as xenografted pancreatic tumors (Wagner et al. *Gastroenterology,* 1998, 114, 798). Overexpression and amplification of the FGFR1 gene in human breast tumors (Jacquemier et al. *Int J Cancer,* 1994, 59, 373) and bladder cancers (Simon et al. *Cancer Res,* 2001, 61, 4514), has been reported whereas translocation of FGFR1 resulting in an activated chimeric kinase has been identified in myeloproliferative disorders with lymphoma (Gausch et al. *Mol Cell Biol* 2001, 21, 8129) and Chronic Myelogenous Leukemias (CML, Demiroglu et al., *Blood,* 2001, 98, 3778).

The activation of FGFR1 by FGF induces both the MAPK/ERK and the PI3K/Akt pathways. In contrast to Ang1, which is not a mitogen, FGF stimulates cell proliferation via the MAPK/ERK pathway (Bikfalvi et al., *Endocr Rev,* 1997, 18, 26). Activation of FGFR1 leads to the recruitment of adaptor proteins FRS2 and GRB2, which recruit SOS to the plasma membrane leading to the activation of RAS (Kouhara et al., *Cell,* 1997, 89, 693). Activated RAS, which subsequently activates RAF, MEK, then ERK, leads to cell proliferation. The activation of p38 MAPK has also been reported to be involved in FGF-induced cell proliferation (Maher, *J Biol Chem,* 1999, 274, 17491). The recruitment of GRB2 to activated FGFR1 also recruits Gab1, which induces the PBK/Akt pathway (Ong et al., *Mol Cell Biol,* 2000, 20, 979), and promotes cell survival. This effect of Akt on cell survival is mediated, in part through mTOR and $p70^{S6K}$ (Gausch et al., *Mol Cell, Biol,* 2001, 21, 8129). The effects of FGF on cell migration have been shown to be mediated, in part, by ERK activation and c-Fes (reviewed in Javerzat et al., *Trends in Molecular Medicine,* 2002, 8, 483).

PDGF is another key regulator of stromal formation which is secreted by many tumors in a paracrine fashion and is believed to promote the growth of fibroblasts, smooth muscle and endothelial cells, promoting stroma formation and angiogenesis. PDGF was originally identified as the v-sis oncogene product of the simian sarcoma virus (Heldin, C. H., et al., *J Cell Sci Suppl,* 1985, 3, 65-76). The growth factor is made up of two peptide chains, referred to as A or B chains which share 60% homology in their primary amino acid sequence. The chains are disulfide cross linked to form the 30 kDa mature protein composed of either AA, BB or AB homo- or heterodimers. PDGF is found at high levels in platelets, and is expressed by endothelial cells and vascular smooth muscle cells. In addition, the production of PDGF is up regulated under low oxygen conditions such as those found in poorly vascularized tumor tissue (Kourembanas, S., et al., *Kidney Int,* 1997, 51 (2), 438-43). PDGF binds with high affinity to the PDGF receptor, a 1106 amino acid 124 kDa transmembrane tyrosine kinase receptor (Heldin, C. H., A. Ostman, and L. Ronnstrand, *Biochim Biophys Acta,* 1998. 1378 (1), 79-113). PDGFR is found as homo- or heterodimer chains which have 30% homology overall in their amino acid sequence and 64% homology between their kinase domains (Heldin, C. H., et al. *Embo J,* 1988, 7 (5), 1387-93). PDGFR is a member of a family of tyrosine kinase receptors with split kinase domains that includes VEGFR2 (KDR), VEGFR3 (Flt4), c-Kit, and FLT3. The PDGF receptor is expressed primarily on fibroblast, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. *Biochemistry,* 1999, 38 (6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, it is believed the major function of PDGF is to facilitate and increase the rate of wound healing and to maintain blood vessel homeostasis (Baker, E. A. and D. J. Leaper, *Wound Repair Regen,* 2000. 8 (5), 392-8; Yu, J., A. Moon, and H. R. Kim, *Biochem Biophys Res Commun,* 2001. 282 (3), 697-700). PDGF is found at high concentrations in platelets and is a potent chemoattractant for fibroblast, smooth muscle cells, neutrophils and macrophages. In addition to its role in wound healing PDGF is known to help maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis PDGF controls interstitial fluid pressure, regulating the permeability of vessels through its regulation of the interaction between connective tissue cells and the extracellular matrix. Inhibiting PDGFR activity can lower interstitial pressure and facilitate the influx of cytotoxics into tumors improving the anti-tumor efficacy of these agents (Pietras, K., et al. *Cancer Res,* 2002. 62 (19), 5476-84; Pietras, K., et al. *Cancer Res,* 2001. 61 (7), 2929-34).

PDGF can promote tumor growth through either the paracrine or autocrine stimulation of PDGFR receptors on stromal cells or tumor cells directly, or through the amplification of the receptor or activation of the receptor by recombination. Over expressed PDGF can transform human melanoma cells and keratinocytes (Forsberg, K., et al. *Proc Natl Acad Sci USA.,* 1993. 90 (2), 393-7; Skobe, M. and N. E. Fusenig, *Proc Natl Acad Sci USA,* 1998. 95 (3), 1050-5), two cell types that do not express PDGF receptors, presumably by the direct effect of PDGF on stroma formation and induction of angiogenesis. This paracrine stimulation of tumor stroma is also observed in carcinomas of the colon, lung, breast, and prostate (Bhardwaj, B., et al. *Clin Cancer Res,* 1996, 2 (4), 773-82; Nakanishi, K., et al. *Mod Pathol,* 1997, 10 (4), 341-7; Sundberg, C, et al. *Am J Pathol,* 1997, 151 (2), 479-92; Lindmark, G., et al. *Lab Invest,* 1993, 69 (6), 682-9; Vignaud, J. M., et al, *Cancer Res,* 1994, 54 (20), 5455-63) where the tumors express PDGF, but not the receptor. The autocrine stimulation of tumor cell growth, where a large faction of tumors analyzed express both the ligand PDGF and the receptor, has been reported in glioblastomas (Fleming, T. P., et al. *Cancer Res,* 1992, 52 (16), 4550-3), soft tissue sarcomas (Wang, J., M. D. Coltrera, and A. M. Gown, *Cancer Res,* 1994, 54 (2), 560-4) and cancers of the ovary (Henriksen, R., et al. *Cancer Res,* 1993, 53 (19), 4550-4), prostate (Fudge, K., C. Y. Wang, and M. E. Stearns, *Mod Pathol,* 1994, 7 (5), 549-54), pancreas (Funa, K., et al. *Cancer Res,* 1990, 50 (3), 748-53) and lung (Antoniades, H. N., et al., *Proc Natl Acad Sci USA,* 1992, 89 (9), 3942-6). Ligand independent activation of the receptor is found to a lesser extent but has been reported in chronic myelomonocytic leukemia (CMML) where the a chromosomal translocation event forms a fusion protein between the Ets-like transcription factor TEL and the PDGF receptor. In addition, activating mutations in PDGFR have been found in gastrointestinal stromal tumors in which c-Kit activation is not involved (Heinrich, M. C., et al., *Science,* 2003, 9, 9).

Certain PDGFR inhibitors will interfere with tumor stromal development and are believed to inhibit tumor growth and metastasis.

Several new drugs that are directed at various molecular targets have been approved over the past several years for the treatment of cancer. Imatinib is an inhibitor of the Abl tyrosine kinase and was the first small molecule tyrosine kinase inhibitor to be approved for the treatment of chronic myeloid leukemia (CML). Based on additional activity of imatinib against the receptor tyrosine kinase activated in gastrointestinal stromal tumors (GIST), c-KIT, it was subsequently approved for the treatment of advanced GIST. Erlotinib, a small molecule inhibitor of EGFR, was approved in late 2004 for the treatment of non-small cell lung carcinoma (NSCLC). Sorafenib, an inhibitor of multiple kinases including c-Raf and VEGFR2 was approved for the treatment of advanced renal cell carcinoma (RCC) in December, 2005. Recently in January of 2006, Sunitinib, a multi-kinase inhibitor was approved for the treatment of refractory- or resistant-GIST and advanced RCC. These small molecule inhibitors demonstrate that targeted approaches are successful for the treatment of different types of cancers.

Despite advancements in the art, there remains a need for cancer treatments and anti-cancer compounds.

Compounds and compositions described herein, including salts, metabolites, solvates, solvates of salts, hydrates, prodrugs such as esters, polymorphs, and stereoisomeric forms thereof, exhibit anti-proliferative and anti-angiogenic activity, and are thus useful to prevent or treat the disorders associated with hyper-proliferation and angiogenesis.

DESCRIPTION OF THE INVENTION

In embodiment one, the present invention provides a compound of formula (I)

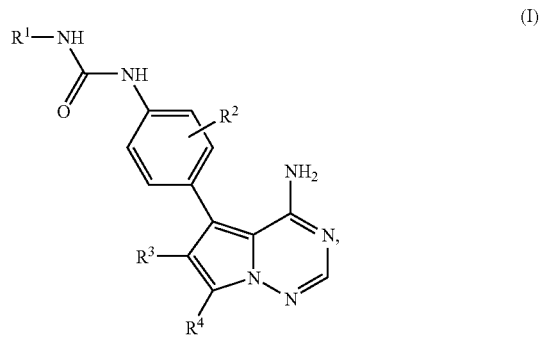

wherein $R^1$ represents 1.1) phenyl or a bicyclic carbocycle of 9-10 ring members, in which at least one ring is aromatic, $R^1$ optionally bearing up to 4 substituents independently selected from the group consisting of 1.1.a) $(C_1-C_4)$alkyl, which may optionally bear up to 3 substituents independently selected from 1.1.a1) halogen;

1.1.a2) $OR^5$ wherein $R^5$ represents H or $(C_1-C_3)$alkyl which may optionally bear halogen or $—(C_1-C_3)$ mono- or di-alkylamino;

1.1.a3) $—NR^6R^7$ in which $R^6$ and $R^7$ are independently H or $—(C_1-C_3)$alkyl which may optionally bear halogen or $OR^{7a}$ wherein $R^{7a}$ represents H or $(C_1-C_3)$alkyl, or $R^6$ and $R^7$ may be joined and taken together with the N atom to which they are attached form a 5-6 membered ring which may optionally contain a ring member selected from O, S, and $NR^8$ wherein $R^8$ represents H or $(C_1-C_3)$alkyl; and 1.1.a4) a 5-6 membered heteroaromatic containing up to two heteroatoms selected from O, S, and N;

1.1.b) —$(C_3$-$C_6)$cycloalkyl which may optionally bear up to 2 substituents independently selected from 1.1.b1) halogen; and 1.1.b2) $OR^9$ wherein $R^9$ represents H or $(C_1$-$C_3)$alkyl which may optionally bear halogen or $(C_1$-$C_3)$ mono- or di-alkylamino;

1.1.c) $OR^{10}$ wherein $R^{10}$ represents H; phenyl; benzyl; $(C_3$-$C_6)$cycloalkyl; or $(C_1$-$C_4)$alkyl which may optionally bear up to 3 substituents independently selected from 1.1.c1) halogen;

1.1.c2) $OR^{11}$ wherein $R^{11}$ represents H or $(C_1$-$C_3)$ alkyl which may optionally bear $(C_1$-$C_3)$mono- or di-alkylamino; and 1.1.c3) $NR^{12}R^{13}$ in which $R^{12}$ and $R^{13}$ are independently H or —$(C_1$-$C_3)$alkyl which may optionally bear halogen, or $R^{12}$ and $R^{13}$ may be joined and taken together with the N atom to which they are attached form a 5-6 membered ring which may optionally contain a ring member selected from O, S, and $NR^{14}$ wherein $R^{14}$ represents H or $(C_1$-$C_3)$ alkyl;

1.1.d) —C(O)—$OR^{15}$ wherein $R^{15}$ represents H or —$(C_1$-$C_4)$alkyl which may optionally bear up to 3 halogens;

1.1.e) —C(O)—$NR^{16}R^{17}$ wherein $R^{16}$ represents H or $(C_1$-$C_3)$alkyl which may optionally bear halogen; and $R^{17}$ represents H or —$(C_1$-$C_4)$alkyl which is optionally substituted with 1.1.e1) halogen;

1.1.e2) a 5-6 membered heteroaromatic containing up to two heteroatoms selected from O, S, and N;

1.1.e3) phenyl;

1.1.e4) —$SO_2CH_3$;

1.1.e5) —$OR^{18}$ wherein $R^{18}$ represents H or $(C_1$-$C_3)$ alkyl which may optionally bear halogen; or 1.1.e6) —$NR^{19}R^{20}$ in which $R^{19}$ and $R^{20}$ are independently H or —$(C_1$-$C_3)$alkyl which may optionally bear halogen, or $R^{19}$ and $R^{20}$ may be joined and taken together with the N atom to which they are attached form a 5-6 membered ring which may optionally contain a ring member selected from O, S, and $NR^{21}$ wherein $R^{21}$ represents H or $(C_1$-$C_3)$ alkyl;

1.1.f) —N($R^{22}$)—C(O)—$R^{23}$ wherein $R^{22}$ represents H or $(C_1$-$C_3)$alkyl; and $R^{23}$ represents optionally substituted phenyl, or $(C_1$-$C_4)$alkyl which is optionally substituted with 1.1.f1) optionally substituted phenyl, 1.1.f2) $OR^{24}$ wherein $R^{24}$ represents H or $(C_1$-$C_3)$ alkyl, or 1.1.f3) $NR^{25}R^{26}$ wherein $R^{25}$ and $R^{26}$ are independently H or —$(C_1$-$C_3)$alkyl which may optionally bear halogen, or $R^{25}$ and $R^{26}$ may be joined and taken together with the N atom to which they are attached form a 5-6 membered ring which may optionally contain a ring member selected from O, S, and $NR^{27}$ wherein $R^{27}$ represents H or $(C_1$-$C_3)$ alkyl;

1.1.g) —$SO_2NR^{28}R^{29}$ wherein $R^{28}$ represents H or $(C_1$-$C_3)$alkyl which may optionally bear halogen; and $R^{29}$ represents H or —$(C_1$-$C_4)$alkyl which is optionally substituted with:

1.1.g1) halogen;

1.1.g2) a 5-6 membered heteroaromatic containing up to two heteroatoms selected from O, S, and N;

1.1.g3) phenyl;

1.1.g4) —$SO_2CH_3$;

1.1.g5) —$OR^{30}$ wherein $R^{30}$ represents H or $(C_1$-$C_3)$ alkyl which may optionally bear halogen; or 1.1.g6) —$NR^{31}R^{32}$ in which $R^{31}$ and $R^{32}$ are independently H or —$(C_1$-$C_3)$alkyl which may optionally bear halogen, or $R^{31}$ and $R^{32}$ may be joined and taken together with the N atom to which they are attached form a 5-6 membered ring which may optionally contain a ring member selected from O, S, and $NR^{33}$ wherein $R^{33}$ represents H or $(C_1$-$C_3)$ alkyl;

1.1.h) —N($R^{34}$)—$SO_2$—$R^{35}$ wherein $R^{34}$ represents H or $(C_1$-$C_3)$alkyl, and $R^{35}$ represents optionally substituted phenyl, or $(C_1$-$C_4)$alkyl which is optionally substituted with 1.1.h1) halogen;

1.1.h2) optionally substituted phenyl, 1.1.h3) $OR^{36}$ wherein $R^{36}$ represents H or $(C_1$-$C_3)$ alkyl, or 1.1.h4) $NR^{37}R^{38}$ wherein $R^{37}$ and $R^{38}$ are independently H or —$(C_1$-$C_3)$alkyl which may optionally bear halogen, or $R^{37}$ and $R^{38}$ may be joined and taken together with the N atom to which they are attached form a 5-6 membered ring which may optionally contain a ring member selected from O, S, and $NR^{39}$ wherein $R^{39}$ represents H or $(C_1$-$C_3)$ alkyl;

1.1.i) —$NR^{40}R^{41}$ in which $R^{40}$ and $R^{41}$ are independently H or —$(C_1$-$C_3)$alkyl which may optionally bear halogen or $OR^{42}$ in which $R^{42}$ represents H or $(C_1$-$C_3)$alkyl, or $R^{40}$ and $R^{41}$ may be joined and taken together with the N atom to which they are attached form a 5-6 membered ring which may optionally contain a ring member selected from O, S, and $NR^{43}$ wherein $R^{43}$ represents H or $(C_1$-$C_3)$alkyl;

1.1.j) halogen;

1.1.k) optionally substituted phenyl;

1.1.l) $NO_2$;

1.1.m) CN; and 1.1.n) a 5-6 membered heteroaromatic containing up to two heteroatoms selected from O, S, and N;

or $R^1$ represents 1.2) a 5-6 membered aromatic heterocycle containing up to 3 heteroatoms independently selected from the group consisting of N, O, and S; or a bicyclic heterocycle of 8-10 ring members in which at least one ring is aromatic and contains up to 3 moieties independently selected from the group consisting of N, N→O, O, and S, and any non-aromatic ring of said bicyclic heterocycle optionally contains up to three moieties independently selected from the group consisting of O, S, S(O), S(O)$_2$, and $NR^{44}$ wherein $R^{44}$ represents H or —$(C_1$-$C_3)$alkyl; said $R^1$ heterocycle optionally bearing up to 4 substituents independently selected from the group consisting of 1.2.a) $(C_1-C_4)$alkyl, which may optionally bear up to 3 substituents independently selected from
  1.2.a1) halogen;
  1.2.a2) $OR^{45}$ wherein $R^{45}$ represents H or $(C_1-C_3)$ alkyl which may optionally bear halogen or —$(C_1-C_3)$mono- or di-alkylamino;
  1.2.a3) —$NR^{46}R^{47}$ in which $R^{46}$ and $R^{47}$ are independently H or —$(C_1-C_3)$alkyl which may optionally bear halogen or $OR^{47a}$ wherein $R^{47a}$ represents H or $(C_1-C_3)$alkyl, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or $(C_1-C_3)$alkyl; and
  1.2.a4) a 5-6 membered heteroaromatic containing up to two heteroatoms selected from O, S, and N;
1.2.b) —$(C_3-C_6)$cycloalkyl which may optionally bear up to 2 substituents independently selected from
  1.2.b1) halogen; and
  1.2.b2) $OR^{49}$ wherein $R^{49}$ represents H or $(C_1-C_3)$ alkyl which may optionally bear halogen or —$(C_1-C_3)$mono- or di-alkylamino;
1.2.c) $OR^{50}$ wherein
  $R^{50}$ represents H; phenyl; benzyl; —$(C_3-C_6)$cycloalkyl; or —$(C_1-C_4)$alkyl which may optionally bear up to 3 substituents independently selected from
  1.2.c1) halogen;
  1.2.c2) $OR^{51}$ wherein $R^{51}$ represents H or $(C_1-C_3)$ alkyl which may optionally bear —$(C_1-C_3)$mono- or di-alkylamino; and
  1.2.c3) —$NR^{52}R^{53}$ in which $R^{52}$ and $R^{53}$ are independently H or —$(C_1-C_3)$alkyl which may optionally bear halogen, or $R^{52}$ and $R^{53}$ may be joined and taken together with the N atom to which they are attached form a 5-6 membered ring which may optionally contain a ring member selected from O, S, and $NR^{54}$ wherein $R^{54}$ represents H or $(C_1-C_3)$alkyl;
1.2.d) —C(O)—$OR^{55}$ wherein $R^{55}$ represents H or —$(C_1-C_4)$alkyl which may optionally bear up to 3 halogens;
1.2.e) —C(O)—$NR^{56}R^{57}$ wherein
  $R^{56}$ represents H or $(C_1-C_3)$alkyl which may optionally bear halogen; and
  $R^{57}$ represents H or —$(C_1-C_4)$alkyl which is optionally substituted with
  1.2.e1) halogen;
  1.2.e2) a 5-6 membered heteroaromatic containing up to two heteroatoms selected from O, S, and N;
  1.2.e3) phenyl;
  1.2.e4) —$SO_2CH_3$;
  1.2.e5) —$OR^{58}$ wherein $R^{58}$ represents H or $(C_1-C_3)$ alkyl which may optionally bear halogen; or
  1.2.e6) —$NR^{59}R^{60}$ in which $R^{59}$ and $R^{60}$ are independently H or —$(C_1-C_3)$alkyl which may optionally bear halogen, or $R^{59}$ and $R^{60}$ may be joined and taken together with the N atom to which they are attached form a 5-6 membered ring which may optionally contain a ring member selected from O, S, and $NR^{61}$ wherein $R^{61}$ represents H or $(C_1-C_3)$ alkyl;
1.2.f) —N($R^{62}$)—C(O)—$R^{63}$ wherein
  $R^{62}$ represents H or $(C_1-C_3)$alkyl; and
  $R^{63}$ represents optionally substituted phenyl, or $(C_1-C_4)$alkyl which is optionally substituted with
  1.2.f1) optionally substituted phenyl,
  1.2.f2) $OR^{64}$ wherein $R^{64}$ represents H or $(C_1-C_3)$ alkyl, or
  1.2.f3) $NR^{65}R^{66}$ wherein $R^{65}$ and $R^{66}$ are independently H or —$(C_1-C_3)$alkyl which may optionally bear halogen, or $R^{65}$ and $R^{66}$ may be joined and taken together with the N atom to which they are attached form a 5-6 membered ring which may optionally contain a ring member selected from O, S, and $NR^{67}$ wherein $R^{67}$ represents H or $(C_1-C_3)$ alkyl;
1.2.g) —$SO_2NR^{68}R^{69}$ wherein
  $R^{68}$ represents H or $(C_1-C_3)$alkyl which may optionally bear halogen; and
  $R^{69}$ represents H or —$(C_1-C_4)$alkyl which is optionally substituted with
  1.2.g1) halogen;
  1.2.g2) a 5-6 membered heteroaromatic containing up to two heteroatoms selected from O, S, and N;
  1.2.g3) phenyl;
  1.2.g4) —$SO_2CH_3$;
  1.2.g5) —$OR^{70}$ wherein $R^{70}$ represents H or $(C_1-C_3)$ alkyl which may optionally bear halogen; or
  1.2.g6 —$NR^{71}R^{72}$ in which $R^{71}$ and $R^{72}$ are independently H or —$(C_1-C_3)$alkyl which may optionally bear halogen, or $R^{71}$ and $R^{72}$ may be joined and taken together with the N atom to which they are attached form a 5-6 membered ring which may optionally contain a ring member selected from O, S, and $NR^{73}$ wherein $R^{73}$ represents H or $(C_1-C_3)$ alkyl;
1.2.h) —N($R^{74}$)—$SO_2$—$R^{75}$ wherein
  $R^{74}$ represents H or $(C_1-C_3)$alkyl, and
  $R^{75}$ represents optionally substituted phenyl, or $(C_1-C_4)$alkyl which is optionally substituted with
  1.2.h1) halogen;
  1.2.h2) optionally substituted phenyl,
  1.2.h3) $OR^{76}$ wherein $R^{76}$ represents H or $(C_1-C_3)$ alkyl, or
  1.2.h4) $NR^{77}R^{78}$ wherein $R^{77}$ and $R^{78}$ are independently H or —$(C_1-C_3)$alkyl which may optionally bear halogen, or $R^{77}$ and $R^{78}$ may be joined and taken together with the N atom to which they are attached form a 5-6 membered ring which may optionally contain a ring member selected from O, S, and $NR^{79}$ wherein $R^{79}$ represents H or $(C_1-C_3)$ alkyl;
1.2.i) —$NR^{80}R^{81}$ in which $R^{80}$ and $R^{81}$ are independently H or —$(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$alkyl;
1.2.j) halogen;
1.2.k) optionally substituted phenyl;
1.2.l) $NO_2$;
1.2.m) CN; and
1.2.n) a 5-6 membered heteroaromatic containing up to two heteroatoms selected from O, S, and N;

$R^2$ represents halogen; —($C_1$-$C_5$)alkyl which may optionally bear halogen; or —O($C_1$-$C_3$)alkyl which may optionally bear halogen;

$R^3$ represents 3.1) —($C_1$-$C_5$)alkyl which is optionally substituted with
  3.1.a) -halogen;
  3.1.b) phenyl optionally substituted with halogen, —($C_1$-$C_3$)alkyl, or —($C_1$-$C_3$)alkoxy,
  3.1.c) a 5-6 membered heteroaromatic containing up to two heteroatoms selected from O, S, and N, optionally substituted with halogen or —($C_1$-$C_3$)alkyl,
  3.1.d) —CN,
  3.1.e) —$OR^{83}$ wherein $R^{83}$ represents H or —($C_1$-$C_3$)alkyl which may optionally bear up to 3 substituents independently selected from
    3.1.e1) halogen;
    3.1.e2) optionally substituted phenyl;
    3.1.e3) —S(O)$_2$CH$_3$;
    3.1.e4) $OR^{84}$ wherein $R^{84}$ represents H or ($C_1$-$C_3$)alkyl which may optionally bear halogen or —($C_1$-$C_3$)mono- or di-alkylamino; and
    3.1.e5) —$NR^{85}R^{86}$ in which $R^{85}$ and $R^{86}$ are independently H or —($C_1$-$C_3$)alkyl which may optionally bear halogen, or $R^{85}$ and $R^{86}$ may be joined and taken together with the N atom to which they are attached form a 5-6 membered ring which may optionally contain a ring member selected from O, S, and $NR^{87}$ wherein $R^{87}$ represents H or ($C_1$-$C_3$)alkyl;
  3.1.f) —($C_3$-$C_5$)cycloalkyl which may optionally bear halogen or $OR^{88}$ wherein $R^{88}$ represents H or ($C_1$-$C_3$)alkyl; or
  3.1.g) —$NR^{89}R^{90}$ wherein
    $R^{89}$ represents H or —($C_1$-$C_3$)alkyl which may optionally bear halogen; and
    $R^{90}$ represents H or —($C_1$-$C_4$)alkyl which is optionally substituted with
      3.1.g1) halogen;
      3.1.g2) a 5-6 membered heteroaromatic containing up to two heteroatoms selected from O, S, and N;
      3.1.g3) phenyl;
      3.1.g4) —SO$_2$CH$_3$;
      3.1.g5) —$OR^{91}$ wherein $R^{91}$ represents H or ($C_1$-$C_3$)alkyl which may optionally bear halogen; or
      3.1.g6) —$NR^{92}R^{93}$ in which $R^{92}$ and $R^{93}$ are independently H or —($C_1$-$C_3$)alkyl which may optionally bear halogen, or $R^{92}$ and $R^{93}$ may be joined and taken together with the N atom to which they are attached form a 5-6 membered ring which may optionally contain a ring member selected from O, S, and $NR^{94}$ wherein $R^{94}$ represents H or ($C_1$-$C_3$)alkyl; or
      3.1.g7) $R^{89}$ and $R^{90}$ may be joined and taken together with the N to which they are attached form an aromatic or nonaromatic 5-6 membered ring which may optionally contain a ring member selected from O, S, and $NR^{95}$ wherein $R^{95}$ represents H or ($C_1$-$C_3$)alkyl;

3.2)

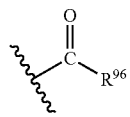

wherein
$R^{96}$ represents
  3.2.a) H,
  3.2.b) —($C_3$-$C_5$)cycloalkyl which may optionally bear halogen or —($C_1$-$C_3$)alkoxy; or
  3.2.c) —($C_1$-$C_5$)alkyl which may optionally bear up to 3 substituents independently selected from
    3.2.c1) halogen;
    3.2.c2) a 5-6 membered heteroaromatic containing up to two heteroatoms selected from O, S, and N;
    3.2.c3) phenyl;
    3.2.c4) —S(O)$_2$CH$_3$;
    3.2.c5) —$OR^{97}$ wherein $R^{97}$ represents H or ($C_1$-$C_3$)alkyl which may optionally bear halogen or —($C_1$-$C_3$)mono- or di-alkylamino; and
    3.2.c6) —$NR^{98}R^{99}$ in which $R^{98}$ and $R^{99}$ are independently H or —($C_1$-$C_3$)alkyl which may optionally bear halogen or $OR^{99a}$ wherein $R^{99a}$ represents H or ($C_1$-$C_3$)alkyl, or $R^{98}$ and $R^{99}$ may be joined and taken together with the N atom to which they are attached form a 5-6 membered ring which may optionally contain a ring member selected from O, S, and $NR^{100}$ wherein $R^{100}$ represents H or ($C_1$-$C_3$)alkyl;

3.3)

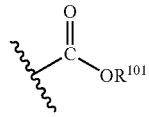

wherein $R^{101}$ represents H or —($C_1$-$C_5$)alkyl which may optionally bear up to 3 substituents independently selected from
  3.3.a) halogen; and
  3.3.b) phenyl;

3.4)

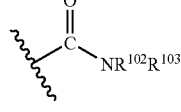

wherein
$R^{102}$ represents H or —($C_1$-$C_3$)alkyl which may optionally bear halogen; and
$R^{103}$ represents H or —($C_1$-$C_5$)alkyl which may optionally bear up to 3 substituents independently selected from
  3.4.a) halogen;
  3.4.b) a 5-6 membered heteroaromatic containing up to two heteroatoms selected from O, S, and N;
  3.4.c) phenyl;
  3.4.d) —S(O)$_2$CH$_3$;
  3.4.e) $OR^{104}$ wherein $R^{104}$ represents H or ($C_1$-$C_3$)alkyl which may optionally bear halogen; and 3.4.f) —NR$^{105}$R$^{106}$ in which R$^{105}$ and R$^{106}$ are independently H or —(C$_1$-C$_3$)alkyl which may optionally bear halogen, or R$^{105}$ and R$^{106}$ may be joined and taken together with the N atom to which they are attached form a 5-6 membered ring which may optionally contain a ring member selected from O, S, and NR$^{107}$ wherein R$^{107}$ represents H or (C$_1$-C$_3$)alkyl;

3.5) optionally substituted phenyl;

3.6) a 5-6 membered heteroaromatic containing up to two heteroatoms selected from O, S, and N;

3.7) halogen;

3.8) —CN; or 3.9) —CH=N—OR$^{108}$ wherein R$^{108}$ represents H or —C(O)—(C$_1$-C$_3$)alkyl;

R$^4$ represents 4.1) —(C$_3$-C$_5$)alkyl which is optionally substituted with 4.1.a) —(C$_3$-C$_5$)cycloalkyl which may optionally bear halogen or OR$^{109}$ wherein R$^{109}$ represents H or (C$_1$-C$_3$)alkyl;

4.1.b) -halogen;

4.1.c) —OR$^{110}$ wherein R$^{110}$ represents H or —(C$_1$-C$_3$)alkyl which may optionally bear up to 3 substituents independently selected from 4.1.c1) halogen;

4.1.c2) phenyl;

4.1.c3) —S(O)$_2$CH$_3$;

4.1.c4) OR$^{111}$ wherein R$^{111}$ represents H or (C$_1$-C$_3$)alkyl which may optionally bear halogen; and 4.1.c5) —NR$^{112}$R$^{113}$ in which R$^{112}$ and R$^{113}$ are independently H or —(C$_1$-C$_3$)alkyl which may optionally bear halogen, or R$^{112}$ and R$^{113}$ may be joined and taken together with the N atom to which they are attached form a 5-6 membered ring which may optionally contain a ring member selected from O, S, and NR$^{114}$ wherein R$^{114}$ represents H or (C$_1$-C$_3$)alkyl;

4.1.d) —NR$^{115}$R$^{116}$ wherein

R$^{115}$ represents H or —(C$_1$-C$_3$)alkyl which may optionally bear halogen and R$^{116}$ represents H, optionally substituted phenyl, or —(C$_1$-C$_5$)alkyl which may optionally bear up to 3 substituents independently selected from 4.1.d1) halogen;

4.1.d2) —S(O)$_2$CH$_3$;

4.1.d3) OR$^{117}$ wherein R$^{117}$ represents H or (C$_1$-C$_3$)alkyl which may optionally bear halogen; and 4.1.d4) —NR$^{118}$R$^{119}$ in which R$^{118}$ and R$^{119}$ are independently H or —(C$_1$-C$_3$)alkyl which may optionally bear halogen, or R$^{118}$ and R$^{119}$ may be joined and taken together with the N atom to which they are attached form a 5-6 membered ring which may optionally contain a ring member selected from O, S, and NR$^{120}$ wherein R$^{120}$ represents H or (C$_1$-C$_3$)alkyl;

4.1.e) optionally substituted phenyl; or 4.1.f) a 5-6 membered aromatic heterocycle containing up to two heteroatoms selected from O, S, and N;

4.2)

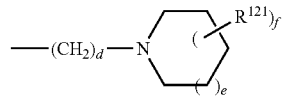

wherein R$^{121}$ represents —(C$_1$-C$_3$)alkyl which may optionally bear halogen or —OR$^{122}$ in which R$^{122}$ represents H or —(C$_1$-C$_3$)alkyl;

d represents 1, 2, or 3;

e represents 0 or 1;

f represents 0, 1, or 2;

4.3)

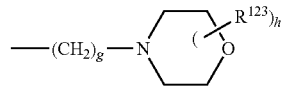

wherein R$^{123}$ represents —(C$_1$-C$_3$)alkyl which may optionally bear halogen or —OR$^{124}$ in which R$^{124}$ represents H or —(C$_1$-C$_3$)alkyl;

g represents 1, 2, or 3;

h represents 0, 1, or 2;

4.4)

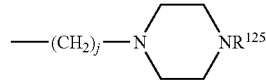

wherein

R$^{125}$ represents 4.4.a) H;

4.4.b) —(C$_1$-C$_3$)alkyl which may optionally bear halogen or —OR$^{126}$ in which R$^{126}$ represents H or —(C$_1$-C$_3$)alkyl which in turn is optionally substituted with halogen;

4.4.c) —SO$_2$R$^{127}$ wherein R$^{127}$ represents optionally substituted phenyl, or —(C$_1$-C$_3$)alkyl which may optionally bear halogen or OR$^{128}$ wherein R$^{128}$ represents H or (C$_1$-C$_3$)alkyl;

4.4.d) —C(O)R$^{129}$ wherein

R$^{129}$ represents 4.4.d1) optionally substituted phenyl, 4.4.d2) —(C$_1$-C$_3$)alkyl which may optionally bear up to 3 substituents independently selected from 4.4.d2.1) halogen;

4.4.d2.2) optionally substituted phenyl;

4.4.d2.3) —S(O)$_2$CH$_3$;

4.4.d2.4) —OR$^{130}$ wherein R$^{130}$ represents H or (C$_1$-C$_3$)alkyl which may optionally bear halogen; and 4.4.d2.5) —NR$^{131}$R$^{132}$ in which R$^{131}$ and R$^{132}$ are independently H or —(C$_1$-C$_3$)alkyl which may optionally bear halogen, or R$^{131}$ and R$^{132}$ may be joined and taken together with the N atom to which they are attached form a 5-6 membered ring which may optionally contain a ring member selected from O, S, and NR$^{133}$ wherein R$^{133}$ represents H or (C$_1$-C$_3$)alkyl;

4.4.d3) —OR$^{134}$ wherein R$^{134}$ represents H or (C$_1$-C$_3$)alkyl which may optionally bear halogen; or 4.4.d4) NR$^{135}$R$^{136}$ wherein R$^{135}$ and R$^{136}$ are independently H or —(C$_1$-C$_3$)alkyl which may optionally bear halogen, or $R^{135}$ and $R^{136}$ may be joined and taken together with the N atom to which they are attached form a 5-6 membered ring which may optionally contain a ring member selected from O, S, and $NR^{137}$ wherein $R^{137}$ represents H or $(C_1-C_3)$alkyl; and j represents 1, 2, or 3;

4.5)

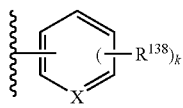

wherein

X represents C or N;

$R^{138}$ represents 4.5.a) $(C_1-C_4)$alkyl, which may optionally bear up to 3 substituents independently selected from
- 4.5.a1) halogen;
- 4.5.a2) $OR^{139}$ wherein $R^{139}$ represents H or $(C_1-C_3)$ alkyl which may optionally bear halogen or —$(C_1-C_3)$mono- or di-alkylamino;
- 4.5.a3) —$NR^{140}R^{141}$ in which $R^{140}$ and $R^{141}$ are independently H or —$(C_1-C_3)$alkyl which may optionally bear halogen or $OR^{141a}$ wherein $R^{141a}$ represents H or $(C_1-C_3)$alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or $(C_1-C_3)$alkyl; and
- 4.5.a4) a 5-6 membered heteroaromatic containing up to two heteroatoms selected from O, S, and N;

4.5.b) —$(C_3-C_6)$cycloalkyl which may optionally bear up to 2 substituents independently selected from
- 4.5.b1) halogen; and
- 4.5.b2) $OR^{143}$ wherein $R^{143}$ represents H or $(C_1-C_3)$ alkyl which may optionally bear halogen;

4.5.c) $OR^{144}$ wherein
$R^{144}$ represents H; phenyl; benzyl; $(C_3-C_6)$cycloalkyl; or $(C_1-C_4)$alkyl which may optionally bear up to 3 substituents independently selected from
- 4.5.c1) halogen;
- 4.5.c2) $OR^{145}$ wherein $R^{145}$ represents H or $(C_1-C_3)$ alkyl which may optionally bear $(C_1-C_3)$mono- or di-alkylamino; and
- 4.5.c3) $NR^{146}R^{147}$ in which $R^{146}$ and $R^{147\textit{a}}$ are independently H or —$(C_1-C_3)$alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or $(C_1-C_3)$ alkyl;

4.5.d) —$C(O)$—$OR^{149}$ wherein $R^{149}$ represents H or —$(C_1-C_4)$alkyl which may optionally bear up to 3 halogens;

4.5.e) —$C(O)$—$NR^{150}R^{151}$ wherein
$R^{150}$ represents H or $(C_1-C_3)$alkyl which may optionally bear halogen; and
$R^{151}$ represents H or —$(C_1-C_4)$alkyl which is optionally substituted with
- 4.5.e1) halogen;
- 4.5.e2) a 5-6 membered heteroaromatic containing up to two heteroatoms selected from O, S, and N;
- 4.5.e3) phenyl;
- 4.5.e4) —$SO_2CH_3$;
- 4.5.e5) —$OR^{152}$ wherein $R^{152}$ represents H or $(C_1-C_3)$alkyl which may optionally bear halogen; or
- 4.5.e6) —$NR^{153}R^{154}$ in which $R^{153}$ and $R^{154}$ are independently H or —$(C_1-C_3)$alkyl which may optionally bear halogen, or $R^{153}$ and $R^{154}$ may be joined and taken together with the N atom to which they are attached form a 5-6 membered ring which may optionally contain a ring member selected from O, S, and $NR^{155}$ wherein $R^{155}$ represents H or $(C_1-C_3)$alkyl;

4.5.f) —$N(R^{156})$—$C(O)$—$R^{157}$ wherein
$R^{156}$ represents H or $(C_1-C_3)$alkyl; and
$R^{157}$ represents H, optionally substituted phenyl, or $(C_1-C_4)$alkyl which is optionally substituted with
- 4.5.f1) optionally substituted phenyl,
- 4.5.f2) $OR^{158}$ wherein $R^{158}$ represents H or $(C_1-C_3)$ alkyl, or
- 4.5.f3) $NR^{159}R^{160}$ wherein $R^{159}$ and $R^{160}$ are independently H or —$(C_1-C_3)$alkyl which may optionally bear halogen, or $R^{159}$ and $R^{160}$ may be joined and taken together with the N atom to which they are attached form a 5-6 membered ring which may optionally contain a ring member selected from O, S, and $NR^{161}$ wherein $R^{161}$ represents H or $(C_1-C_3)$ alkyl;

4.5.g) —$SO_2NR^{162}R^{163}$ wherein
$R^{162}$ represents H or $(C_1-C_3)$alkyl which may optionally bear halogen; and
$R^{163}$ represents H or —$(C_1-C_4)$alkyl which is optionally substituted with
- 4.5.g1) halogen;
- 4.5.g2) a 5-6 membered heteroaromatic containing up to two heteroatoms selected from O, S, and N;
- 4.5.g3) phenyl;
- 4.5.g4) —$SO_2CH_3$;
- 4.5.g5) —$OR^{164}$ wherein $R^{164}$ represents H or $(C_1-C_3)$alkyl which may optionally bear halogen; or
- 4.5.g6) —$NR^{165}R^{166}$ in which $R^{165}$ and $R^{166}$ are independently H or —$(C_1-C_3)$alkyl which may optionally bear halogen, or $R^{165}$ and $R^{166}$ may be joined and taken together with the N atom to which they are attached form a 5-6 membered ring which may optionally contain a ring member selected from O, S, and $NR^{167}$ wherein $R^{167}$ represents H or $(C_1-C_3)$alkyl;

4.5.h) —$N(R^{168})$—$SO_2$—$R^{169}$ wherein
$R^{168}$ represents H or $(C_1-C_3)$alkyl, and
$R^{169}$ represents H, optionally substituted phenyl, or $(C_1-C_4)$alkyl which is optionally substituted with
- 4.5.h1) halogen,
- 4.5.h2) optionally substituted phenyl,
- 4.5.h3) $OR^{170}$ wherein $R^{170}$ represents H or $(C_1-C_3)$ alkyl which may optionally bear halogen, or
- 4.5.h4) $NR^{171}R^{172}$ wherein $R^{171}$ and $R^{172}$ are independently H or —$(C_1-C_3)$alkyl which may optionally bear halogen, or $R^{171}$ and $R^{172}$ may be joined and taken together with the N atom to which they are attached form a 5-6 membered ring which may optionally contain a ring member selected from O, S, and NR$^{173}$ wherein R$^{173}$ represents H or (C$_1$-C$_3$)alkyl;

4.5.i) —NR$^{174}$R$^{175}$ in which R$^{174}$ and R$^{175}$ are independently H or —(C$_1$-C$_3$)alkyl which may optionally bear halogen or OR$^{175a}$ wherein R$^{175a}$ represents H or (C$_1$-C$_3$)alkyl, or R$^{174}$ and R$^{175}$ may be joined and taken together with the N atom to which they are attached form a 5-6 membered ring which may optionally contain a ring member selected from O, S, and NR$^{176}$ wherein R$^{176}$ represents H or (C$_1$-C$_3$)alkyl;

4.5.j) halogen;
4.5.k) optionally substituted phenyl;
4.5.l) NO$_2$;
4.5.m) CN; or
4.5.n) a 5-6 membered heteroaromatic containing up to two heteroatoms selected from O, S, and N; and k represents 0, 1, or 2;

4.6)

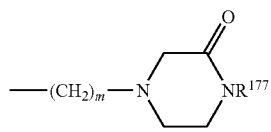

wherein R$^{177}$ represents H or —(C$_1$-C$_3$)alkyl; and
m represents 1, 2, or 3;

4.7)

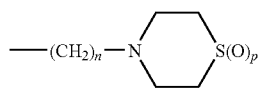

wherein
n represents 1, 2, or 3; and
p represents 0, 1, or 2;

4.8)

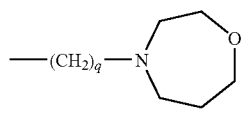

wherein
q represents 1, 2, or 3;

4.9)

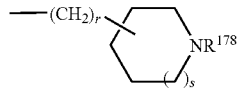

wherein
R$^{178}$ represents
4.9.a) H;
4.9.b) —(C$_1$-C$_3$)alkyl which may optionally bear halogen or —OR$^{179}$ in which R$^{179}$ represents H or (C$_1$-C$_3$)alkyl optionally substituted with halogen;

4.9.c) —SO$_2$R$^{180}$ wherein R$^{180}$ represents optionally substituted phenyl or —(C$_1$-C$_3$)alkyl, which may be substituted with halogen or —OR$^{181}$ wherein R$^{181}$ represents H or (C$_1$-C$_3$)alkyl which may optionally bear halogen;

4.9.d) —C(O)R$^{182}$ wherein R$^{182}$ represents optionally substituted phenyl or —(C$_1$-C$_3$)alkyl which may optionally bear up to 3 substituents independently selected from
4.9.d1) halogen;
4.9.d2) optionally substituted phenyl;
4.9.d3) —S(O)$_2$CH$_3$;
4.9.d4) OR$^{183}$ wherein R$^{183}$ represents H or (C$_1$-C$_3$)alkyl which may optionally bear halogen; and
4.9.d5) —NR$^{184}$R$^{185}$ in which R$^{184}$ and R$^{185}$ are independently H or —(C$_1$-C$_3$)alkyl which may optionally bear halogen or OR$^{185a}$ wherein R$^{185a}$ represents H or (C$_1$-C$_3$)alkyl, or R$^{184}$ and R$^{185}$ may be joined and taken together with the N atom to which they are attached form a 5-6 membered ring which may optionally contain a ring member selected from O, S, and NR$^{186}$ wherein R$^{186}$ represents H or (C$_1$-C$_3$)alkyl;

4.9e) —C(O)OR$^{187}$ wherein R$^{187}$ represents (C$_1$-C$_3$)alkyl; or
4.9.f) —C(O)—NR$^{188}$R$^{189}$ wherein R$^{188}$ and R$^{189}$ each independently represents H or —(C$_1$-C$_3$)alkyl which may optionally bear halogen, or R$^{188}$ and R$^{189}$ may be joined and taken together with the N atom to which they are attached form a 5-6 membered ring which may optionally contain a ring member selected from O, S, and NR$^{190}$ wherein R$^{190}$ represents H or (C$_1$-C$_3$)alkyl;

r represents 0, 1, or 2; and
s represents 0 or 1;

4.10)

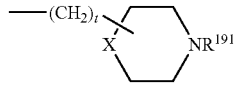

wherein
R$^{191}$ represents
4.10.a) H;
4.10.b) —(C$_1$-C$_3$)alkyl which may optionally bear halogen or —OR$^{192}$ in which R$^{192}$ represents H or (C$_1$-C$_3$)alkyl;
4.10c) —SO$_2$R$^{193}$ wherein R$^{193}$ represents phenyl or —(C$_1$-C$_3$)alkyl, both of which may be substituted with halogen or —(C$_1$-C$_3$)alkyl;
4.10.d) —C(O)R$^{194}$ wherein R$^{194}$ represents (C$_1$-C$_3$)alkyl which may optionally bear up to 3 substituents independently selected from
4.10.d1) halogen;
4.10.d2) phenyl;
4.10.d3) —S(O)$_2$CH$_3$;
4.10.d4) OR$^{195}$ wherein R$^{195}$ represents H or (C$_1$-C$_3$)alkyl which may optionally bear halogen; and
4.10.d5) —NR$^{196}$R$^{197}$ in which R$^{196}$ and R$^{197}$ are independently H or —(C$_1$-C$_3$)alkyl which may optionally bear halogen or OR$^{197a}$ wherein R$^{197a}$ represents H or (C$_1$-C$_3$)alkyl, or R$^{196}$ and R$^{197}$ may be joined and taken together with the N atom to which they are attached form a 5-6 membered ring which may optionally contain a ring member selected from O, S, and $NR^{198}$ wherein $R^{198}$ represents H or $(C_1-C_3)$alkyl;

4.10.e) $-C(O)OR^{199}$ wherein $R^{199}$ represents $(C_1-C_3)$alkyl; or 4.10.f) $-C(O)-NR^{200}R^{201}$ wherein $R^{200}$ and $R^{201}$ each independently represents H or $-(C_1-C_3)$alkyl which may optionally bear halogen, or $R^{200}$ and $R^{201}$ may be joined and taken together with the N atom to which they are attached form a 5-6 membered ring which may optionally contain a ring member selected from O, S, and $NR^{202}$ wherein $R^{202}$ represents H or $(C_1-C_3)$alkyl; and X represents O, S, S(O), $S(O)_2$, or $NR^{203}$ wherein $R^{203}$ represents H or $-(C_1-C_3)$alkyl; and t represents 0, 1, or 2;

4.11) halogen; or 4.12) CN;

or a pharmaceutically acceptable salt thereof.

In embodiment two, the present invention provides a compound of formula (I)

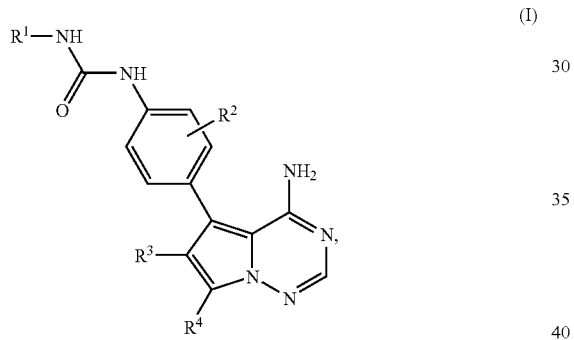

wherein $R^1$ represents 1.1) phenyl which may optionally bear up to 4 substituents independently selected from the group consisting of 1.1.a) $(C_1-C_4)$alkyl, which may optionally bear up to 3 substituents independently selected from 1.1.a1) halogen;

1.1.a2) $OR^5$ wherein $R^5$ represents H or $(C_1-C_3)$alkyl which may optionally bear halogen or $-(C_1-C_3)$ mono- or di-alkylamino;

1.1.a3) $-NR^6R^7$ in which $R^6$ and $R^7$ are independently H or $-(C_1-C_3)$alkyl which may optionally bear halogen or $OR^{7a}$ wherein $R^{7a}$ represents H or $(C_1-C_3)$alkyl, or $R^6$ and $R^7$ may be joined and taken together with the N atom to which they are attached form a 5-6 membered ring which may optionally contain a ring member selected from O, S, and $NR^8$ wherein $R^8$ represents H or $(C_1-C_3)$alkyl; and 1.1.a4) a 5-6 membered heteroaromatic containing up to two heteroatoms selected from O, S, and N;

1.1.b) $-(C_3-C_6)$cycloalkyl which may optionally bear up to 2 substituents independently selected from 1.1.b1) halogen;

1.1.c) $OR^{10}$ wherein $R^{10}$ represents H; phenyl; benzyl; $(C_3-C_6)$cycloalkyl; or $(C_1-C_4)$alkyl which may optionally bear up to 3 substituents independently selected from 1.1.c1) halogen;

1.1.c2) $OR^{11}$ wherein $R^{11}$ represents H or $(C_1-C_3)$alkyl which may optionally bear $(C_1-C_3)$mono- or di-alkylamino; and 1.1.c3) $NR^{12}R^{13}$ in which $R^{12}$ and $R^{13}$ are independently H or $-(C_1-C_3)$alkyl which may optionally bear halogen, or $R^{12}$ and $R^{13}$ may be joined and taken together with the N atom to which they are attached form a 5-6 membered ring which may optionally contain a ring member selected from O, S, and $NR^{14}$ wherein $R^{14}$ represents H or $(C_1-C_3)$alkyl;

1.1.e) $-C(O)-NR^{16}R^{17}$ wherein $R^{16}$ represents H or $(C_1-C_3)$alkyl which may optionally bear halogen; and $R^{17}$ represents H or $-(C_1-C_4)$alkyl which is optionally substituted with 1.1.e1) halogen;

1.1.e3) phenyl;

1.1.e4) $-SO_2CH_3$;

1.1.e5) $-OR^{18}$ wherein $R^{18}$ represents H or $(C_1-C_3)$alkyl which may optionally bear halogen; or 1.1.e6) $-NR^{19}R^{20}$ in which $R^{19}$ and $R^{20}$ are independently H or $-(C_1-C_3)$alkyl which may optionally bear halogen, or $R^{19}$ and $R^{20}$ may be joined and taken together with the N atom to which they are attached form a 5-6 membered ring which may optionally contain a ring member selected from O, S, and $NR^{21}$ wherein $R^{21}$ represents H or $(C_1-C_3)$alkyl;

1.1.f) $-N(R^{22})-C(O)-R^{23}$ wherein $R^{22}$ represents H or $(C_1-C_3)$alkyl; and $R^{23}$ represents optionally substituted phenyl, or $(C_1-C_4)$alkyl which is optionally substituted with 1.1.f1) optionally substituted phenyl, 1.1.f2) $OR^{24}$ wherein $R^{24}$ represents H or $(C_1-C_3)$alkyl, or 1.1.f3) $NR^{25}R^{26}$ wherein $R^{25}$ and $R^{26}$ are independently H or $-(C_1-C_3)$alkyl which may optionally bear halogen, or $R^{25}$ and $R^{26}$ may be joined and taken together with the N atom to which they are attached form a 5-6 membered ring which may optionally contain a ring member selected from O, S, and $NR^{27}$ wherein $R^{27}$ represents H or $(C_1-C_3)$alkyl;

1.1.g) $-SO_2NR^{28}R^{29}$ wherein $R^{28}$ represents H or $(C_1-C_3)$alkyl which may optionally bear halogen; and $R^{29}$ represents H or $-(C_1-C_4)$alkyl which is optionally substituted with:

1.1.g1) halogen;

1.1.g3) phenyl;

1.1.g4) $-SO_2CH_3$;

1.1.g5) $-OR^{30}$ wherein $R^{30}$ represents H or $(C_1-C_3)$alkyl which may optionally bear halogen; or 1.1.g6) $-NR^{31}R^{32}$ in which $R^{31}$ and $R^{32}$ are independently H or $-(C_1-C_3)$alkyl which may optionally bear halogen, or $R^{31}$ and $R^{32}$ may be joined and taken together with the N atom to which they are attached form a 5-6 membered ring which may optionally contain a ring member selected from O, S, and $NR^{33}$ wherein $R^{33}$ represents H or $(C_1-C_3)$alkyl;

1.1.h) —N($R^{34}$)—$SO_2$—$R^{35}$ wherein
   $R^{34}$ represents H or ($C_1$-$C_3$)alkyl, and
   $R^{35}$ represents optionally substituted phenyl, or ($C_1$-$C_4$)alkyl which is optionally substituted with
   1.1.h1) halogen;
   1.1.h2) optionally substituted phenyl,
   1.1.h3) $OR^{36}$ wherein $R^{36}$ represents H or ($C_1$-$C_3$)alkyl, or
   1.1.h4) $NR^{37}R^{38}$ wherein $R^{37}$ and $R^{38}$ are independently H or —($C_1$-$C_3$)alkyl which may optionally bear halogen, or $R^{37}$ and $R^{38}$ may be joined and taken together with the N atom to which they are attached form a 5-6 membered ring which may optionally contain a ring member selected from O, S, and $NR^{39}$ wherein $R^{39}$ represents H or ($C_1$-$C_3$)alkyl;
1.1.i) —$NR^{40}R^{41}$ in which $R^{40}$ and $R^{41}$ are independently H or —($C_1$-$C_3$)alkyl which may optionally bear halogen or $OR^{42}$ in which $R^{42}$ represents H or ($C_1$-$C_3$)alkyl, or $R^{40}$ and $R^{41}$ may be joined and taken together with the N atom to which they are attached form a 5-6 membered ring which may optionally contain a ring member selected from O, S, and $NR^{43}$ wherein
   $R^{43}$ represents H or ($C_1$-$C_3$)alkyl;
1.1.j) halogen;
1.1.l) $NO_2$;
1.1.m) CN; and
1.1.n) a 5-6 membered heteroaromatic containing up to two heteroatoms selected from O, S, and N;

or
$R^1$ represents
1.2) a 5-6 membered aromatic heterocycle containing up to 3 heteroatoms independently selected from the group consisting of N, O, and S; said $R^1$ heterocycle optionally bearing up to 4 substituents independently selected from the group consisting of
   1.2.a) ($C_1$-$C_4$)alkyl, which may optionally bear up to 3 substituents independently selected from
      1.2.a1) halogen;
      1.2.a2) $OR^{45}$ wherein $R^{45}$ represents H or ($C_1$-$C_3$)alkyl which may optionally bear halogen or —($C_1$-$C_3$)mono- or di-alkylamino;
      1.2.a3) —$NR^{46}R^{47}$ in which $R^{46}$ and $R^{47}$ are independently H or —($C_1$-$C_3$)alkyl which may optionally bear halogen or $OR^{47a}$ wherein $R^{47a}$ represents H or ($C_1$-$C_3$)alkyl, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or ($C_1$-$C_3$)alkyl; and
      1.2.a4) a 5-6 membered heteroaromatic containing up to two heteroatoms selected from O, S, and N;
   1.2.b) —($C_3$-$C_6$)cycloalkyl which may optionally bear up to 2 substituents independently selected from
      1.2.b1) halogen;
   1.2.c) $OR^{50}$ wherein
      $R^{50}$ represents H; phenyl; benzyl; —($C_3$-$C_6$)cycloalkyl; or —($C_1$-$C_4$)alkyl which may optionally bear up to 3 substituents independently selected from
      1.2.c1) halogen;
      1.2.c2) $OR^{51}$ wherein $R^{51}$ represents H or ($C_1$-$C_3$)alkyl which may optionally bear —($C_1$-$C_3$)mono- or di-alkylamino; and
      1.2.c3) —$NR^{52}R^{53}$ in which $R^{52}$ and $R^{53}$ are independently H or —($C_1$-$C_3$)alkyl which may optionally bear halogen, or $R^{52}$ and $R^{53}$ may be joined and taken together with the N atom to which they are attached form a 5-6 membered ring which may optionally contain a ring member selected from O, S, and $NR^{54}$ wherein $R^{54}$ represents H or ($C_1$-$C_3$)alkyl;
   1.2.e) —C(O)—$NR^{56}R^{57}$ wherein
      $R^{56}$ represents H or ($C_1$-$C_3$)alkyl which may optionally bear halogen; and
      $R^{57}$ represents H or —($C_1$-$C_4$)alkyl which is optionally substituted with
      1.2.e1) halogen;
      1.2.e3) phenyl;
      1.2.e4) —$SO_2CH_3$;
      1.2.e5) —$OR^{58}$ wherein $R^{58}$ represents H or ($C_1$-$C_3$)alkyl which may optionally bear halogen; or
      1.2.e6) —$NR^{59}R^{60}$ in which $R^{59}$ and $R^{60}$ are independently H or —($C_1$-$C_3$)alkyl which may optionally bear halogen, or $R^{59}$ and $R^{60}$ may be joined and taken together with the N atom to which they are attached form a 5-6 membered ring which may optionally contain a ring member selected from O, S, and $NR^{61}$ wherein $R^{61}$ represents H or ($C_1$-$C_3$)alkyl;
   1.2.f) —N($R^{62}$)—C(O)—$R^{63}$ wherein
      $R^{62}$ represents H or ($C_1$-$C_3$)alkyl; and
      $R^{63}$ represents optionally substituted phenyl, or ($C_1$-$C_4$)alkyl which is optionally substituted with
      1.2.f1) optionally substituted phenyl,
      1.2.f2) $OR^{64}$ wherein $R^{64}$ represents H or ($C_1$-$C_3$)alkyl, or
      1.2.f3) $NR^{65}R^{66}$ wherein $R^{65}$ and $R^{66}$ are independently H or —($C_1$-$C_3$)alkyl which may optionally bear halogen, or $R^{65}$ and $R^{66}$ may be joined and taken together with the N atom to which they are attached form a 5-6 membered ring which may optionally contain a ring member selected from O, S, and $NR^{67}$ wherein $R^{67}$ represents H or ($C_1$-$C_3$)alkyl;
   1.2.g) —$SO_2NR^{68}R^{69}$ wherein
      $R^{68}$ represents H or ($C_1$-$C_3$)alkyl which may optionally bear halogen; and
      $R^{69}$ represents H or —($C_1$-$C_4$)alkyl which is optionally substituted with
      1.2.g1) halogen;
      1.2.g3) phenyl;
      1.2.g4) —$SO_2CH_3$;
      1.2.g5) —$OR^{70}$ wherein $R^{70}$ represents H or ($C_1$-$C_3$)alkyl which may optionally bear halogen; or
      1.2.g6) —$NR^{71}R^{72}$ in which $R^{71}$ and $R^{72}$ are independently H or —($C_1$-$C_3$)alkyl which may optionally bear halogen, or $R^{71}$ and $R^{72}$ may be joined and taken together with the N atom to which they are attached form a 5-6 membered ring which may optionally contain a ring member selected from O, S, and $NR^{73}$ wherein $R^{73}$ represents H or ($C_1$-$C_3$)alkyl;
   1.2.h) —N($R^{74}$)—$SO_2$—$R^{75}$ wherein
      $R^{74}$ represents H or ($C_1$-$C_3$)alkyl, and
      $R^{75}$ represents optionally substituted phenyl, or ($C_1$-$C_4$)alkyl which is optionally substituted with
      1.2.h1) halogen;
      1.2.h2) optionally substituted phenyl,
      1.2.h3) $OR^{76}$ wherein $R^{76}$ represents H or ($C_1$-$C_3$)alkyl, or 1.2.h4) $NR^{77}R^{78}$ wherein $R^{77}$ and $R^{78}$ are independently H or —$(C_1-C_3)$alkyl which may optionally bear halogen, or $R^{77}$ and $R^{78}$ may be joined and taken together with the N atom to which they are attached form a 5-6 membered ring which may optionally contain a ring member selected from O, S, and $NR^{79}$ wherein $R^{79}$ represents H or $(C_1-C_3)$alkyl;

1.2.i) —$NR^{80}R^{81}$ in which $R^{80}$ and $R^{81}$ are independently H or —$(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$alkyl;

1.2.j) halogen;

1.2.k) optionally substituted phenyl;

1.2.l) $NO_2$;

1.2.m) CN; and 1.2.n) a 5-6 membered heteroaromatic containing up to two heteroatoms selected from O, S, and N;

$R^2$ represents halogen; —$(C_1-C_5)$alkyl which may optionally bear halogen; or —$O(C_1-C_3)$alkyl which may optionally bear halogen;

$R^3$ represents 3.1) —$(C_1-C_5)$alkyl which is optionally substituted with 3.1.a) -halogen;

3.1.b) phenyl optionally substituted with halogen, —$(C_1-C_3)$alkyl, or —$(C_1-C_3)$alkoxy, 3.1.c) a 5-6 membered heteroaromatic containing up to two heteroatoms selected from O, S, and N, optionally substituted with halogen or —$(C_1-C_3)$alkyl, 3.1.d) —CN, 3.1.e) —$OR^{83}$ wherein $R^{83}$ represents H or —$(C_1-C_3)$ alkyl which may optionally bear up to 3 substituents independently selected from 3.1.e1) halogen;

3.1.e2) optionally substituted phenyl;

3.1.e3) —$S(O)_2CH_3$;

3.1.e4) $OR^{84}$ wherein $R^{84}$ represents H or $(C_1-C_3)$ alkyl which may optionally bear halogen or —$(C_1-C_3)$mono- or di-alkylamino; and 3.1.e5) —$NR^{85}R^{86}$ in which $R^{85}$ and $R^{86}$ are independently H or —$(C_1-C_3)$alkyl which may optionally bear halogen, or $R^{85}$ and $R^{86}$ may be joined and taken together with the N atom to which they are attached form a 5-6 membered ring which may optionally contain a ring member selected from O, S, and $NR^{87}$ wherein $R^{87}$ represents H or $(C_1-C_3)$ alkyl;

3.1.f) —$(C_3-C_5)$cycloalkyl which may optionally bear halogen; or 3.1.g) —$NR^{89}R^{90}$ wherein $R^{89}$ represents H or —$(C_1-C_3)$alkyl which may optionally bear halogen; and $R^{90}$ represents H or —$(C_1-C_4)$alkyl which is optionally substituted with 3.1.g1) halogen;

3.1.g2) a 5-6 membered heteroaromatic containing up to two heteroatoms selected from O, S, and N;

3.1.g3) phenyl;

3.1.g4) —$SO_2CH_3$;

3.1.g5) —$OR^{91}$ wherein $R^{91}$ represents H or $(C_1-C_3)$alkyl which may optionally bear halogen; or 3.1.g6) —$NR^{92}R^{93}$ in which $R^{92}$ and $R^{93}$ are independently H or —$(C_1-C_3)$alkyl which may optionally bear halogen, or $R^{92}$ and $R^{93}$ may be joined and taken together with the N atom to which they are attached form a 5-6 membered ring which may optionally contain a ring member selected from O, S, and $NR^{94}$ wherein $R^{94}$ represents H or $(C_1-C_3)$alkyl; or 3.1.g7) $R^{89}$ and $R^{90}$ may be joined and taken together with the N to which they are attached form an aromatic or nonaromatic 5-6 membered ring which may optionally contain a ring member selected from O, S, and $NR^{95}$ wherein $R^{95}$ represents H or $(C_1-C_3)$alkyl;

3.2)

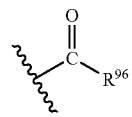

wherein
$R^{96}$ represents 3.2.a) H, 3.2.b) —$(C_3-C_5)$cycloalkyl which may optionally bear halogen; or 3.2.c) —$(C_1-C_5)$alkyl which may optionally bear up to 3 substituents independently selected from 3.2.c1) halogen;

3.2.c2) a 5-6 membered heteroaromatic containing up to two heteroatoms selected from O, S, and N;

3.2.c3) phenyl;

3.2.c5) —$OR^{97}$ wherein $R^{97}$ represents H or $(C_1-C_3)$ alkyl which may optionally bear halogen or —$(C_1-C_3)$mono- or di-alkylamino; and 3.2.c6) —$NR^{98}R^{99}$ in which $R^{98}$ and $R^{99}$ are independently H or —$(C_1-C_3)$alkyl which may optionally bear halogen or $OR^{99a}$ wherein $R^{99a}$ represents H or $(C_1-C_3)$alkyl, or $R^{98}$ and $R^{99}$ may be joined and taken together with the N atom to which they are attached form a 5-6 membered ring which may optionally contain a ring member selected from O, S, and $NR^{100}$ wherein $R^{100}$ represents H or $(C_1-C_3)$ alkyl;

3.3)

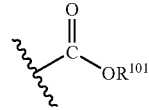

wherein $R^{101}$ represents H or —$(C_1-C_5)$alkyl which may optionally bear up to 3 substituents independently selected from 3.3.a) halogen; and 3.3.b) phenyl;

3.4)

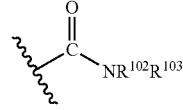

wherein
R$^{102}$ represents H or —(C$_1$-C$_3$)alkyl which may optionally bear halogen; and
R$^{103}$ represents H or —(C$_1$-C$_5$)alkyl which may optionally bear up to 3 substituents independently selected from
3.4.a) halogen;
3.4.b) a 5-6 membered heteroaromatic containing up to two heteroatoms selected from O, S, and N;
3.4.c) phenyl;
3.4.d) —S(O)$_2$CH$_3$;
3.4.e) OR$^{104}$ wherein R$^{104}$ represents H or (C$_1$-C$_3$)alkyl which may optionally bear halogen; and
3.4.f) —NR$^{105}$R$^{106}$ in which R$^{105}$ and R$^{106}$ are independently H or —(C$_1$-C$_3$)alkyl which may optionally bear halogen, or R$^{105}$ and R$^{106}$ may be joined and taken together with the N atom to which they are attached form a 5-6 membered ring which may optionally contain a ring member selected from O, S, and NR$^{107}$ wherein R$^{107}$ represents H or (C$_1$-C$_3$)alkyl;
3.6) a 5-6 membered heteroaromatic containing up to two heteroatoms selected from O, S, and N;
3.7) halogen; or
3.8) —CN;
R$^4$ represents
4.1) —(C$_1$-C$_5$)alkyl which is optionally substituted with
4.1.a) —(C$_3$-C$_5$)cycloalkyl which may optionally bear halogen or OR$^{109}$ wherein R$^{109}$ represents H or (C$_1$-C$_3$)alkyl;
4.1.b) -halogen;
4.1.c) —OR$^{110}$ wherein R$^{110}$ represents H or —(C$_1$-C$_3$)alkyl which may optionally bear up to 3 substituents independently selected from
4.1.c1) halogen;
4.1.c2) phenyl;
4.1.c4) OR$^{111}$ wherein R$^{111}$ represents H or (C$_1$-C$_3$)alkyl which may optionally bear halogen; and
4.1.c5) —NR$^{112}$R$^{113}$ in which R$^{112}$ and R$^{113}$ are independently H or —(C$_1$-C$_3$)alkyl which may optionally bear halogen, or R$^{112}$ and R$^{113}$ may be joined and taken together with the N atom to which they are attached form a 5-6 membered ring which may optionally contain a ring member selected from O, S, and NR$^{114}$ wherein R$^{114}$ represents H or (C$_1$-C$_3$)alkyl;
4.1.d) —NR$^{115}$R$^{116}$ wherein
R$^{115}$ represents H or —(C$_1$-C$_3$)alkyl which may optionally bear halogen and
R$^{116}$ represents H, optionally substituted phenyl, or —(C$_1$-C$_5$)alkyl which may optionally bear up to 3 substituents independently selected from
4.1.d1) halogen;
4.1.d2) —S(O)$_2$CH$_3$;
4.1.d3) OR$^{117}$ wherein R$^{117}$ represents H or (C$_1$-C$_3$)alkyl which may optionally bear halogen; and
4.1.d4) —NR$^{118}$R$^{119}$ in which R$^{118}$ and R$^{119}$ are independently H or —(C$_1$-C$_3$)alkyl which may optionally bear halogen, or R$^{118}$ and R$^{119}$ may be joined and taken together with the N atom to which they are attached form a 5-6 membered ring which may optionally contain a ring member selected from O, S, and NR$^{120}$ wherein R$^{120}$ represents H or (C$_1$-C$_3$)alkyl; or
4.1.f) a 5-6 membered aromatic heterocycle containing up to two heteroatoms selected from O, S, and N;

4.2)

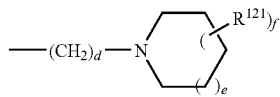

wherein R$^{121}$ represents —(C$_1$-C$_3$)alkyl which may optionally bear halogen or —OR$^{122}$ in which R$^{122}$ represents H or —(C$_1$-C$_3$)alkyl;
d represents 1, 2, or 3;
e represents 0 or 1;
f represents 0, 1, or 2;

4.3)

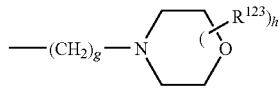

wherein R$^{123}$ represents —(C$_1$-C$_3$)alkyl which may optionally bear halogen or —OR$^{124}$ in which R$^{124}$ represents H or —(C$_1$-C$_3$)alkyl;
g represents 1, 2, or 3;
h represents 0, 1, or 2;

4.4)

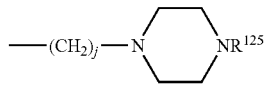

wherein
R$^{125}$ represents
4.4.a) H;
4.4.b) —(C$_1$-C$_3$)alkyl which may optionally bear halogen or —OR$^{126}$ in which R$^{126}$ represents H or —(C$_1$-C$_3$)alkyl which in turn is optionally substituted with halogen;
4.4.c) —SO$_2$R$^{127}$ wherein R$^{127}$ represents optionally substituted phenyl, or —(C$_1$-C$_3$)alkyl which may optionally bear halogen or OR$^{128}$ wherein R$^{128}$ represents H or (C$_1$-C$_3$)alkyl;
4.4.d) —C(O)R$^{129}$ wherein
R$^{129}$ represents
4.4.d1) optionally substituted phenyl,
4.4.d2) —(C$_1$-C$_3$)alkyl which may optionally bear up to 3 substituents independently selected from
4.4.d2.1) halogen;
4.4.d2.4) —OR$^{130}$ wherein R$^{130}$ represents H or (C$_1$-C$_3$)alkyl which may optionally bear halogen; and
4.4.d2.5) —NR$^{131}$R$^{132}$ in which R$^{131}$ and R$^{132}$ are independently H or —(C$_1$-C$_3$)alkyl which may optionally bear halogen, or R$^{131}$ and R$^{132}$ may be joined and taken together with the N atom to which they are attached form a 5-6 membered ring which may optionally contain a ring member selected from O, S, and NR$^{133}$ wherein R$^{133}$ represents H or (C$_1$-C$_3$)alkyl;
4.4.d3) —OR$^{134}$ wherein R$^{134}$ represents (C$_1$-C$_3$)alkyl which may optionally bear halogen; or
4.4.d4) NR$^{135}$R$^{136}$ wherein R$^{135}$ and R$^{136}$ are independently H or —(C$_1$-C$_3$)alkyl which may optionally bear halogen, or R$^{135}$ and R$^{136}$ may be joined and taken together with the N atom to which they are attached form a 5-6 membered ring which may optionally contain a ring member selected from O, S, and $NR^{137}$ wherein $R^{137}$ represents H or $(C_1-C_3)$alkyl; and j represents 1, 2, or 3;

4.5)

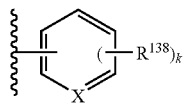

wherein

X represents C or N;

$R^{138}$ represents 4.5.a) $(C_1-C_4)$alkyl, which may optionally bear up to 3 substituents independently selected from
- 4.5.a1) halogen;
- 4.5.a2) $OR^{139}$ wherein $R^{139}$ represents H or $(C_1-C_3)$ alkyl which may optionally bear halogen or $-(C_1-C_3)$mono- or di-alkylamino;
- 4.5.a3) $-NR^{140}R^{141}$ in which $R^{140}$ and $R^{141}$ are independently H or $-(C_1-C_3)$alkyl which may optionally bear halogen or $OR^{141a}$ wherein $R^{141a}$ represents H or $(C_1-C_3)$alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or $(C_1-C_3)$alkyl; and
- 4.5.a4) a 5-6 membered heteroaromatic containing up to two heteroatoms selected from O, S, and N;

4.5.b) $-(C_3-C_6)$cycloalkyl which may optionally bear up to 2 substituents independently selected from
- 4.5.b1) halogen;

4.5.c) $OR^{144}$ wherein
$R^{144}$ represents H; phenyl; benzyl; $(C_3-C_6)$cycloalkyl; or $(C_1-C_4)$alkyl which may optionally bear up to 3 substituents independently selected from
- 4.5.c1) halogen;
- 4.5.c2) $OR^{145}$ wherein $R^{145}$ represents H or $(C_1-C_3)$ alkyl which may optionally bear $(C_1-C_3)$mono- or di-alkylamino; and
- 4.5.c3) $NR^{146}R^{147}$ in which $R^{146}$ and $R^{1473}$ are independently H or $-(C_1-C_3)$alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or $(C_1-C_3)$alkyl;

4.5.e) $-C(O)-NR^{150}R^{151}$ wherein
$R^{150}$ represents H or $(C_1-C_3)$alkyl which may optionally bear halogen; and
$R^{151}$ represents H or $-(C_1-C_4)$alkyl which is optionally substituted with
- 4.5.e1) halogen;
- 4.5.e3) phenyl;
- 4.5.e4) $-SO_2CH_3$;
- 4.5.e5) $-OR^{152}$ wherein $R^{152}$ represents H or $(C_1-C_3)$alkyl which may optionally bear halogen; or
- 4.5.e6) $-NR^{153}R^{154}$ in which $R^{153}$ and $R^{154}$ are independently H or $-(C_1-C_3)$alkyl which may optionally bear halogen, or $R^{153}$ and $R^{154}$ may be joined and taken together with the N atom to which they are attached form a 5-6 membered ring which may optionally contain a ring member selected from O, S, and $NR^{155}$ wherein $R^{155}$ represents H or $(C_1-C_3)$ alkyl;

4.5.f) $-N(R^{156})-C(O)-R^{157}$ wherein
$R^{156}$ represents H or $(C_1-C_3)$alkyl; and
$R^{157}$ represents H, optionally substituted phenyl, or $(C_1-C_4)$alkyl which is optionally substituted with
- 4.5.f1) optionally substituted phenyl,
- 4.5.f2) $OR^{158}$ wherein $R^{158}$ represents H or $(C_1-C_3)$ alkyl, or
- 4.5.f3) $NR^{159}R^{160}$ wherein $R^{159}$ and $R^{160}$ are independently H or $-(C_1-C_3)$alkyl which may optionally bear halogen, or $R^{159}$ and $R^{160}$ may be joined and taken together with the N atom to which they are attached form a 5-6 membered ring which may optionally contain a ring member selected from O, S, and $NR^{161}$ wherein $R^{161}$ represents H or $(C_1-C_3)$ alkyl;

4.5.g) $-SO_2NR^{162}R^{163}$ wherein
$R^{162}$ represents H or $(C_1-C_3)$alkyl which may optionally bear halogen; and
$R^{163}$ represents H or $-(C_1-C_4)$alkyl which is optionally substituted with
- 4.5.g1) halogen;
- 4.5.g3) phenyl;
- 4.5.g4) $-SO_2CH_3$;
- 4.5.g5) $-OR^{164}$ wherein $R^{164}$ represents H or $(C_1-C_3)$alkyl which may optionally bear halogen; or
- 4.5.g6) $-NR^{165}R^{166}$ in which $R^{165}$ and $R^{166}$ are independently H or $-(C_1-C_3)$alkyl which may optionally bear halogen, or $R^{165}$ and $R^{166}$ may be joined and taken together with the N atom to which they are attached form a 5-6 membered ring which may optionally contain a ring member selected from O, S, and $NR^{167}$ wherein $R^{167}$ represents H or $(C_1-C_3)$alkyl;

4.5.h) $-N(R^{168})-SO_2-R^{169}$ wherein
$R^{168}$ represents H or $(C_1-C_3)$alkyl, and
$R^{169}$ represents H, optionally substituted phenyl, or $(C_1-C_4)$alkyl which is optionally substituted with
- 4.5.h1) halogen,
- 4.5.h2) optionally substituted phenyl,
- 4.5.h3) $OR^{170}$ wherein $R^{170}$ represents H or $(C_1-C_3)$ alkyl which may optionally bear halogen, or
- 4.5.h4) $NR^{171}R^{172}$ wherein $R^{171}$ and $R^{172}$ are independently H or $-(C_1-C_3)$alkyl which may optionally bear halogen, or $R^{171}$ and $R^{172}$ may be joined and taken together with the N atom to which they are attached form a 5-6 membered ring which may optionally contain a ring member selected from O, S, and $NR^{173}$ wherein $R^{173}$ represents H or $(C_1-C_3)$ alkyl;

4.5.i) $-NR^{174}R^{175}$ in which $R^{174}$ and $R^{175}$ are independently H or $-(C_1-C_3)$alkyl which may optionally bear halogen or $OR^{175a}$ wherein $R^{175a}$ represents H or $(C_1-C_3)$alkyl, or $R^{174}$ and $R^{175}$ may be joined and taken together with the N atom to which they are attached form a 5-6 membered ring which may optionally contain a ring member selected from O, S, and $NR^{176}$ wherein $R^{176}$ represents H or $(C_1-C_3)$ alkyl;

4.5.j) halogen;
4.5.l) $NO_2$;
4.5.m) CN; or
4.5.n) a 5-6 membered heteroaromatic containing up to two heteroatoms selected from O, S, and N; and k represents 0, 1, or 2;

4.6)

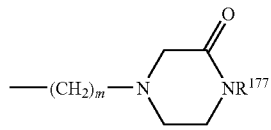

wherein $R^{177}$ represents H or —$(C_1$-$C_3)$alkyl; and
m represents 1, 2, or 3;

4.7)

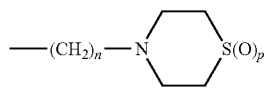

wherein
n represents 1, 2, or 3; and
p represents 0, 1, or 2;

4.8)

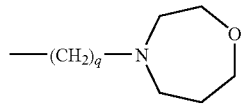

wherein
q represents 1, 2, or 3;

4.9)

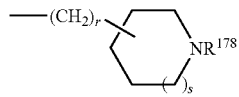

wherein
$R^{178}$ represents
 4.9.a) H;
 4.9.b) —$(C_1$-$C_3)$alkyl which may optionally bear halogen or —$OR^{179}$ in which $R^{179}$ represents H or $(C_1$-$C_3)$alkyl optionally substituted with halogen;
 4.9.c) —$SO_2R^{180}$ wherein $R^{180}$ represents optionally substituted phenyl or —$(C_1$-$C_3)$alkyl, which may be substituted with halogen or —$OR^{181}$ wherein $R^{181}$ represents H or $(C_1$-$C_3)$alkyl which may optionally bear halogen;
 4.9.d) —$C(O)R^{182}$ wherein $R^{182}$ represents optionally substituted phenyl or —$(C_1$-$C_3)$alkyl which may optionally bear up to 3 substituents independently selected from
  4.9.d1) halogen;
  4.9.d2) optionally substituted phenyl;
  4.9.d4) $OR^{183}$ wherein $R^{183}$ represents H or $(C_1$-$C_3)$alkyl which may optionally bear halogen; and
  4.9.d5) —$NR^{184}R^{185}$ in which $R^{184}$ and $R^{185}$ are independently H or —$(C_1$-$C_3)$alkyl which may optionally bear halogen or $OR^{185a}$ wherein $R^{185a}$ represents H or $(C_1$-$C_3)$alkyl, or $R^{184}$ and $R^{185}$ may be joined and taken together with the N atom to which they are attached form a 5-6 membered ring which may optionally contain a ring member selected from O, S, and $NR^{186}$ wherein $R^{186}$ represents H or $(C_1$-$C_3)$alkyl;
 4.9e) —$C(O)OR^{187}$ wherein $R^{187}$ represents $(C_1$-$C_3)$alkyl; or
 4.9.f) —$C(O)$—$NR^{188}R^{189}$ wherein $R^{188}$ and $R^{189}$ each independently represents H or —$(C_1$-$C_3)$alkyl which may optionally bear halogen, or $R^{188}$ and $R^{189}$ may be joined and taken together with the N atom to which they are attached form a 5-6 membered ring which may optionally contain a ring member selected from O, S, and $NR^{190}$ wherein $R^{190}$ represents H or $(C_1$-$C_3)$alkyl;

r represents 0, 1, or 2; and
s represents 0 or 1;

4.10)

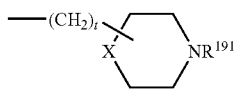

wherein
$R^{191}$ represents
 4.10.a) H;
 4.10.b) —$(C_1$-$C_3)$alkyl which may optionally bear halogen or —$OR^{192}$ in which $R^{192}$ represents H or $(C_1$-$C_3)$alkyl;
 4.10c) —$SO_2R^{193}$ wherein $R^{193}$ represents phenyl or —$(C_1$-$C_3)$alkyl, both of which may be substituted with halogen or —$(C_1$-$C_3)$alkyl;
 4.10.d) —$C(O)R^{194}$ wherein $R^{194}$ represents $(C_1$-$C_3)$alkyl which may optionally bear up to 3 substituents independently selected from
  4.10.d1) halogen;
  4.10.d2) phenyl;
  4.10.d4) $OR^{195}$ wherein $R^{195}$ represents H or $(C_1$-$C_3)$alkyl which may optionally bear halogen; and
  4.10.d5) —$NR^{196}R^{197}$ in which $R^{196}$ and $R^{197}$ are independently H or —$(C_1$-$C_3)$alkyl which may optionally bear halogen or $OR^{197a}$ wherein $R^{197a}$ represents H or $(C_1$-$C_3)$alkyl, or $R^{196}$ and $R^{197}$ may be joined and taken together with the N atom to which they are attached form a 5-6 membered ring which may optionally contain a ring member selected from O, S, and $NR^{198}$ wherein $R^{198}$ represents H or $(C_1$-$C_3)$alkyl;
 4.10.e) —$C(O)OR^{199}$ wherein $R^{199}$ represents $(C_1$-$C_3)$alkyl; or
 4.10.f) —$C(O)$—$NR^{200}R^{201}$ wherein $R^{200}$ and $R^{201}$ each independently represents H or —$(C_1$-$C_3)$alkyl which may optionally bear halogen, or $R^{200}$ and $R^{201}$ may be joined and taken together with the N atom to which they are attached form a 5-6 membered ring which may optionally contain a ring member selected from O, S, and $NR^{202}$ wherein $R^{202}$ represents H or $(C_1$-$C_3)$alkyl; and X represents O, S, S(O)$_2$, or NR$^{203}$ wherein
R$^{203}$ represents H or —(C$_1$-C$_3$)alkyl; and
t represents 0, 1, or 2;
4.11) halogen; or
4.12) —CN;
or a pharmaceutically acceptable salt thereof.

In embodiment three, the present invention provides a compound of formula (I)

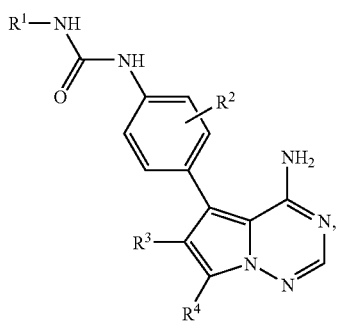

(I)

wherein
R$^1$ represents
1.1) phenyl which may optionally bear up to 4 substituents independently selected from the group consisting of
   1.1.a) (C$_1$-C$_4$)alkyl, which may optionally bear up to 3 substituents independently selected from
      1.1.a1) halogen;
      1.1.a2) OR$^5$ wherein R$^5$ represents H or (C$_1$-C$_3$)alkyl which may optionally bear halogen;
      1.1.a3) —NR$^6$R$^7$ in which R$^6$ and R$^7$ are independently H or —(C$_1$-C$_3$)alkyl which may optionally bear halogen or R$^6$ and R$^7$ may be joined and taken together with the N atom to which they are attached form a 5-6 membered ring which may optionally contain a ring member selected from O, S, and NR$^8$ wherein R$^8$ represents H or (C$_1$-C$_3$)alkyl; and
      1.1.a4) an imidazole, thiazole, oxazole, pyridine, pyrazole, pyrimidine, isoxazole, isothiazole, thiophene, or furan;
   1.1.b) —(C$_3$-C$_6$)cycloalkyl which may optionally bear up to 2 substituents independently selected from
      1.1.b1) halogen;
   1.1.c) OR$^{10}$ wherein
      R$^{10}$ represents H; phenyl; benzyl; (C$_3$-C$_6$)cycloalkyl; or (C$_1$-C$_4$)alkyl which may optionally bear up to 3 substituents independently selected from
      1.1.c1) halogen;
      1.1.c2) OR$^{11}$ wherein R$^{11}$ represents H or (C$_1$-C$_3$)alkyl; and
      1.1.c3) NR$^{12}$R$^{13}$ in which R$^{12}$ and R$^{13}$ are independently H or —(C$_1$-C$_3$)alkyl which may optionally bear halogen, or R$^{12}$ and R$^{13}$ may be joined and taken together with the N atom to which they are attached form a 5-6 membered ring which may optionally contain a ring member selected from O, S, and NR$^{14}$ wherein R$^{14}$ represents H or (C$_1$-C$_3$)alkyl;
   1.1.e) —C(O)—NR$^{16}$R$^{17}$ wherein
      R$^{16}$ represents H or (C$_1$-C$_3$)alkyl which may optionally bear halogen; and
      R$^{17}$ represents H or —(C$_1$-C$_4$)alkyl which is optionally substituted with
      1.1.e1) halogen;
      1.1.e5) —OR$^{18}$ wherein R$^{18}$ represents H or (C$_1$-C$_3$) alkyl which may optionally bear halogen; or
      1.1.e6) —NR$^{19}$R$^{20}$ in which R$^{19}$ and R$^{20}$ are independently H or —(C$_1$-C$_3$)alkyl which may optionally bear halogen, or R$^{19}$ and R$^{20}$ may be joined and taken together with the N atom to which they are attached form a 5-6 membered ring which may optionally contain a ring member selected from O, S, and NR$^{21}$ wherein R$^{21}$ represents H or (C$_1$-C$_3$) alkyl;
   1.1.f) —N(R$^{22}$)—C(O)—R$^{23}$ wherein
      R$^{22}$ represents H or (C$_1$-C$_3$)alkyl; and
      R$^{23}$ represents optionally substituted phenyl, or (C$_1$-C$_4$)alkyl;
   1.1.g) —SO$_2$NR$^{28}$R$^{29}$ wherein
      R$^{28}$ represents H or (C$_1$-C$_3$)alkyl which may optionally bear halogen; and
      R$^{29}$ represents H or —(C$_1$-C$_4$)alkyl which is optionally substituted with:
      1.1.g1) halogen;
      1.1.g4) —SO$_2$CH$_3$;
      1.1.g5) —OR$^{30}$ wherein R$^{30}$ represents H or (C$_1$-C$_3$) alkyl which may optionally bear halogen; or
      1.1.g6) —NR$^{31}$R$^{32}$ in which R$^{31}$ and R$^{32}$ are independently H or —(C$_1$-C$_3$)alkyl which may optionally bear halogen, or R$^{31}$ and R$^{32}$ may be joined and taken together with the N atom to which they are attached form a 5-6 membered ring which may optionally contain a ring member selected from O, S, and NR$^{33}$ wherein R$^{33}$ represents H or (C$_1$-C$_3$) alkyl;
   1.1.h) —N(R$^{34}$)—SO$_2$—R$^{35}$ wherein
      R$^{34}$ represents H or (C$_1$-C$_3$)alkyl, and
      R$^{35}$ represents optionally substituted phenyl, or (C$_1$-C$_4$)alkyl which is optionally substituted with
      1.1.h1) halogen;
   1.1.i) —NR$^{40}$R$^{41}$ in which R$^{40}$ and R$^{41}$ are independently H or —(C$_1$-C$_3$)alkyl which may optionally bear halogen or OR$^{42}$ in which R$^{42}$ represents H or (C$_1$-C$_3$)alkyl, or R$^{40}$ and R$^{41}$ may be joined and taken together with the N atom to which they are attached form a 5-6 membered ring which may optionally contain a ring member selected from O, S, and NR$^{43}$ wherein R$^{43}$ represents H or (C$_1$-C$_3$)alkyl;
   1.1.j) halogen;
   1.1.l) NO$_2$;
   1.1.m) CN; and
   1.1.n) an imidazole, thiazole, oxazole, pyridine, pyrazole, pyrimidine, isoxazole, isothiazole, thiophene, or furan;
or
R$^1$ represents
1.2) a 5-6 membered aromatic heterocycle selected from imidazole, thiazole, oxazole, pyridine, pyrazole, pyrimidine, isoxazole, isothiazole, thiophene, and furan; said R$^1$ heterocycle optionally bearing up to 4 substituents independently selected from the group consisting of 1.2.a) $(C_1-C_4)$alkyl, which may optionally bear up to 3 substituents independently selected from
   1.2.a1) halogen;
   1.2.a2) $OR^{45}$ wherein $R^{45}$ represents H or $(C_1-C_3)$alkyl which may optionally bear halogen;
   1.2.a3) —$NR^{46}R^{47}$ in which $R^{46}$ and $R^{47}$ are independently H or —$(C_1-C_3)$alkyl which may optionally bear halogen, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or $(C_1-C_3)$alkyl; and
   1.2.a4) an imidazole, thiazole, oxazole, pyridine, pyrazole, pyrimidine, isoxazole, isothiazole, thiophene, or furan;
1.2.b) —$(C_3-C_6)$cycloalkyl which may optionally bear up to 2 substituents independently selected from
   1.2.b1) halogen;
1.2.c) $OR^{50}$ wherein
   $R^{50}$ represents H; phenyl; benzyl; —$(C_3-C_6)$cycloalkyl; or —$(C_1-C_4)$alkyl which may optionally bear up to 3 substituents independently selected from
      1.2.c1) halogen;
1.2.e) —C(O)—$NR^{56}R^{57}$ wherein
   $R^{56}$ represents H or $(C_1-C_3)$alkyl which may optionally bear halogen; and
   $R^{57}$ represents H or —$(C_1-C_4)$alkyl which is optionally substituted with
      1.2.e1) halogen; or
      1.2.e5) —$OR^{58}$ wherein $R^{58}$ represents H or $(C_1-C_3)$alkyl which may optionally bear halogen;
1.2.f) —$N(R^{62})$—C(O)—$R^{63}$ wherein
   $R^{62}$ represents H or $(C_1-C_3)$alkyl; and
   $R^{63}$ represents optionally substituted phenyl, or $(C_1-C_4)$alkyl;
1.2.g) —$SO_2NR^{68}R^{69}$ wherein
   $R^{68}$ represents H or $(C_1-C_3)$alkyl which may optionally bear halogen; and
   $R^{69}$ represents H or —$(C_1-C_4)$alkyl which is optionally substituted with
      1.2.g1) halogen; or
      1.2.g5) —$OR^{70}$ wherein $R^{70}$ represents H or $(C_1-C_3)$alkyl which may optionally bear halogen;
1.2.h) —$N(R^{74})$—$SO_2$—$R^{75}$ wherein
   $R^{74}$ represents H or $(C_1-C_3)$alkyl, and
   $R^{75}$ represents optionally substituted phenyl, or $(C_1-C_4)$alkyl which is optionally substituted with
      1.2.h1) halogen;
1.2.i) —$NR^{80}R^{81}$ in which $R^{80}$ and $R^{81}$ are independently H or —$(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$alkyl;
1.2.j) halogen;
1.2.k) optionally substituted phenyl;
1.2.l) $NO_2$;
1.2.m) CN; and
1.2.n) an imidazole, thiazole, oxazole, pyridine, pyrazole, pyrimidine, isoxazole, isothiazole, thiophene, or furan;

$R^2$ represents halogen; —$(C_1-C_5)$alkyl which may optionally bear halogen; or —$O(C_1-C_3)$alkyl which may optionally bear halogen;

$R^3$ represents
3.1) —$(C_1-C_5)$alkyl which is optionally substituted with
   3.1.a) -halogen;
   3.1.b) phenyl optionally substituted with halogen, —$(C_1-C_3)$alkyl, or —$(C_1-C_3)$alkoxy,
   3.1.c) a 5-6 membered heteroaromatic containing up to two heteroatoms selected from O, S, and N, optionally substituted with halogen or —$(C_1-C_3)$alkyl,
   3.1.d) —CN,
   3.1.e) —$OR^{83}$ wherein $R^{83}$ represents H or —$(C_1-C_3)$alkyl which may optionally bear up to 3 substituents independently selected from
      3.1.e1) halogen;
      3.1.e2) optionally substituted phenyl;
      3.1.e3) —$S(O)_2CH_3$;
      3.1.e4) $OR^{84}$ wherein $R^{84}$ represents H or $(C_1-C_3)$alkyl which may optionally bear halogen or —$(C_1-C_3)$mono- or di-alkylamino; and
      3.1.e5) —$NR^{85}R^{86}$ in which $R^{85}$ and $R^{86}$ are independently H or —$(C_1-C_3)$alkyl which may optionally bear halogen, or $R^{85}$ and $R^{86}$ may be joined and taken together with the N atom to which they are attached form a 5-6 membered ring which may optionally contain a ring member selected from O, S, and $NR^{87}$ wherein $R^{87}$ represents H or $(C_1-C_3)$alkyl;
   3.1.f) —$(C_3-C_5)$cycloalkyl which may optionally bear halogen; or
   3.1.g) —$NR^{89}R^{90}$ wherein
      $R^{89}$ represents H or —$(C_1-C_3)$alkyl which may optionally bear halogen; and
      $R^{90}$ represents H or —$(C_1-C_4)$alkyl which is optionally substituted with
         3.1.g1) halogen;
         3.1.g2) a 5-6 membered heteroaromatic containing up to two heteroatoms selected from O, S, and N;
         3.1.g3) phenyl;
         3.1.g4) —$SO_2CH_3$;
         3.1.g5) —$OR^{91}$ wherein $R^{91}$ represents H or $(C_1-C_3)$alkyl which may optionally bear halogen; or
         3.1.g6) —$NR^{92}R^{93}$ in which $R^{92}$ and $R^{93}$ are independently H or —$(C_1-C_3)$alkyl which may optionally bear halogen, or $R^{92}$ and $R^{93}$ may be joined and taken together with the N atom to which they are attached form a 5-6 membered ring which may optionally contain a ring member selected from O, S, and $NR^{94}$ wherein $R^{94}$ represents H or $(C_1-C_3)$alkyl; or
      3.1.g7) $R^{89}$ and $R^{90}$ may be joined and taken together with the N to which they are attached form an aromatic or nonaromatic 5-6 membered ring which may optionally contain a ring member selected from O, S, and $NR^{95}$ wherein $R^{95}$ represents H or $(C_1-C_3)$alkyl;
3.2)

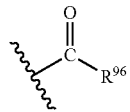

wherein
R$^{96}$ represents
3.2.a) H,
3.2.b) —(C$_3$-C$_5$)cycloalkyl which may optionally bear halogen; or
3.2.c) —(C$_1$-C$_5$)alkyl which may optionally bear up to 3 substituents independently selected from
3.2.c1) halogen;
3.2.c2) a 5-6 membered heteroaromatic containing up to two heteroatoms selected from O, S, and N;
3.2.c3) phenyl;
3.2c5) —OR$^{97}$ wherein R$^{97}$ represents H or (C$_1$-C$_3$)alkyl which may optionally bear halogen or —(C$_1$-C$_3$)mono- or dl-alkylamino; and
3.2.c6) —NR$^{98}$R$^{99}$ in which R$^{98}$ and R$^{99}$ are independently H or —(C$_1$-C$_3$)alkyl which may optionally bear halogen or OR$^{99a}$ wherein R$^{99a}$ represents H or (C$_1$-C$_3$)alkyl, or R$^{98}$ and R$^{99}$ may be joined and taken together with the N atom to which they are attached form a 5-6 membered ring which may optionally contain a ring member selected from O, S, and NR$^{100}$ wherein R$^{100}$ represents H or (C$_1$-C$_3$)alkyl;

3.3)

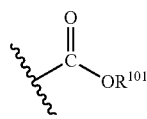

wherein R$^{101}$ represents H or —(C$_1$-C$_5$)alkyl which may optionally bear up to 3 substituents independently selected from
3.3.a) halogen; and
3.3.b) phenyl;

3.4)

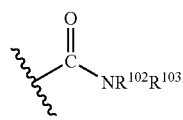

wherein
R$^{102}$ represents H or —(C$_1$-C$_3$)alkyl which may optionally bear halogen; and
R$^{103}$ represents H or —(C$_1$-C$_5$)alkyl which may optionally bear up to 3 substituents independently selected from
3.4.a) halogen;
3.4.b) a 5-6 membered heteroaromatic containing up to two heteroatoms selected from O, S, and N;
3.4.c) phenyl;
3.4.d) —S(O)$_2$CH$_3$;
3.4.e) OR$^{104}$ wherein R$^{104}$ represents H or (C$_1$-C$_3$)alkyl which may optionally bear halogen; and
3.4.f) —NR$^{105}$R$^{106}$ in which R$^{105}$ and R$^{106}$ are independently H or —(C$_1$-C$_3$)alkyl which may optionally bear halogen, or R$^{105}$ and R$^{106}$ may be joined and taken together with the N atom to which they are attached form a 5-6 membered ring which may optionally contain a ring member selected from O, S, and NR$^{107}$ wherein R$^{107}$ represents H or (C$_1$-C$_3$)alkyl;

3.6) a 5-6 membered heteroaromatic containing up to two heteroatoms selected from O, S, and N;
3.7) halogen; or
3.8) —CN;

R$^4$ represents
4.1) —(C$_1$-C$_5$)alkyl which is optionally substituted with
4.1.a) —(C$_3$-C$_5$)cycloalkyl which may optionally bear halogen or OR$^{109}$ wherein R$^{109}$ represents H or (C$_1$-C$_3$)alkyl;
4.1.b) -halogen;
4.1.c) —OR$^{110}$ wherein R$^{110}$ represents H or —(C$_1$-C$_3$)alkyl which may optionally bear up to 3 substituents independently selected from
4.1.c1) halogen;
4.1.c2) phenyl;
4.1.c4) OR$^{111}$ wherein R$^{111}$ represents H or (C$_1$-C$_3$)alkyl which may optionally bear halogen; and
4.1.c5) —NR$^{112}$R$^{113}$ in which R$^{112}$ and R$^{113}$ are independently H or —(C$_1$-C$_3$)alkyl which may optionally bear halogen, or R$^{112}$ and R$^{113}$ may be joined and taken together with the N atom to which they are attached form a 5-6 membered ring which may optionally contain a ring member selected from O, S, and NR$^{114}$ wherein R$^{114}$ represents H or (C$_1$-C$_3$)alkyl;
4.1.d) —NR$^{115}$R$^{116}$ wherein
R$^{115}$ represents H or —(C$_1$-C$_3$)alkyl which may optionally bear halogen and
R$^{116}$ represents H, optionally substituted phenyl, or —(C$_1$-C$_5$)alkyl which may optionally bear up to 3 substituents independently selected from
4.1.d1) halogen;
4.1.d2) —S(O)$_2$CH$_3$;
4.1.d3) OR$^{117}$ wherein R$^{117}$ represents H or (C$_1$-C$_3$)alkyl which may optionally bear halogen; and
4.1.d4) —NR$^{118}$R$^{119}$ in which R$^{118}$ and R$^{119}$ are independently H or —(C$_1$-C$_3$)alkyl which may optionally bear halogen, or R$^{118}$ and R$^{119}$ may be joined and taken together with the N atom to which they are attached form a 5-6 membered ring which may optionally contain a ring member selected from O, S, and NR$^{120}$ wherein R$^{120}$ represents H or (C$_1$-C$_3$)alkyl; or
4.1.f) a 5-6 membered aromatic heterocycle containing up to two heteroatoms selected from O, S, and N;

4.2)

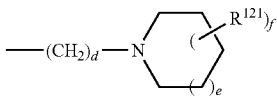

wherein R$^{121}$ represents —(C$_1$-C$_3$)alkyl which may optionally bear halogen or —OR$^{122}$ in which R$^{122}$ represents H or —(C$_1$-C$_3$)alkyl;

d represents 1, 2, or 3;

e represents 0 or 1;

f represents 0, 1, or 2;

4.3)

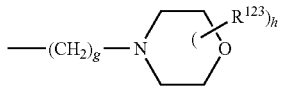

wherein $R^{123}$ represents —$(C_1$-$C_3)$alkyl which may optionally bear halogen or —$OR^{124}$ in which $R^{124}$ represents H or —$(C_1$-$C_3)$alkyl;

g represents 1, 2, or 3;

h represents 0, 1, or 2;

4.4)

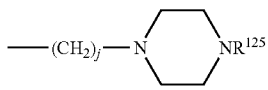

wherein $R^{125}$ represents 4.4.a) H;

4.4.b) —$(C_1$-$C_3)$alkyl which may optionally bear halogen or —$OR^{126}$ in which $R^{126}$ represents H or —$(C_1$-$C_3)$alkyl which in turn is optionally substituted with halogen;

4.4.c) —$SO_2R^{127}$ wherein $R^{127}$ represents optionally substituted phenyl, or —$(C_1$-$C_3)$alkyl which may optionally bear halogen or $OR^{128}$ wherein $R^{128}$ represents H or $(C_1$-$C_3)$alkyl;

4.4.d) —$C(O)R^{129}$ wherein $R^{129}$ represents 4.4.d1) optionally substituted phenyl, 4.4.d2) —$(C_1$-$C_3)$alkyl which may optionally bear up to 3 substituents independently selected from 4.4.d2.1) halogen;

4.4.d2.4) —$OR^{130}$ wherein $R^{130}$ represents H or $(C_1$-$C_3)$alkyl which may optionally bear halogen; and 4.4.d2.5) —$NR^{131}R^{132}$ in which $R^{131}$ and $R^{132}$ are independently H or —$(C_1$-$C_3)$alkyl which may optionally bear halogen, or $R^{131}$ and $R^{132}$ may be joined and taken together with the N atom to which they are attached form a 5-6 membered ring which may optionally contain a ring member selected from O, S, and $NR^{133}$ wherein $R^{133}$ represents H or $(C_1$-$C_3)$alkyl;

4.4.d3) —$OR^{134}$ wherein $R^{134}$ represents $(C_1$-$C_3)$alkyl which may optionally bear halogen; or 4.4.d4) $NR^{135}R^{136}$ wherein $R^{135}$ and $R^{136}$ are independently H or —$(C_1$-$C_3)$alkyl which may optionally bear halogen, or $R^{135}$ and $R^{136}$ may be joined and taken together with the N atom to which they are attached form a 5-6 membered ring which may optionally contain a ring member selected from O, S, and $NR^{137}$ wherein $R^{137}$ represents H or $(C_1$-$C_3)$alkyl; and j represents 1, 2, or 3;

4.5)

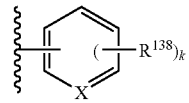

wherein

X represents C or N;

$R^{138}$ represents 4.5.a) $(C_1$-$C_4)$alkyl, which may optionally bear up to 3 substituents independently selected from 4.5.a1) halogen;

4.5.a2) $OR^{139}$ wherein $R^{139}$ represents H or $(C_1$-$C_3)$alkyl which may optionally bear halogen or —$(C_1$-$C_3)$mono- or di-alkylamino;

4.5.a3) —$NR^{140}R^{141}$ in which $R^{140}$ and $R^{141}$ are independently H or —$(C_1$-$C_3)$alkyl which may optionally bear halogen or $OR^{141a}$ wherein $R^{141a}$ represents H or $(C_1$-$C_3)$alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or $(C_1$-$C_3)$alkyl; and 4.5.a4) a 5-6 membered heteroaromatic containing up to two heteroatoms selected from O, S, and N;

4.5.b) —$(C_3$-$C_6)$cycloalkyl which may optionally bear up to 2 substituents independently selected from 4.5.b1) halogen;

4.5.c) $OR^{144}$ wherein $R^{144}$ represents H; phenyl; benzyl; $(C_3$-$C_6)$cycloalkyl; or $(C_1$-$C_4)$alkyl which may optionally bear up to 3 substituents independently selected from 4.5.c1) halogen;

4.5.c2) $OR^{145}$ wherein $R^{145}$ represents H or $(C_1$-$C_3)$alkyl which may optionally bear $(C_1$-$C_3)$mono- or di-alkylamino; and 4.5.c3) $NR^{146}R^{147}$ in which $R^{146}$ and $R^{1473}$ are independently H or —$(C_1$-$C_3)$alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or $(C_1$-$C_3)$alkyl;

4.5.e) —$C(O)$—$NR^{150}R^{151}$ wherein $R^{150}$ represents H or $(C_1$-$C_3)$alkyl which may optionally bear halogen; and $R^{151}$ represents H or —$(C_1$-$C_4)$alkyl which is optionally substituted with 4.5.e1) halogen;

4.5.e3) phenyl;

4.5.e4) —$SO_2CH_3$;

4.5.e5) —$OR^{152}$ wherein $R^{152}$ represents H or $(C_1$-$C_3)$alkyl which may optionally bear halogen; or 4.5.e6) —$NR^{153}R^{154}$ in which $R^{153}$ and $R^{154}$ are independently H or —$(C_1$-$C_3)$alkyl which may optionally bear halogen, or $R^{153}$ and $R^{154}$ may be joined and taken together with the N atom to which they are attached form a 5-6 membered ring which may optionally contain a ring member selected from O, S, and $NR^{155}$ wherein $R^{155}$ represents H or $(C_1$-$C_3)$alkyl;

4.5.f) —N($R^{156}$)—C(O)—$R^{157}$ wherein
   $R^{156}$ represents H or ($C_1$-$C_3$)alkyl; and
   $R^{157}$ represents H, optionally substituted phenyl, or ($C_1$-$C_4$)alkyl which is optionally substituted with
     4.5.f1) optionally substituted phenyl,
     4.5.f2) $OR^{158}$ wherein $R^{158}$ represents H or ($C_1$-$C_3$)alkyl, or
     4.5.f3) $NR^{159}R^{160}$ wherein $R^{159}$ and $R^{160}$ are independently H or —($C_1$-$C_3$)alkyl which may optionally bear halogen, or $R^{159}$ and $R^{160}$ may be joined and taken together with the N atom to which they are attached form a 5-6 membered ring which may optionally contain a ring member selected from O, S, and $NR^{161}$ wherein $R^{161}$ represents H or ($C_1$-$C_3$)alkyl;
4.5.g) —$SO_2NR^{162}R^{163}$ wherein
   $R^{162}$ represents H or ($C_1$-$C_3$)alkyl which may optionally bear halogen; and
   $R^{163}$ represents H or —($C_1$-$C_4$)alkyl which is optionally substituted with
     4.5.g1) halogen;
     4.5.g3) phenyl;
     4.5.g4) —$SO_2CH_3$;
     4.5.g5) —$OR^{164}$ wherein $R^{164}$ represents H or ($C_1$-$C_3$)alkyl which may optionally bear halogen; or
     4.5.g6) —$NR^{165}R^{166}$ in which $R^{165}$ and $R^{166}$ are independently H or —($C_1$-$C_3$)alkyl which may optionally bear halogen, or $R^{165}$ and $R^{166}$ may be joined and taken together with the N atom to which they are attached form a 5-6 membered ring which may optionally contain a ring member selected from O, S, and $NR^{167}$ wherein $R^{167}$ represents H or ($C_1$-$C_3$)alkyl;
4.5.h) —N($R^{168}$)—$SO_2$—$R^{169}$ wherein
   $R^{168}$ represents H or ($C_1$-$C_3$)alkyl, and
   $R^{169}$ represents H, optionally substituted phenyl, or ($C_1$-$C_4$)alkyl which is optionally substituted with
     4.5.h1) halogen,
     4.5.h2) optionally substituted phenyl,
     4.5.h3) $OR^{170}$ wherein $R^{170}$ represents H or ($C_1$-$C_3$)alkyl which may optionally bear halogen, or
     4.5.h4) $NR^{171}R^{172}$ wherein $R^{171}$ and $R^{172}$ are independently H or —($C_1$-$C_3$)alkyl which may optionally bear halogen, or $R^{171}$ and $R^{172}$ may be joined and taken together with the N atom to which they are attached form a 5-6 membered ring which may optionally contain a ring member selected from O, S, and $NR^{173}$ wherein $R^{173}$ represents H or ($C_1$-$C_3$)alkyl;
4.5.i) —$NR^{174}R^{175}$ in which $R^{174}$ and $R^{175}$ are independently H or —($C_1$-$C_3$)alkyl which may optionally bear halogen or $OR^{175a}$ wherein $R^{175a}$ represents H or ($C_1$-$C_3$)alkyl, or $R^{174}$ and $R^{175}$ may be joined and taken together with the N atom to which they are attached form a 5-6 membered ring which may optionally contain a ring member selected from O, S, and $NR^{176}$ wherein $R^{176}$ represents H or ($C_1$-$C_3$)alkyl;
4.5.j) halogen;
4.5.l) $NO_2$;
4.5.m) CN; or
4.5.n) a 5-6 membered heteroaromatic containing up to two heteroatoms selected from O, S, and N; and
k represents 0, 1, or 2;

4.6)

—$(CH_2)_m$—N[piperazinone ring]$NR^{177}$ wherein $R^{177}$ represents H or —($C_1$-$C_3$)alkyl; and
m represents 1, 2, or 3;

4.7)

—$(CH_2)_n$—N[thiomorpholine ring]$S(O)_p$ wherein
n represents 1, 2, or 3; and
p represents 0, 1, or 2;

4.8)

—$(CH_2)_q$—N[homomorpholine ring]O wherein
q represents 1, 2, or 3;

4.9)

—$(CH_2)_r$—[piperidine ring with ($)_s$]$NR^{178}$ wherein
$R^{178}$ represents
   4.9.a) H;
   4.9.b) —($C_1$-$C_3$)alkyl which may optionally bear halogen or —$OR^{179}$ in which $R^{179}$ represents H or ($C_1$-$C_3$)alkyl optionally substituted with halogen;
   4.9.c) —$SO_2R^{180}$ wherein $R^{180}$ represents optionally substituted phenyl or —($C_1$-$C_3$)alkyl, which may be substituted with halogen or —$OR^{181}$ wherein $R^{181}$ represents H or ($C_1$-$C_3$)alkyl which may optionally bear halogen;
   4.9.d) —C(O)$R^{182}$ wherein $R^{182}$ represents optionally substituted phenyl or —($C_1$-$C_3$)alkyl which may optionally bear up to 3 substituents independently selected from
     4.9.d1) halogen;
     4.9.d2) optionally substituted phenyl;
     4.9.d4) $OR^{183}$ wherein $R^{183}$ represents H or ($C_1$-$C_3$)alkyl which may optionally bear halogen; and
     4.9.d5) —$NR^{184}R^{185}$ in which $R^{184}$ and $R^{185}$ are independently H or —($C_1$-$C_3$)alkyl which may optionally bear halogen or $OR^{185a}$ wherein $R^{185a}$ represents H or ($C_1$-$C_3$)alkyl, or $R^{184}$ and $R^{185}$ may be joined and taken together with the N atom to which they are attached form a 5-6 membered ring which may optionally contain a ring member selected from O, S, and $NR^{186}$ wherein $R^{186}$ represents H or ($C_1$-$C_3$)alkyl;

4.9e) —C(O)OR$^{187}$ wherein R$^{187}$ represents (C$_1$-C$_3$) alkyl; or 4.9.f) —C(O)—NR$^{188}$R$^{189}$ wherein R$^{188}$ and R$^{189}$ each independently represents H or —(C$_1$-C$_3$)alkyl which may optionally bear halogen, or R$^{188}$ and R$^{189}$ may be joined and taken together with the N atom to which they are attached form a 5-6 membered ring which may optionally contain a ring member selected from O, S, and NR$^{190}$ wherein R$^{190}$ represents H or (C$_1$-C$_3$)alkyl;

r represents 0, 1, or 2; and s represents 0 or 1;

4.10)

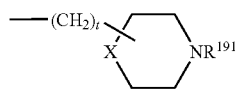

wherein

R$^{191}$ represents 4.10.a) H;

4.10.b) —(C$_1$-C$_3$)alkyl which may optionally bear halogen or —OR$^{192}$ in which R$^{192}$ represents H or (C$_1$-C$_3$)alkyl;

4.10c) —SO$_2$R$^{193}$ wherein R$^{193}$ represents phenyl or —(C$_1$-C$_3$)alkyl, both of which may be substituted with halogen or —(C$_1$-C$_3$)alkyl;

4.10.d) —C(O)R$^{194}$ wherein R$^{194}$ represents (C$_1$-C$_3$) alkyl which may optionally bear up to 3 substituents independently selected from 4.10.d1) halogen;

4.10.d2) phenyl;

4.10.d4) OR$^{195}$ wherein R$^{195}$ represents H or (C$_1$-C$_3$)alkyl which may optionally bear halogen; and 4.10.d5) —NR$^{196}$R$^{197}$ in which R$^{196}$ and R$^{197}$ are independently H or —(C$_1$-C$_3$)alkyl which may optionally bear halogen or OR$^{197a}$ wherein R$^{197a}$ represents H or (C$_1$-C$_3$)alkyl, or R$^{196}$ and R$^{197}$ may be joined and taken together with the N atom to which they are attached form a 5-6 membered ring which may optionally contain a ring member selected from O, S, and NR$^{198}$ wherein R$^{198}$ represents H or (C$_1$-C$_3$)alkyl;

4.10.e) —C(O)OR$^{199}$ wherein R$^{199}$ represents (C$_1$-C$_3$)alkyl; or 4.10.f) —C(O)—NR$^{200}$R$^{201}$ wherein R$^{200}$ and R$^{201}$ each independently represents H or —(C$_1$-C$_3$)alkyl which may optionally bear halogen, or R$^{200}$ and R$^{201}$ may be joined and taken together with the N atom to which they are attached form a 5-6 membered ring which may optionally contain a ring member selected from O, S, and NR$^{202}$ wherein R$^{202}$ represents H or (C$_1$-C$_3$)alkyl; and X represents O, S, S(O)$_2$, or NR$^{203}$ wherein R$^{203}$ represents H or —(C$_1$-C$_3$)alkyl; and t represents 0, 1, or 2;

4.11) halogen; or 4.12) —CN;

or a pharmaceutically acceptable salt thereof.

In embodiment four, the present invention provides a compound of formula (I)

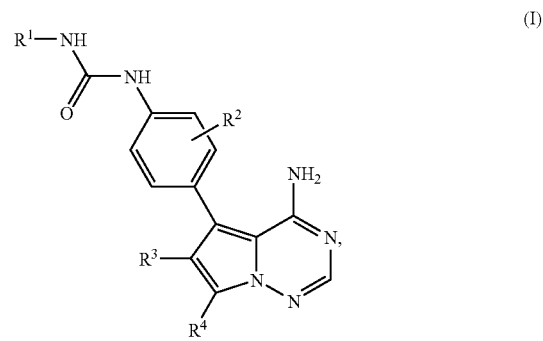

wherein

R$^1$ represents 1.1) phenyl which may optionally bear up to 4 substituents independently selected from the group consisting of 1.1.a) (C$_1$-C$_4$)alkyl, which may optionally bear up to 3 substituents independently selected from 1.1.a1) halogen;

1.1.a2) OR$^5$ wherein R$^5$ represents H or (C$_1$-C$_3$)alkyl which may optionally bear halogen;

1.1.a3) —NR$^6$R$^7$ in which R$^6$ and R$^7$ are independently H or —(C$_1$-C$_3$)alkyl which may optionally bear halogen or R$^6$ and R$^7$ may be joined and taken together with the N atom to which they are attached form a 5-6 membered ring which may optionally contain a ring member selected from O, S, and NR$^8$ wherein R$^8$ represents H or (C$_1$-C$_3$)alkyl; and 1.1.a4) an imidazole, thiazole, oxazole, pyridine, pyrazole, pyrimidine, isoxazole, isothiazole, thiophene, or furan;

1.1.b) —(C$_3$-C$_6$)cycloalkyl which may optionally bear up to 2 substituents independently selected from 1.1.b1) halogen;

1.1.c) OR$^{10}$ wherein

R$^{10}$ represents H; phenyl; benzyl; (C$_3$-C$_6$)cycloalkyl; or (C$_1$-C$_4$)alkyl which may optionally bear up to 3 substituents independently selected from 1.1.c1) halogen;

1.1.c2) OR$^{11}$ wherein R$^{11}$ represents H or (C$_1$-C$_3$) alkyl; and 1.1.c3) NR$^{12}$R$^{13}$ in which R$^{12}$ and R$^{13}$ are independently H or —(C$_1$-C$_3$)alkyl which may optionally bear halogen, or R$^{12}$ and R$^{13}$ may be joined and taken together with the N atom to which they are attached form a 5-6 membered ring which may optionally contain a ring member selected from O, S, and NR$^{14}$ wherein R$^{14}$ represents H or (C$_1$-C$_3$) alkyl;

1.1.e) —C(O)—NR$^{16}$R$^{17}$ wherein

R$^{16}$ represents H or (C$_1$-C$_3$)alkyl which may optionally bear halogen; and R$^{17}$ represents H or —(C$_1$-C$_4$)alkyl which is optionally substituted with 1.1.e1) halogen;

1.1.e5) —OR$^{18}$ wherein R$^{18}$ represents H or (C$_1$-C$_3$) alkyl which may optionally bear halogen; or 1.1.e6) —NR$^{19}$R$^{20}$ in which R$^{19}$ and R$^{20}$ are independently H or —(C$_1$-C$_3$)alkyl which may optionally bear halogen, or R$^{19}$ and R$^{20}$ may be joined and taken together with the N atom to which they are attached form a 5-6 membered ring which may optionally contain a ring member selected from O, S, and $NR^{21}$ wherein $R^{21}$ represents H or $(C_1-C_3)$alkyl;

1.1.f) —$N(R^{22})$—C(O)—$R^{23}$ wherein
$R^{22}$ represents H or $(C_1-C_3)$alkyl; and
$R^{23}$ represents optionally substituted phenyl, or $(C_1-C_4)$alkyl;

1.1.g) —$SO_2NR^{28}R^{29}$ wherein
$R^{28}$ represents H or $(C_1-C_3)$alkyl which may optionally bear halogen; and
$R^{29}$ represents H or —$(C_1-C_4)$alkyl which is optionally substituted with:
  1.1.g1) halogen;
  1.1.g4) —$SO_2CH_3$;
  1.1.g5) —$OR^{30}$ wherein $R^{30}$ represents H or $(C_1-C_3)$alkyl which may optionally bear halogen; or
  1.1.g6) —$NR^{31}R^{32}$ in which $R^{31}$ and $R^{32}$ are independently H or —$(C_1-C_3)$alkyl which may optionally bear halogen, or $R^{31}$ and $R^{32}$ may be joined and taken together with the N atom to which they are attached form a 5-6 membered ring which may optionally contain a ring member selected from O, S, and $NR^{33}$ wherein $R^{33}$ represents H or $(C_1-C_3)$alkyl;

1.1.h) —$N(R^{34})$—$SO_2$—$R^{35}$ wherein
$R^{34}$ represents H or $(C_1-C_3)$alkyl, and
$R^{35}$ represents optionally substituted phenyl, or $(C_1-C_4)$alkyl which is optionally substituted with
  1.1.h1) halogen;

1.1.i) —$NR^{40}R^{41}$ in which $R^{40}$ and $R^{41}$ are independently H or —$(C_1-C_3)$alkyl which may optionally bear halogen or $OR^{42}$ in which $R^{42}$ represents H or $(C_1-C_3)$alkyl, or $R^{40}$ and $R^{41}$ may be joined and taken together with the N atom to which they are attached form a 5-6 membered ring which may optionally contain a ring member selected from O, S, and $NR^{43}$ wherein $R^{43}$ represents H or $(C_1-C_3)$alkyl;

1.1.j) halogen;
1.1.l) $NO_2$;
1.1.m) CN; and
1.1.n) an imidazole, thiazole, oxazole, pyridine, pyrazole, pyrimidine, isoxazole, isothiazole, thiophene, or furan;

or
$R^1$ represents 1.2) a 5-6 membered aromatic heterocycle selected from imidazole, thiazole, oxazole, pyridine, pyrazole, pyrimidine, isoxazole, isothiazole, thiophene, and furan; said $R^1$ heterocycle optionally bearing up to 4 substituents independently selected from the group consisting of 1.2.a) $(C_1-C_4)$alkyl, which may optionally bear up to 3 substituents independently selected from
  1.2.a1) halogen;
  1.2.a2) $OR^{45}$ wherein $R^{45}$ represents H or $(C_1-C_3)$alkyl which may optionally bear halogen;
  1.2.a3) —$NR^{46}R^{47}$ in which $R^{46}$ and $R^{47}$ are independently H or —$(C_1-C_3)$alkyl which may optionally bear halogen, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or $(C_1-C_3)$alkyl; and
  1.2.a4) an imidazole, thiazole, oxazole, pyridine, pyrazole, pyrimidine, isoxazole, isothiazole, thiophene, or furan;

1.2.b) —$(C_3-C_6)$cycloalkyl which may optionally bear up to 2 substituents independently selected from
  1.2.b1) halogen;

1.2.c) $OR^{50}$ wherein
$R^{50}$ represents H; phenyl; benzyl; —$(C_3-C_6)$cycloalkyl; or —$(C_1-C_4)$alkyl which may optionally bear up to 3 substituents independently selected from
  1.2.c1) halogen;

1.2.e) —C(O)—$NR^{56}R^{57}$ wherein
$R^{56}$ represents H or $(C_1-C_3)$alkyl which may optionally bear halogen; and
$R^{57}$ represents H or —$(C_1-C_4)$alkyl which is optionally substituted with
  1.2.e1) halogen; or
  1.2.e5) —$OR^{58}$ wherein $R^{58}$ represents H or $(C_1-C_3)$alkyl which may optionally bear halogen;

1.2.f) —$N(R^{62})$—C(O)—$R^{63}$ wherein
$R^{62}$ represents H or $(C_1-C_3)$alkyl; and
$R^{63}$ represents optionally substituted phenyl, or $(C_1-C_4)$alkyl;

1.2.g) —$SO_2NR^{68}R^{69}$ wherein
$R^{68}$ represents H or $(C_1-C_3)$alkyl which may optionally bear halogen; and
$R^{69}$ represents H or —$(C_1-C_4)$alkyl which is optionally substituted with
  1.2.g1) halogen; or
  1.2.g5) —$OR^{70}$ wherein $R^{70}$ represents H or $(C_1-C_3)$alkyl which may optionally bear halogen;

1.2.h) —$N(R^{74})$—$SO_2$—$R^{75}$ wherein
$R^{74}$ represents H or $(C_1-C_3)$alkyl, and
$R^{75}$ represents optionally substituted phenyl, or $(C_1-C_4)$alkyl which is optionally substituted with
  1.2.h1) halogen;

1.2.i) —$NR^{80}R^{81}$ in which $R^{80}$ and $R^{81}$ are independently H or —$(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$alkyl;

1.2.j) halogen;
1.2.k) optionally substituted phenyl;
1.2.l) $NO_2$;
1.2.m) CN; and
1.2.n) an imidazole, thiazole, oxazole, pyridine, pyrazole, pyrimidine, isoxazole, isothiazole, thiophene, or furan;

$R^2$ represents halogen; —$(C_1-C_5)$alkyl which may optionally bear halogen; or —$O(C_1-C_3)$alkyl which may optionally bear halogen;

$R^3$ represents 3.1) —$(C_1-C_5)$alkyl which is optionally substituted with
  3.1.a) -halogen;
  3.1.c) a 5-6 membered heteroaromatic containing up to two heteroatoms selected from O, S, and N, optionally substituted with halogen or —$(C_1-C_3)$alkyl;
  3.1.d) —CN;
  3.1.e) —$OR^{83}$ wherein $R^{83}$ represents H or —$(C_1-C_3)$alkyl which may optionally bear up to 3 substituents independently selected from
    3.1.e1) halogen; or
    3.1.e4) $OR^{84}$ wherein $R^{84}$ represents H or $(C_1-C_3)$alkyl which may optionally bear halogen;
  3.1.f) —$(C_3-C_5)$cycloalkyl which may optionally bear halogen; or 3.1.g) —NR$^{89}$R$^{90}$ wherein
  R$^{89}$ represents H or —(C$_1$-C$_3$)alkyl which may optionally bear halogen; and
  R$^{90}$ represents H or —(C$_1$-C$_4$)alkyl which is optionally substituted with
    3.1.g1) halogen;
    3.1.g4) —SO$_2$CH$_3$;
    3.1.g5) —OR$^{91}$ wherein R$^{91}$ represents H or (C$_1$-C$_3$)alkyl which may optionally bear halogen; or
    3.1.g7) R$^{89}$ and R$^{90}$ may be joined and taken together with the N to which they are attached form an aromatic or nonaromatic 5-6 membered ring which may optionally contain a ring member selected from O, S, and NR$^{95}$ wherein R$^{95}$ represents H or (C$_1$-C$_3$)alkyl;
3.2)

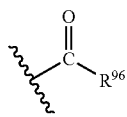

wherein
R$^{96}$ represents
  3.2.b) —(C$_3$-C$_5$)cycloalkyl which may optionally bear halogen; or
  3.2.c) —(C$_1$-C$_5$)alkyl which may optionally bear up to 3 substituents independently selected from
    3.2.c1) halogen; and
    3.2.c5) —OR$^{97}$ wherein R$^{97}$ represents H or (C$_1$-C$_3$)alkyl which may optionally bear halogen;
3.3)

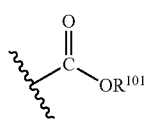

wherein R$^{101}$ represents H or —(C$_1$-C$_5$)alkyl;
3.4)

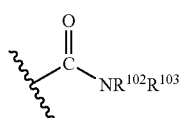

wherein
R$^{102}$ represents H or —(C$_1$-C$_3$)alkyl which may optionally bear halogen; and
R$^{103}$ represents H or —(C$_1$-C$_5$)alkyl which may optionally bear up to 3 substituents independently selected from
  3.4.a) halogen;
  3.4.d) —S(O)$_2$CH$_3$; and
  3.4.e) OR$^{104}$ wherein R$^{104}$ represents H or (C$_1$-C$_3$)alkyl which may optionally bear halogen;
3.7) halogen; or
3.8) —CN;

R$^4$ represents
  4.1) —(C$_1$-C$_5$)alkyl which is optionally substituted with
    4.1.a) —(C$_3$-C$_5$)cycloalkyl which may optionally bear halogen or OR$^{109}$ wherein R$^{109}$ represents H or (C$_1$-C$_3$)alkyl;
    4.1.b) -halogen;
    4.1.c) —OR$^{110}$ wherein R$^{110}$ represents H or —(C$_1$-C$_3$)alkyl which may optionally bear up to 3 substituents independently selected from
      4.1.c1) halogen;
      4.1.c2) phenyl;
      4.1.c4) OR$^{111}$ wherein R$^{111}$ represents H or (C$_1$-C$_3$)alkyl which may optionally bear halogen; and
      4.1.c5) —NR$^{112}$R$^{113}$ in which R$^{112}$ and R$^{113}$ are independently H or —(C$_1$-C$_3$)alkyl which may optionally bear halogen, or R$^{112}$ and R$^{113}$ may be joined and taken together with the N atom to which they are attached form a 5-6 membered ring which may optionally contain a ring member selected from O, S, and NR$^{114}$ wherein R$^{114}$ represents H or (C$_1$-C$_3$)alkyl;
    4.1.d) —NR$^{115}$R$^{116}$ wherein
      R$^{115}$ represents H or —(C$_1$-C$_3$)alkyl which may optionally bear halogen and
      R$^{116}$ represents H, optionally substituted phenyl, or —(C$_1$-C$_5$)alkyl which may optionally bear up to 3 substituents independently selected from
        4.1.d1) halogen;
        4.1.d2) —S(O)$_2$CH$_3$;
        4.1.d3) OR$^{117}$ wherein R$^{117}$ represents H or (C$_1$-C$_3$)alkyl which may optionally bear halogen; and
        4.1.d4) —NR$^{118}$R$^{119}$ in which R$^{118}$ and R$^{119}$ are independently H or —(C$_1$-C$_3$)alkyl which may optionally bear halogen, or R$^{118}$ and R$^{119}$ may be joined and taken together with the N atom to which they are attached form a 5-6 membered ring which may optionally contain a ring member selected from O, S, and NR$^{120}$ wherein R$^{120}$ represents H or (C$_1$-C$_3$)alkyl; or
    4.1.f) a 5-6 membered aromatic heterocycle containing up to two heteroatoms selected from O, S, and N;
  4.2)

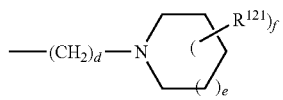

wherein R$^{121}$ represents —(C$_1$-C$_3$)alkyl which may optionally bear halogen or —OR$^{122}$ in which R$^{122}$ represents H or —(C$_1$-C$_3$)alkyl;
d represents 1, 2, or 3;
e represents 0 or 1;
f represents 0, 1, or 2;
  4.3)

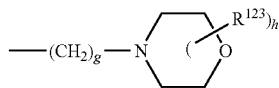

wherein R$^{123}$ represents —(C$_1$-C$_3$)alkyl which may optionally bear halogen or —OR$^{124}$ in which R$^{124}$ represents H or —(C$_1$-C$_3$)alkyl;
g represents 1, 2, or 3;
h represents 0, 1, or 2;

4.4)

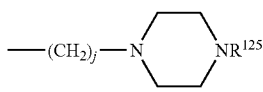

wherein
R$^{125}$ represents
4.4.a) H;
4.4.b) —(C$_1$-C$_3$)alkyl which may optionally bear halogen or —OR$^{126}$ in which R$^{126}$ represents H or —(C$_1$-C$_3$)alkyl which in rum is optionally substituted with halogen;
4.4.c) —SO$_2$R$^{127}$ wherein R$^{127}$ represents optionally substituted phenyl, or —(C$_1$-C$_3$)alkyl which may optionally bear halogen or OR$^{128}$ wherein R$^{128}$ represents H or (C$_1$-C$_3$)alkyl;
4.4.d) —C(O)R$^{129}$ wherein R$^{129}$ represents
  4.4.d1) optionally substituted phenyl,
  4.4.d2) —(C$_1$-C$_3$)alkyl which may optionally bear up to 3 substituents independently selected from
    4.4.d2.1) halogen;
    4.4.d2.4) —OR$^{130}$ wherein R$^{130}$ represents H or (C$_1$-C$_3$)alkyl which may optionally bear halogen; and
    4.4.d2.5) —NR$^{131}$R$^{132}$ in which R$^{131}$ and R$^{132}$ are independently H or —(C$_1$-C$_3$)alkyl which may optionally bear halogen, or R$^{131}$ and R$^{132}$ may be joined and taken together with the N atom to which they are attached form a 5-6 membered ring which may optionally contain a ring member selected from O, S, and NR$^{133}$ wherein R$^{133}$ represents H or (C$_1$-C$_3$)alkyl;
  4.4.d3) —OR$^{134}$ wherein R$^{134}$ represents (C$_1$-C$_3$)alkyl which may optionally bear halogen; or
  4.4.d4) NR$^{135}$R$^{136}$ wherein R$^{135}$ and R$^{136}$ are independently H or —(C$_1$-C$_3$)alkyl which may optionally, bear halogen, or R$^{135}$ and R$^{136}$ may be joined and taken together with the N atom to which they are attached form a 5-6 membered ring which may optionally contain a ring member selected from O, S, and NR$^{137}$ wherein R$^{137}$ represents H or (C$_1$-C$_3$)alkyl; and
j represents 1, 2, or 3;

4.5)

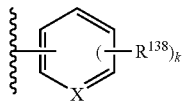

wherein
X represents C or N;
R$^{138}$ represents
4.5.a) (C$_1$-C$_4$)alkyl, which may optionally bear up to 3 substituents independently selected from
  4.5.a1) halogen;
  4.5.a2) OR$^{139}$ wherein R$^{139}$ represents H or (C$_1$-C$_3$)alkyl which may optionally bear halogen or —(C$_1$-C$_3$)mono- or di-alkylamino;
  4.5.a3) —NR$^{140}$R$^{141}$ in which R$^{140}$ and R$^{141}$ are independently H or —(C$_1$-C$_3$)alkyl which may optionally bear halogen or OR$^{141a}$ wherein R$^{141a}$ represents H or (C$_1$-C$_3$)alkyl, or R$^{140}$ and R$^{141}$ may be joined and taken together with the N atom to which they are attached form a 5-6 membered ring which may optionally contain a ring member selected from O, S, and NR$^{142}$ wherein R$^{142}$ represents H or (C$_1$-C$_3$)alkyl; and
  4.5.a4) a 5-6 membered heteroaromatic containing up to two heteroatoms selected from O, S, and N;
4.5.b) —(C$_3$-C$_6$)cycloalkyl which may optionally bear up to 2 substituents independently selected from
  4.5.b1) halogen;
4.5.c) OR$^{144}$ wherein
R$^{144}$ represents H; phenyl; benzyl; (C$_3$-C$_6$)cycloalkyl; or (C$_1$-C$_4$)alkyl which may optionally bear up to 3 substituents independently selected from
  4.5.c1) halogen;
  4.5.c2) OR$^{145}$ wherein R$^{145}$ represents H or (C$_1$-C$_3$)alkyl which may optionally bear (C$_1$-C$_3$) mono- or di-alkylamino; and
  4.5.c3) NR$^{146}$R$^{147}$ in which R$^{146}$ and R$^{1473}$ are independently H or —(C$_1$-C$_3$)alkyl which may optionally bear halogen, or R$^{146}$ and R$^{147}$ may be joined and taken together with the N atom to which they are attached form a 5-6 membered ring which may optionally contain a ring member selected from O, S, and NR$^{148}$ wherein R$^{148}$ represents H or (C$_1$-C$_3$)alkyl;
4.5.e) —C(O)—NR$^{150}$R$^{151}$ wherein
R$^{150}$ represents H or (C$_1$-C$_3$)alkyl which may optionally bear halogen; and
R$^{151}$ represents H or —(C$_1$-C$_4$)alkyl which is optionally substituted with
  4.5.e1) halogen;
  4.5.e3) phenyl;
  4.5.e4) —SO$_2$CH$_3$;
  4.5.e5) —OR$^{152}$ wherein R$^{152}$ represents H or (C$_1$-C$_3$)alkyl which may optionally bear halogen; or
  4.5.e6) —NR$^{153}$R$^{154}$ in which R$^{153}$ and R$^{154}$ are independently H or —(C$_1$-C$_3$)alkyl which may optionally bear halogen, or R$^{153}$ and R$^{154}$ may be joined and taken together with the N atom to which they are attached form a 5-6 membered ring which may optionally contain a ring member selected from O, S, and NR$^{155}$ wherein R$^{155}$ represents H or (C$_1$-C$_3$)alkyl;
4.5.f) —N(R$^{156}$)—C(O)—R$^{157}$ wherein
R$^{156}$ represents H or (C$_1$-C$_3$)alkyl; and
R$^{157}$ represents H, optionally substituted phenyl, or (C$_1$-C$_4$)alkyl which is optionally substituted with
  4.5.f1) optionally substituted phenyl,
  4.5.f2) OR$^{158}$ wherein R$^{158}$ represents H or (C$_1$-C$_3$) alkyl, or
  4.5.f3) NR$^{159}$R$^{160}$ wherein R$^{159}$ and R$^{160}$ are independently H or —(C$_1$-C$_3$)alkyl which may optionally bear halogen, or R$^{159}$ and R$^{160}$ may be joined and taken together with the N atom to which they are attached form a 5-6 membered ring which may optionally contain a ring member selected from O, S, and NR$^{161}$ wherein R$^{161}$ represents H or (C$_1$-C$_3$) alkyl;

4.5.g) —SO$_2$NR$^{162}$R$^{163}$ wherein

R$^{162}$ represents H or (C$_1$-C$_3$)alkyl which may optionally bear halogen; and R$^{163}$ represents H or —(C$_1$-C$_4$)alkyl which is optionally substituted with 4.5.g1) halogen;

4.5.g3) phenyl;

4.5.g4) —SO$_2$CH$_3$;

4.5.g5) —OR$^{164}$ wherein R$^{164}$ represents H or (C$_1$-C$_3$)alkyl which may optionally bear halogen; or 4.5.g6) —NR$^{165}$R$^{166}$ in which R$^{165}$ and R$^{166}$ are independently H or —(C$_1$-C$_3$)alkyl which may optionally bear halogen, or R$^{165}$ and R$^{166}$ may be joined and taken together with the N atom to which they are attached form a 5-6 membered ring which may optionally contain a ring member selected from O, S, and NR$^{167}$ wherein R$^{167}$ represents H or (C$_1$-C$_3$)alkyl;

4.5.h) —N(R$^{168}$)—SO$_2$—R$^{169}$ wherein

R$^{168}$ represents H or (C$_1$-C$_3$)alkyl, and

R$^{169}$ represents H, optionally substituted phenyl, or (C$_1$-C$_4$)alkyl which is optionally substituted with 4.5.h1) halogen, 4.5.h2) optionally substituted phenyl, 4.5.h3) OR$^{170}$ wherein R$^{170}$ represents H or (C$_1$-C$_3$) alkyl which may optionally bear halogen, or 4.5.h4) NR$^{171}$R$^{172}$ wherein R$^{171}$ and R$^{172}$ are independently H or —(C$_1$-C$_3$)alkyl which may optionally bear halogen, or R$^{171}$ and R$^{172}$ may be joined and taken together with the N atom to which they are attached form a 5-6 membered ring which may optionally contain a ring member selected from O, S, and NR$^{173}$ wherein R$^{173}$ represents H or (C$_1$-C$_3$) alkyl;

4.5.i) —NR$^{174}$R$^{175}$ in which R$^{174}$ and R$^{175}$ are independently H or —(C$_1$-C$_3$)alkyl which may optionally bear halogen or OR$^{175a}$ wherein R$^{175a}$ represents H or (C$_1$-C$_3$)alkyl, or R$^{174}$ and R$^{175}$ may be joined and taken together with the N atom to which they are attached form a 5-6 membered ring which may optionally contain a ring member selected from O, S, and NR$^{176}$ wherein R$^{176}$ represents H or (C$_1$-C$_3$) alkyl;

4.5.j) halogen;

4.5.l) NO$_2$;

4.5.m) CN; or 4.5.n) a 5-6 membered heteroaromatic containing up to two heteroatoms selected from O, S, and N; and k represents 0, 1, or 2;

4.6)

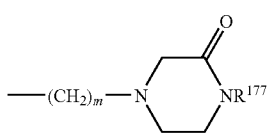

wherein R$^{177}$ represents H or —(C$_1$-C$_3$)alkyl; and m represents 1, 2, or 3;

4.7)

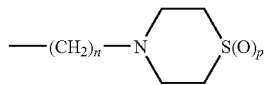

wherein n represents 1, 2, or 3; and p represents 0, 1, or 2;

4.8)

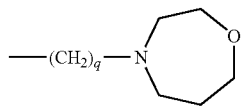

wherein q represents 1, 2, or 3;

4.9)

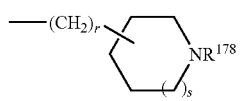

wherein

R$^{178}$ represents 4.9.a) H;

4.9.b) —(C$_1$-C$_3$)alkyl which may optionally bear halogen or —OR$^{179}$ in which R$^{179}$ represents H or (C$_1$-C$_3$)alkyl optionally substituted with halogen;

4.9.c) —SO$_2$R$^{180}$ wherein R$^{180}$ represents optionally substituted phenyl or —(C$_1$-C$_3$)alkyl, which may be substituted with halogen or —OR$^{181}$ wherein R$^{181}$ represents H or (C$_1$-C$_3$)alkyl which may optionally bear halogen;

4.9.d) —C(O)R$^{182}$ wherein R$^{182}$ represents optionally substituted phenyl or —(C$_1$-C$_3$)alkyl which may optionally bear up to 3 substituents independently selected from 4.9.d1) halogen;

4.9.d2) optionally substituted phenyl;

4.9.d4) OR$^{183}$ wherein R$^{183}$ represents H or (C$_1$-C$_3$)alkyl which may optionally bear halogen; and 4.9.d5) —NR$^{184}$R$^{185}$ in which R$^{184}$ and R$^{185}$ are independently H or —(C$_1$-C$_3$)alkyl which may optionally bear halogen or OR$^{185a}$ wherein R$^{185a}$ represents H or (C$_1$-C$_3$)alkyl, or R$^{184}$ and R$^{185}$ may be joined and taken together with the N atom to which they are attached form a 5-6 membered ring which may optionally contain a ring member selected from O, S, and NR$^{186}$ wherein R$^{186}$ represents H or (C$_1$-C$_3$)alkyl;

4.9e) —C(O)OR$^{187}$ wherein R$^{187}$ represents (C$_1$-C$_3$) alkyl; or 4.9.f) —C(O)—NR$^{188}$R$^{189}$ wherein R$^{188}$ and R$^{189}$ each independently represents H or —(C$_1$-C$_3$)alkyl which may optionally bear halogen, or R$^{188}$ and R$^{189}$ may be joined and taken together with the N atom to which they are attached form a 5-6 membered ring which may optionally contain a ring member selected from O, S, and NR$^{190}$ wherein R$^{190}$ represents H or (C$_1$-C$_3$)alkyl;

r represents 0, 1, or 2; and s represents 0 or 0.1;

4.10)

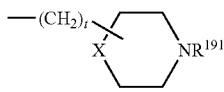

wherein
R$^{191}$ represents
  4.10.a) H;
  4.10.b) —(C$_1$-C$_3$)alkyl which may optionally bear halogen or —OR$^{192}$ in which R$^{192}$ represents H or (C$_1$-C$_3$)alkyl;
  4.10c) —SO$_2$R$^{193}$ wherein R$^{193}$ represents phenyl or —(C$_1$-C$_3$)alkyl, both of which may be substituted with halogen or —(C$_1$-C$_3$)alkyl;
  4.10.d) —C(O)R$^{194}$ wherein R$^{194}$ represents (C$_1$-C$_3$)alkyl which may optionally bear up to 3 substituents independently selected from
    4.10.d1) halogen;
    4.10.d2) phenyl;
    4.10.d4) OR$^{195}$ wherein R$^{195}$ represents H or (C$_1$-C$_3$)alkyl which may optionally bear halogen; and
    4.10.d5) —NR$^{196}$R$^{197}$ in which R$^{196}$ and R$^{197}$ are independently H or —(C$_1$-C$_3$)alkyl which may optionally bear halogen or OR$^{197a}$ wherein R$^{197a}$ represents H or (C$_1$-C$_3$)alkyl, or R$^{196}$ and R$^{197}$ may be joined and taken together with the N atom to which they are attached form a 5-6 membered ring which may optionally contain a ring member selected from O, S, and NR$^{198}$ wherein R$^{198}$ represents H or (C$_1$-C$_3$)alkyl;
  4.10.e) —C(O)OR$^{199}$ wherein R$^{199}$ represents (C$_1$-C$_3$)alkyl; or
  4.10.f) —C(O)—NR$^{200}$R$^{201}$ wherein R$^{200}$ and R$^{201}$ each independently represents H or —(C$_1$-C$_3$)alkyl which may optionally bear halogen, or R$^{200}$ and R$^{201}$ may be joined and taken together with the N atom to which they are attached form a 5-6 membered ring which may optionally contain a ring member selected from O, S, and NR$^{202}$ wherein R$^{202}$ represents H or (C$_1$-C$_3$)alkyl; and
X represents O, S, S(O)$_2$, or NR$^{203}$ wherein R$^{203}$ represents H or —(C$_1$-C$_3$)alkyl; and
t represents 0, 1, or 2;
4.11) halogen; or
4.12) —CN;
or a pharmaceutically acceptable salt thereof.

In embodiment five, the present invention provides a compound of formula (I)

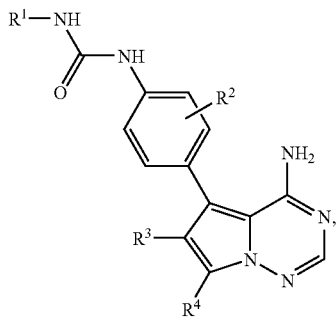

(I)

wherein
R$^1$ represents
  1.1) phenyl which may optionally bear up to 4 substituents independently selected from the group consisting of
    1.1.a) (C$_1$-C$_4$)alkyl, which may optionally bear up to 3 substituents independently selected from
      1.1.a1) halogen;
      1.1.a2) OR$^5$ wherein R$^5$ represents H or (C$_1$-C$_3$)alkyl which may optionally bear halogen;
      1.1.a3) —NR$^6$R$^7$ in which R$^6$ and R$^7$ are independently H or —(C$_1$-C$_3$)alkyl which may optionally bear halogen or R$^6$ and R$^7$ may be joined and taken together with the N atom to which they are attached form a 5-6 membered ring which may optionally contain a ring member selected from O, S, and NR$^8$ wherein R$^8$ represents H or (C$_1$-C$_3$)alkyl; and
      1.1.a4) an imidazole, thiazole, oxazole, pyridine, pyrazole, pyrimidine, isoxazole, isothiazole, thiophene, or furan;
    1.1.b) —(C$_3$-C$_6$)cycloalkyl which may optionally bear up to 2 substituents independently selected from
      1.1.b1) halogen;
    1.1.c) OR$^{10}$ wherein
      R$^{10}$ represents H; phenyl; benzyl; (C$_3$-C$_6$)cycloalkyl; or (C$_1$-C$_4$)alkyl which may optionally bear up to 3 substituents independently selected from
      1.1.c1) halogen;
      1.1.c2) OR$^{11}$ wherein R$^{11}$ represents H or (C$_1$-C$_3$)alkyl; and
      1.1.c3) NR$^{12}$R$^{13}$ in which R$^{12}$ and R$^{13}$ are independently H or —(C$_1$-C$_3$)alkyl which may optionally bear halogen, or R$^{12}$ and R$^{13}$ may be joined and taken together with the N atom to which they are attached form a 5-6 membered ring which may optionally contain a ring member selected from O, S, and NR$^{14}$ wherein R$^{14}$ represents H or (C$_1$-C$_3$)alkyl;
    1.1.e) —C(O)—NR$^{16}$R$^{17}$ wherein
      R$^{16}$ represents H or (C$_1$-C$_3$)alkyl which may optionally bear halogen; and
      R$^{17}$ represents H or —(C$_1$-C$_4$)alkyl which is optionally substituted with
        1.1.e1) halogen;
        1.1.e5) —OR$^{18}$ wherein R$^{18}$ represents H or (C$_1$-C$_3$)alkyl which may optionally bear halogen; or
        1.1.e6) —NR$^{19}$R$^{20}$ in which R$^{19}$ and R$^{20}$ are independently H or —(C$_1$-C$_3$)alkyl which may optionally bear halogen, or R$^{19}$ and R$^{20}$ may be joined and taken together with the N atom to which they are attached form a 5-6 membered ring which may optionally contain a ring member selected from O, S, and NR$^{21}$ wherein R$^{21}$ represents H or (C$_1$-C$_3$)alkyl;
    1.1.f) —N(R$^{22}$)—C(O)—R$^{23}$ wherein
      R$^{22}$ represents H or (C$_1$-C$_3$)alkyl; and
      R$^{23}$ represents optionally substituted phenyl, or (C$_1$-C$_4$)alkyl;
    1.1.g) —SO$_2$NR$^{28}$R$^{29}$ wherein
      R$^{28}$ represents H or (C$_1$-C$_3$)alkyl which may optionally bear halogen; and
      R$^{29}$ represents H or —(C$_1$-C$_4$)alkyl which is optionally substituted with:
        1.1.g1) halogen;
        1.1.g4) —SO$_2$CH$_3$;
        1.1.g5) —OR$^{30}$ wherein R$^{30}$ represents H or (C$_1$-C$_3$)alkyl which may optionally bear halogen; or
        1.1.g6) —NR$^{31}$R$^{32}$ in which R$^{31}$ and R$^{32}$ are independently H or —(C$_1$-C$_3$)alkyl which may optionally bear halogen, or R$^{31}$ and R$^{32}$ may be joined and taken together with the N atom to which they are attached form a 5-6 membered ring which may optionally contain a ring member selected from O, S, and NR$^{33}$ wherein R$^{33}$ represents H or (C$_1$-C$_3$)alkyl;

1.1.h) —N(R$^{34}$)—SO$_2$—R$^{35}$ wherein
R$^{34}$ represents H or (C$_1$-C$_3$)alkyl, and
R$^{35}$ represents optionally substituted phenyl, or (C$_1$-C$_4$)alkyl which is optionally substituted with
1.1.h1) halogen;
1.1.i) —NR$^{40}$R$^{41}$ in which R$^{40}$ and R$^{41}$ are independently H or —(C$_1$-C$_3$)alkyl which may optionally bear halogen or OR$^{42}$ in which R$^{42}$ represents H or (C$_1$-C$_3$)alkyl, or R$^{40}$ and R$^{41}$ may be joined and taken together with the N atom to which they are attached form a 5-6 membered ring which may optionally contain a ring member selected from O, S, and NR$^{43}$ wherein R$^{43}$ represents H or (C$_1$-C$_3$)alkyl;
1.1.j) halogen;
1.1.l) NO$_2$;
1.1.m) CN; and
1.1.n) an imidazole, thiazole, oxazole, pyridine, pyrazole, pyrimidine, isoxazole, isothiazole, thiophene, or furan;

or

R$^1$ represents
1.2) a 5-6 membered aromatic heterocycle selected from imidazole, thiazole, oxazole, pyridine, pyrazole, pyrimidine, isoxazole, isothiazole, thiophene, and furan; said R$^1$ heterocycle optionally bearing up to 4 substituents independently selected from the group consisting of
1.2.a) (C$_1$-C$_4$)alkyl, which may optionally bear up to 3 substituents independently selected from
1.2.a1) halogen;
1.2.a2) OR$^{45}$ wherein R$^{45}$ represents H or (C$_1$-C$_3$) alkyl which may optionally bear halogen;
1.2.a3) —NR$^{46}$R$^{47}$ in which R$^{46}$ and R$^{47}$ are independently H or —(C$_1$-C$_3$)alkyl which may optionally bear halogen, or R$^{46}$ and R$^{47}$ may be joined and taken together with the N atom to which they are attached form a 5-6 membered ring which may optionally contain a ring member selected from O, S, and NR$^{48}$ wherein R$^{48}$ represents H or (C$_1$-C$_3$) alkyl; and
1.2.a4) an imidazole, thiazole, oxazole, pyridine, pyrazole, pyrimidine, isoxazole, isothiazole, thiophene, or furan;
1.2.b) —(C$_3$-C$_6$)cycloalkyl which may optionally bear up to 2 substituents independently selected from
1.2.b1) halogen;
1.2.c) OR$^{50}$ wherein
R$^{50}$ represents H; phenyl; benzyl; —(C$_3$-C$_6$)cycloalkyl; or —(C$_1$-C$_4$)alkyl which may optionally bear up to 3 substituents independently selected from
1.2.c1) halogen;
1.2.e) —C(O)—NR$^{56}$R$^{57}$ wherein
R$^{56}$ represents H or (C$_1$-C$_3$)alkyl which may optionally bear halogen; and
R$^{57}$ represents H or —(C$_1$-C$_4$)alkyl which is optionally substituted with
1.2.e1) halogen; or
1.2.e5) —OR$^{58}$ wherein R$^{58}$ represents H or (C$_1$-C$_3$) alkyl which may optionally bear halogen;
1.2.f) —N(R$^{62}$)—C(O)—R$^{63}$ wherein
R$^{62}$ represents H or (C$_1$-C$_3$)alkyl; and
R$^{63}$ represents optionally substituted phenyl, or (C$_1$-C$_4$)alkyl;
1.2.g) —SO$_2$NR$^{68}$R$^{69}$ wherein
R$^{68}$ represents H or (C$_1$-C$_3$)alkyl which may optionally bear halogen; and
R$^{69}$ represents H or —(C$_1$-C$_4$)alkyl which is optionally substituted with
1.2.g1) halogen; or
1.2.g5) —OR$^{70}$ wherein R$^{70}$ represents H or (C$_1$-C$_3$) alkyl which may optionally bear halogen; or
1.2.h) —N(R$^{74}$)—SO$_2$—R$^{75}$ wherein
R$^{74}$ represents H or (C$_1$-C$_3$)alkyl, and
R$^{75}$ represents optionally substituted phenyl, or (C$_1$-C$_4$)alkyl which is optionally substituted with
1.2.h1) halogen;
1.2.i) —NR$^{80}$R$^{81}$ in which R$^{80}$ and R$^{81}$ are independently H or —(C$_1$-C$_3$)alkyl which may optionally bear halogen or OR$^{81a}$ wherein R$^{81a}$ represents H or (C$_1$-C$_3$)alkyl, or R$^{80}$ and R$^{81}$ may be joined and taken together with the N atom to which they are attached form a 5-6 membered ring which may optionally contain a ring member selected from O, S, and NR$^{82}$ wherein R$^{82}$ represents H or (C$_1$-C$_3$)alkyl;
1.2.j) halogen;
1.2.k) optionally substituted phenyl;
1.2.l) NO$_2$;
1.2.m) CN; and
1.2.n) an imidazole, thiazole, oxazole, pyridine, pyrazole, pyrimidine, isoxazole, isothiazole, thiophene, or furan;
R$^2$ represents halogen; —(C$_1$-C$_5$)alkyl which may optionally bear halogen; or —O(C$_1$-C$_3$)alkyl which may optionally bear halogen;
R$^3$ represents
3.1) —(C$_1$-C$_5$)alkyl which is optionally substituted with
3.1.a) -halogen;
3.1.b) phenyl optionally substituted with halogen, —(C$_1$-C$_3$)alkyl, or —(C$_1$-C$_3$)alkoxy,
3.1.c) a 5-6 membered heteroaromatic containing up to two heteroatoms selected from O, S, and N, optionally substituted with halogen or —(C$_1$-C$_3$)alkyl,
3.1.d) —CN,
3.1.e) —OR$^{83}$ wherein R$^{83}$ represents H or —(C$_1$-C$_3$) alkyl which may optionally bear up to 3 substituents independently selected from
3.1.e1) halogen;
3.1.e2) optionally substituted phenyl;
3.1.e3) —S(O)$_2$CH$_3$;
3.1.e4) OR$^{84}$ wherein R$^{84}$ represents H or (C$_1$-C$_3$) alkyl which may optionally bear halogen or —(C$_1$-C$_3$)mono- or di-alkylamino; and
3.1.e5) —NR$^{85}$R$^{86}$ in which R$^{85}$ and R$^{86}$ are independently H or —(C$_1$-C$_3$)alkyl which may optionally bear halogen, or R$^{85}$ and R$^{86}$ may be joined and taken together with the N atom to which they are attached form a 5-6 membered ring which may optionally contain a ring member selected from O, S, and NR$^{87}$ wherein R$^{87}$ represents H or (C$_1$-C$_3$) alkyl;
3.1.f) —(C$_3$-C$_5$)cycloalkyl which may optionally bear halogen; or
3.1.g) —NR$^{89}$R$^{90}$ wherein
R$^{89}$ represents H or —(C$_1$-C$_3$)alkyl which may optionally bear halogen; and
R$^{90}$ represents H or —(C$_1$-C$_4$)alkyl which is optionally substituted with
3.1.g1) halogen;
3.1.g2) a 5-6 membered heteroaromatic containing up to two heteroatoms selected from O, S, and N;
3.1.g3) phenyl;
3.1.g4) —SO$_2$CH$_3$;

3.1.g5) —$OR^{91}$ wherein $R^{91}$ represents H or ($C_1$-$C_3$)alkyl which may optionally bear halogen; or 3.1.g6) —$NR^{92}R^{93}$ in which $R^{92}$ and $R^{93}$ are independently H or —($C_1$-$C_3$)alkyl which may optionally bear halogen, or $R^{92}$ and $R^{93}$ may be joined and taken together with the N atom to which they are attached form a 5-6 membered ring which may optionally contain a ring member selected from O, S, and $NR^{94}$ wherein $R^{94}$ represents H or ($C_1$-$C_3$)alkyl; or 3.1.g7) $R^{89}$ and $R^{90}$ may be joined and taken together with the N to which they are attached form an aromatic or nonaromatic 5-6 membered ring which may optionally contain a ring member selected from O, S, and $NR^{95}$ wherein $R^{95}$ represents H or ($C_1$-$C_3$)alkyl;

3.2)

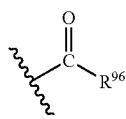

wherein $R^{96}$ represents 3.2.a) H, 3.2.b) —($C_3$-$C_5$)cycloalkyl which may optionally bear halogen; or 3.2.c) —($C_1$-$C_5$)alkyl which may optionally bear up to 3 substituents independently selected from 3.2.c1) halogen;

3.2.c2) a 5-6 membered heteroaromatic containing up to two heteroatoms selected from O, S, and N;

3.2.c3) phenyl;

3.2.c5) —$OR^{97}$ wherein $R^{97}$ represents H or ($C_1$-$C_3$)alkyl which may optionally bear halogen or —($C_1$-$C_3$)mono- or di-alkylamino; and 3.2.c6) —$NR^{98}R^{99}$ in which $R^{98}$ and $R^{99}$ are independently H or —($C_1$-$C_3$)alkyl which may optionally bear halogen or $OR^{99a}$ wherein $R^{99a}$ represents H or ($C_1$-$C_3$)alkyl, or $R^{98}$ and $R^{99}$ may be joined and taken together with the N atom to which they are attached form a 5-6 membered ring which may optionally contain a ring member selected from O, S, and $NR^{100}$ wherein $R^{100}$ represents H or ($C_1$-$C_3$)alkyl;

3.3)

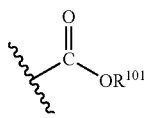

wherein $R^{101}$ represents H or —($C_1$-$C_5$)alkyl which may optionally bear up to 3 substituents independently selected from 3.3.a) halogen; and 3.3.b) phenyl;

3.4)

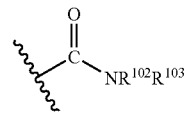

wherein $R^{102}$ represents H or —($C_1$-$C_3$)alkyl which may optionally bear halogen; and $R^{103}$ represents H or —($C_1$-$C_5$)alkyl which may optionally bear up to 3 substituents independently selected from 3.4.a) halogen;

3.4.b) a 5-6 membered heteroaromatic containing up to two heteroatoms selected from O, S, and N;

3.4.c) phenyl;

3.4.d) —$S(O)_2CH_3$;

3.4.e) $OR^{104}$ wherein $R^{104}$ represents H or ($C_1$-$C_3$) alkyl which may optionally bear halogen; and 3.4.f) —$NR^{105}R^{106}$ in which $R^{105}$ and $R^{106}$ are independently H or —($C_1$-$C_3$)alkyl which may optionally bear halogen, or $R^{105}$ and $R^{106}$ may be joined and taken together with the N atom to which they are attached form a 5-6 membered ring which may optionally contain a ring member selected from O, S, and $NR^{107}$ wherein $R^{107}$ represents H or ($C_1$-$C_3$) alkyl;

3.6) a 5-6 membered heteroaromatic containing up to two heteroatoms selected from O, S, and N;

3.7) halogen; or 3.8) —CN;

$R^4$ represents 4.1) —($C_1$-$C_5$)alkyl which is optionally substituted with 4.1.b) -halogen;

4.1.c) —$OR^{110}$ wherein $R^{110}$ represents H or —($C_1$-$C_3$) alkyl which may optionally bear up to 3 substituents independently selected from 4.1.c1) halogen; and 4.1.c5) —$NR^{112}R^{113}$ in which $R^{112}$ and $R^{113}$ are independently H or —($C_1$-$C_3$)alkyl which may optionally bear halogen, or $R^{112}$ and $R^{113}$ may be joined and taken together with the N atom to which they are attached form a 5-6 membered ring which may optionally contain a ring member selected from O, S, and $NR^{114}$ wherein $R^{114}$ represents H or ($C_1$-$C_3$) alkyl; or 4.1.d) —$NR^{115}R^{116}$ wherein $R^{115}$ represents H or —($C_1$-$C_3$)alkyl which may optionally bear halogen and $R^{116}$ represents H, optionally substituted phenyl, or —($C_1$-$C_5$)alkyl which may optionally bear up to 3 substituents independently selected from 4.1.d1) halogen;

4.1.d2) —$S(O)_2CH_3$;

4.1.d3) $OR^{117}$ wherein $R^{117}$ represents H or ($C_1$-$C_3$)alkyl which may optionally bear halogen; and 4.1.d4) —$NR^{118}R^{119}$ in which $R^{118}$ and $R^{119}$ are independently H or —($C_1$-$C_3$)alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or ($C_1$-$C_3$)alkyl;

4.2)

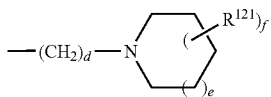

wherein R$^{121}$ represents —(C$_1$-C$_3$)alkyl which may optionally bear halogen;
d represents 1, 2, or 3;
e represents 0 or 1;
f represents 0, 1, or 2;

4.3)

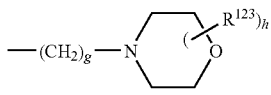

wherein R$^{123}$ represents —(C$_1$-C$_3$)alkyl which may optionally bear halogen;
g represents 1, 2, or 3;
h represents 0, 1, or 2;

4.4)

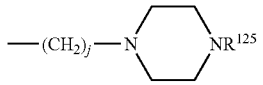

wherein
R$^{125}$ represents
  4.4.a) H;
  4.4.b) —(C$_1$-C$_3$)alkyl which may optionally bear halogen;
  4.4.c) —SO$_2$R$^{127}$ wherein R$^{127}$ represents optionally substituted phenyl, or —(C$_1$-C$_3$)alkyl which may optionally bear halogen;
  4.4.d) —C(O)R$^{129}$ wherein
    R$^{129}$ represents
      4.4.d1) optionally substituted phenyl,
      4.4.d2) —(C$_1$-C$_3$)alkyl which may optionally bear up to 3 substituents independently selected from
        4.4.d2.1) halogen; and
        4.4.d2.4) —OR$^{130}$ wherein R$^{130}$ represents H or (C$_1$-C$_3$)alkyl which may optionally bear halogen;
      4.4.d3) —OR$^{134}$ wherein R$^{134}$ represents (C$_1$-C$_3$)alkyl; or
      4.4.d4) NR$^{135}$R$^{136}$ wherein R$^{135}$ and R$^{136}$ are independently H or —(C$_1$-C$_3$)alkyl which may optionally bear halogen; and
j represents 1, 2, or 3;

4.5)

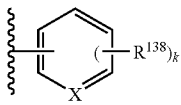

wherein
X represents C or N;
R$^{138}$ represents
4.5.a) (C$_1$-C$_4$)alkyl, which may optionally bear up to 3 substituents independently selected from
  4.5.a1) halogen;
  4.5.a2) OR$^{139}$ wherein R$^{139}$ represents H or (C$_1$-C$_3$)alkyl which may optionally bear halogen; and
  4.5.a3) —NR$^{140}$R$^{141}$ in which R$^{140}$ and R$^{141}$ are independently H or —(C$_1$-C$_3$)alkyl, or R$^{140}$ and R$^{141}$ may be joined and taken together with the N atom to which they are attached form a 5-6 membered ring which may optionally contain a ring member selected from O, S, and NR$^{142}$ wherein R$^{142}$ represents H or (C$_1$-C$_3$)alkyl;
4.5.b) —(C$_3$-C$_6$)cycloalkyl which may optionally bear up to 2 substituents independently selected from
  4.5.b1) halogen;
4.5.c) OR$^{144}$ wherein
  R$^{144}$ represents H; phenyl; benzyl; (C$_3$-C$_6$)cycloalkyl; or (C$_1$-C$_4$)alkyl which may optionally bear up to 3 substituents independently selected from
    4.5.c1) halogen;
    4.5.c2) OR$^{145}$ wherein R$^{145}$ represents H or (C$_1$-C$_3$)alkyl; and
    4.5.c3) NR$^{146}$R$^{147}$ in which R$^{146}$ and R$^{1473}$ are independently H or —(C$_1$-C$_3$)alkyl which may optionally bear halogen, or R$^{146}$ and R$^{147}$ may be joined and taken together with the N atom to which they are attached form a 5-6 membered ring which may optionally contain a ring member selected from O, S, and NR$^{148}$ wherein R$^{148}$ represents H or (C$_1$-C$_3$)alkyl;
4.5.e) —C(O)—NR$^{150}$R$^{151}$ wherein
  R$^{150}$ represents H or (C$_1$-C$_3$)alkyl which may optionally bear halogen; and
  R$^{151}$ represents H or —(C$_1$-C$_4$)alkyl which is optionally substituted with
    4.5.e1) halogen; or
    4.5.e6) —NR$^{153}$R$^{154}$ in which R$^{153}$ and R$^{154}$ are independently H or —(C$_1$-C$_3$)alkyl which may optionally bear halogen, or R$^{153}$ and R$^{154}$ may be joined and taken together with the N atom to which they are attached form a 5-6 membered ring which may optionally contain a ring member selected from O, S, and NR$^{155}$ wherein R$^{155}$ represents H or (C$_1$-C$_3$)alkyl;
4.5.f) —N(R$^{156}$)—C(O)—R$^{157}$ wherein
  R$^{156}$ represents H or (C$_1$-C$_3$)alkyl; and
  R$^{157}$ represents H, optionally substituted phenyl, or (C$_1$-C$_4$)alkyl;
4.5.g) —SO$_2$NR$^{162}$R$^{163}$ wherein
  R$^{162}$ represents H or (C$_1$-C$_3$)alkyl which may optionally bear halogen; and
  R$^{163}$ represents H or —(C$_1$-C$_4$)alkyl which is optionally substituted with
    4.5.g1) halogen; or
    4.5.g6) —NR$^{165}$R$^{166}$ in which R$^{165}$ and R$^{166}$ are independently H or —(C$_1$-C$_3$)alkyl which may optionally bear halogen, or R$^{165}$ and R$^{166}$ may be joined and taken together with the N atom to which they are attached form a 5-6 membered ring which may optionally contain a ring member selected from O, S, and NR$^{167}$ wherein R$^{167}$ represents H or (C$_1$-C$_3$)alkyl;
4.5.h) —N(R$^{168}$)—SO$_2$—R$^{169}$ wherein
  R$^{168}$ represents H or (C$_1$-C$_3$)alkyl, and
  R$^{169}$ represents H, optionally substituted phenyl, or (C$_1$-C$_4$)alkyl which is optionally substituted with 4.5.h1) halogen; or 4.5.h4) $NR^{171}R^{172}$ wherein $R^{171}$ and $R^{172}$ are independently H or —$(C_1-C_3)$alkyl which may optionally bear halogen, or $R^{171}$ and $R^{172}$ may be joined and taken together with the N atom to which they are attached form a 5-6 membered ring which may optionally contain a ring member selected from O, S, and $NR^{173}$ wherein $R^{173}$ represents H or $(C_1-C_3)$alkyl;

4.5.i) —$NR^{174}R^{175}$ in which $R^{174}$ and $R^{175}$ are independently H or —$(C_1-C_3)$alkyl which may optionally bear halogen or $OR^{175a}$ wherein $R^{175a}$ represents H or $(C_1-C_3)$alkyl, or $R^{174}$ and $R^{175}$ may be joined and taken together with the N atom to which they are attached form a 5-6 membered ring which may optionally contain a ring member selected from O, S, and $NR^{176}$ wherein $R^{176}$ represents H or $(C_1-C_3)$alkyl;

4.5.j) halogen;

4.5.l) $NO_2$;

4.5.m) CN; or 4.5.n) an imidazole, thiazole, oxazole, pyridine, pyrazole, pyrimidine, isoxazole, isothiazole, thiophene, or furan; and k represents 0, 1, or 2;

4.6)

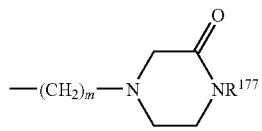

wherein $R^{177}$ represents H or —$(C_1-C_3)$alkyl; and
m represents 1, 2, or 3;

4.7)

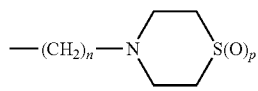

wherein
n represents 1, 2, or 3; and
p represents 0, 1, or 2;

4.8)

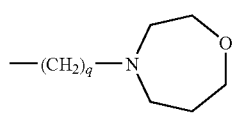

wherein
q represents 1, 2, or 3;

4.9)

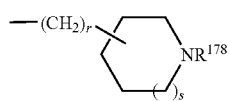

wherein
$R^{178}$ represents 4.9.a) H;

4.9.b) —$(C_1-C_3)$alkyl which may optionally bear halogen;

4.9.c) —$SO_2R^{180}$ wherein $R^{180}$ represents optionally substituted phenyl or —$(C_1-C_3)$alkyl, which may be substituted with halogen;

4.9.d) —$C(O)R^{182}$ wherein $R^{182}$ represents optionally substituted phenyl or —$(C_1-C_3)$alkyl which may optionally bear up to 3 substituents independently selected from 4.9.d1) halogen; and 4.9.d4) $OR^{183}$ wherein $R^{183}$ represents H or $(C_1-C_3)$alkyl which may optionally bear halogen;

4.9e) —$C(O)OR^{187}$ wherein $R^{187}$ represents $(C_1-C_3)$alkyl; or 4.9.f) —$C(O)$—$NR^{188}R^{189}$ wherein $R^{188}$ and $R^{189}$ each independently represents H or —$(C_1-C_3)$alkyl which may optionally bear halogen;

r represents 0, 1, or 2; and s represents 0 or 1;

4.10)

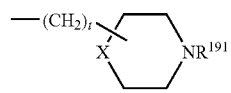

wherein
$R^{191}$ represents 4.10.a) H;

4.10.b) —$(C_1-C_3)$alkyl which may optionally bear halogen;

4.10c) —$SO_2R^{193}$ wherein $R^{193}$ represents phenyl or —$(C_1-C_3)$alkyl, both of which may be substituted with halogen;

4.10.d) —$C(O)R^{194}$ wherein $R^{194}$ represents $(C_1-C_3)$alkyl which may optionally bear up to 3 substituents independently selected from 4.10.d1) halogen;

4.10.d2) phenyl; and 4.10.d4) $OR^{195}$ wherein $R^{195}$ represents H or $(C_1-C_3)$alkyl which may optionally bear halogen;

4.10.e) —$C(O)OR^{199}$ wherein $R^{199}$ represents $(C_1-C_3)$alkyl; or 4.10.f) —$C(O)$—$NR^{200}R^{201}$ wherein $R^{200}$ and $R^{201}$ each independently represents H or —$(C_1-C_3)$alkyl which may optionally bear halogen;

X represents O, S, $S(O)_2$, or $NR^{203}$ wherein $R^{203}$ represents H or —$(C_1-C_3)$alkyl; and t represents 0, 1, or 2;

4.11) halogen; or 4.12) —CN;

or a pharmaceutically acceptable salt thereof.

In embodiment six, the present invention provides a compound of formula (I)

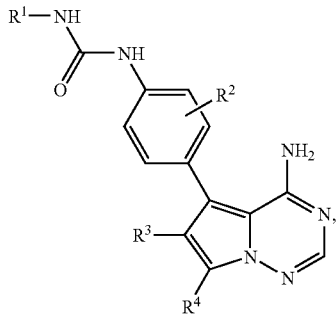

wherein
R$^1$ represents
1.1) phenyl which may optionally bear up to 4 substituents independently selected from the group consisting of
   1.1.a) (C$_1$-C$_4$)alkyl, which may optionally bear up to 3 substituents independently selected from
      1.1.a1) halogen;
      1.1.a2) OR$^5$ wherein R$^5$ represents H or (C$_1$-C$_3$)alkyl which may optionally bear halogen;
      1.1.a3) —NR$^6$R$^7$ in which R$^6$ and R$^7$ are independently H or —(C$_1$-C$_3$)alkyl which may optionally bear halogen or R$^6$ and R$^7$ may be joined and taken together with the N atom to which they are attached form a 5-6 membered ring which may optionally contain a ring member selected from O, S, and NR$^8$ wherein R$^8$ represents H or (C$_1$-C$_3$)alkyl; and
      1.1.a4) an imidazole, thiazole, oxazole, pyridine, pyrazole, pyrimidine, isoxazole, isothiazole, thiophene, or furan;
   1.1.b) —(C$_3$-C$_6$)cycloalkyl which may optionally bear up to 2 substituents independently selected from
      1.1.b1) halogen;
   1.1.c) OR$^{10}$ wherein
      R$^{10}$ represents H; phenyl; benzyl; (C$_3$-C$_6$)cycloalkyl; or (C$_1$-C$_4$)alkyl which may optionally bear up to 3 substituents independently selected from
      1.1.c1) halogen;
      1.1.c2) OR$^{11}$ wherein R$^{11}$ represents H or (C$_1$-C$_3$) alkyl; and
      1.1.c3) NR$^{12}$R$^{13}$ in which R$^{12}$ and R$^{13}$ are independently H or —(C$_1$-C$_3$)alkyl which may optionally bear halogen, or R$^{12}$ and R$^{13}$ may be joined and taken together with the N atom to which they are attached form a 5-6 membered ring which may optionally contain a ring member selected from O, S, and NR$^{14}$ wherein R$^{14}$ represents H or (C$_1$-C$_3$) alkyl;
   1.1.e) —C(O)—NR$^{16}$R$^{17}$ wherein
      R$^{16}$ represents H or (C$_1$-C$_3$)alkyl which may optionally bear halogen; and
      R$^{17}$ represents H or —(C$_1$-C$_4$)alkyl which is optionally substituted with
      1.1.e1) halogen;
      1.1.e5) —OR$^{18}$ wherein R$^{18}$ represents H or (C$_1$-C$_3$) alkyl which may optionally bear halogen; or
      1.1.e6) —NR$^{19}$R$^{20}$ in which R$^{19}$ and R$^{20}$ are independently H or —(C$_1$-C$_3$)alkyl which may optionally bear halogen, or R$^{19}$ and R$^{20}$ may be joined and taken together with the N atom to which they are attached form a 5-6 membered ring which may optionally contain a ring member selected from O, S, and NR$^{21}$ wherein R$^{21}$ represents H or (C$_1$-C$_3$) alkyl;
   1.1.f) —N(R$^{22}$)—C(O)—R$^{23}$ wherein
      R$^{22}$ represents H or (C$_1$-C$_3$)alkyl; and
      R$^{23}$ represents optionally substituted phenyl, or (C$_1$-C$_4$)alkyl;
   1.1.g) —SO$_2$NR$^{28}$R$^{29}$ wherein
      R$^{28}$ represents H or (C$_1$-C$_3$)alkyl which may optionally bear halogen; and
      R$^{29}$ represents H or —(C$_1$-C$_4$)alkyl which is optionally substituted with:
      1.1.g1) halogen;
      1.1.g4) —SO$_2$CH$_3$;
      1.1.g5) —OR$^{30}$ wherein R$^{30}$ represents H or (C$_1$-C$_3$) alkyl which may optionally bear halogen; or
      1.1.g6) —NR$^{31}$R$^{32}$ in which R$^{31}$ and R$^{32}$ are independently H or —(C$_1$-C$_3$)alkyl which may optionally bear halogen, or R$^{31}$ and R$^{32}$ may be joined and taken together with the N atom to which they are attached form a 5-6 membered ring which may optionally contain a ring member selected from O, S, and NR$^{33}$ wherein R$^{33}$ represents H or (C$_1$-C$_3$) alkyl;
   1.1.h) —N(R$^{34}$)—SO$_2$—R$^{35}$ wherein
      R$^{34}$ represents H or (C$_1$-C$_3$)alkyl, and
      R$^{35}$ represents optionally substituted phenyl, or (C$_1$-C$_4$)alkyl which is optionally substituted with
      1.1.h1) halogen;
   1.1.i) —NR$^{40}$R$^{41}$ in which R$^{40}$ and R$^{41}$ are independently H or —(C$_1$-C$_3$)alkyl which may optionally bear halogen or OR$^{42}$ in which R$^{42}$ represents H or (C$_1$-C$_3$)alkyl, or R$^{40}$ and R$^{41}$ may be joined and taken together with the N atom to which they are attached form a 5-6 membered ring which may optionally contain a ring member selected from O, S, and NR$^{43}$ wherein R$^{43}$ represents H or (C$_1$-C$_3$)alkyl;
   1.1.j) halogen;
   1.1.l) NO$_2$;
   1.1.m) CN; and
   1.1.n) an imidazole, thiazole, oxazole, pyridine, pyrazole, pyrimidine, isoxazole, isothiazole, thiophene, or furan;
or
R$^1$ represents
1.2) a 5-6 membered aromatic heterocycle selected from imidazole, thiazole, oxazole, pyridine, pyrazole, pyrimidine, isoxazole, isothiazole, thiophene, and furan; said R$^1$ heterocycle optionally bearing up to 4 substituents independently selected from the group consisting of
   1.2.a) (C$_1$-C$_4$)alkyl, which may optionally bear up to 3 substituents independently selected from
      1.2.a1) halogen;
      1.2.a2) OR$^{45}$ wherein R$^{45}$ represents H or (C$_1$-C$_3$) alkyl which may optionally bear halogen;
      1.2.a3) —NR$^{46}$R$^{47}$ in which R$^{46}$ and R$^{47}$ are independently H or —(C$_1$-C$_3$)alkyl which may optionally bear halogen, or R$^{46}$ and R$^{47}$ may be joined and taken together with the N atom to which they are attached form a 5-6 membered ring which may optionally contain a ring member selected from O, S, and NR$^{48}$ wherein R$^{48}$ represents H or (C$_1$-C$_3$) alkyl; and
      1.2.a4) an imidazole, thiazole, oxazole, pyridine, pyrazole, pyrimidine, isoxazole, isothiazole, thiophene, or furan;

1.2.b) —$(C_3-C_6)$cycloalkyl which may optionally bear up to 2 substituents independently selected from
  1.2.b1) halogen;
1.2.c) $OR^{50}$ wherein
  $R^{50}$ represents H; phenyl; benzyl; —$(C_3-C_6)$cycloalkyl; or —$(C_1-C_4)$alkyl which may optionally bear up to 3 substituents independently selected from
    1.2.c1) halogen;
1.2.e) —$C(O)$—$NR^{56}R^{57}$ wherein
  $R^{56}$ represents H or $(C_1-C_3)$alkyl which may optionally bear halogen; and
  $R^{57}$ represents H or —$(C_1-C_4)$alkyl which is optionally substituted with
    1.2.e1) halogen; or
    1.2.e5) —$OR^{58}$ wherein $R^{58}$ represents H or $(C_1-C_3)$alkyl which may optionally bear halogen;
1.2.f) —$N(R^{62})$—$C(O)$—$R^{63}$ wherein
  $R^{62}$ represents H or $(C_1-C_3)$alkyl; and
  $R^{63}$ represents optionally substituted phenyl, or $(C_1-C_4)$alkyl;
1.2.g) —$SO_2NR^{68}R^{69}$ wherein
  $R^{68}$ represents H or $(C_1-C_3)$alkyl which may optionally bear halogen; and
  $R^{69}$ represents H or —$(C_1-C_4)$alkyl which is optionally substituted with
    1.2.g1) halogen; or
    1.2.g5) —$OR^{70}$ wherein $R^{70}$ represents H or $(C_1-C_3)$alkyl which may optionally bear halogen;
1.2.h) —$N(R^{74})$—$SO_2$—$R^{75}$ wherein
  $R^{74}$ represents H or $(C_1-C_3)$alkyl, and
  $R^{75}$ represents optionally substituted phenyl, or $(C_1-C_4)$alkyl which is optionally substituted with
    1.2.h1) halogen;
1.2.i) —$NR^{80}R^{81}$ in which $R^{80}$ and $R^{81}$ are independently H or —$(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$alkyl;
1.2.j) halogen;
1.2.k) optionally substituted phenyl;
1.2.l) $NO_2$;
1.2.m) CN; and
1.2.n) an imidazole, thiazole, oxazole, pyridine, pyrazole, pyrimidine, isoxazole, isothiazole, thiophene, or furan;

$R^2$ represents halogen; —$(C_1-C_5)$alkyl which may optionally bear halogen; or —$O(C_1-C_3)$alkyl which may optionally bear halogen;

$R^3$ represents
3.1) —$(C_1-C_5)$alkyl which is optionally substituted with
  3.1.a) -halogen;
  3.1.c) a 5-6 membered heteroaromatic containing up to two heteroatoms selected from O, S, and N, optionally substituted with halogen or —$(C_1-C_3)$alkyl,
  3.1.d) —CN,
  3.1.e) —$OR^{83}$ wherein $R^{83}$ represents H or —$(C_1-C_3)$alkyl which may optionally bear up to 3 substituents independently selected from
    3.1.e1) halogen; and
    3.1.e4) $OR^{84}$ wherein $R^{84}$ represents H or $(C_1-C_3)$alkyl which may optionally bear halogen;
  3.1.f) —$(C_3-C_5)$cycloalkyl which may optionally bear halogen; or
  3.1.g) —$NR^{89}R^{90}$ wherein
    $R^{89}$ represents H or —$(C_1-C_3)$alkyl which may optionally bear halogen; and
    $R^{90}$ represents H or —$(C_1-C_4)$alkyl which is optionally substituted with
      3.1.g1) halogen;
      3.1.g4) —$SO_2CH_3$;
      3.1.g5) —$OR^{91}$ wherein $R^{91}$ represents H or $(C_1-C_3)$alkyl which may optionally bear halogen; or
      3.1.g7) $R^{89}$ and $R^{90}$ may be joined and taken together with the N to which they are attached form an aromatic or nonaromatic 5-6 membered ring which may optionally contain a ring member selected from O, S, and $NR^{95}$ wherein $R^{95}$ represents H or $(C_1-C_3)$alkyl;
3.2)

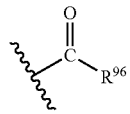

wherein
$R^{96}$ represents
3.2.b) —$(C_3-C_5)$cycloalkyl which may optionally bear halogen; or
3.2.c) —$(C_1-C_5)$alkyl which may optionally bear up to 3 substituents independently selected from
  3.2.c1) halogen; and
  3.2.c5) —$OR^{97}$ wherein $R^{97}$ represents H or $(C_1-C_3)$alkyl which may optionally bear halogen;
3.3)

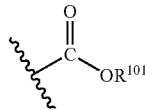

wherein $R^{101}$ represents H or —$(C_1-C_5)$alkyl;
3.4)

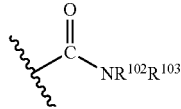

wherein
$R^{102}$ represents H or —$(C_1-C_3)$alkyl which may optionally bear halogen; and
$R^{103}$ represents H or —$(C_1-C_5)$alkyl which may optionally bear up to 3 substituents independently selected from
  3.4.a) halogen;
  3.4.d) —$S(O)_2CH_3$; and
  3.4.e) $OR^{104}$ wherein $R^{104}$ represents H or $(C_1-C_3)$alkyl which may optionally bear halogen;
3.6) a 5-6 membered aromatic heterocycle selected from imidazole, thiazole, oxazole, pyridine, pyrazole, pyrimidine, isoxazole, isothiazole, thiophene, and furan;
3.7) halogen; or
3.8) —CN;

$R^4$ represents
- 4.1) —$(C_1\text{-}C_5)$alkyl which is optionally substituted with
  - 4.1.b) -halogen;
  - 4.1.c) —$OR^{110}$ wherein $R^{110}$ represents H or —$(C_1\text{-}C_3)$alkyl which may optionally bear up to 3 substituents independently selected from
    - 4.1.c1) halogen; and
    - 4.1.c5) —$NR^{112}R^{113}$ in which $R^{112}$ and $R^{113}$ are independently H or —$(C_1\text{-}C_3)$alkyl which may optionally bear halogen, or $R^{112}$ and $R^{113}$ may be joined and taken together with the N atom to which they are attached form a 5-6 membered ring which may optionally contain a ring member selected from O, S, and $NR^{114}$ wherein $R^{114}$ represents H or $(C_1\text{-}C_3)$alkyl; or
  - 4.1.d) —$NR^{115}R^{116}$ wherein
    - $R^{115}$ represents H or —$(C_1\text{-}C_3)$alkyl which may optionally bear halogen and
    - $R^{116}$ represents H, optionally substituted phenyl, or —$(C_1\text{-}C_5)$alkyl which may optionally bear up to 3 substituents independently selected from
      - 4.1.d1) halogen;
      - 4.1.d2) —$S(O)_2CH_3$;
      - 4.1.d3) $OR^{117}$ wherein $R^{117}$ represents H or $(C_1\text{-}C_3)$alkyl which may optionally bear halogen; and
      - 4.1.d4) —$NR^{118}R^{119}$ in which $R^{118}$ and $R^{119}$ are independently H or —$(C_1\text{-}C_3)$alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or $(C_1\text{-}C_3)$alkyl;
- 4.2)

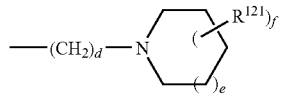

wherein $R^{121}$ represents —$(C_1\text{-}C_3)$alkyl which may optionally bear halogen;
d represents 1, 2, or 3;
e represents 0 or 1;
f represents 0, 1, or 2;
- 4.3)

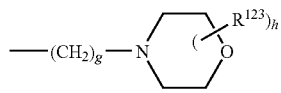

wherein $R^{123}$ represents —$(C_1\text{-}C_3)$alkyl which may optionally bear halogen;
g represents 1, 2, or 3;
h represents 0, 1, or 2;
- 4.4)

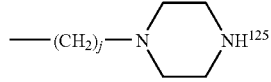

wherein
$R^{125}$ represents
- 4.4.a) H;
- 4.4.b) —$(C_1\text{-}C_3)$alkyl which may optionally bear halogen;
- 4.4.c) —$SO_2R^{127}$ wherein $R^{127}$ represents optionally substituted phenyl, or —$(C_1\text{-}C_3)$alkyl which may optionally bear halogen;
- 4.4.d) —$C(O)R^{129}$ wherein
  $R^{129}$ represents
  - 4.4.d1) optionally substituted phenyl,
  - 4.4.d2) —$(C_1\text{-}C_3)$alkyl which may optionally bear up to 3 substituents independently selected from
    - 4.4.d2.1) halogen; and
    - 4.4.d2.4) —$OR^{130}$ wherein $R^{130}$ represents H or $(C_1\text{-}C_3)$alkyl which may optionally bear halogen;
  - 4.4.d3) —$OR^{134}$ wherein $R^{134}$ represents $(C_1\text{-}C_3)$alkyl; or
  - 4.4.d4) $NR^{135}R^{136}$ wherein $R^{135}$ and $R^{136}$ are independently H or —$(C_1\text{-}C_3)$alkyl which may optionally bear halogen; and
j represents 1, 2, or 3;
- 4.5)

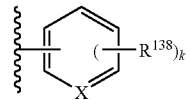

wherein
X represents C or N;
$R^{138}$ represents
- 4.5.a) $(C_1\text{-}C_4)$alkyl, which may optionally bear up to 3 substituents independently selected from
  - 4.5.a1) halogen;
  - 4.5.a2) $OR^{139}$ wherein $R^{139}$ represents H or $(C_1\text{-}C_3)$alkyl which may optionally bear halogen; and
  - 4.5.a3) —$NR^{140}R^{141}$ in which $R^{140}$ and $R^{141}$ are independently H or —$(C_1\text{-}C_3)$alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or $(C_1\text{-}C_3)$alkyl;
- 4.5.b) —$(C_3\text{-}C_6)$cycloalkyl which may optionally bear up to 2 substituents independently selected from
  - 4.5.b1) halogen;
- 4.5.c) $OR^{144}$ wherein
  $R^{144}$ represents H; phenyl; benzyl; $(C_3\text{-}C_6)$cycloalkyl; or $(C_1\text{-}C_4)$alkyl which may optionally bear up to 3 substituents independently selected from
  - 4.5.c1) halogen;
  - 4.5.c2) $OR^{145}$ wherein $R^{145}$ represents H or $(C_1\text{-}C_3)$alkyl; and
  - 4.5.c3) $NR^{146}R^{147}$ in which $R^{146}$ and $R^{1473}$ are independently H or —$(C_1\text{-}C_3)$alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or $(C_1\text{-}C_3)$alkyl;

4.5.e) —C(O)—NR$^{150}$R$^{151}$ wherein
  R$^{150}$ represents H or (C$_1$-C$_3$)alkyl which may optionally bear halogen; and
  R$^{151}$ represents H or —(C$_1$-C$_4$)alkyl which is optionally substituted with
    4.5.e1) halogen; or
    4.5.e6) —NR$^{153}$R$^{154}$ in which R$^{153}$ and R$^{154}$ are independently H or —(C$_1$-C$_3$)alkyl which may optionally bear halogen, or R$^{153}$ and R$^{154}$ may be joined and taken together with the N atom to which they are attached form a 5-6 membered ring which may optionally contain a ring member selected from O, S, and NR$^{155}$ wherein R$^{155}$ represents H or (C$_1$-C$_3$)alkyl;
4.5.f) —N(R$^{156}$)—C(O)—R$^{157}$ wherein
  R$^{156}$ represents H or (C$_1$-C$_3$)alkyl; and
  R$^{157}$ represents H, optionally substituted phenyl, or (C$_1$-C$_4$)alkyl;
4.5.g) —SO$_2$NR$^{162}$R$^{163}$ wherein
  R$^{162}$ represents H or (C$_1$-C$_3$)alkyl which may optionally bear halogen; and
  R$^{163}$ represents H or —(C$_1$-C$_4$)alkyl which is optionally substituted with
    4.5.g1) halogen; or
    4.5.g6) —NR$^{165}$R$^{166}$ in which R$^{165}$ and R$^{166}$ are independently H or —(C$_1$-C$_3$)alkyl which may optionally bear halogen, or R$^{165}$ and R$^{166}$ may be joined and taken together with the N atom to which they are attached form a 5-6 membered ring which may optionally contain a ring member selected from O, S, and NR$^{167}$ wherein R$^{167}$ represents H or (C$_1$-C$_3$)alkyl;
4.5.h) —N(R$^{168}$)—SO$_2$—R$^{169}$ wherein
  R$^{168}$ represents H or (C$_1$-C$_3$)alkyl, and
  R$^{169}$ represents H, optionally substituted phenyl, or (C$_1$-C$_4$)alkyl which is optionally substituted with
    4.5.h1) halogen; or
    4.5.h4) NR$^{171}$R$^{172}$ wherein R$^{171}$ and R$^{172}$ are independently H or —(C$_1$-C$_3$)alkyl which may optionally bear halogen, or R$^{171}$ and R$^{172}$ may be joined and taken together with the N atom to which they are attached form a 5-6 membered ring which may optionally contain a ring member selected from O, S, and NR$^{173}$ wherein R$^{173}$ represents H or (C$_1$-C$_3$)alkyl;
4.5.i) —NR$^{174}$R$^{175}$ in which R$^{174}$ and R$^{175}$ are independently H or —(C$_1$-C$_3$)alkyl which may optionally bear halogen or OR$^{175a}$ wherein R$^{175a}$ represents H or (C$_1$-C$_3$)alkyl, or R$^{174}$ and R$^{175}$ may be joined and taken together with the N atom to which they are attached form a 5-6 membered ring which may optionally contain a ring member selected from O, S, and NR$^{176}$ wherein R$^{176}$ represents H or (C$_1$-C$_3$) alkyl;
4.5.j) halogen;
4.5.l) NO$_2$;
4.5.m) CN; or
4.5.n) a 5-6 membered aromatic heterocycle selected from imidazole, thiazole, oxazole, pyridine, pyrazole, pyrimidine, isoxazole, isothiazole, thiophene, and furan; and
k represents 0, 1, or 2;

4.6)

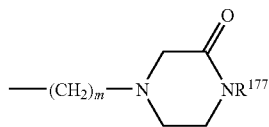

wherein R$^{177}$ represents H or —(C$_1$-C$_3$)alkyl; and
m represents 1, 2, or 3;

4.7)

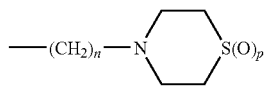

wherein
n represents 1, 2, or 3; and
p represents 0, 1, or 2;

4.8)

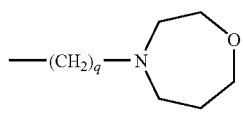

wherein
q represents 1, 2, or 3;

4.9)

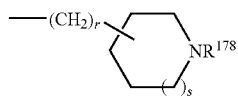

wherein
R$^{178}$ represents
  4.9.a) H;
  4.9.b) —(C$_1$-C$_3$)alkyl which may optionally bear halogen;
  4.9.c) —SO$_2$R$^{180}$ wherein R$^{180}$ represents optionally substituted phenyl or —(C$_1$-C$_3$)alkyl, which may be substituted with halogen;
  4.9.d) —C(O)R$^{182}$ wherein R$^{182}$ represents optionally substituted phenyl or (C$_1$-C$_3$)alkyl which may optionally bear up to 3 substituents independently selected from
    4.9.d1) halogen; and
    4.9.d4) OR$^{183}$ wherein R$^{183}$ represents H or (C$_1$-C$_3$)alkyl which may optionally bear halogen;
  4.9e) —C(O)OR$^{187}$ wherein R$^{187}$ represents (C$_1$-C$_3$)alkyl; or
  4.9.f) —C(O)—NR$^{188}$R$^{189}$ wherein R$^{188}$ and R$^{189}$ each independently represents H or —(C$_1$-C$_3$)alkyl which may optionally bear halogen;
r represents 0, 1, or 2; and
s represents 0 or 1;

4.10)

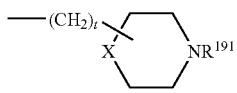

wherein
R$^{191}$ represents
  4.10.a) H;
  4.10.b) —(C$_1$-C$_3$)alkyl which may optionally bear halogen;
  4.10c) —SO$_2$R$^{193}$ wherein R$^{193}$ represents phenyl or —(C$_1$-C$_3$)alkyl, both of which may be substituted with halogen;
  4.10.d) —C(O)R$^{194}$ wherein R$^{194}$ represents (C$_1$-C$_3$) alkyl which may optionally bear up to 3 substituents independently selected from
    4.10.d1) halogen;
    4.10.d2) phenyl; and
    4.10.d4) OR$^{195}$ wherein R$^{195}$ represents H or (C$_1$-C$_3$)alkyl which may optionally bear halogen;
  4.10.e) —C(O)OR$^{199}$ wherein R$^{199}$ represents (C$_1$-C$_3$)alkyl; or
  4.10.f) —C(O)—NR$^{200}$R$^{201}$ wherein R$^{200}$ and R$^{201}$ each independently represents H or —(C$_1$-C$_3$)alkyl which may optionally bear halogen;
X represents O, S, S(O)$_2$, or NR$^{203}$ wherein
  R$^{203}$ represents H or —(C$_1$-C$_3$)alkyl; and
t represents 0, 1, or 2;
4.11) halogen; or
4.12) —CN;
or a pharmaceutically acceptable salt thereof.

In embodiment seven, the present invention provides a compound of formula (I)

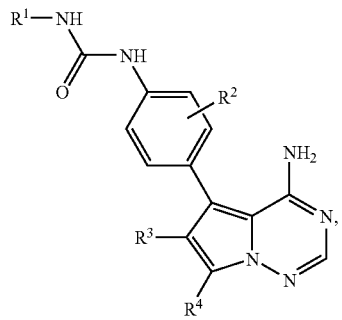

(I)

wherein.
R$^1$ represents
  1.1) phenyl which may optionally bear up to 4 substituents independently selected from the group consisting of
    1.1.a) (C$_1$-C$_4$)alkyl, which may optionally bear up to 3 substituents independently selected from
      1.1.a1) halogen;
    1.1.b) —(C$_3$-C$_6$)cycloalkyl which may optionally bear up to 2 substituents independently selected from
      1.1.b1) halogen;
    1.1.c) OR$^{10}$ wherein
      R$^{10}$ represents H, or (C$_1$-C$_4$)alkyl which may optionally bear up to 3 substituents independently selected from
        1.1.c1) halogen;
    1.1.i) —NR$^{40}$R$^{41}$ in which R$^{40}$ and R$^{41}$ are independently H or —(C$_1$-C$_3$)alkyl which may optionally bear halogen;
    1.1.j) halogen;
    1.1.l) NO$_2$; and
    1.1.m) CN;
or
R$^1$ represents
  1.2) a 5-6 membered aromatic heterocycle selected from thiazole, oxazole, pyridine, pyrazole, pyrimidine, isoxazole, isothiazole, and thiophene; said R$^1$ heterocycle optionally bearing up to 4 substituents independently selected from the group consisting of
    1.2.a) (C$_1$-C$_4$)alkyl, which may optionally bear up to 3 substituents independently selected from
      1.2.a1) halogen; and
      1.2.a4) an imidazole, thiazole, oxazole, pyridine, pyrazole, pyrimidine, isoxazole, isothiazole, thiophene, or furan;
    1.2.b) —(C$_3$-C$_6$)cycloalkyl which may optionally bear up to 2 substituents independently selected from
      1.2.b1) halogen;
    1.2.c) OR$^{50}$ wherein
      R$^{50}$ represents —(C$_1$-C$_4$)alkyl which may optionally bear up to 3 substituents independently selected from
        1.2.c1) halogen;
    1.2.i) —NR$^{80}$R$^{81}$ in which R$^{80}$ and R$^{81}$ are independently H or —(C$_1$-C$_3$)alkyl which may optionally bear halogen;
    1.2.j) halogen;
    1.2.k) optionally substituted phenyl;
    1.2.l) NO$_2$; and
    1.2.m) CN;
R$^2$ represents halogen or —(C$_1$-C$_5$)alkyl;
R$^3$ represents
  3.1) —(C$_1$-C$_5$)alkyl which is optionally substituted with
    3.1.a) -halogen;
    3.1.d) —CN; or
    3.1.e) —OR$^{83}$ wherein R$^{83}$ represents H or —(C$_1$-C$_3$) alkyl which may optionally bear up to 3 substituents independently selected from
      3.1.e1) halogen;
    3.1.g) —NR$^{89}$R$^{90}$ wherein
      R$^{89}$ represents H; and
      R$^{90}$ represents —(C$_1$-C$_4$)alkyl which is optionally substituted with —OR$^{91}$ wherein R$^{91}$ represents H or (C$_1$-C$_3$)alkyl;
  3.2)

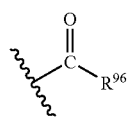

wherein
R$^{96}$ represents
  3.2.b) —(C$_3$-C$_5$)cycloalkyl which may optionally bear halogen; or
  3.2.c) —(C$_1$-C$_5$)alkyl;

3.3)

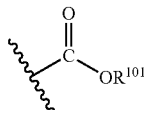

wherein $R^{101}$ represents H or —$(C_1$-$C_5)$alkyl;

3.4)

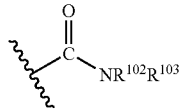

wherein
$R^{102}$ represents H or —$(C_1$-$C_3)$alkyl which may optionally bear halogen; and
$R^{103}$ represents H or —$(C_1$-$C_5)$alkyl which may optionally bear up to 3 substituents independently selected from
3.4.a) halogen;
3.6) a 5-6 membered aromatic heterocycle selected from imidazole, thiazole, oxazole, pyrazole, isoxazole, and isothiazole;
3.7) halogen; or
3.8) —CN;
$R^4$ represents
4.1) —$(C_1$-$C_5)$alkyl which is optionally substituted with
4.1.b) -halogen;
4.1.c) —$OR^{110}$ wherein $R^{110}$ represents H or —$(C_1$-$C_3)$ alkyl which may optionally bear up to 3 substituents independently selected from
4.1.c1) halogen; or
4.1.d) —$NR^{115}R^{116}$ wherein
$R^{115}$ represents H or —$(C_1$-$C_3)$alkyl which may optionally bear halogen, and
$R^{116}$ represents H, optionally substituted phenyl, or —$(C_1$-$C_5)$alkyl which may optionally bear up to 3 substituents independently selected from
4.1.d1) halogen;
4.1.d3) $OR^{117}$ wherein $R^{117}$ represents H or $(C_1$-$C_3)$ alkyl which may optionally bear halogen; and
4.1.d4) —$NR^{118}R^{119}$ in which $R^{118}$ and $R^{119}$ are independently H or —$(C_1$-$C_3)$alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or $(C_1$-$C_3)$ alkyl;

4.2)

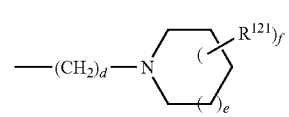

wherein $R^{121}$ represents —$(C_1$-$C_3)$alkyl which may optionally bear halogen;
d represents 1, 2, or 3;
e represents 0 or 1;
f represents 0, 1, or 2;

4.3)

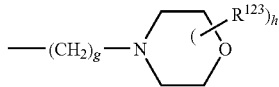

wherein $R^{123}$ represents —$(C_1$-$C_3)$alkyl which may optionally bear halogen;
g represents 1, 2, or 3;
h represents 0, 1, or 2;

4.4)

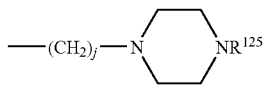

wherein
$R^{125}$ represents
4.4.a) H;
4.4.b) —$(C_1$-$C_3)$alkyl;
4.4.c) —$SO_2R^{127}$ wherein $R^{127}$ represents optionally substituted phenyl, or —$(C_1$-$C_3)$alkyl;
4.4.d) —$C(O)R^{129}$ wherein
$R^{129}$ represents
4.4.d2) —$(C_1$-$C_3)$alkyl which may optionally bear
4.4.d2.4) —$OR^{130}$ wherein $R^{130}$ represents H or $(C_1$-$C_3)$alkyl;
4.4.d3) —$OR^{134}$ wherein $R^{134}$ represents $(C_1$-$C_3)$ alkyl; or
4.4.d4) $NR^{135}R^{136}$ wherein $R^{135}$ and $R^{136}$ are independently H or —$(C_1$-$C_3)$; and
j represents 1, 2, or 3;

4.5)

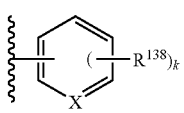

wherein
X represents C or N;
$R^{138}$ represents
4.5.a) $(C_1$-$C_4)$alkyl, which may optionally bear up to 3 substituents independently selected from
4.5.a1) halogen;
4.5.b) —$(C_3$-$C_6)$cycloalkyl which may optionally bear up to 2 substituents independently selected from
4.5.b1) halogen;
4.5.c) $OR^{144}$ wherein
$R^{144}$ represents H, or $(C_1$-$C_4)$alkyl which may optionally bear up to 3 substituents independently selected from
4.5.c1) halogen;
4.5.i) —$NR^{174}R^{175}$ in which $R^{174}$ and $R^{175}$ are independently H or —$(C_1$-$C_3)$alkyl which may optionally bear halogen;
4.5.j) halogen;
4.5.l) $NO_2$; or
4.5.m) CN; and
k represents 0, 1, or 2;

4.6)

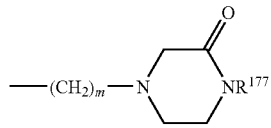

wherein
$R^{177}$ represents H or —$(C_1-C_3)$alkyl; and
m represents 1, 2, or 3;

4.7)

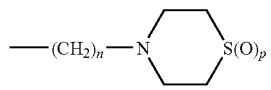

wherein
n represents 1, 2, or 3; and
p represents 0, 1, or 2;

4.8)

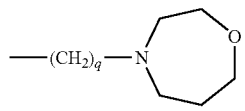

wherein
q represents 1, 2, or 3;

4.9)

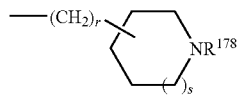

wherein
$R^{178}$ represents
4.9.a) H;
4.9.b) —$(C_1-C_3)$alkyl;
4.9.c) —$SO_2R^{180}$ wherein $R^{180}$ represents —$(C_1-C_3)$alkyl;
4.9.d) —$C(O)R^{182}$ wherein $R^{182}$ represents —$(C_1-C_3)$alkyl which may optionally bear up to 3 substituents independently selected from
    4.9.d4) $OR^{183}$ wherein $R^{183}$ represents H or $(C_1-C_3)$alkyl;
4.9e) —$C(O)OR^{187}$ wherein $R^{187}$ represents —$(C_1-C_3)$alkyl; or
4.9.f) —$C(O)$—$NR^{188}R^{189}$ wherein $R^{188}$ and $R^{189}$ each independently represents H or —$(C_1-C_3)$alkyl;
r represents 0, 1, or 2; and
s represents 0 or 1;

4.10)

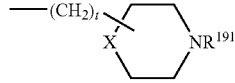

wherein
$R^{191}$ represents
4.10.a) H;
4.10.b) —$(C_1-C_3)$alkyl;
4.10c) —$SO_2R^{193}$ wherein $R^{193}$ represents —$(C_1-C_3)$alkyl;
4.10.d) —$C(O)R^{194}$ wherein $R^{194}$ represents $(C_1-C_3)$alkyl which may optionally bear up to 3 substituents independently selected from
    4.10.d4) $OR^{195}$ wherein $R^{195}$ represents H or $(C_1-C_3)$alkyl;
4.10.e) —$C(O)OR^{199}$ wherein $R^{199}$ represents $(C_1-C_3)$alkyl; or
4.10.f) —$C(O)$—$NR^{200}R^{201}$ wherein $R^{200}$ and $R^{201}$ each independently represents H or —$(C_1-C_3)$alkyl;
X represents O, S, $S(O)_2$, or $NR^{203}$ wherein $R^{203}$ represents H or —$(C_1-C_3)$alkyl; and
t represents 0, 1, or 2;
4.11) halogen; or
4.12) —CN;
or a pharmaceutically acceptable salt thereof.

An intermediate which is useful in the synthesis of the compounds of the invention has the general formula shown below as Q1

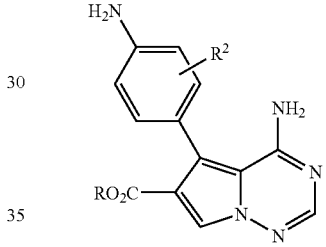

(Q1)

wherein
R represents H or $(C_1-C_5)$alkyl; and
$R^2$ represents halogen; —$(C_1-C_5)$alkyl which may optionally bear halogen; or —$O(C_1-C_3)$alkyl which may optionally bear halogen.

A second intermediate which is useful in the synthesis of the compounds of the invention has the general formula shown below as Q2

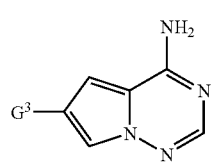

(Q2)

wherein
G3 represents halogen, $(C_1-C_5)$alkyl, —CN, —$C(O)(C_1-C_5)$alkyl, or —C(O)H.

DEFINITIONS

Where the plural form of the word compounds, salts, polymorphs, hydrates, solvates and the like, is used herein, this is taken to mean also a single compound, salt, polymorph, isomer, hydrate, solvate or the like.

The compounds of this invention may contain one or more asymmetric centers, depending upon the location and nature of the various substituents desired. Asymmetric carbon atoms may be present in the (R) or (S) configuration, resulting in racemic mixtures in the case of a single asymmetric center, and diastereomeric mixtures in the case of multiple asymmetric centers. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivitization, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of this invention can likewise be obtained by chiral syntheses utilizing optically active starting materials.

The present invention also relates to useful forms of the compounds as disclosed herein, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

The term "solvates" for the purposes of the invention are those forms of the compounds that coordinate with solvent molecules to form a complex in the solid or liquid state. Hydrates are a specific form of solvates, wherein the solvent is water.

The term "alkyl" refers to a straight-chain or branched saturated hydrocarbon radical having generally 1 to 6, 1 to 4 or 1 to 3 carbon atoms, illustratively representing methyl, ethyl, n-propyl, isopropyl, tert-butyl, n-pentyl and n-hexyl.

The term "cycloalkyl" refers to saturated carbocyclic groups. Preferred cycloalkyl groups include $C_3$-$C_6$ rings, illustratively representing cyclopropyl, cyclopentyl, and cyclohexyl.

The term "alkoxy" refers to a straight-chain or branched hydrocarbon radical having 1 to 6, 1 to 4 or 1 to 3 carbon atoms and bound via an oxygen atom, illustratively representing methoxy, ethoxy, propoxy, isopropoxy, butoxy, isobutoxy, pentoxy, isopentoxy, hexoxy, isohexoxy. The terms "alkoxy" and "alkyloxy" are often used synonymously.

The term "alkylamino" refers to an amino radical having one or two (independently selected) alkyl substituents, illustratively representing methylamino, ethylamino, n-propylamino, isopropylamino, tert-butylamino, n-pentylamino, n-hexylamino, N,N-dimethylamino, N,N-dimethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

The term "alkylaminocarbonyl" refers to an alkylaminocarbonyl radical having one or two (independently selected) alkyl substituents, illustratively representing methylaminocarbonyl, ethylaminocarbonyl, n-propylaminocarbonyl, isopropylaminocarbonyl, tert-butylamino-carbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-t-butyl-N-methylaminocarbonyl, N-ethyl-N-n-pentylamino-carbonyl and N-n-hexyl-N-methylaminocarbonyl.

The term "alkylaminosulfonyl" refers to an aminosulfonyl radical having one or two (independently selected) alkyl substitutents on the amino moiety, illustratively representing methylaminosulfonyl, ethylaminosulfonyl, n-propylaminosulfonyl, isopropylaminosulfonyl, tert-butylaminosulfonyl, n-pentylaminosulfonyl, n-hexyl-aminosulfonyl, N,N-dimethylaminosulfonyl, N,N-diethylaminosulfonyl, N-ethyl-N-methylaminosulfonyl, N-methyl-N-n-propylaminosulfonyl, N-isopropyl-N-n-propylaminosulfonyl, N-t-butyl-N,N-methylaminosulfonyl, N-ethyl-N-n-pentylaminosulfonyl and N-n-hexyl-N-methylaminosulfonyl.

The term "alkylsulfonylamino" refers to a sulfonylamino radical having an alkyl substitutent on the sulfonylamino moiety, illustratively representing methylsulfonylamino, ethylsulfonylamino, n-propylsulfonylamino, isopropylsulfonylamino, tert-butyl-sulfonylamino, n-pentylsulfonylamino and n-hexylsulfonylamino.

The term "alkoxycarbonyl" refers to a carbonyl radical being substituted with an alkoxy radical, illustratively representing methoxycarbonyl, ethoxycarbonyl, n-propoxycarbonyl, isopropoxycarbonyl, tert-butoxycarbonyl, n-pentoxycarbonyl and n-hexoxycarbonyl.

The term "alkoxycarbonylamino" refers to a carbonylamino radical being substituted with an alkoxy radical on the carbonyl moiety, illustratively representing methoxycarbonylamino, ethoxycarbonylamino, n-propoxycarbonylamino, isopropoxycarbonylamino, tert-butoxy-carbonylamino, n-pentoxycarbonylamino and n-hexoxycarbonylamino.

The term "heteroaryl" refers to a mono- or bicyclic radical having 5 to 10 or 5 or 6 ring atoms and up to 4 hetero atoms selected from the group consisting of nitrogen, oxygen and sulfur, which is aromatic at least in one ring. It can be attached via a ring carbon atom or a ring nitrogen atom. If it represents a bicycle, wherein one ring is aromatic and the other one is not, it can be attached at either ring. Illustrative examples of such groups are the thiophene, furan, pyrrole, thiazole, oxazole, imidazole, pyridine, pyrimidine, pyridazine, indole, indazole, benzofuran, benzothiophene, quinoline and isoquinoline groups.

Language reciting a 5-6 membered aromatic heterocycle containing up to 3 heteroatoms independently selected from the group consisting of N, O, and S is meant to refer to aromatic heterocycles such as furan, thiophene, pyrrole, pyrazole, triazole, isoxazole, oxazole, thiazole, isothiazole, imidaxole, an oxadiazole, 1,3,2-dioxazole, 1,2,5-oxathiazole, 1,2-pyrone, 1,4-pyrone, pyridine, pyridazine, pyrimidine, pyrazine, a triazine, o- and p-isoxazines, 1,2,5-oxathiazine, 1,2,4-oxadiazine, and the like.

Language reciting a bicyclic heterocycle of 8-10 ring members in which at least one ring is aromatic and contains up to 3 moieties independently selected from the group consisting of N, N→O, O, and S, and any non-aromatic ring of said bicyclic heterocycle optionally contains up to three moieties independently selected from the group consisting of O, S, S(O), S(O)$_2$, and NR, is meant to refer to bicyclic heterocycles in which at least one ring is a 5-6-membered aromatic heterocycle as discussed above, which is fused to a second ring which may be aromatic or nonaromatic. Where this second ring is aromatic, it may also optionally contain up to 3 moieties independently selected from the group consisting of N, N→O, O, and S, and where this second ring is nonaromatic, it may optionally contain up to three moieties independently selected from O, S, S(O), S(O)$_2$, and NR.

The term "heterocyclyl" refers to a saturated or partially unsaturated mono- or bicyclic heterocyclic ring which contains 3 to 8 or 5 to 6 ring atoms and 1 to 3 heteroatoms or hetero groups selected independently from the group consisting of nitrogen, oxygen and sulfur, CO, SO and SO$_2$, such as tetrahydrofuran-2-yl, pyrrolidin-2-yl, pyrrolidin-3-yl, pyrrolinyl, piperidinyl, morpholinyl, or perhydroazepinyl. It can be attached via a ring carbon atom or a ring nitrogen atom.

The terms "halo" and "halogen" refer to fluorine, chlorine, bromine or iodine.

A bicyclic carbocycle of 9-10 ring members in which at least one ring is aromatic is a compound such as indene, isoindene, and tetrahydronaphthalene.

Language stating that an alkyl or alkoxy group may optionally bear halogen or may be substituted with halogen means that the group may bear one or more halogens, up to perhalo.

Language reciting that in a group —NRR, the two R groups may be joined and taken together with the N atom to which they are attached form a 5-6 membered ring which may optionally contain a ring member selected from O, S, and NR$^x$ wherein R$^x$ represents H or (C$_1$-C$_3$)alkyl, is meant to indicate formation of groups such as pyrrolidine, imidazolidine, piperidine piperazine, morpholine, thiomorpholine, and the like.

Language indicating that two substituent groups of a tertiary amino moiety may be joined and taken together with the N to which they are attached form an aromatic or nonaromatic 5-6 membered ring which may optionally contain a ring member selected from O, S, and NR is meant to indicate the possibility of forming 5-6-membered N-containing heterocycles such as pyrrole, pyrazole, piperazine, morpholine, piperidine, imidazole, pyrrolidine, imidazolidene, and the like.

When NR is indicated as being part of a heterocycle, this means that the N atom is the ring member and R is a substituent.

Language reciting a 5-6 membered heteroaromatic containing up to two heteroatoms selected from O, S, and N is meant to refer to groups such as furan, thiophene, pyrrole, pyrazole, oxazole, isoxazole, thiazole, isothiazole, imidazole, pyridine, pyridazine, pyrimidine, pyrazine, isoxazine, and the like.

The term "aryl" refers to a mono- to tricyclic carbocyclic radical, which is aromatic at least in one ring, having generally 6 to 14 carbon atoms, illustratively representing phenyl, naphthyl and phenanthrenyl.

The term "substituted phenyl" refers to an phenyl radical having one or more (but typically not more than three) groups independently selected from halogen; alkyl such as (C$_1$-C$_3$) alkyl; alkoxy such as O(C$_1$-C$_3$)alkyl; CN; cycloalkyl; heteroaryl; heterocyclyl; amino; alkylamino such as mono- or di-(C$_1$-C$_3$)alkylamino; acylamino wherein for example the acyl group is —C(O)(C$_1$-C$_3$)alkyl or —C(O)phenyl alkoxycarbonyl; CN; NO$_2$; alkynyl; alkenyl; C(O)NH$_2$; C(O)NH (C$_1$-C$_3$)alkyl; C(O)N((C$_1$-C$_3$)alkyl)$_2$; C(O)NH-phenyl; —NHC(O)NH$_2$; alkylaminosulfonyl; alkylsulfonylamino; and alkoxycarbonylamino, and in these groups, alkyl and phenyl groups may be further substituted with halogen.

Language stating that phenyl may be optionally substituted with halogen means that the phenyl group optionally may bear one or more substituents independently selected from fluorine, chlorine, bromine and iodine, up to a maximum of perhalo, but typically not more than three such groups.

Language stating that a cycloalkyl group may optionally bear halogen or alkoxy is meant to indicate that the cycloalkyl group may be bear one or more halogen substituents, up to perhalo, and/or it may bear one or more alkoxy groups, generally up to a maximum of three.

The skilled in the art understand that when two heteroatoms are attached to a single aliphatic carbon atom, the resulting material is usually not stable. Accordingly, in this invention, when an aliphatic group bears two heteroatom-containing substituents (such as amino and alkoxy, for example) in which the heteroatoms are joined to the aliphatic group, such heteroatom-containing substituents will generally need to be located on different carbon atoms of the aliphatic material.

A wavy line across the end of a line which indicates a chemical bond extending from a chemical substructure or functional group means that the substructure or group is attached to the remainder of the molecule via that bond.

A carbonyl group is indicated as C=O in a chemical structure or substructure, or by C(O) in a typed formula.

In naming a multiunit functional group by listing the constituent units, the terminal unit is recited first, then the adjacent unit is recited, etc. An example of this style of nomenclature would be "alkylphenyl", which connotes an alkyl group located on a phenyl group, which is in turn connected to the remainder of the molecule. Conversely, the term "phenylalkyl" would connote a phenyl group located on an alkyl group which is in turn connected to the remainder of the molecule. Another example would be "cycloalkylalkyl", which connotes a cycloalkyl group connected to an alkyl group which is in turn connected to the remainder of the molecule.

In this document, for the sake of simplicity, the names of substituent groups are generally (but not always) given as names of the parent compounds rather than using nomenclature which indicates their status as substituents. Thus, for example, if a substituent in a compound of the invention were a pyridine ring, it would generally be termed a "pyridine" substituent rather than a being referred to as a "pyridyl" group. Where the nomenclature indicating status as a substituent is not employed, and a substituent is named in terms of its parent, its status as a substituent will be clear from the context.

Salts of the compounds identified herein can be obtained by isolating the compounds as hydrochloride salts, prepared by treatment of the free base with anhydrous HCl in a suitable solvent such as THF. Generally, a desired salt of a compound of this invention can be prepared in situ during the final isolation and purification of a compound by means well known in the art. Or, a desired salt can be prepared by separately reacting the purified compound in its free base form with a suitable organic or inorganic acid and isolating the salt thus formed. These methods are conventional and would be readily apparent to one skilled in the art.

If used as active compounds, the compounds according to the invention are preferably isolated in more or less pure form, that is more or less free from residues from the synthetic procedure. The degree of purity can be determined by methods known to the chemist or pharmacist (see especially Remington's Pharmaceutical Sciences, 18$^{th}$ ed. 1990, Mack Publishing Group, Enolo). Preferably the compounds are greater than 99% pure (w/w), while purities of greater than 95%, 90% or 85% can be employed if necessary.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of claim 1" is meant to include the simultaneous treatment of more than one disease as well as the administration of more than one compound of claim 1.

The compounds according to the invention exhibit an unforeseeable, useful pharmacological and pharmacokinetic activity spectrum. They are therefore suitable for use as medicaments for the treatment and/or prophylaxis of disorders in humans and animals.

Pharmaceutical Compositions of the Compounds of the Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52 (5), 238-311; Strickley, R. G "Parenteral Formulations of Small Molecule Therapeutics Marketed in the United States (1999)-Part-1" *PDA Journal of Pharmaceutical Science & Technology* 1999, 53 (6), 324-349; and Nema, S. et al, "Excipients and Their Use in Injectable Products" *PDA Journal of Pharmaceutical Science & Technology* 1997, 51 (4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lyophilized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyperproliferative disorders include but are not limited to, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also, provides methods for the treatment of disorders associated with aberrant kinase activity (such as tyrosine kinase activity), including, FGFR1, FGFR2, FGFR3, FGFR4, VEGFR1, VEGFR2, VEGFR3, Tie2, PDGFR, Aurora A, Aurora B, EphB4, EphA2, p70S6K, RSK, TrkA, Trk B, RET, Src, c-Yes and Fyn.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of FGFR1, FGFR2, FGFR3, FGFR4, VEGFR1, VEGFR2, VEGFR3, Tie2, PDGFR, Aurora A, Aurora B, EphB4, EphA2, p70S6K, RSK, TrkA, Trk B, RET, Src, c-Yes and Fyn comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), age-related macular degeneration (AMD; see, Lopez et al. *Invest. Opththalmol. Vis. Sci.* 1996, 37, 855), neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. For example, the compounds of this invention can be combined with known anti-hyper-proliferative or other indication agents, and the like, as well as with admixtures and combinations thereof.

The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofuran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, trednoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY 43-9006 (sorafenib), avastin, CCI-779, CDC-501, Celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be added to the composition include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemo-therapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

EXPERIMENTAL

Abbreviations and Acronyms

A comprehensive list of the abbreviations used by organic chemists of ordinary skill in the art appears in The ACS Style Guide (third edition) or the Guidelines for Authors for the *Journal of Organic Chemistry*. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:

Abbreviations and Acronyms $^{1}$H-NMR proton nuclear magnetic resonance spectroscopy
$^{31}$P-NMR phosphorus-31 nuclear magnetic resonance spectroscopy
AcOH acetic acid
(Ac)$_2$O acetic anhydride
abs absolute
aq aqueous
ap approximate
atm atmosphere
br broad
BOP benzotriazole-1-yloxy-tris(dimethylamino)phosphonium hexafluorophosphate
Bu butyl
ACN acetonitrile
Ac$_2$O acetic anhydride
AcOH acetic acid
Celite® brand of diatomaceous earth from Celite Corp.
CD$_3$CN acetonitrile-d$_3$
CD$_3$OD methanol-d$_4$
d doublet
DCE dichloroethane
DCM dichloromethane
dd double doublet
DIBAL diisobutylaluminum hydride
DMF N,N-dimethylformamide
DMSO dimethylsulfoxide
DMSO-d$_6$ dimethylsulfoxide-d$_6$
equiv equivalent(s)
ES-MS electrospray mass spectrometry
Et$_3$N triethylamine
Et$_2$O diethyl ether
EtOAc ethyl acetate
EtOH ethanol
FBS fetal bovine serum
g gram(s)
h hour(s)
HPLC high performance liquid chromatography
Hz hertz
J NMR coupling constant
L liter(s)
LCMS liquid chromatography-mass spectrometry
LHMDS lithium hexamethyldisilazide
L-Selectride lithium tri-sec-butylborohydride
M molar
Me methyl
MeOH methanol
mg milligram(s)
MHz megahertz
min minute(s)
mL milliliter
mmol millimole
MPLC medium pressure liquid chromatography
MS mass spectrometry
Ms methanesulfonyl
N normal
nM nanomolar
Pr propyl
py-BOP benzotriazol-1-yl-oxytripyrrolidineophosphonium hexafluorophosphate
q quartet
Ra-Ni Raney-Nickel
R$_f$ TLC retention factor
Rochelle's salt potassium sodium tartrate
RP Reverse phase
RPMI Roswell Park Memorial Institute
RT retention time
rt room temperature
s singlet
t triplet
TEA triethylamine
TFA trifluoroacetic acid
THF tetrahydrofuran
TLC thin layer chromatography
TosMIC Tosylmethyl isocyanide
TPP triphenylphosphine
Ts p-toluenesulfonyl
v/v volume-to-volume proportion
v/v/v volume-to-volume-to-volume proportion
μL microliter
μm micrometer The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated under reduced pressure" refers to use of a Buchi rotary evaporator at approximately 15 mm of Hg. All temperatures are reported uncorrected in degrees Celsius (° C.). Thin layer chromatography (TLC) was performed on pre-coated glass-backed silica gel 60 A F-254 250 μm plates.

The structures of compounds of this invention were confirmed using one or more of the following procedures.

NMR

NMR spectra were acquired for each compound and were consistent with the structures shown.

Routine one-dimensional NMR spectroscopy was performed on either 300 or 400 MHz Varian® Mercury-plus spectrometers. The samples were dissolved in deuterated solvents. Chemical shifts were recorded on the ppm scale and were referenced to the appropriate solvent signals, such as 2.49 ppm for DMSO-d6, 1.93 ppm for CD3CN, 3.30 ppm for CD3OD, 5.32 ppm for CD2Cl2 and 7.26 ppm for CDCl3 for 1H spectra.

GC/MS

Electron impact mass spectra (EI-MS) were obtained with a Hewlett Packard 5973 mass spectrometer equipped Hewlett Packard 6890 Gas Chromatograph with a J & W HP-5 column (0.25 uM coating; 30 m×0.32 mm). The ion source was maintained at 250° C. and spectra were scanned from 50-550 amu at 0.34 sec per scan.

LC/MS

Unless otherwise noted, all retention times are obtained from the LC/MS and correspond to the molecular ion. High pressure liquid chromatography-electrospray mass spectra (LC/MS) were obtained using one of the following:

Method A (LCQ)

Hewlett-Packard 1100 HPLC equipped with a quaternary pump, a variable wavelength detector set at 254 nm, a Waters Sunfire C18 column (2.1×30 mm, 3.5 □m), a Gilson autosampler and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA, and B: 2% water in acetonitrile with 0.018% TFA. Gradient elution from 10% B to 95% B over 3.5 minutes at a flow rate of 1.0 mL/min was used with an initial hold of 0.5 minutes and a final hold at 95% B of 0.5 minutes. Total run time was 6.5 minutes.

Method B (LCQ5)

Agilent 1100 HPLC system. The Agilent 1100 HPLC system was equipped with an Agilent 1100 autosampler, quaternary pump, a variable wavelength detector set at 254 nm. The HPLC column used was a Waters Sunfire C-18 column (2.1×30 mm, 3.5 □m). The HPLC eluent was directly coupled without splitting to a Finnigan LCQ DECA ion trap mass spectrometer with electrospray ionization. Spectra were scanned from 140-1200 amu using a variable ion time according to the number of ions in the source using positive ion mode. The eluents were A: 2% acetonitrile in water with 0.02% TFA, and B: 2% water in acetonitrile with 0.02% TFA. Gradient elution from 10% B to 90% B over 3.0 minutes at a flow rate of 1.0 mL/min was used with an initial hold of 1.0 minutes and a final hold at 95% B of 1.0 minutes. Total run time was 7.0 minutes.

Method C (LTQ)

Agilent 1100 HPLC system. The Agilent 1100 HPLC system was equipped with an Agilent 1100 autosampler, quaternary pump, and a diode array. The HPLC column used was a Waters Sunfire C18 column (2.1×30 mm, 3.5 □m). The HPLC eluent was directly coupled with a 1:4 split to a Finnigan LTQ ion trap mass spectrometer with electrospray ionization. Spectra were scanned from 50-800 amu using a variable ion time according to the number of ions in the source using positive or negative ion mode. The eluents were A: water with 0.1 formic acid, and B: acetonitrile with 0.1% formic acid. Gradient elution from 10% B to 90% B over 3.0 minutes at a flowrate of 1.0 mL/min was used with an initial hold of 2.0 minutes and a final hold at 95% B of 1.0 minutes. Total ran time was 8.0 minutes.

Method D

Gilson HPLC system equipped with a variable wavelength detector set at 254 nm, a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluants were A: 2% acetonitrile in water with 0.02% TFA and B: 2% water in acetonitrile with 0.018% TFA. Gradient elution from 10% B to 95% over 3.5 minutes at a flow rate of 1.0 mL/min was used with an initial hold of 0.5 minutes and a final hold at 95% B of 0.5 minutes. Total run time was 6.5 minutes.

Method E

Agilent 1100 HPLC system. The Agilent 1100 HPLC system was equipped with an Agilent 1100 autosampler, quaternary pump, and a diode array. The HPLC column used was a Waters Sunfire (2.1×30 mm, 3.5 □m). The HPLC eluent was directly coupled with a 1:4 split to a Finnigan LTQ ion trap mass spectrometer with electrospray ionization. Spectra were scanned from 50-1000 amu using a variable ion time according to the number of ions in the source in either positive or negative ion mode. The eluents were A: water with 0.1 formic acid, and B: acetonitrile with 0.1% formic acid. Gradient elution from 10% B to 90% B over 3.0 minutes at a flow rate of 1.0 mL/min was used with an initial hold of 2.0 minutes and a final hold at 95% B of 1.0 minutes. Total run time was 8.0 minutes.

Preparative HPLC:

Preparative HPLC was carried out in reversed phase mode, typically using a Gilson HPLC system equipped with two Gilson 322 pumps, a Gilson 215 Autosampler, a Gilson diode array detector, and a C-18 column (e.g. YMC Pro 20×150 mm, 120 A). Gradient elution was used with solvent A as water with 0.1% TFA, and solvent B as acetonitrile with 0.1% TFA. Following injection onto the column as a solution, the compound was typically eluted with a mixed solvent gradient, such as 10-90% Solvent B in Solvent A over 15 minutes with flow rate of 25 mL/min. The fraction(s) containing the desired product were collected by UV monitoring at 254 or 220 nm.

Preparative MPLC:

Preparative medium pressure liquid chromatography (MPLC) was carried out by standard silica gel "flash chromatography" techniques (e.g., Still, W. C. et al. *J. Org. Chem.* 1978, 43, 2923-5), or by using silica gel cartridges and devices such as the Biotage Flash systems. A variety of eluting solvents were used, as described in the experimental protocols.

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

Synthetic transformations that may be employed in the synthesis of compounds of this invention and in the synthesis of intermediates involved in the synthesis of compounds of this invention are known by or accessible to one skilled in the art. Collections of synthetic transformations may be found in compilations, such as:

J. March. *Advanced Organic Chemistry,* 4th ed.; John Wiley: New York (1992)

R. C. Larock. *Comprehensive Organic Transformations,* 2nd ed.; Wiley-VCH: New York (1999)

F. A. Carey; R. J. Sundberg. *Advanced Organic Chemistry,* 2nd ed.; Plenum Press: New York (1984)

T. W. Greene; P. G. M. Wuts. *Protective Groups in Organic Synthesis,* 3rd ed.; John Wiley: New York (1999)

L. S. Hegedus. *Transition Metals in the Synthesis of Complex Organic Molecules*, 2nd ed.; University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*; Pergamon Press: Oxford, UK (1984)

A. R. Katritzky; C. W. Rees; E. F. V. Scriven, Eds. *Comprehensive Heterocyclic Chemistry II*; Pergamon Press: Oxford, UK (1996)

C. Hansen; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts*, which may be searched using either CAS OnLine or SciFinder, *Handbuch der Organischen Chemie* (Beilstein), which may be searched using SpotFire, and REACCS.

Methods for preparing pyrrolotriazines are also disclosed in published U.S. application Ser. No. 10/289,010 (Publication No. US 2003-0186982 A1), U.S. Pat. No. 6,670,357 (U.S. application Ser. No. 10/036,293), as well as WO 2003/042172, WO 2004/009542, WO2004/009601, WO 2004/009784, WO 2004/013145 and WO 2005/121147 all of which are hereby incorporated by reference in their entirety.

General Methods of Preparation of Invention Compounds

It is also to be understood that starting materials are commercially available or readily prepared by standard methods well known in the art. Such methods include, but are not limited to the transformations listed herein.

If not mentioned otherwise, the reactions are usually carried out in inert organic solvents which do not change under the reaction conditions. These include ethers, such as diethyl ether, 1,4-dioxane or tetrahydrofuran, halogenated hydrocarbons, such as dichloromethane, trichloromethane, carbon tetrachloride, 1,2-dichloroethane, trichloroethane or tetrachloroethane, hydrocarbons, such as benzene, toluene, xylene, hexane, cyclohexane or mineral oil fractions, alcohols, such as methanol, ethanol or iso-propanol, nitromethane, dimethylformamide or acetonitrile. It is also possible to use mixtures of the solvents.

The reactions are generally carried out in a temperature range of from 0° C. to 150° C., preferably from 0° C. to 70° C. The reactions can be carried out under atmospheric, elevated or under reduced pressure (for example from 0.5 to 5 bar). In general, they are carried out under atmospheric pressure of air or inert gas, typically nitrogen.

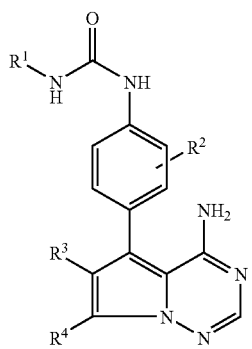

Compounds of the present invention of formula I can be prepared by straightforward means as described in the reaction schemes below or by means well known to those skilled in the art. In these reaction schemes, unless otherwise specifically defined, the meanings of $R^1$, $R^2$, $R^3$ and $R^4$ are identical to those described above.

Reaction Scheme 1 illustrates a general method of preparing compounds of formula I from the corresponding anilino compounds of formula 1-1 by methods of urea formation well known in the art. Thus, reaction of anilines of formula-1 with either an isocyanate of formula 1-2 or preferably a carbamate of formula 1-3, generally in an inert solvent, provides compounds of formula I-1 directly.

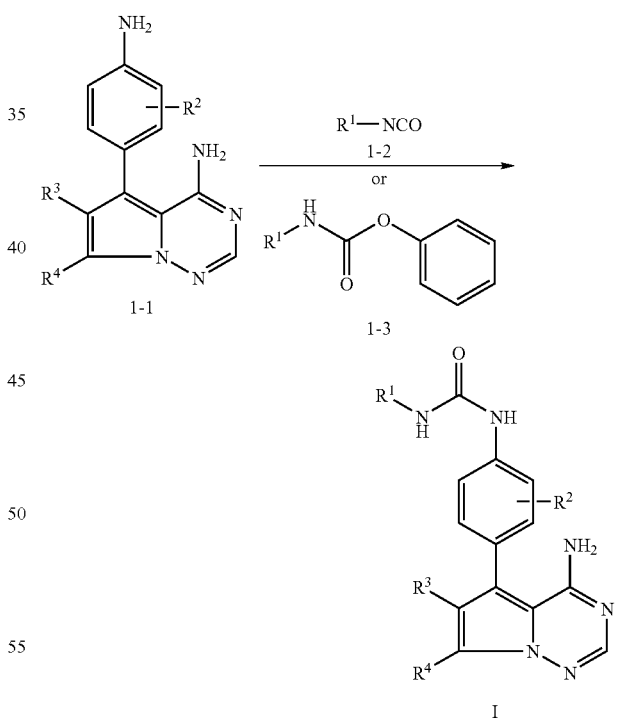

Reaction Scheme 2 outlines an alternate method for preparing compounds of formula I, starting from bromides of formula 2-1, where PG is an optional protecting group known in the art (or alternatively NHPG=NO$_2$). Thus, Suzuki reaction of 2-1 with boronates of formula 2-3 under conditions well known in the art provides compounds of formula I. Alternatively, Suzuki reactions of boronates of formula 2-3 under conditions well known in the art provides anilino-compounds of formula 1-1. Such compounds can be converted to the ureas of Formula I by reaction with isocyanates of formula 1-2 or carbamates of formula 1-3, as described in Scheme 1. If necessary, the protecting group (PG) can be removed first by methods well known in the art (e.g. acid catalyzed removal of BOC carbamates).

or the like and an animating reagent such as $(Ph)_2P(O)$—O—$NH_2$ (compound 3-5) or the like, to provide N-amino nitriles of formula 3-6. Reaction of 3-6 with formamide provides pyrrolotriazine intermediates of formula 3-7. Selective reduction of the nitro substituent of the phenyl ring can be accomplished by many methods known to those skilled in the art, (e.g. Raney nickel or tin(II) chloride) providing intermediates of formula 3-8.

Reaction Scheme 2

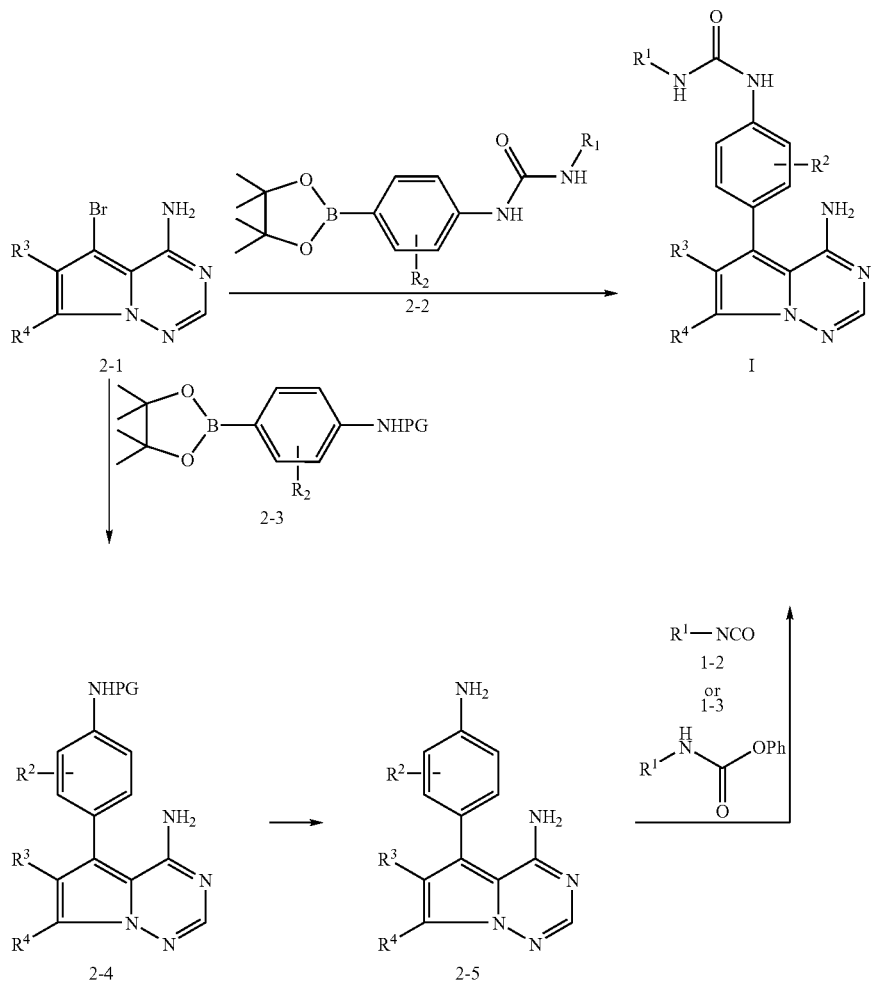

Reaction Schemes 3 outlines the preparation of intermediates of general formula 3-8, but where $R^4$ has been replaced by H and $R^3$ is described as a carboxylic acid derivative (e.g an ester). Thus, beginning with 4-nitrocinnamate compounds of formula 5-5, treatment with isocyanide reagents of formula 3-1 in the presence of a strong base such as lithium hexamethyldisdazide or the like in an aprotic solvent such as THF or the like provides pyrroles of formula 3-2. Formylation of 3-2 under Vilsmeier conditions well known in the art (e.g., DMF, $POCl_3$) gives 2-formylpyrrole compounds of formula 3-3. Compounds of formula 3-3 are converted to nitriles of Formula 3-4 by reaction with hydroxylamine hydrochloride in a solvent such as pyridine to form an intermediate oxime, which is dehydrated in situ to provide the nitrile, using a reagent such as acetic anhydride or the like. Compounds of formula 3-4 are N-aminated using a strong base such as NaH Reaction Scheme 3

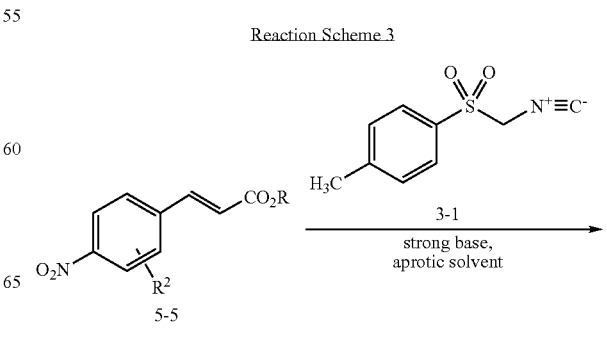

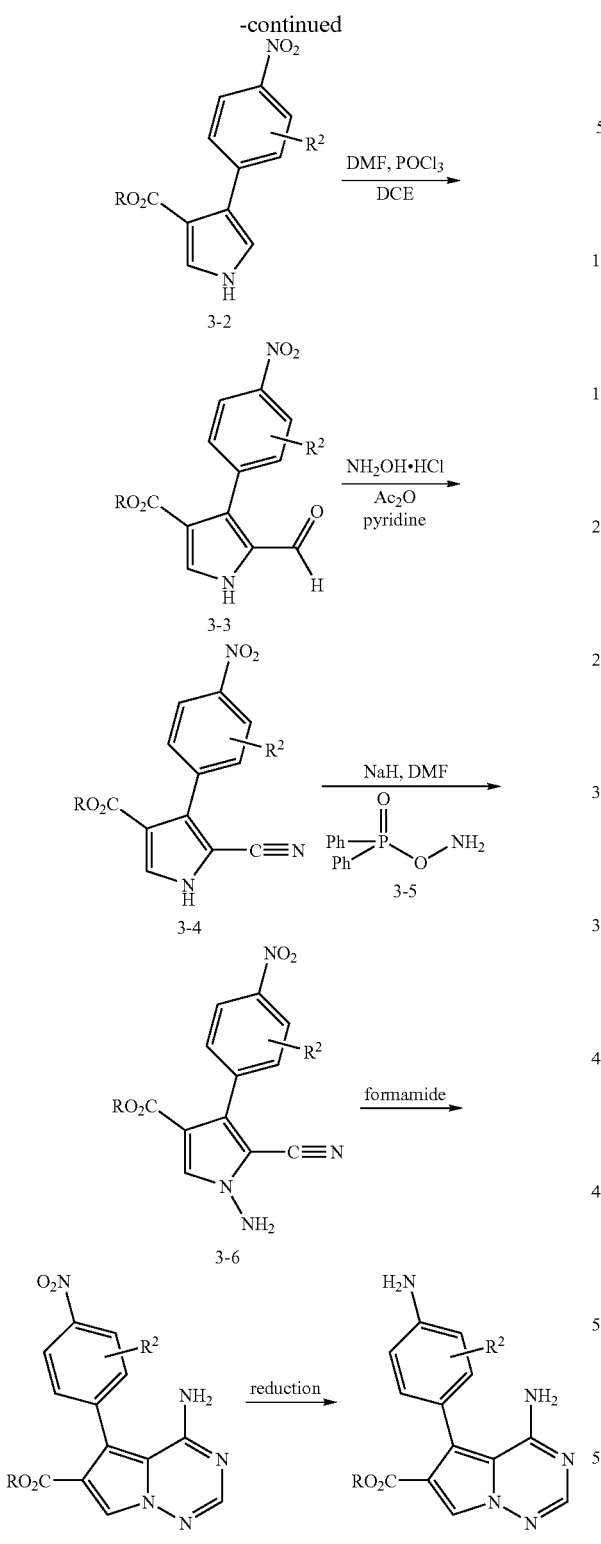

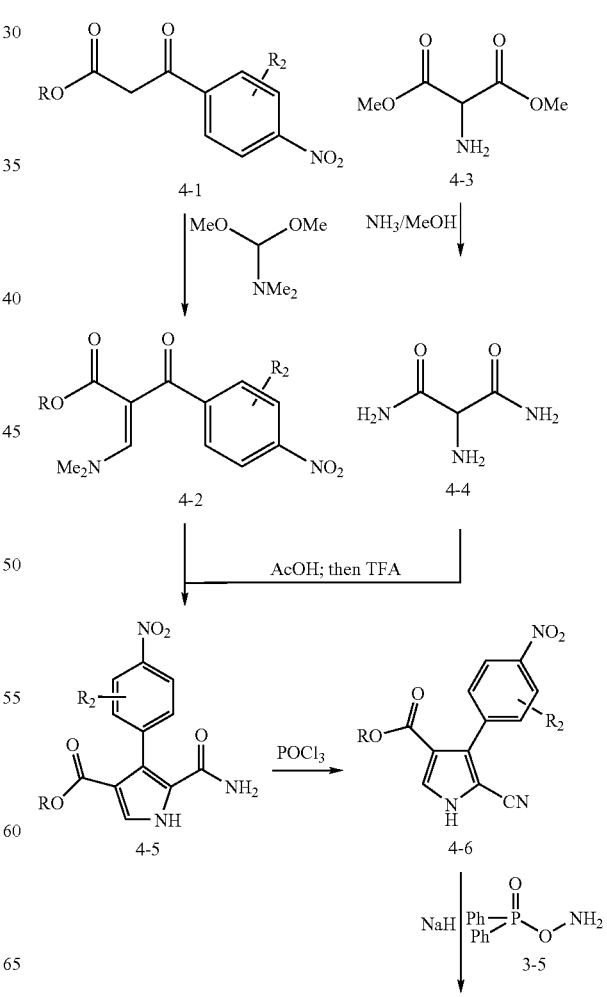

by an acid such as trifluoroacetic or the like provides pyrolles of formula 4-5. Treatment of 4-5 with a reagent such as phosphorous oxychloride provides compounds of formula 4-6. Compounds of formula 4-6 are N-aminated using a strong base such as NaH or the like and an aminating reagent such as $(Ph)_2P(O)$—O—$NH_2$ (compound 3-5) or the like, to provide N-amino nitriles of formula 4-7. Cyclization of 4-7 can be affected by treatment with a formamiding derivative such as formamidine acetate or the like in a solvent such as EtOH to provide pyrrolotriazine intermediates of formula 3-7.

The cinnamates of formula 5-5 are either commercially available or can be prepared as shown in Reaction Scheme 5. In this sequence, substituted nitrotoluenes of formula 5-1 are oxidized with a reagent such as potassium permanganate or the like to give the corresponding acids of formula 5-2. This acid can in turn be reduced to alcohols of formula 5-3 with a reducing agent such as borane or the like in a suitable solvent such as THF or the like. Treatment of these compounds with an oxidizing reagent such as the Dess-Martin periodinane provides aldehydes of formula 5-4. Wadsworth-Emmons type reaction of 5-4 using $(EtO)_2P(O)CH_2CO_2Et$ or the like and a strong base such as LiH or the like provides cinnamates of formula 5-5.

Schemes 4 outlines the preparation of intermediates of formula 3-7, where $R^4$ has been replaced by H and $R^3$ is described as a carboxylic acid derivative (e.g an ester). Thus, treatment of with β-ketoesters of formula 4-1 with N,N-dimethylformamide dimethylacetal or the like provides compounds of formula 4-2. Reaction of 4-2 with compounds of formula 4-4 in the presence of an acid such as AcOH followed

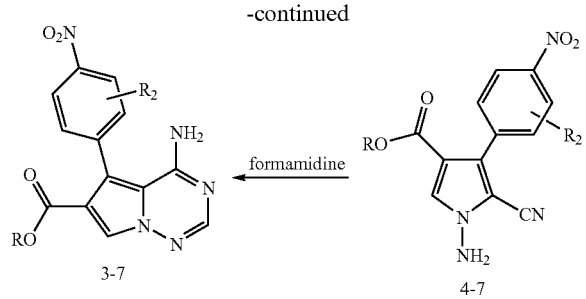

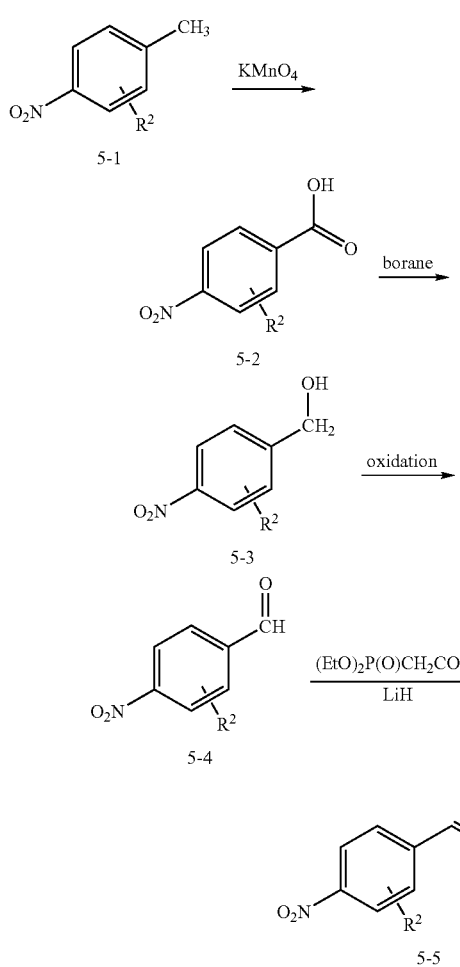

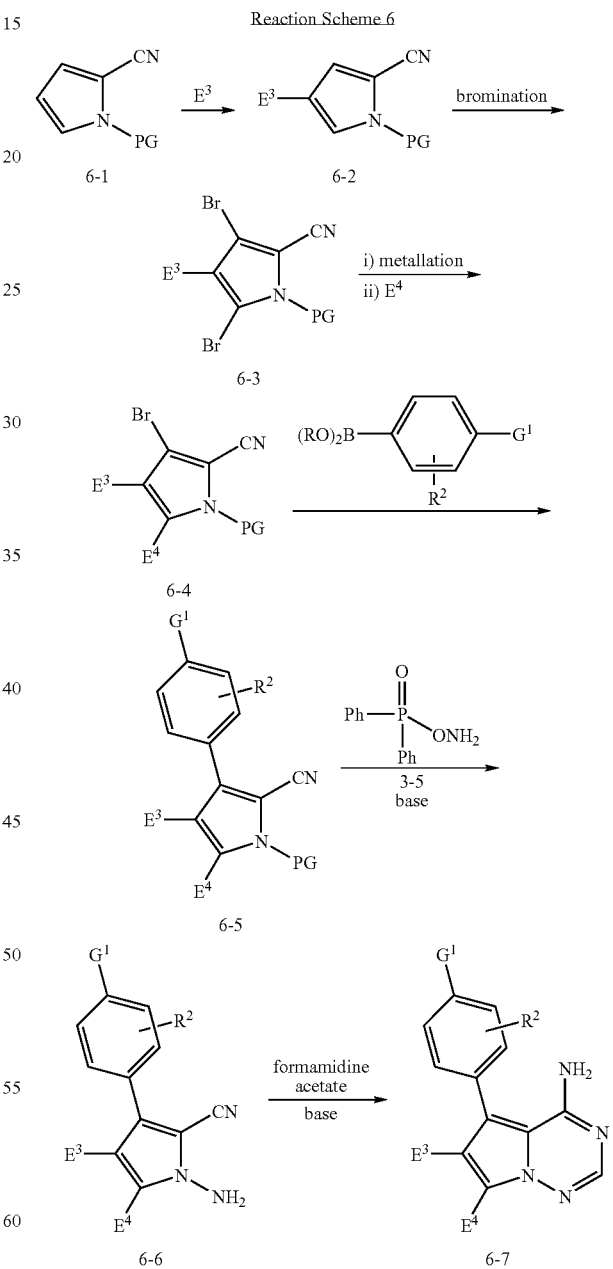

reagent such as n-butyllithium or the like in a solvent such as THF or the like, followed by addition of an appropriate electrophile $E^4$ (e.g. substituted alkyl halide or simply a proton) provides substituted pyrolles of formula 6-4. Compounds of formula 6-4 are N-aminated using a strong base such as NaH or the like and an aminating reagent such as $(Ph)_2P(O)$—O—$NH_2$ (compound 3-5) or the like, to provide N-amino nitriles of formula 6-6 If necessary, the protecting group (PG) can be removed first using methods well known to those versed in the art. Treatment of 6-6 with a reagent such as formamidine preferably in the presence of a base such as potassium carbonate provides compounds of formula 6-7.

Reaction Scheme 6 outlines a preparation of intermediate compounds of general formula 6-7, where $E^3$ is described as a subset of $R^3$, $E^4$ is defined as a subset of $R^4$ which also includes H, and $G^1$ is described as $NH_2$, NHPG, $NO_2$ or $NH(CO)NHR^1$. Thus, treatment of pyrrole 6-1 (where PG is an optional protecting group such as 2,2-(trimethylsilyl) ethoxymethyl) with an appropriate electrophile $E^3$ (e.g. chlorosulfonyl isocyanate) under conditions well known to those familiar with the art, provides compounds of formula 6-2. Treatment of 6-2 with a brominating reagent such as 1,3-dibromo-5,5-dimethylhydantoin or the like, in a solvent, such as DMF or the like, provides dibromides of formula 6-3. Regioselective metallation of 6-3 with an organometallic Reaction Scheme 7 outlines a preparation of intermediate compounds of general formula 7-8. These compounds are described as having the same general structure as compounds 2-1, but here $G^3$ is defined as a subset of $R^3$ and $E^4$ is defined as a subset of R⁴. Treatment of a suitably protected (e.g. a protecting group well known to those skilled in the art) hydrazine derivative with a 2,5-dialkoxy tetrahydrofuran derivative in the presence of an acid, such as HCl or the like in a solvent such as 1,4-dioxane or the like provides the protected aminopyrrole derivative 7-1. Cyanation using chlorosulfonyl isocyanate in a solvent such as acetonitrile or the like provides 2-cyano derivatives of formula 7-2. Treatment of 6-2 with a brominating reagent such as 1,3-dibromo-5,5-dimethylhydantoin or the like, in a solvent, such as DMF or the like, provides bromides of formula 7-3, which upon deprotection (using procedures/reagents known in the art) liberate aminopyrrole products of formula 7-4. Reaction of 7-4 with a formamidine reagent in the presence of a base such as potassium phosphate or the like in a solvent such as ethanol or similar provides compounds of structure 7-5. Reaction of 7-5 with organometallic reagents, (e.g. methylzinc chloride) under palladium catalyzed conditions well known to those skilled in the art, provides compounds of formula 7-6. Reaction of 7-6 with an appropriate electrophile E⁴ (e.g. Mannich conditions) provides compounds of formula 7-7. Bromination of 7-7 with brominating reagent, such as 1,3-dibromo-5,5-dimethylhydantoin or another appropriate agent in an appropriate solvent, such as DMF or the like, and provides 7-8. The following schemes demonstrate the interconversion of compounds of formula 6-7 and 7-8 to yield a variety of functionalities.

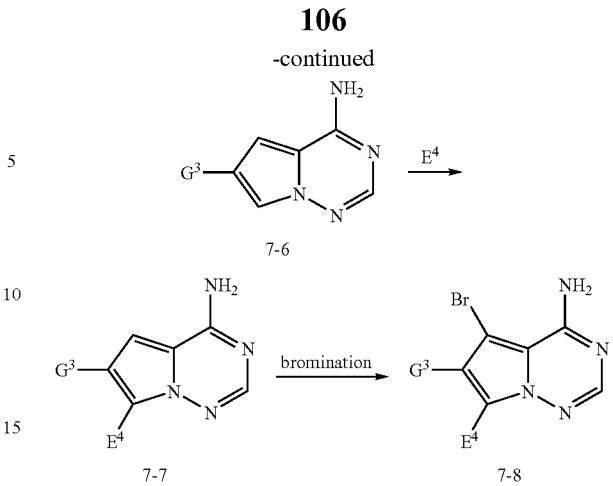

Reaction Scheme 8 describes methods in which the R⁴ functionality can be introduced and modified into a variety of functionalities, where G¹ is defined as —NH₂, NO₂, NH(CO)NHR¹, or NHPG and G² is defined as in Scheme 8 and where Z⁴ is defined as an aryl or heteroaryl group. Beginning with compounds of formula 8-1, treatment with with an appropriate brominating reagent, such as 1,3-dibromo-5,5-dimethylhydantoin or the like, in a solvent, such as DMF or the like, provides bromide compounds of formula 8-2. Bromides of formula 8-2 can be further functionalized in several ways. First, Suzuki reaction of I-2 with aryl boronic acids under conditions well known in the art provides compounds of formula 8-3. Alternatively, treatment of 8-2 with cyanide salts such as copper(I) cyanide or the like in a solvent such as DMF or the like provides cyano compounds of formula 8-4. Similarly, metallation of 8-2 by treatment with an organometallic such as n-butyllithium or the like, followed by treatment with an electrophile such as DMF or the like, provides aldehydes of formula 8-5.

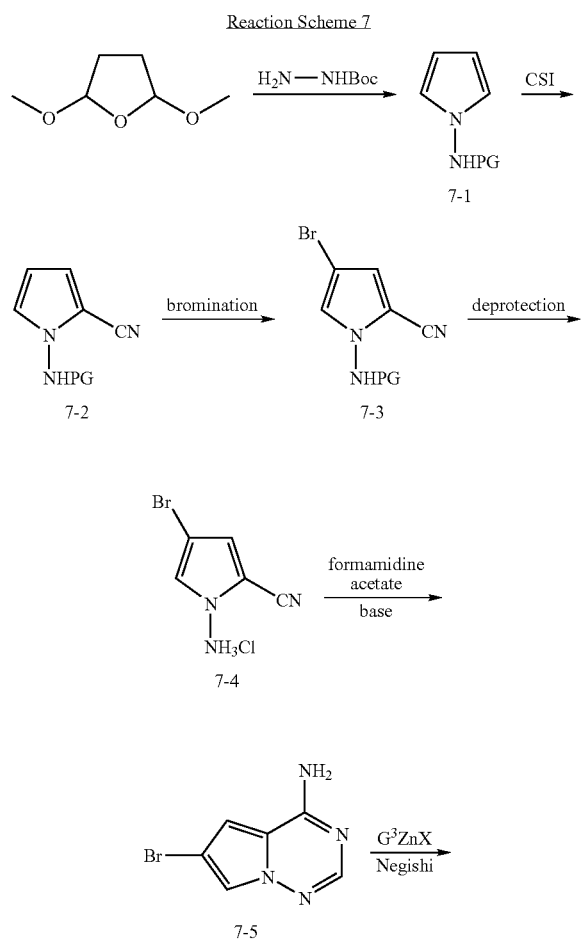

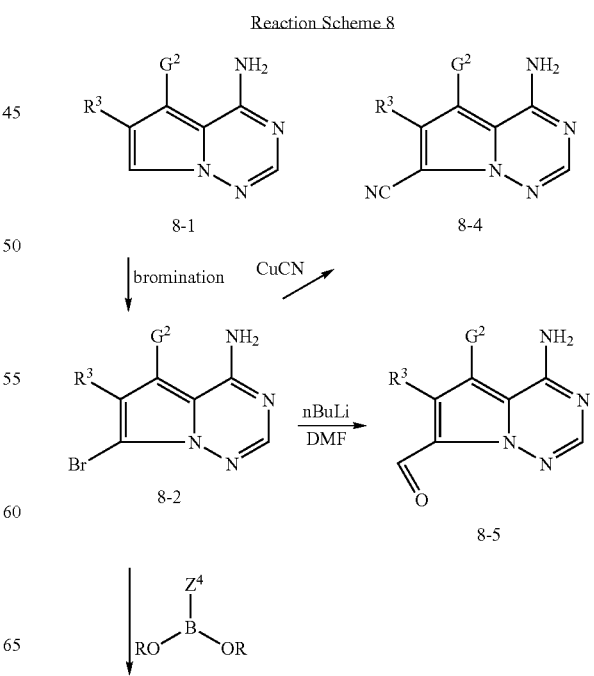

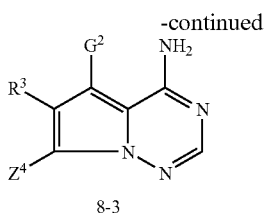

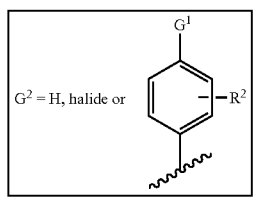

Reaction Scheme 9 describes the preparation of ketone compounds of formula 9-2, where $G^2$ is defined as above in Scheme 8. Thus, treatment of compounds of formula 8-5 with an organometallic such as a Grignard reagent or the like, in an appropriate solvent such as THF or the like provides alcohols of formula 9-1. Oxidation of these compounds with a reagent such as the Dess-Martin periodinane or the like in a solvent such as THF provides ketones of formula 9-2.

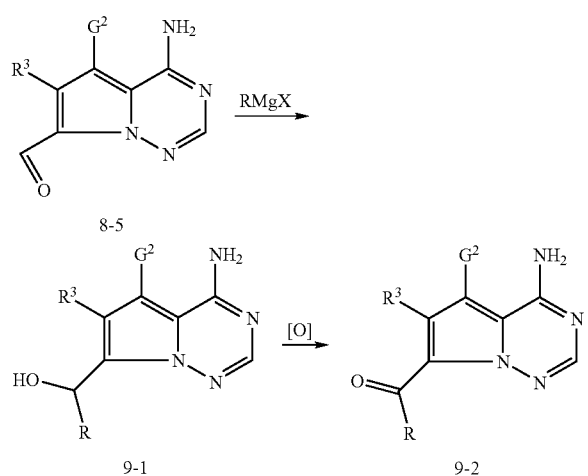

Reaction Scheme 10 outlines some of the ways in which functionality at the $R^4$ position can be introduced and modified. In all cases $G^2$ is defined as above in Scheme 8. Thus, treatment of compounds of formula 8-5 with a reducing agent, preferably DIBAL-H, in a solvent such as THF or the like will provide primary alcohols of formula 10-1. Halogenation of 10-1 with a reagent such as thionyl chloride or the like in a suitable solvent such as $CH_2Cl_2$ provides α-halo compounds of formula 10-2 (X=Cl, Br or I). Treatment of 10-2 with alcohols in a suitable solvent such as DMF or the like, in the presence of a base such as Hunigs base or the like and optionally with a catalyst such as potassium iodide or the like provides ethers of formula 10-3. Alternatively, treatment of 10-2 with an amine, such as a primary or secondary (cyclic or acyclic) amine, in the presence of a suitable base, such as Hunigs base or the like provides compounds of structure 10-4. Compounds of formula 10-4 can be directly prepared from 8-5 by treatment with an amine, such as a primary or secondary (cyclic or acyclic) amine, under reductive amination conditions well know in the art (sodium triacetoxyborohydride, e.g.).

Compounds of formula 10-4 can also be prepared directly from compounds of formula 10-5 using Mannich conditions, such as by treatment with an amine, such as a primary or secondary (cyclic or acyclic) amine, and formaldehyde in a solvent such as acetic acid or the like.

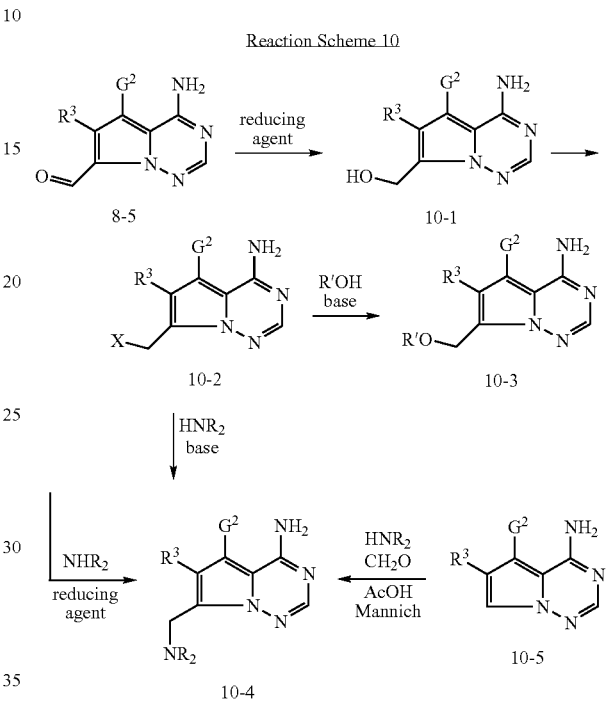

Reaction Scheme 11 outlines the preparation of compounds of 11-6 wherein $R^4$ is described as a heteroatom functionality attached to a 2 carbon linker and $G^2$ is defined as above in Scheme 8. Metallation of compounds of formula 11-1 with an organometallic reagent such as isopropylmagnesium chloride or the like in the presence of an in situ protecting group such as chlortrimethylsilane or the like followed by treatment with Weinreb amide 11-2 provides α-haloketones of formula 11-3. These compounds can be converted to compounds of formula 11-4 by treatment with a nucleophile Nu, wherein Nu is defined as an amine, such as a primary or secondary (cyclic or acyclic) amine, or as an alcohol, in a suitable solvent such as DMF or the like and optionally in the presence of a catalyst such as potassium iodide and/or a base such as potassium carbonate or the like. Treatment of 11-4 with a reducing agent such as DIBAL-H or the like in a solvent such as THF or the like provides compounds of formula 11-5. These compounds can be converted to their reduced analogs of formula 11-7 by a variety of methods familiar to those skilled in the art. For example, activation of 11-5 with a halogenating agent such as thionyl chloride or the like in a suitable solvent such as $CH_2Cl_2$ or the like provides chlorides of formula 11-6. These compounds can in rum be reduced to compounds of formula 11-7 by treatment with a suitable reducing agent such as lithium triethylborohydride or the like in a suitable solvent such as THF or the like. Alternatively, compounds of formula 11-5 can be reduced under H2 gas in the presence of a suitable catalyst such as palladium on carbon using methods well known in the art.

Reaction Scheme 11

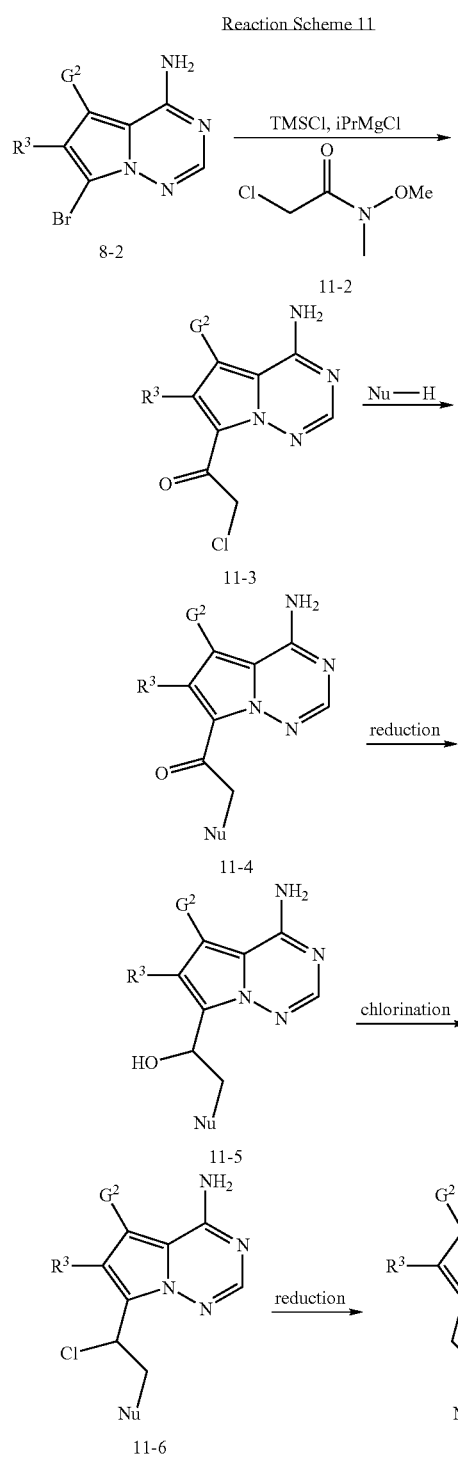

Reaction Scheme 12 outlines the preparation of compounds of formula 12-5 wherein $R^4$ is described as an heteroatom functionality connected by a 3 or 4 carbon linker and G is defined as above in Scheme 8. Metallation of compounds of formula 8-2 with an organometallic reagent such as isopropylmagnesium chloride or the like in the presence of an in situ protecting group such as chlortrimethylsilane or the like followed by treatment with an aldehyde of formula 12-1 (where PG=a suitable protecting group, e.g. a trialkylsilyl group) provides alcohols of formula 12-2. Conversion of 12-2 to compounds of formula 12-3 can be effected by treatment with triethylsilane in the presence of an acid such as trifluoracetic acid or the like or by a two step procedure analogous to that described previously in Scheme 11. The protecting groups (PG) used until this point in the sequence can then be removed under various well-precedented procedures (acid-catalyzed removal of trialkylsilanes, e.g.), to provide alcohols of formula 12-3. Conversion of 12-3 to compounds of formula 12-4 (where LG is a suitable leaving group, e.g. Cl) can be carried out by methods known in the art. Compounds of formula 12-5 are prepared by treatment of 12-4 with various nucleophiles (e.g., Nu=ROH or HNR'$_2$) in an appropriate solvent such as DMF or the like and in the presence of a base such as potassium carbonate or the like.

Reaction Scheme 12

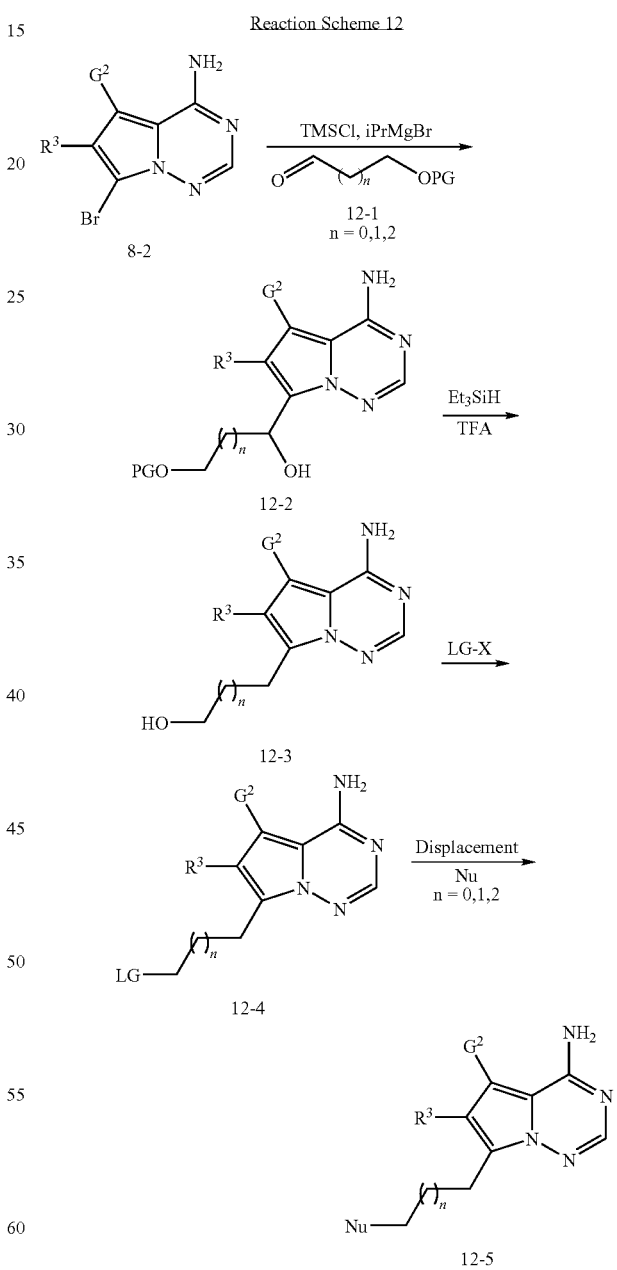

Reaction Scheme 13 outlines some methods for the modification of the $R^3$ functionality, wherein $G^2$ is defined as above in Scheme 8 and $G^4$ is defined as $R^4$ or H. Thus, treatment of esters of formula 13-1 with a reducing agent such as diisobutylaluminium hydride or the like in a solvent such as THF or the like provides compounds of structure 13-2. Oxidation of these to the aldehyde using Dess-Martin periodinane or the like in a solvent such as THF or the like provides compounds of formula 13-3. Such aldehydes can be converted to cyano compounds of formula 13-4 by treatment with hydroxylamine and a reagent such as acetic anhydride or the like in a solvent such as pyridine or the like. Alternatively, hydrolysis of 13-1 with a base such as sodium hydroxide or the like in a solvent such as ethanol or the like provides acids of formula 13-5. These compounds can be treated with amines, such as a primary or secondary (cyclic or acyclic) amine, and a peptide coupling reagent such as py-BOP or the like in a solvent such as DMF to provide amides of formula 13-6.

Reaction Scheme 13

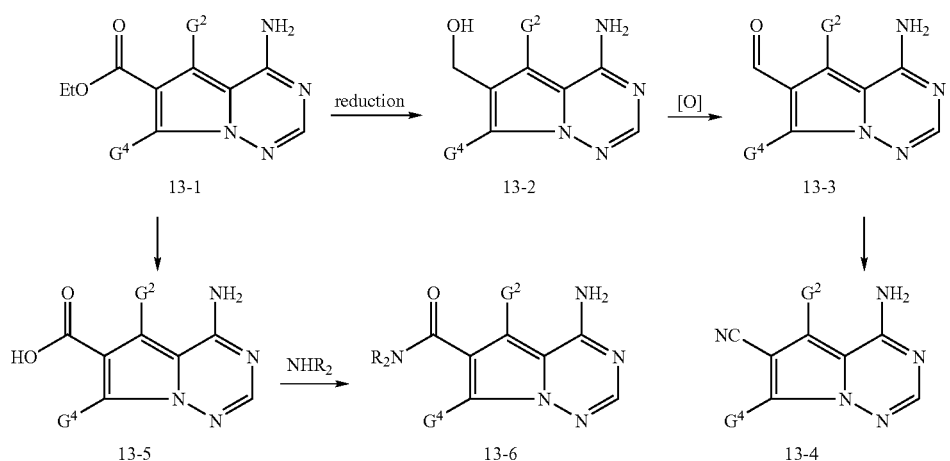

Reaction Scheme 14 outlines some methods for the modification of the $R^3$ functionality, wherein $G^2$ is defined as above in Scheme 8 and $G^4$ is defined as $R^4$ or H. Thus, compounds of formula 13-2 can be converted to the corresponding fluorides of formula 14-1 by treatment with a suitable fluorinating reagent such as Deoxo-Fluor™ or the like in a suitable solvent such as THF or the like. Aldehydes of formula 13-3 can be converted to difluoride compounds of formula 14-2 using analogous procedures. Alternatively, treatment of 13-3 with organometallic reagents such as a Grignard reagent or the like in a suitable solvent such as THF or the like, followed by oxidation of the intermediate alcohol by treatment with a reagent such as the Dess-Martin periodinane or the like provides ketones of formula 14-3. As in the previous examples, ketones of formula 14-3 can be converted to fluorides of formula 14-4 via treatment with a suitable fluorinating agent such as Deoxo-Fluor™ or the like.

Reaction Scheme 14

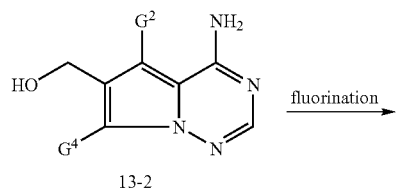

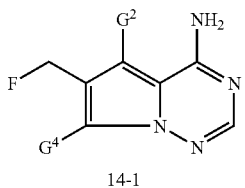

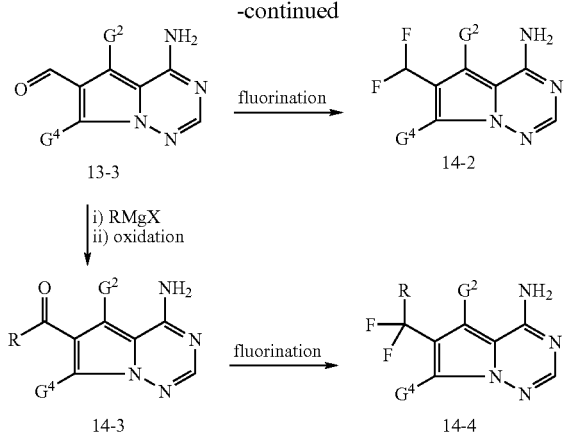

Reaction Scheme 15 outlines some methods for the modification of the $R^3$ functionality, wherein $G^2$ is defined as above in Scheme 8 and $G^4$ is defined as $R^4$ or H. Treatment of compounds of formula 13-2 with a chlorinating agent such as thionyl chloride or the like in a suitable solvent such as $CH_2Cl_2$ or the like provides chlorides of formula 15-1. Treatment of 15-1 with an appropriate nucleophile (wherein Nu=$R^2$NH, ROH, $CN^-$, RSH) in the presence of a suitable base such as Hunigs base or the like in a solvent such as DMF or the like provides compounds of formula 15-2. Alternatively, treatment of 15-1 with a reducing agent such as a lithium triethylborohydride or the like in a suitable solvent such as THF or the like provides compounds of formula 15-3. Treatment of 15-1 with an amine, such as a primary or secondary (cyclic or acyclic) amine, in the presence of a suitable base such as potassium carbonate or the like or a tertiary amine, such as Hunig's base or the like provides compounds of formula 15-4. Alternatively, amines of formula 15-4 can be prepared from the corresponding aldehydes of formula 13-3 by treatment with an amine, such as a primary or secondary (cyclic or acyclic) amine, in the presence of a suitable reducing agent, such as sodium triacetoxyborohydride or the like in a suitable solvent such as dichloroethane or the like.

Reaction Scheme 15

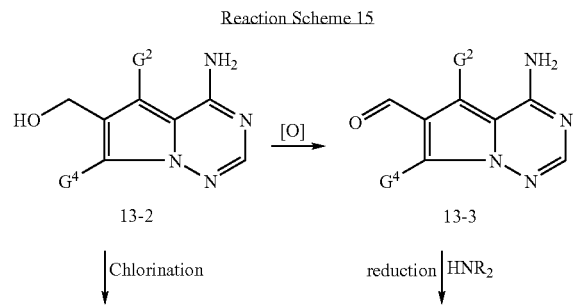

Reaction Scheme 16 outlines some methods for the modification of the $R^3$ functionality, wherein $G^2$ is defined as above in Scheme 8 and $G^4$ is defined as $R^4$ or H. Thus, treatment of 13-3 with (p-tolylsulfonyl)methyl isocyanate or the like in the presence of a base such as sodium hydride or the like in a suitable solvent such as THF or the like provides oxazole compounds of formula 16-1. Treatment of 13-3 with a Grignard reagent or the like in a suitable solvent such as THF or the like provides alcohols of formula 16-2. Oxidation of 16-2 with a reagent such as the Dess-Martin periodinane or the like in a solvent such as THF or the like provides ketones of formula 16-3. Alternatively, treatment of amides of formula 16-2 with organometallics such as Grignard reagents under similar conditions provides ketones of formula 16-3 directly.

-continued

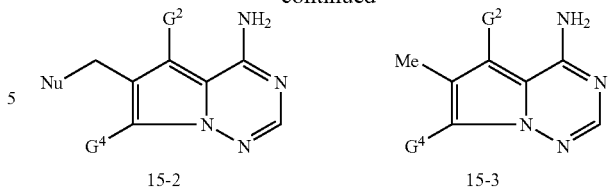

Reaction Scheme 16

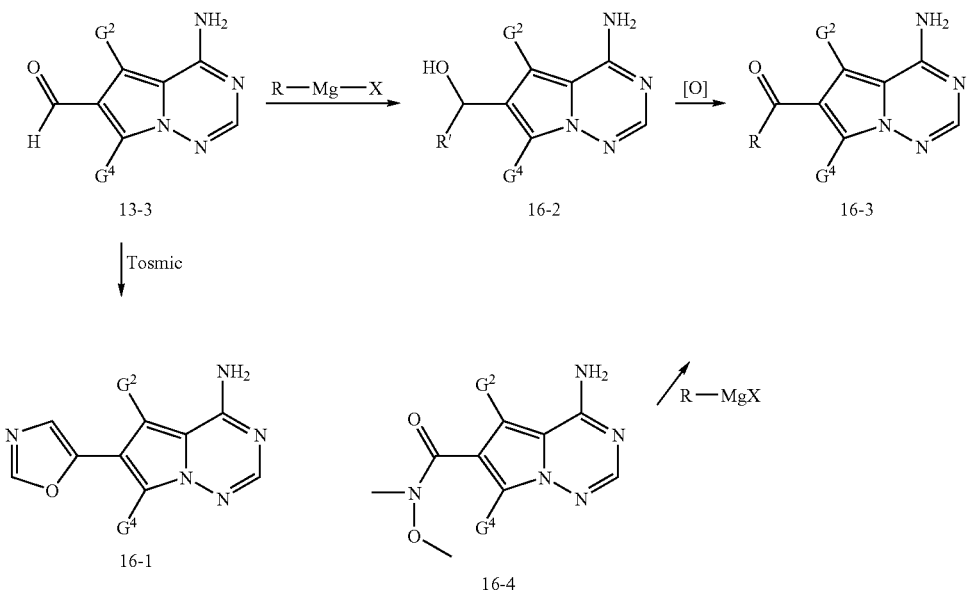

-continued

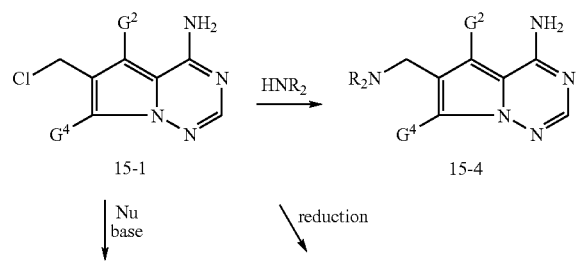

Reaction Scheme 17 outlines methods for the preparation of compounds of formula 17-5, wherein $G^2$ is defined as above in Scheme 8. Thus, reaction of compounds of formula 8-2 with an appropriate terminal acetylene of formula 17-1 (wherein X=H or a suitable protecting groups such as a trialkylsilane) in presence of a Pd(II) catalyst, a Cu(I) co-catalyst and an amine base such as pyrrolidine or triethylamine or the like, in a solvent such as DMF or the like provides compounds of formula 17-2. Reduction of the triple bond using hydrogen gas in the presence of a metal catalyst such as $PtO_2$ or the like in a solvent such as acetic acid or the like provides compounds of formula 17-3. Conversion of 17-3 to compounds of formula 17-4 (where LG is a suitable leaving group) can be carried out by methods known in the art. If necessary, a protecting group (PG) can be removed by methods known in the art prior to the conversion to 17-4. Treatment of 17-4 with a primary or secondary amine, or a primary alcohol, in the presence of a suitable base such as potassium phosphate or the like or a tertiary amine, such as Hunigs Base or the like provides compounds of formula 17-5.

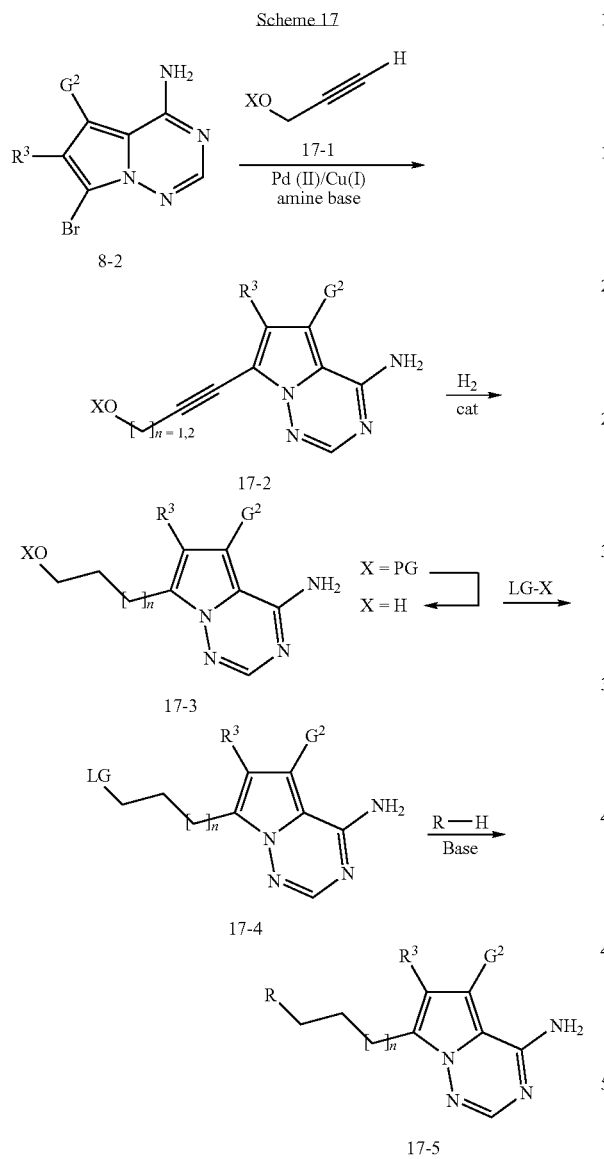

Reaction Scheme 18 describes the preparation of compounds of formula 18-5 ($R^4$=unsubstituted piperidine, pyrollidine or azetadine) or 18-6 ($R^5$=optionally substituted piperidine, pyrollidine or azetadine) wherein $G^2$ is defined as above in Scheme 8. Treatment of compound 8-2 with a boronate such as 18-1 under conditions well known in the art provides the appropriately protected di-dehydrocyclic amines of formula 18-3. Alternatively, such protected amines can be prepared by conversion of 8-2 to a Grignard reagent, which can be carried out by reaction with an appropriate Grignard reagent such as isopropylmagnesium chloride, in the presence of a temporary protecting agent such as trimethylsilyl chloride in a solvent such as THF. This Grignard reagent formed from 8-2 is reacted with a protected piperidone of formula 18-2 to provide, after an electrophilic workup which eliminates the intermediate hydroxy compound, compounds of formula 18-3. Reduction of the double bond of 18-3 with hydrogen in the presence of a catalyst such as $PtO_2$ or the like in a solvent such as acetic acid or the like provides cyclic amines of formula 18-4. Deprotection of 18-4 using procedures well known in the art (acid catalyzed deprotection of BOC carbamate, e.g.) provides compounds of formula 18-5. Reaction of compounds of formula 18-4 with an appropriate alkylating agent such as ethylene carbonate in the presence of a suitable base such as sodium hydroxide provides compounds of the formula 18-6. Compounds of formula 18-6 are also prepared by treatment of compounds of the formula 18-5 with an aldehyde such as formaldehyde and the like and a reducing agent such as sodium triacetoxyborohydride or the like in a solvent such as 1,2-dichloroethane or the like. Compounds of formula 18-6 can also be prepared by the reaction of the amines of formula 18-5 with an acylating or sulfonating reagent, such as an acyl anhydride, acyl chloride, sulfonyl chloride or the like, in the presence of a suitable base such as pyridine, potassium carbonate, a tertiary amine or the like, in appropriate solvents such as THF, dichloromethane, or others.

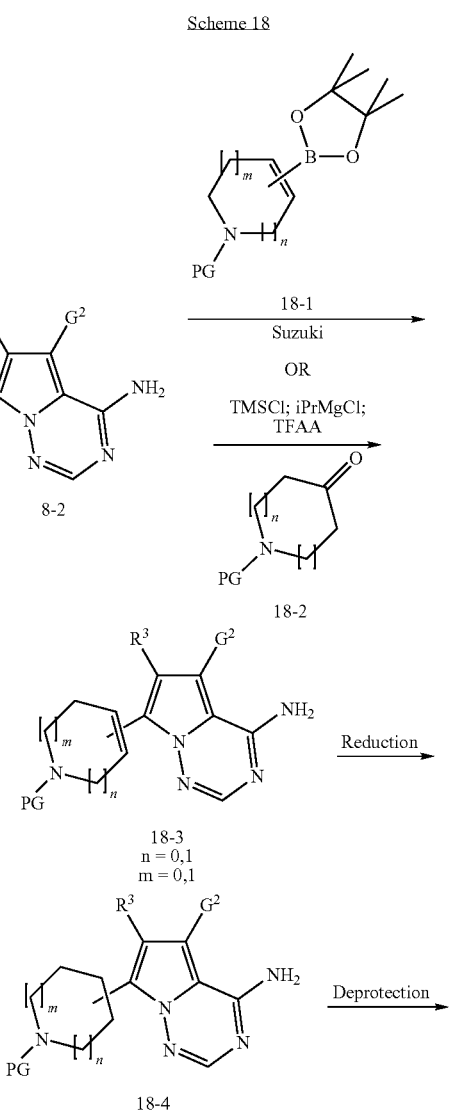

117

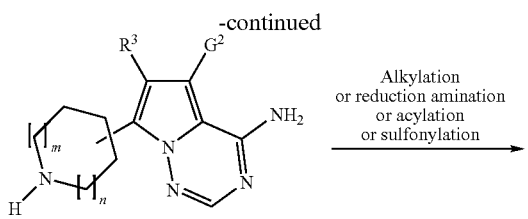

18-5

Alkylation
or reduction amination
or acylation
or sulfonylation
→

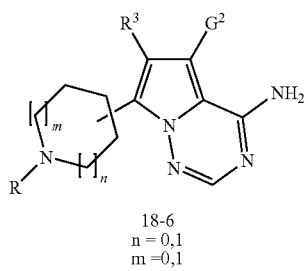

18-6
n = 0,1
m = 0,1

Reaction Scheme 19 describes the preparation of compounds of formula 19-2, where $Z^3$ is defined as a subset of $R^3$ containing aryl and heteroaryl functionalities, $G^2$ is defined as above in Scheme 8 and $G^4$ is defined as $R^4$ or H. Such compounds can be prepared by reaction of bromides of formula 19-1 with boronates or bonronic acids of formula H3-B(OR)$_2$ under Suzuki coupling conditions well known to those versed in the art. Alternatively, carbonyl compounds of formula 19-3 (R=alkyl or H) can be converted to compounds of formula 19-3 using many routes well known to those versed in the art (as shown in Scheme 16, e.g.)

Reaction Scheme 19

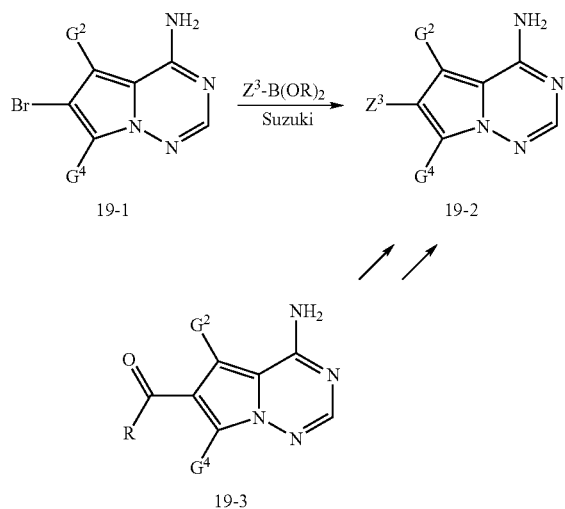

Additionally, sensitive or reactive groups on the compound of this invention may need to be protected and deprotected during any of the above methods. Protecting groups in general may be added and removed by conventional methods well known in the art (see, for example, T. W. Greene and P. G. M. Wuts, *Protective Groups in Organic Synthesis*; Wiley: New York, (1999).

In order that this invention may be better understood, the following examples are set forth. These examples are for the purpose of illustration only, and are not to be construed as limiting the scope of the invention in any manner. All publications mentioned herein are incorporated by reference in their entirety.

PREPARATION OF INTERMEDIATES

Intermediate A

Preparation of ethyl
5-cyano-4-(nitrophenyl)-1H-pyrrole-3-carboxylate

Preparation 1

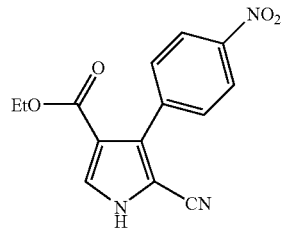

Step 1: Preparation of 2-aminomalonamide

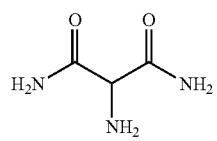

A 5 L 4-neck round bottomed flask equipped with an over head stirrer was charged with commercially available diethyl amino malonate hydrochloride (338 g, 1.596 mol). 7N ammonia in MeOH (2 L) was removed from the freezer and added cold in one portion. All of the inlet ports were covered with plastic caps. Over 1 h the reaction mixture turned to a clear yellow color. The flask was vented once with no observable increase in pressure. The mixture was allowed to stir over night. A precipitate had formed, which was isolated by filtration. The powder was washed with MeOH (500 mL). The light yellow powder was dried over night in vacuo to provide diamide 2 (170 g, 1.45 mol, 91% yield).

Step 2: Preparation of ethyl
3-(dimethylamino)-2-(4-nitrobenzoyl)acrylate

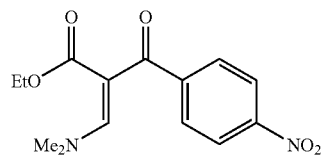

To a solution of Ethyl 4-nitro benzoylacetate (50 g, 210.8 mmol) in toluene (500 mL) was added dimethylformamide dimethyl acetal (42.3 mL, 316.2 mmol). The reaction was heated to 80° C. over night. The mixture was concentrated in vacuo and purified by flash column chromatography (100% Hexane to 10% EtOAc; 90% Hexane until non-polar impurities were removed, then 75% EtOAc; 25% Hex to 100% EtOAc for product) to provide a yellow solid in 87% yield (54 g, 184.8 mmol). $^1$H-NMR (DMSO-d$_6$) δ 8.26-8.22 (m, 2H), 7.78 (s, 1H), 7.75-7.73 (m, 2H), 3.83 (q, J=7.2 Hz, 2H), 3.27 (br s, 3H), 2.69 (br s, 3H), 0.83 (t, J=7.2, 3H); LCMS RT=2.80 rain; MS {M+H}$^+$=292.9.

Step 3: Preparation of title ethyl 5-(aminocarbonyl)-4-(4-nitrophenyl)-1H-pyrrole-3-carboxylate

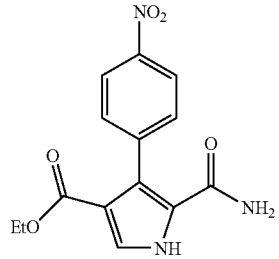

A 3 L round bottomed flask was charged with ethyl 3-(dimethylamino)-2-(4-nitrobenzoyl)acrylate (63.59 g, 217.5 mmol) and 2-aminomalonamide (33.12 g, 282.8 mmol) and AcOH (800 mL). The reaction mixture was heated to 80° C. over night. The starting material appeared consumed by TLC. The AcOH was removed under reduced pressure and TFA (400 mL) was added. The mixture was heated over night at 60° C. The reaction was cooled to room temperature and the TFA was removed under reduced pressure. The orange oil was washed with saturated aqueous NaHCO$_3$ (1 L) and solid NaHCO$_3$ was added until the solution was neutral. The solids were filtered and placed in a 1 L erlenmeyer flask. The solids were washed with H$_2$O (3×1 L) and the water was decanted off through the filter. On the last washing the solids were poured onto the filter and allowed to air dry. The solids were once again removed from the filter and washed with Et$_2$O (4×500 mL). The Et$_2$O was decanted off through the filter and on the final washing the solids were transferred to the filter. An addition portion of Et$_2$O (200 mL) was used to wash the flask and the filter cake. The product was dried in a vacuum oven at 40° C. over P$_2$O$_5$ for 4 h affording ethyl 5-(aminocarbonyl)-4-(4-nitrophenyl)-1H-pyrrole-3-carboxylate as a tan solid (55.2 g, 182 mmol, 83.7%). $^1$H-NMR (DMSO-d$_6$) δ 12.33 (br s, 1H), 8.19-8.15 (m, 2H), 7.57 (d, J=3.6 Hz, 1H), 7.53-7.49 (m, 2H), 7.29 (br s, 1H), 6.41 (br s, 1H), 3.99 (q, J=7.2 Hz, 2H), 1.03 (t, J=7.2 Hz, 3H); LCMS RT=2.79 min; MS {M+H}$^+$=304.2.

Step 4: Preparation of Title Compound

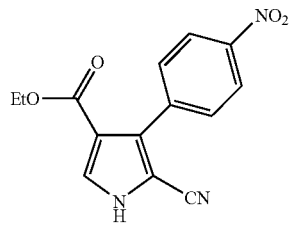

A solution of ethyl 5-(aminocarbonyl)-4-(4-nitrophenyl)-1H-pyrrole-3-carboxylate (55.0 g, 181.3 mmol) in POCl$_3$ (500 mL) was heated to 70° C. for 2 h. TLC analysis indicated that there was complete conversion of starting material. Excess POCl$_3$ was removed under reduced pressure and the remaining solids were poured over ice. The pH was adjusted to 8 using 5N NaOH and the solution was filtered. The product was dried over P$_2$O$_5$ under reduced pressure to afford a tight brown solid (50.9 g, 178 mmol) in 98% yield. $^1$H-NMR (DMSO-d$_6$) δ 12.24 (br s, 1H), 8.28-8.24 (m, 2H), 7.89 (d, J=3.2 Hz, 1H), 7.72-7.68 (m, 2H), 4.10 (q, J=7.2 Hz, 2H), 1.14 (t, J=7.2 Hz, 3H); LCMS*RT=4.74 min; MS {M-H}$^-$=284.0.

Intermediate A

Preparation of ethyl 5-cyano-4-(nitrophenyl)-LET-pyrrole-3-carboxylate

Preparation 2

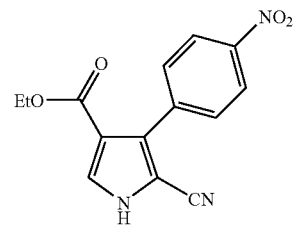

Step 1: Preparation of ethyl 4-(4-nitrophenyl)-1H-pyrrole-3-carboxylate

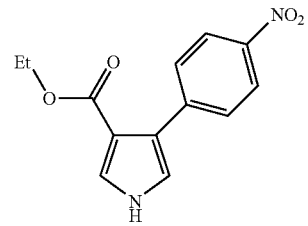

To a solution of 1M lithium hexamethyldisilazide in THF (102.4 mL, 102.4 mmol) cooled to −77° C. was added 1-[(isocyanomethyl)sulfonyl]-4-methylbenzene (20.0 g, 102.4 mmol) as a solution in THF (100 mL) dropwise over 30 min. The solution was allowed to stir an additional 15 min, and then ethyl (2E)-3-(4-nitrophenyl)acrylate was added dropwise (22.66 g, 102.4 mmol) as a solution in THF (250 mL) over 1 h. The reaction was allowed to warm to rt over 17 h. Aqueous saturated NaHCO$_3$ (200 mL) was added to the reaction mixture followed by EtOAc (500 mL). The solution was transferred to a separatory funnel, and the organic layer was collected and washed with H$_2$O (100 mL). The aqueous layers were back extracted with EtOAc (2×150 mL). The combined organic layers dried (MgSO$_4$), concentrated onto silica gel, and purified by flash column chromatography (100% CH$_2$Cl$_2$ ramping to 95:5 v/v CH$_2$Cl$_2$-EtOAc) to afford 16.65 g of the above compound as an orange/yellow solid (63.98 mmol, yield 62%). $^1$H-NMR (DMSO-d$_6$) δ 11.78 (br s, 1H), 8.19 to 8.15 (m, 2H), 7.76 to 7.73 (m, 2H), 7.57 to 7.56 (m, 1H), 7.22 to 7.21 (m, 1H), 4.18 to 4.13 (q, J=7.1 Hz, 2H), 1.21 (t, J=7.1 Hz, 3H); LCMS RT=2.90 min; TLC $R_f$=0.47 (95:5 v/v CH$_2$Cl$_2$-EtOAc).

Step 2: Preparation of ethyl 5-formyl-4-(nitrophenyl)-1H-pyrrole-3-carboxylate

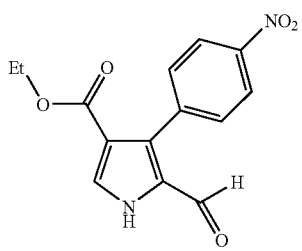

To a solution of DCE (100 mL) was added DMF (14.96 mL, 194.4 mmol), which was cooled in an ice-salt bath. As POCl$_3$ (18.12 mL, 194.4 mmol) was slowly added a white precipitate formed. The solution was allowed to warm to rt while vigorously stirring over 30 min. The slurry was again cooled in an ice-salt bath. Ethyl 4-(4-nitrophenyl)-1H-pyrrole-3-carboxylate (46.00 g, 176.8 mmol) was added as a suspension in DCE (500 mL). The reaction proceeded while cooling in an ice-salt bath for 1 h, and then was allowed to warm to rt over 17 h. Sodium Acetate (79.75 g, 972.2 mmol) in water (600 mL) was then added to the reaction and the solution was heated to 80° C. for 1 h. Upon cooling to rt, the solution was transferred to a separatory funnel and the organic layer was isolated while the aqueous layer was back extracted with CH$_2$Cl$_2$ (2×150 mL). The combined organic layers were dried (MgSO$_4$), filtered, and concentrated to dryness. The crude material was heated to reflux in toluene (2 L) and to the hot solution was added hexanes (200 mL). The solution was allowed to slowly cool, and over the following 2 days crystals formed. The crystals were collected, washed with Et$_2$O (500 mL), and dried under vacuum to afford 25.53 g of the above compound as golden needles (88.57 mmol, yield 50%). $^1$H-NMR (DMSO-d$_6$) δ 12.94 (br s, 1H), 9.29 (d, J=0.8 Hz, 1H), 8.25 to 8.22 (m, 2H), 7.81 (d, J=2.7 Hz, 1H), 7.74 to 7.71 (m, 2H), 4.12 to 4.06 (q, J=7.1 Hz, 2H), 1.15 to 1.11 (t, J=7.0 Hz, 3H); LCMS RT=2.75 min; TLC $R_f$=0.16 (95:5 v/v CH$_2$Cl$_2$-EtOAc).

Step 3: Preparation of ethyl 5-cyano-4-(nitrophenyl)-1H-pyrrole-3-carboxylate

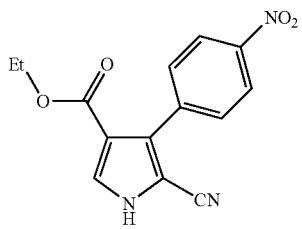

To a solution of pyridine (400 mL) was added ethyl 5-formyl-4-(nitrophenyl)-1H-pyrrole-3-carboxylate (24.55 g, 85.17 mmol) followed by hydroxylamine hydrochloride (6.51 g, 93.7 mmol). The solution was stirred at rt for 2 h, acetic anhydride (17.68 mL, 187.4 mmol) was added, and the solution was heated to 80° C. for 17 h. Upon cooling to rt, the reaction mixture was partially concentrated in vacuo and then diluted with EtOAc (300 mL) and H$_2$O (300 mL). The solution was transferred to a separatory funnel, and the organic layer was isolated while the aqueous layers were back extracted with EtOAc (2×100 mL). The combined organic layers were dried (Na$_2$SO$_4$), filtered, and concentrated to dryness. The crude material was then triturated with CH$_2$Cl$_2$-Et$_2$O (1:1 v/v, 300 mL). The solid was collected, washed with Et$_2$O (150 mL), and dried under vacuum to afford 18.94 g of the above compound as a fluffy white solid (66.40 mmol, yield 78%). $^1$H-NMR (DMSO-d$_6$) δ 13.24 (br s, 1H), 8.30 to 8.27 (m, 2H), 7.92 (s, 1H), 7.74 to 7.71 (m, 2H), 4.16 to 4.10 (q, J=7.2 Hz, 2H), 1.18 to 1.15 (t, J=7.0 Hz, 3H); LCMS RT=2.97 min; TLC $R_f$=0.20 (95:5 v/v CH$_2$Cl$_2$-EtOAc).

Intermediate B

Preparation of ethyl 4-amino-5-(4-nitrophenyl)pyrrolo[2,1-f][1,2,4]triazine-6-carboxylate

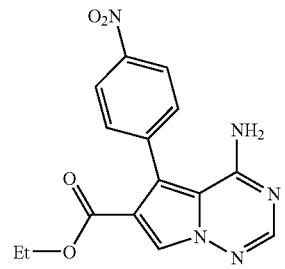

Step 1: Preparation of (aminooxy)(diphenyl)phosphine oxide

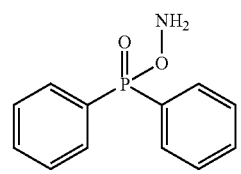

A 5 L 4-neck round bottom flask (rbf) fitted with an overhead stirrer & a thermocouple was charged with; (1) a solution of NaOH (60.85 g, 1.52 mol, 2.4 eq) in 180 mL water, (2) a solution of hydroxylamine-HCl (110.12 g, 1.58 mol, 2.5 eq) in 180 mL water and (3) 180 mL dioxane. The mixture was cooled in an ice/acetone bath to 0° C. 150 g of ice was added, followed by a precooled (to about 10° C.) solution of diphenylphosphinic chloride (150.0 g, 0.634 mol, 1 eq) in 180 mL dioxane (added all at once). The reaction became very thick with a white precipitate, requiring vigorous stirring. The internal temperature rose to 22° C. After 5 additional minutes stirring (10 minutes maximum), the reaction mixture was diluted with 2.5 L of ice cold water and filtered thru a large fritted funnel (15 cm diameter). The crude material was left on the frit to drain for one hour, then transferred back into the 5 L rbf. The solid was suspended in 500 mL ice cold 0.25N NaOH solution and vigorously stirred for five minutes (no more than 10 min), then filtered again, washing 2× with ice cold water and left to dry overnight on the fritted filter. The partially dried material was dried for 12 h in a vacuum oven (50° C., 0.1 torr) and then well crushed with a mortar & pestle. An additional 16 h of drying in the vacuum oven afforded 122 g (82%) the above compound as a white powder.

Step 2: Preparation of ethyl 1-amino-5-cyano-4-(nitrophenyl)-1H-pyrrole-3-carboxylate

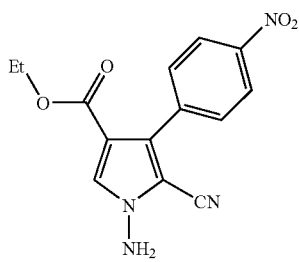

A 3 L 3 neck round bottomed flask was fitted with a reflux condenser and overhead stirrer and charged with ethyl 5-cyano-4-(nitrophenyl)-1H-pyrrole-3-carboxylate (20 g, 70.11 mmol). To a rapidly stirred solution in DMF (1 L) was added NaH (5×500 mg, 98 mmol) portion wise over 20 min. The dark brown solution was allowed to stir for an additional 10 min. The aminating reagent ((aminooxy)(diphenyl)phosphine oxide) was added in one portion (21.26 g, 91.14 mmol). The reaction mixture immediately solidified. Upon heating to 60° C. the solids began to disperse. The mixture was eventually heated to 80° C. and stirred over night. The reaction mixture was cooled and the solids were filtered off. The filter cake was washed with EtOAc (200 mL) and the filtrate was concentrated in vacuo. The resulting solid was suspended in Et$_2$O (300 mL) and filtered to provide a 69% yield of the product (14.37 g, 47.86 mmol) as a light tan powder. The product was used without further purification. $^1$H-NMR (DMSO-d$_6$) δ 8.29-8.24 (m, 2H), 7.72 (s, 1H), 7.71-7.68 (m, 2H), 6.71 (s, 2H), 4.09 (q, J=7.2 Hz, 2H), 1.12 (t, J=7.2 Hz, 3H); HPLC RT=3.15 min.

Step 3: Preparation of the Title Compound

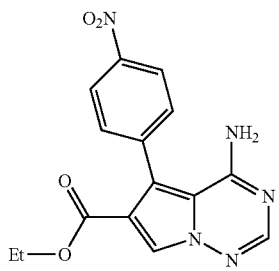

To a stirred suspension of ethyl 1-amino-5-cyano-4-(nitrophenyl)-1H-pyrrole-3-carboxylate (14.37 g, 47.86 mmol) in EtOH (800 mL) was added formamidinium acetate (40 g, 383 mmol). The mixture was heated to 80° C. and allowed to stir over the weekend. The reaction was complete by LCMS. The reaction mixture was cooled to room temperature and then filtered. The reaction vessel was rinsed with H$_2$O (200 mL). The filter cake was placed in a beaker and washed with H$_2$O (300 mL). The yellow suspension was filtered again and the filter cake was washed with H$_2$O (2×250 mL). The yellow solid was dried over night under reduced pressure to provide 83% yield of the title compound (13 g, 39.72 mmol). $^1$H-NMR (DMSO-d$_6$) δ 8.27-8.24 (m, 2H), 8.20 (s, 1H), 7.97 (s, 1H), 7.66-7.62 (m, 2H), 4.07 (q, J=7.2 Hz, 2H), 1.06 (t, J=7.2 Hz, 3H); LCMS RT=2.87 min; MS {M+H}$^+$=328.2.

Intermediate C

Preparation of ethyl 4-amino-5-(3-fluoro-4-nitrophenyl)-pyrrolo[2,1-f][1,2,4]triazine-6-carboxylate

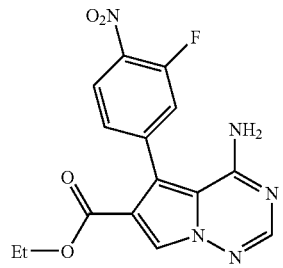

Step 1: Preparation of 3-fluoro-4-nitrobenzoyl chloride

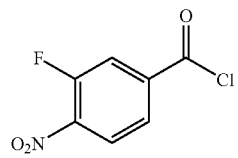

To a suspension of 3-fluoro-4-nitrobenzoic acid (30 g, 162.0 mmol) in toluene (500 mL) was added SOCl$_2$ (35 mL, 486 mmol). The reaction was heated to 110° C. at which point the reaction became homogeneous. The reaction was stirred at 110° C. for 3 h. The reaction had not gone to completion so an additional portion of SOCl$_2$ (10 mL) was added. The reaction was stirred for an additional 3 h. A small amount of stalling material remained thus a final portion of SOCl$_2$ (10 mL) was added and the reaction was heated for 2 h. The resulting green solution was cooled to room temperature and allowed to stand over night. The reaction mixture was filtered and concentrated in vacuo. Toluene (300 mL) was added to the resulting oil and removed under reduced pressure (2×). The product was used without further purification.

Step 2: Preparation of ethyl 3-(3-fluoro-4-nitrophenyl)-3-oxopropanoate

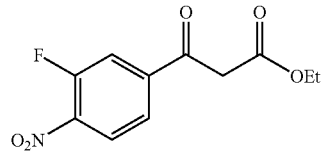

A 2 L round bottomed flask was fitted with a mechanical stir motor and nitrogen inlet. To a 10° C. solution of potassium 3-ethoxy-3-oxopropanoate (55.15 g, 324 mmol) in THF (500 mL) was added MgCl$_2$ (38.56 g, 405 mmol) and Et$_3$N (45 mL, 324 mmoL). The reaction mixture was allowed to warm to 23° C. and stir for 3 h. A solution of 3-fluoro-4-nitrobenzoyl chloride (~162 mmol) in THF (200 mL) was added. The reaction turned yellow instantly and a precipitate formed. THF (200 mL) was added to ensure that stirring was not impeded. TLC analysis indicated that the reaction had gone to completion however the reaction was allowed to stir over night. The reaction was quenched with 2N HCl (1 L) and extracted with EtOAc (2×500 mL). The organic layer was washed with saturated NaHCO$_3$ (500 mL), H$_2$O (300 mL) and brine (200 mL). The organic layer was dried (Na$_2$SO$_4$) and concentrated in vacuo. The desired product (37.65 g, 147 mmol) was isolated by flash column chromatography in 91% yield (1:1 Hex EtOAc) as a yellow solid as a mixture of keto (75%) and enol (25%) tautomers. $^1$H-NMR (DMSO-d$_6$) Keto tautomer δ 8.29 (dd, J=8.6, 7.4 Hz, 1H), 8.10 (dd, J=11.6, 2.0 Hz, 1H), 7.94 (m, 1H), 4.30 (s, 2H), 4.11 (q, J=7.2 Hz, 2H), 1.17 (t, J=7.2 Hz, 3H); Enol tautomer δ 12.44 (br s, 1H), 8.22 (app t, J=8.2 Hz, 1H), 8.05 (dd, J=12.6, 2.0 Hz, 1H), 7.90 (m, 1H), 6.22 (s, 1H), 4.25 (q, J=7.2 Hz, 2H), 1.26 (t, J=7.2 Hz, 3H); LCMS RT=3.14 min; MS {M+H}$^+$=311.0.

Step 3: Preparation of ethyl 3-(dimethylamino)-2-(3-fluoro-4-nitrobenzoyl)acrylate

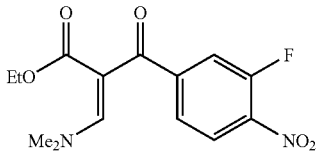

To a solution of ethyl 3-fluoro-4-nitro benzoylacetate (39.0 g, 153.0 mmol) in toluene (300 mL) was added dimethylformamide dimethylacetal (30.7 mL, 229.5 mmol). The reaction was heated to 80° C. over night. The mixture was concentrated in vacuo and purified by flash column chromatography (100% Hexane to 10% EtOAc; 90% Hexane until non-polar impurities were removed, then 75% EtOAc; 25% Hex to 100% EtOAc for product) to provide the desired product as a yellow solid in 95% yield (45.21 g, 145.7 mmol). $^1$H-NMR (DMSO-d$_6$) δ 8.17 (dd, J=8.4, 7.8 Hz, 1H), 7.82 (s, 1H), 7.62 (dd, J=11.6, 1.6 Hz, 1H), 7.50 (dd, J=8.4, 1.6 Hz, 1H), 3.87 (q, J=7.2 Hz, 2H), 3.32 (br s, 3H), 2.71 (br s, 1H), 0.89 (t, J=7.2 Hz, 3H); LCMS*RT=4.52 min; MS {M+H}$^+$=311.1.

Step 4: Preparation of Ethyl 5-(aminocarbonyl)-4-(3-fluoro-4-nitrophenyl)-1H-pyrrole-3-carboxylate

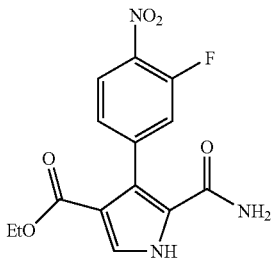

A 50 mL round bottomed flask was charged with of ethyl 3-(dimethylamino)-2-(3-fluoro-4-nitrobenzoyl)acrylate (51.74 g, 166.75 mmol) and 2-aminomalonamide (23.4 mg, 200 mmol) and AcOH (1 L). The reaction mixture was heated to 80° C. over night. The starting material appeared consumed by TLC. The AcOH was removed under reduced pressure and TFA (300 mL) was added. The mixture was heated over night at 60° C. The reaction was cooled to room temperature and the TFA was removed under reduced pressure. The orange oil was treated with saturated aqueous NaHCO$_3$ (1 L), then solid NaHCO$_3$ was added until the solution was neutral. The solids were filtered and placed in a 1 L erlenmeyer flask. The solids were washed with H$_2$O (3×1 L) and the water was decanted off through the filter. On the last washing the solids were poured onto the filter and allowed to air dry. The solids were once again removed from the filter and washed with Et$_2$O (4×500 mL). The Et$_2$O was decanted off through the filter and on the final washing the solids were transferred to the filter. An addition portion of Et$_2$O (200 mL) was used to wash the flask and the filter cake. The desired product was dried in a vacuum oven at 40° C. to provide a light tan solid (36.8 g, 114.5 mmol, 69% yield). $^1$H-NMR (DMSO-d$_6$) δ 12.28 (br s, 1H), 8.07 (app t, J=8.4 Hz, 1H), 7.57 (s, 1H), 7.46 (dd, J=12.6, 1.6 Hz, 1H), 7.28 (dd, J=8.4, 1.6 Hz, 1H), 7.25 (br s, 1H), 6.72 (br s, 1H), 4.01 (q, J=7.2 Hz, 2H), 1.07 (t, J=7.2 Hz, 3H); LCMS*RT=4.45 min; MS {M−H}$^-$=320.1.

Step 5: Preparation of Ethyl 5-cyano-4-(3-fluoro-4-nitrophenyl)-1H pyrrole-3-carboxylate

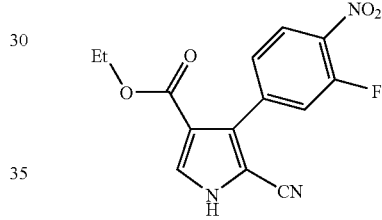

A solution of intermediate ethyl 5-(aminocarbonyl)-4-(3-fluoro-4-nitrophenyl)-1H-pyrrole-3-carboxylate (36.8 mg, 114.5 mmol) in POCl$_3$ (500 mL) was heated to 70° C. for 2 h. TLC analysis indicated that there was complete conversion of starting material. Excess POCl$_3$ was removed under reduced pressure and the remaining solids were poured over ice. The pH was adjusted to 8 using 5 N NaOH and the solution was filtered. The product was dried over night under reduced pressure to afford a light brown solid (33.85 g, 111.6 mmol) in 97% yield. $^1$H-NMR (DMSO-d$_6$) δ 13.32 (br s, 1H), 8.21 (app t, J=8.4 Hz, 1H), 7.90 (s, 1H), 7.73 (dd, J=12.4, 2.0 Hz, 1H), 7.51 (m, 1H), 4.13 (q, J=7.2 Hz, 2H), 1.15 (t, J=7.2 Hz, 3H); HPLC RT=3.16 min.

Step 6: Preparation of Ethyl 1-amino-5-cyano-4-(3-fluoro-4-nitrophenyl)-1H-pyrrole-3-carboxylate

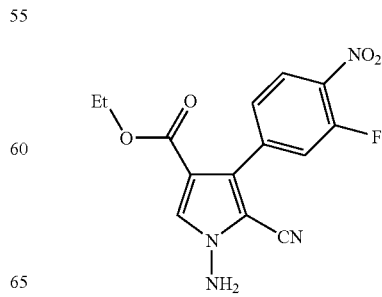

To a solution of ethyl 5-cyano-4-(3-fluoro-4-nitrophenyl)-1H pyrrole-3-carboxylate (31.9 g, 105.2 mmol) in DMF (1.5 L) was slowly added NaH (34.54 g, 136.7 mmol). After the evolution of gas had ceased (aminooxy)(diphenyl)phosphine oxide (34.4 g, 147.3 mmol) was added in one portion. Upon addition of (aminooxy)(diphenyl)phosphine oxide the reaction mixture solidified. The reaction mixture was heated to 80° C. during which time the solids broke up and mixture stirred freely. The reaction was heated for 3 h, then cooled and the DMF was removed under reduced pressure. The remaining slurry was dissolved in EtOAc (500 mL) and filtered to remove a majority of the phosphinic acid. The filter cake was washed with EtOAc and the organics were concentrated in vacuo. The product was purified by crystallization from hot ACN to provide a tan solid (24.0 g, 75.31 mmol) in 71% yield. $^1$H-NMR (DMSO-$d_6$) δ 8.21 (app t, J=8.4 Hz, 1H), 7.73 (s, 1H), 7.71 (dd, J=12.4, 2.0 Hz, 1H), 7.48 (m, 1H), 6.72 (s, 2H), 4.11 (q, J=7.2 Hz, 2H), 1.14 (t, J=7.2 Hz, 3H).

Step 7: Preparation of the Title Compound

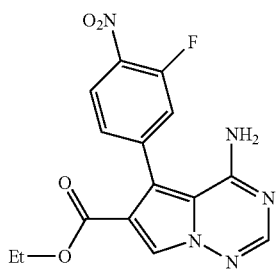

To a suspension of ethyl 1-amino-5-cyano-4-(3-fluoro-4-nitrophenyl)-1H-pyrrole-3-carboxylate (19.8 g, 62.2 mmol) in EtOH (600 mL) was added formadine acetate (51.8 g, 497.7 mmol). The reaction mixture was heated to 70° C. overnight. The reaction was not complete so an additional portion of formadine acetate (10.0 g, 96.1 mmol) was added. The reaction mixture was heated to 70° C. for an additional 8 h. The reaction mixture was cooled and the EtOH was removed under reduced pressure. The remaining solids were suspended in H$_2$O (1 L). The suspension was filtered to provide the title compound (19.6 g, 56.76 mmol) as a yellow solid in 91% yield. $^1$H-NMR (DMSO-$d_6$) δ 8.21 (s, 1H), 8.19 (app t, J=8.4 Hz, 1H), 7.98 (s, 1H), 7.66 (dd, J=12.4, 2.0 Hz, 1H), 7.41 (m, 1H), 4.09 (q, J=7.2 Hz, 2H), 1.10 (t, J=7.2 Hz, 3H); LCMS RT=2.90 min; MS {M+H}$^+$=346.0.

Intermediate D

Preparation of methyl 4-bromo-5-cyano-1-{[2-(trimethylsilyl)ethoxy]methyl}-1H-pyrrole-3-carboxylate

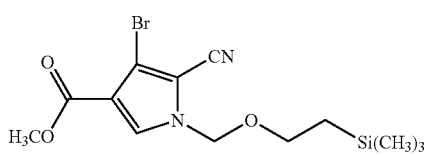

Step 1: Preparation of 4-(trichloroacetyl)-1H-pyrrole-2-carbonitrile

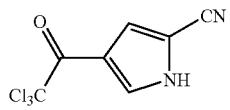

Trichloracetyl chloride (44.4 g, 27.3 mL, 244 mmol) in dichloromethane (75 mL) was added over 20 min to a mechanically stirred suspension of aluminum trichloride (54.3 g, 407 mmol) in dichloromethane (150 mL). The resulting mixture was stirred for 30 min, and then 2-cyanopyrrole (15.0 g, 163 mmol) in dichloromethane (75 mL) was added over 30 min. The reaction was heated at reflux for 5 h and then allowed to cool. The reaction was diluted with ethyl acetate (600 mL) and then quenched slowly with water (300 mL). The layers were separated and then the organic layer was washed with water and brine, dried (magnesium sulfate) and evaporated under reduced pressure to afford a quantitative yield of desired product (39.0 g, 100%) containing trace impurities. This material was used in the next step without further purification. $^1$H NMR (DMSO-$d_6$) δ 8.14 (s, 1H), 7.55 (s, 1H).

Step 2: Preparation of methyl 5-cyano-1H-pyrrole-3-carboxylate

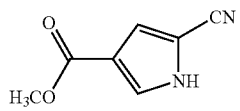

Sodium methoxide (17.8 g, 329 mmol) was added to a solution of 4-(trichloroacetyl)-1H-pyrrole-2-carbonitrile (39.0 g, 164 mmol) in methanol (350 mL). The reaction was stirred for 16 h and then the methanol was evaporated under reduced pressure. The residue was dissolved in ethyl acetate (800 mL) and the solution was adjusted to pH 6 using 1 M hydrochloric acid. The layers were separated and then the organic layer was washed with water and brine, dried (magnesium sulfate) and evaporated under reduced pressure to afford the expected product (24.2 g, 98%). $^1$H NMR (DMSO-$d_6$) δ 7.76 (s, 1H), 7.28 (s, 1H), 3.72 (s, 3H).

Step 3: Preparation of methyl 2,4-dibromo-5-cyano-1H-pyrrole-3-carboxylate

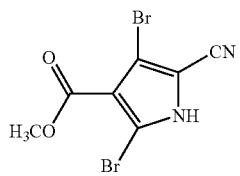

Bromine (54.1 g, 17.4 mL, 338 mmol) was added slowly (20 min) to a cooled (0° C.) solution of methyl 5-cyano-1H-pyrrole-3-carboxylate (24.2 g, 161 mmol) in 1 M aqueous sodium hydroxide solution (500 mL). The cold bath was removed and the reaction was stirred for 2 h. The reaction was quenched by addition of 1 M hydrochloric acid (400 mL) and the resulting precipitate was collected by filtration. The material was washed with 1 M hydrochloric acid to give the desired product (44.8 g, 90%). $^1$H NMR (DMSO-$d_6$) δ 3.77 (s, 3H).

Step 4: Preparation of methyl 2,4-dibromo-5-cyano-1-{[2-(trimethylsilyl)-ethoxy]methyl}-1H-pyrrole-3-carboxylate

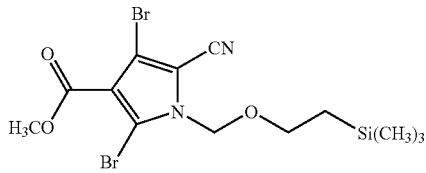

Potassium carbonate (56.5 g, 409 mmol) was added to a 0° C. solution of methyl 2,4-dibromo-5-cyano-1H-pyrrole-3-carboxylate (42.0 g, 136 mmol) in dimethylformamide (250 mL). After gas evolution ceased, 2-(chloromethoxy)ethyl](trimethyl)silane (34.1 g, 36.1 mL, 205 mmol) was added over 20 min. The reaction was stirred for 2 h and then poured into water (3 L). The product was extracted with ethyl acetate (3×500 mL) and then the combined organic extracts were washed with water, dried (magnesium sulfate) and evaporated under reduced pressure. The residue was triturated with hexane to afford the desired product (44.1 g, 73%). $^1$H NMR (DMSO-$d_6$) δ 5.51 (s, 2H), 3.83 (s, 3H), 3.62, (t, J=7.9 Hz, 2H), 0.91, (t, J=7.9 Hz, 2H), 0.00 (s, 9H).

Intermediate E

Preparation of ethyl 2,4-dibromo-5-cyano-1-{[2-(trimethyl-silyl)ethoxy]methyl}-1H-pyrrole-3-carboxylate

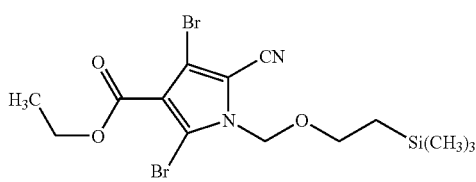

The procedure used for the preparation of Intermediate D was used to prepare the title compound by substituting ethanol for methanol in step 2.

Intermediate F

Preparation of 1-[2-fluoro-4-(4,4,5,5-tetramethyl-1,3,2-dioxaborolan-2-yl)phenyl]-3-[2-fluoro-5-(trifluoromethyl)phenyl]urea Preparation 1

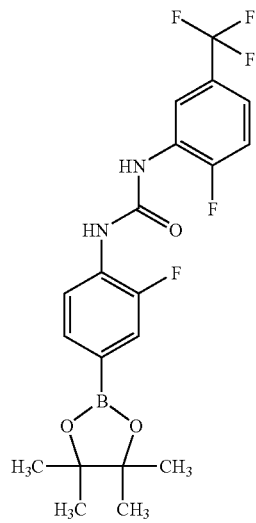

Step 1: Preparation of 2-fluoro-4-(4,4,5,5-tetramethyl-1,3,2-dioxaborolan-2-yl)aniline

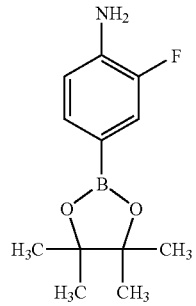

4-Bromo-2-fluoroaniline (45.00 g, 236.8 mmol) and 4,4,4',4',5,5,5',5'-octamethyl-2,2'-bi-1,3,2-dioxaborolane (66.15 g, 260.5 mmol, 1.1 eq) were added as solids to a flask then dissolved in 1,4-dioxanes (250 mL) and placed under $N_2$. The reaction was taken through five purge-fill cycles using high vacuum and nitrogen. To this solution was added potassium acetate (69.72 g, 710.4 mmol, 3 eq) and the reaction was again taken through three purge-fill cycles using high vacuum and nitrogen. To the reaction was added 1,1-bis(diphenylphosphino)ferrocene (5.20 g, 7.1 mmol, 0.03 eq). The reaction was taken one final time through five purge-fill cycles using high vacuum and nitrogen. The reaction was heated at 80° C. overnight (17 hr). After cooling to rt, EtOAc was added (1000 mL) and the reaction was partitioned between EtOAc and water. The organic phase was washed with brine, dried ($Na_2SO_4$), filtered, concentrated in vacuo. The crude material was dissolved in dichloromethane and the desired product (50.84 g, 90.6% yield) was obtained after flash column chromatography (9:1 Hexanes:EtOAc). $^1$H-NMR (DMSO-$d_6$) δ 7.17 (dd, J=7.8, 1.4 Hz, 1H), 7.12 (dd, 12.1, 1.2 Hz, 1H), 6.70 (t, 7.9 Hz, 1H) 5.56 (s, 2H), 1.22 (s, 12H); MS [M+H]$^+$=238, LCMS RT=3.35 min.

Step 2: Preparation of Title Compound

To a solution of 2-fluoro-4-(4,4,5,5-tetramethyl-1,3,2-dioxaborolan-2-yl)aniline (7.65 g, 32.3 mmol, 1 eq) in 1,2-dichloroethane (76.5 mL) was added 1-fluoro-2-isocyanato-4-(trifluoromethyl)benzene (4.9 ml, 33.9 mmol, 1.05 eq). The reaction was allowed to stir overnight. White solids precipitated from the reaction mixture and were filtered and washed with hexanes (3×). The solids were dried under vacuum to obtain 8.75 g (61.3% yield) of the desired product. $^1$H-NMR (DMSO-d$_6$) δ 9.45 (d, J=2.7 Hz, 1H), 9.32 (d, J=2.76 Hz, 1H), 8.63 (dd, J=7.2, 2.2 Hz, 1H), 8.28 (t, J=8.0 Hz, 1H), 7.50-7.34 (m, 4H), 1.27 (s, 12H); MS [M+H]$^+$=443, LCMS RT=4.50 min

Intermediate F

Preparation of N-[2-fluoro-4-(4,4,5,5-tetramethyl-1,3,2-dioxaborolan-2-yl)phenyl]-N'-[2-fluoro-5-(trifluoromethyl)phenyl]urea Preparation 2

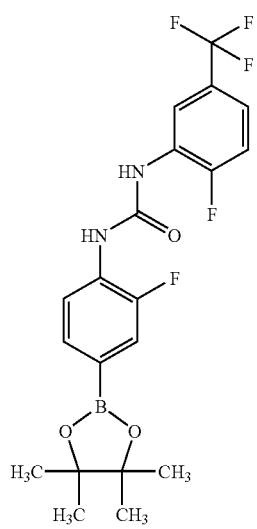

Step 1. Preparation of N-(4-bromo-2-fluorophenyl)-N'-[2-fluoro-5-(trifluoromethyl) phenyl]urea

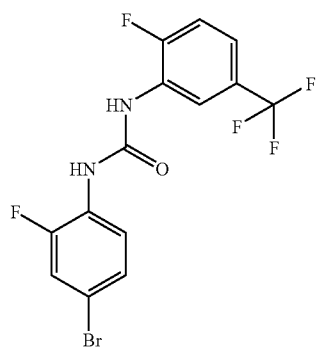

To a solution of 1,2 dichloroethane (100 mL) was added 4-bromo-2-fluoroaniline (5.00 g, 26.31 mmol) followed by 2-fluoro-5-trifluoromethyl phenylisocyante (5.67 g, 27.63 mmol) in one portion. The solution was allowed to stir overnight at rt, and the resulting solids were filtered and rinsed with 1,2 dichloroethane (3×5 mL). A second crop of product was obtained by concentrating the mother liquor and redissolving in 1,2-dichloroethane (20 mL). The solution was briefly heated to reflux and upon cooling the desired product precipitated. The solid was filtered and rinsed with 1,2 dichloroethane (3×5 mL). Total amount of white solids obtained was 10.13 g (25.64 mmol, 97.4% yield). $^1$H-NMR (DMSO-d$_6$) δ 9.37 (s, 1H), 9.23 (s, 1H), 8.60 (d, J=7.2 Hz 1H), 8.15 (t, J=8.8 Hz, 1H), 7.58 to 7.50 (dd, J=8.9, 2.2 1H), 7.48 (m, 1H), 7.40 to 7.32 (m, 2H); LCMS RT=4.22 min.

Step 2: Preparation of Title Compound

To a solution of 1,4-dioxane (60 mL) was added Intermediate B (N-(4-bromo-2-fluorophenyl)-N'-[2-fluoro-5-(trifluoromethyl)phenyl]urea) (10.00 g, 25.31 mmol). DMF was added dropwise until the solution was homogeneous a the reaction was degassed 3 times. To this solution was added bis(pinacolato)diboron (7.71 g, 30.37 mmol) in one portion. The reaction was degassed 5 times and potassium acetate (7.45 g, 75.92 mmol) was then added in one portion. The reaction was again degassed 3 times. To this heterogeneous reaction was added 1,1'-Bis(diphenylphosphino)ferrocenepalladium dichloride (925 mg, 1.26 mmol) and the reaction was degassed 5 additional times and was then heated at 80° C. overnight (17 hr). After cooling to rt, the reaction was filtered through a thin pad of silica to remove solids and then purified via flash column chromatography (15:1 to 5:1 Hex:EtOAc) to afford the desired product as a white solid. (12.24 g, 27.68 mmol). $^1$H-NMR (DMSO-d$_6$) δ 9.46 (s, 1H), 9.33 (s, 1H), 8.63 (d, J=7.4 Hz 1H), 8.28 (t, J=8.2 Hz, 1H), 7.52 to 7.35 (br m, 4H), 1.27 (s, 12H); MS [M+H]$^+$=443; LCMS RT=4.31 min.

Intermediate G

Preparation ethyl 4-amino-5-(4-amino-3-fluorophenyl)pyrrolo[2,1-f][1,2,4]triazine-6-carboxylate hydrochloride

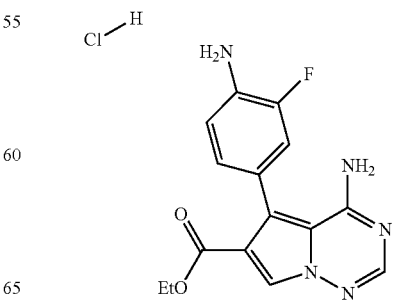

Step 1: Preparation of ethyl 4-bromo-5-cyano-1-{[2-(trimethylsilyl)ethoxy]-methyl}-1H-pyrrole-3-carboxylate

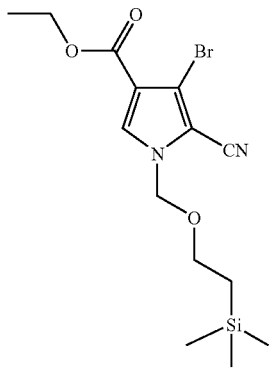

A solution of Intermediate E (ethyl 2,4-dibromo-5-cyano-1-{[2-(trimethylsilyl)ethoxy]methyl}-1H-pyrrole-3-carboxylate (42.10 g, 92.9 mmol)) in 1.0 L THF was cooled to −65 C and a solution of n-butyllithium in hexanes (1.6M, 87.09 mL, 139.3 mmol) was added dropwise over 20 min. After 15 additional minutes, the reaction was quenched by addition of methanol (14.86 mL, 464 mmol). The reaction was diluted with Et₂O (1 L) and brine (200 mL). The organic layer was separated, dried (Na₂SO₄) and filtered through a plug of silica. Evaporation of the solvent afforded the title compound as a brown solid (33.91 g, 97.8% yield). $^1$H-NMR (DMSO-d$_6$) δ8.18 (s, 1H), 5.50 (s, 2H), 4.28 (q, J=7 Hz, 2H), 3.55 (t, J=8 Hz, 2H), 1.32 (t, J=7 Hz, 2H), 0.89 (t, J=8 Hz, 2H), 0.00 (s, 9H); GCMS [M+H]$^+$=372.9; GCMS RT=5.43. LCMS RT=3.94.

Step 2: Preparation of ethyl 4-{4-[(tertbutoxycarbonylamino]-3-fluorophenyl}-5-cyano-1-{[2-(trimethylsilyl)ethoxy]methyl}-1H-pyrrole-3-carboxylate

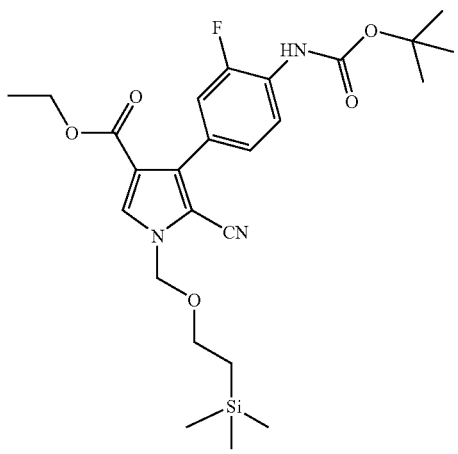

A degassed suspension of palladium(II) acetate (1.86 g, 8.304 mmol) in dioxane (20 mL) was treated with triphenylphosphine (8.71 g, 33.2 mmol) and the mixture allowed to stir for 15 min. The yellow suspension was then diluted with dioxane (500 mL) and treated with ethyl 4-bromo-5-cyano-1-{[2-(trimethylsilyl)ethoxy]-methyl}-1H-pyrrole-3-carboxylate (31.70 g, 83.04 mmol) and Intermediate F (t-butyl[2-fluoro-4-(4,4,5,5-tetramethyl-1,3,2-dioxaborolan-2-yl)phenyl]carbamate (27.83 g, 87.19 mmol)). The solution was degassed and backfilled with N₂ (2x) before treatment with aqueous sodium carbonate (2N, 83.04 mL, 166.1 mmol). The reaction mixture was again degassed and backfilled with N₂ (2x) then heated to 80 C for 16 h. The reaction mixture was cooled to rt and diluted with EtOAc (200 mL) and hexanes (200 mL). After washing with sodium bicarbonate (1x) and brine (1x) the organic layer was filtered passed through a large pad of silica gel. Evaporation of the solvent gave the title compound as a viscous, semi-solid (31.0 g, 75.2%). $^1$H-NMR (DMSO-d$_6$) δ9.15 (s, 1H), 8.14 (, 1H), 7.71 (t, J=8 Hz, 1H), 7.31 (dd, J=12, 2 Hz, 1H), 7.21 (dd, J=8, 2 Hz, 1H), 5.50 (s, 1H), 4.16 (q, J=7 Hz, 2H), 3.59 (t, J=8 Hz, 2H), 1.20 (t, J=7 Hz, 3H), 1.50 (s, 9H), 0.90 (t, J=8 Hz, 2H), 0.00 (s 9H); MS [M+Na]$^+$=526.4; LCMS RT=4.09.

Step 3: Preparation of ethyl 4-{4-[(tert-butoxycarbonyl)amino]-3-fluorophenyl}-5-cyano-1H-pyrrole-3-carboxylate

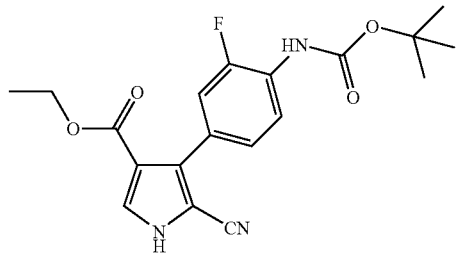

Ethyl 4-{4-[(tertbutoxycarbonylamino]-3-fluorophenyl}-5-cyano-1-{[2-(trimethyl-silyl)-ethoxy]methyl}-1H-pyrrole-3-carboxylate (31.00 g, 63.8 mmol) was taken up in 400 mL solution of tert-butylammonium fluoride in THF (1N, 400 mL, 400 mmol) which had been dried with activated 3 A MS. After 10 min the reaction appeared complete by TLC. The reaction was diluted with EtOAc and washed with aqueous 1N Na₂HPO₄ (1x) and water (3x). The organic layer was dried with Na₂SO₄, filtered thru a plug of silica and concentrated to afford a faintly orange solid. The solids were trituration with ether:hexanes (1:3) to provided the title compound as a yellowish solid free of impurities (20.13 g, 88.7% yield) $^1$H-NMR (DMSO-d$_6$) δ9.07 (s, 1H), 7.01 (s, 1H), 7.62 (t, J=8 Hz, 1H), 7.26 (dd, J=12, 2 Hz, 1H), 7.16 (dd, J=9, 2 Hz, 1H), 4.10 (q, J=7 Hz, 2H), 1.45 (s, 9H), 1.14 (t, J=7 Hz, 3H); MS [M+Na]$^+$=395.9; LCMS RT=3.45.

Step 4: Preparation of ethyl 1-amino-4-{4-[(tert-butoxycarbonyl)amino]-3-fluorophenyl}-5-cyano-1H-pyrrole-3-carboxylate

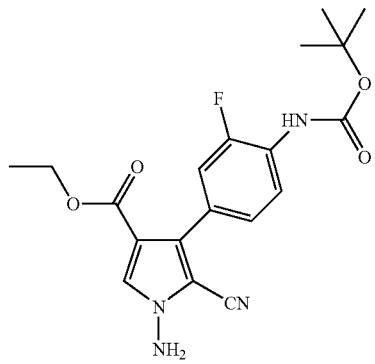

A 1-L 3-neck rbf was fitted with an overhead stirrer and charged with sodium hydride (60% dispersion in mineral oil, 2.19 g, 54.6 mmol) and DMF (550 mL). Ethyl 4-{4-[(tert-butoxycarbonyl)amino]-3-fluorophenyl}-5-cyano-1H-pyrrole-3-carboxylate (10.00 g, 45.5 mmol) was added and the mixture was left to stir at rt for 15 min. The reaction mixture was treated with (aminooxy)(diphenyl) phosphine oxide (12.74 g, 54.6 mmol) and heated to 60° C. The very thick reaction mixture gradually became a readily stirred suspension. After 1 h analysis by RP-HPLC indicated that all starting material had been consumed. The reaction was cooled to rt and diluted with 1.5 L EtOAc and aq. sodium bicarbonate. The aqueous layer was back extracted with EtOAc (2×) and the combined organic layers were dried (sodium sulfate) and filtered through a silica plug. Trituration with ether:hexanes (1:2) gave the title compound as a yellowish powder (18.06 g, 46.5 mmol, 93.7%). $^1$H-NMR (DMSO-$d_6$) δ9.13 (s, 1H), 7.68 (s, 1H, 7.68 (t, J=8 Hz, 1H), 7.29 (dd, J=12, 2 Hz, 1H), 7.19 (dd, J=8 Hz, 1H), 6.67 (s, 2H), 4.14 (q, J=7 Hz, 2H), 1.50 (s, 9H), 1.18 (s, 3H); MS [M+Na]$^+$=411.0; LCMS RT=3.48.

Step 5: Preparation of ethyl 4-amino-5-{4-[(tert-butoxycarbonyl)amino]-3-fluorophenyl}pyrrolo[2,1-f][1,2,4]triazine-6-carboxylate

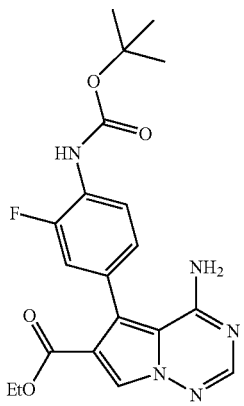

A mixture of ethyl 1-amino-4-{4-[(tert-butoxycarbonyl)amino]-3-fluorophenyl}-5-cyano-1H-pyrrole-3-carboxylate (18.06 g, 46.5 mmol), formamidine acetate (48.41 g, 464.9 mmol) and finely ground potassium phosphate (19.74 g, 93.0 mmol) in ethanol (350 mL) was heated at 80° C. overnight. After 16 h, the reaction mixture was cooled to rt and diluted with 1.8 L water. The resulting precipitate was filtered thru a glass frit and washed with water. Drying in a vacuum oven provided the title compound as a gray solid (15.6 g, 80.8%) $^1$H-NMR (DMSO-$d_6$) δ9.11 (s, 1H), 8.13 (s, 1H), 7.93 (s, 1H), 7.72 (t, J=8 Hz, 1H), 7.26 (dd, J=12, 2 Hz, 1H), 7.12 (dd, J=8, 2 Hz, 1H), 4.07 (q, J=7 Hz, 2H), 1.47 (s, 9H), 1.09 (t, J=7 Hz, 3H); MS [M+H]$^+$ 415.8=; LCMS RT=3.05.

Step 6: Preparation of Title Compound

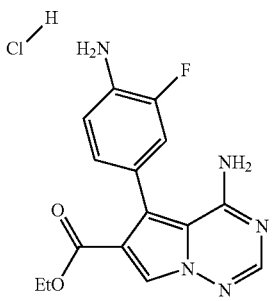

A suspension of ethyl 4-amino-5-{4-[(tert-butoxycarbonyl)amino]-3-fluorophenyl}pyrrolo[2,1-f][1,2,4]triazine-6-carboxylate (400 mg, 0.963 mmol) in 4N HCl in dioxane (9.63 mL, 38.5 mmol) was heated to 60° C. for 5 min, then cooled to rt and diluted with 40 mL ether. Filtration through a teflon membrane filter gave the title compound as a yellow solid (310 mg, 91.5% yield). $^1$H-NMR (DMSO-$d_6$) δ8.33 (s, 1H), 8.14 (s, 1H), 7.16 (d, J=12 Hz, 1H), 6.96 to 7.03 (m, 2H), 4.13 (q, J=8 Hz, 2H), 1.15 (t, J=8 Hz, 3H); MS [M+H]$^+$=316.1; LCMS RT=2.39.

Intermediate H

Preparation of ethyl 4-amino-5-(4-aminophenyl)pyrrolo[2,1-f][1,2,4]triazine-6-carboxylate

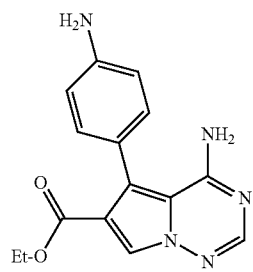

Raney nickel (several spatulas) was added to a flask containing 20 mL of EtOH. The catalyst was triturated with abs EtOH (3×20 mL). A suspension of Intermediate B (ethyl 4-amino-5-(4-nitrophenyl)pyrrolo[2,1-f][1,2,4]triazine-6-carboxylate (4.0 g, 12.2 mmol)) in abs EtOH (600 mL)/THF (200 mL) was added to the flask with the catalyst. The flask was evacuated and refilled with hydrogen gas (3×) and the reaction was then placed under a hydrogen atmosphere (1 atm) and allowed to stir at rt overnight. The reaction was filtered through a Celite® pad and washed with copious amounts of EtOH/THF (3:1) to afford 3.60 g of the above compound as a brown solid (yield 96%) $^1$H-NMR (DMSO-$d_6$) δ 8.05 (s, 1H), 8.04 (br s, 2H), 7.88 (s, 1H), 7.01 (d, J=8.0 Hz, 2H), 6.61 (d, J=8.0 Hz, 2H), 5.31 (br s, 2H), 4.07 (q, J=7.4 Hz, 2H), 1.12 (t, J=7.2 Hz, 3H); MS [M+H]$^+$=298; LCMS RT=1.64 min; TLC $R_f$=0.30 (Acetone/CH$_2$Cl$_2$ 1:3).

Intermediate I

Preparation of ethyl 4-amino-5-(4-amino-3-fluorophenyl)pyrrolo[2,1-f][1,2,4]triazine-6-carboxylate

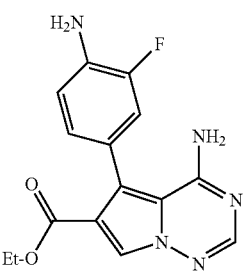

The procedure used for the preparation of Intermediate H was used to prepare the title compound by substituting Intermediate C for Intermediate B. ¹H-NMR (DMSO-d₆) δ 8.07 (s, 1H), 7.90 (s, 1H), 7.04 to 7.01 (d, J=12.3 Hz, 1H), 6.88 to 6.85 (m, 2H), 6.81 to 6.77 (m, 1H), 5.36 (s, 2H), 4.11 to 4.06 (q, J=7.1 Hz, 2H), 1.15 to 1.11 (t, J=7.0 Hz, 3H); MS [M+H]⁺=316.1; LCMS RT=2.16 min.

Intermediate J

Preparation of ethyl 4-amino-5-{4-[({[2-fluoro-5-(trifluoromethyl)phenyl]amino}carbonyl)amino]phenyl}pyrrolo[2,1-f]-[1,2,4]triazine-6-carboxylate

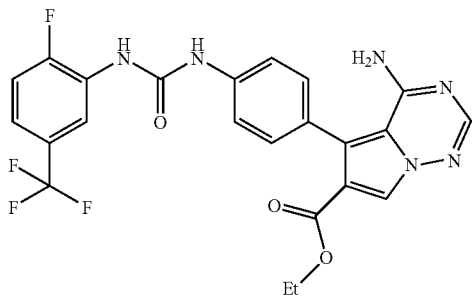

To a solution of DCE (200 mL) was added intermediate H (ethyl 4-amino-5-(4-aminophenyl)pyrrolo[2,1-f][1,2,4]triazine-6-carboxylate (6.40 g. 21.5 mmol)) followed by 2-fluoro-5-(trifluoromethyl)phenyl isocyanate (6.38 mL, 44.13 mmol). The solution was heated at 80° C. for 17 h. To the reaction mixture was added DMF (200 mL) and aq 2 N HCl (10.8 mL, 21.5 mmol), and the solution was heated to 80° C. for 2.5 h. The reaction mixture was evaporated under reduced pressure and then triturated with THF/Et₂O. A white solid formed which was collected and washed with Et₂O. Upon drying under vacuum 9.14 g of product was isolated (18.2 mmol, 85%). ¹H-NMR (DMSO-d₆) δ9.33 (s, 1H), 8.97 (d, J=4.0 Hz, 1H), 8.62 (d, J=12.0 Hz, 1H), 8.12 (s, 1H), 8.11 (br s, 1H), 7.92 (s, 1H), 7.6-7.3 (m, 5H), 4.10 (q, J=8.0 Hz, 2H), 1.11 (t, J=8.0 Hz, 3H); MS [M+H]⁺=503; LCMS RT=3.50 min; TLC R_f=0.40 (3:1 v/v CH₂Cl₂-Acetone).

Intermediate K

Preparation of N-{4-[4-amino-6-(hydroxymethyl)pyrrolo[2,1-f][1,2,4]triazin-5-yl]phenyl}-N'-[2-fluoro-5-(trifluoromethyl)phenyl]urea

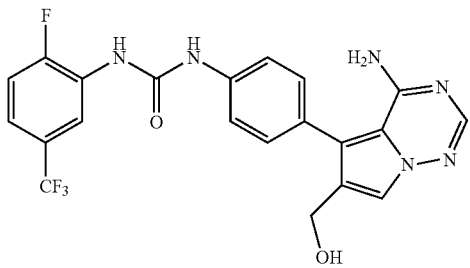

To a solution of THF (8.0 mL) was added Intermediate J (80.0 mg, 0.16 mmol) followed by DIBAL (0.8 mL, 0.8 mmol, 1.0M solution in THF). The reaction was stirred at it with addition of DIBAL (2.4 mL, 2.4 mmol, 1.0M solution in THF) in three batches until HPLC indicated completion of reaction. The reaction was diluted with EtOAc and quenched with saturated aqueous Rochelle's salt. Reaction was extracted with EtOAc (4×). Organic was dried (Na₂SO₄) and evaporated to give a crude oil that was purified via HPLC (10-90% ACN/H₂O) yielding a yellow solid (40.0 mg, 55%). ¹H-NMR (CD₃CN) δ8.61 (d, J=8.0 Hz, 1H), 7.80 (s, 1H), 7.66-7.60 (m, 3H), 7.42-7.32 (m, 4H), 4.50 (s, 2H); MS [M+H]⁺=461; LCMS RT=2.87 min.

Intermediate L

Preparation of ethyl 4-amino-5-{3-fluoro-4-[({[2-fluoro-5-(trifluoromethyl)phenyl]amino}carbonyl)amino]phenyl}pyrrolo[2,1-f][1,2,4]triazine-6-carboxylate

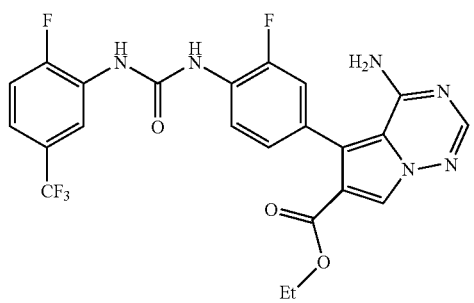

The procedure used for the preparation of Intermediate J was used to prepare the title compound by substituting Intermediate I for Intermediate H. ¹H-NMR (DMSO-d₆) δ 9.42 (s, 1H), 9.28 (s, 1H), 8.65 to 8.63 (m, 1H), 8.27 to 8.22 (m, 1H), 8.13 (s, 1H), 7.93 (s, 1H), 4.11 to 4.06 (m, 2H), 1.14 to 1.10 (m, 3H); MS [M+H]⁺=521.3; LCMS RT=2.98 min.

Intermediate M

Preparation of N-{4-[4-amino-6-(hydroxymethyl)pyrrolo-[2,1-f][1,2,4]triazin-5-yl]-2-fluorophenyl}-N'-[2-fluoro-5-(trifluoromethyl)-phenyl]urea

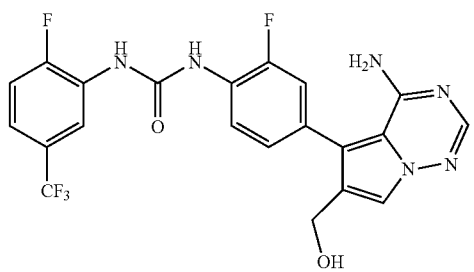

The procedure used for the preparation of Intermediate K was used to prepare the title compound by substituting Intermediate L for Intermediate J. ¹H-NMR (DMSO-d₆) δ 9.41 (s, 1H), 9.40 (s, 1H), 9.26 to 8.63 (m, 1H), 8.28 to 8.24 (m, 1H), 7.83 (s, 1H), 7.66 (s, 1H), 7.53 to 7.48 (m, 1H), 7.41 to 7.33

(m, 2H), 7.18 (d, J=8.2 Hz, 1H), 5.01 to 4.98 (m, 1H), 4.37 (d, J=5.0 Hz, 2H); MS [M+H]⁺=479.1; LCMS RT=2.49 min.

Intermediate N

Preparation of N-[4-(4-amino-6-formylpyrrolo[2,1-f][1,2,4]triazin-5-yl)-2-fluorophenyl]-N'-[2-fluoro-5-(trifluoromethyl)phenyl]urea

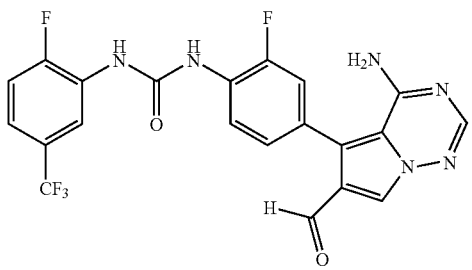

Intermediate M (N-{4-[4-amino-6-(hydroxymethyl)pyrrolo[2,1-f][1,2,4]triazin-5-yl]-2-fluoro-phenyl}-N'-[2-fluoro-5-(trifluoromethyl)phenyl]urea) (1.02 g, 2.13 mmol) was dissolved in THF (500 mL) and to it was added Dess-Martin Periodinane reagent (0.99 g, 2.35 mmol). The reaction was stirred at rt for 1 h. The reaction was then diluted with EtOAc and saturated aqueous NaHCO₃/Na₂S₂O₃ 1:1 which was stirred for 30 min and then transferred to a separatory funnel. The organic layer was washed with aqueous NaHCO₃/Na₂S₂O₃ 1:1 and water. The organic layer was dried (MgSO₄), filtered, and evaporated to give 0.99 g of product (2.10 mmol, 98%). ¹H-NMR (DMSO-d₆) δ 9.75 (s, 1H), 9.45 (s, 1H), 9.33 (s, 1H), 8.65 to 8.64 (d, J=7.1 Hz, 1H), 8.34 to 8.29 (m, 2H), 7.97 (s, 1H), 7.54 to 7.40 (m, 3H), 7.27 to 7.25 (d, J=9.4 Hz, 1H); MS [M+H]⁺=477.1; LCMS RT=3.07 min.

Intermediate O

Preparation of N-{4-[4-amino-6-(1,3-oxazol-5-yl)pyrrolo[2,1-f][1,2,4]triazin-5-yl]-2-fluorophenyl}-N'-[2-fluoro-5-(trifluoromethyl)-phenyl]urea

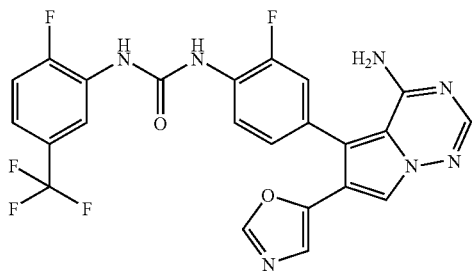

To a solution of MeOH (20 mL), THF (20 mL), and 0.5 M sodium methoxide in MeOH (6.30 mL, 3.15 mmol) cooled in an ice bath was added tosylmethyl isocyanide (0.61 g, 6.30 mmol) and Intermediate N(N-[4-(4-amino-6-formylpyrrolo[2,1-f][1,2,4]triazin-5-yl)-2-fluorophenyl]-N'-[2-fluoro-5-(trifluoro-methyl)phenyl]urea (500 mg, 1.05 mmol)). The solution was allowed to stir at 0° C. for 5 min and was then heated to 60° C. for 6 h. Upon cooling to rt, the solution was partially evaporated and a solid formed which was collected and washed with MeOH. The solid was dried under vacuum producing 140 mg of white powder (0.27 mmol, yield 26%). ¹H-NMR (DMSO-d₆) δ 9.46 (s, 1H), 9.32 (s, 1H), 8.65 to 8.64 (d, J=7.4 Hz, 1H), 8.35 to 8.30 (t, J=8.5 Hz, 1H), 8.30 (s, 1H), 8.09 (s, 1H), 7.90 (s, 1H), 7.53 to 7.48 (m, 1H), 7.42 to 7.39 (m, 1H), 7.37 to 7.34 (d, J=12.0 Hz, 1H), 7.21 to 7.19 (d, J=8.4 Hz, 1H), 6.62 (s, 1H); MS [M+H]⁺=516.1; LCMS RT=3.01 min.

Intermediate P

Preparation of N-[4-(4-amino-6-formylpyrrolo[2,1-f][1,2,4]triazin-5-yl)phenyl]-N'-[2-fluoro-5-(trifluoromethyl)phenyl]urea

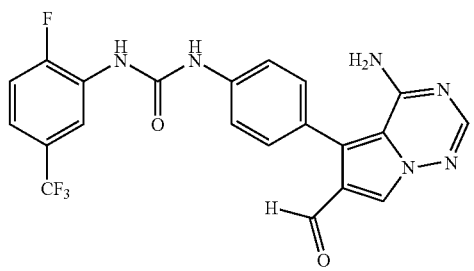

Intermediate K (N-{4-[4-amino-6-(hydroxymethyl)pyrrolo[2,1-f][1,2,4]triazin-5-yl]phenyl}-N'-[2-fluoro-5-(trifluoromethyl)phenyl]urea (40.0 mg, 0.09 mmol)) was dissolved in THF (5.0 mL) and to it was added Dess-Martin Periodinane reagent (44.0 mg, 0.10 mmol). The reaction was stirred at rt until HPLC indicated completion of reaction. Reaction was diluted with EtOAc and washed with saturated aqueous NaHCO₃/Na₂S₂O₃ 1:1 (3×). The aqueous layer was back extracted with EtOAc (2×). The combined organic layer was dried (Na₂SO₄) and evaporated to give a crude oil that was purified via HPLC (10-90% ACN/H₂O) to give a yellow solid (35.0 mg, 88%). ¹H-NMR (CD₃OD) δ 9.76 (s, 1H), 8.61 (d, J=8.0 Hz, 1H), 8.11 (s, 1H), 7.87 (s, 1H), 7.65 (d, J=8.0 Hz, 1H), 7.46 (d, J=8.0 Hz, 1H), 7.30 (d, J=8.0 Hz, 1H); MS [M+H]⁺=459; LCMS RT=2.95 min.

Intermediate Q

Preparation of N-{4-[4-amino-6-(1,3-oxazol-5-yl)pyrrolo[2,1-f][1,2,4]triazin-5-yl]phenyl}-N'-[2-fluoro-5-(trifluoromethyl)phenyl]urea

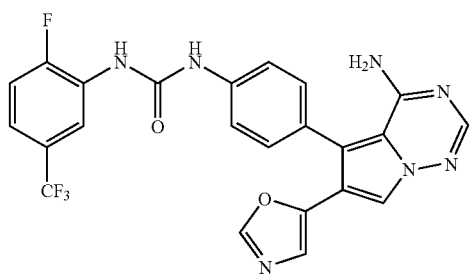

The procedure used for the preparation of Intermediate O was used to prepare the title compound by substituting Intermediate P for Intermediate N. ¹H-NMR (CD₃OD) δ 8.63 (d, J=6.8 Hz, 1H), 8.13 (s, 1H), 7.98 (s, 1H), 7.83 (s, 1H), 7.69 (d, J=8.5 Hz, 2H), 7.42 (d, J=8.4 Hz, 2H), 7.35 (d, J=8.3 Hz, 2H), 6.49 (s, 1H); MS [M+H]⁺=498.1; LCMS RT=2.82.

Intermediate R

Preparation of N-[4-(4-amino-6-cyanopyrrolo[2,1-f][1,2,4]triazin-5-yl)phenyl]-N'-[2-fluoro-5-(trifluoromethyl)phenyl]urea

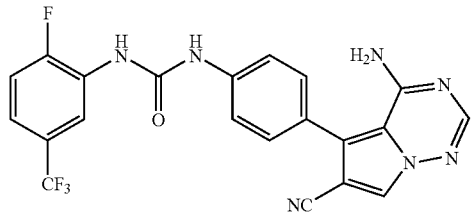

To a solution of pyridine (40 mL) was added Intermediate P(N-[4-(4-amino-6-formylpyrrolo[2,1-f][1,2,4]triazin-5-yl)phenyl]-N'-[2-fluoro-5-(trifluoromethyl)-phenyl]urea (2.64 g, 5.76 mmol)) followed by hydroxylamine hydrochloride (0.63 g, 6.33 mmol). The reaction was stirred at ambient temperature for 1 h, and then acetic anhydride (1.20 mL, 12.67 mmol) was added. The solution was heated at 80° C. for 1 h. Additional acetic anhydride (0.27 mL, 2.88 mmol) was added and the solution was heated at 80° C. for 1 h. Upon cooling to rt, the solution was concentrated to half the original volume in vacuo, and subsequently EtOAc (100 mL) and aq NaHCO₃ (100 mL) were added to the reaction, which was then transferred to a separatory funnel. The organic layer was collected and washed with water (50 mL). The aqueous layer was back extracted with EtOAc, which was washed with water. The organic layers were combined, dried (MgSO₄), filtered, concentrated to dryness, and purified by flash chromatography (9:1 v/v CH₂Cl-MeOH). The resulting purified fractions were combined and triturated in EtOH. The material was washed with cold EtOH and dried under vacuum yielding 1.45 g of a pale yellow solid (3.18 mmol, yield 55%). ¹H-NMR (CD₃OD) δ 8.62 (d, J=7.0 Hz, 1H), 8.19 (s, 1H), 7.91 (s, 1H), 7.69 (d, J=8.6 Hz, 2H), 7.50 (d, J=8.6 Hz, 2H), 7.34 (d, J=8.7 Hz, 2H); MS [M+H]⁺=456.1; LCMS RT=3.10.

Intermediate S

Preparation of 4-amino-5-{4-[({[2-fluoro-5-(trifluoromethyl)-phenyl]amino}carbonyl)amino]phenyl}pyrrolo[2,1-f][1,2,4]triazine-6-carboxylic acid

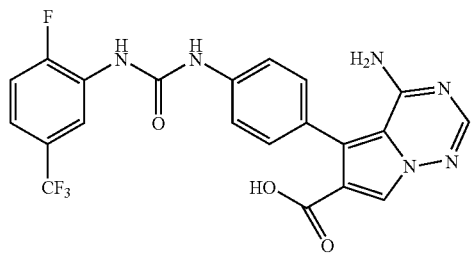

To a solution of Intermediate J (720.0 mg, 1.433 mmol) in MeOH (5 mL) and THF (3 mL) was added 1M NaOH (3.58 mL, 3.58 mmoL) and the reaction left to stir at 60° C. for 12 h. The reaction mixture was cooled and partitioned between CHCl₃ and pH 2 sulfate buffer. The organic layer was washed with brine, dried (Na₂SO₄) and concentrated to yield a brown solid (623 mg, 92% yield). ¹H-NMR (DMSO-d₆) δ 12.17 (bs, 1H), 9.34 (s, 1H), 8.98 (d, J=2 Hz, 1H), 8.62 (dd, J=2 Hz, 8 Hz, 1H), 8.07 (3, 1H), 8.0 (bs, 1H), 7.91 (s, 1H), 7.53 (d, J=8 Hz, 2H), 7.55-7.45 (m, 1H), 7.42-7.35 (m, 1H), 7.32 (d, J=8 Hz, 2H), 5.0 (bs, 1H); MS [M+H]⁺=475.2; LCMS RT=2.56 min; TLC R_f=0.26 (1:1:0.02 v/v/v THF:CH₂Cl₂:MeOH).

Intermediate T

Preparation of 4-amino-5-{4-[({[2-fluoro-5-(trifluoromethyl)phenyl]amino}carbonyl)amino]phenyl}-N-(2,2,2-trifluoroethyl)-pyrrolo[2,1-f][1,2,4]triazine-6-carboxamide

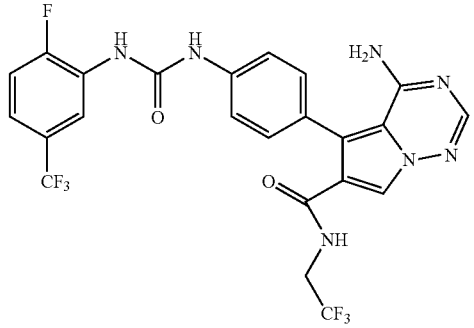

To a solution of Intermediate S (2.92 g, 6.16 mmol) in DMF (100 mL) was added benzotriazol-1-yloxytris(dimethylamino)phosphonium hexafluorophosphate (2.72 g, 6.16 mmoL), 4-methylmorpholine (0.68 ml, 6.16 mmol), and 2,2,2-trifluoroethylamine (0.48 mL, 6.16 mmol). The solution was allowed to stir at rt for 17 h. The crude reaction mixture was reduced in vacuo and purified by flash column chromatography (50:45:5 v/v/v CH₂Cl₂-EtOAc-MeOH). The purified fractions were combined and triturated with CH₂Cl₂/hexanes. The white solid was collected and washed with hexanes and upon drying under vacuum yielded 2.18 g (3.92 mmol, 64% yield). ¹H-NMR (DMSO-d₆) δ 9.29 (s, 1H), 8.93 (s, 1H), 8.64-8.58 (m, 1H), 8.51 (t, J=6 Hz, 1H), 8.18 (s, 1H), 8.00 (bs, 1H), 7.91 (s, 1H), 7.52 (d, J=8 Hz, 2H), 7.51 to 7.46 (m, 1H), 7.40 to 7.30 (m, 1H), 7.28 (d, J=8 Hz, 2H), 5.05 (bs, 1H), 4.00 to 3.85 (m, 2H). MS [M+H]⁺=556.2; LCMS RT=3.32 min; TLC R_f=0.33 (2:1 v/v CH₂Cl₂-THF).

Intermediate U

Preparation of 4-amino-5-{3-fluoro-4-[({[2-fluoro-5-(trifluoromethyl)phenyl]amino}carbonyl)amino]phenyl}pyrrolo[2,1-f][1,2,4]triazine-6-carboxylic acid

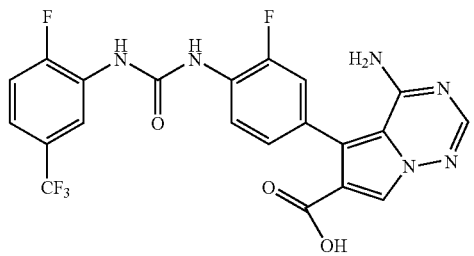

The procedure used for the preparation of Intermediate S was used to prepare the title compound by substituting Intermediate L for Intermediate J. $^1$H-NMR (DMSO-d$_6$) δ 12.3 (s, 1H), 9.43 (s, 1H), 9.27 (s, 1H), 8.65 to 8.63 (m, 1H), 8.25 to 8.20 (m, 1H), 8.07 (s, 1H), 8.02 (s, 1H); MS [M+H]$^+$=433.1; LCMS RT=2.58 min.

Intermediate V

Preparation of phenyl[4-(trifluoromethyl)pyridin-2-yl]carbamate

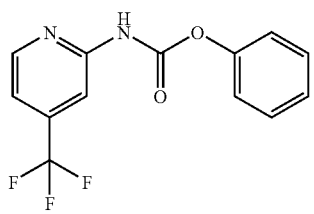

A solution of the commercially available 2-amino-4-trifluoromethylpyridine (20.86 g, 128.7 mmol) in 250 mL CH$_2$Cl$_2$ was treated with phenylchloroformate (17.81 mL, 141.5 mmol) and pyridine (22.85 mL, 283 mmol). During addition of the pyridine a yellow precipitate formed and a considerable exotherm was observed. After 0.5 h the homogeneous reaction was diluted with 1 L Et$_2$O and washed with 1N bisulfate buffer (pH 2) and sat. NaHCO$_3$. The organic layer was dried with Na$_2$SO$_4$ and evaporated to yield a gray solid. Trituration with Et$_2$O:hexanes (1:5) gave the title compound as white crystals (33.5 g, 92% Yield). $^1$H-NMR (DMSO-d$_6$) δ11.28 (s, 1H), 8.60 (d, J=5.1 Hz, 1H), 8.12 (bs, 1H), 7.40 to 7.48 (m, 3H), 7.22 to 7.31 (m, 3H); MS [M+H]$^+$=283.1; LCMS RT=3.51.

Intermediate W

Preparation of ethyl 4-amino-5-{4-[({[4-(trifluoromethyl)pyridin-2-yl]amino}carbonyl)amino]phenyl}pyrrolo[2,1-f][1,2,4]triazine-6-carboxylate

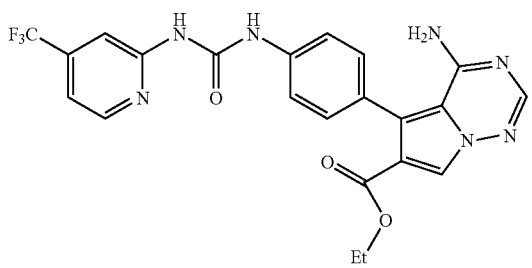

To a solution of THF (100 mL) was added phenyl[4-(trifluoromethyl)pyridin-2-yl]carbamate (1.27 g, 4.48 mmol), Intermediate H (ethyl 4-amino-5-(4-aminophenyl)pyrrolo[2,1-f][1,2,4]triazine-6-carboxylate (1.33 g, 4.48 mmol)) and triethylamine (0.63 mL, 4.48 mmol). The solution was heated at 60° C. for 3 h. Upon cooling to rt the solution was triturated with THF/Et$_2$O. The precipitate was collected and washed with Et$_2$O. Upon drying under vacuum 1.65 g of product was isolated (3.40 mmol, 76%). $^1$H-NMR (DMSO-d$_6$) δ 10.19 (s, 1H), 9.89 (s, 1H), 8.52 (d, J=5.4 Hz, 1H), 8.12 (s, 1H), 8.12 to 8.10 (m, 2H), 7.93 (s, 1H), 7.59 (d, J=6.9 Hz, 2H), 7.48 to 7.30 (m, 3H), 5.15 to 5.10 (m, 1H), 4.06 (q, J=7.2 Hz, 2H), 1.11 (t, J=7.2 Hz, 3H); MS [M+H]$^+$=486.1; LCMS RT=3.33 min; TLC R$_f$=0.27 (3:7 v/v THF—CH$_2$Cl$_2$).

Intermediate X

Preparation of 4-amino-5-{4-[({[4-(trifluoromethyl)pyridin-2-yl]amino}carbonyl)amino]phenyl}pyrrolo[2,1-f][1,2,4]triazine-6-carboxylic acid

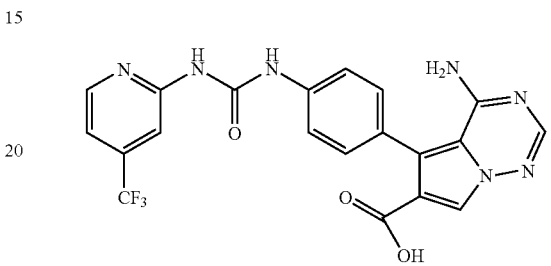

The procedure used for the preparation of Intermediate S was used to prepare the title compound by substituting Intermediate W for Intermediate J. $^1$H-NMR (DMSO-d$_6$) δ 12.3 (s, 1H), 9.87 (s, 1H), 9.75 (s, 1H), 8.53 (d, J=5.3 Hz, 2H), 8.07 to 8.06 (m, 3H), 7.86 (s, 1H), 7.58 to 7.56 (m, 2H), 7.36 to 7.33 (m, 3H); MS [M+H]$^+$=458.0; LCMS RT=2.28 min.

Intermediate Y

Preparation of N-{4-[4-amino-6-(hydroxymethyl)pyrrolo[2,1-f][1,2,4]triazin-5-yl]phenyl}-N'-[4-(trifluoromethyl)pyridin-2-yl]urea

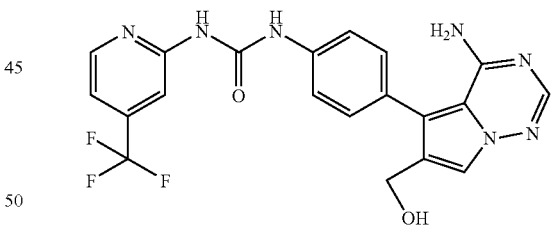

Intermediate W (0.25 g, 0.515 mmol) was suspended in THF (5 mL) and treated with 1M solution of DIBAL in THF (2 mL, 2.06 mmol). The resulting solution was stirred at room temperature for 3 hours and quenched with saturated NH$_4$Cl solution. The mixture was stirred for 1 hour. The mixture was transferred to a sep. funnel and the crude product was extracted with EtOAc. The organic layer was then washed with water and saturated NaCl solution. The organic layer was then dried over MgSO$_4$, filtered and concentrated under reduced pressure. The remaining solid was then triturated with EtOAc and filtered providing 0.22 g of product as a tan solid (0.496 mmol, 96% yield). $^1$H-NMR (DMSO) δ 11.66 (s, 1H), 9.86 (s, 1H), 9.73 (s, 1H), 8.53 (d, J=8.7 Hz, 1H), 8.05 (s, 1H), 7.82 (s, 1H), 7.65 (s, 1H), 7.61 (d, J=6.6 Hz, 2H), 7.38-7.35 (m, 3H), 4.95 (t, J=5.2 Hz, 1H), 4.37 (d, J=5.1 Hz, 2H); MS [M+H]⁺=444.0; LCMS RT=2.3 min.

Intermediate Z

Preparation of N-{4-[4-amino-6-(methoxymethyl) pyrrolo[2,1-f][1,2,4]triazin-5-yl]phenyl}-N'-[4-(trifluoromethyl)pyridin-2-yl]urea

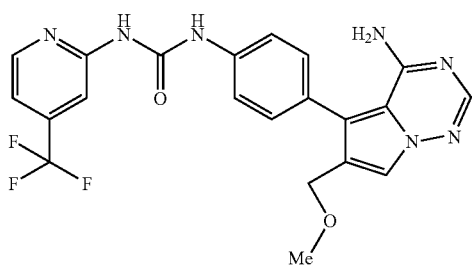

To a solution of THF (200 mL) was added Intermediate Y (N-{4-[4-amino-6-(hydroxymethyl)pyrrolo[2,1-f][1,2,4]triazin-5-yl]phenyl}-N'-[4-(trifluoromethyl)-pyridin-2-yl]urea (1.77 g, 3.98 mmol)) followed by 2M thionyl chloride in CH₂Cl₂ (19.9 mL, 39.8 mmol). The reaction was stirred at ambient temperature for 30 min, and then concentrated by rotary evaporation chasing with CH₂Cl₂. The reaction material was diluted with MeOH (100 mL) and triethyl amine (1.67 mL, 11.9 mmol) was added. The solution was heated at 60° C. for 1 h. Upon cooling to rt, the solution was concentrated in vacuo and purified by flash column chromatography (5:4:1 v/v/v CH₂Cl₂-EtOAc-MeOH). The resulting purified fractions were combined and evaporated to dryness producing 1.14 g of a pale yellow solid (2.49 mmol, yield 63%). ¹H-NMR (CD₃OD) δ 8.52 (d, J=5.4 Hz, 1H), 7.79 (s, 1H), 7.76 (s, 1H), 7.71 to 7.67 (m, 3H), 7.43 (d, J=8.6 Hz, 2H), 7.28 (d, J=5.3 Hz, 1H), 4.36 (s, 2H), 3.29 (s, 3H); MS [M+H]⁺=458.1; LCMS RT=2.66.

Intermediate AA

Preparation of N-{4-[4-amino-6-(methoxymethyl) pyrrolo[2,1-f][1,2,4]triazin-5-yl]phenyl}-N'-[2-fluoro-5-(trifluoromethyl)phenyl]urea

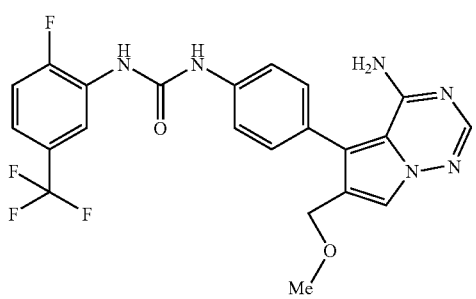

The procedure used for the preparation of intermediate Z was used to prepare the title compound by substituting Intermediate K for Intermediate Y. ¹H-NMR (CD₃OD) δ8.61 (d, J=7.6 Hz, 1H), 7.78 (s, 1H), 7.68 (s, 1H), 7.62 (d, J=8.7 Hz, 2H), 7.40 (d, J=8.6 Hz, 2H), 7.33 (d, J=8.7 Hz, 2H), 4.35 (s, 2H), 3.30 (s, 3H); MS [M+H]⁺=475.2; LCMS RT=2.81.

Intermediate AB

Preparation of N-{4-[4-amino-6-(methoxymethyl) pyrrolo[2,1-f][1,2,4]triazin-5-yl]-2-fluorophenyl}-N'-[2-fluoro-5-(trifluoromethyl)-phenyl]urea

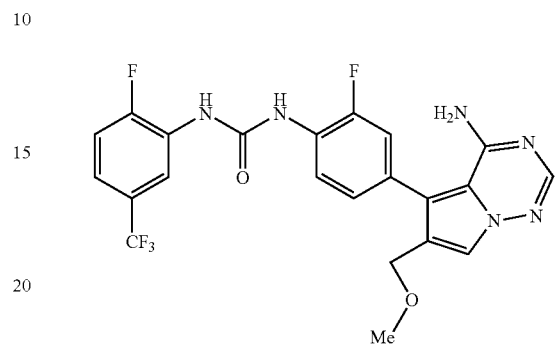

The procedure used for the preparation of Intermediate Z was used to prepare the title compound by substituting Intermediate M for Intermediate Y. ¹H-NMR (CD₃OD) δ 8.65 (d, J=8.0 Hz, 1H), 8.31 to 8.27 (m, 1H), 7.80 (s, 1H), 7.70 (s, 1H), 7.35 to 7.23 (m, 4H), 4.37 (s, 2H), 3.33 (s, 3H); MS [M+H]⁺=493.1; LCMS RT=2.84 min.

Intermediate AC

Preparation of N-{4-[4-amino-6-(cyanomethyl)pyrrolo[2,1-f][1,2,4]triazin-5-yl]-2-fluorophenyl}-N'-[2-fluoro-5-(trifluoromethyl)-phenyl]urea

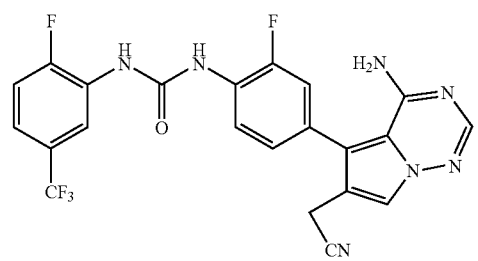

Thionyl chloride (0.31 mL, 4.18 mmol) was added dropwise to a vigorously stirring slurry of Intermediate M (1.00 g, 2.09 mmol) in THF (20 mL) and CH₂Cl₂ (20 mL). The reaction mixture was allowed to stir for 30 min where upon HPLC indicated that the reaction was complete. The reaction was concentrated and re-suspended in dichloroethane (3×). The resulting light brown powder was dissolved in 20 mL of DMSO and the NaCN (512.1 mg, 10.45 mmol) was added as a fine powder. The solution was sonicated for 10 minutes after which, HPLC indicated the reaction was complete. The reaction was diluted with 10 volumes of EtOAc and the organic layer was washed with H₂O (3×). The organic layer was dried over Na₂SO₄ and concentrated to give a light brown powder (933.0 mg, 1.91 mmol, 91%). ¹H-NMR (DMSO-d₆). δ 9.50 (d, J=3 Hz, 1H), 9.37 (d, J=2 Hz, 1H), 8.71 (dd, J=3, 7.2 Hz, 1H), 7.94 (s, 1H), 7.82 (s, 1H), 7.60-7.53 (m, 1H), 7.50-7.44 (m, 1H), 7.40 (dd, J=2, 12.6 Hz, 1H), 7.24 (dd, J=2, 8.4 Hz, 1H), 3.92 (s, 2H). MS [M+H]⁺=488; LCMS RT=3.10 min.

Intermediate AD

Preparation of N-{4-[4-amino-6-(cyanomethyl)pyrrolo[2,1-f]-[1,2,4]triazin-5-yl]phenyl}-N'-[2-fluoro-5-(trifluoromethyl)phenyl]urea

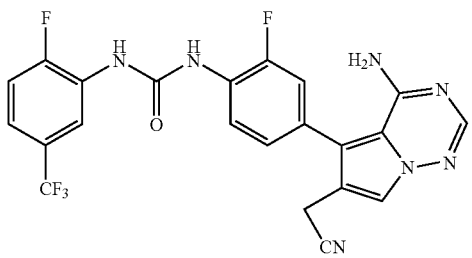

The procedure used for the preparation of Intermediate AC was used to prepare the title compound by substituting Intermediate K for Intermediate M. $^1$H-NMR (DMSO-d$_6$) δ 9.41 (s, 1H), 9.01 (d, J=3 Hz, 1H), 8.62 (d, J=3, 8 Hz, 1H), 7.81 (s, 1H), 7.77 (s, 1H), 7.61 (d, J=9 Hz, 2H), 7.47 to 7.54 (m, 1H), 7.38 to 7.42 (m, 1H), 7.35 (d, J=9 Hz, 2H), 5.35 (dd, J=2, 6 Hz), 3.82 (s, 2H); MS [M+H]$^+$=470.1; LCMS RT=2.80 min.

Intermediate AE

Preparation of N-{4-[4-amino-6-(cyanomethyl)pyrrolo[2,1-f][1,2,4]triazin-5-yl]phenyl}-N'-[4-(trifluoromethyl)pyridin-2-yl]urea

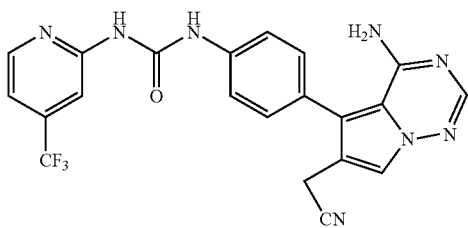

The procedure used for the preparation of Intermediate AC was used to prepare the title compound by substituting Intermediate Y for Intermediate M. $^1$H-NMR (DMSO-d$_6$) δ 8.54 (d, J=5 Hz, 1H), 8.07 (s, 1H), 7.87 (s, 1H), 7.77 (s, 1H), 7.66 (d, J=9 Hz, 2H), 7.36 (d, J=9 Hz, 2H), 7.34 to 7.36 (m, 1H), 3.81 (s, 2H); MS [M+H]$^+$=453.1; LCMS RT=2.67 min.

Intermediate AF

Preparation of N-[4-(4-amino-6-formylpyrrolo[2,1-f][1,2,4]-triazin-5-yl)phenyl]-N'-[4-(trifluoromethyl)pyridin-2-yl]urea

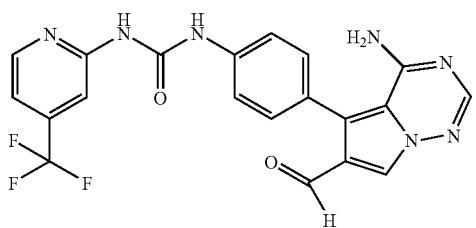

Intermediate Y (1.9 g, 4.29 mmol) was suspended in THF (20 mL) and treated with Dess-Martin periodinane (2.0 g, 4.71 mmol). The mixture was stirred at room temperature overnight and quenched with saturated NHCO$_3$ solution with Na$_2$S$_2$O$_3$. The mixture was stirred for 1 hour then transferred to a sep. funnel. The crude product was extracted with EtOAc and washed with water and saturated NaCl solution. The organic layer was then dried over MgSO$_4$, filtered and concentrated under reduced pressure. The remaining solid was then triturated with EtOAc and filtered providing 1.8 g of product as a tan solid (4.08 mmol, 95% yield). $^1$H-NMR (DMSO) δ 10.05 (bs, 1H), 9.82 (s, 1H), 9.72 (s, 1H), 8.52 (d, J=5.1 Hz, 1H), 8.26 (s, 1H), 8.07 (s, 1H), 7.95 (s, 1H), 7.64 (d, J=8.6 Hz, 2H), 7.44 (d, J=8.6 Hz, 2H), 7.35 (d, J=5.8 Hz, 1H); MS [M+H]$^+$=442.0; LCMS RT=2.81 min.

Intermediate AG

Preparation of N-{4-[4-amino-6-(1,3-oxazol-5-yl)-pyrrolo[2,1-f][1,2,4]triazin-5-yl]phenyl}-N'-[4-(trifluoromethyl)pyridin-2-yl]urea

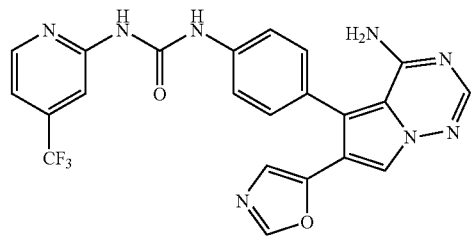

The procedure used for the preparation of Intermediate O was used to prepare the title compound by substituting Intermediate AF for Intermediate N. $^1$H-NMR (CD$_3$OD) δ 8.50 (d, J=5.3 Hz, 1H), 8.12 (s, 1H), 7.98 (s, 1H), 7.84 (s, 1H), 7.77 (s, 1H), 7.76 (d, J=8.1 Hz, 2H), 7.45 (d, J=8.0 Hz, 2H), 7.29 (d, J=6.3 Hz, 1H), 6.51 (s, 1H); MS [M+H]$^+$=481.0; LCMS RT=2.70.

Intermediate AH

Preparation of 4-amino-N-(2,2,2-trifluoroethyl)-5-{4-[({[4-(trifluoromethyl)pyridin-2-yl]amino}carbonyl)amino]phenyl}pyrrolo[2,1-f][1,2,4]triazine-6-carboxamide

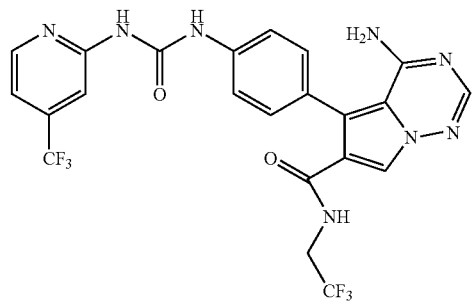

The procedure used for the preparation of Intermediate T was used to prepare the title compound by substituting Intermediate X for Intermediate S. $^1$H-NMR (CD$_3$OD) δ 8.54 (d, J=5.1 Hz, 1H), 8.19 (s, 1H), 8.06 (br s, 1H), 7.91 (s, 1H), 7.60 (d, J=8.7 Hz, 2H), 7.35 (d, J=5.6 Hz, 2H), 7.31 (d, J=8.9 Hz, 2H), 3.94 (q, J=9.2 Hz, 2H); MS [M+H]$^+$=539.0; LCMS RT=2.77.

Intermediate AI

Preparation of ethyl 4-amino-5-{3-fluoro-4-[({[4-(trifluoromethyl)pyridin-2-yl]amino}carbonyl) amino]phenyl}pyrrolo[2,1-f][1,2,4]triazine-6-carboxylate

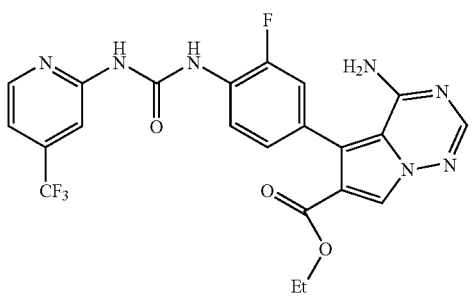

The procedure used for the preparation of Intermediate W was used to prepare the title compound by substituting Intermediate I for Intermediate H. $^1$H-NMR (DMSO-d$_6$) δ 10.14 (s, 1H), 10.11 to 10.04 (br s, 1H), 8.54 to 8.53 (d, J=5.3 Hz, 1H), 8.28 to 8.23 (t, J=8.4 Hz, 1H), 8.14 (s, 1H), 8.01 (s, 1H), 7.94 (s, 1H), 7.39 to 7.33 (m, 2H), 7.18 to 7.16 (d, J=10.0 Hz, 1H), 4.12 to 4.06 (q, J=8.3 Hz, 2H), 1.14 to 1.10 (t, J=7.1 Hz, 3H); MS [M+H]$^+$=504.1; LCMS RT=3.12 min.

Intermediate AJ

Preparation of N-{4-[4-amino-6-(hydroxymethyl)-pyrrolo[2,1-f][1,2,4]triazin-5-yl]-2-fluorophenyl}-N'-[4-(trifluoromethyl)pyridin-2-yl]urea

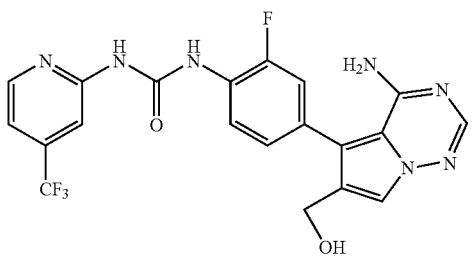

The procedure used for the preparation of Intermediate Y was used to prepare the title compound by substituting Intermediate AI for Intermediate W. $^1$H-NMR (DMSO-d$_6$) δ 10.13 (s, 1H), 10.07 to 10.02 (br s, 1H), 8.54 to 8.53 (d, J=5.3 Hz, 1H), 8.29 to 8.24 (t, J=8.5 Hz, 1H), 8.03 (s, 1H), 7.84 (s, 1H), 7.67 (s, 1H), 7.39 (s, 1H), 7.38 to 7.35 (d, J=8.7 Hz, 1H), 7.21 to 7.19 (d, J=9.7 Hz, 1H), 5.02 to 5.00 (t, J=5.1 Hz, 1H), 4.39 to 4.37 (d, J=5.2 Hz, 2H); MS [M+H]$^+$=462.0; LCMS RT=2.44 min.

Intermediate AK

Preparation of N-{4-[4-amino-6-(1,3-oxazol-5-yl) pyrrolo[2,1-f][1,2,4]triazin-5-yl]-2-fluorophenyl}-N'-[4-(trifluoromethyl)pyridin-yl]urea

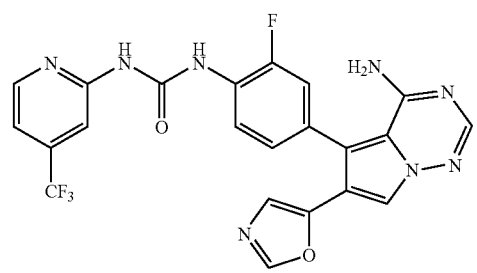

Step 1: Preparation of N-[4-(4-amino-6-formylpyrrolo[2,1-f][1,2,4]triazin-5-yl)-2-fluorophenyl]-N'-[4-(trifluoromethyl)pyridin-2-yl]urea

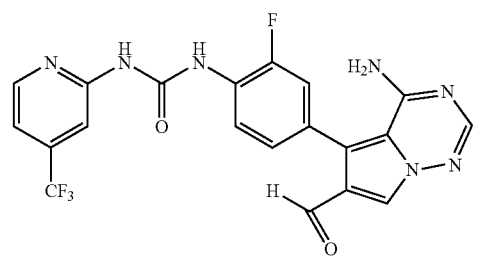

The procedure used for the preparation of Intermediate AF was used to prepare the title compound by substituting Intermediate AJ for Intermediate Y. $^1$H-NMR (DMSO-d$_6$) δ 10.16 (s, 1H), 10.13 to 10.08 (br s, 1H), 9.76 (s, 1H), 8.55 to 8.54 (d, J=5.3 Hz, 1H), 8.34 to 8.29 (t, J=8.6 Hz, 1H), 8.28 (s, 1H), 8.01 (s, 1H), 7.97 (s, 1H), 7.48 to 7.45 (d, J=11.2 Hz, 1H), 7.39 to 7.38 (d, J=5.7 Hz, 1H), 7.29 to 7.27 (d, J=8.1 Hz, 1H); MS [M+H]$^+$=459.9; LCMS RT=2.96 min.

Step 2: Preparation of Title Compound

To a solution of THF (10 mL) and MeOH (10 mL) cooled in an ice/water bath was added 0.5 M sodium methoxide in MeOH (0.96 mL, 0.48 mmol) followed by TosMIC (93 mg, 0.48 mmol). The solution was allowed to stir for 5 min and then N-[4-(4-amino-6-formylpyrrolo[2,1-f][1,2,4]triazin-5-yl)-2-fluorophenyl]-N'-[4-(trifluoromethyl)pyridin-2-yl] urea (73 mg, 0.16 mmol) was added. The solution was heated to 60° C. for 17 h. The reaction mixture was allowed to cool and was transferred to a separatory funnel, diluted with EtOAc (20 mL), washed with aq saturated NaHCO$_3$ (20 mL) and H$_2$O (20 mL). The aqueous layer was back extracted with EtOAc (2×20 mL). The combined organic layers were dried (MgSO$_4$), filtered, evaporated in vacuo and purified by flash chromatography 5:4:1 v/v/v DCM/EtOAc/MeOH the resulting purified fractions were combined and evaporated providing 26 mg of the title compound as a white solid (0.052 mmol, yield 33%). ¹H-NMR (DMSO-d₆) δ 10.18 (s, 1H), 10.16 to 10.12 (br s, 1H), 8.55 to 8.54 (d, J=5.4 Hz, 1H), 8.35 to 8.31 (t, J=8.3 Hz, 1H), 8.30 (s, 1H), 8.10 (s, 1H), 8.01 (s, 1H), 7.91 (s, 1H), 7.39 to 7.36 (m, 2H), 7.23 to 7.21 (d, J=10.4 Hz, 1H), 6.63 (s, 1H); MS [M+H]⁺=499.0; LCMS RT=2.85 min.

Intermediate AL

Preparation of N-{4-[4-amino-6-(methoxymethyl)pyrrolo[2,1-f][1,2,4]triazin-5-yl]-2-fluorophenyl}-N'-[4-(trifluoromethyl)pyridin-2-yl]urea

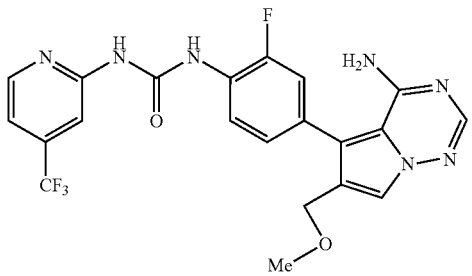

The procedure used for the preparation of Intermediate Z was used to prepare the title compound by substituting Intermediate AJ for Intermediate Y. ¹H-NMR (DMSO-d₆) δ 10.14 (s, 1H), 10.09 to 10.04 (br s, 1H), 8.54 to 8.53 (d, J=5.5 Hz, 1H), 8.30 to 8.26 (t, J=8.5 Hz, 1H), 8.00 (s, 1H), 7.86 (s, 1H), 7.76 (s, 1H), 7.39 to 7.38 (d, J=5.2 Hz, 1H), 7.35 to 7.32 (d, J=12.0 Hz, 1H), 7.21 to 7.18 (d, J=10.2 Hz, 1H), 4.28 (s, 2H), 3.22 (s, 3H); MS [M+H]⁺=476.1; LCMS RT=2.77 min.

Intermediate AM

Preparation of N-{4-[4-amino-6-(cyanomethyl)pyrrolo[2,1-f][1,2,4]triazin-5-yl]-2-fluorophenyl}-N'-[4-(trifluoromethyl)pyridin-2-yl]urea

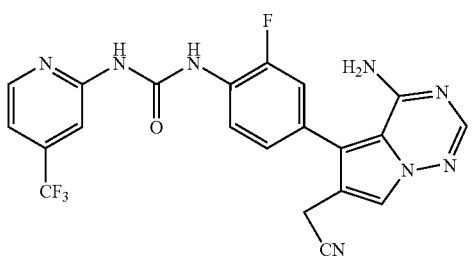

The procedure used for the preparation of Intermediate AC was used to prepare the title compound by substituting Intermediate AJ for Intermediate M. ¹H-NMR (Acetone-d₆) δ 10.99 (s, 1H), 9.39 (s, 1H), 8.59 to 8.58 (d, J=5.1 Hz, 1H), 8.51 to 8.47 (t, J=8.5 Hz, 1H), 7.84 (s, 1H), 7.82 to 7.81 (d, J=6.4 Hz, 1H), 7.75 (s, 1H), 7.38 to 7.35 (m, 2H), 7.30 to 7.28 (d, J=8.4 Hz, 1H), 3.86 (s, 2H); MS [M+H]⁺=471.0; LCMS RT=2.75 min.

Intermediate AN

Preparation of ethyl 4-amino-5-{4-[({[6-(trifluoromethyl)pyridin-2-yl]amino}carbonyl)amino]phenyl}pyrrolo[2,1-f][1,2,4]triazine-6-carboxylate

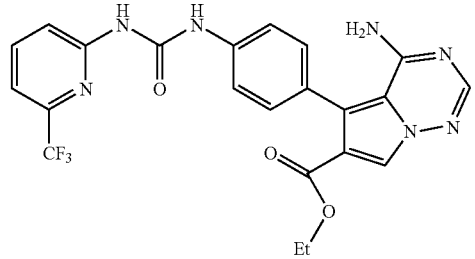

The procedure used for the preparation of Intermediate W was used to prepare the title compound by substituting phenyl [6-(trifluoromethyl)pyridin-2-yl]carbamate for phenyl (4-tert-butylpyridin-2-yl)carbamate. ¹H-NMR (DMSO-d₆) δ 9.89 (s, 1H), 9.74 (s, 1H), 8.13 (s, 1H), 8.02 to 7.97 (m, 2H), 7.92 (s, 1H), 7.55 (d, J=9 Hz, 2H), 7.53 to 7.50 (m, 1H), 7.35 (d, J=9 Hz, 2H), 5.12 (bs, 1H), 4.07 (q, J=7 Hz, 2H), 1.09 (t, J=7 Hz, 3H); MS [M+H]⁺=486.0; LCMS RT=2.92 min; TLC R_f=0.38 (3:1 v/v CH₂Cl₂-THF).

Intermediate AO

Preparation of 4-amino-5-{4-[({[6-(trifluoromethyl)-pyridin-2-yl]amino}carbonyl)amino]phenyl}pyrrolo[2,1-f][1,2,4]triazine-6-carboxylic acid

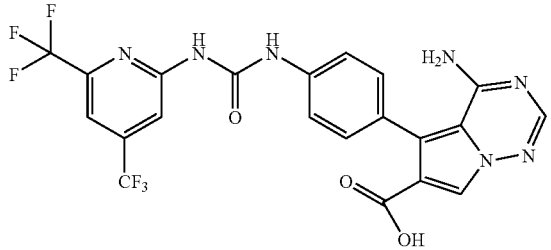

The procedure used for the preparation of Intermediate S was used to prepare the title compound by substituting Intermediate AN for Intermediate J. ¹H-NMR (DMSO) δ 10.29 (bs, 1H), 8.03 to 7.96 (m, 3H), 7.86 (s, 1H), 7.53 (d, J=8.5 Hz, 2H), 7.45 (d, J=7.0 Hz, 1H), 7.33 (d, J=8.6 Hz, 2H); MS [M+H]⁺=458.1; LCMS RT=2.51 min.

Intermediate AP

Preparation of 4-amino-N-(2,2,2-trifluoroethyl)-5-{4-[({[6-(trifluoromethyl)pyridin-2-yl]amino}carbonyl)-amino]phenyl}pyrrolo-[2,1-f][1,2,4]triazine-6-carboxamide

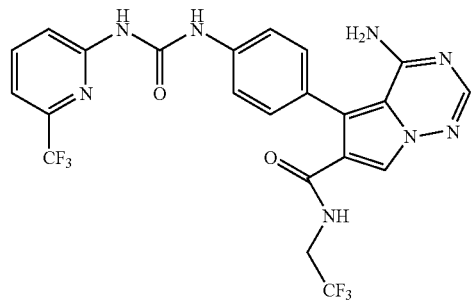

The procedure used for the preparation of Intermediate T was used to prepare the title compound by substituting Intermediate AO for Intermediate S. ¹H-NMR (CD₃OD) δ 8.05 (s, 1H), 7.97 (s, 1H), 7.85 (s, 1H), 7.67 (d, J=8.7 Hz, 2H), 7.56 (d, J=8.7 Hz, 1H), 7.46 to 7.41 (m, 3H), 3.94 (q, J=8.9 Hz, 2H); MS [M+H]⁺=539.0; LCMS RT=2.71.

Intermediate AQ

-{4-[4-amino-6-(methoxymethyl)pyrrolo[2,1-f][1,2,4]triazin-5-yl]phenyl}-N'-[6-(trifluoromethyl)pyridin-2-yl]urea

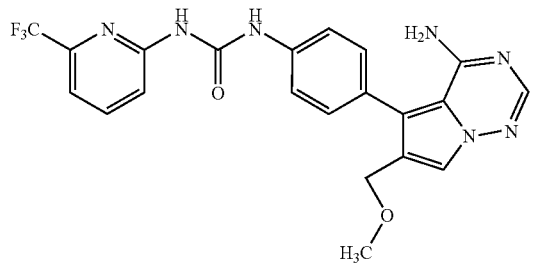

Step 1: Preparation of N-{4-[4-amino-6-(hydroxymethyl)pyrrolo[2,1-f][1,2,4]triazin-5-yl]phenyl}-N'-[6-(trifluoromethyl)pyridin-2-yl]urea

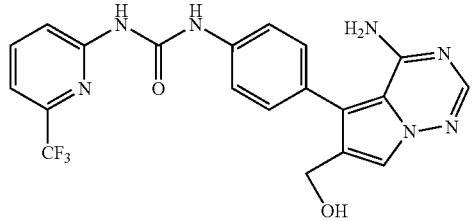

The procedure used for the preparation of Intermediate Y was used to prepare the title compound by substituting Intermediate AN for Intermediate W. ¹H-NMR (DMSO-d₆) δ 9.87 (s, 1H), 9.71 (s, 1H), 8.03 to 7.99 (m, 3H), 7.82 (s, 1H), 7.65 (s, 1H), 7.57 to 7.55 (m, 3H), 7.50 to 7.47 (m, 1H), 7.37 (d, J=8.5 Hz, 2H), 4.97 to 4.94 (m, 1H), 4.36 (d, J=5.2 Hz, 2H); MS [M+H]⁺=444.0; LCMS RT=2.24 min.

Step 2: Preparation of Title Compound

The procedure used for the preparation of Intermediate Z was used to prepare the title compound by substituting N-{4-[4-amino-6-(hydroxymethyl)pyrrolo[2,1-f][1,2,4]triazin-5-yl]phenyl}-N'-[6-(trifluoromethyl)pyridin-2-yl]urea for Intermediate Y. ¹H-NMR (DMSO-d₆) δ 9.90 (s, 1H), 9.74 (s, 1H), 8.05 to 7.99 (m, 2H); 7.85 (s, 1H), 7.75 (s, 1H), 7.58 (d, J=8.8, 2H), 7.50 (dd, J=8.8, J=6.8, 1.2, 1H), 7.37 (d, J=8.0, 2H), 4.26 (s, 2H), 3.19 (s, 3H); MS [M+H]⁺=457.9; LCMS RT=2.70.

Intermediate AR

Preparation of N-{4-[4-amino-6-(methoxymethyl)-pyrrolo[2,1-f][1,2,4]triazin-5-yl]phenyl}-N'-[2-chloro-5-(trifluoromethyl)-phenyl]urea

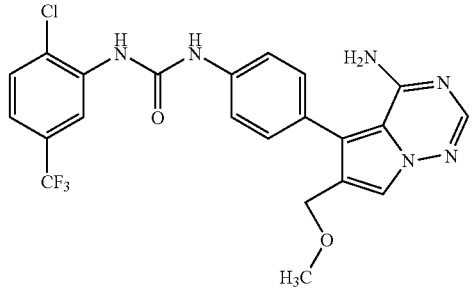

Step 1: Preparation of ethyl 4-amino-5-{4-[({[2-chloro-5-(trifluoromethyl)phenyl]amino}carbonyl)amino]phenyl}pyrrolo[2,1-f][1,2,4]triazine-6-carboxylate

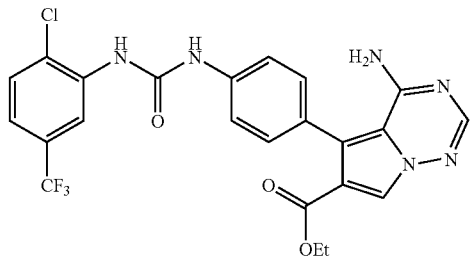

To a solution of DCE (5 mL) was added Intermediate H (300 mg, 1.01 mmol) followed by 2-chloro-1-isocyanato-4-(trifluoromethyl)benzene (0.32 mL, 2.12 mmol). The reaction was stirred under N₂ at rt for 1 h, and then aq 2N HCl (0.50 mL, 1.01 mmol) was added to the reaction followed by DMF (5 mL). The solution was heated for an additional 1 h. Upon cooling to rt, the solution was diluted with EtOAc, transferred to a separatory funnel, and washed with aq saturated NaHCO₃. The aq layer was back extracted with EtOAc. The combined organic layers were collected, dried, concentrated, and purified by column chromatography (95:5 v/v CH₂Cl₂-MeOH). The resulting fractions containing product were concentrated and triturated using CH₂Cl₂ and hexanes. The product was filtered and dried in vacuo to afford 408 mg of the above compound as a white solid (0.79 mmol, yield 78%). ¹H-NMR (DMSO-d₆) δ 9.72 (s, 1H), 8.67 (s, 1H), 8.64 (s, 1H), 8.13 (s, 1H), 8.08 (br s, 1H), 7.93 (s, 1H), 7.72 (d, J=8.5 Hz, 1H), 7.56 (d, J=8.8 Hz, 2H), 7.39 to 7.36 (m, 1H), 7.34 (d, J=8.6 Hz, 2H), 5.10 (br s, 1H), 4.09 (q, J=7.0 Hz, 2H), 1.12 (t, J=7.1 Hz, 3H); MS [M+H]⁺=519; LCMS RT=3.58 min; TLC R_f=0.26 (95:5 v/v CH₂Cl₂-MeOH).

Step 2: Preparation of N-{4-[4-amino-6-(hydroxymethyl)pyrrolo[2,1-f][1,2,4]triazin-5-yl]phenyl}-N'-[2-chloro-5-(trifluoromethyl)phenyl]urea

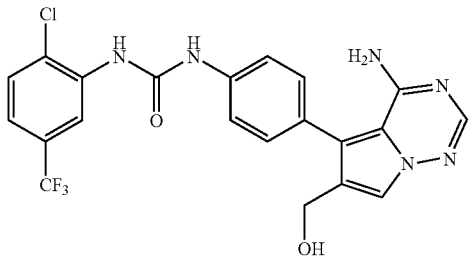

The procedure used for the preparation of Intermediate Y was used to prepare by substituting ethyl 4-amino-5-{4-[({[2-chloro-5-(trifluoromethyl)-phenyl]amino}carbonyl)-amino]phenyl}pyrrolo[2,1-f][1,2,4]triazine-6-carboxylate for Intermediate W.

Step 3: Preparation of Title Compound

The procedure used for the preparation of Intermediate Z was used to prepare the title compound by substituting N-{4-[4-amino-6-(hydroxymethyl)pyrrolo[2,1-f]-[1,2,4]triazin-5-yl]phenyl}-N'-[2-chloro-5-(trifluoromethyl)-phenyl]urea for Intermediate Y. ¹H-NMR (DMSO-d₆) δ 8.55 (s, 1H), 7.84 (s, 1H), 7.74 (s, 1H); 7.68 to 7.62 (m, 3H), 7.33 to 7.28 (m, 3H), 4.26 (s, 2H), 3.19 (s, 3H); MS [M+H]⁺=491.1; LCMS RT=3.25.

Intermediate AS

Preparation of N-{4-[4-amino-6-(cyanomethyl)pyrrolo[2,1-f][1,2,4]triazin-5-yl]-2-fluorophenyl}-N'-[2-chloro-5-(trifluoromethyl)phenyl]urea

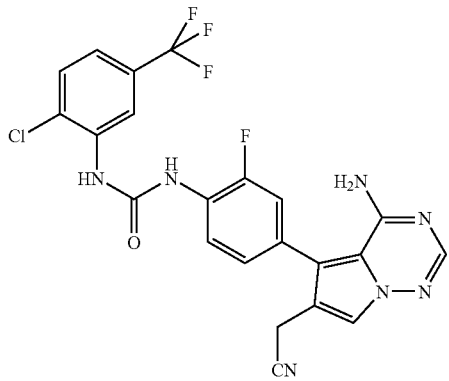

Step 1: Preparation of ethyl 4-amino-5-{4-[({[2-chloro-5-(trifluoromethyl)phenyl]amino}carbonyl)amino]-3-fluorophenyl}pyrrolo[2,1-f][1,2,4]triazine-6-carboxylate

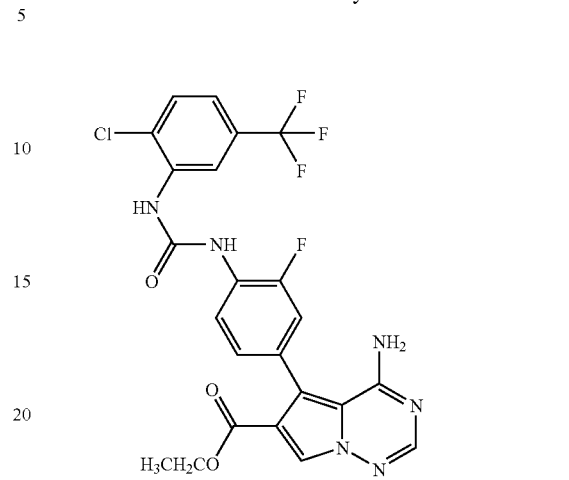

The procedure used for the preparation of Intermediate AR, step 1 was used to prepare ethyl 4-amino-5-{4-[({[2-chloro-5-(trifluoromethyl)phenyl]amino}-carbonyl)-amino]-3-fluorophenyl}pyrrolo[2,1-f][1,2,4]triazine-6-carboxylate by substituting Intermediate I for Intermediate H. ¹H-NMR (CD₃OD) δ 9.46 (s, 1H), 8.91 (d, J=4.8 Hz, 1H), 8.65 (d, J=2.4 Hz, 1H), 8.31-8.27 (m, 2H), 8.01 (s, 1H), 7.63 (d, J=8.0 Hz, 1H), 7.35-7.23 (m, 3H), 4.18 (q, J=8.0 Hz, 2H), 1.20 (t, J=8.0 Hz, 3H); MS [M+H]⁺=537.2; LCMS RT=3.76.

Step 2: Preparation of N-{4-[4-amino-6-(hydroxymethyl)pyrrolo[2,1-f][1,2,4]triazin-5-yl]-2-fluorophenyl}-N'-[2-chloro-5-(trifluoromethyl)phenyl]urea

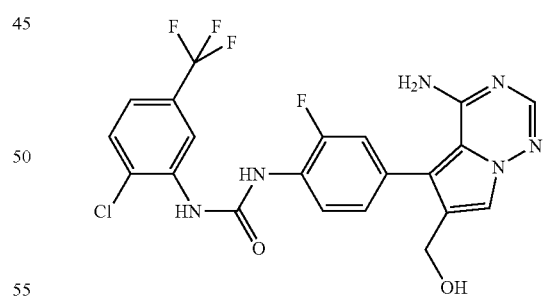

The procedure used for the preparation of Intermediate AR, step 2 was used to prepare the intermediate methyl alcohol derivative by substituting ethyl 4-amino-5-{4-[({[2-chloro-5-(trifluoromethyl)phenyl]amino}carbonyl)amino]-3-fluorophenyl}-pyrrolo-[2,1-f][1,2,4]triazine-6-carboxylate for ethyl 4-amino-5-{4-[({[2-chloro-5-(trifluoro-methyl)-phenyl]amino}carbonyl)amino]phenyl}pyrrolo[2,1-f][1,2,4]-triazine-carboxylate. ¹H-NMR (CD₃OD) δ8.65 (d, J=2.4 Hz, 1H), 8.31 (t, J=8.4 Hz, 1H), 7.89 (s, 1H), 7.82 (s, 1H), 7.63 (d, J=8.4 Hz, 1H), 7.38-7.28 (m, 3H), 4.54 (s, 2H); MS [M+H]⁺=495.2; LCMS RT=3.08.

Step 3: Preparation of Title Compound

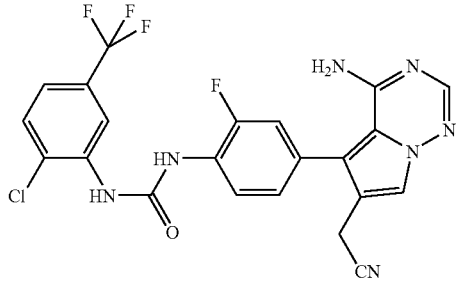

The procedure used for the preparation of Intermediate AC was used to prepare the title compound by substituting N-{4-[4-amino-6-(hydroxymethyl)pyrrolo[2,1-f][1,2,4]triazin-5-yl]-2-fluorophenyl}-N'-[2-chloro-5-(trifluoromethyl)phenyl]urea for Intermediate M. ¹H-NMR (CD₃OD) δ 9.48 (s, 1H), 8.92 (s, 1H), 8.66 (s, 1H), 8.40-8.35 (m, 1H), 7.94 (s, 1H), 7.89 (s, 1H), 7.64 (d, J=9.2 Hz, 1H), 7.36 (d, J=2.0 Hz, 1H), 7.34-7.32 (m, 1H), 7.29-7.26 (m, 1H), 3.82 (s, 2H); MS [M+H]⁺=504; LCMS RT=3.10.

Intermediate AT

Preparation of 4-amino-7-bromo-5-{4-[({[2-fluoro-5-(trifluoromethyl)-phenyl]amino}carbonyl)amino]phenyl}-N-(2,2,2-trifluoroethyl)pyrrolo[2,1-f][1,2,4]triazine-6-carboxamide

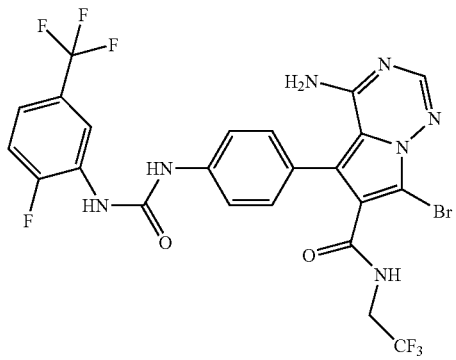

To a suspension of Intermediate T (4-amino-5-{4-[({[2-fluoro-5-(trifluoromethyl)phenyl]amino}carbonyl)amino]phenyl}-N-(2,2,2-trifluoroethyl)-pyrrolo-[2,1-f][1,2,4]triazine-6-carboxamide (505 mg, 0.9 mmol)) in acetonitrile (20 ml) was added N-bromosuccinimide (177 mg, 1.0 mmol) and the reaction mixture was heated at 60° C. in a sealed vial for 1 h. After cooling to 0° C., the crude was filtered and washed with cold CH₃CN (3×) and subsequently ethyl ether to afford 550 mg as solid. No further purification was needed. MS [M+H]⁺=634.1; LCMS RT=3.12 min.

Intermediate AU

Preparation of 4-amino-5-4-[({[2-fluoro-5-(trifluoromethyl)-phenyl]aminocarbonyl)amino]phenyl-7-formyl-N-(2,2,2-trifluoroethyl)pyrrolo-[2,1-f][1,2,4]triazine-6-carboxamide

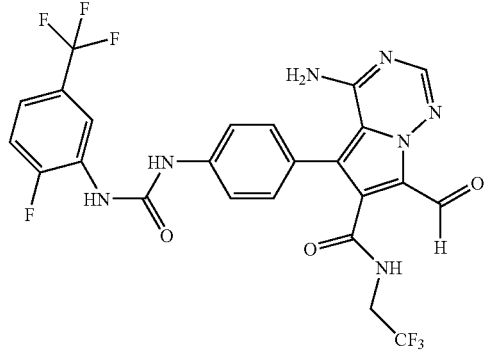

To a solution Intermediate AT ((4-amino-7-bromo-5-{4-[({[2-fluoro-5-(trifluoromethyl)phenyl]amino}carbonyl)amino]phenyl}-N-(2,2,2-trifluoro-ethyl)-pyrrolo-[2,1-f][1,2,4]triazine-6-carboxamide (400 mg, 0.63 mmol)) in THF (10 ml) at −78° C. under N₂ was added n-BuLi (1.26 ml, 3.15 mmol) slowly. After 15 min., DMF was added and the reaction mixture was allowed to warm up to rt. The reaction was diluted with EtOAc and was washed with H₂O (3×). The organic layer was dried (Na₂SO₄), concentrated and purified via flash column chromatography (95:5 v/v CH₂Cl₂-MeOH) to afford 230 mg of the title compound (yield 62%). ¹H-NMR (DMSO-d₆) δ10.36 (s, 1H), 9.33 (s, 1H), 9.05 (dd, J=6 Hz, 1H), 9.93 (d, J=3 Hz, 1H), 8.63 to 8.59 (m, 1H), 8.21 (s, 1H), 7.93 (s, 3H), 7.55 to 7.32 (m, 6H), 3.98 to 3.92 (m, 2H); MS [M+H]⁺=584.0; LCMS RT=3.21 min.

Intermediate AV

Preparation of N-{4-[4-amino-7-bromo-6-(methoxymethyl)-pyrrolo[2,1-f][1,2,4]triazin-5-yl]phenyl}-N'-[2-fluoro-5-(trifluoromethyl)-phenyl]urea

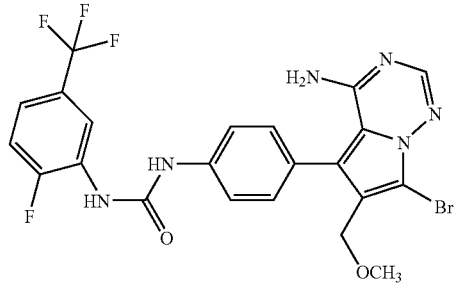

To a suspension of Intermediate AA (N-{4-[4-amino-6-(methoxymethyl)pyrrolo[2,1-f][1,2,4]triazin-5-yl]phenyl}-N'-[2-fluoro-5-(trifluoro-methyl)phenyl]urea (750 mg, 1.58 mmol)) in acetonitrile (7 ml) was added N-bromosuccinimide (365 mg, 2.0 mmol) and the mixture was heated at 60 C in a sealed vial for 1 h. After cooling to 0° C., the reaction was filtered and washed with cold $CH_3CN$ and ethyl ether (3×) to give the crude product as a solid, which was purified via flash column chromatography (95:5 v/v $CH_2Cl_2$-MeOH) to afford additional 50 mg of the title compound. $^1$H-NMR (DMSO-$d_6$) δ 9.34 (s, 1H), 8.95 (d, J=3 Hz, 1H), 8.6 (m, 1H), 7.98 (s, 1H), 7.60 (d, J=3 Hz, 1H), 7.57 to 7.58 (m, 1H), 7.49 (m, 1H), 7.38 to 7.34 (m, 2H), 4.21 (s, 2H), 3.16 (s, 3H); MS [M+H]$^+$=553; LCMS RT=3.24 min.

Intermediate AW

Preparation of N-{4-[4-amino-7-formyl-6-(methoxymethyl)-pyrrolo[2,1-f][1,2,4]triazin-5-yl]phenyl}-N'-[2-fluoro-5-(trifluoromethyl)-phenyl]urea

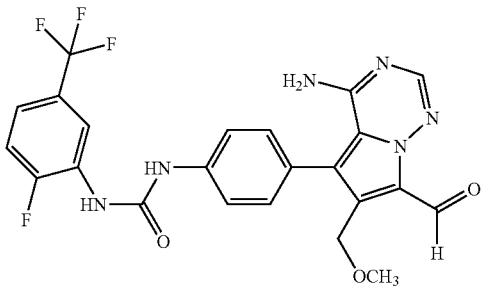

The procedure used for the preparation of Intermediate AU was used to prepare the title compound by substituting Intermediate AV (N-{4-[4-amino-7-bromo-6-(methoxymethyl)pyrrolo[2,1-f][1,2,4]triazin-5-yl]phenyl}-N'-[2-fluoro-5-(trifluoro-methyl)phenyl]urea) for Intermediate AT (4-amino-7-bromo-5-{4-[({[2-fluoro-5-(trifluoromethyl)phenyl]amino}carbonyl)amino]phenyl}-N-(2,2,2-trifluoroethyl)-pyrrolo-[2,1-f][1,2,4]triazine-6-carboxamide). The title compound was obtained as isolated and was used without further purification. MS [M+H]$^+$=503; LCMS RT=3.21 min.

Intermediate AX

Preparation of 1-[4-amino-5-(4-amino-3-fluorophenyl)-7-(morpholin-4-ylmethyl)pyrrolo[2,1-f][1,2,4]triazin-6-yl]ethanone

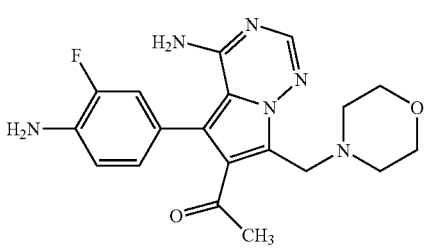

Step 1: Preparation of 1H-pyrrole-2,4-dicarbonitrile

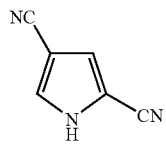

To a solution of ACN (15 mL) was added pyrrole (1.03 mL, 14.9 mmol) which was cooled in an ice/salt bath. Chlorosulfonyl isocyanate (2.73 mL, 31.3 mmol) was diluted in ACN (5 mL) and then added to the reaction dropwise over the following 30 min. The ice/salt bath was removed and the solution was allowed to warm to rt over the next 1.5 h. The solution was then cooled in an ice/salt bath and DMF (5.00 mL, 65.0 mmol) was slowly added via an addition funnel. The solution was allowed to slowly warm to rt over 17 h. The solution was cooled in an ice/salt bath and aq 1N NaOH (50 mL) was added followed by EtOAc (50 mL). The solution was transferred to a separatory funnel, and the organic layer was isolated and the aqueous layer was back extracted with EtOAc (2×). The collected organic was washed with aq saturated $NaHCO_3$ followed by $H_2O$ (100 mL). The aqueous layers were back extracted with EtOAc (2×50 mL). The combined organic layers were collected, dried ($MgSO_4$), concentrated onto silica gel, and purified by column chromatography (9:1 v/v $CH_2Cl_2$-EtOAc) to afford 1.28 g of the above compound as a white solid (10.9 mmol, yield 73%). $^1$H-NMR (DMSO-$d_6$) δ 13.29 (br s, 1H), 8.00 (s, 1H), 7.49 (s, 1H); LCMS RT=1.65 min.

Step 2: Preparation of 1-amino-1H-pyrrole-2,4-dicarbonitrile

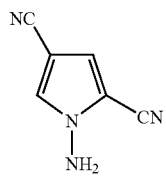

To a solution of DMF (100 mL) was added 1H-pyrrole-2,4-dicarbonitrile (1.00 g, 8.54 mmol) followed by NaH, 60% dispersion in mineral oil (0.51 g, 12.8 mmol). The solution was stirred at rt for 15 min and then (aminooxy)(diphenyl)phosphine oxide (2.99 g, 12.8 mmol) was added, and the solution was heated to 80° C. for 2 h. Upon cooling to rt the solution was filtered washing with $CH_2Cl_2$. The solution was partially concentrated and a white precipitate formed which was filtered. The mother liquor was then evaporated under vacuum and subsequently purified by MPLC (Isco) 100% $CH_2Cl_2$ ramping to 9:1 v/v $CH_2Cl_2$-EtOAc. The resulting purified fractions were combined and concentrated in vacuo yielding 0.92 g of a white solid (6.98 mmol, yield 82%). $^1$H-NMR (DMSO-$d_6$) δ7.92 (d, J=1.8 Hz, 1H), 7.39 (d, J=1.9 Hz, 1H), 6.66 (s, 2H); MS [M+H]$^+$=133.0; LCMS RT=0.96 min.

Step 3: Preparation of 4-aminopyrrolo[2,1-f][1,2,4]triazine-6-carbonitrile

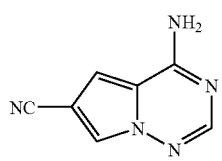

To a solution of EtOH (50 mL) was added 1-amino-1H-pyrrole-2,4-dicarbonitrile (1.00 g, 7.57 mmol) followed by formamidine acetate (9.46 g, 90.8 mmol) and potassium carbonate (14.6 g, 106.0 mmol). The solution was heated to 80° C. for 2 h. Upon cooling to rt, the reaction mixture was diluted with EtOAc transferred to a separatory funnel and washed with water. The organic layer was collected, dried (MgSO$_4$), filtered, and concentrated to dryness. The crude material was then triturated with EtOH-water. The solid was collected, washed with water, and dried under vacuum to afford 0.91 g of the above compound as a yellow-orange solid (5.70 mmol, yield 75%). $^1$H-NMR (DMSO-d$_6$) δ 8.37 (d, J=1.8 Hz, 1H), 8.19 (d, J=17.4, 2H), 7.93 (s, 1H), 7.27 (d, J=1.8 Hz, 1H); LCMS RT=1.14 min.

Step 4: Preparation of 4-aminopyrrolo[2,1-f][1,2,4]triazine-6-carbaldehyde

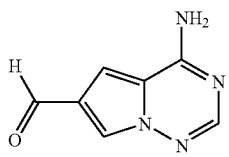

To a solution of THF (200 mL) was added 4-aminopyrrolo[2,1-f][1,2,4]triazine-6-carbonitrile (1.00 g, 6.28 mmol). The solution was heated until all stalling material was in solution and was then cooled in an ice-water bath. 1M Diisobutylaluminum hydride in THF (50.3 mL, 50.3 mmol) was then added to the solution which was stirred for 1 h. EtOAc was added to the solution and it was then allowed to warm to it. Wet silica gel was carefully pipetted into the solution, and the reaction mixture was heated to 50° C. for 30 min, filtered through Celite, and washed with excess EtOAc. The solution was transferred to a separatory funnel and washed with water. The organic layer was collected, dried (MgSO$_4$), filtered, and concentrated to dryness yielding 0.92 g of yellow solid (5.69 mmol, yield 91%). $^1$H-NMR (DMSO-d$_6$) δ9.91 (s, 1H) 7.92 (d, J=1.7 Hz, 1H), 8.14 (d, J=35.3 Hz, 2H), 7.89 (s, 1H), 7.30 (d, J=1.8 Hz, 1H); MS [M+H]$^+$=163.3; LCMS RT=1.07 min.

Step 5: Preparation of 1-(4-aminopyrrolo[2,1-f][1,2,4]triazin-6-yl)ethanol

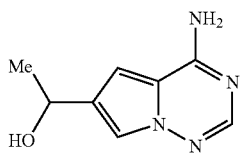

To a solution of THF (100 mL) was added 3.0 M methylmagnesium bromide in diethyl ether (14.0 mL, 41.9, mmol) cooled in an ice bath. Then 4-aminopyrrolo[2,1-f][1,2,4]triazine-6-carbaldehyde (0.68 g, 4.19 mmol) was added as a solution in THF (200 mL) via an addition funnel. The reaction was allowed to slowly warm to rt over the following 17 h. The reaction was carefully treated with MeOH (10 mL) followed by aq saturated NH$_4$Cl (50 mL) and EtOAc (50 mL). The solution was transferred to a separatory funnel and the organic layer was isolated while the aqueous layer was back extracted with EtOAc (4×20 mL). The combined organic layers were collected, dried (MgSO$_4$), filtered, and concentrated to dryness. The crude material was then purified by flash chromatography (85:15 v/v CH$_2$Cl$_2$-MeOH). The purified fractions were concentrated in vacuo and then dried under vacuum to afford 422 mg of the above compound (2.37 mmol, yield 56%). $^1$H-NMR (DMSO-d$_6$) δ 7.72 (s, 1H), 7.59 (br s, 2H), 7.45 (dd, J=0.5 Hz, 1.7 Hz, 1H), 6.76 (dd, J=0.5 Hz, 1.7 Hz, 1H), 5.03 (d, J=4.7 Hz, 1H), 4.79 (m, 1H), 1.38 (d, J=6.5 Hz, 3H); MS [M+H]$^+$=179.3; LCMS RT=1.04 min.

Step 6: Preparation of 1-[4-amino-7-(morpholin-4-ylmethyl)pyrrolo[2,1-f][1,2,4]triazin-6-yl]ethanol

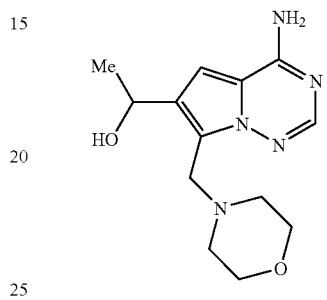

To a solution of AcOH (70 mL) was added 1-(4-aminopyrrolo[2,1-f][1,2,4]triazin-6-yl)ethanol (611 mg, 3.43 mmol) followed by the addition of a 0.5 M solution of 37% formaldehyde in water (0.26 mL, 3.43 mmol) and morpholine (0.30 mL, 3.43 mmol) in AcOH (6.86 mL) was added. The reaction was heated to 60° C. for 1.5 h. The solution was allowed to cool to rt and was then evaporated via rotary evaporation chasing the remaining AcOH with toluene. The crude material was purified by column chromatography (85:15 v/v CH$_2$Cl$_2$-EtOAc) to afford 633 mg of the above compound (2.28 mmol, yield 67%). $^1$H-NMR (DMSO-d$_6$) δ 7.79 (s, 1H), 7.57 (br s, 2H), 6.85 (s, 1H), 4.94 (m, 1H), 3.84 (m, 2H), 3.49 (m, 4H), 2.37 (m, 4H), 1.41 (d, J=6.6 Hz, 3H); MS [M+H]$^+$=278.0; LCMS RT=1.01 min.

Step 7: Preparation of ethyl 1-[4-amino-5-bromo-7-(morpholin-4-ylmethyl)-pyrrolo[2,1-f][1,2,4]triazin-6-yl]ethanol

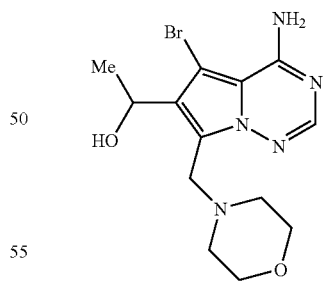

To a solution of THF (500 mL) was added 1-[4-amino-7-(morpholin-4-ylmethyl)pyrrolo[2,1-f][1,2,4]triazin-6-yl]ethanol (2.49 g, 8.99 mmol), which was cooled in an ACN-dry ice bath. Then 1,3-dibromo-5,5-dimethylhydantoin (1.29 g, 4.50 mmol) was added and in two batches 20 min apart and the reaction stirred for a total of 45 min. The reaction was quenched with aq saturated Na$_2$SO$_3$ (500 mL) as the solution warmed to rt. EtOAc (500 mL) was added to the reaction and the solution was transferred to a separatory funnel and the organic layer was isolated while the aqueous layer was back extracted with EtOAc (2×200 mL). The combined organic layers were collected, dried (MgSO₄), filtered, and concentrated to dryness. The crude material was purified by MPLC (Isco) 100% CH₂Cl₂ to 9:1 v/v CH₂Cl₂-MeOH. The resulting purified fractions were combined and concentrated in vacuo yielding 2.52 g of the above compound (7.09 mmol, yield 79%). ¹H-NMR (DMSO-d₆) δ 7.85 (s, 1H), 5.85 (d, J=5.3, 1H), 4.91 (m, 1H), 4.01 (d, J=13.6 Hz, 1H), 3.87 (d, J=13.2 Hz, 1H), 3.50 (m, 2H), 2.50 (m, 4H), 2.39 (m, 4H), 1.45 (d, J=6.5 Hz, 3H); MS [M+H]⁺=355.9; LCMS RT=1.08 min.

Step 8: Preparation of 1-[4-amino-5-bromo-7-(morpholin-4-ylmethyl)-pyrrolo[2,1-f][1,2,4]triazin-6-yl] ethanone

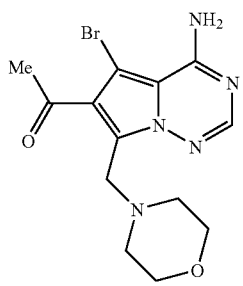

To a solution of THF (100 mL) was added ethyl 1-[4-amino-5-bromo-7-(morpholin-4-ylmethyl)pyrrolo[2,1-f][1,2,4]triazin-6-yl]ethanol (419 mg, 1.18 mmol) followed by Dess-Martin periodinane (748 mg, 1.76 mmol). The solution was stirred at rt for 1 h and then quenched by addition of aqueous saturated sodium thiosulfate and NaHCO₃ (100 mL) followed by EtOAc (100 mL) to the reaction. The solution was stirred for 30 min at rt and then transferred to a separatory funnel. The organic layer was isolated while the aqueous layers were back extracted with EtOAc (2×50 mL). The combined organic layers were collected, dried (MgSO₄), filtered, and concentrated to dryness. The crude material was then triturated with THF-Et₂O. The solid was collected, washed with Et₂O (150 mL), and dried under vacuum. The mother liquor was concentrated and purified by MPLC (Isco) 100% CH₂Cl₂ to 9:1 v/v CH₂Cl₂-MeOH. The resulting purified fractions were combined with the solid and concentrated in vacuo yielding 344 mg of the above compound (0.97 mmol, yield 83%). ¹H-NMR (DMSO-d₆) δ 8.35 (br s, 1H), 7.94 (s, 1H), 7.13 (br s, 1H), 4.02 (s, 2H), 3.47 (m, 4H), 2.64 (s, 3H), 2.35 (m, 4H); MS [M+H]⁺=354.0; LCMS RT=1.11 min.

Step 9: Preparation of tert-butyl {4-[6-acetyl-4-amino-7-(morpholin-4-ylmethyl)pyrrolo[2,1-f][1,2,4]triazin-5-yl]-2-fluorophenyl}carbamate

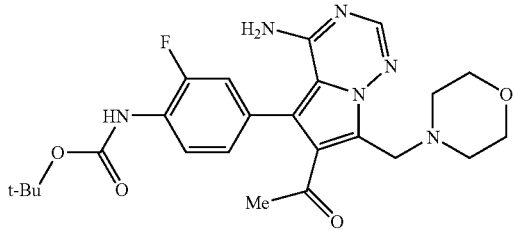

To a solution of 1,4-dioxane (30 mL) was added 1-[4-amino-5-bromo-7-(morpholin-4-ylmethyl)pyrrolo[2,1-f][1,2,4]triazin-6-yl]ethanone (222 mg, 0.627 mmol), tert-butyl [3-fluoro-4-(4,4,5,5-tetramethyl-1,3,2-dioxaborolan-2-yl)phenyl]carbamate (423 mg, 1.25 mmol), and Na₂CO₃ (199 mg, 1.88 mmol). N₂ was bubbled through the solution for 15 min, and then tetrakis(triphenylphosphine)palladium(0) and water (3.0 mL) were added. N₂ was again bubbled through the solution for 15 min, and then the solution was heated to 80° C. for 17 h. Upon cooling to rt EtOAc (50 mL) and water (50 mL) were added to the reaction mixture which was then transferred to a separatory funnel. The organic layer was isolated while the aqueous layer was back extracted with EtOAc (2×50 mL). The combined organic layers were collected, dried (MgSO₄), filtered, and concentrated to dryness. The crude material was then purified by column chromatography (5:4:1 v/v/v CH₂Cl₂-EtOAc-MeOH. The resulting purified fractions were combined and concentrated in vacuo yielding 305 mg of the above compound as a white solid (0.63 mmol, yield 100%). ¹H-NMR (DMSO-d₆) δ 9.16 (s, 1H), 7.97 (s, 1H), 7.78 (t, J=8.4 Hz, 1H), 7.28 (dd, J=1.7 Hz, 11.1 Hz, 1H), 7.15 (dd, J=2.0 Hz, 8.4 Hz, 1H), 4.06 (s, 2H), 3.49 (m, 4H), 2.42 (m, 4H), 2.15 (s, 3H), 1.49 (s, 9H); MS [M+H]⁺=485.1; LCMS RT=2.28 min.

Step 10: Preparation of the Title Compound

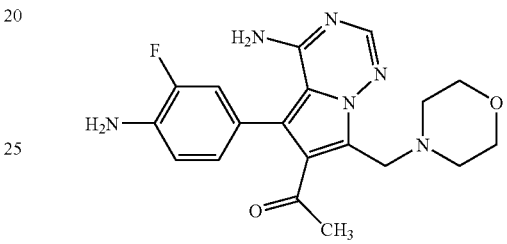

To a solution of CH₂Cl₂ (50 mL) was added of tert-butyl {4-[6-acetyl-4-amino-7-(morpholin-4-ylmethyl)pyrrolo[2,1-f][1,2,4]triazin-5-yl]-2 fluorophenyl}-carbamate (291 mg, 0.60 mmol) followed by trifluoroacetic acid (5 mL). The solution was allowed to stir for 30 min at rt. Aq saturated NaHCO₃ was added to the solution until bubbling stopped. Additionally CH₂Cl₂ was added and the solution was then transferred to a separatory funnel. The organic layer was isolated while the aqueous layer was back extracted with CH₂Cl₂ (2×25 mL). The combined organic layers were collected, dried (MgSO₄), filtered, and concentrated to dryness yielding 214 mg of the above compound as a white solid (0.56 mmol, yield 93%). ¹H-NMR (DMSO-d₆) δ 7.95 (s, 1H), 7.08 (dd, J=1.7 Hz, 10.3 Hz, 1H), 6.92 (dd, J=1.8 Hz, 7.9 Hz, 1H), 6.86 (t, J=8.7 Hz, 1H), 5.47 (s, 2H), 4.05 (s, 2H), 3.49 (m, 4H), 2.41 (m, 4H), 2.06 (s, 3H); MS [M+H]⁺=385.1; LCMS RT=1.16 min.

Intermediate AY. Preparation of Ethyl 4-amino-7-bromo-5-{4-[({[4-(trifluoromethyl)pyridin-2-yl]amino}carbonyl)amino]phenyl}pyrrolo[2,1-f]-[1,2,4]triazine-6-carboxylate

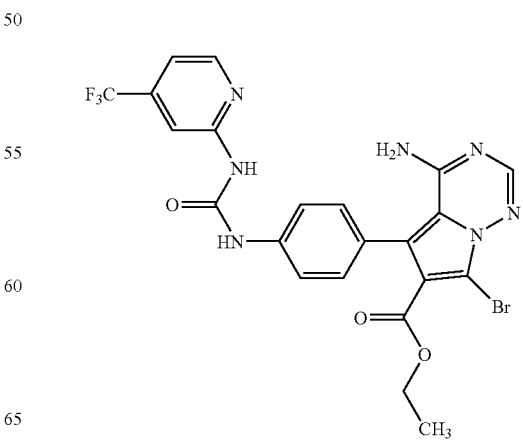

Step 1: Preparation of Ethyl 4-amino-7-bromo-5-(4-nitrophenyl)pyrrolo[2,1-f][1,2,4]triazine-6-carboxylate

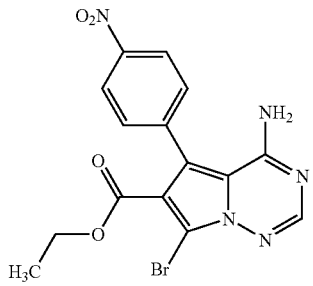

Ethyl 4-amino-5-(4-nitrophenyl)pyrrolo[2,1-f][1,2,4]triazine-6-carboxylate (2.0 g, 6.11 mmol) was suspended in ACN and treated with N-bromosuccinimide (1.20 g, 6.72 mmol). The dark suspension was heated to 60° C. for 1 h. The suspension was cooled and filtered. The brown solid was washed with ACN and MeOH. The product was collected by filtration to give 2.06 g of a yellow brown solid (83%). $^1$H-NMR (DMSO-$d_6$) δ 8.26 (d, J=8.8, 2H), 8.07 (s, 1H), 7.64 (d, J=8.8, 2H), 4.02 (q, J=7.0, 2H), 0.95 (t, J=7.0, 3H); MS [M+H]$^+$=406.1, 408.0; LCMS RT=2.93.

Step 2: Preparation of Ethyl 4-amino-5-(4-aminophenyl)-7-bromopyrrolo[2,1-f][1,2,4]triazine-6-carboxylate

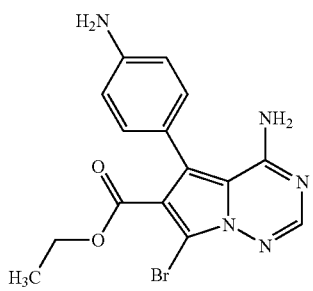

Ethyl-4-amino-7-bromo-5-(4-nitrophenyl)pyrrolo[2,1-f][1,2,4]triazine-6-carboxylate (2.06 g, 5.07 mmol) was suspended in EtOH (30 mL) and treated with tin(II)chloride dihydrate (3.66 g. 16.2 mmol). The mixture was heated to reflux for 18 h. The mixture was concentrated then diluted with EtOAc and saturated NaHCO$_3$ solution. The emulsion was filtered and the filtrate was transferred to a separatory funnel. The organic layer was washed with water and saturated NaCl solution, dried then (MgSO$_4$) and concentrated to afford 1.5 g of the desired product as tan solid (79%). $^1$H-NMR (DMSO-$d_6$) δ 8.00 (s, 1H), 7.00 (d, J=8.6, 1H), 6.62 (d, J=9.2, 3H), 5.40 (bd, 2H), 5.19 (bs, 2H), 4.05 (q, J=7.0, 2H), 1.03 (t, J=7.0, 3H); MS [M+H]$^+$=376.0, 378.0; LCMS RT=2.02.

Step 3. Preparation of Title Compound

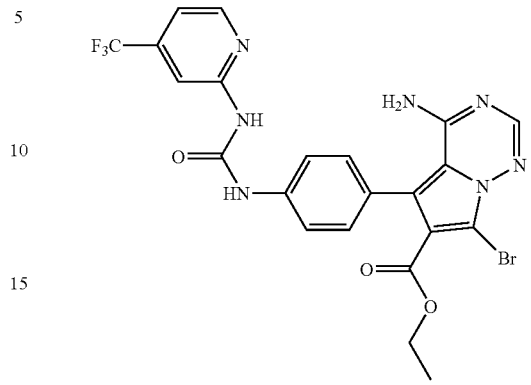

Ethyl-4-amino-5-(4-aminophenyl)-7-bromopyrrolo[2,1-f][1,2,4]triazine-6-carboxylate (1.5 g, 3.99 mmol) was suspended in THF (20 mL) and treated with triethylamine (0.56 mL, 3.99 mmol) and phenyl[4-(trifluoromethyl)pyridin-2-yl]carbamate (1.13 g, 3.99 mmol). The mixture was heated to 70° C. for 18 h. After cooling to rt, the mixture was concentrated then suspended in EtOAc. The product was collected by filtration to give 2.0 g of a tan solid (89%). $^1$H-NMR (DMSO-$d_6$) δ 9.91 (s, 1H) 9.75 (s, 1H), 8.53 (d, J=5.4, 1H), 8.06 (s, 1H), 8.04 (s, 1H), 7.60 (d, J=11, 2H), 7.37-7.31 (m, 3H), 5.15 (bs, 2H), 4.04 (q, J=7.1, 2H), 0.99 (t, J=7.2, 3H); MS [M+H]$^+$=563.9, 565.9; LCMS RT=3.22.

Intermediate AZ

Preparation of ethyl 4-amino-7-bromo-5-{4-[({[4-(trifluoromethyl)pyridin-2-yl]amino}carbonyl)amino]phenyl}pyrrolo[2,1-f][1,2,4]triazine-6-carboxylate

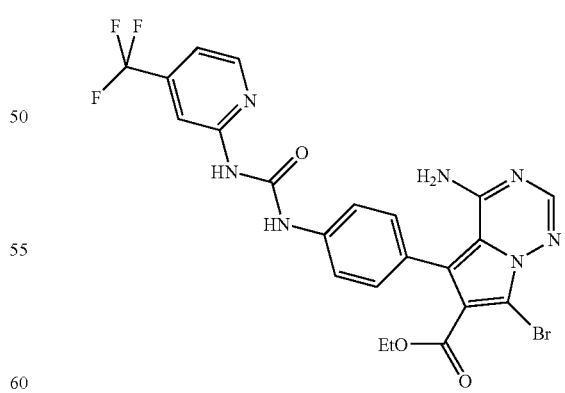

The procedure used for the preparation of Intermediate AT was used to prepare the title compound by substituting Intermediate W for Intermediate T.

Intermediate AAA 5-bromo-6-(methoxymethyl)-7-(morpholin-4-ylm-ethyl)-pyrrolo[2,1-f][1,2,4]triazin-4-amine

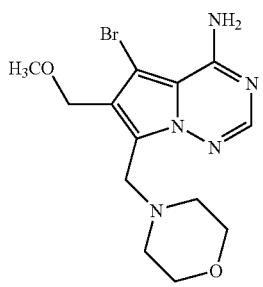

Step 1: Preparation of (4-aminopyrrolo[2,1-f][1,2,4]triazin-6-yl)methanol

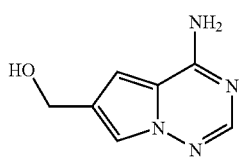

To a solution of THF (150 mL) was added ethyl 4-aminopyrrolo[2,1-f][1,2,4]triazine-6-carboxylate (2.29 g, 4.65 mmol) followed by 1 M DIBAL in THF (28.8 mL, 28.8 mmol). The solution was stirred at rt for 1 h. The rxn mixture was treated with EtOAc followed by aq Rochelle's salt. This heterogeneous mixture was then heated at 60° C. for 30 min. The solution was transferred to a separatory funnel, separated and washed with water. The aq layer was back extracted with EtOAc. The organic layer was dried (MgSO$_4$), filtered, and concentrated to yield 550 mg (93%) of the desired product. MS [M+H]$^+$=165; LCMS RT=1.03.

Step 2: Preparation of [4-amino-7-(morpholin-4-ylmethyl)pyrrolo[2,1-f][1,2,4]triazin-6-yl]methanol

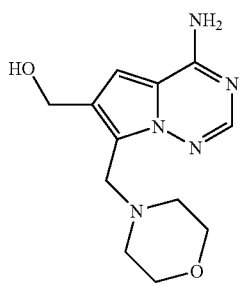

To a solution of DMF (50 mL) was added (4-aminopyrrolo[2,1-f][1,2,4]triazin-6-yl)methanol (550 mg, 3.35 mmol) and 4-methylenemorpholin-4-ium chloride (*Eur. J. Med. Chem.* 1989, 24, 379-384) (636 mg, 4.69 mmol). The solution was stirred at rt for 1 h and then the solvent was evaporated. The oil was triturated with CH$_2$Cl$_2$ and a white solid was collected. The free based was obtained by stirring over a Dowex 66 solid support resin in MeOH. The material was filtered and evaporated yielding 794 mg (90%) of the desired product as a white solid. MS [M+H]$^+$=264; LCMS RT=1.07.

Step 3: Preparation of 6-(methoxymethyl)-7-(morpholin-4-ylmethyl)pyrrolo[2,1-f][1,2,4]triazin-4-amine

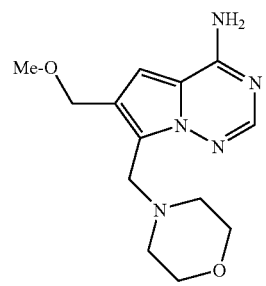

The procedure used for the preparation of Intermediate Z was used to prepare the title compound by substituting [4-amino-7-(morpholin-4-ylmethyl)pyrrolo[2,1-f][1,2,4]triazin-6-yl]methanol for Intermediate Y (N-{4-[4-amino-6-(hydroxyl-methyl)pyrrolo[2,1-f][1,2,4]triazin-5-yl]phenyl}-N'-[4-(trifluoromethyl)-pyridin-2-yl]urea. MS [M+H]$^+$=278; LCMS RT=1.07.

Step 4. Preparation of Title Compound

The procedure used for the preparation of the product of step 7 in Intermediate AX (ethyl 1-[4-amino-5-bromo-7-(morpholin-4-ylmethyl)-pyrrolo[2,1-f][1,2,4]triazin-6-yl]-ethanol) was used to prepare the title compound by substituting 6-(methoxymethyl)-7-(morpholin-4-ylmethyl)pyrrolo[2,1-f][1,2,4]triazin-4-amine for 1-[4-amino-7-(morpholin-4-ylmethyl)pyrrolo[2,1-f][1,2,4]triazin-6-yl]ethanol. MS [M+H]$^+$=356; LCMS RT=1.12.

Intermediate AAB

Preparation of 1-[2,5-difluoro-4-(4,4,5,5-tetramethyl-1,3,2-dioxaborolan-2-yl)phenyl]-3-[2-fluoro-5-(trifluoromethyl)phenyl]urea

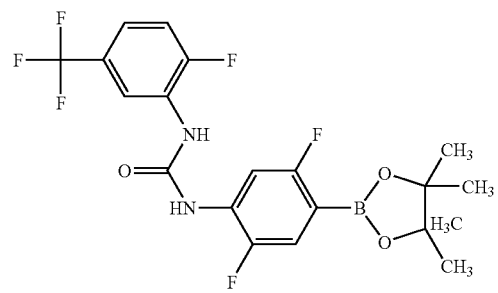

Step 1: Preparation of 2,5-difluoro-4-(4,4,5,5-tetramethyl-1,3,2-dioxaborolan-2-yl)aniline

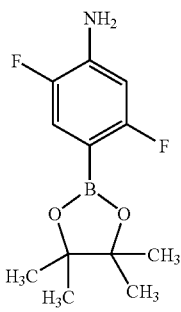

Potassium acetate (3 eq) and 4,4,4',4',5,5,5',5'-octamethyl-2,2'-bi-1,3,2-dioxaborolane (1.1 eq) were added as solids to a flask then placed under $N_2$. 4-Bromo-2-5-difluoroaniline (1 eq) in DMSO (0.4 M) was then added to the flask. The reaction was taken through three purge-fill cycles using high vacuum then nitrogen and Pd(dppf)$CH_2Cl_2$ (0.01 eq) was added. The reaction was again placed under vacuum then blanketed with nitrogen. The reaction was heated at 80° C. until the TLC showed the complete consumption of starting bromide (approximately 90 minutes). After cooling to rt, EtOAc was added and the reaction was partitioned between EtOAc and saturated aqueous bicarbonate. The organic layer was washed with brine seven times to remove DMSO. The material was then dried ($Na_2SO_4$) and concentrated under vacuum. The desired product was obtained after column chromatography (0-100% v/v $CH_2Cl_2$/Hexanes). $^1$H-NMR (DMSO-$d_6$) $^1$H-NMR (DMSO-$d_6$) δ 7.03 (dd, J=11.7 Hz, 5.4 Hz, 1H), 6.38 (dd, 10.8 Hz, 3.9 Hz, 1H), 5.91 (s 2H) 1.22 (s, 12H); MS [M+H]$^+$=256.3, LCMS RT=3.13 min.

Step 2: Preparation of the Title Compound

To a solution of 2,5-difluoro-4-(4,4,5,5-tetramethyl-1,3,2-dioxaborolan-2-yl)aniline (1 eq) in THF (1 M) was added 2-fluoro-5-trifluoromethyl phenylisocyante (1.2 eq). The reaction was stirred at room temperature overnight. The desire product was precipitated from the reaction mixture by the addition of 1:2 ether/hexanes. The desired title compound was obtained as a solid after filtration and drying in vacuo. MS [M+H]$^+$=461.2, LCMS RT=4.38 min.

Intermediate AAC

1-{4-[4-amino-7-formyl-6-(methoxymethyl)pyrrolo[2,1-f][1,2,4]triazin-5-yl]-2-fluorophenyl}-3-[2-fluoro-5-(trifluoromethyl)phenyl]urea

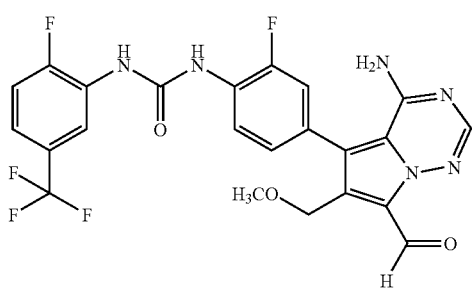

Step 1: Preparation of 1-{4-[4-amino-7-bromo-6-(methoxymethyl)pyrrolo[2,1-f][1,2,4]triazin-5-yl]-2-fluorophenyl}-3-[2-fluoro-5-(trifluoromethyl)phenyl]urea

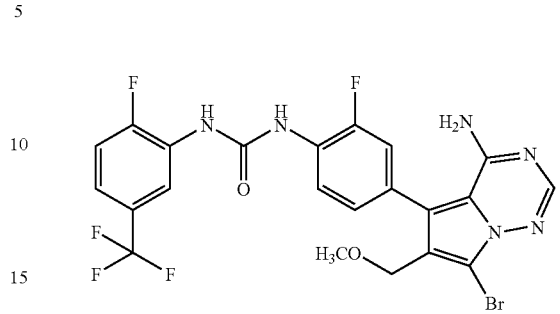

To a solution of THF (500 mL) was added 1-{4-[4-amino-6-(methoxymethyl)pyrrolo[2,1-f][1,2,4]triazin-5-yl]-2-fluorophenyl}-3-[2-fluoro-5-(trifluoromethyl)phenyl]urea (2.29 g, 4.65 mmol). The solution was cooled to −40° C. and then 1,3-dibromo-5,5-dimethylhydantoin (665 mg, 2.33 mmol) was added in two batches 20 min apart. The reaction was stirred at −40° C. for 1 h and then allowed to warm to rt over the following 2 h. Aq saturated $Na_2SO_3$ was added to the reaction followed by EtOAc. The layers were separated and the aqueous layer was back extracted with EtOAc. The organic layer was washed with 1N NaOH and water, dried ($Na_2SO_4$), filtered and evaporated to yield 2.83 g crude (107%) of the desired product. MS [M+H]$^+$=571; LCMS RT=3.54.

Step 2. Preparation of Title Compound

To a solution of THF (35 mL) was added 1-{4-[4-amino-7-bromo-6-(methoxymethyl)pyrrolo[2,1-f][1,2,4]triazin-5-yl]-2-fluorophenyl}-3-[2-fluoro-5-(trifluoromethyl)phenyl]urea (200 mg, 0.35 mmol). The solution was cooled to −77° C., and then 2.5 M n-BuLi in hexanes (0.70 mL, 1.75 mmol) was added. The reaction was stirred for 1 min and then DMF (0.16 mL, 2.1 mmol) was added. The solution was stirred for an additional 5 min, and the ice bath was removed. The reaction was allowed to warm to rt over the following 1 h. EtOAc was added to the solution followed by water. The solution was separated and the aqueous layer was back extracted with EtOAc. The combined organic fractions were dried (MgSO$_4$), filtered, and evaporated yielding the title compound as crude material (216 mg, 119%). MS [M+H]$^+$=521; LCMS RT=3.49.

Intermediate AAD 5-bromo-6-chloro-7-(morpholin-4-ylmethyl)pyrrolo[2,1-f][1,2,4]triazin-4-amine

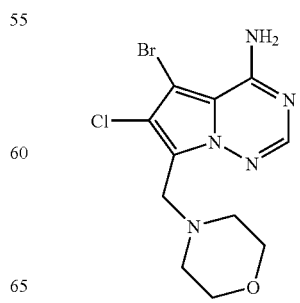

Step 1: Preparation of 2,2,2-trichloro-1-(4-chloro-1H-pyrrol-2-yl)ethanone

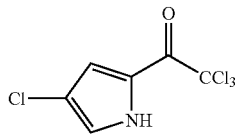

To a solution of 2-(trichloroacetyl)pyrrole (4.0 g, 18.83 mmol) in chloroform (28 ml) at 0° C. was added sulfuryl chloride (13 mL, 13.2 mmol). The mixture was stirred for 17 hours at room temperature. TLC analysis indicated 50% conversion of starting material. Sulfuryl chloride (13 mL, 13.2 mmol) was added and the reaction mixture was stirred for another 4 hours at room temperature. The reaction was quenched with distilled water (50 mL). $CH_2Cl_2$ (50 mL) was added to the reaction and the solution was transferred to a separatory funnel and the organic layer was isolated while the aqueous layer was back extracted with $CH_2Cl_2$ (2×50 mL). The combined organic layers were collected, dried ($MgSO_4$), filtered, and concentrated in vacuo to yield 3.5 g of the above compound (14.18 mmol, yield 75%). $^1$H-NMR ($CDCl_3$-$d_1$) δ 9.45 (s, 1H), 7.27 (dd, J=2.8, 1.6, 1H), 7.12 (dd, J=3.2, 1.6 Hz, 1H).

Step 2. Preparation of 4-chloro-1H-pyrrole-2-carboxamide

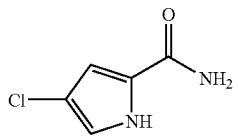

A solution of 2,2,2-trichloro-1-(4-chloro-1H-Pyrrol-2-yl)ethanone (14.0 g, 56.7 mmol) in THF (100 mL) was bubbled with ammonium gas for 2 h at room temperature. TLC analysis indicated that there was complete conversion of starting material. The reaction mixture was concentrated in vacuo to yield 7.5 g of the above compound (51.88 mmol, yield 92%). $^1$H-NMR (Acetone-$d_6$) δ 10.92 (br s, 1H), 7.21 (br s, 1H), 7.02 (s, 1H), 6.84 (s, 1H), 6.57 (br s, 1H).

Step 3. Preparation of 4-chloro-1H-pyrrole-2-carbonitrile

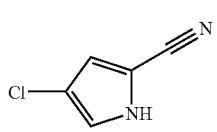

To a solution of 4-chloro-1H-pyrrole-2-carboxamide (7.5 g, 51.88 mmol) in toluene (50 mL) was added $POCl_3$ (5.8 mL, 62.26 mmol). The mixture was heated to 80° C. for 4 hours. TLC analysis indicated that there was complete conversion of starting material. Toluene and excess $POCl_3$ were removed under reduced pressure and the remaining solids were dissolved in EtOAc (30 mL). The pH was adjusted to 8 using 1N NaOH and the solution was transferred to a separatory funnel and the organic layer was isolated while the aqueous layer was back extracted with EtOAc, (2×50 mL). The combined organic layers were collected, dried ($MgSO_4$), filtered, and concentrated in vacuo. The crude material was purified by column chromatography (60% EtOAc/Hexanes) to afford 3.6 g of the above compound (28.45 mmol, yield 55%). $^1$H-NMR (Acetone-$d_6$) δ 11.62 (br s, 1H), 7.25 (dd, J=2.8, 1.2 Hz, 1H), 6.93 (dd, J=2.8, 1.2 Hz, 1H).

Step 4. Preparation of 1-amino-4-chloro-1H-pyrrole-2-carbonitrile

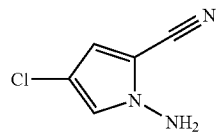

To a rapidly stirred solution of 4-chloro-1H-pyrrole-2-carbonitrile (3.6 g, 28.4 mmol) in DMF (75 mL) was added NaH (1.7 g, 42.7 mmol) portion wise over 20 min. The dark brown solution was allowed to stir for an additional 10 min. The aminating reagent ((aminooxy)(diphenyl)phosphine oxide) (10 g, 42.7 mmol) was added in one portion. The mixture was heated to 80° C. for 6 hours. The reaction was quenched with distilled water (100 mL). EtOAc (50 mL) was added to the reaction and the solution was transferred to a separatory funnel and the organic layer was isolated while the aqueous layer was back extracted with EtOAc (2×50 mL). The combined organic layers were collected, dried ($MgSO_4$), filtered, and concentrated in vacuo to yield 3.4 g of the above compound (24.02 mmol, yield 84%).

Step 5. Preparation of 6-chloropyrrolo[2,1-f][1,2,4]triazin-4-amine

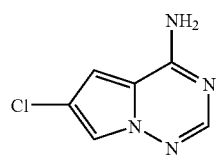

To a stirred suspension of 1-amino-4-chloro-1H-pyrrole-2-carbonitrile (3.4 g, 24.02 mmol) in EtOH (160 mL) was added formamidinium acetate (25 g, 240.2 mmol). The mixture was heated to 80° C. over night. TLC analysis indicated that there was complete conversion of starting material. The reaction mixture was cooled to room temperature and then filtered. Ethanol was removed under reduced pressure and the remaining solids were purified by column chromatography (EtOAc) to afford 2.2 g of the above compound (13.1 mmol, yield 54%). $^1$H-NMR (MeOD-$d_4$) δ 7.77 (s, 1H), 7.56 (d, J=1.6 Hz, 1H), 6.82 (d, J=1.6 Hz, 1H); LCMS RT=1.30 min; MS {M+H}$^+$=168.8

Step 6. Preparation of 6-chloro-7-(morpholin-4-ylmethyl)pyrrolo[2,1-f][1,2,4]triazin-4-amine

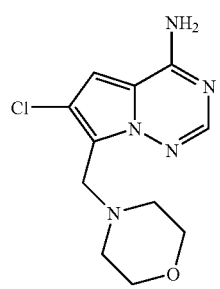

To a solution of AcOH (30 mL) was added formaldehyde (1.2 g, 14.95 mmol). The reaction mixture was allowed to stir for 20 minutes at room temperature. 6-chloropyrrolo[2,1-f][1,2,4]triazin-4-amine (2.1 g, 12.46 mmol) was introduced and the reaction mixture was heated to 80° C. over night. TLC analysis indicated that there was complete conversion of starting material. The solution was allowed to cool to rt and was then neutralized by 1N NaOH. EtOAc (30 mL) was added to the reaction and the solution was transferred to a separatory funnel and the organic layer was isolated while the aqueous layer was back extracted with EtOAc (2×50 mL). The combined organic layers were collected, dried (MgSO$_4$), filtered, and concentrated in vacuo to yield 3.0 g of the above compound (11.2 mmol, yield 90%). $^1$H-NMR (MeOD-d$_4$) δ 8.05 (s, 1H), 7.13 (s, 1H), 4.75 (s, 2H), 3.90 (br s, 4H), 3.42 (br s, 4H); MS [M+H]$^+$=267.8; LCMS RT=1.08 min.

Step 7. Preparation of Title Compound

To a solution of 6-chloro-7-(morpholin-4-ylmethyl)pyrrolo[2,1-f][1,2,4]triazin-4-amine (0.9 g, 3.36 mmol) in DMF (5 mL) at −20° C. was added 1,3-dibromo-5,5-dimethylhydantoin (0.43 g, 1.51 mmol) portion wise over 30 min. The reaction mixture was stirred for 20 minutes at that temperature. TLC analysis indicated that there was complete conversion of starting material. The reaction was quenched with distilled water (30 mL) as the solution warmed to rt. CH$_2$Cl$_2$ (30 mL) was added to the reaction and the solution was transferred to a separatory funnel and the organic layer was isolated while the aqueous layer was back extracted with CH$_2$Cl$_2$ (4×20 mL). The combined organic layers were collected, dried (MgSO$_4$), filtered, and concentrated to dryness. The crude material was washed with diethyl ether (10 mL). The white precipitate was collected and dried under vacuum to yield 0.6 g of the above compound (1.73 mmol, yield 51%). $^1$H-NMR (CD$_3$OD-d$_4$) δ 7.94 (s, 1H), 3.79 (s, 2H), 3.05 (t, J=4.8 Hz, 4H), 2.39 (t, J=4.8 Hz, 4H); MS [M+H]$^+$=347.7; LCMS RT=1.21 min.

Intermediate AAE

Preparation of
6-Bromopyrrolo[2,1-f][1,2,4]triazin-4-amine

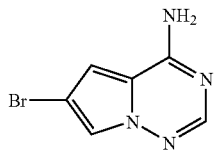

Step 1: Preparation of Pyrrol-1-yl-carbamic acid tert-butyl ester

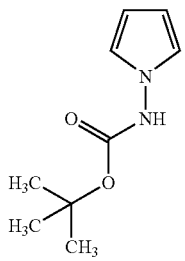

A flask (fitted with a Dean-Stark trap) containing a stirred solution of tert-butylcarbazate (100, 0.757 mol), 2,5-dimethoxytetrahydrofuran (108 g, 0.832 mol) and 2N HCl (10 mL) in 1,4-dioxane (700 mL) was heated under nitrogen at 90° C. As the reaction progressed over several hours, the solution changed from pale yellow to orange and began to reflux. The reaction was monitored by the amount of distillate collected in the D/S trap (primarily CH$_3$OH, 2 moles/1 mole reagent). As methanol collection approached the theoretical amount (50 mL) a sample was analyzed by TLC (silica gel, 1:3 EtOAc/hexane, ninhydrin stain) to confirm reaction completion. Heating was shut off and the reaction was allowed to cool somewhat before adding saturated sodium bicarbonate solution (~25 mL) to neutralize the hydrochloric acid. The quenched mixture was filtered through a sintered-glass funnel and concentrated in vacuo to leave an orange, semi-solid residue. The residue was suspended in diethyl ether (minimum volume) and the nearly colorless solids were collected by suction filtration, washed with hexane and air-dried to afford 60.2 g (40%) of product. A second crop (yellow-tan solids) from the mother liquors was isolated: 29.0 g, (19%). Additional material which was present in the mother liquors could be recovered by silica gel chromatography to increase the yield. $^1$H-NMR (CD$_3$OD): δ 10.23 (br s, 1H), 6.66 (t, 2H, J=2.2 Hz), 5.94 (t, 2H, J=2.2), 1.42 (s, 9H); MS: GC/MS (+esi): m/z=182.9 [MH]$^+$ Step 2: Preparation of
(2-Cyano-pyrrol-1-yl)-carbamic acid, tert-butyl ester

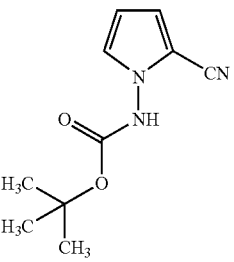

A 2 L, 3-neck RB was fitted w/ stir bar, N$_2$ inlet, rubber septum low-temp, thermometer and ice/acetone cooling bath. Pyrrol-1-yl-carbamic acid tert-butyl ester (99.0 g, 0.543 mol) was added to the reactor, dissolved w/ anhydrous acetonitrile (700 mL) and the stirred solution was cooled to 0° C. Chlorosulfonyl isocyanate (49.7 mL, 0.57 mol) was added dropwise via syringe (maintaining an internal temp, below 5° C.); after ~20 minutes a suspension was observed. After 45 minutes N,N-dimethylformamide (anhydrous, 100 mL) was added dropwise via addition funnel (keeping internal temp, below 5° C.) and the reaction mixture became a solution. Stirring @ 0° C. was continued for 45 minutes, then the reaction was allowed to warm to RT; monitoring by TLC (silica gel, 1:3 ethyl acetate/hexane, UV, ninhydrin stain) of a quenched sample indicated that the reaction had progressed to completion. The mixture was poured onto ice (~2 L) and stirred with addition of EtOAc (2 L). The layers were separated and the organic layer was dried over magnesium sulfate. The dried solution was filtered through a pad of 30/40 Magnesol and the filtrate was concentrated to dryness in vacuo, then the residue was dissolved in a minimum volume of dichloromethane and chromatographed on a plug of silica gel, eluting with ethyl acetate/hexane, 0-50% ethyl acetate. The clean, product-containing fractions were combined and concentrated to dryness in vacuo, to afford the desired product as a white solid, 69.8 g (62%). A somewhat impure fraction provided additional material, 16.8 g (15%), bringing the total recovery to 86.6 g, (77%). $^1$H-NMR (CD$_3$OD): δ 7.01 (dd, 1H, J=3.0, 1.6 Hz), 6.82 (dd, 1H, J=4.4, 1.7 Hz), 6.19 (dd, 1H, J=4.2, 2.9 Hz), 4.88 (s, 1H, H$_2$O+NH—), 1.50 (br s, 9H, HN—BOC); MS: LC/MS (+esi), m/z=207.9 [M+H].

Step 3: Preparation of tert-Butyl (4-bromo-2-cyano-1H-pyrrol-1-yl)carbamate

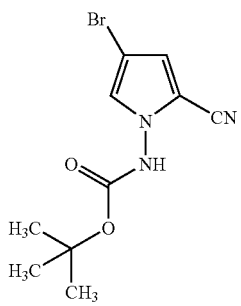

A 1 L, 3-neck RB flask was fitted with a mechanical stirrer, nitrogen inlet, thermocouple/JKEM thermocontroller, and a dry-ice acetonitrile cooling. 2-Cyano-pyrrol-1-yl)-carbamic acid, tert-butyl ester (20 g, 96.5 mmol) was added and dissolved in 350 mL acetonitrile. The resulting solution and cooled to below −30° C. 1,3-Dibromo-5,5-dimethylhydantoin (13.79 g, 48.26 mmol) was added as a solid, and the reaction was allowed to warm to rt over 2 h. Analysis by RP-HPLC at 2 h indicated that about 10% starting material remained. The reaction was cooled again to below −30° C. and treated with additional 1,3-dibromo-5,5-dimethylhydantoin (1.3 g, 4.8 mmol). The reaction was allowed to warm slowly to rt over 3 h. Once RP-HPLC indicated that all starting material had been consumed, the reaction was diluted with 500 mL EtOAc and transferred to a separatory funnel. The organic was washed with 1N sodium carbonate, water and brine and then dried with sodium sulfate. Filtration of the organic layer thru silica gel removed much of the colored impurities. Evaporation of the solvent under vacuum provided a reddish oil, which provided orange-brown crystals of the desired product upon seeding (27.16 g, 98% yield). This material proved to be only about 90% pure by $^1$H-NMR. $^1$H-NMR (DMSO): δ 10.95 (bs, 1H), 7.61 (d, 1H, J=2.0 Hz), 7.16 (d, 1H, J=2 Hz), 1.44 (s, 9H, J=4.4, 1.7 Hz).

Step 4: Preparation of 1-Amino-4-bromo-1H-pyrrole-2-carbonitrile hydrochloride

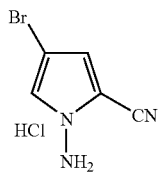

A 1 L, 3-neck RB flask was fitted with a mechanical stirrer, nitrogen inlet, thermocouple/JKEM thermocontroller, cooling bath and an addition funnel. tert-Butyl (4-bromo-2-cyano-1H-pyrrol-1-yl)carbamate (19 g, 66 mmol) was added and dissolved with 1,4-dioxane (50 mL), then the stirred orange solution was cooled to 0° C. and HCl/dioxane (4N, 100 mL, 8 eq.) was slowly added from the addition funnel, maintaining an internal temperature around 25° C. After 2 hours the solution became cloudy and stirring @ room temperature was continued for 7 hours; the reaction was monitored for completion by TLC (silica gel, GHLF, 1:3 EtOAc/hexane, UV; Note: the free base may be observed as a high-Rf spot and can be misinterpreted as incomplete reaction). The reaction mixture was diluted with diethyl ether (150 mL) and the precipitated solids were collected by suction filtration and washed with ether (200 mL). Drying (vacuum oven @ 50° C.) afforded the desired product as 10.9 g (93%) of a white solid. $^1$H-NMR (DMSO): δ 7.24 (d, 1H, J=2 Hz), 6.93 (d, 1H, J=2 Hz), 6.2 (bs, 3H, J=2.8, 4.4 Hz).

Step 5: Preparation of the Title Compound

To a stirred suspension of 1-Ammo-4-bromo-1H-pyrrole-2-carbonitrile hydrochloride (17 g, 61.1 mmol) in absolute ethanol (350 mL) was added formamidine acetate (31.8 g, 305 mmol) and potassium phosphate (64.9 g, 305 mol). The suspension was heated for 18 hours @ 78° C. (under N2), then cooled, filtered and concentrated to dryness in vacuo. The residue was mixed with ice water (2 L) and the dark grayish-brown solids were collected by suction filtration. The solids were taken up in refluxing MeOH and treated with decolorizing carbon, then filtered thru Celite and concentrated dryness in vacuo. The solids were taken up in THF:DCE (1:3) and filtered thru a pad of silica. Removal of the solvent in vacuo provided a yellowish-brown solid. This material was recrystallized from THF:hexanes to provide the desired compound as a yellow solid (9.86 g, 75% yield). (81%). $^1$H-NMR (DMSO): δ 7.85 (bs, 2H), 7.81 (s, 1H), 7.80 (d, 1H, J=2 Hz), 6.96 (d, 1H, J=2 Hz).

Intermediate AAF

Preparation of 1-[2-fluoro-4-(4,4,5,5-tetramethyl-1,3,2-dioxaborolan-2-yl)phenyl]-3-[4-(trifluoromethyl)pyridin-2-yl]urea

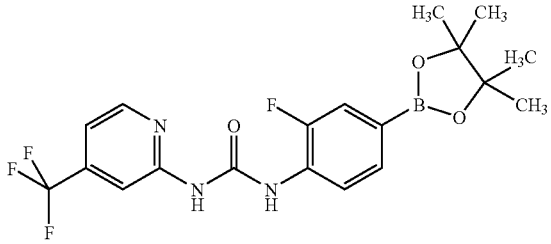

To a solution of 2-fluoro-4-(4,4,5,5-tetramethyl-1,3,2-dioxaborolan-2-yl)aniline (8.00 g, 33.7 mmol, 1 eq) (product of Step 1 Intermediate F (preparation 1)) in 1,2-dichloroethane (80 ml) was added Intermediate V (phenyl[4-(trifluoromethyl)pyridin-2-yl]carbamate) (10.10 g, 35.4 mmol, 1.05 eq). Triethylamine (4.70 ml, 33.7 mmol, 1 eq) was then added and reaction was allowed to stir at 60° C. for 4 hours. The reaction was cooled in an ice bath and the resulting white solids collected by filtration. The solids were washed with 1,2-dichloroethane and hexanes then dried under vacuum to obtain the desired product (10.86 g, 75.7% yield). $^1$H-NMR (DMSO-δ6) δ 10.18 (s, 1H), 8.52 (d, J=5.2 Hz, 1H), 8.28 (t, J=8.0 Hz, 1H), 7.97 (s, 1H), 7.46 (dd, =8.1, 1.0 Hz, 1H), 7.40-7.36 (m, 2H), 1.27 (s, 12H); MS [M+H]$^+$=426, LCMS RT=4.33 min.

The following boronates were prepared in the same manner as Intermediate F by substituting the appropriate bromide for N-(4-bromo-2-fluorophenyl)-N'-[2-fluoro-5-(trifluoromethyl)phenyl]urea and by substituting the appropriate isocyanate or carbamate for 1-fluoro-2-isocyanato-4-(trifluoromethyl)benzene.

| Intermediate | Structure | IUPAC Name | LC-MS m/z[M + H], RT, Method |
|---|---|---|---|
| AAG | 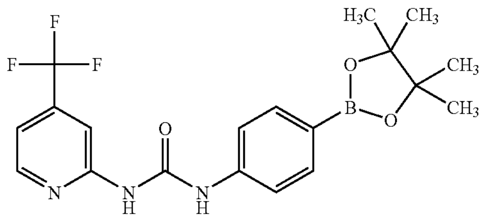 | 1-[4-(4,4,5,5-tetramethyl-1,3,2-dioxaborolan-2-yl)phenyl]-3-[4-(trifluoromethyl)pyridin-2-yl]urea | 407.09, 3.93 min, A |
| AAH | 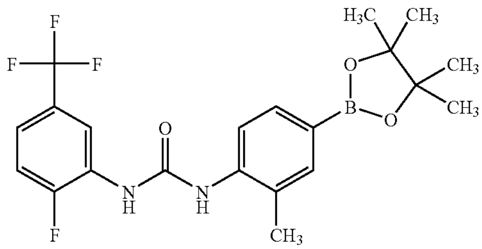 | 1-[2-fluoro-5-(trifluoromethyl)phenyl]-3-[2-methyl-4-(4,4,5,5-tetramethyl-1,3,2-dioxaborolan-2-yl)phenyl]urea | 439.2, 3.81 min, A |
| AAI | 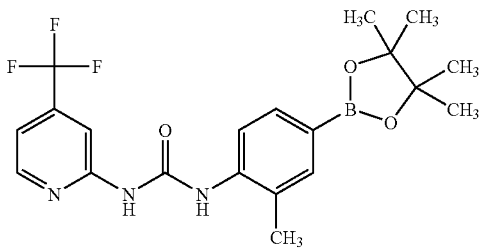 | 1-[2-methyl-4-(4,4,5,5-tetramethyl-1,3,2-dioxaborolan-2-yl)phenyl]-3-[4-(trifluoromethyl)pyridin-2-yl]urea | 422.2, 3.77 min, A |
| AAJ | 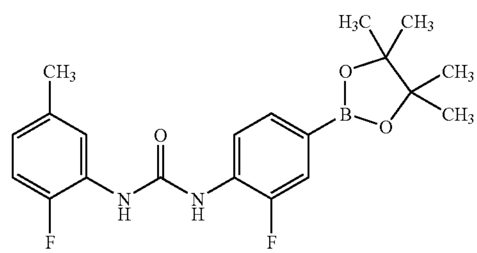 | 1-(2-fluoro-5-methylphenyl)-3-[2-fluoro-4-(4,4,5,5-tetramethyl-1,3,2-dioxaborolan-2-yl)phenyl]urea | 389.3, 3.83 min, A |
| AAK | 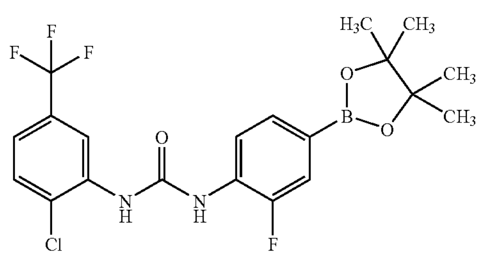 | 1-[2-chloro-5-(trifluoromethyl)phenyl]-3-[2-fluoro-4-(4,4,5,5-tetramethyl-1,3,2-dioxaborolan-2-yl)phenyl]urea | 459.1, 4.53 min, A |
| AAL | 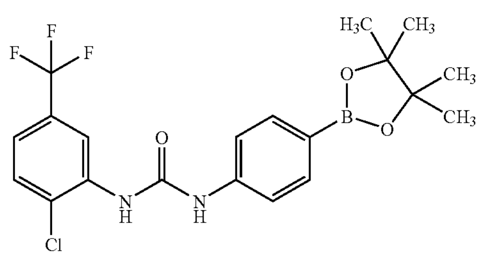 | 1-[2-chloro-5-(trifluoromethyl)phenyl]-3-[4-(4,4,5,5-tetramethyl-1,3,2-dioxaborolan-2-yl)phenyl]urea | 441, 4.38 min, A |

-continued

| Intermediate | Structure | IUPAC Name | LC-MS m/z[M + H], RT, Method |
|---|---|---|---|
| AAM | 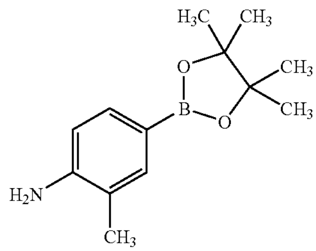 | 2-methyl-4-(4,4,5,5-tetramethyl-1,3,2-dioxaborolan-2-yl)aniline | 234.2, 3.06 min, A |
| AAN | 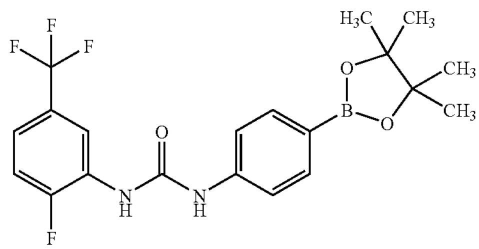 | 1-[2-fluoro-5-(trifluoromethyl)phenyl]-3-[4-(4,4,5,5-tetramethyl-1,3,2-dioxaborolan-2-yl)phenyl]urea | 425, 4.11 min, A |
| AAO | 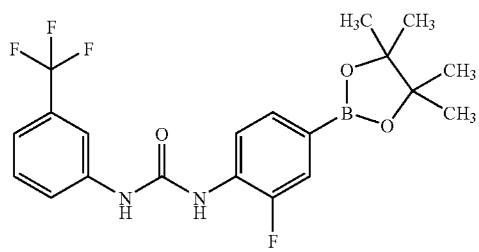 | 1-[3-(trifluoromethyl)phenyl]-3-[2-fluoro-4-(4,4,5,5-tetramethyl-1,3,2-dioxaborolan-2-yl)phenyl]urea | 425, 4.24 min, A |
| AAP | 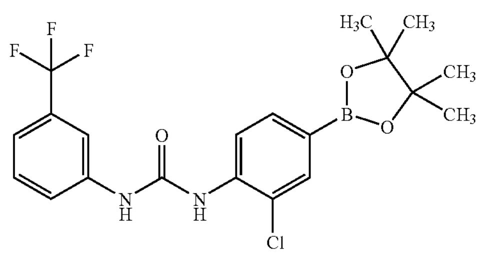 | 1-[3-(trifluoromethyl)phenyl]-3-[2-chloro-4-(4,4,5,5-tetramethyl-1,3,2-dioxaborolan-2-yl)phenyl]urea | 441, 4.48 min, A |

Example 1

Preparation of Ethyl 4-amino-7-(3-fluorophenyl)-5-{4-[({[4-(trifluoromethyl)pyridin-2-yl]amino}carbonyl)amino]phenyl}-pyrrolo[2,1-f][1,2,4]triazine-6-carboxylate

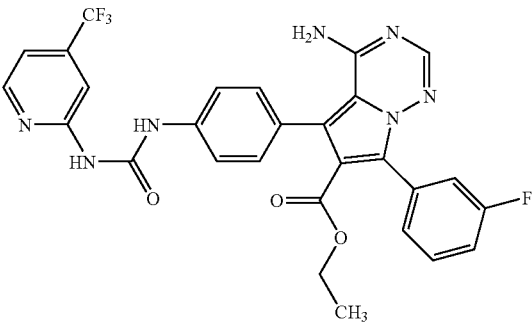

Palladium(II)acetate (0.002 g, 0.009 mmol) was dissolved in dioxane (0.5 mL), and treated with triphenylphosphine (0.009 g, 0.035 mmol). The mixture was degassed twice before adding ethyl Intermediate AY (4-amino-7-bromo-5-{4-[({[4-(trifluoromethyl)pyridin-2-yl]amino}carbonyl)amino]phenyl}pyrrolo[2,1-f][1,2,4-]triazine-6-carboxylate (0.05 g, 0.009 mmol)), 3-fluorophenylboronic acid (0.014 g, 0.097 mmol) and aq. Na$_2$CO$_3$ solution (0.11 mL, 0.22 mmol, 2M). The mixture was heated to 80° C. overnight. The reaction was then cooled and filtered through silica. The filtrate was concentrated then triturated with EtOAc. The product was collected by filtration to give 20 mg of a tan solid (39%). $^1$H-NMR (THF-d$_8$) δ 10.59 (bs, 1H) 9.08 (s, 1H), 8.47 (d, J=5.1, 1H), 7.79 (s, 1H), 7.73-7.68 (m, 3H), 7.41-7.37 (m, 5H), 7.23 (d, J=5.2, 1H), 7.13-7.08 (m, 1H), 3.94 (q, J=7.1, 2H), 0.90 (t, J=7.1, 3H); MS [M+H]$^+$=580.0; LCMS RT=3.41.

Example 2

Preparation of Ethyl 4-amino-7-(4-fluorophenyl)-5-{4-[({[4-(trifluoromethyl)pyridin-2-yl]amino}carbonyl)amino]phenyl}-pyrrolo[2,1-f][1,2,4]triazine-6-carboxylate

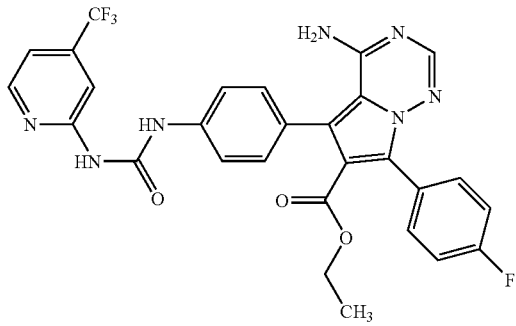

The procedure used for the preparation of Example 1 was used to prepare the title compound by substituting 4-fluorophenylboronic acid for -fluorophenylboronic acid. $^1$H-NMR (THF-d$_8$) δ 9.08 (bs, 1H) 8.47 (d, J=5.5, 1H), 7.76 (s, 1H), 7.72-7.69 (m, 2H), 7.62 (d, J=8.5, J=5.6, 2H), 7.39 (d, J=8.7, 2H), 7.23 (d, J=5.3, 1H), 7.14 (t, J=8.8, 3H) 3.92 (q, J=7.1, 2H), 0.89 (t, J=7.1, 3H); MS [M+H]$^+$=579.9; LCMS RT=3.31.

Example 3

Preparation of ethyl 4-amino-7-[3-(trifluoromethyl)phenyl]-5-{4-[({[4-(trifluoromethyl)pyridin-2-yl]amino}-carbonyl)amino]phenyl}pyrrolo[2,1-f][1,2,4]triazine-6-carboxylate

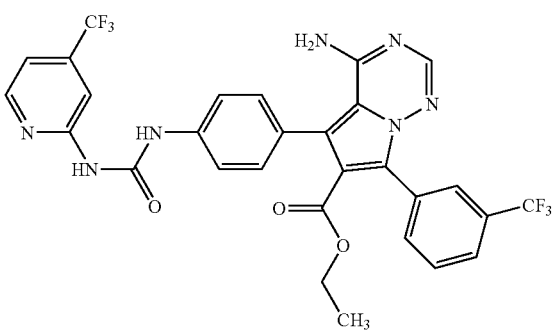

The procedure used for the preparation of Example 1 was used to prepare the title compound by substituting 3-fluorophenylboronic acid with (3-trifluoromethylphenyl)boronic acid. $^1$H-NMR (THF-d$_8$) δ 9.08 (bs, 1H) 8.47 (d, J=5.0, 1H), 7.94 (s, 1H), 7.86 (d, J=7.7, 2H), 7.79 (s, 1H), 7.73-7.67 (m, 3H), 7.61 (d, J=7.7, 1H), 7.40 (d, J=8.5, 1H) 7.22 (d, J=5.0, 1H), 3.92 (q, J=7.1, 2H), 0.88 (t, J=7.1, 3H); MS [M+H]$^+$=592.0; LCMS RT=3.26.

Example 4

Preparation of ethyl 4-amino-7-(4-methoxyphenyl)-5-{4-[({[4-(trifluoromethyl)pyridin-2-yl]amino}carbonyl)amino]-phenyl}pyrrolo[2,1-f][1,2,4]triazine-6-carboxylate

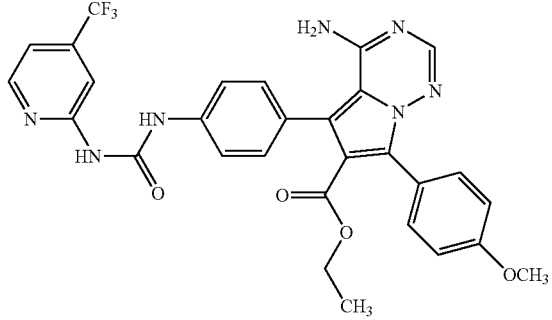

The procedure used for the preparation of Example 1 was used to prepare the title compound by substituting 3-fluorophenylboronic acid with (4-methoxyphenyl)boronic acid. $^1$H-NMR (THF-d$_8$) δ 9.07 (bs, 1H) 8.46 (d, J=5.2, 1H), 7.74 (s, 1H), 7.70 (d, J=8.7, 2H), 7.53 (d, J=8.9, 2H), 7.38 (d, J=8.6, 2H), 7.22 (d, J=5.6, 1H), 6.94 (d, J=9.0, 2H) 3.92 (q, J=7.1, 2H), 3.83 (s, 3H), 0.90 (t, J=7.1, 3H); MS [M+H]$^+$=592.0; LCMS RT=3.20.

Example 5

Preparation of 4-amino-7-cyano-5-4-[([2-fluoro-5-(trifluoromethyl)phenyl]aminocarbonyl)amino]phenyl-N-(2,2-trifluoroethyl)-pyrrolo[2,1-f][1,2,4]triazine-6-carboxamide

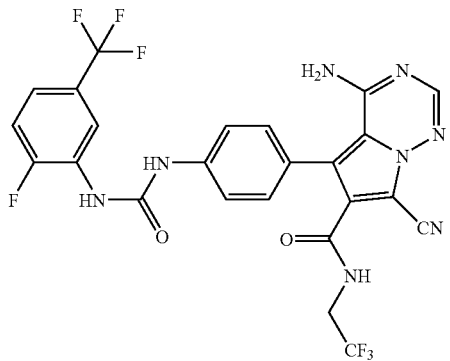

To a solution of Intermediate AT (4-amino-7-bromo-5-{4-[({[2-fluoro-5-(trifluoromethyl)-phenyl]amino}carbonyl) amino]phenyl}-N-(2,2,2-trifluoroethyl)-pyrrolo-[2,1-f]-[1,2,4]triazine-6-carboxamide (46 mg, 0.07 mmol)) in 1-methyl-2-pyrrolidinone (3 ml) was added copper cyanide (I) (25 mg, 0.14 mmol). The reaction was heated at 170° C. in a sealed tube for 2 h. After cooling to rt, ethyl acetate was added and the mixture was washed with $H_2O$ (3×). The combined organic layer was dried ($Na_2SO_4$), concentrated and purified via column chromatography (95:5 v/v $CH_2Cl_2$-MeOH) to afford 13 mg of the above compound (yield 30%). $^1$H-NMR (DMSO-$d_6$) δ9.36 (s, 1H), 8.94 (d, J=3 Hz, 1H), 8.73 (m, 1H), 8.61 to 8.58 (m, 1H), 8.20 (s, 1H), 7.57 (d, J=8 Hz, 2H), 7.31-50 (m, 3H), 3.97 (m, 2H); MS [M+H]$^+$=581.0; LCMS RT=3.37 min.

Example 6

Preparation of ethyl 4-amino-7-cyano-5-{4-[({[4-(trifluoromethyl)pyridin-2-yl]amino}carbonyl) amino]phenyl}pyrrolo[2,1-f][1,2,4]triazine-6-carboxylate

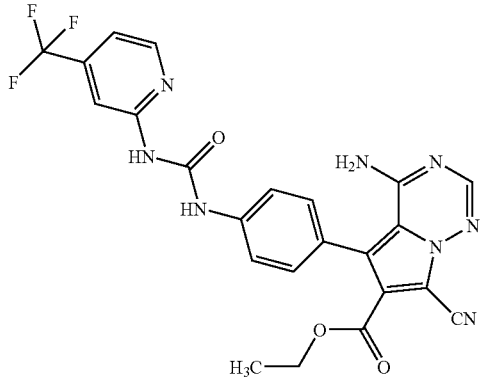

The procedure used for the preparation of Example 5 was used to prepare the title compound by substituting Intermediate AZ for Intermediate AT. $^1$H-NMR (DMSO-$d_6$) δ 9.98 (s, 1H), 9.79 (s, 1H), 8.58 (bs, 1H), 8.53 (d, J=5.4 Hz, 1H), 8.21 (S, 1H), 8.07 (s, 1H), 7.61 (d, J=8.4 Hz, 2H), 7.36 (m, 1H), 7.35 (d, J=8.4 Hz, 2H), 5.39 (bs, 1H), 4.11 (qt, J=6.9 Hz, 2H), 1.07 (t, J=6.9 Hz, 3H); MS [M+H]$^+$=511.1; LCMS RT=3.60.

Example 7

Preparation of 4-amino-7-cyano-N-(2,2,2-trifluoroethyl)-5-{4-[({[4-(trifluoromethyl)pyridin-2-yl]amino}carbonyl)-amino]phenyl}pyrrolo[2,1-f][1,2,4]triazine-6-carboxamide

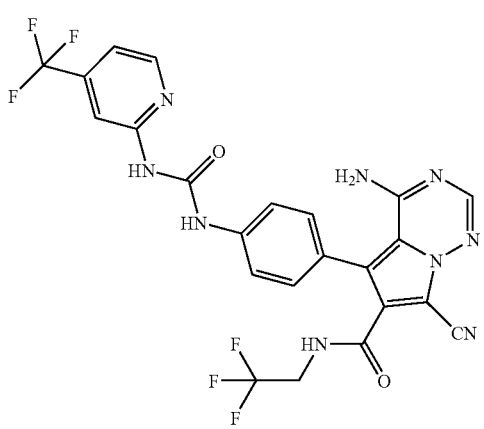

Step 1: Preparation of 4-amino-7-bromo-N-(2,2,2-trifluoroethyl)-5-{4-[({[4-(trifluoromethyl)pyridin-2-yl]amino}carbonyl)amino]phenyl}pyrrolo[2,1-f]-[1,2,4]triazine-6-carboxamide

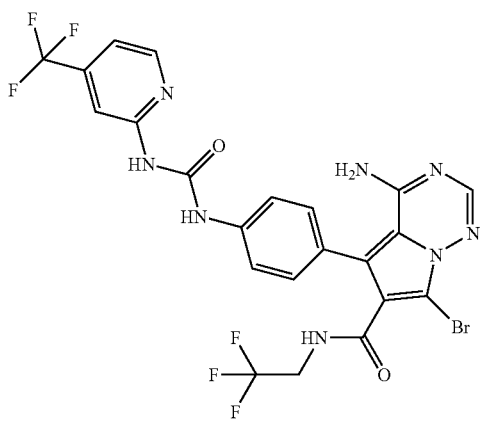

The procedure used for the preparation of Intermediate AT was used to prepare the title compound by substituting Intermediate AH for Intermediate T.

Step 2: Preparation of Title Compound

The procedure used for the preparation of Example 5 was used to prepare the title compound by substituting 4-amino-7-bromo-N-(2,2,2-trifluoroethyl)-5-{4-[({[4-(trifluoromethyl)pyridin-2-yl]amino}carbonyl)amino]phenyl}pyrrolo[2,1-f]-[1,2,4]-triazine-6-carboxamide for Intermediate AT.

¹H-NMR (DMSO-d₆) δ 9.90 (s, 1H), 9.74 (s, 1H), 8.78 (t, J=4.5 Hz, 1H), 8.20 (s, 1H), 8.05 (s, 1H), 7.60 (d, J=6.6 Hz, 2H), 7.37 (m, 1H), 7.34 (d, J=7 Hz, 2H), 5.60 (bs, 1H), 4.04 to 3.95 (m, 2H); MS [M+H]⁺=564.0; LCMS RT=3.17.

Example 8

Preparation of 4-amino-7-cyano-5-{4-[({[4-(trifluoromethyl)pyridin-2-yl]amino}carbonyl)amino]phenyl}pyrrolo[2,1-f][1,2,4]triazine-6-carboxylic acid

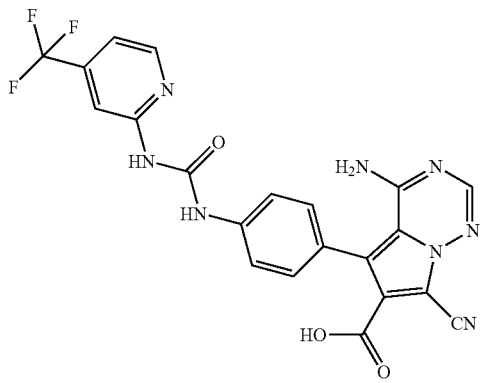

Step 1: Preparation of 4-amino-7-bromo-5-{4-[({[4-(trifluoromethyl)pyridin-2-yl]amino}carbonyl)amino]phenyl}pyrrolo[2,1-f][1,2,4]triazine-6-carboxylic acid

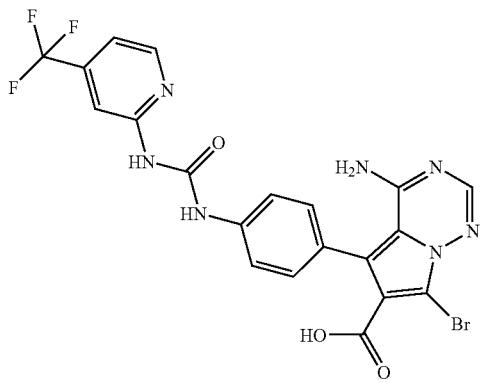

The procedure used for the preparation of Intermediate AT was used to prepare the title compound by substituting Intermediate X for Intermediate T.

Step 2: Preparation of Title Compound

The procedure used for the preparation of Example 5 was used to prepare the title compound by substituting 4-amino-7-bromo-5-{4-[({[4-(trifluoromethyl)pyridin-2-yl]amino}carbonyl)amino]phenyl}pyrrolo[2,1-f][1,2,4]triazine-6-carboxylic acid for Intermediate AT. ¹H-NMR (DMSO-d₆) δ9.92 (s, 1H), 9.77 (s, 1H), 8.53 (d, J=5.4 Hz, 1H), 8.19 (s, 1H), 8.06 (s, 1H), 7.60 (d, J=8.7 Hz, 2H), 7.36 (d, J=8.7 Hz, 2H), 7.36 (m, 1H) 5.30 (bs, 1H); MS [M+H]⁺=483.0; LCMS RT=2.87.

Example 9

Preparation of 4-amino-5-{4-[({[2-fluoro-5-(trifluoromethyl)-phenyl]amino}carbonyl)amino]phenyl}-7-(morpholin-4-ylmethyl)-N-(2,2,2-trifluoroethyl)pyrrolo[2,1-f][1,2,4]triazine-6-carboxamide

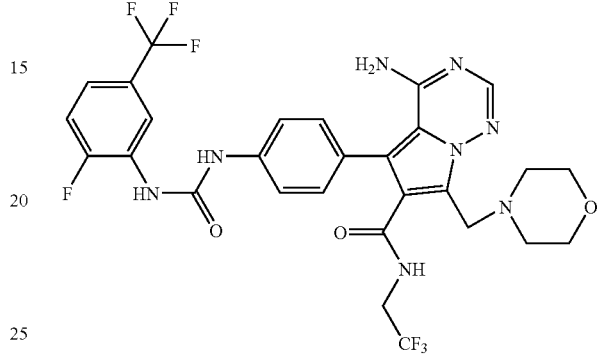

To a suspension of Intermediate AU (4-amino-5-4-[([2-fluoro 5(trifluoromethyl)phenyl]aminocarbonyl)amino]phenyl-7-formyl-N-(2,2,2-trifluoro-ethyl)pyrrolo[2,1-f]-[1,2,4]triazine-6-carboxamide (35 mg, 0.06 mmol)) and morpholine (0.013 ml, 0.015 mmol) in dichloroethane (2 ml) was added sodium triacetoxyborohydride (50 mg, 0.24 mmol). The reaction was stirred under N₂ at rt for 16 h. The reaction mixture was diluted with CH₂Cl₂ and quenched with aq. saturated NaHCO₃. The organic layer was collected, dried over (Na₂SO₄) and concentrated by rotary evaporation. The crude was purified via column chromatography (95:5 v/v CH₂Cl₂-MeOH) to afford 15.5 mg of the title compound (yield 39%). ¹H-NMR (DMSO-d₆) δ 9.98 (dd, J=6 Hz, 1H), 9.29 (s, 1H), 8.95 (d, J=3 Hz, 1H), 8.64 to 8.61 (dd, J=3 Hz, 1H), 7.94 (s, 1H), 7.53 to 7.46 (m, 2H), 7.36-7.46 (m, 1H), 7.28 (d, J=9 Hz, 2H), 4.06 to 4.04 (m, 2H), 4.01 (s, 2H), 3.57 (d, J=7 Hz, 4H), 2.47 to 2.25 (m, 4H) ppm; MS [M+H]⁺=655.1; LCMS RT=2.64 min.

Example 10

Preparation of 4-amino-5-{4-[({[2-fluoro-5-(trifluoromethyl)-phenyl]amino}carbonyl)amino]phenyl}-7-[(4-methylpiperazin-1-yl)methyl]-N-(2,2,2-trifluoroethyl)pyrrolo[2,1-f][1,2,4]triazine-6-carboxamide

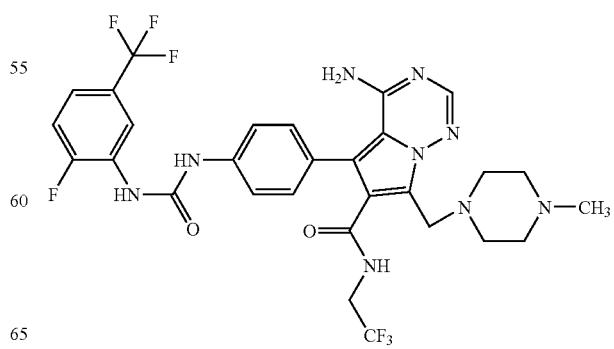

The procedure used for the preparation of Example 9 was used to prepare the title compound by substituting reagent N-methyl piperazine for morpholine. $^1$H-NMR (MeOH-d$_4$) δ 8.61 (d, J=8 Hz, 1H), 7.88 (s, 1H), 7.58 to 7.55 (m, 2H), 7.38 to 7.32 (m, 4H), 4.15 (s, 2H), 4.10 to 4.00 (m, 2H), 2.63 to 2.46 (m, 8H), 2.30 (s, 3H); MS [M+H]$^+$=668.0; LCMS RT=2.55 min.

Example 11

Preparation of N-4-[4-amino-7-cyano-6-(methoxymethyl)pyrrolo[2,1-f][1,2,4]triazin-5-yl]phenyl-N'-[2-fluoro-5-(trifluoromethyl)-phenyl]urea

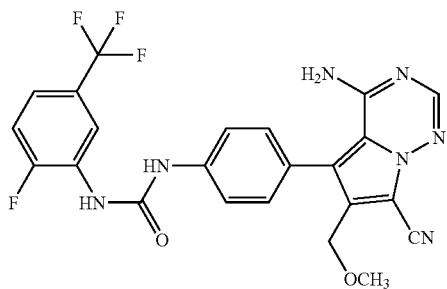

To a solution of Intermediate AV (N-{4-[4-amino-7-bromo-6-(methoxymethyl)pyrrolo[2,1-f][1,2,4]triazin-5-yl]phenyl}-N-[2-fluoro-5-(trifluoro-methyl)phenyl]urea (500 mg, 0.90 mmol)) in 1-methyl-2-pyrrolidinone (3 ml) was added CuCN (321 mg, 1.80 mmol). The reaction was heated at 170° C. in a flask for 2 h. After cooling to rt, EtOAc was added and the mixture was washed with H$_2$O (3×). The combined organic layer was dried (Na$_2$SO$_4$), concentrated and purified via column chromatography (95:5 v/v CH$_2$Cl$_2$-MeOH) to afford 64 mg of the titled compound (yield 13%). $^1$H-NMR (Acetone-d$_6$) δ 8.85 (s, 1H), 8.79 (d, J=8 Hz, 1H), 8.43 (s, 1H), 7.75 to 7.71 (m, 2H), 7.47 to 7.38 (m, 4H), 4.39 (s, 2H), 3.31 (s, 3H); MS [M+H]$^+$=500.1; LCMS RT=3.41 min.

Example 12

Preparation of N-{4-[4-amino-6-(methoxymethyl)-7-(morpholin-4-ylmethyl)pyrrolo[2,1-f][1,2,4]triazin-5-yl]phenyl}-N'-[2-fluoro-5-(trifluoromethyl)phenyl]urea

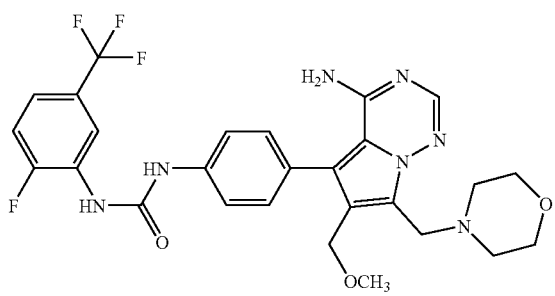

To a suspension of Intermediate AW (N-{4-[4-amino-7-formyl-6-(methoxymethyl)pyrrolo[2,1-f][1,2,4]triazin-5-yl]phenyl}-N'-[2-fluoro-5-(trifluoro-methyl)phenyl]urea (50 mg, 0.1 mmol)) and morpholine (0.01 ml, 0.12 mmol) in dichloroethane (3 ml) was added sodium triacetoxyborohydride (67 mg, 0.31 mmol). The reaction was stirred under N$_2$ at rt for 16 h. The reaction mixture was diluted with CH$_2$Cl$_2$ and subsequently quenched with aqueous saturated NaHCO$_3$. The organic phase was collected, dried (Na$_2$SO$_4$), concentrated and purified via column chromatography (95:5 v/v CH$_2$Cl$_2$-MeOH) to afford 26 mg of the title compound (yield 46%). $^1$H-NMR (DMSO-d$_6$) δ9.32 (s, 1H), 8.96 (d, J=2 Hz, 1H), 8.64 to 8.61 (dd, J=8, 2 Hz, 1H), 7.90 (s, 1H), 7.59 to 7.34 (m, 6H), 4.29 (s, 2H), 3.86 (s, 2H), 3.55 to 3.50 (m, 4H), 3.14 (s, 3H), 2.47-2.41 (m, 4H); MS [M+H]$^+$=573.9; LCMS RT=2.53 min.

Example 13

Preparation of N-(4-{4-amino-6-(methoxymethyl)-7-[(4-methylpiperazin-1-yl)methyl]pyrrolo[2,1-f][1,2,4]triazin-5-yl}phenyl)-N'-[2-fluoro-5-(trifluoro-methyl)phenyl]urea

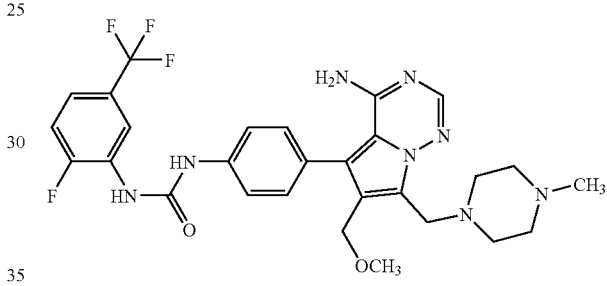

The procedure used for the preparation of Example 12 was used to prepare the title compound by substituting N-methyl piperazine for morpholine. $^1$H-NMR (MeOH-d$_4$) δ8.62 (d, J=8 Hz, 1H), 7.83 (s, 1H), 7.63 to 7.59 (m, 2H), 7.42 to 7.32 (m, 4H), 4.39 (s, 2H), 4.01 (s, 2H), 3.27 (s, 3H), 2.64 to 2.43 (br, 8H), 2.25 (s, 3H); MS [M+H]$^+$=587.0; LCMS RT=2.37 min.

Example 14

Preparation of N-{4-[4-amino-6-(methoxymethyl)-7-(pyrrolidin-1-ylmethyl)pyrrolo[2,1-f][1,2,4]triazin-5-yl]phenyl}-N'-[2-fluoro-5-(trifluoromethyl)phenyl]urea

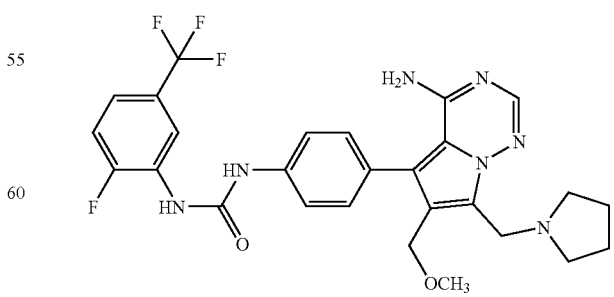

The procedure used for the preparation of Example 12 was used to prepare the title compound by substituting pyrrolidine for morpholine. $^1$H-NMR (MeOH-d$_4$) δ8.62 (d, J=8 Hz, 1H), 7.90 (s, 1H), 7.65 to 7.62 (m, 2H), 7.42 to 7.33 (m, 4H), 4.42 (s, 4H), 3.29 (s, 3H), 3.00 (s, 4H), 1.96 to 1.90 (m, 4H); MS [M+H]$^+$=558.0; LCMS RT=2.49 min.

Example 15

Preparation of N-{4-[4-amino-7-{[(2-methoxyethyl)amino]methyl}-6-(methoxymethyl)pyrrolo[2,1-f][1,2,4]triazin-5-yl]phenyl}-N'-[2-fluoro-5-(trifluoromethyl)phenyl]urea

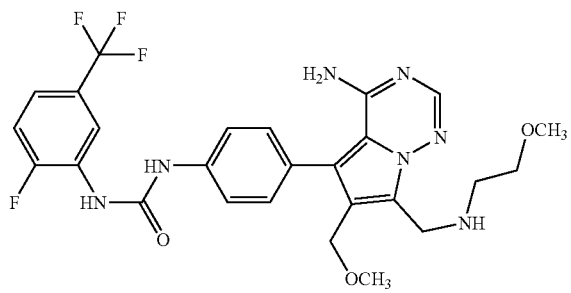

The procedure used for the preparation of Example 12 was used to prepare the title compound by substituting reagent methoxyethylamine for morpholine. $^1$H-NMR (DMSO-d$_6$) δ9.34 (s, 1H), 8.96 (d, J=3 Hz, 1H), 8.64 to 8.61 (m, 1H), 7.90 (s, 1H), 7.60 to 7.31 (m, 6H), 4.27 (s, 2H), 4.05 (s, 2H), 3.40-3.34 (m, 2H), 3.18 (s, 3H), 3.16 (s, 3H); MS [M+H]$^+$=561.9; LCMS RT=2.51 min.

Example 16

Preparation of N-{4-[4-amino-7-[(cyclopropylamino)methyl]-6-(methoxymethyl)pyrrolo[2,1-f][1,2,4]triazin-5-yl]phenyl}-N'-[2-fluoro-5-(trifluoromethyl)phenyl]urea

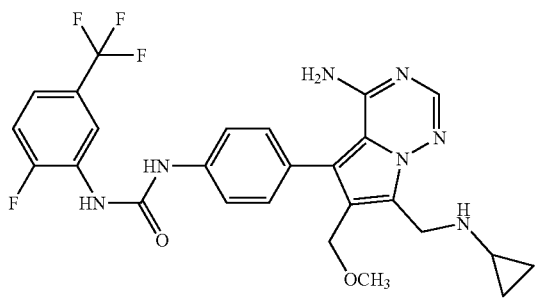

The procedure used for the preparation of Example 12 was used to prepare the title compound by substituting reagent cyclopropylamine for morpholine. $^1$H-NMR (CH$_3$OH-d$_4$) δ8.62 (d, J=6 Hz, 1H), 7.86 (s, 1H), 7.64 to 7.60 (m, 2H), 7.42 to 7.32 (m, 4H), 4.40 (s, 2H), 4.22 (s, 2H), 3.36 (s, 3H), 2.14 to 2.09 (m, 1H), 0.52 to 0.40 (m, 4H) ppm; MS [M+H]$^+$=543.9; LCMS RT=2.45 min

Example 17

Preparation of N-{4-[4-amino-7-{[bis(2-methoxyethyl)-amino]methyl}-6-(methoxymethyl)pyrrolo[2,1-f][1,2,4]triazin-5-yl]phenyl}-N'-[2-fluoro-5-(trifluoromethyl)phenyl]urea

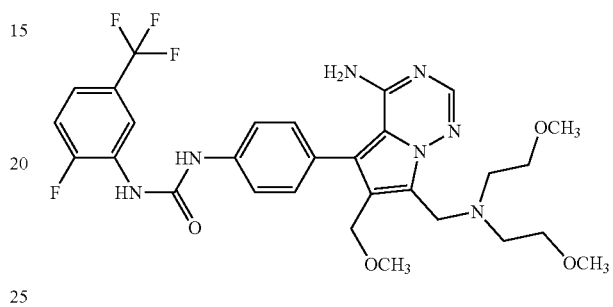

The procedure used for the preparation of Example 12 was used to prepare the title compound by substituting N-(2-methoxyethyl)methylamine for morpholine. $^1$H-NMR (DMSO-d$_6$) δ 9.32 (s, 1H), 8.96 (d, J=3 Hz, 1H), 8.63 (dd, J=8, 3 Hz, 2H), 7.89 (s, 1H), 7.58 (d, J=8 Hz, 2H), 7.50 to 7.33 (m, 3H), 4.31 (s, 2H), 4.03 (s, 2H), 3.20 to 3.40 (m, 13H), 2.6 (t, J=5 Hz, 4H) ppm; MS [M+H]$^+$=619.9; LCMS RT=2.69 min.

Example 18

Preparation of N-{4-[4-amino-7-[(2,6-dimethylmorpholin-4-yl)methyl]-6-(methoxymethyl)pyrrolo[2,1-f][1,2,4]triazin-5-yl]phenyl}-N'-[2-fluoro-5-(trifluoromethyl)phenyl]urea

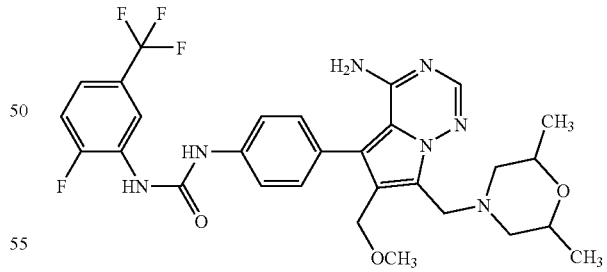

The procedure used for the preparation of Example 12 was used to prepare the title compound by substituting 2,4-dimethylmorpholine for morpholine. $^1$H-NMR (CH$_3$OH-d$_4$) δ8.63 (dd, J=6, 1 Hz, 1H), 7.84 (s, 1H), 7.62 (dd, J=6, 2 Hz, 2H), 7.42 (dd, J=6, 2 Hz, 2H), 7.34 (dd, J=7, 2 Hz, 2H), 4.39 (s, 2H), 3.99 (s, 2H), 3.68 to 3.63 (m, 2H), 3.28 (s, 3H), 2.86 (d, J=11 Hz, 2H), 1.91 (t, J=11 Hz, 2H), 1.1 (d, J=6 Hz, 6H) ppm; MS [M+H]$^+$=602.0; LCMS RT=2.73 min.

Example 19

Preparation of N-(4-{4-amino-6-(methoxymethyl)-7-[(3-oxopiperazin-1-yl)methyl]pyrrolo[2,1-f][1,2,4]triazin-5-yl}phenyl)-N'-[2-fluoro-5-(trifluoromethyl)phenyl]urea

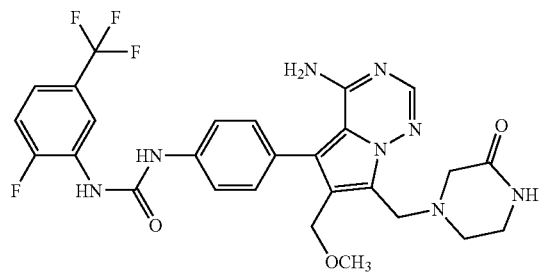

The procedure used for the preparation of Example 12 was used to prepare the title compound by substituting 2-oxopiperizine for morpholine. $^1$H-NMR (DMSO-$d_6$) δ9.32 (s, 1H), 8.96 (d, J=3 Hz, 1H), 8.62 (dd, J=7, 2 Hz, 1H), 7.91 (s, 1H), 7.70 (s, 1H), 7.60 (d, J=3 Hz, 2H), 7.57 to 7.35 (m, 3H), 4.29 (s, 2H), 3.93 (s, 2H), 3.19 (s, 3H), 3.09 (m, 2H), 2.98 (m, 2H), 2.62 (m, 2H) ppm; MS [M+H]$^+$=587; LCMS RT=2.59 min.

Example 20

Preparation of N-[4-(4-amino-6-(methoxymethyl)-7-{[4-(methylsulfonyl)piperazin-1-yl]methyl}pyrrolo[2,1-f][1,2,4]triazin-5-yl)phenyl]-N'-[2-fluoro-5-(trifluoromethyl)phenyl]urea

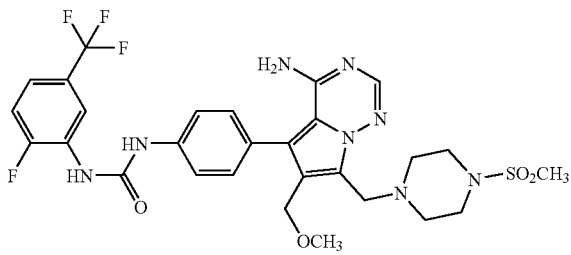

The procedure used for the preparation of Example 12 was used to prepare the title compound by substituting 1-(methylsulfonyl)piperazine for morpholine. $^1$H-NMR (CH$_3$OH-$d_4$) δ8.62 (dd, J=7, 1 Hz, 1H), 7.84 (s, 1H), 7.64 to 7.61 (m, 2H), 7.43 to 7.41 (m, 4H), 4.39 (s, 2H), 4.03 (s, 3H), 3.21 (t, J=5 Hz, 4H), 2.81 (s, 3H), 2.66 (t, J=5 Hz, 4H) ppm; MS [M+H]$^+$=651; LCMS RT=2.61 min.

Example 21

Preparation of N-{4-[7-[(4-acetylpiperazin-1-yl)methyl]-4-amino-6-(methoxymethyl)pyrrolo[2,1-f][1,2,4]triazin-5-yl]phenyl}-N'-[2-fluoro-5-(trifluoromethyl)phenyl]urea

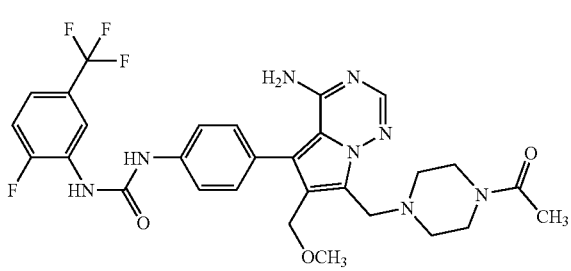

The procedure used for the preparation of Example 12 was used to prepare the title compound by substituting 1-acetylpiperazine for morpholine. $^1$H-NMR (CH$_3$OH-$d_4$) δ 8.62 (d, J=3 Hz, 1H), 7.82 (s, 1H), 7.62 (d, J=5 Hz, 2H), 7.42 (d, J=5 Hz, 2H), 7.38 (d, J=5 Hz, 2H), 4.42 (s, 2H), 4.02 (s, 2H), 3.58 to 3.44 (m, 4H), 2.62 to 2.58 (m, 4H), 2.08 (s, 3H) ppm; MS [M+H]$^+$=614.9; LCMS RT=2.58 min.

Example 22

Preparation of N-{4-[4-amino-7-{[(2-methoxyethyl)(methyl)amino]methyl}-6-(methoxymethyl)pyrrolo[2,1-f][1,2,4]triazin-5-yl]phenyl}-N'-[2-fluoro-5-(trifluoromethyl)phenyl]urea

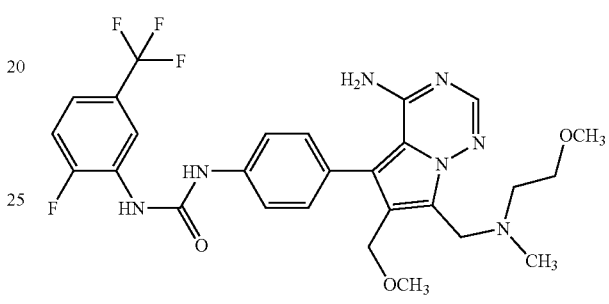

The procedure used for the preparation of Example 12 was used to prepare the title compound by substituting 2-methoxy-N-methylethanamine for morpholine. $^1$H-NMR (DMSO-$d_6$) δ9.32 (d, 1H), 8.96 (d, J=2 Hz, 1H), 8.63 (dd, J=7 Hz, 1H), 7.89 (s, 1H), 7.58 (d, J=8 Hz, 2H), 7.50 to 7.34 (m, 4H), 4.30 (s, 2H), 3.89 (br, 2H), 3.46 to 3.48 (m, 2H), 3.20 (s, 3H), 3.16 (s, 3H), 2.58 to 2.55 (m, 2H), 2.17 (s, 3H) ppm; MS [M+H]$^+$=575.9; LCMS RT=2.57 min.

Example 23

Preparation of N-{4-[4-amino-7-(hydroxymethyl)-6-(methoxymethyl)-pyrrolo[2,1-f][1,2,4]triazin-5-yl]phenyl}-N'-[2-fluoro-5-(trifluoromethyl)-phenyl]urea

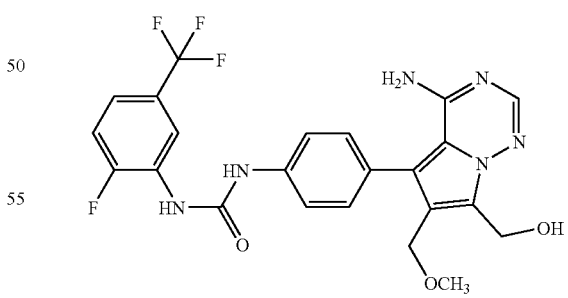

To a solution of Intermediate AW (N-{4-[4-amino-7-formyl-6-(methoxymethyl)pyrrolo[2,1-f][1,2,4]triazin-5-yl]phenyl}-N'-[2-fluoro-5-(trifluoro-methyl)phenyl]urea (50 mg, 0.1 mmol)) in THF at −78° C. under N$_2$ was added DIBAL-H (0.5 ml, 0.5 mmol). The reaction mixture was stirred for 30 min. and was allowed to warm up to 0° C. The reaction was diluted with ethyl acetate (5 mL) and quenched with aqueous saturated Rochelle's salt (5 ml). The reaction mixture was stirred for 10 min at 0° C. and then warmed to rt. The organic layer was collected and washed with aqueous Rochelle's salt (2×), dried ($Na_2SO_4$) and concentrated. The crude concentrate was purified via column chromatography (5:95, v/v MeOH—$CH_2Cl_2$) to afford 25 mg of the title compound (yield 49%). $^1$H-NMR (DMSO-$d_6$) δ 9.32 (s, 1H), 8.96 (d, J=3 Hz, 1H), 8.63 (d, J=5 Hz, 1H), 7.90 (s, 1H), 7.58 (d, J=7 Hz, 2H), 7.50 to 7.32 (m, 3H), 5.0 (t, J=5 Hz, 1H), 4.79 (d, J=5 Hz, 2H), 4.30 (s, 3H), 3.16 (s, 2H) ppm; MS [M+H]$^+$=505.1; LCMS RT=2.66 min.

Example 24

Preparation of N-{4-[4-amino-6,7-bis(methoxymethyl)pyrrolo[2,1-f]-[1,2,4]triazin-5-yl]phenyl}-N'-[2-fluoro-5-(trifluoromethyl)phenyl]urea

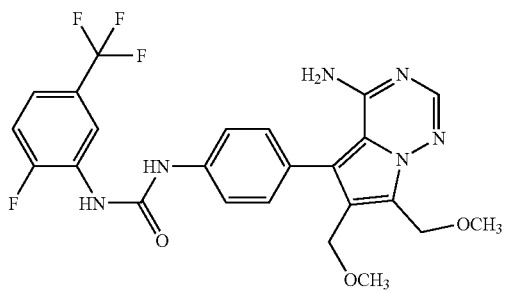

To a solution of Example 23 (N-{4-[4-amino-7-(hydroxymethyl)-6-(methoxy-methyl)pyrrolo[2,1-f][1,2,4]triazin-5-yl]phenyl}-N'-[2-fluoro-5-(trifluoro-methyl)-phenyl]urea (22 mg, 0.04 mmol)) in anhydrous THF (1 mL) and $CH_2Cl_2$ (1 mL) was added $SOCl_2$ (0.006 ml, 0.08 mmol). After 20 min, analytical HPLC showed half of the starting material remained. Additional $SOCl_2$ (0.01 ml) was added and the reaction was stirred at rt for 2.5 h until completion. The mixture was evaporated to dryness and $CH_2Cl_2$ (3 ml) was added. The solvent was evaporated to dryness and the crude concentrate was re-suspended in $CH_2Cl_2$ and evaporated to remove the excess $SOCl_2$ completely. To the resulting solid was added anhydrous MeOH (1 ml) and Hunig's base (0.008 ml), the reaction was stirred at 70° C. overnight. After 16 h, the reaction was cooled to rt and solvent was evaporated. The crude material was taken up in ethyl acetate, washed with aq. saturated sodium bicarbonate three times and dried over $Na_2SO_4$. After concentration, the resulting crude was purified via column chromatography (5:95 v/v MeOH—$CH_2Cl_2$) to afford 12 mg of the title compound (yield 53%). $^1$H-NMR (DMSO-$d_6$) δ 9.32 (s, 1H), 8.96 (d, J=3 Hz, 1H), 8.63 (dd, J=7, 3 Hz, 1H), 7.92 (s, 1H), 7.59 (t, J=3 Hz, 2H), 7.57 to 7.32 (m, 4H), 4.73 (s, 2H), 4.28 (s, 2H), 3.26 (s, 3H), 3.24 (s, 3H) ppm; MS [M+H]$^+$=519.1; LCMS RT=2.84 rain Example 25

Preparation of N-{4-[4-amino-7-(1-hydroxyethyl)-6-(methoxymethyl)pyrrolo[2,1-f][1,2,4]triazin-5-yl]phenyl}-N'-[2-fluoro-5-(trifluoromethyl)phenyl]urea

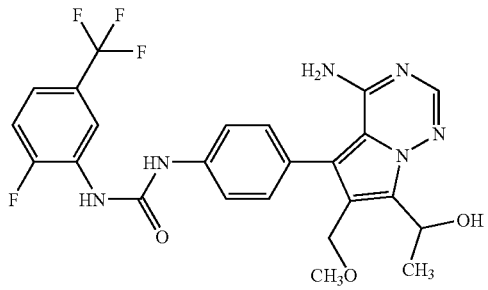

To a solution of Intermediate AW (N-{4-[4-amino-7-formyl-6-(methoxymethyl)pyrrolo[2,1-f][1,2,4]triazin-5-yl]phenyl}-N'-[2-fluoro-5-(trifluoro-methyl)phenyl]urea (25 mg, 0.05 mmol)) in THF (1 ml) at −78 C under $N_2$ was added methyllithium (0.18 ml, 0.25 mmol) and stirred for 10 min. The reaction was quenched by the addition of $H_2O$ and after warming to rt, the reaction mixture was extracted with ethyl acetate. The organic layer was dried ($Na_2SO_4$), concentrated and purified via column chromatography (5:95 v/v MeOH—$CH_2Cl_2$) to afford 13 mg of the title compound (yield 50%). $^1$H-NMR (DMSO-$d_6$) δ9.32 (s, 1H), 8.97 (d, J=2 Hz, 1H), 8.63 (dd, J=8, 2 Hz, 1H), 7.87 (s, 1H), 7.55 (d, J=8 Hz, 2H), 7.53 to 7.31 (m, 4H), 5.49 to 5.45 (m, 1H), 5.19 (d, J=6 Hz, 1H), 4.52 (d, J=10 Hz, 1H), 4.19 (d, J=10 Hz, 1H), 3.16 (s, 3H), 1.50 (d, J=6 Hz, 3H) ppm; MS [M+H]$^+$=519.1; LCMS RT=2.74 min.

Example 26

Preparation of N-4-[4-amino-7-(morpholin-4-ylmethyl)-6-(1,3-oxazol-5-yl)pyrrolo[2,1-f][1,2,4]triazin-5-yl]phenyl-N'-[2-fluoro-5-(trifluoromethyl)phenyl]urea

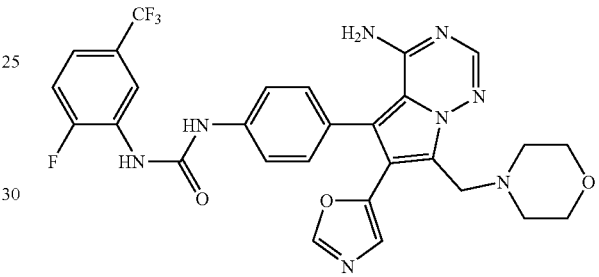

To a solution of formaldehyde (37% solution in water, (14 uL, 0.19 mmol) and morpholine (12 ul, 0.19 mmol) in AcOH (0.5 mL) was added to a stirring solution of Intermediate Q in AcOH (1 mL). The reaction was heated to 60° C. overnight. The solvent was removed under vacuum and the residue was dissolved in DCM and washed with sat. $NaHCO_3$ and brine. The organic layer was collected, dried, and concentrated under vacuum. The crude material was purified by silica gel chromatography using 100% EtOAc. The product fractions were collected and the solvent removed under vacuum to give Example 60 (46% yield). $^1$H-NMR (DMSO-$d_6$) δ 9.35 (s, 1H), 9.00 to 8.95 (m, 1H), 8.363 to 8.59 (m, 1H), 8.28 (s, 1H), 7.96 (s, 1H), 7.93 (br s, 1H), 7.59 to 7.54 (m, 2H), 7.52-7.46 (m, 1H), 7.41 to 7.36 (m, 1H), 7.34 to 7.29 (m, 2H), 6.93 (s, 1H), 5.07 (br s, 1H), 3.94 (s, 2H), 3.54 to 3.47 (m, 4H), 2.44 to 2.36 (m, 4H); MS [M+H]$^+$=597.0; LCMS RT=2.45.

Example 27

Preparation of N-4-[4-amino-7-(morpholin-4-ylmethyl)-6-(1,3-oxazol-5-yl)pyrrolo[2,1-f][1,2,4]triazin-5-yl]phenyl-N'-[4-(trifluoromethyl)pyridin-2-yl]urea

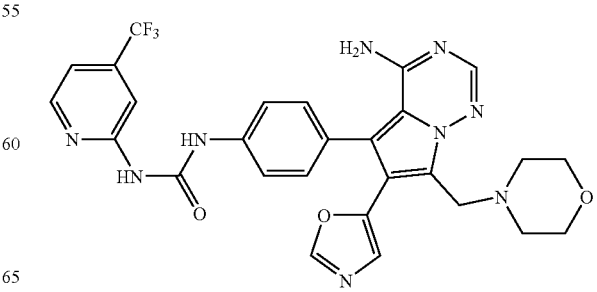

The procedure used for the preparation of Example 26 was used to prepare the title compound by substituting Intermediate AG for Intermediate Q. ¹H-NMR (DMSO-d₆) δ 9.94 (s, 1H), 9.79 (s, 1H), 8.53 (d, J=5.3, 1H), 8.27 (s, 1H), 8.04 (s, 1H), 7.96 (s, 1H), 7.93 (br s, 1H), 7.63 to 7.58 (m, 2H), 7.36 (d, J=5.3 (1H), 7.34 to 7.31 (m, 2H), 6.93 (s, 1H), 5.09 (br s, 1H), 3.93 (s, 2H), 3.52 to 3.47 (m, 4H), 2.43 to 2.37 (m, 4H); MS [M+H]⁺=579.9; LCMS RT=2.42.

Example 28

Preparation of N-4-[4-amino-7-(morpholin-4-ylmethyl)-6-(1,3-oxazol-5-yl)pyrrolo[2,1-f][1,2,4]triazin-5-yl]phenyl-N'-[3-(trifluoromethoxy)-phenyl]urea

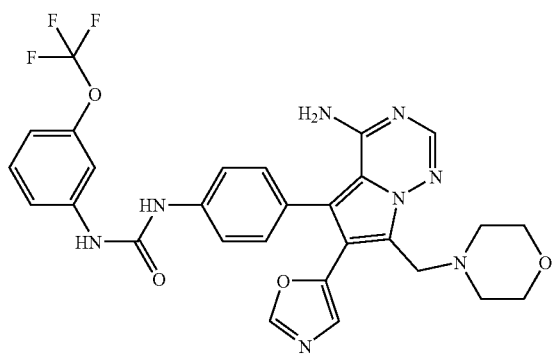

Step 1: Preparation of N-{4-[4-amino-6-(1,3-oxazol-5-yl)pyrrolo[2,1-f][1,2,4]-triazin-5-yl]phenyl}-N'-[3-(trifluoromethoxy)phenyl]urea

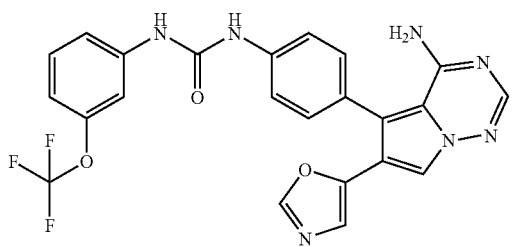

The sequence of procedures used for the preparation of Intermediate O was used to prepare N-{4-[4-amino-6-(1,3-oxazol-5-yl)pyrrolo[2,1-f][1,2,4]triazin-5-yl]phenyl}-N'-[3-(trifluoromethoxy)phenyl]urea by substituting the initial core Intermediate H for initial core intermediate I. ¹H-NMR (DMSO-d₆) δ 9.11 (s, 1H), 9.02 (s, 1H), 8.30 (s, 1H), 8.08 (s, 1H), 7.90 (s, 1H), 7.71 (s, 1H), 7.62 to 7.60 (d, J=8.4 Hz, 2H), 7.42 to 7.38 (t, J=8.1 Hz, 1H), 7.36 to 7.34 (d, J=8.7 Hz, 2H), 7.32 to 7.29 (d, J=9.1 Hz, 1H), 6.96 to 6.93 (d, J=10.6, 1H), 6.55 (s, 1H); MS [M+H]⁺=496.1; LCMS RT=2.89 min.

Step 2: Preparation of Title Compound

The procedure used for the preparation of Example 26 was used to prepare the title compound by substituting N-{4-[4-amino-6-(1,3-oxazol-5-yl)pyrrolo[2,1-f][1,2,4]triazin-5-yl]phenyl}-N'-[3-(trifluoromethoxy)phenyl]urea for Intermediate Q. ¹H-NMR (DMSO-d₆) δ 9.13 (s, 1H), 8.99 (s, 1H), 8.28 (s, 1H), 7.96 (s, 1H), 7.91 (br s, 1H), 7.71 to 7.69 (m, 1H), 7.57 to 7.53 (m, 2H), 7.38 (t, J=8.4, 1H), 7.32 to 7.37 (m, 3H), 6.95 to 6.91 (m, 2H). 5.07 (br s, 1H), 3.93 (s, 2H), 3.53 to 3.47 (m, 4H), 2.43 to 2.37 (m, 4H); MS [M+H]⁺=594.9; LCMS RT=2.57.

Example 29

Preparation of N-4-[4-amino-7-(morpholin-4-ylmethyl)-6-(1,3-oxazol-5-yl)pyrrolo[2,1-f][1,2,4]triazin-5-yl]phenyl-N'-[3-fluoro-5-(trifluoromethyl)phenyl]urea

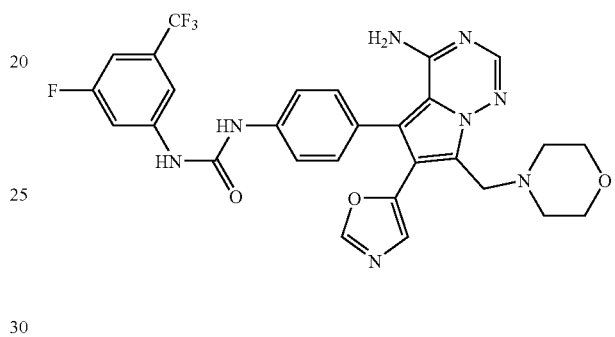

Step 1: Preparation of N-{4-[4-amino-6-(1,3-oxazol-5-yl)pyrrolo[2,1-f][1,2,4]triazin-5-yl]phenyl}-N'-[3-fluoro-5-(trifluoromethyl)phenyl]urea

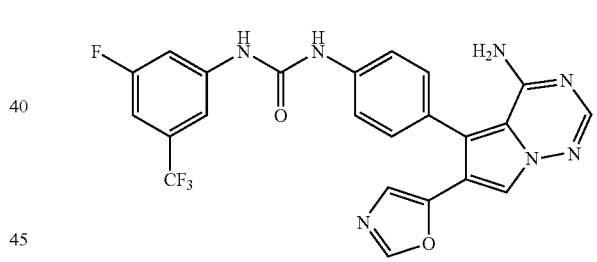

The sequence of procedures used for the preparation of Intermediate O was used to prepare N-{4-[4-amino-6-(1,3-oxazol-5-yl)pyrrolo[2,1-f][1,2,4]triazin-5-yl]phenyl}-N'-[3-fluoro-5-(trifluoromethyl)phenyl]urea by substituting the initial core Intermediate H for initial core intermediate I. ¹H-NMR (CD₃OD) δ 8.12 (s, 1H), 7.97 (s, 1H), 7.83 (s, 1H), 7.71 to 7.60 (m, 4H), 7.42 (d, J=8.2 Hz, 2H), 7.05 (d, J=8.1 Hz, 1H), 6.49 (s, 1H); MS [M+H]⁺=498.2; LCMS RT=2.90.

Step 2: Preparation of Title Compound

The procedure used for the preparation of Example 26 was used to prepare the title compound by substituting N-{4-[4-amino-6-(1,3-oxazol-5-yl)pyrrolo[2,1-f]-[1,2,4]triazin-5-yl]phenyl}-N'-[3-fluoro-5-(trifluoromethyl)phenyl]urea for Intermediate Q. ¹H-NMR (DMSO-d₆) δ 9.36 (s, 1H), 9.14 (s, 1H), 8.28 (s, 1H), 7.96 (s, 1H), 7.94 (br s, 1H), 7.71 (s, 1H), 7.64 to 7.59 (m, 1H), 7.58 to 7.54 (m, 2H), 7.33 to 7.28 (m, 2H), 7.25 to 7.20 (m, 1H), 6.92 (s, 1H), 5.07 (br s, 1H), 3.93

(s, 2H), 3.54 to 3.46 (m, 4H), 2.44 to 2.36 (m, 4H); MS [M+H]⁺=569.9; LCMS RT=2.63.

Example 30

Preparation of N-4-[4-amino-7-[(2,6-dimethylmorpholin-4-yl)methyl]-6-(1,3-oxazol-5-yl)pyrrolo[2,1-f][1,2,4]triazin-5-yl]phenyl-N'-[2-fluoro-5-(trifluoromethyl)phenyl]urea

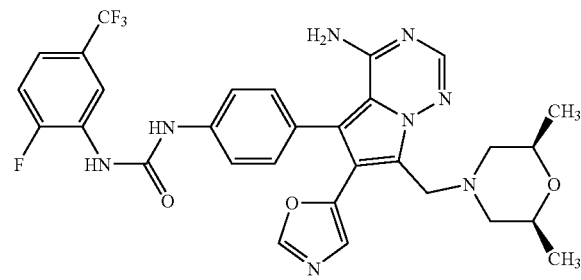

The procedure used for the preparation of Example 26 was used to prepare the title compound by substituting 2,4-dimethylmorpholine for morpholine. ¹H-NMR (DMSO-d₆) δ 9.35 (s, 1H), 8.97 (d, J=2.4, 1H), 8.62 to 8.59 (m, 1H), 8.27 (s, 1H), 7.97 (s, 1H), 7.91 (br s, 1H), 7.58 to 7.53 (m, 2H), 7.52 to 7.46 (m, 1H), 7.41 to 7.36 (m, 1H), 7.33 to 7.29 (m, 2H), 6.94 (s, 1H), 5.05 (br s, 1H), 3.90 (s, 2H), 3.50 to 3.42 (m, 2H), 2.65 (d, J=10.9, 2H), 1.76 (t, J=10.9, 2H), 1.01 (s, 3H), 0.99 (s, 3H); MS [M+H]⁺=625.0; LCMS RT=2.69.

Example 31

Preparation of N-4-[4-amino-7-[(4-methylpiperazin-1-yl)methyl]-6-(1,3-oxazol-5-yl)pyrrolo[2,1-f][1,2,4]triazin-5-yl]phenyl-N'-[2-fluoro-5-(trifluoromethyl)phenyl]urea

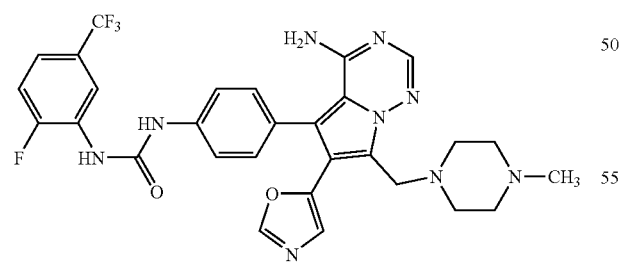

The procedure used for the preparation of Example 26 was used to prepare the title compound by substituting N-methyl piperazine for morpholine. ¹H-NMR (DMSO-d₆) δ 9.34 (s, 1H), 8.97 (d, J=2.4, 1H), 8.63 to 8.59 (m, 1H), 8.27 (s, 1H), 7.45 (s, 1H), 7.58 to 7.54 (m, 2H), 7.52 to 7.46 (m, 1H), 7.41 to 7.36 (m, 1H), 7.33 to 7.29 (m, 2H), 6.94 (s, 1H), 3.92 (s, 2H), 2.46 to 2.16 (m, 8H), 2.10 (s, 3H); MS [M+H]⁺=610.0; LCMS RT=2.49.

Example 32

Preparation of N-4-[7-[(4-acetylpiperazin-1-yl)methyl]-4-amino-6-(1,3-oxazol-5-yl)pyrrolo[2,1-f][1,2,4]triazin-5-yl]phenyl-N'-[2-fluoro-5-(trifluoromethyl)phenyl]urea

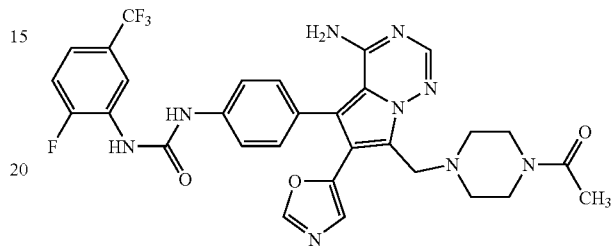

The procedure used for the preparation of Example 26 was used to prepare the title compound by substituting 1-acetylpiperazine for morpholine. ¹H-NMR (DMSO-d₆) δ 9.34 (s, 1H), 8.97 (d, J=2.4, 1H), 8.63 to 8.59 (m, 1H), 8.28 (s, 1H), 7.96 (s, 1H), 7.92 (br s, 1H), 7.58 to 7.54 (m, 2H), 7.53 to 7.47 (m, 1H), 7.41 to 7.36 (m, 1H), 7.34 to 7.30 (m, 2H), 6.91 (s, 1H), 5.09 (br s, 1H), 3.97 (s, 2H), 3.39 to 3.32 (m, 4H), 2.44 to 2.39 (m, 2H), 2.38 to 2.33 (m, 2H); MS [M+H]⁺=637.9; LCMS RT=2.57.

Example 33

N-4-[4-amino-7-(morpholin-4-ylmethyl)-6-(1,3-oxazol-5-yl)pyrrolo[2,1-f][1,2,4]triazin-5-yl]-2-fluorophenyl-N'-[4-(trifluoromethyl)pyridin-2-yl]urea

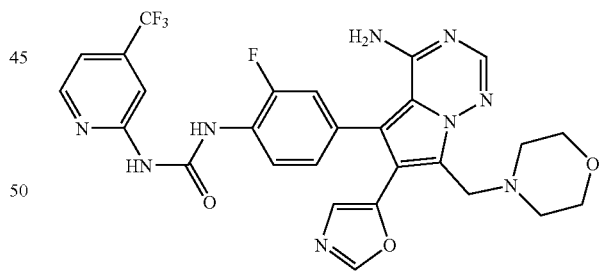

The procedure used for the preparation of Example 26 was used to prepare the title compound by substituting Intermediate AK (N-{4-[4-amino-6-(1,3-oxazol-5-yl)pyrrolo[2,1-f][1,2,4]triazin-5-yl]-2-fluorophenyl}-N'-[2-fluoro-5-(trifluoromethyl)-phenyl]urea) for Intermediate Q. ¹H-NMR (DMSO-d₆) δ 10.16 (s, 1H), 10.12 (br s, 1H), 8.53 (d, J=4.4 Hz, 1H), 8.29 (m, 1H), 8.28 (m, 1H), 7.99 (br s, 1H), 7.97 (m, 1H), 7.38 (d, J=2.2 Hz, 1H), 7.31 (d, J=12.4 Hz, 1H), 7.16 (d, J=8.2 Hz, 1H), 7.00 (m, 1H), 3.92 (s, 2H), 3.51 (m, 4H), 2.41 (m, 4H); MS [M+H]⁺=598.0; LCMS RT=2.89.

Example 34

N-4-[4-amino-6-(hydroxymethyl)-7-(morpholin-4-ylmethyl)-pyrrolo[2,1-f][1,2,4]triazin-5-yl]phenyl-N'-[2-fluoro-5-(trifluoromethyl)-phenyl]urea

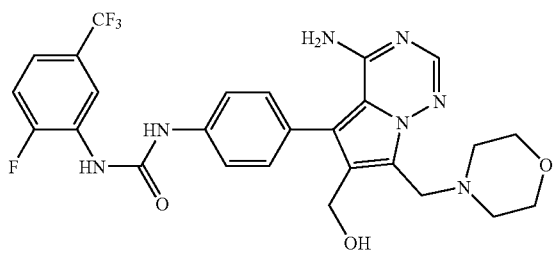

The procedure used for the preparation of Example 26 was used to prepare the title compound by substituting Intermediate K (N-{4-[4-amino-6-(hydroxymethyl)pyrrolo[2,1-f][1,2,4]-triazin-5-yl]phenyl}-N'-[2-fluoro-5-(trifluoro-methyl)phenyl]-urea) for Intermediate Q. $^1$H-NMR (DMSO-d$_6$) δ 9.35 (s, 1H), 8.98 (d, J=2.7 Hz, 1H), 8.64 (dd, J=7.3, 2.5 Hz, 1H), 7.91 (s, 1H), 7.60 (m, 2H), 7.52 (m, 1H), 7.41 (m, 1H), 7.39 (m, 2H), 5.08 (br s, 1H), 4.40 (s, 2H), 3.95 (s, 2H), 3.53 (m, 4H), 2.45 (m, 4H); MS [M+H]$^+$=560.0; LCMS RT=2.43.

Example 35

Preparation of N-4-[4-amino-6-(methoxymethyl)-7-(morpholin-4-ylmethyl)pyrrolo[2,1-f][1,2,4]triazin-5-yl]phenyl-N'-[4-(trifluoromethyl)pyridin-2-yl]urea

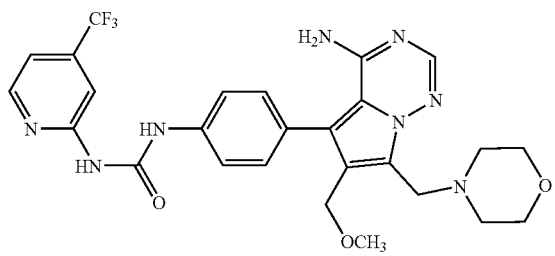

The procedure used for the preparation of Example 26 was used to prepare the title compound by substituting Intermediate Z for Intermediate Q. $^1$H-NMR (DMSO-d$_6$) δ9.91 (s, 1H), 9.76 (s, 1H), 8.46 to 8.58 (m, 1H), 8.03 (s, 1H), 7.88 (s, 1H), 7.54 to 7.71 (m, 2H), 7.28 to 7.45 (m, 3H), 4.29 (s, 2H), 3.85 (s, 2H), 3.44 to 3.63 (m, 4H), 3.17 (s, 3H), 2.35 to 2.50 (m, 4H). MS [M+H]$^+$=556.91; LCMS RT=2.35.

Example 36

N-4-[4-amino-7-[(2R,6S)-2,6-dimethylmorpholin-4-yl]methyl-6-(methoxymethyl)pyrrolo[2,1-f][1,2,4]triazin-5-yl]phenyl-N'-[4-(trifluoromethyl)pyridin-2-yl]urea

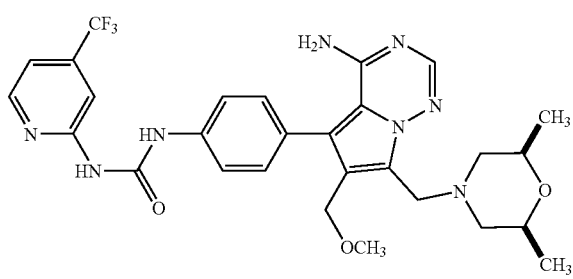

The procedure used for the preparation of Example 26 was used to prepare the title compound by substituting Intermediate Z for Intermediate Q and by substituting 2,4-dimethylmorpholine for morpholine. $^1$H-NMR (DMSO-d$_6$) δ9.89 (s, 1H), 9.75 (s, 1H), 8.48 to 8.59 (m, 1H), 8.04 (s, 1H), 7.89 (s, 1H), 7.53 to 7.70 (m, 2H), 7.25 to 7.47 (m, 3H), 4.29 (s, 2H), 3.84 (s, 2H), 3.41 to 3.59 (m, 2H), 3.18 (s, 3H), 2.68 to 2.85 (d, J=9.6 Hz, 2H), 1.67 to 1.87 (m, 2H), 0.99-1.07 (d, J=6.8 Hz, 6H). MS [M+H]$^+$=584.90; LCMS RT=2.58.

Example 37

N-4-[7-[(4-acetylpiperazin-1-yl)methyl]-4-amino-6-(methoxy-methyl)pyrrolo[2,1-f][1,2,4]triazin-5-yl]phenyl-N'-[4-(trifluoromethyl)pyridin-2-yl]urea

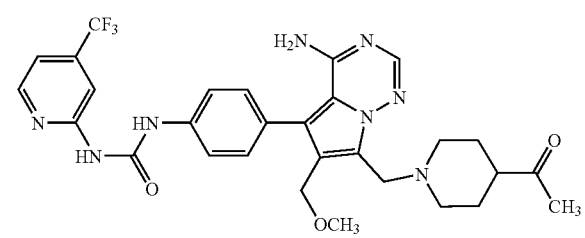

The procedure used for the preparation of Example 26 was used to prepare the title compound by substituting Intermediate Z for Intermediate Q and by substituting N-methyl piperazine for morpholine. $^1$H-NMR (CD$_3$OD-d$_6$) δ 8.49 to 8.55 (d, J=5 Hz, 1H), 7.84 (s, 1H), 7.75 (s, 1H), 7.66 to 7.72 (m, 2H), 7.40 to 7.48 (m, 2H), 7.26 to 7.30 (d, J=5 Hz, 1H), 4.42 (s, 2H), 4.04 (s, 2H), 3.50 to 3.64 (m, 4H), 3.27 (s, 3H), 2.54 to 2.67 (m, 4H), 2.09 (s, 3H). MS [M+H]$^+$=597.98; LCMS RT=2.43.

Example 38

N-[4-(4-amino-6-(methoxymethyl)-7-[(2R)-2-(methoxy-methyl)pyrrolidin-1-yl]methylpyrrolo[2,1-f][1,2,4]triazin-5-yl)phenyl]-N'-[4-(trifluoromethyl)pyridin-2-yl]urea

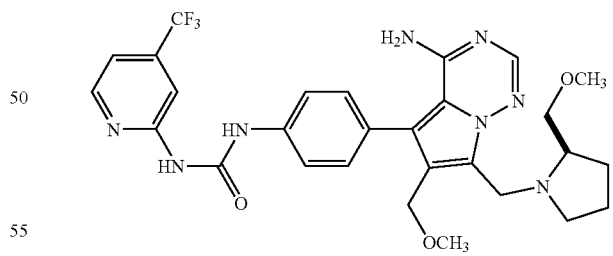

The procedure used for the preparation of Example 26 was used to prepare the title compound by substituting Intermediate Z for Intermediate Q and by substituting (2R)-2-(methoxymethyl)pyrrolidine for morpholine. $^1$H-NMR (DMSO-d$_6$) δ 9.89 (s, 1H), 9.77 (s, 1H), 8.49 to 8.57 (d, J=5 Hz, 1H), 8.05 (s, 1H), 7.87 (s, 1H), 7.58 to 7.66 (m, 2H), 7.31 to 7.42 (m, 3H), 4.18 (m, 2H), 3.86 to 3.96 (d, J=12.8 Hz, 1H), 3.37 to 3.45 (m, 1H), 3.25 (s, 3H), 3.18 (s, 3H), 2.69 to 2.83 (m, 2H), 2.28 to 2.41 (m, 2H), 1.77 to 1.91 (m, 1H), 1.42 to 1.69 (m, 3H). MS [M+H]$^+$=584.95; LCMS RT=2.54.

Example 39

Preparation of N-[4-(4-amino-6-(methoxymethyl)-7-{[4-(trifluoro-methyl)piperidin-1-yl]methyl}pyrrolo[2,1-f][1,2,4]triazin-5-yl)phenyl]-N'-[4-(trifluoromethyl)pyridin-2-yl]urea

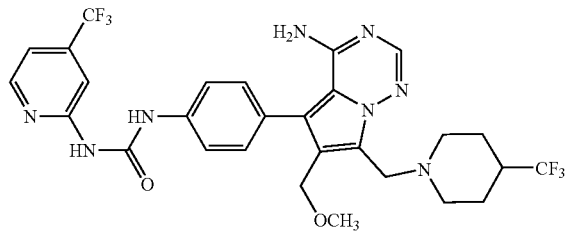

The procedure used for the preparation of Example 26 was used to prepare the title compound by substituting Intermediate Z for Intermediate Q and by substituting 4-(trifluoromethyl)piperidine for morpholine. $^1$H-NMR (DMSO-$d_6$) δ 9.99 (s, 1H), 9.85 (s, 1H), 8.54 (d, J=5.2, 1H), 8.07 (s, 1H), 7.91 (s, 1H), 7.64 (d, J=8.8, 2H); 7.39 to 7.36 (m, 3H), 4.29 (s, 2H), 3.89 (s, 2H), 3.17 (s, 3H), 2.94 (d, J=11.2, 2H), 2.26 to 2.22 (m, 1H), 2.08 (t, J=10.8, 2H), 1.75 (d, J=12.8, 2H), 1.39 (dq, J=8.4, 3.6, 2H); MS [M+H]$^+$=623.2; LCMS RT=3.01.

Example 40

Preparation of N-{4-[4-amino-7-[(4,4-difluoropiperidin-1-yl)methyl]-6-(methoxymethyl)pyrrolo[2,1-f][1,2,4]triazin-5-yl]phenyl}-N'-[4-(trifluoromethyl)pyridin-2-yl]urea

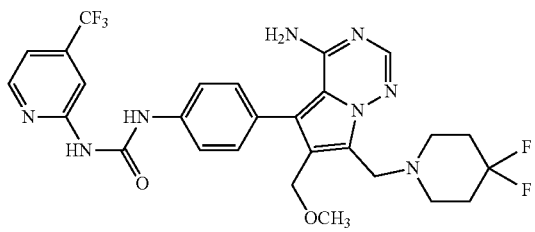

The procedure used for the preparation of Example 26 was used to prepare the title compound by substituting Intermediate Z for Intermediate Q and by substituting 4,4-difluoropiperidine for morpholine. $^1$H-NMR (DMSO-$d_6$) δ 10.06 (s, 1H), 9.93 (s, 1H), 8.54 (d, J=5.2, 1H), 8.08 (s, 1H), 7.91 (s, 1H), 7.64 (d, J=8.8, 2H); 7.39 to 7.36 (m, 3H), 4.30 (s, 2H), 3.95 (s, 2H), 3.18 (s, 3H), 2.58 to 2.57 (m, 4H), 2.01 to 1.82 (m, 4H); MS [M+H]$^+$=591.1; LCMS RT=2.98.

Example 41

Preparation of N-(4-{4-amino-6-(methoxymethyl)-7-[(3-oxopiperazin-1-yl)methyl]pyrrolo[2,1-f][1,2,4]triazin-5-yl}phenyl)-N'-[4-(trifluoromethyl)pyridin-2-yl]urea

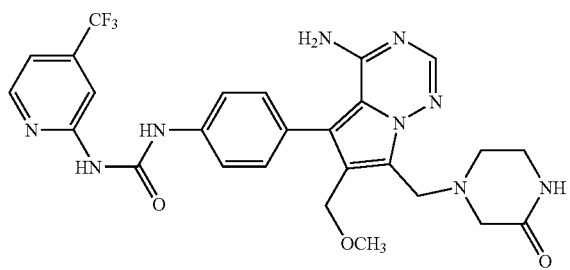

The procedure used for the preparation of Example 26 was used to prepare the title compound by substituting Intermediate Z for Intermediate Q and by substituting 2-oxopiperizine for morpholine. $^1$H-NMR (DMSO-$d_6$) δ 8.52 (d, J=5.6, 1H), 8.10 (s, 1H), 7.92 (s, 1H), 7.66 (d, J=8.4, 2H); 7.38 to 7.31 (m, 3H), 4.30 (s, 2H), 3.95 (s, 2H), 3.18 (s, 3H), 3.10 (t, J=5.2, 2H), 3.00 (s, 2H), 2.63 (t, J=5.2, 2H); MS [M+H]$^+$=570.1; LCMS RT=2.86.

Example 42

Preparation of N-{4-[4-amino-7-{[4-(methoxyacetyl)piperazin-1-yl]methyl}-6-(methoxymethyl)pyrrolo[2,1-f][1,2,4]triazin-5-yl]phenyl}-N'-[4-(trifluoromethyl)pyridin-2-yl]urea

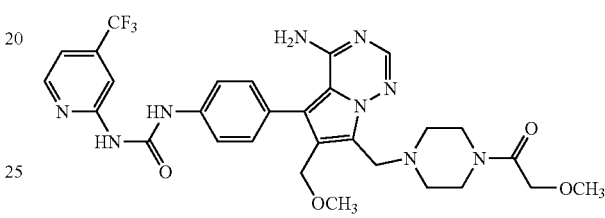

The procedure used for the preparation of Example 26 was used to prepare the title compound by substituting Intermediate Z for Intermediate Q and by substituting 1-(methoxyacetyl)piperazine for morpholine. $^1$H-NMR (DMSO-$d_6$) δ 9.92 (s, 1H), 9.78 (s, 1H), 8.55 (d, J=4.8, 1H), 8.07 (s, 1H), 7.92 (s, 1H), 7.64 (d, J=8.4, 2H); 7.40 to 7.37 (m, 3H), 4.30 (s, 2H), 4.05 (s, 2H), 3.90 (s, 2H), 3.40 to 3.36 (m, 4H), 3.25 (s, 3H), 3.18 (s, 3H), 2.46 to 2.41 (m, 4H); MS [M+H]$^+$=628.1; LCMS RT=2.48.

Example 43

Preparation of N-{4-[4-amino-7-[(1,1-dioxidothiomorpholin-4-yl)methyl]-6-(methoxymethyl)pyrrolo[2,1-f][1,2,4]triazin-5-yl]-2-fluorophenyl}-N'-[2-fluoro-5-(trifluoromethyl)phenyl]urea

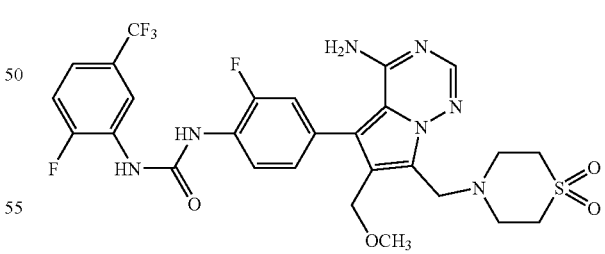

The procedure used for the preparation of Example 26 was used to prepare the title compound by substituting Intermediate AB for Intermediate Q and by substituting thiomorpholine 1,1-dioxide for morpholine. $^1$H-NMR (DMSO-$d_6$) δ 9.48 (s, 1H), 9.33 (s, 1H), 8.66 (dd, J=7.2, 2.0, 1H), 8.30 (t, J=8.4, 1H), 7.94 (s, 1H), 7.52 (t, J=9.2, 1H); 7.43 to 7.40 (m, 1H), 7.34 (dd, J=12.0, 2.0, 1H), 7.20 (dd, J=8.4, 1.2.1H), 4.31 (s, 2H), 4.08 (s, 2H), 3.21 (s, 3H), 3.09 (d, J=5.6, 4H), 2.98 (d, J=5.6, 4H); MS [M+H]$^+$=640.1; LCMS RT=2.87.

Example 44

Preparation of N-(4-{4-amino-6-(methoxymethyl)-7-[(3-oxopiperazin-1-yl)methyl]pyrrolo[2,1-f][1,2,4]triazin-5-yl}-2-fluorophenyl)-N'-[2-fluoro-5-(trifluoromethyl)phenyl]urea

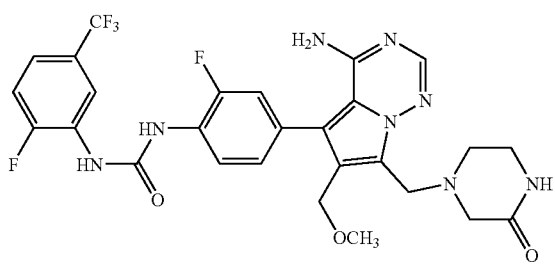

The procedure used for the preparation of Example 26 was used to prepare the title compound by substituting Intermediate AB for Intermediate Q and by substituting 2-oxopiperizine for morpholine. $^1$H-NMR (DMSO-$d_6$) δ 9.45 (s, 1H), 9.30 (s, 1H), 8.67 (dd, J=7.2, 2.4, 1H), 8.30 (t, J=8.8, 1H), 7.94 (s, 1H), 7.52 (t, J=9.2, 1H); 7.43 to 7.40 (m, 1H), 7.35 (dd, J=12.8, 2.0, 1H), 7.21 (dd, J=7.6, 1.6, 1H), 4.31 (s, 2H), 3.95 (s, 2H), 3.20 (s, 3H), 3.10 (t, J=6.0, 2H), 2.99 (s, 2H), 2.63 (t, J=5.2, 2H); MS [M+H]$^+$=605.0; LCMS RT=2.59.

Example 45

Preparation of N-{4-[4-amino-6-(methoxymethyl)-7-(morpholin-4-ylmethyl)pyrrolo[2,1-f][1,2,4]triazin-5-yl]-2-fluorophenyl}-N'-[2-fluoro-5-(trifluoromethyl)phenyl]urea

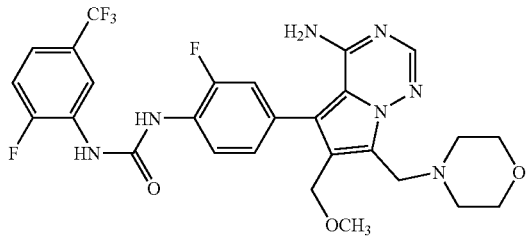

The procedure used for the preparation of Example 26 was used to prepare the title compound by substituting Intermediate AB for Intermediate Q. $^1$H-NMR (DMSO-$d_6$) δ 8.64 (dd, J=7.2, 2.0, 1H), 8.26 (t, J=8.8, 1H), 7.92 (s, 1H), 7.51 (t, J=8.8, 1H); 7.42 to 7.38 (m, 1H), 7.33 (dd, J=12.0, 1.6, 1H), 7.19 (dd, J=8.4, 1.6.1H), 4.31 (s, 2H), 3.87 (s, 2H), 3.52 (t, J=4.0, 4H), 3.20 (s, 3H), 2.43 (t, J=4.0, 4H); MS [M+H]$^+$=591.9; LCMS RT=2.74.

Example 46

Preparation of N-{4-[4-amino-7-{[(2R,6S)-2,6-dimethylmorpholin-4-yl]methyl}-6-(methoxymethyl)pyrrolo[2,1-f][1,2,4]triazin-5-yl]-2-fluoro-phenyl}-N'-[2-fluoro-5-(trifluoromethyl)phenyl]urea

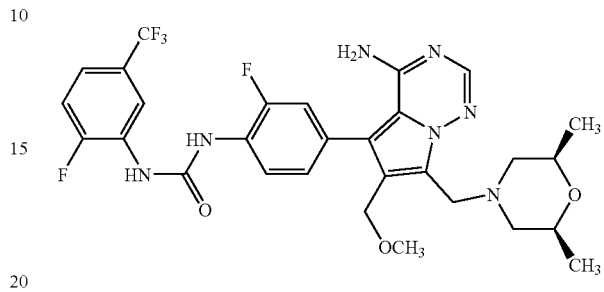

The procedure used for the preparation of Example 26 was used to prepare the title compound by substituting Intermediate AB for Intermediate Q and by substituting 2,4-dimethylmorpholine for morpholine. $^1$H-NMR (CD$_3$OD-$d_4$) δ 9.16 to 9.15 (m, 1H), 9.09 to 9.08 (m, 1H), 8.65 (d, J=8.0, 1H), 8.36 (t, J=8.4, 1H), 8.11 (s, 1H), 7.37 to 7.33 (m, 3H), 7.27 (d, J=8.0, 1H); 4.86 (s, 2H), 4.46 (s, 2H), 9.93 to 9.79 (m, 2H), 3.56 (d, J=12.4, 2H), 3.40 (s, 3H), 3.24 (d, J=12.0, 2H), 1.24 (d, J=6.4, 6H); MS [M+H]$^+$=619.8; LCMS RT=2.73.

Example 47

Preparation of N-{4-[4-amino-7-{[2-(hydroxymethyl)morpholin-4-yl]methyl}-6-(methoxymethyl)pyrrolo[2,1-f][1,2,4]triazin-5-yl]-2-fluorophenyl}-N'-[2-fluoro-5-(trifluoromethyl)-phenyl]urea

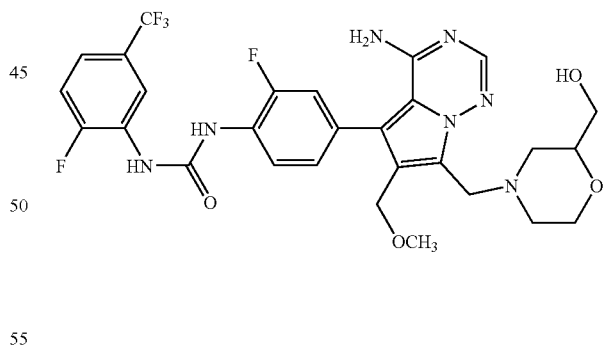

The procedure used for the preparation of Example 26 was used to prepare the title compound by substituting Intermediate AB for Intermediate Q and by substituting morpholin-2-ylmethanol for morpholine. $^1$H-NMR (DMSO-$d_6$) δ 9.57 to 9.52 (m, 1H), 9.41 to 9.37 (m, 1H), 8.67 (dd, J=6.8, 1.6, 1H); 8.31 (t, J=8.8, 1H), 7.99 (s, 1H), 7.52 (t, J=8.8, 1H), 7.44 to 7.41 (m, 1H), 7.33 (d, J=12.4, 1H), 7.21 (d, J=8.8, 1H), 4.82 (s, 2H), 4.79 to 4.74 (m, 1H), 4.55 (s, 2H), 4.19 to 4.10 (m, 4H), 3.69 (d, J=10.8, 2H), 3.18 (s, 3H), 2.90 (d, J=10.4, 1H), 2.77 (d, J=10.4, 1H); MS [M+H]$^+$=622.1; LCMS RT=2.70.

Example 48

Preparation of N-(4-{4-amino-6-(methoxymethyl)-7-[(4-methylpiperazin-1-yl)methyl]pyrrolo[2,1-f][1,2,4]triazin-5-yl}-2-fluorophenyl)-N'-[2-fluoro-5-(trifluoromethyl)phenyl]urea

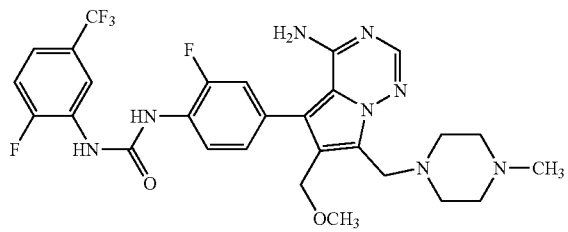

The procedure used for the preparation of Example 26 was used to prepare the title compound by substituting Intermediate AB for Intermediate Q and by substituting N-methyl piperazine for morpholine. $^1$H-NMR (CD$_3$OD-d$_4$) δ 8.66 (d, J=8.0, 1H), 8.30 (t, J=8.8, 1H), 7.86 (s, 1H), 7.35 (dd, J=7.6, 1.2, 2H); 7.31 (dd, J=12.0, 2.0, 1H), 7.24 (dd, J=8.4, 1.2, 1H), 4.39 (s, 2H), 4.07 (s, 2H), 2.82 to 2.73 (m, 8H), 2.52 (s, 3H), 1.94 (s, 3H); MS [M+H]$^+$=605.0; LCMS RT=2.63.

Example 49

Preparation of N-{4-[4-amino-6-(methoxymethyl)-7-(morpholin-4-ylmethyl)pyrrolo[2,1-f][1,2,4]triazin-5-yl]phenyl}-N'-[2-chloro-5-(trifluoromethyl)phenyl]urea

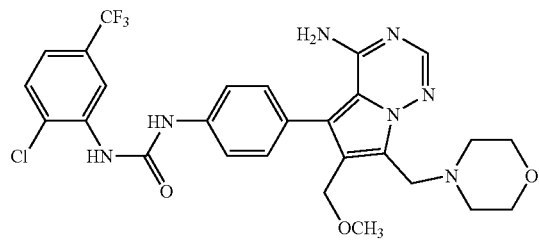

The procedure used for the preparation of Example 26 was used to prepare the title compound by substituting Intermediate AR for Intermediate Q. $^1$H-NMR (CD3OD-d$_4$) δ 8.67 (d, J=2.4, 1H), 7.84 (s, 1H), 7.66 to 7.62 (m, 3H), 7.44 to 7.41 (m, 2H); 7.32 (dd, J=8.0, 0.8, 1H), 4.41 (s, 2H), 4.01 (s, 2H), 3.68 (t, J=4.4, 4H), 3.29 (s, 3H), 2.59 (t, J=4.4, 4H); MS [M+H]$^+$=591.8; LCMS RT=2.63.

Example 50

Preparation of N-{4-[4-amino-6-(methoxymethyl)-7-(morpholin-4-ylmethyl)pyrrolo[2,1-f][1,2,4]triazin-5-yl]-2-fluorophenyl}-N'-[6-(trifluoro-methyl)pyridin-2-yl]urea

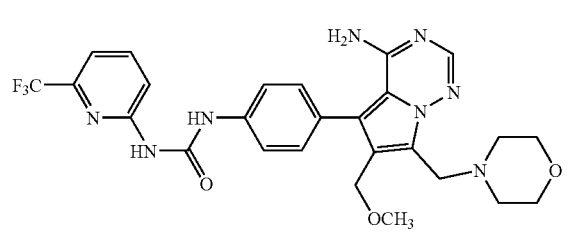

The procedure used for the preparation of Example 26 was used to prepare the title compound by substituting Intermediate AQ for Intermediate Q. $^1$H-NMR (DMSO-d$_6$) δ 10.14 to 10.05 (m, 1H), 9.93 to 9.88 (m, 1H), 8.04 (t, J=9.2, 3H); 7.61 (d, J=8.0, 2H), 7.51 (dd, J=6.4, 1.6, 1H), 7.36 (d, J=8.8, 2H), 4.74 (s, 2H), 4.38 (s, 2H), 4.03 to 3.92 (m, 2H), 3.76 to 3.66 (m, 2H), 3.52 to 3.41 (m, 2H), 3.38 to 3.28 (m, 2H), 3.22 (s, 3H); MS [M+H]$^+$=556.8; LCMS RT=2.37.

Example 51

Preparation of N-{4-[4-amino-7-(morpholin-4-ylmethyl)-6-(1,3-oxazol-5-yl)pyrrolo[2,1-f][1,2,4]triazin-5-yl]-2-fluorophenyl}-N'-[2-fluoro-5-(trifluoromethyl)phenyl]urea

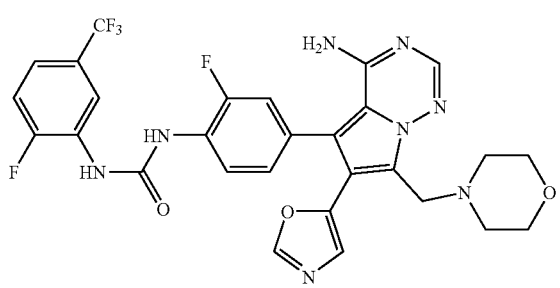

The procedure used for the preparation of Example 26 was used to prepare the title compound by substituting Intermediate O for Intermediate Q. $^1$H-NMR (DMSO-d$_6$) δ 9.45 (s, 1H), 9.30 (s, 1H), 8.66 to 8.61 (m, 1H), 8.32 to 8.24 (m, 2H), 7.97 (s, 1H), 7.54 to 7.47 (m, 1H), 7.43 to 7.37 (m, 1H), 7.31 to 7.26 (m, 1H), 7.17 to 7.12 (m, 1H), 6.99 (s, 1H), 3.92 (s, 2H), 3.53 to 3.47 (m, 4H), 2.43 to 2.36 (m, 4H); MS [M+H]$^+$=615.0; LCMS RT=2.65.

Example 52

Preparation of 4-amino-7-(morpholin-4-ylmethyl)-N-(2,2,2-trifluoroethyl)-5-{4-[({[6-(trifluoromethyl)pyridin-2-yl]amino}-carbonyl)-amino]phenyl}pyrrolo[2,1-f][1,2,4]triazine-6-carboxamide

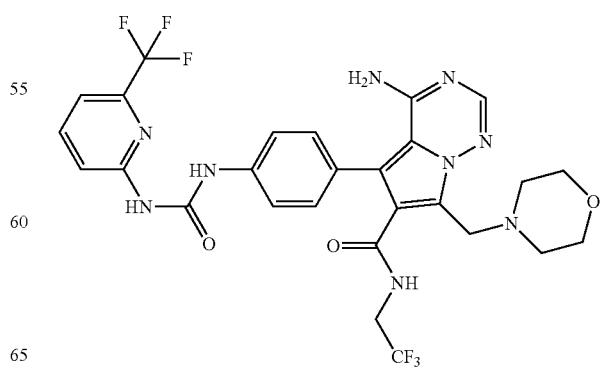

To a solution of morpholine (80.9 mg, 0.93 mmol) in acetic acid (1 mL) was added a 37% aqueous formaldehyde solution (0.07 mL, 0.93 mmol). The mixture was stirred at rt under nitrogen for 20 min and was added to a solution of Intermediate AP (4-amino-N-(2,2,2-trifluoroethyl)-5-{4-[({[6-(trifluoromethyl)pyridin-2-yl]amino}-carbonyl)-amino]phenyl}pyrrolo[2,1-f][1,2,4]triazin-6-carboxamide (50.0 mg, 0.093 mmol)) in acetic acid (2 mL). The resultant solution was heated (60° C.) overnight and concentrated. The crude material was directly purified by HPLC using a gradient of 35-40% MeCN in water containing 0.1% trifluoroacetic acid. The combined fractions were concentrated under reduced pressure. The residue was dissolved in EtOAc (15 mL). The organic layer was washed with a 2.0 M $Na_2CO_3$ aqueous solution (15 mL), brine (15 mL), dried ($Na_2SO_4$) and concentrated under reduced pressure to yield 18.7 mg (32%) of the title compound. $^1$H-NMR (DMSO-$d_6$) δ10.0 (t, J=6.3 Hz, 1H), 9.89 (bs, 1H), 9.71 (bs, 1H), 8.05-8.00 (m, 2H), 7.98 (s, 1H), 7.52-7.49 (m, 3H), 7.31 (d, J=8.6 Hz, 2H), 4.12-3.98 (m, 4H), 3.56 (bs, 4H), 2.44 ((bs, 4H); MS [M+H]$^+$=638.1; LCMS RT=2.92 min.

Example 53

Preparation of 4-amino-7-[(dimethylamino)methyl]-N-(2,2,2-trifluoroethyl)-5-{4-[({[6-(trifluoromethyl)-pyridin-2-yl]amino}carbonyl)-amino]phenyl}pyrrolo[2,1-f][1,2,4]triazine-6-carboxamide

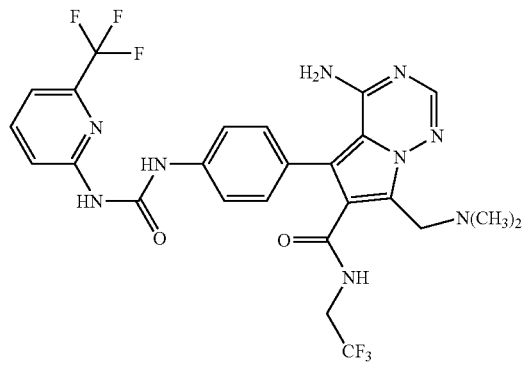

The procedure used for the preparation of Example 52 was used to prepare the title compound by substituting dimethylamine for morpholine. $^1$H-NMR (DMSO-$d_6$) δ 10.24 (t, J=6.0 Hz, 1H), 9.92 (s, 1H), 9.73 (s, 1H), 8.07-8.00 (m, 2H), 7.99 (s, 1H), 7.53-7.51 (m, 3H), 7.33 (d, J=8.6 Hz, 2H), 4.08-4.02 (m, 2H), 3.95 (s, 2H), 2.23 (s, 6H); MS [M+H]$^+$=595.8; LCMS RT=2.48 min.

Example 54

Preparation of N-4-[4-amino-6-cyano-7-(morpholin-4-ylmethyl)pyrrolo[2,1-f][1,2,4]triazin-5-yl]phenyl-N'-[2-fluoro-5-(trifluoromethyl)phenyl]urea

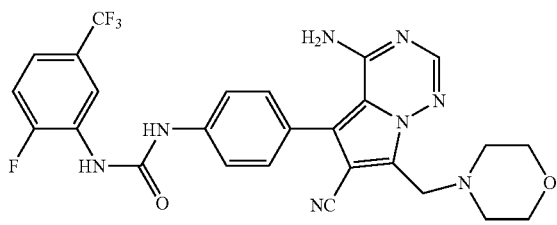

Step 1: Preparation of N-[4-(4-amino-7-bromo-6-cyanopyrrolo[2,1-f][1,2,4]triazin-5-yl)phenyl]-N'-[2-fluoro-5-(trifluoromethyl)phenyl]urea

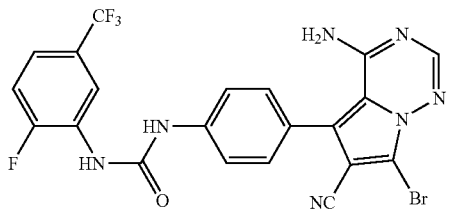

To a solution of acetonitrile (6.5 mL) was added Intermediate R(N-[4-(4-amino-6-cyanopyrrolo[2,1-f][1,2,4]triazin-5-yl)phenyl]-N'-[2-fluoro-5-(trifluoromethyl)-phenyl]urea) (300 mg, 0.659 mmol) followed by N-bromosuccinimide (129 mg, 0.725 mmol). The solution was heated at 60° C. for 1 h. Upon cooling to rt the solution was diluted with ethyl acetate (30 mL) and transferred to a separatory funnel. The organic layer was washed with aq 1N NaOH (20 mL) followed by water (20 mL). The organic was isolated, dried (MgSO$_4$), filtered, and concentrated to dryness. The crude material was then purified by flash column chromatography eluting with 95:5 v/v dichloromethane-methanol producing 267 mg (0.500 mmol, yield 76%) of purified solid. $^1$H-NMR (DMSO-$d_6$) δ 9.41 (s, 1H), 8.99 (d, J=2.6 Hz, 1H), 8.61 (dd, J=7.3, 2.3 Hz, 1H), 8.41 (br s, 1H), 8.11 (s, 1H), 7.65 (d, J=8.6 Hz, 2H), 7.50 (m, 1H), 7.45 (d, J=8.7 Hz, 2H), 7.39 (m, 1H), 5.87 (br s, 1H); MS [M+H]$^+$=534.0; LCMS RT=3.51.

Step 2: Preparation of N-[4-(4-amino-6-cyano-7-formylpyrrolo[2,1-f][1,2,4]triazin-5-yl)phenyl]-N'-[2-fluoro-5-(trifluoromethyl)phenyl]urea

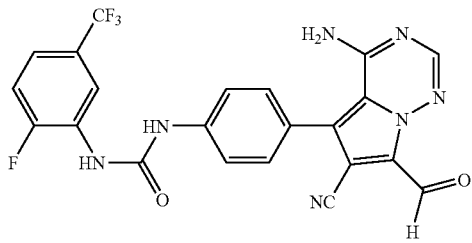

To a solution of THF (20 mL) was added N-[4-(4-amino-7-bromo-6-cyanopyrrolo[2,1-f][1,2,4]triazin-5-yl)phenyl]-N'-[2-fluoro-5-(trifluoromethyl)phenyl]urea (230 mg, 0.430 mmol) which was cooled to −77° C. n-BuLi (2.5 M in hexanes, 0.86 mL, 2.15 mmol) was slowly added to the solution via syringe. The solution was stirred for 10 min and then DMF (0.20 mL, 2.58 mmol) was added. The cooling bath was removed and the reaction was allowed to warm to ambient temperature over the following 17 h. EtOAc (20 mL) and water (20 mL) were added to the reaction which was then transferred to a separatory funnel. The organic layer was washed with aq 1N NaOH (20 mL) followed by water (20 mL). The organic was isolated, dried (MgSO$_4$), filtered, and concentrated to dryness yielding 207 mg (0.428 mmol, yield 99%) of product. $^1$H-NMR (DMSO-$d_6$) δ 10.38 (s, 1H), 9.43 (s, 1H), 8.99 (d, J=2.7 Hz, 1H), 8.68 (br s, 1H), 8.61 (dd, J=6.8, 1.8 Hz, 1H), 8.27 (s, 1H), 7.66 (d, J=8.6 Hz, 2H), 7.52 (m, 1H), 7.47 (d, J=8.6 Hz, 2H), 7.40 (m, 1H), 6.06 (br s, 1H); MS [M+H]$^+$=484.1; LCMS RT=3.34.

Step 3: Preparation of the Title Compound

To a solution of N-[4-(4-amino-6-cyano-7-formylpyrrolo[2,1-f][1,2,4]triazin-5-yl)phenyl]-N'-[2-fluoro-5-(trifluoromethyl)phenyl]urea (40.0 mg, 0.083 mmol) in THF (1.0 mL) was added AcOH (47 μL, 0.83 mmol) and morpholine (36 μL, 0.41 mmol). The reaction was heated at 60° C. for 1 h after which sodium cyanoborohydride (26.0 mg, 0.41 mmol) was added. The reaction was heated at 60° C. for an additional 1 h. The reaction was diluted with EtOAc, transferred to a separatory funnel and washed with saturated aq NaHCO$_3$ (2×). The organic was dried (MgSO$_4$) and evaporated to give a crude oil that was purified by flash column chromatography eluting with 5:4:1 v/v/v CH$_2$Cl$_2$-EtOAc-MeOH. The resulting purified fractions were combined and evaporated producing 22 mg (0.039 mmol, yield 48%) of the title compound as a white solid. $^1$H-NMR (DMSO-d$_6$) δ 9.41 (s, 1H), 9.00 (d, J=2.9 Hz, 1H), 8.64 (dd, J=7.2, 2.3 Hz, 1H), 8.27 (br s, 1H), 8.06 (s, 1H), 7.66 (m, 2H), 7.53 (m, 1H), 7.47 (m, 2H), 7.41 (m, 1H), 5.72 (br s, 1H), 3.95 (s, 2H), 3.57 (m, 4H), 2.49 (m, 4H); MS [M+H]$^+$=555.0; LCMS RT=2.55.

Example 55

N-(4-4-amino-6-cyano-7-[(4-methylpiperazin-1-yl)methyl]-pyrrolo[2,1-f][1,2,4]triazin-5-ylphenyl)-N'-[2-fluoro-5-(trifluoromethyl)-phenyl]urea

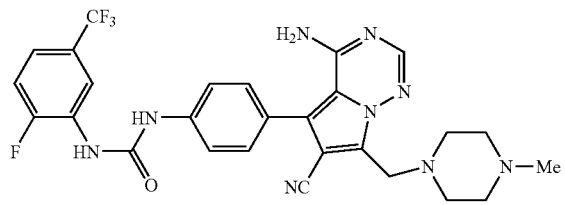

The procedure used for the preparation of Example 54, Step 3 was used to prepare the title compound by substituting 1-methylpiperazine for morpholine. $^1$H-NMR (DMSO-d$_6$) δ 9.39 (s, 1H), 8.98 (d, J=3.0 Hz, 1H), 8.62 (dd, J=6.8, 2.2 Hz, 1H), 8.23 (br s, 1H), 8.04 (s, 1H), 7.64 (m, 2H), 7.51 (m, 1H), 7.45 (m, 2H), 7.40 (m, 1H), 5.71 (br s, 1H), 3.93 (s, 2H), 2.49 (m, 4H), 2.33 (m, 4H), 2.14 (s, 3H); MS [M+H]$^+$=568.1; LCMS RT=2.60.

Example 56

N-[4-(4-amino-6-cyano-7-[(2,2,2-trifluoroethyl)-amino]methylpyrrolo[2,1-f][1,2,4]triazin-5-yl)phenyl]-N'-[2-fluoro-5-(trifluoromethyl)phenyl]urea

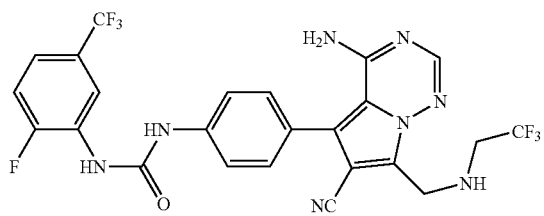

The procedure used for the preparation of Example 54, Step 3 was used to prepare the title compound by substituting 2,2,2-trifluoroethanamine for morpholine. $^1$H-NMR (DMSO-d$_6$) δ 9.49 (s, 1H), 9.02 (d, J=2.5 Hz, 1H), 8.62 (dd, J=7.1, 2.3 Hz, 1H), 8.35 (br s, 1H), 8.08 (s, 1H), 7.65 (m, 2H), 7.50 (m, 1H), 7.43 (m, 2H), 7.40 (m, 1H), 5.88 (br s, 1H), 4.26 (s, 2H), 3.45 (br s, 2H); MS [M+H]$^+$=567.2; LCMS RT=3.35.

Example 57

N-4-[6-acetyl-4-amino-7-(morpholin-4-ylmethyl)pyrrolo[2,1-f]-[1,2,4]triazin-5-yl]-2-fluorophenyl-N'-[2-fluoro-5-(trifluoromethyl)phenyl]urea

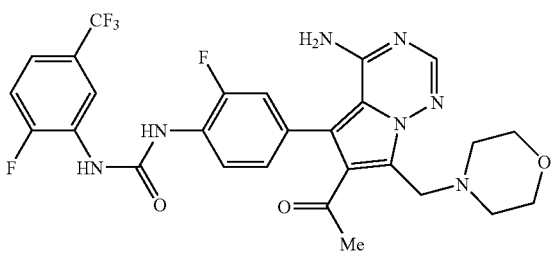

To a solution of DCE (1 mL) was added Intermediate AX (1-[4-amino-5-(4-amino-3-fluorophenyl)-7-(morpholin-4-ylmethyl)pyrrolo[2,1-f][1,2,4]triazin-6-yl]-ethanone (40 mg, 0.10 mmol)) followed by 1-fluoro-2-isocyanato-4-(trifluoromethyl)benzene (32 μL, 0.22 mmol). The reaction was heated at 80° C. for 17 h, and then aq 2N HCl (52 μL, 0.10 mmol) was added to the reaction followed by DMF (1 mL). The solution was heated for an additional 2.5 h. Upon cooling to rt, the solution was concentrated in vacuo and subsequently purified by MPLC (100% CH$_2$Cl$_2$ to 5:4:1 v/v/v CH$_2$Cl$_2$-EtOAc-MeOH). The resulting purified fractions were combined and evaporated producing 44 mg (0.075 mmol, yield 72%) of a white solid. $^1$H-NMR (DMSO-d$_6$) δ 9.48 (m, 1H), 9.34 (m, 1H), 8.67 (m, 1H), 8.32 (t, J=8.4 Hz, 1H), 7.99 (s, 1H), 7.53 (m, 1H), 7.42 (m, 1H), 7.38 (m, 1H), 7.20 (m, 1H), 4.07 (s, 2H), 3.50 (m, 4H), 2.42 (m, 4H), 2.15 (s, 3H); MS [M+H]$^+$=590.0; LCMS RT=2.62.

Example 58

N-4-[6-acetyl-4-amino-7-(morpholin-4-ylmethyl)pyrrolo[2,1-f][1,2,4]triazin-5-yl]-2-fluorophenyl-N'-[3-(trifluoromethyl)phenyl]urea

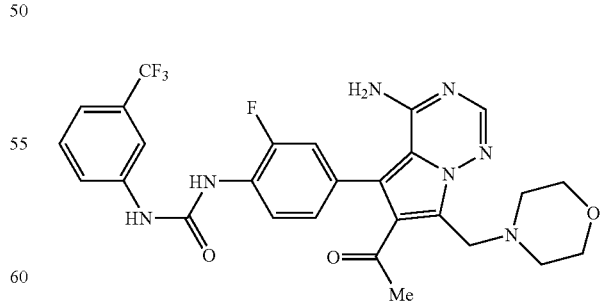

The procedure used for the preparation of Example 57 was used to prepare the title compound by substituting 1-isocyanato-3-(trifluoromethyl)benzene for 1-fluoro-2-isocyanato-4-(trifluoromethyl)benzene. $^1$H-NMR (DMSO-d$_6$) δ 9.51 (s, 1H), 8.82 (m, 1H), 8.27 (t, J=8.7 Hz, 1H), 8.06 (s, 1H), 7.99

(s, 1H), 7.56 (m, 2H), 7.37 (m, 2H), 7.19 (m, 1H), 4.07 (s, 2H), 3.50 (m, 4H), 2.42 (m, 4H), 2.15 (s, 3H); MS [M+H]⁺=572.0; LCMS RT=2.67.

Example 59

N-4-[6-acetyl-4-amino-7-(morpholin-4-ylmethyl)pyrrolo[2,1-f][1,2,4]triazin-5-yl]-2-fluorophenyl-N'-[4-(trifluoromethoxy)phenyl]urea

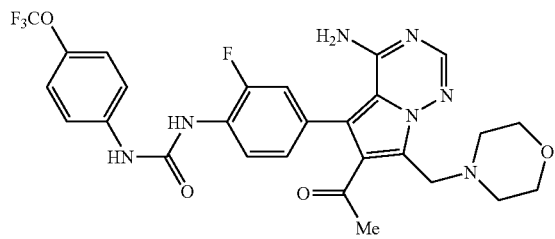

The procedure used for the preparation of Example 57 was used to prepare the title compound by substituting 1-isocyanato-4-(trifluoromethoxy)benzene for 1-fluoro-2-isocyanato-4-(trifluoromethyl)benzene. ¹H-NMR (DMSO-d₆) δ 9.35 (s, 1H), 8.77 (m, 1H), 8.28 (t, J=8.7 Hz, 1H), 7.99 (s, 1H), 8.06 (s, 1H), 7.58 (m, 2H), 7.36 (m, 1H), 7.32 (m, 2H), 7.19 (m, 1H), 4.07 (s, 2H), 3.50 (m, 4H), 2.42 (m, 4H), 2.15 (s, 3H); MS [M+H]⁺=588.1; LCMS RT=3.04.

Example 60

N-4-[6-acetyl-4-amino-7-(morpholin-4-ylmethyl)pyrrolo[2,1-f][1,2,4]triazin-5-yl]-2-fluorophenyl-N'-[4-(trifluoromethyl)pyridin-2-yl]urea

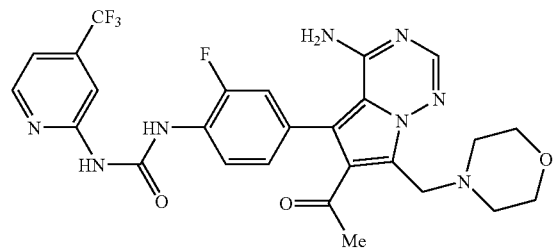

To a solution of THF (0.2 mL) was added Intermediate AX (1-[4-amino-5-(4-amino-3-fluorophenyl)-7-(morpholin-4-ylmethyl)pyrrolo[2,1-f][1,2,4]triazin-6-yl]ethanone (43 mg, 0.11 mmol)) followed by Intermediate V (phenyl[4-(trifluoromethyl)pyridin-2-yl]carbamate (32 mg, 0.11 mmol)) and triethylamine (16 μL, 0.11 mmol). The reaction was heated while stirring at 50° C. for 4.5 h. The solution was concentrated in vacuo and subsequently purified by MPLC (100% CH₂Cl₂ to 5:4:1 v/v/v CH₂Cl₂-EtOAc-MeOH). The resulting purified fractions were combined and evaporated producing 25 mg (0.043 mmol, yield 39%) of a white solid. ¹H-NMR (DMSO-d₆) δ 10.19 (s, 1H), 10.15 (br s, 1H), 8.56 (d, J=5.4 Hz, 1H), 8.32 (t, J=8.4 Hz, 1H), 8.02 (s, 1H), 7.99 (s, 1H), 7.41 (m, 1H), 7.39 (m, 1H), 7.21 (m, 1H), 4.07 (s, 2H), 3.50 (m, 4H), 2.42 (m, 4H), 2.15 (s, 3H); MS [M+H]⁺=573.0; LCMS RT=2.57.

Example 61

N-4-[6-acetyl-4-amino-7-(morpholin-4-ylmethyl)pyrrolo[2,1-f][1,2,4]triazin-5-yl]-2-fluorophenyl-N'-[6-(trifluoromethyl)pyridin-2-yl]urea

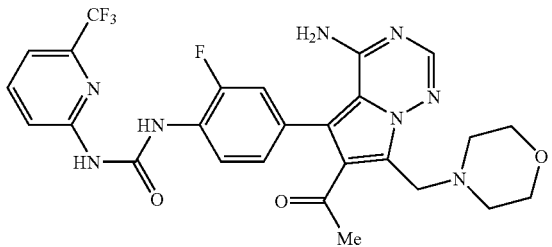

The procedure used for the preparation of Example 60 was used to prepare the title compound by substituting phenyl[6-(trifluoromethyl)pyridin-2-yl]carbamate for phenyl[4-(trifluoromethyl)pyridin-2-yl]carbamate. ¹H-NMR (DMSO-d₆) δ 10.34 (s, 1H), 10.23 (br s, 1H), 8.35 (t, J=8.4 Hz, 1H), 8.05 (t, J=6.3 Hz, 1H), 7.98 (s, 1H), 7.84 (d, J=8.7 Hz, 1H), 7.54 (d, J=7.4 Hz, 1H), 7.39 (m, 1H), 7.20 (m, 1H), 4.06 (s, 2H), 3.49 (m, 4H), 2.41 (m, 4H), 2.14 (s, 3H); MS [M+H]⁺=573.0; LCMS RT=2.50.

Example 62

Preparation of N-{4-[4-amino-6-(hydroxymethyl)-7-(morpholin-4-ylmethyl)pyrrolo[2,1-f][1,2,4]triazin-5-yl]phenyl}-N'-[4-(trifluoromethyl)-pyridin-2-yl]urea

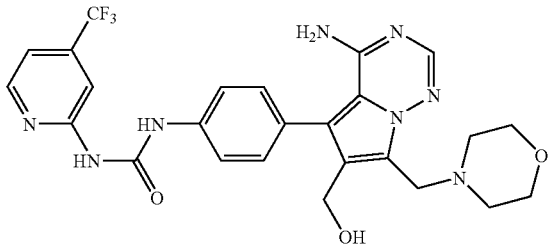

A solution of formaldehyde (20 μL, 0.271 mmol, 37% in H₂O) and morpholine (24 μL, 0.271 mmol) in AcOH (0.5 mL) was added to a stirring solution of Intermediate Y (100 mg, 0.23 mmol) in AcOH (1.5 mL) at 60° C. The reaction was allowed to stir until all starting material had been consumed as shown by HPLC. The reaction mixture was quenched by diluting with EtOAc and washing 3× with saturated sodium carbonate solution. The organic layer was dried (Na₂SO₄) and concentrated to a brown powder. The crude product was purified by HPLC (10-70% ACN/H₂O) to yield 25.3 mg (0.5 mmol, 20.7%). ¹H-NMR (DMSO-d₆). δ 9.98 (s, 1H), 9.84 (s, 1H), 8.60 (d, J=5.1 Hz, 1H), 8.13 (s, 1H), 7.95 (s, 1H), 7.69 (d, J=8.1 Hz, 2H), 7.45-7.38 (m, 3H), 5.105 (s, 1H), 4.45 (s, 2H), 3.99 (s, 2H), 3.61-3.52 (m, 4H), 2.55-2.44 (m, 4H). MS [M+H]⁺=543; LCMS RT=2.29 min.

Example 63

N-{4-[4-amino-6-(cyanomethyl)-7-(morpholin-4-ylmethyl)-pyrrolo[2,1-f][1,2,4]triazin-5-yl]phenyl}-N'-[4-(trifluoromethyl)-pyridin-2-yl]urea

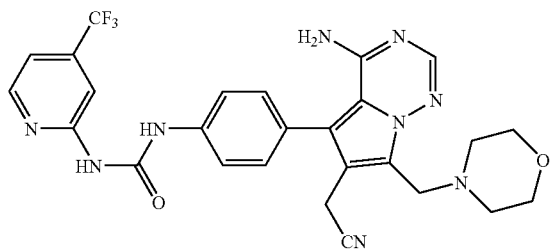

The procedure used to prepare Example 62 was used to prepare the title compound by substituting Intermediate AE for Intermediate Y. The crude product was purified by HPLC (10-70% ACN/H$_2$O). $^1$H-NMR (DMSO-d$_6$). δ 10.11 (s, 1H), 9.95 (s, 1H), 8.59 (d, J=4.8 Hz, 1H), 8.15 (s, 1H), 7.98 (s, 1H), 7.75 (d, J=8.4 Hz, 2H), 7.44-7.49 (m, 3H), 3.99 (s, 2H), 3.89 (s, 2H), 3.65-3.60 (m, 4H), 2.50-2.43 (m, 4H). MS [M+Na]$^+$=574; LCMS RT=2.46 min.

Example 64

N-(4-{4-amino-6-(cyanomethyl)-7-[(2,6-dimethyl-morpholin-4-yl)methyl]pyrrolo[2,1-f][1,2,4]triazin-5-yl}phenyl)-N'-[4-(trifluoromethyl)-pyridin-2-yl]urea

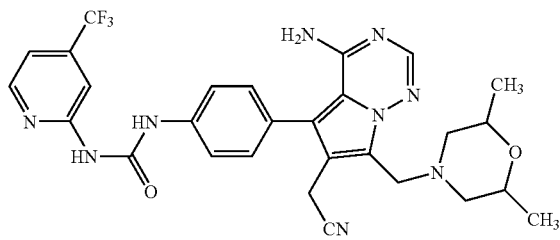

The procedure used to prepare Example 62 was used to prepare the title compound by substituting Intermediate AE for Intermediate Y and 2,6-dimethylmorpholine for morpholine. The crude product was purified by HPLC (10-70% ACN/H$_2$O). $^1$H-NMR (DMSO-d$_6$). δ 10.02 (s, 1H), 9.86 (s, 1H), 8.60 (d, J=5.4 Hz, 1H), 8.12 (s, 1H), 7.97 (s, 1H), 7.73 (d, J=8.1 Hz, 2H), 7.50-7.40 (m, 3H), 3.95 (s, 2H), 3.87 (s, 2H), 3.69-3.55 (m, 2H), 2.74 (d, J=10.5 Hz, 4H), 1.06 (d, J=5.7 Hz, 6H). MS [M+H]$^+$=580; LCMS RT=2.58 min.

Example 65

N-{4-[7-[(4-acetylpiperazin-1-yl)methyl]-4-amino-6-(cyanomethyl)-pyrrolo[2,1-f][1,2,4]triazin-5-yl]phenyl}-N'-[4-(trifluoromethyl)-pyridin-2-yl]urea

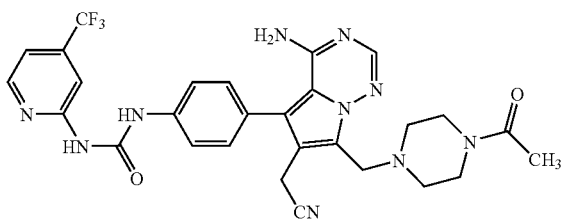

The procedure used to prepare Example 62 was used to prepare the title compound by substituting Intermediate AE for Intermediate Y and 1-acetylpiperazine for morpholine. The crude product was purified by HPLC (10-70% ACN/H$_2$O). $^1$H-NMR (DMSO-d$_6$). δ 10.05 (s, 1H), 9.89 (s, 1H), 8.60 (d, J=5.1 Hz, 1H), 8.13 (s, 1H), 7.98 (s, 1H), 7.74 (d, J=8.7 Hz, 2H), 7.46-7.40 (m, 3H), 4.02 (s, 2H), 3.89 (s, 2H), 3.52-3.42 (m, 4H), 2.52-2.45 (m, 2H), 2.45-2.40 (m, 2H), 2.02 (s, 3H). MS [M+Na]$^+$=616; LCMS RT=2.37 min.

Example 66

N-(4-{4-amino-6-(cyanomethyl)-7-[(3-oxopiperazin-1-yl)methyl]-pyrrolo[2,1-f][1,2,4]triazin-5-yl}phenyl)-N'-[4-(trifluoromethyl)pyridin-2-yl]urea

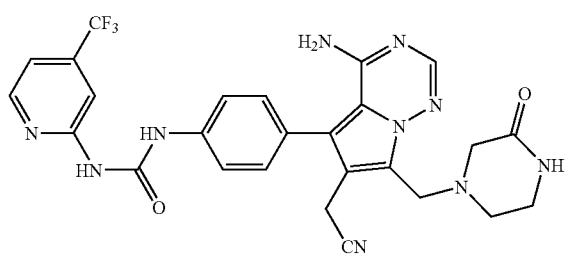

The procedure used to prepare Example 62 was used to prepare the title compound by substituting Intermediate AE for Intermediate Y and 2-oxopiperazine for morpholine. The crude product was purified by HPLC (10-70% ACN/H$_2$O). $^1$H-NMR (DMSO-d$_6$) δ 10.06 (s, 1H), 9.90 (s, 1H), 8.61-8.58 (m, 1H), 8.12 (s, 1H), 7.99 (s, 1H), 7.81-7.73 (m, 2H), 7.48-7.40 (m, 3H), 4.73 (s, 2H), 4.04 (s, 2H), 3.91 (s, 2H), 3.20-3.12 (m, 2H), 2.75-2.63 (m, 2H). MS [M+Na]$^+$=587; LCMS RT=2.44 min.

Example 67

N-[4-(4-amino-6-(cyanomethyl)-7-{[4-(methylsulfonyl)piperazin-1-yl]methyl}pyrrolo[2,1-f][1,2,4]triazin-5-yl)phenyl]-N'-[4-(trifluoromethyl)pyridin-2-yl]urea

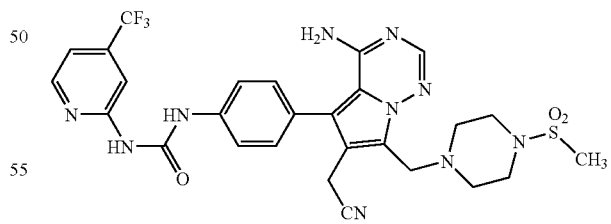

The procedure used to prepare Example 62 was used to prepare the title compound by substituting Intermediate AE for Intermediate Y and 1-methanesulfonylpiperaizne for morpholine. The crude product was purified by HPLC (10-70% ACN/H$_2$O). $^1$H-NMR (DMSO-d$_6$). δ 8.58 (d, J=5.1 Hz, 1H), 8.14 (s, 1H), 7.98 (s, 1H), 7.75 (d, J=8.4 Hz, 2H), 7.44-7.37 (m, 3H), 4.05 (s, 2H), 3.89 (s, 2H), 3.20-3.11 (m, 4H), 2.89 (s, 3H), 2.61-2.55 (m, 4H). MS [M+Na]$^+$=651; LCMS RT=2.92 min.

Example 68

N-{4-[4-amino-6-(cyanomethyl)-7-(morpholin-4-ylmethyl)-pyrrolo[2,1-f][1,2,4]triazin-5-yl]phenyl}-N'-[2-fluoro-5-(trifluoromethyl)-phenyl]urea

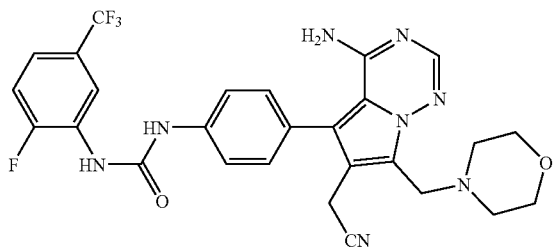

The procedure used to prepare Example 62 was used to prepare the title compound by substituting Intermediate AD for Intermediate Y. The crude product was purified by HPLC (10-70% ACN/H$_2$O). $^1$H-NMR (DMSO-d$_6$). δ 8.55 (d, J=7.2 Hz, 1H), 7.97 (s, 1H), 7.79-7.73 (m, 3H), 7.55-7.37 (m, 3H), 3.98 (s, 2H), 3.88 (s, 2H), 3.62-3.55 (m, 4H), 2.50-2.41 (m, 4H). MS [M+H]$^+$=569; LCMS RT=2.62 min.

Example 69

N-{4-[4-amino-6-(cyanomethyl)-7-(morpholin-4-ylmethyl)-pyrrolo[2,1-f][1,2,4]triazin-5-yl]-2-fluorophenyl}-N'-[2-fluoro-5-(trifluoromethyl)phenyl]urea

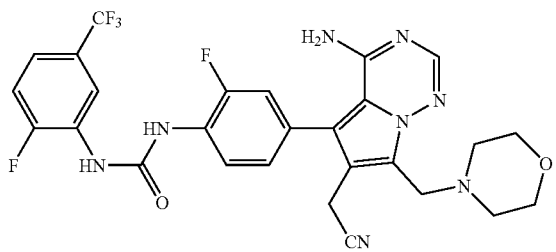

The procedure used to prepare Example 62 was used to prepare the title compound by substituting Intermediate AC for Intermediate Y. The crude product was purified by HPLC (10-70% ACN/H$_2$O). $^1$H-NMR (DMSO-d$_6$). δ 9.60-9.30 (br s, 2H), 8.71 (d, J=6.3 Hz, 1H), 8.39 (t, J=8.6 Hz, 1H), 7.98 (s, 1H), 7.60-7.38 (m, 4H), 7.25 (d, J=7.5 Hz, 1H), 3.98 (s, 2H), 3.93 (s, 2H), 3.75-3.45 (m, 4H), 2.50-2.41 (m, 4H). MS [M+H]$^+$=587; LCMS RT=2.76 min.

Example 70

Preparation of N-(4-{4-amino-6-(cyanomethyl)-7-[(3-oxopiperazin-1-yl)methyl]pyrrolo[2,1-f][1,2,4]triazin-5-yl}phenyl)-N'-[2-fluoro-5-(trifluoromethyl)phenyl]urea

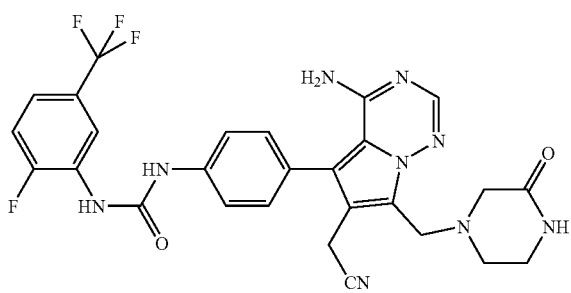

The procedure used for the preparation of Example 62 was used to prepare the title compound by substituting Intermediate AD for Intermediate Y and by substituting 2-oxopiperazine for morpholine. $^1$H-NMR (CD$_3$OD) δ 8.62 (d, J=8.4 Hz, 1H), 8.04 (s, 1H), 7.72 (d, J=8.8 Hz, 2H), 7.45 (d, J=8.8 Hz, 2H), 7.36 (d, J=8.4 Hz, 2H), 4.47 (s, 2H), 3.87 (s, 2H), 3.48-3.44 (m, 4H), 3.15-3.09 (m, 2H); MS [M+H]$^+$=582; LCMS RT=2.58.

Example 71

Preparation of N-(4-{4-amino-6-(cyanomethyl)-7-[(2,6-dimethyl-morpholin-4-yl)methyl]pyrrolo[2,1-f][1,2,4]triazin-5-yl}phenyl)-N'-[2-fluoro-5-(trifluoromethyl)phenyl]urea

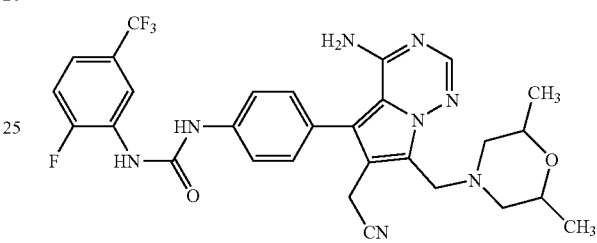

The procedure used for the preparation of Example 62 was used to prepare the title compound by substituting Intermediate AD for Intermediate Y and by substituting 2,6-dimethylmorpholine for morpholine. $^1$H-NMR (CD$_3$OD) δ 8.62 (d, J=7.6 Hz, 1H), 8.04 (s, 1H), 7.70 (d, J=8.4 Hz, 2H), 7.44 (d, J=8.0 Hz, 2H), 7.36 (d, J=8.0 Hz, 2H), 4.85 (s, 2H), 3.91 (s, 2H), 3.51 (d, J=11.6 Hz, 2H), 2.94 (t, J=11.6 Hz, 2H), 1.25 (d, J=6.4 Hz, 6H); MS [M+H]$^+$=597.2; LCMS RT=2.97.

Example 72

Preparation of N-[4-(4-amino-6-(cyanomethyl)-7-{[2-(hydroxymethyl)morpholin-4-yl]methyl}pyrrolo[2,1-f][1,2,4]triazin-5-yl)phenyl]-N'-[2-fluoro-5-(trifluoromethyl)phenyl]urea

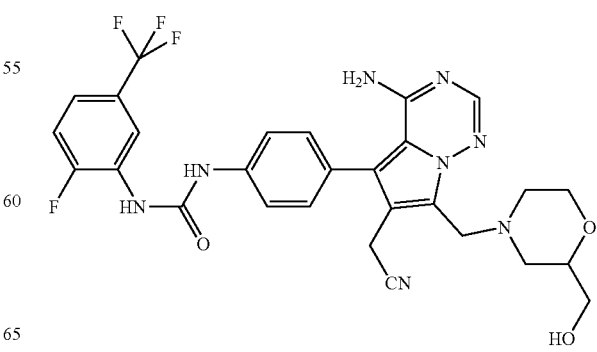

The procedure used for the preparation of Example 62 was used to prepare the title compound by substituting Intermediate AD for Intermediate Y and by substituting morpholin-2-ylmethanol for morpholine. $^1$H-NMR (CD$_3$OD) δ 8.62 (d, J=7.2 Hz, 1H), 8.06 (s, 1H), 7.71 (d, J=8.8 Hz, 2H), 7.44 (d, J=8.4 Hz, 2H), 7.36 (d, J=8.4 Hz, 2H), 4.16 (dd, J=12.8, 4.00 Hz, 1H), 3.91 (s, 2H), 3.90-3.82 (m, 2H), 3.65 (s, 2H), 3.62-3.47 (m, 4H), 3.26-3.18 (m, 2H); MS [M+H]$^+$=599.1; LCMS RT=2.91.

Example 73

Preparation of N-(4-{4-amino-6-(cyanomethyl)-7-[(1,1-dioxidothiomorpholin-4-yl)methyl]pyrrolo[2,1-f][1,2,4]triazin-5-yl}phenyl)-N'-[2-fluoro-5-(trifluoromethyl)phenyl]urea

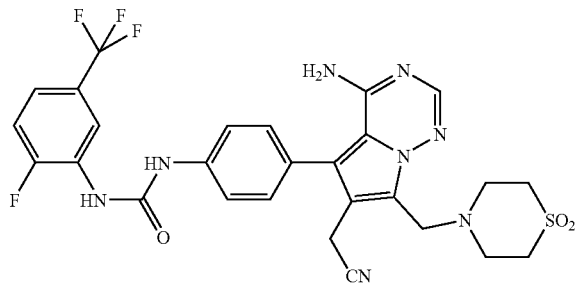

The procedure used for the preparation of Example 62 was used to prepare the title compound by substituting Intermediate AD for Intermediate Y and by substituting thiomorpholine 1,1-dioxide for morpholine. $^1$H-NMR (CD$_3$OD) δ 8.62 (d, J=7.2 Hz, 1H), 8.06 (s, 1H), 7.72 (d, J=8.8 Hz, 2H), 7.45 (d, J=8.8 Hz, 2H), 7.36 (d, J=8.4 Hz, 2H), 4.27 (s, 2H), 3.84 (s, 2H), 3.20-3.15 (m, 4H), 3.13-3.06 (m, 4H); MS [M+H]$^+$=617.2; LCMS RT=3.12.

Example 74

Preparation of N-(4-{4-amino-6-(cyanomethyl)-7-[(4-methylpiperazin-1-yl)methyl]pyrrolo[2,1-f][1,2,4]triazin-5-yl}phenyl)-N'-[2-fluoro-5-(trifluoromethyl)phenyl]urea

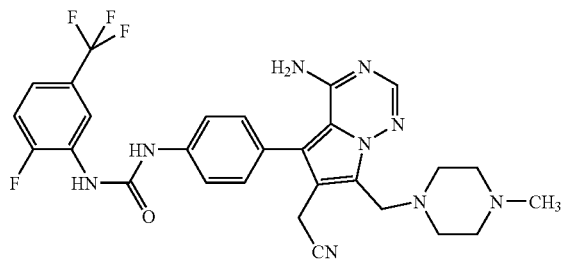

The procedure used for the preparation of Example 62 was used to prepare the title compound by substituting Intermediate AD for Intermediate Y and by substituting N-methyl piperazine for morpholine. $^1$H-NMR (CD$_3$OD) δ 8.61 (d, J=8.0 Hz, 1H), 8.07 (s, 1H), 7.72 (d, J=8.8 Hz, 2H), 7.45 (d, J=8.8 Hz, 2H), 7.36 (d, J=8.8 Hz, 2H), 4.20 (s, 2H), 3.83 (s, 2H), 3.48-3.32 (m, 2H), 3.30-3.16 (m, 4H), 2.90 (s, 3H), 2.88-2.80 (m, 2H); MS [M+H]$^+$=582; LCMS RT=2.64.

Example 75

Preparation of N-(4-{4-amino-6-(cyanomethyl)-7-(piperazin-1-ylmethyl)pyrrolo[2,1-f][1,2,4]triazin-5-yl}phenyl)-N'-[2-fluoro-5-(trifluoromethyl)phenyl]urea

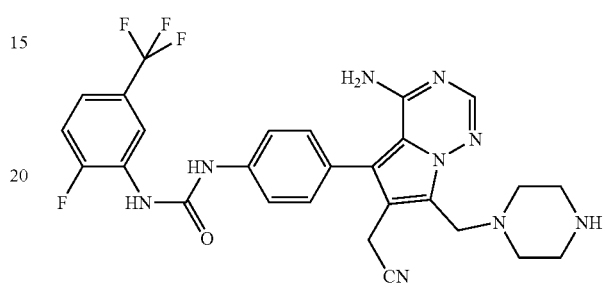

The procedure used for the preparation of Example 62 was used to prepare the title impound by substituting Intermediate AD for Intermediate Y and by substituting piperazine for morpholine. $^1$H-NMR (CD$_3$OD) δ 8.61 (d, J=8.8 Hz, 1H), 8.02 (s, 1H), 7.72 (d, J=8.0 Hz, 2H), 7.44 (d, J=8.0 Hz, 2H), 7.36 (d, J=8.0 Hz, 2H), 4.19 (s, 2H), 3.82 (s, 2H), 3.28 (t, J=6.0 Hz, 4H), 2.81 (t, J=6.0 Hz, 4H); MS [M+H]$^+$=568; LCMS RT=2.64.

Example 76

Preparation of N-(4-{4-amino-6-(cyanomethyl)-7-[(4-isopropylsulfonylpiperazin-1-yl)methyl]pyrrolo[2,1-f][1,2,4]triazin-5-yl}phenyl)-N'-[2-fluoro-5-(trifluoromethyl)phenyl]urea

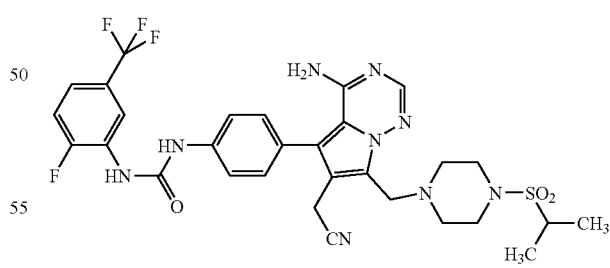

The procedure used for the preparation of Example 62 was used to prepare the title compound by substituting Intermediate AD for Intermediate Y and by substituting 1-(isopropylsulfonyl)piperazine for morpholine. $^1$H-NMR (CD$_3$OD) δ 8.62 (d, J=8.0 Hz, 1H), 8.04 (s, 1H), 7.71 (d, J=8.8 Hz, 2H), 7.45 (d, J=8.8 Hz, 2H), 7.35 (d, J=6.8 Hz, 2H), 5.42 (s, 2H), 4.09-3.90 (m, 3H), 3.91 (s, 2H), 3.79-3.62 (m, 4H), 3.35-3.32 (m, 2H), 1.35 (d, J=6.8 Hz, 6H); MS [M+H]$^+$=674; LCMS RT=2.98.

Example 77

Preparation of t-butyl 4-[(4-amino-6-(cyanomethyl)-5-{4-[({[2-fluoro-5-(trifluoromethyl)phenyl]amino}carbonyl)-amino]phenyl}pyrrolo[2,1-f][1,2,4]triazin-7-yl)methyl]piperazine-1-carboxylate

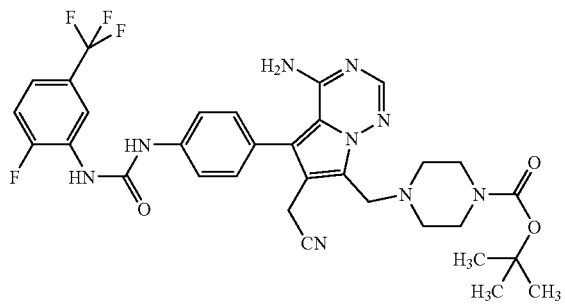

The procedure used for the preparation of Example 62 was used to prepare the title compound by substituting Intermediate AD for Intermediate Y and by substituting tert-butyl piperazine-1-carboxylate for morpholine. $^1$H-NMR (CD$_3$OD) δ 8.62 (d, J=8.0 Hz, 1H), 7.95 (s, 1H), 7.68 (d, J=8.8 Hz, 2H), 7.44 (d, J=8.8 Hz, 2H), 7.35 (d, J=8.8 Hz, 2H), 5.01 (s, 2H), 4.07 (s, 2H), 4.01 (s, 2H), 3.66-3.63 (m, 4H), 3.31-3.29 (m, 2H), 1.47 (s, 9H); MS [M+H]$^+$=668.1; LCMS RT=3.09.

Example 78

Preparation of N-(4-{4-amino-6-(cyanomethyl)-7-[(4-methylpiperazin-1-yl)methyl]pyrrolo[2,1-f][1,2,4]triazin-5-yl}2-fluoro-phenyl)-N'-[2-fluoro-5-(trifluoromethyl)phenyl]urea

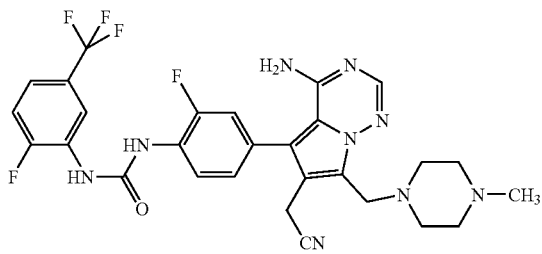

The procedure used for the preparation of Example 62 was used to prepare the title compound by substituting Intermediate AC for Intermediate Y and by substituting N-methyl piperazine for morpholine. $^1$H-NMR (CD$_3$OD) δ 8.64 (d, J=8.4 Hz, 1H), 8.42 (t, J=8.4 Hz, 1H), 8.08 (s, 1H), 7.37-7.27 (m, 4H), 4.20 (s, 2H), 3.86 (s, 2H), 3.42-3.22 (m, 6H), 2.90 (s, 3H), 2.88-2.75 (m, 2H); MS [M+H]$^+$=600.1; LCMS RT=2.93.

Example 79

Preparation of N-(4-{4-amino-6-(cyanomethyl)-7-[(1,1-dioxidothiomorpholin-4-yl)methyl]pyrrolo[2,1-f][1,2,4]triazin-5-yl}-2-fluorophenyl)-N'-[2-fluoro-5-(trifluoromethyl)phenyl]urea

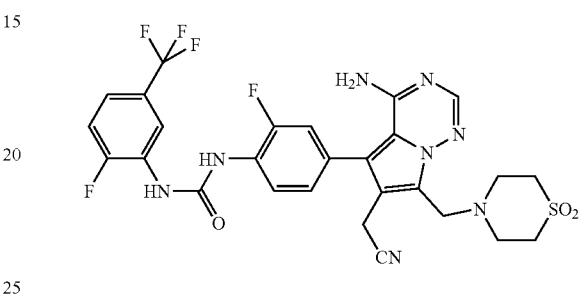

The procedure used for the preparation of Example 62 was used to prepare the title compound by substituting Intermediate AC for Intermediate Y and by substituting thiomorpholine 1,1-dioxide for morpholine. $^1$H-NMR (CD$_3$OD) δ 8.65 (d, J=6.4 Hz, 1H), 8.41 (t, J=8.4 Hz, 1H), 8.04 (s, 1H), 7.37-7.26 (m, 4H), 4.26 (s, 2H), 3.86 (d, J=2.4 Hz, 2H), 3.20-3.15 (m, 4H), 3.11-3.08 (m, 4H); MS [M+H]$^+$=635.2; LCMS RT=3.19.

Example 80

Preparation of N-(4-{4-amino-6-(cyanomethyl)-7-[(3-oxopiperazin-1-yl)methyl]pyrrolo[2,1-f][1,2,4]triazin-5-yl}-2-fluorophenyl)-N'-[2-fluoro-5-(trifluoromethyl)phenyl]urea

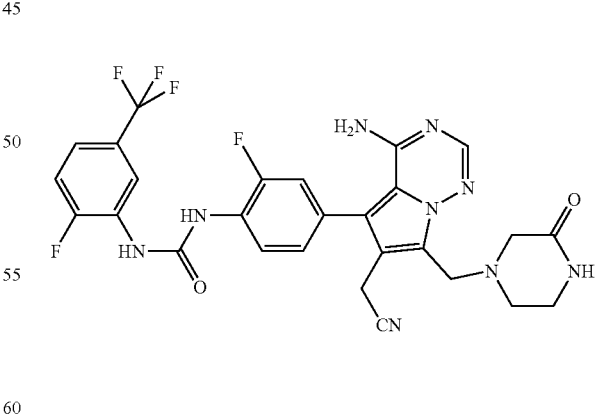

The procedure used for the preparation of Example 62 was used to prepare the title compound by substituting Intermediate AC for Intermediate Y and by substituting 2-oxopiperazine for morpholine. $^1$H-NMR (CD$_3$OD) δ 9.14 (d, J=2.4 Hz, 1H), 9.09 (d, J=2.8 Hz, 1H), 8.65 (d, J=6.8 Hz, 1H), 8.43-8.37 (m, 1H), 8.04 (s, 1H), 7.37-7.25 (m, 4H), 4.45 (s, 2H), 3.89 (s, 2H), 3.48 (s, 2H), 3.44 (t, J=4.8 Hz, 2H), 3.09 (t, J=4.8 Hz, 2H); MS [M+H]⁺=600; LCMS RT=3.01.

Example 81

Preparation of N-(4-{4-amino-6-(cyanomethyl)-7-{[2-(hydroxymethyl)morpholin-4-yl]methyl}pyrrolo[2,1-f][1,2,4]triazin-5-yl}-2-fluorophenyl)-N'-[2-fluoro-5-(trifluoromethyl)phenyl]urea

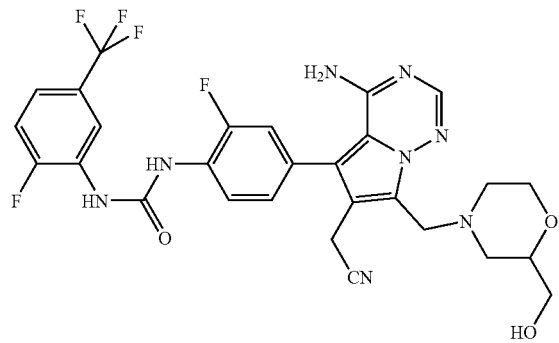

The procedure used for the preparation of Example 62 was used to prepare the title compound by substituting Intermediate AC for Intermediate Y and by substituting morpholin-2-ylmethanol for morpholine. ¹H-NMR (CD₃OD) δ 8.65 (d, J=7.6 Hz, 1H), 8.41 (t, J=8.0 Hz, 1H), 8.08 (s, 1H), 7.37-7.26 (m, 4H), 4.15 (dd, J=13.2, 2.4 Hz, 1H), 3.96 (s, 2H), 3.92-3.84 (m, 2H), 3.64 (t, J=3.2 Hz, 2H), 3.60-3.50 (m, 2H), 3.38-3.19 (m, 4H); MS [M+H]⁺=617; LCMS RT=2.96.

Example 82

Preparation of N-(4-{4-amino-6-(cyanomethyl)-7-[(2,6-dimethylmorpholin-4-yl)methyl]pyrrolo[2,1-f][1,2,4]triazine-5-yl}-2-fluorophenyl)-N'-[2-fluoro-5-(trifluoromethyl)phenyl]urea

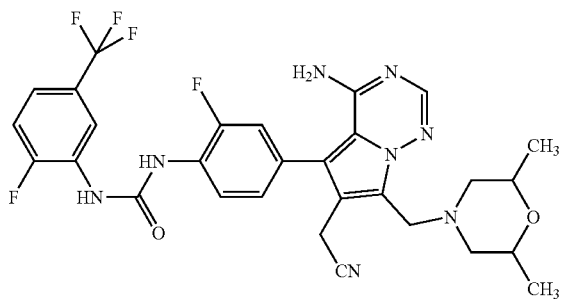

The procedure used for the preparation of Example 62 was used to prepare the title compound by substituting Intermediate AC for Intermediate Y and by substituting 2,6-dimethylmorpholine for morpholine. ¹H-NMR (CD₃OD) δ 8.67 (d, J=8.0 Hz, 1H), 8.41 (t, J=8.0 Hz, 1H), 8.06 (s, 1H), 7.37-7.26 (m, 4H), 4.85 (s, 2H), 3.94 (s, 2H), 3.91-3.88 (m, 2H), 3.52 (d, J=12.0 Hz, 2H), 2.93 (d, J=12.0 Hz, 2H), 1.24 (d, J=6.4 Hz, 6H); MS [M+H]⁺=615.1; LCMS RT=3.08.

Example 83

Preparation of N-(4-{4-amino-6-(cyanomethyl)-7-[(1,1-dioxidothiomorpholin-4-yl)methyl]pyrrolo[2,1-f][1,2,4]triazin-5-yl}-2-fluorophenyl)-N'-[2-chloro-5-(trifluoromethyl)phenyl]urea

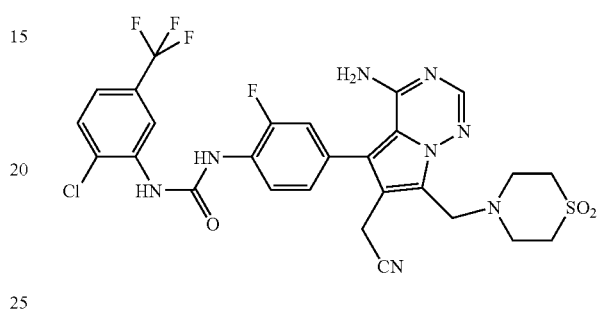

The procedure used for the preparation of Example 62 was used to prepare the title compound by substituting Intermediate AS for Intermediate Y and by substituting thiomorpholine 1,1-dioxide for morpholine. ¹H-NMR (CD₃OD) δ 9.53 (s, 1H), 8.95 (s, 1H), 8.66 (s, 1H), 8.43-8.38 (m, 1H), 8.06 (s, 1H), 7.64 (d, J=8.0 Hz, 1H), 7.35-7.24 (m, 3H), 4.26 (s, 2H), 3.87 (m, 4H), 3.96 (d, J=2.8 Hz, 2H), 3.20-3.17 (m, 4H), 3.12-3.09 (m, 4H); MS [M+H]⁺=650.9; LCMS RT=3.04.

Example 84

Preparation of N-(4-{4-amino-6-(cyanomethyl)-7-[(morpholin-4-yl)methyl]pyrrolo[2,1-f][1,2,4]triazin-5-yl}-2-fluorophenyl)-N'-[2-chloro-5-(trifluoromethyl)phenyl]urea

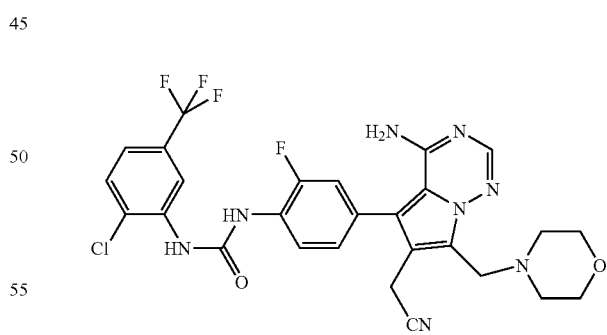

The procedure used for the preparation of Example 62 was used to prepare the title compound by substituting Intermediate AS for Intermediate Y. ¹H-NMR (CD₃OD) δ 9.52 (s, 1H), 8.95 (s, 1H), 8.66 (s, 1H), 8.42-8.38 (m, 1H), 8.06 (s, 1H), 7.64 (d, J=8.0 Hz, 1H), 7.35-7.24 (m, 3H), 4.90 (s, 2H), 4.02-3.85 (m, 4H), 3.96 (s, 2H), 3.48-3.44 (m, 4H); MS [M+H]⁺=602.8; LCMS RT=2.68.

Example 85

Preparation of N-{4-[4-amino-6-formyl-7-(morpholin-4-ylmethyl)pyrrolo[2,1-f][1,2,4]triazin-5-yl]phenyl}-N'-[4-(trifluoro-methyl)pyridin-2-yl]urea

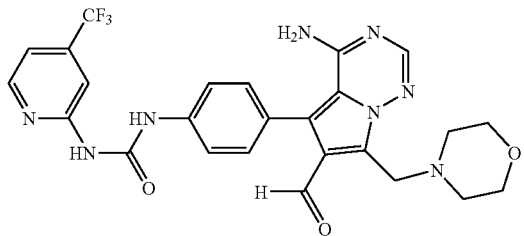

Dess-Martin periodinane (703.6 mg, 1.66 mmol) was added to a stirring solution of Example 62 (600 mg, 1.11 mmol) dissolved in DMSO (3 mL). After 1 hour HPLC indicated that the reaction was complete. The reaction was diluted with EtOAc (200 mL) washed with aq. Sodium thiosulfate solution (2M) (2×), and saturated NaHCO₃ solution (2×). The organic layer was dried (Na₂SO₄) and concentrated to give a brown powder which was triturated with 10% Et₂O/Hexanes to afford 450 mg (0.83 mmol, 75.3%) of the title compound. $^1$H-NMR (DMSO-d$_6$). δ 10.00 (s, 1H), 9.95 (s, 1H), 9.84 (s, 1H), 8.60 (d, J=5.4 Hz, 1H), 8.12 (s, 1H), 8.07 (s, 1H), 7.89 (d, J=8.7 Hz, 2H), 7.49 (d, J=8.4 Hz, 2H), 7.43 (d, J=5.1 Hz, 1H), 4.18 (s, 2H), 3.57-3.54 (m, 4H), 2.55-2.51 MS [M+H]$^+$=541; LCMS RT=2.50 min.

Example 86

N-{4-[4-amino-6-isobutyryl-7-(morpholin-4-ylmethyl)pyrrolo[2,1-f][1,2,4]triazin-5-yl]phenyl}-N'-[4-(trifluoromethyl)-pyridin-2-yl]urea

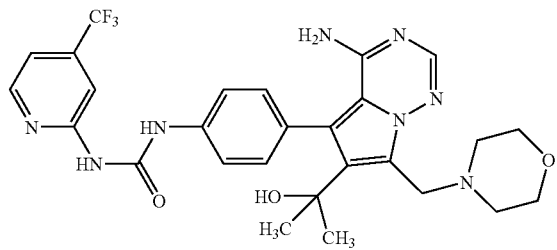

Step 1: Preparation of N-{4-[4-amino-6-(1-hydroxy-1-methylethyl)pyrrolo[2,1-f][1,2,4]triazin-5-yl]phenyl}-N'-[4-(trifluoromethyl)-pyridin-2-yl]urea

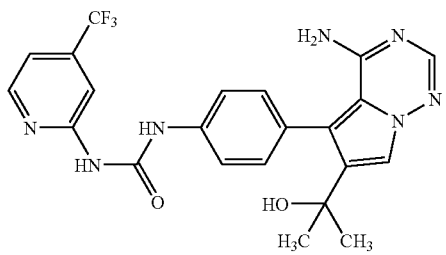

Methylmagnesium bromide (2.75 mL, 8.24 mmol, 3.0 M in Et₂O) was added drop wise to a stirring solution of Intermediate W (200 mg, 0.412 mmol) in THF (5 mL) at rt. The solution was heated to 60° C. for 2 h, after which TLC indicated the reaction was complete. The reaction was quenched with EtOAc and washed with saturated NH₄Cl solution (3×). The organic layer was dried (Na₂SO₄) and concentrated to a solid which was triturated with Et₂O to give an off-white powder which was used directly in the next step.

Step 2: Preparation of the Title Compound

The procedure used to prepare Example 62 was used to prepare the title compound by substituting N-{4-[4-amino-6-(1-hydroxy-1-methylethyl)pyrrolo[2,1-f]-[1,2,4]triazin-5-yl]phenyl}-N'-[4-(trifluoromethyl)pyridin-2-yl]urea for Intermediate Y. The crude product was purified by recrystallization in acetonitrile. $^1$H-NMR (DMSO-d$_6$). δ 8.55 (d, J=4.8 Hz, 1H), 8.27 (s, 1H), 7.89 (s, 1H), 7.74 (d, J=8.4 Hz, 2H), 7.34-7.31 (m, 3H), 6.82 (s, 1H), 4.16 (s, 2H), 3.65-3.58 (m, 4H), 2.60-2.41 (m, 4H), 1.72 (s, 3H), 1.29 (s, 3H). MS [M+H]$^+$=571; LCMS RT=2.49 min.

Example 87

N-{4-[4-amino-6-(difluoromethyl)-7-(morpholin-4-ylmethyl)-pyrrolo[2,1-f][1,2,4]triazin-5-yl]phenyl}-N'-[4-(trifluoromethyl)-pyridin-2-yl]urea

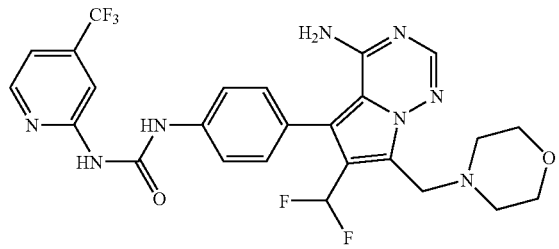

Deoxo-Fluor™ (0.38 mL, 0.740 mmol) was added to a stirring solution of Example 85 (N-{4-[4-amino-6-formyl-7-(morpholin-4-ylmethyl)pyrrolo[2,1-f]-[1,2,4]triazin-5-yl]-phenyl}-N'-[4-(trifluoro-methyl)pyridin-2-yl]urea) (200 mg, 0.37 mmol) in THF (3 mL). The reaction mixture was stirred until no starting material remained by HPLC (5 minutes). The reaction was diluted with EtOAc (150 mL) and washed with NaHCO₃ (3×). The organic layer was dried (Na₂SO₄) and concentrated to give a brown powder which was purified by HPLC (10-70% ACN/H₂O) to yield 21.1 mg (0.04 mmol, 10.1%). $^1$H-NMR (DMSO-d$_6$). δ 10.1-9.8 (s, 2H, br), 8.60 (d, J=5.1 Hz, 1H), 8.13 (s, 1H), 7.68 (d, J=9 Hz, 2H), 7.46-7.40 (m, 3H), 7.18 (t, J=54 Hz, 1H), 4.03 (s, 2H), 3.60-3.57 (m, 4H), 2.49-2.46 (m, 4H), MS [M+H]$^+$=563; LCMS RT=2.94 min.

Example 88

N-{4-[6-acetyl-4-amino-7-(morpholin-4-ylmethyl)pyrrolo[2,1-f][1,2,4]triazin-5-yl]phenyl}-N'-[4-(trifluoromethyl)-pyridin-2-yl]urea

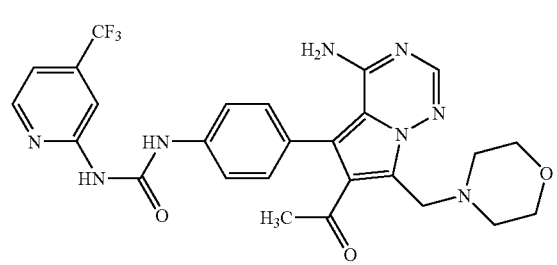

Step 1: Preparation of N-{4-[4-amino-6-(1-hydroxyethyl)pyrrolo[2,1f][1,2,4]-triazin-5-yl]phenyl}-N'-[4-(trifluoromethyl)pyridin-2-yl]urea

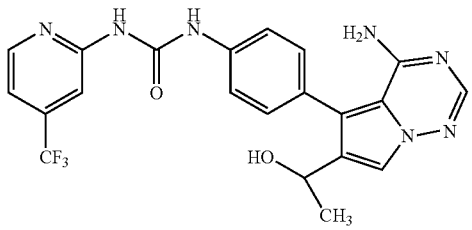

A solution of Intermediate AF (60 mg, 0.136 mmol) in 5 mL THF was treated with methylmagnesium bromide (0.68 mL, 2.1 mmol, 3 M in Et$_2$O) dropwise over 2 min. The reaction was allowed to stir for 15 min, then quenched with MeOH, diluted with EtOAc and washed with aq. NH$_4$Cl. The organic layer was dried with sodium sulfate and evaporated to dryness. The residue was triturated with Et$_2$O to provide 50.1 mg of the title compound (82% yield). $^1$H-NMR (DMSO) δ 10.05 (s, 1H), 9.82 (s, 1H), 8.52 (d, J=5 Hz, 1H), 8.09 (s, 1H), 7.81 (s, 1H), 7.64 (s, 1H), 7.61 (d, J=9 Hz, 2H), 7.34 (d, J=9 Hz, 2H), 4.96 (d, J=5 Hz, 1H), 4.63 (dq, J=5, 6 Hz, 1H), 1.24 (d, J=6 Hz, 3H); MS [M+H]$^+$=458.0; LCMS RT=2.41.

Step 2: Preparation of N-{4-[4-amino-6-(1-hydroxyethyl)-7-(morpholin-4-ylmethyl)pyrrolo[2,1-f][1,2,4]triazin-5-yl]phenyl}-N'-[4-(trifluoromethyl)-pyridin-2-yl]urea

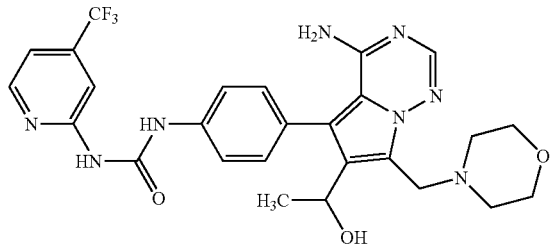

The procedure used to prepare Example 62 was used to prepare the above compound by substituting N-{4-[4-amino-6-(1-hydroxyethyl)pyrrolo[2,1-f][1,2,4]-triazin-5-yl]phenyl}-N'-[4-(trifluoromethyl)pyridin-2-yl]urea for Intermediate Y. The crude product was used directly in the next step. $^1$H-NMR (DMSO-d$_6$). δ 9.97 (s, 1H), 9.82 (s, 1H), 8.59 (d, J=5.1 Hz, 1H), 8.13 (s, 1H), 7.88 (s, 1H), 7.67 (d, J=9 Hz, 2H), 7.45-7.41 (m, 3H), 5.03 (d, J=4.8 Hz, 1H), 4.74-4.68 (m, 1H), 1.31 (d, J=6.0 Hz, 3H). MS [M+H]$^+$=557; LCMS RT=2.70 min.

Step 3: Preparation of the Title Compound

Dess-Martin periodinane (342.9 mg, 0.809 mmol) was added to a stirring solution of N-{4-[4-amino-6-(1-hydroxyethyl)-7-(morpholin-4-ylmethyl)pyrrolo[2,1-f][1,2,4]-triazin-5-yl]phenyl}-N'-[4-(trifluoromethyl)-pyridin-2-yl]urea (300 mg, 0.54 mmol) in DMSO (3 mL). The reaction was allowed to stir until complete by HPLC. Saturated aq. NaHCO$_3$ solution (0.25 volumes) was added until a lot of solid had crashed out. Then 2 volumes of EtOAc and 0.5 volumes of H$_2$O was added. This was allowed to stir overnight and the next day the excess liquid was removed via pipette. Careful addition of 5-10 mL of Et$_2$O and 2 mL of CH$_2$Cl$_2$ provided an off white suspension. This was filtered to give a the title compound (100 mg, 0.18 mmol, 31% yield, 2 steps) as pure white powder. $^1$H-NMR (DMSO-d$_6$). δ 10.20 (s, 1H), 10.04 (s, 1H), 8.67 (d, J=5.1 Hz, 1H), 8.20 (s, 1H), 8.10 (s, 1H), 7.78 (d, J=8.7 Hz, 2H), 7.52-7.48 (m, 3H), 4.19 (s, 2H), 3.63-3.60 (m, 4H), 2.56-2.53 (m, 4H), 2.19 (s, 3H). MS [M+H]$^+$=555; LCMS RT=2.51 min.

Example 89

N-{4-[4-amino-6-(cyclopropylcarbonyl)-7-(morpholin-4-ylmethyl)pyrrolo[2,1-f][1,2,4]triazin-5-yl]phenyl}-N'-[4-(trifluoromethyl)pyridin-2-yl]urea

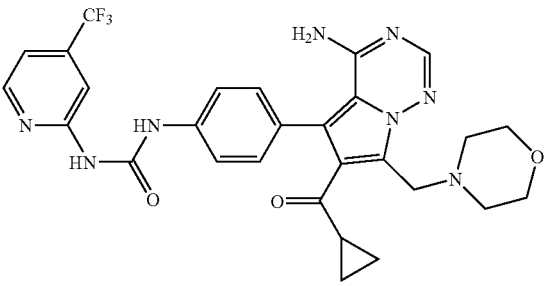

Cyclopropyl magnesium bromide (7.40 mL, 3.70 mmol, 0.5 M in diethyl ether) was added dropwise to a stirring solution of Example 85 (200 mg, 0.37 mmol) in THF (10 mL). This was allowed to stir until the reaction was complete by HPLC (1 hour). Additional amounts of the grinard reagent were added as needed. The reaction was quenched with methanol and was worked up by adding 1 volume of saturated NH$_4$Cl solution and 5 volumes of EtOAc. The organic layer was washed 2× with NH$_4$Cl and 1× with sodium carbonate soln. The organic layer was dried over Na$_2$SO$_4$ and concentrated. The crude intermediate was dissolved in DMSO (3 mL) and treated with Dess-Martin periodinane (174.7 mg, 0.412 mmol). The reaction was allowed to stir until the reaction was complete by HPLC (2 hours). The reaction was diluted with EtOAc (200 mL) and washed 2× with both saturated NaHCO$_3$ and 2M sodium thiosulfate solution. The organic layer was dried over Na$_2$SO$_4$ and concentrated to give a crude solid which was purified by HPLC (10-70% ACN/H$_2$O) to give 26.3 mg of the above compound (0.04 mmol, 12.3% yield). $^1$H-NMR (DMSO-d$_6$). δ 9.98 (s, 1H), 9.82 (s, 1H), 8.60 (d, J=5.4 Hz, 1H), 8.11 (s, 1H), 8.03 (s, 1H), 7.69 (d, J=8.4 Hz, 2H), 0.745-7.41 (m, 3H), 4.08 (s, 2H), 3.55-3.52 (m, 4H), 2.46-2.43 (m, 4H), 2.07-1.97 (m, 1H), 0.95-0.91 (m, 2H), 0.74-0.69 (m, 2H). MS [M+H]$^+$=581; LCMS RT=2.68 min.

Example 90

N-{4-[4-amino-7-(morpholin-4-ylmethyl)-6-propionylpyrrolo[2,1-f][1,2,4]triazin-5-yl]phenyl}-N'-[4-(trifluoromethyl)-pyridin-2-yl]urea

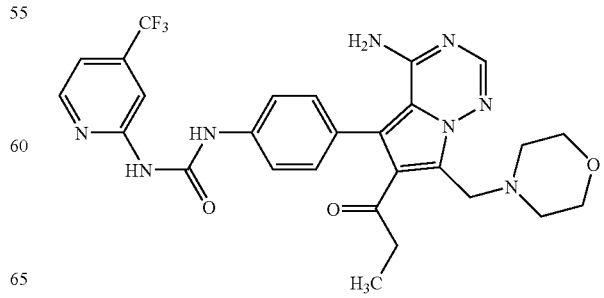

The procedure used to prepare Example 89 was used to prepare the title compound by substituting ethyl magnesium bromide (3.0 M in diethyl ether) for cyclopropyl magnesium bromide. The crude product was purified by recrystallizing it in acetonitrile. $^1$H-NMR (DMSO-d$_6$). δ 10.00 (s, 1H), 9.84 (s, 1H), 8.60 (d, J=5.4 Hz, 1H), 8.12 (s, 1H), 8.02 (s, 1H), 7.69 (d, J=9.0 Hz, 2H), 7.43-7.40 (m, 3H), 4.08 (s, 2H), 3.55-3.52 (m, 4H), 2.53-2.41 (m, 6H), 0.91 (t, J=7.4 Hz, 3H). MS [M+H]$^+$=569; LCMS RT=2.56 min.

Example 91

N-{4-[4-amino-6-isobutyryl-7-(morpholin-4-ylmethyl)pyrrolo[2,1-f][1,2,4]triazin-5-yl]phenyl}-N'-[4-(trifluoromethyl)-pyridin-2-yl]urea

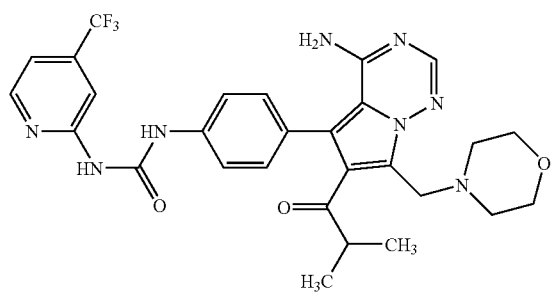

The procedure used to prepare Example 89 was used to prepare the title compound by substituting isopropyl magnesium bromide (2.0M in diethyl ether) for cyclopropyl magnesium bromide. The crude product was purified by HPLC (10-70% ACN/H$_2$O). $^1$H-NMR (DMSO-d$_6$). δ 10.10-9.80 (s, 2H, br), 8.59 (d, J=5.1 Hz, 1H), 8.12 (s, 1H), 8.02 (s, 1H), 7.69 (d, J=8.7 Hz, 2H), 7.42-7.39 (m, 3H), 4.02 (s, 2H), 3.58-3.49 (m, 4H), 2.72-2.61 (m, 1H), 2.49-2.35 (m, 4H), 0.91 (d, J=7.2 Hz, 6H). MS [M+H]$^+$=583; LCMS RT=2.75 min.

Example 92

N-{4-[4-amino-6-(2,2-dimethylpropanoyl)-7-(morpholin-4-ylmethyl)pyrrolo[2,1-f][1,2,4]triazin-5-yl]phenyl}-N'-[4-(trifluoromethyl)-pyridin-2-yl]urea

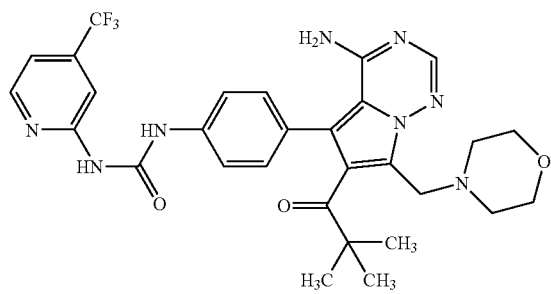

The procedure used to prepare Example 89 was used to prepare the title compound by substituting tert-butyl magnesium chloride (2.0 M in diethyl ether) for cyclopropyl magnesium bromide. The crude product was purified by HPLC (10-70% ACN/H$_2$O). $^1$H-NMR (DMSO-d$_6$). δ 10.00-9.78 (s, 2H, br), 8.59 (d, J=5.4 Hz, 1H), 8.11 (s, 1H), 8.00 (s, 1H), 7.65 (d, J=8.4, 2H), 7.56 (d, J=5.1 Hz, 1H), 7.34 (d, J=8.1 Hz, 2H), 3.82 (s, 2H), 3.59-3.51 (m, 4H), 2.49-2.38 (m, 4H), 0.87 (s, 9H). MS [M+H]$^+$=597; LCMS RT=2.83 min.

Example 93

N-(4-{6-acetyl-4-amino-7-[(2,6-dimethylmorpholin-4-yl)methyl]-pyrrolo[2,1-f][1,2,4]triazin-5-yl}-2-fluorophenyl)-N'-[2-fluoro-5-(trifluoromethyl)phenyl]urea

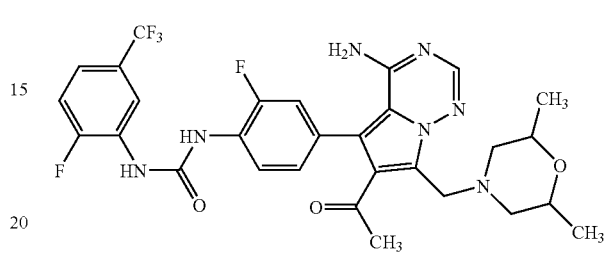

Step 1: Preparation of N-{4-[4-amino-6-(1-hydroxyethyl)pyrrolo[2,1-f][1,2,4]triazin-5-yl]-2-fluorophenyl}-N'-[2-fluoro-5-(trifluoromethyl)-phenyl]urea

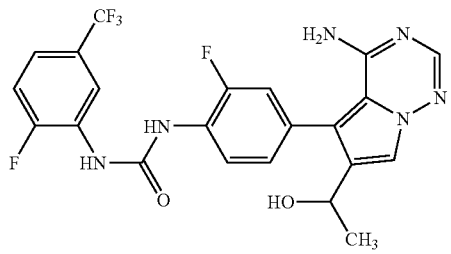

Intermediate N (100 mg, 0.20 mmol) in THF (5 mL) was added to a stirring solution of methylmagnesium bromide (0.80 mL, 2.38 mmol, 3.0 M in Et$_2$O) in THF (10 mL) at 0° C. The reaction was allowed to warm to rt and stir until complete as seen by TLC (1 h). The reaction was quenched with methanol (1 mL) and diluted with 5 volumes of EtOAc, an equal amount of saturated aq. NH$_4$Cl solution, and 1 volume of H$_2$O. The organic layer was dried (Na$_2$SO$_4$) and concentrated to give a off-white solid (80 mg, 0.17 mmol, 81% yield).

Step 2: Preparation of N-{4-[4-amino-7-[(2,6-dimethylmorpholin-4-yl)methyl]-6-(1-hydroxyethyl)pyrrolo[2,1-f][1,2,4]triazin-5-yl]-2-fluorophenyl}-N'-[2-fluoro-5-(trifluoromethyl)phenyl]urea

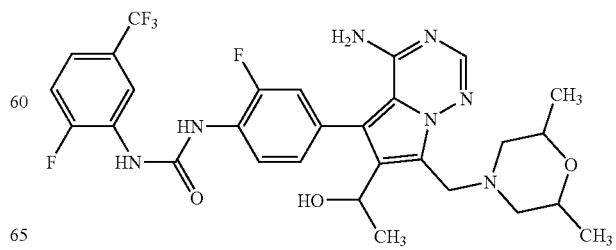

The procedure used to prepare Example 62 was used to prepare the above compound by substituting N-{4-[4-amino-6-(1-hydroxyethyl)pyrrolo[2,1-f][1,2,4]triazin-5-yl]-2-fluorophenyl}-N'-[2-fluoro-5-(trifluoromethyl)-phenyl]urea for Intermediate Y and 2,6-dimethylmorpholine for morpholine. The crude product was used directly in the next reaction. MS [M+H]+=620; LCMS RT=2.72 min.

Step 3: Preparation of Title Compound

The procedure used to prepare Example 88, step 3 was used to prepare the title compound by substituting N-{4-[4-amino-7-[(2,6-dimethylmorpholin-4-yl)methyl]-6-(1-hydroxyethyl)pyrrolo[2,1-f][1,2,4]triazin-5-yl]-2-fluorophenyl}-N'-[2-fluoro-5-(trifluoromethyl)phenyl]urea for N-{4-[4-amino-6-(1-hydroxyethyl)-7-(morpholin-4-ylmethyl)pyrrolo[2,1-f][1,2,4]triazin-5-yl]phenyl}-N'-[4-(trifluoromethyl)-pyridin-2-yl]urea. $^1$H-NMR (DMSO-$d_6$). δ 9.51 (s, 1H), 9.38 (s, 1H), 8.71 (d, J=7.5 Hz, 1H), 8.36 (t, J=8.7 Hz, 1H), 8.03 (s, 1H), 7.61-7.53 (m, 1H), 7.50-7.39 (m, 2H), 7.24 (d, J=8.1 Hz, 1H), 4.08 (s, 2H), 2.70 (d, J=10.2, 2H), 2.19 (s, 3H), 1.83 (t, J=10.5 Hz, 2H), 1.10 (d, J=6.3 Hz, 2H), 1.01 (d, J=11.4 Hz, 6H). MS [M+H]+=618; LCMS RT=2.76 min.

Example 94

4-amino-N-methoxy-N-methyl-7-[(4-methylpiperazin-1-yl)methyl]-5-{4-[({[4-(trifluoromethyl)pyridin-2-yl]amino}-carbonyl)amino]-phenyl}pyrrolo[2,1-f][1,2,4]triazine-6-carboxamide

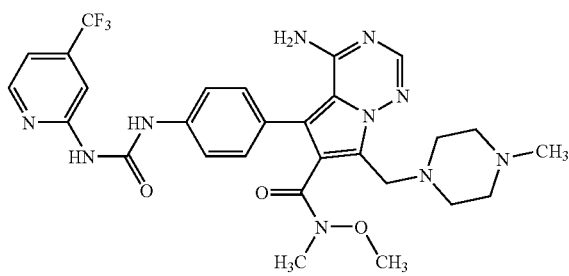

Step 1: Preparation of 4-amino-N-methoxy-N-methyl-5-{4-[({[4-(trifluoromethyl)pyridin-2-yl]amino}carbonyl)amino]phenyl}pyrrolo[2,1-f][1,2,4]triazine-6-carboxamide

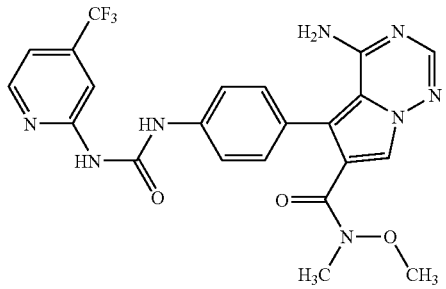

Intermediate X (1235 mg, 2.70 mmol), triethylamine (1.04 mL, 7.53 mmol), and Benzotriazol-1-yloxytos(dimethylamino)-phosphonium hexafluoro-phosphate (BOP, 1220 mg, 2.76 mmol) was combined along with DMF (20 mL). The mixture was allowed to stir until complete by HPLC (1 hour). The reaction mixture was diluted with 5 volumes of EtOAc and washed with pH 7 buffer, brine, and copious amounts of H$_2$O. The organic layer was dried (Na$_2$SO$_4$) and concentrated to give an off-white powder (953 mg, 77% yield).

Step 2: Preparation of the Title Compound

A solution of formaldehyde (0.22 mL, 3.0 mmol, 37% in H$_2$O) and 1-methylpiperazine (0.33 mL, 3.0 mmol) in AcOH (0.5 mL) was added to a stirring solution of 4-amino-N-methoxy-N-methyl-5-{4-[({[4-(trifluoromethyl)pyridin-2-yl]amino}-carbonyl)amino]phenyl}pyrrolo[2,1-f][1,2,4]triazine-6-carboxamide (150 mg, 0.30 mmol) in AcOH (1.5 mL) at 80° C. The reaction was allowed to stir overnight until all starting material had been consumed as shown by HPLC (15 his). The reaction mixture was worked up by diluting with EtOAc and washing 1× with saturated sodium carbonate solution, 1× with saturated sodium bicarbonate solution, and 1× with brine. The organic layer was dried over Na$_2$SO$_4$ and concentrated to a brown powder. The crude product was purified by HPLC (10-70% ACN/H$_2$O) to yield 100 mg (0.16 mmol, 54.5%) of the title compound. $^1$H-NMR (DMSO-$d_6$). δ 10.02 (s, 1H), 9.89 (s, 1H), 8.59 (d, J=5.4 Hz, 1H), 8.14 (s, 1H), 8.06 (s, 1H), 7.67 (d, J=8.4 Hz, 2H), 7.42-7.37 (m, 3H), 3.87 (s, 2H), 2.51-2.38 (m, 4H), 2.35-2.20 (m, 4H), 2.14 (s, 3H). MS [M+H]+=613; LCMS RT=2.37 min.

Example 95

N-[4-(6-acetyl-4-amino-7-{[4-(methylsulfonyl)piperazin-1-yl]methyl}pyrrolo[2,1-f][1,2,4]triazin-5-yl)-2-fluorophenyl]-N'-[2-fluoro-5-(trifluoromethyl)phenyl]urea

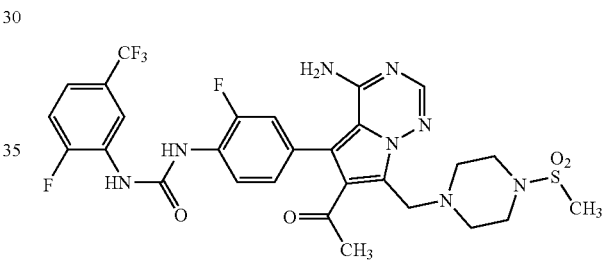

Step 1: Preparation of N-[4-(4-amino-6-(1-hydroxyethyl)-7-{[4-(methylsulfonyl)piperazin-1-yl]methyl}pyrrolo[2,1-f][1,2,4]triazin-5-yl)-2-fluorophenyl]-N'-[2-fluoro-5-(trifluoromethyl)phenyl]urea

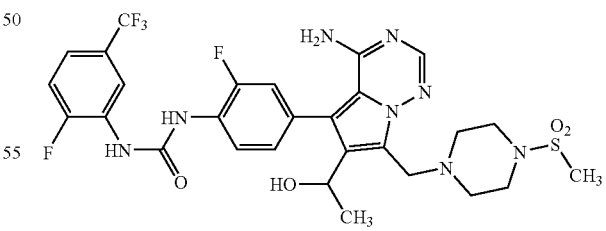

The procedure used to prepare Example 62 was used to prepare the title compound by substituting the product of step 1 in Example 93 (N-{4-[4-amino-6-(1-hydroxyethyl)pyrrolo[2,1-f][1,2,4]triazin-5-yl]-2-fluorophenyl}-N'-[2-fluoro-5-(trifluoromethyl)-phenyl]urea) for Intermediate Y and 1-methanesulfonylpiperazine for 2,6-dimethylmorpholine. The crude product was used directly in the next reaction. MS [M+H]+=669; LCMS RT=2.68 min.

Step 2: Preparation of Title Compound

The procedure used to prepare Example 88, step 3 was used to prepare the title compound by substituting N-[4-(4-amino-6-(1-hydroxyethyl)-7-{[4-(methylsulfonyl)piperazin-1-yl]methyl}pyrrolo[2,1-f][1,2,4]triazin-5-yl)-2-fluoro-phenyl]-N'-[2-fluoro-5-(trifluoromethyl)phenyl]urea for N-{4-[4-amino-6-(1-hydroxyethyl)-7-(morpholin-4-ylmethyl)pyrrolo[2,1-f][1,2,4]triazin-5-yl]phenyl}-N'-[4-(trifluoromethyl)-pyridin-2-yl]urea. ¹H-NMR (DMSO-d₆). δ 8.70 (dd, J=1.8, 7.5 Hz, 1H), 8.36 (t, J=8.4 Hz, 1H), 8.04 (s, 1H), 7.57-7.53 (m, 1H), 7.47-7.39 (m, 2H), 7.24 (dd, J=1.8, 8.4 Hz, 1H), 4.18 (s, 2H), 3.13-3.05 (m, 4H), 2.88 (s, 3H), 2.62-2.55 (m, 4H). MS [M+H]⁺=667; LCMS RT=2.79 min.

Example 96

N-(4-{6-acetyl-4-amino-7-[(4-methylpiperazin-1-yl)methyl]pyrrolo[2,1-f][1,2,4]triazin-5-yl}phenyl)-N'-[4-(trifluoromethyl)-pyridin-2-yl]urea

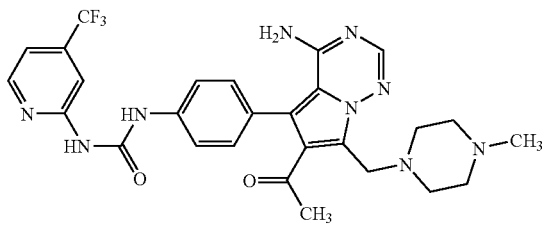

Methyl magnesium bromide (0.54 mL, 1.63 mmol, in 3.0 M in diethyl ether) was added dropwise to a stirring solution of Example 94 (100.0 mg, 0.163 mmol) in THF (2 mL) at rt. The reaction was heated to 60° C. and allowed to stir overnight (15 hrs) or until all starting material had been consumed as seen by HPLC. After cooling to rt, the reaction was quenched with methanol and diluted with 100 mL of EtOAc and washed 3× with saturated NH₄Cl solution. The organic layer was dried over Na₂SO₄, concentrated and purified by HPLC (10-70% ACN/H₂O) to give 37.9 mg (0.07 mmol, 40.9%) of the title compound. ¹H-NMR (DMSO-d₆). δ 10.88 (s, 1H), 10.19 (s, 1H), 8.57 (d, J=5.4 Hz, 1H), 8.27 (s, 1H), 8.03 (s, 1H), 7.70 (d, J=8.1 Hz, 2H), 7.40-7.35 (m, 3H), 4.17 (s, 2H), 3.08-3.04 (m, 4H), 2.73-2.65 (m, 7H), 2.06 (s, 3H). MS [M+H]⁺=568; LCMS RT=2.31 min.

Example 97

4-amino-N-methoxy-N-methyl-7-(morpholin-4-ylmethyl)-5-{4-[({[4-(trifluoromethyl)pyridin-2-yl]amino}carbonyl)-amino]phenyl}pyrrolo[2,1-f][1,2,4]triazine-6-carboxamide

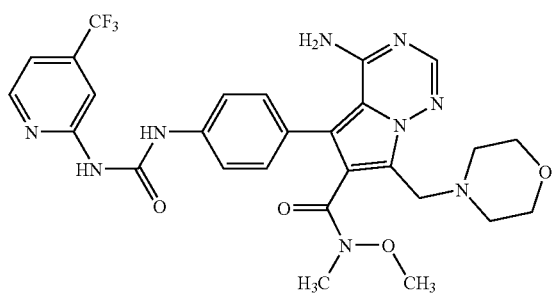

The procedure used to prepare Example 94 was used to prepare the title compound by substituting morpholine for 1-methylpiperazine. ¹H-NMR (DMSO-d₆). δ 8.58 (d, J=5.1 Hz, 1H), 8.17 (s, 1H), 7.72-7.66 (m, 2H), 7.60-7.45 (m, 1H), 7.43-7.36 (m, 3H), 3.88 (s, 2H), 3.61-3.50 (m, 7H), 3.49-3.40 (s, 3H), 2.50-2.38 (m, 4H). MS [M+H]⁺=600; LCMS RT=2.47 min.

Example 98

N-(4-{6-acetyl-4-amino-7-[(2,6-dimethylmorpholin-4-yl)methyl]-pyrrolo[2,1-f][1,2,4]triazin-5-yl}phenyl)-N'-[4-(trifluoromethyl)pyridin-2-yl]urea

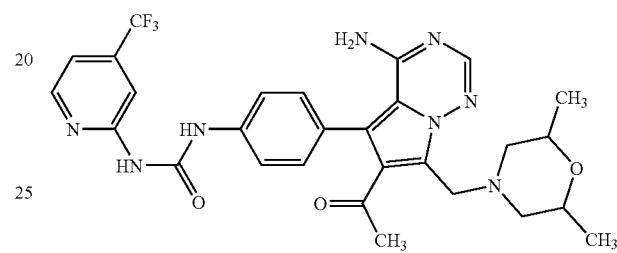

Step 1: Preparation of 4-amino-7-[(2,6-dimethylmorpholin-4-yl)methyl]-N-methoxy-N-methyl-5-{4-[({[4-(trifluoromethyl)pyridin-2-yl]amino}carbonyl)-amino]phenyl}pyrrolo[2,1-f][1,2,4]triazine-6-carboxamide

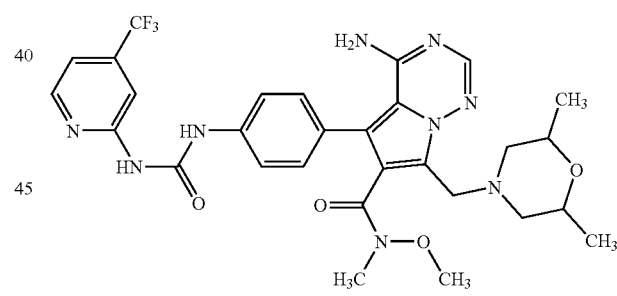

The procedure used to prepare Example 94 was used to prepare the above compound by substituting 2,6-dimethylmorpholine for 1-methylpiperazine. The crude product was used directly in the next reaction. MS [M+H]⁺=628; LCMS RT=2.73 min.

Step 2: Preparation of Title Compound

The procedure used to prepare Example 96 was used to prepare the title compound by substituting 4-amino-7-[(2,6-dimethylmorpholin-4-yl)methyl]-N-methoxy-N-methyl-5-{4-[({[4-(trifluoromethyl)pyridin-2-yl]amino}-carbonyl)amino]-phenyl}pyrrolo[2,1-f][1,2,4]triazine-6-carboxamide for Example 94. ¹H-NMR (Acetone-d₆). δ 8.47 (d, J=5.4 Hz, 1H), 7.78 (s, 1H), 7.77 (s, 1H), 7.68 (d, J=10.8 Hz, 2H), 7.33 (d, J=8.7 Hz, 2H), 7.21 (d, J=6.3 Hz, 1H), 4.02 (s, 2H), 2.61

(d, J=9.9 Hz, 2H), 1.71 (t, J=10.5 Hz, 2H), 0.91 (d, J=6.9 Hz, 2H), 0.90 (d, J=6.3 Hz, 6H). MS [M+H]⁺=583; LCMS RT=2.65 min.

Example 99

N-{4-[4-amino-6-(6-(difluoromethyl)-7-(morpholin-4-ylmethyl)-pyrrolo[2,1-f][1,2,4]triazin-5-yl]-2-fluorophenyl}-N'-[2-fluoro-5-(trifluoromethyl)phenyl]urea

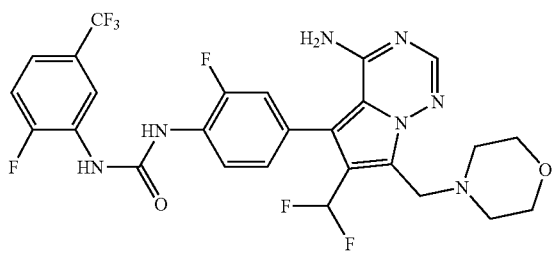

Step 1: Preparation of N-{4-[4-amino-6-formyl-7-(morpholin-4-ylmethyl)pyrrolo[2,1-f][1,2,4]triazin-5-yl]-2-fluorophenyl}-N'-[2-fluoro-5-(trifluoromethyl)phenyl]urea

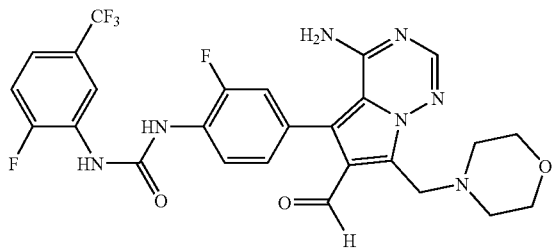

The procedure used to prepare Example 94, step 2 was used to prepare the above compound by substituting morpholine for 1-methylpiperazine and Intermediate N for the product of Step 1, Example 94 (4-amino-N-methoxy-N-methyl-5-{4-[({[4-(trifluoromethyl)pyridin-2-yl]amino}carbonyl)amino]phenyl}pyrrolo[2,1-f][1,2,4]-triazine-6-carboxamide). The crude product was used directly in the next reaction. MS [M+H]⁺=576; LCMS RT=2.82 min.

Step 2: Preparation of the Title Compound

The procedure used to prepare Example 87 was used to prepare the title compound by substituting N-{4-[4-amino-6-formyl-7-(morpholin-4-ylmethyl)pyrrolo[2,1-f][1,2,4]triazin-5-yl]-2-fluorophenyl}-N'-[2-fluoro-5-(trifluoromethyl)phenyl]urea for Example 85. ¹H-NMR (DMSO-d₆). δ 8.70 (dd, J=2.1, 7.2 Hz, 1H), 8.32 (t, J=8.4 Hz, 1H), 8.03 (s, 1H), 7.56-7.46 (m, 1H), 7.50-7.32 (m, 2H), 7.30-7.21 (m, 3H), 4.05 (s, 2H), 3.60-3.56 (m, 4H), 2.50-2.45 (m, 4H). MS [M+H]⁺=598; LCMS RT=3.07 min.

Example 100

N-4-[4-amino-6-formyl-7-(morpholin-4-ylmethyl)pyrrolo[2,1-f][1,2,4]triazin-5-yl]phenyl-N'-[2-fluoro-5-(trifluoromethyl)phenyl]urea

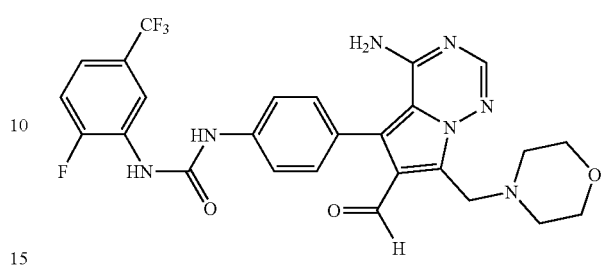

The procedure used for the preparation of Example 85 was used to prepare the title compound by Example 34 for Example 62. ¹H-NMR (DMSO-d₆) δ 9.91 (s, 1H), 9.39 (s, 1H), 8.99 (d, J=2.8 Hz, 1H), 8.64 (dd, J=7.5, 2.0 Hz, 1H), 8.03 (s, 1H), 7.61 (m, 2H), 7.52 (m, 1H), 7.44 (m, 2H), 7.41 (m, 1H), 4.14 (s, 2H), 3.52 (m, 4H), 2.48 (m, 4H); MS [M+H]⁺=558.0; LCMS RT=2.68.

Example 101

N-{4-[4-amino-6-(difluoromethyl)-7-(morpholin-4-ylmethyl)-pyrrolo[2,1-f][1,2,4]triazin-5-yl]phenyl}-N'-[2-fluoro-5-(trifluoromethyl)phenyl]urea

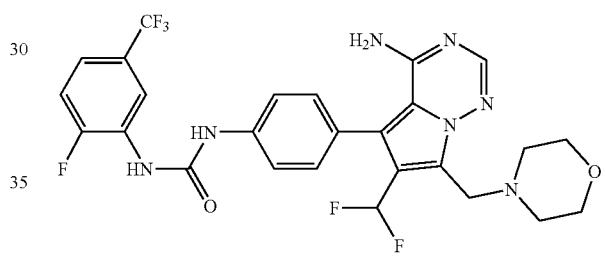

The procedure used to prepare Example 87 was used to prepare the title compound by substituting Example 100 for Example 85. ¹H-NMR (DMSO-d₆). δ 8.67 (dd, J=2.1, 7.5 Hz, 1H), 8.02 (s, 1H), 7.64 (d, J=8.4 Hz, 2H), 7.57-7.51 (m, 1H), 7.45-7.35 (m, 3H), 7.18 (t, J=54 Hz, 1H), 4.03 (s, 2H), 3.61-3.56 (m, 4H), 2.50-2.45 (m, 4H). MS [M+H]⁺=580; LCMS RT=2.69 min.

Example 102

N-4-[4-amino-6-[(E)-(hydroxyimino)methyl]-7-(morpholin-4-ylmethyl)pyrrolo[2,1-f][1,2,4]triazin-5-yl]phenyl-N'-[2-fluoro-5-(trifluoromethyl)phenyl]urea

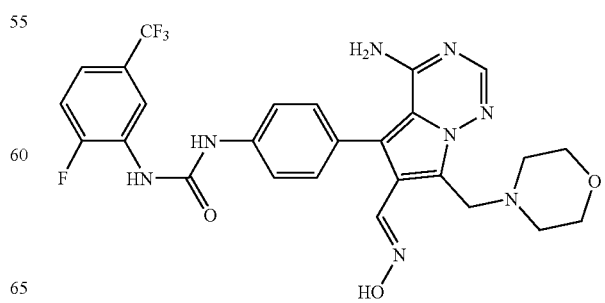

To a solution of pyridine (10 mL) was added the product of Example 100 (2.40 g, 4.31 mmol) followed by hydroxylamine hydrochloride (0.33 g, 4.74 mmol). The reaction was stirred at ambient temperature for 3 h, and then acetic anhydride (0.89 mL, 9.47 mmol) was added. The solution was heated at 80° C. for 2 h. Upon cooling to rt, the solution was concentrated in vacuo and subsequently purified by MPLC (Isco) 100% CH$_2$Cl$_2$ ramping to 9:1 v/v CH$_2$Cl$_2$-MeOH. The resulting purified fractions were combined and evaporated producing 200 mg (0.349 mmol, yield 8%) of a white solid. $^1$H-NMR (DMSO-d$_6$) δ 10.98 (s, 1H), 9.37 (s, 1H), 8.99 (d, J=2.9 Hz, 1H), 8.64 (dd, J=7.6, 2.1 Hz, 1H), 7.95 (s, 2H), 7.60 (m, 2H), 7.51 (m, 1H), 7.41 (m, 2H), 7.34 (m, 2H), 4.06 (s, 2H), 3.52 (m, 4H), 2.48 (m, 4H); MS [M+H]$^+$=572.9; LCMS RT=2.66.

Example 103

N-4-[6-(E)-[(acetyloxy)imino]methyl-4-amino-7-(morpholin-4-ylmethyl)pyrrolo[2,1-f][1,2,4]triazin-5-yl]phenyl-N'-[2-fluoro-5-(trifluoromethyl)phenyl]urea

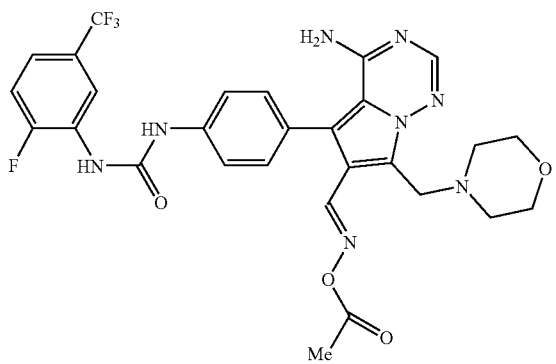

To a solution of pyridine (10 mL) was added Example 100 (2.40 g, 4.31 mmol) followed by hydroxylamine hydrochloride (0.33 g, 4.74 mmol). The reaction was stirred at ambient temperature for 3 h, and then acetic anhydride (0.89 mL, 9.47 mmol) was added. The solution was heated at 80° C. for 2 h. Upon cooling to rt, the solution was concentrated in vacuo and subsequently purified by MPLC (Isco) 100% CH$_2$Cl$_2$ ramping to 9:1 v/v CH$_2$Cl$_2$-MeOH. The resulting purified fractions were combined and evaporated producing 700 mg (1.14 mmol, yield 27%) of a white solid. $^1$H-NMR (DMSO-d$_6$) δ 9.39 (s, 1H), 9.00 (d, J=2.9 Hz, 1H), 8.64 (dd, J=7.4, 2.6 Hz, 1H), 8.29 (s, 1H), 8.00 (s, 1H), 7.62 (m, 2H), 7.52 (m, 1H), 7.42 (m, 1H), 7.38 (m, 2H), 4.12 (s, 2H), 3.51 (m, 4H), 2.53 (m, 4H), 2.07 (s, 3H); MS [M+H]$^+$=615.1; LCMS RT=2.80.

Example 104

N-4-[4-amino-6-(1-hydroxyethyl)-7-(morpholin-4-ylmethyl)-pyrrolo[2,1-f][1,2,4]triazin-5-yl]phenyl-N'-[2-fluoro-5-(trifluoromethyl)-phenyl]urea

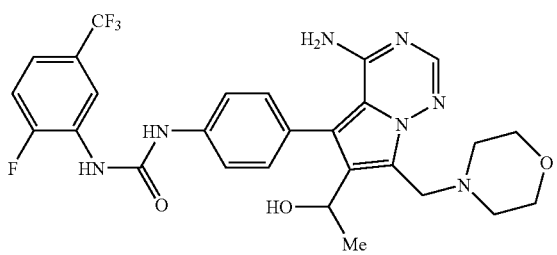

The procedure used to prepare Example 89 (Grignard addition only-no oxidation) was used to prepare the title compound by substituting methyl magnesium bromide (3.0 M in diethyl ether) for cyclopropyl magnesium bromide and by substituting Example 100 for Example 85. $^1$H-NMR (DMSO-d$_6$) δ 9.35 (s, 1H), 8.98 (d, J=2.9 Hz, 1H), 8.64 (dd, J=7.1, 2.1 Hz, 1H), 7.89 (s, 1H), 7.60 (m, 2H), 7.52 (m, 1H), 7.41 (m, 1H), 7.32 (m, 2H), 5.90 (d, J=6.3 Hz, 1H), 4.69 (m, 1H), 4.13 (d, J=13.3 Hz, 1H), 3.94 (d, J=13.4 Hz, 1H), 3.53 (m, 4H), 2.44 (m, 4H), 1.36 (d, J=6.6 Hz, 3H); MS [M+H]$^+$=574.1; LCMS RT=2.91.

Example 105

N-4-[6-acetyl-4-amino-7-(morpholin-4-ylmethyl)pyrrolo[2,1-f][1,2,4]triazin-5-yl]phenyl-N'-[2-fluoro-5-(trifluoromethyl)phenyl]urea

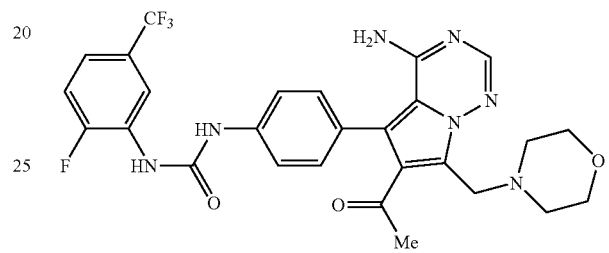

The procedure used to prepare Example 85 was used to prepare the title compound by substituting Example 105 for Example 62. $^1$H-NMR (DMSO-d$_6$) δ 9.39 (s, 1H), 8.99 (d, J=2.9 Hz, 1H), 8.63 (dd, J=7.3, 2.4 Hz, 1H), 7.98 (s, 1H), 7.62 (m, 2H), 7.52 (m, 1H), 7.42 (m, 1H), 7.38 (m, 2H), 4.07 (s, 2H), 3.50 (m, 4H), 2.43 (m, 4H), 2.08 (s, 3H); MS [M+H]$^+$=572.0; LCMS RT=2.70.

Example 106

N-4-[4-amino-6-[cyclopropyl(hydroxy)methyl]-7-(morpholin-4-ylmethyl)pyrrolo[2,1-f][1,2,4]triazin-5-yl]phenyl-N'-[2-fluoro-5-(trifluoromethyl)phenyl]urea

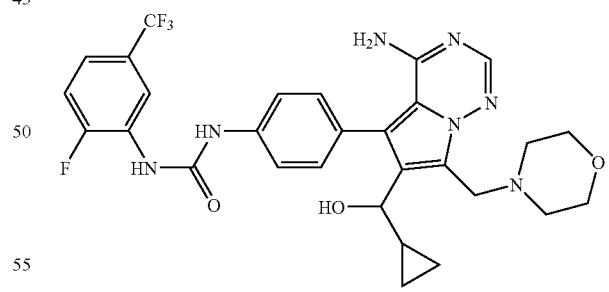

The procedure used to prepare Example 89 (Grignard addition only-no oxidation) was used to prepare the title compound by substituting Example 100 for Example 85. $^1$H-NMR (DMSO-d$_6$) δ 9.36 (s, 1H), 9.00 (d, J=2.1 Hz, 1H), 8.64 (dd, J=7.5, 2.4 Hz, 1H), 7.90 (s, 1H), 7.59 (m, 2H), 7.52 (m, 1H), 7.41 (m, 1H), 7.33 (m, 2H), 5.95 (d, J=7.0 Hz, 1H), 4.11 (d, J=13.1 Hz, 1H), 3.98 (d, J=13.1 Hz, 1H), 3.83 (t, J=7.1 Hz, 1H), 3.53 (m, 4H), 2.40 (m, 4H), 0.86 (m, 1H), 0.43 (m, 1H), 0.23 (m, 2H), −0.09 (m, 1H); MS [M+H]$^+$=600.1; LCMS RT=2.95.

Example 107

N-4-[4-amino-6-(cyclopropylcarbonyl)-7-(morpholin-4-ylmethyl)pyrrolo[2,1-f][1,2,4]triazin-5-yl]phenyl-N'-[2-fluoro-5-(trifluoromethyl)phenyl]urea

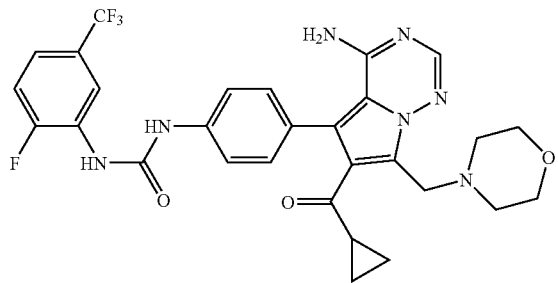

The procedure used to prepare Example 85 was used to prepare the title compound by substituting Example 106 for Example 62. $^1$H-NMR (DMSO-d$_6$) δ 9.37 (s, 1H), 8.98 (d, J=2.5 Hz, 1H), 8.63 (dd, J=7.2, 2.2 Hz, 1H), 7.99 (s, 1H), 7.60 (m, 2H), 7.52 (m, 1H), 7.41 (m, 1H), 7.37 (m, 2H), 4.04 (s, 2H), 3.49 (m, 4H), 2.41 (m, 4H), 1.96 (m, 1H), 0.89 (m, 2H), 0.68 (m, 2H); MS [M+H]$^+$=598.1; LCMS RT=3.07.

Example 108

N-4-[4-amino-6-[(2-methoxyethyl)amino]methyl-7-(morpholin-4-ylmethyl)pyrrolo[2,1-f][1,2,4]triazin-5-yl]phenyl-N'-[2-fluoro-5-(trifluoromethyl)phenyl]urea

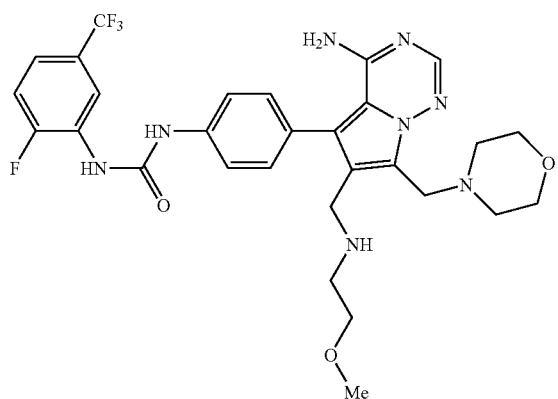

To a solution of Example 100 (N-4-[4-amino-6-formyl-7-(morpholin-4-ylmethyl)pyrrolo[2,1-f][1,2,4]triazin-5-yl]phenyl-N'-[2-fluoro-5-(trifluoromethyl)-phenyl]urea (50.0 mg, 0.090 mmol)) in THF (1.0 mL) was added AcOH (51 μL, 0.90 mmol) and 2-methoxyethanamine (39 μL, 0.45 mmol). The reaction was heated at 60° C. for 3 h after which sodium cyanoborohydride (28 mg, 0.45 mmol) was added. The reaction was heated at 60° C. for an additional 17 h. The crude material was purified by preparative HPLC (10-90ACN/H$_2$O with 0.1% TFA). The resulting fractions were combined and diluted with EtOAc and washed with saturated aq NaHCO$_3$ and water. The organic was dried (MgSO$_4$) and evaporated to give a 31 mg (0.050 mmol, yield 56%) of the title compound as a white solid. $^1$H-NMR (DMSO-d$_6$) δ 9.36 (s, 1H), 8.99 (d, J=2.6 Hz, 1H), 8.64 (dd, J=7.2, 2.5 Hz, 1H), 7.92 (s, 1H), 7.61 (m, 2H), 7.52 (m, 1H), 7.42 (m, 3H), 3.94 (s, 2H), 3.71 (br s, 2H), 3.56 (m, 4H), 3.37 (m, 2H), 3.21 (s, 3H), 2.69 (m, 2H), 2.43 (m, 4H); MS [M+H]$^+$=617.1; LCMS RT=2.81.

Example 109

N-4-[4-amino-6-[(methylamino)methyl]-7-(morpholin-4-ylmethyl)pyrrolo[2,1-f][1,2,4]triazin-5-yl]phenyl-N'-[2-fluoro-5-(trifluoromethyl)phenyl]urea

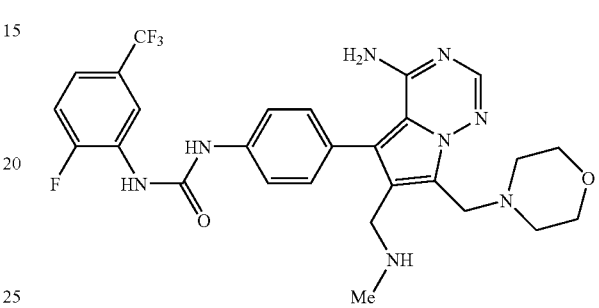

The procedure used for the preparation of Example 108 was used to prepare the title compound by substituting methylamine for morpholine. $^1$H-NMR (DMSO-d$_6$) δ 9.39 (s, 1H), 9.00 (d, J=2.5 Hz, 1H), 8.64 (dd, J=7.2, 2.2 Hz, 1H), 7.94 (s, 1H), 7.63 (m, 2H), 7.53 (m, 1H), 7.42 (m, 1H), 7.39 (m, 2H), 4.00 (s, 2H), 3.82 (s, 2H), 3.56 (m, 4H), 2.47 (m, 4H) 2.37 (s, 3H); MS [M+H]$^+$=573.0; LCMS RT=2.31.

Example 110

N-4-[4-amino-6-[(2-methoxyethyl)(methyl)-amino]methyl-7-(morpholin-4-ylmethyl)pyrrolo[2,1-f][1,2,4]triazin-5-yl]phenyl-N'-[2-fluoro-5-(trifluoromethyl)phenyl]urea

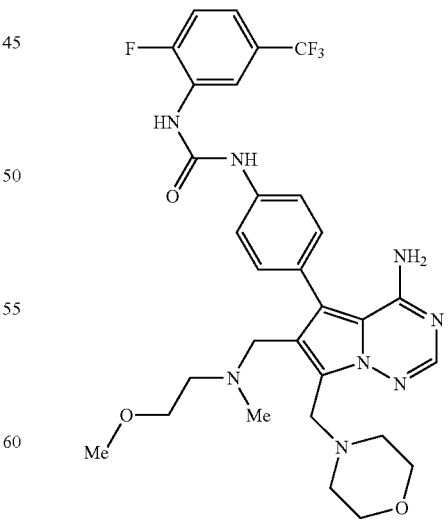

The procedure used for the preparation of Example 108 was used to prepare the title compound by substituting 2-methoxy-N-methylethanamine for morpholine. $^1$H-NMR (DMSO-d₆) δ 9.34 (s, 1H), 8.98 (d, J=2.5 Hz, 1H), 8.64 (dd, J=7.3, 2.6 Hz, 1H), 7.89 (s, 1H), 7.58 (d, J=8.5 Hz, 2H), 7.52 (m, 1H), 7.41 (m, 1H), 7.36 (d, J=8.5 Hz, 2H), 3.93 (s, 2H), 3.54 (m, 4H), 3.43 (m, 2H), 3.31 (m, 2H), 3.17 (s, 3H), 2.43 (m, 4H), 2.39 (m, 2H), 1.99 (s, 1H); MS [M+H]⁺=631.2; LCMS RT=2.79.

Example 111

Preparation of N-{4-[4-amino-6-methyl-7-(morpholin-4-ylmethyl)pyrrolo[2,1-f][1,2,4]triazin-5-yl]phenyl}-N'-[2-fluoro-5-(trifluoromethyl)phenyl]urea

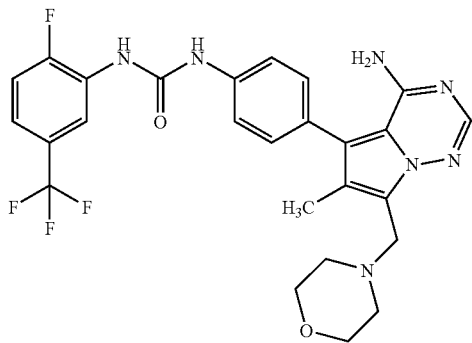

Step 1: Preparation of N-{4-[4-amino-6-(hydroxymethyl)pyrrolo[2,1-f][1,2,4]triazin-5-yl]phenyl}-N'-[2-fluoro-5-(trifluoromethyl)phenyl]urea

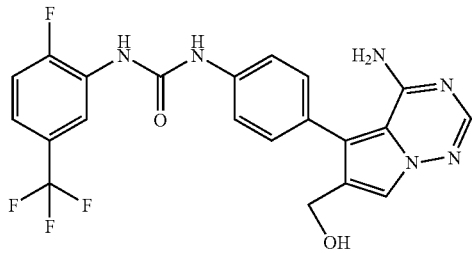

A suspension of Intermediate J (925 mg, 1.84 mmol) in 50 mL tetrahydrofuran was cooled to 0° C. and treated dropwise with 1.0 M DIBAL in THF (18.4 mL, 18.4 mmol). The reaction was allowed to warm to rt over 30 min, then quenched with 1 mL MeOH and diluted with 1 L EtOAc. This solution was stirred vigorously with 1 L of aqueous Rochelle's salt for 18 hours. The organic phase was separated, dried with sodium sulfate and filtered through a plug of silica. Concentration of the solvent and trituration with ether:hexanes (2:1) provided the title compound as a yellowish powder (697 mg, 82% Yield). ¹H-NMR (DMSO-d₆) δ 9.87 (s, 1H), 9.74 (s, 1H), 8.54 (d, J=5 Hz, 1H), 8.06 (s, 1H), 7.83 (s, 1H), 7.66 (s, 1H), 7.62 (d, J=8.7 Hz, 2H), 7.37 (d, J=8.7 Hz, 2H), 7.38 to 7.35 (m, 1H), 4.95 (t, J=5 Hz, 1H), 4.36 (d, J=5 Hz, 2H); MS [M+H]⁺=461; LCMS RT=2.87 min.

Step 2: Preparation of N-[4-(4-amino-6-methylpyrrolo[2,1-f][1,2,4]triazin-5-yl)phenyl]-N'-[2-fluoro-5-(trifluoromethyl)phenyl]urea

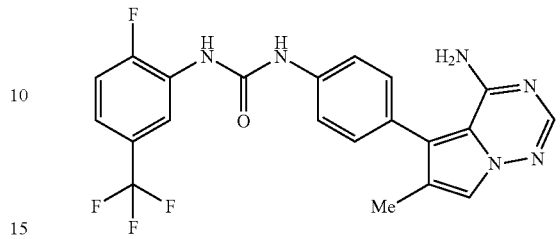

A suspension of N-{4-[4-amino-6-(hydroxymethyl)pyrrolo[2,1-f]-triazin-5-yl]phenyl}-N'-[2-fluoro-5-(trifluoromethyl)phenyl]urea (423 mg, 0.930 mmol) in THF 5 (mL) and 1,2-dichloroethane (5 mL) was treated with thionyl chloride (148 µL, 2.05 mmol) at rt. After 10 min the reaction appeared complete by RP-HPLC. After 30 min the reaction was concentrated under vacuum. The residue was suspended in 1,2-dichloroethane and sonicated briefly, then concentrated again under vacuum (2×). The resulting solid (412 mg, 0.86 mmol) was suspended in THF (20 mL) and cooled to −45° C. This suspension was treated with 1.0 M L-Selectride in THF (8.6 mL, 8.6 mmol). After 15 min the reaction was complete by HPLC. The reaction mixture was removed from the ice bath and quenched with MeOH (1 mL), then treated with 1 M sodium hydroxide (2 mL) and 30% hydrogen peroxide (2 mL). After 15 min stirring, the mixture was diluted with EtOAc (200 mL) and water (200 mL). The organic layer was washed with brine and dried with sodium sulfate. Concentration of the organic layer and trituration with ether:hexanes gave the title compound as an white powder (323 mg, 0.73 mmol, 84% yield). ¹H-NMR (CD₃OD-d₆) δ 8.61 (d, J=8 Hz, 1H), 7.73 (s, 1H), 7.62 (d, J=9 Hz, 2H), 7.48 to 7.50 (m, 1H), 7.35 (d, J=9 Hz, 2H), 7.31 to 7.36 (m, 2H), 2.14 (s, 3H); MS [M+H]⁺=445.1; LCMS RT=2.80.

Step 3: Preparation of Title Compound

A mixture of morpholine (35 mg, 41 mmol) and 100 uL acetic acid were sonicated until homogeneous, then treated with 37% aqueous formaldehyde (30 uL, 33 mg, 41 mmol) and the mixture added to a solution of N-[4-(4-amino-6-methylpyrrolo[2,1-f][1,2,4]triazin-5-yl)phenyl]-N'-[2-fluoro-5-(trifluoromethyl)-phenyl]urea (150 mg, 34 mmol) in 1 mL acetic acid. This mixture was stirred for 16 h at 60° C. and then concentrated in vacuo. The residue was dissolved in methanol with 5 drops of trifluoroacetic acid and purified by RP-HPLC to provide the title compound as a white solid (32.3 mg, 17.1% yield). ¹H-NMR (DMSO-d₆) δ9.34 (d, J=9.6 Hz, 1H), 8.94 (bs, 1H), 8.62 (d, J=7.2 Hz, 1H), 7.92 (s, 1H), 7.85 (s, 1H), 7.61 (d, J=8.7 Hz, 2H), 7.47 to 7.53 (m, m1H), 7.33 to 7.41 (m, 1H), 7.31 (d, J=8.7 Hz, 2H), 3.80 (s, 2H), 3.48 to 3.55 (m, 4H), 2.34 to 2.44 (m, 4H); MS [M+H]⁺=544.1; LCMS RT=2.70.

Example 112

N-{4-[4-amino-6-methyl-7-(morpholin-4-ylmethyl)pyrrolo-[2,1-f][1,2,4]triazin-5-yl]-2-fluorophenyl}-N'-[2-fluoro-5-(trifluoromethyl)phenyl]urea

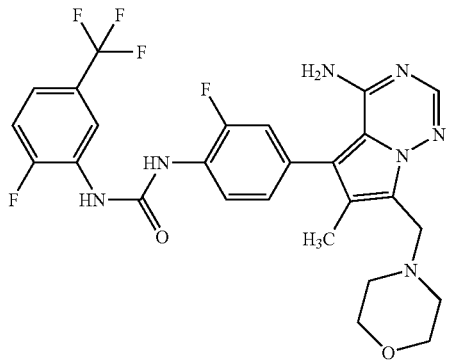

The procedure used for the preparation of Example 111 was used to prepare the title compound by substituting Intermediate L in place of Intermediate J. 700 mg (72%) of the desired product was isolated. $^1$H-NMR (DMSO-d$_6$) δ 8.64 (dd, J=2.1, 7.2 Hz, 1H), 8.28 (t, J=8.7 Hz, 1H), 7.86 (s, 1H), 7.53-7.47 (m, 1H), 7.41-7.37 (m, 1H), 7.28 (dd, J=1.8, 14.1 Hz, 1H), 7.14 (dd, J=1.2, 8.4 Hz, 1H), 3.80 (s, 2H), 3.54-3.50 (m, 4H), 2.43-2.39 (m, 4H), 1.97 (s, 3H); MS [M+H]$^+$=562.2; LCMS RT=2.68.

Example 113

N-{4-[4-amino-6-(fluoromethyl)-7-(morpholin-4-ylmethyl)-pyrrolo[2,1-f][1,2,4]triazin-5-yl]-2-fluorophenyl}-N'-[2-fluoro-5-(trifluoromethyl)phenyl]urea

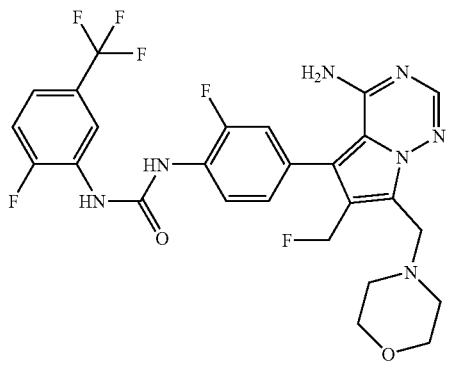

The title compound was prepared in a manner similar to the procedure described for the preparation of Example 87, using N-{4-[4-amino-6-(hydroxymethyl)-7-(morpholin-4-ylmethyl)pyrrolo[2,1-f]-[1,2,4]triazin-5-yl]-[2-fluoro-5-(trifluoromethyl)phenyl]urea (which can be prepared using the procedure used for the preparation of Example 34 substituting Intermediate M for Intermediate K) in place of Example 85 (N-{4-[4-amino-6-formyl-7-(morpholin-4-ylmethyl)pyrrolo[2,1-f]-[1,2,4]triazin-5-yl]phenyl}-N'-[4-(trifluoromethyl)pyridin-2-yl]urea), 45 mg (23%) of the desired product was isolated. $^1$H-NMR (DMSO-d$_6$) δ 8.65 (dd, J=2.4, 6.9 Hz, 1H), 8.31 (t, J=8.4 Hz, 1H), 7.95 (s, 1H), 7.53-7.47 (m, 1H), 7.41-7.37 (m, 1H), 7.30 (dd, J=1.8, 12.3 Hz, 1H), 7.19 (dd, J=1.5, 8.4 Hz, 1H), 5.35 (d, J=49.8 Hz, 2H), 3.92 (s, 2H), 3.54-3.50 (m, 4H), 2.43-2.39 (m, 4H); MS [M+H]$^+$=579.7; LCMS RT=2.63.

Example 114

N-{4-[4-amino-6-(hydroxymethyl)-7-(morpholin-4-ylmethyl)pyrrolo[2,1-f][1,2,4]triazin-5-yl]-2-fluorophenyl}-N'-[4-(trifluoromethyl)pyridin-2-yl]urea

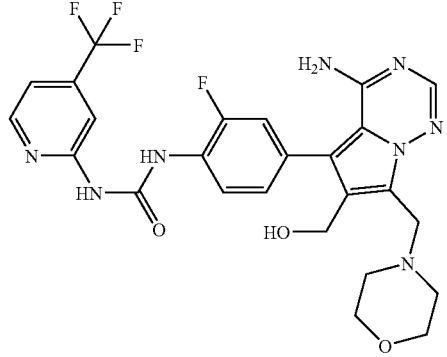

The title compound was prepared in a manner similar to the procedure described for the preparation of Example 62, using Intermediate AJ in place of Intermediate Y, 200 mg (82%) of the desired product was isolated. $^1$H-NMR (DMSO-d$_6$) δ 10.14-10.08 (m, 2H), 8.54 (d, J=5.1 Hz, 1H), 8.30 (q, J=9.3 Hz, 1H), 8.01 (s, 1H), 7.98 (s, 1H), 7.44-7.35 (m, 2H), 7.28-7.19 (m, 1H), 5.06-5.04 (m, 1H), 4.41-4.38 (m, 2H), 3.92 (s, 2H), 3.55-3.52 (m, 4H), 2.45-2.42 (m, 4H); MS [M+H]$^+$=560.9; LCMS RT=2.45.

Example 115

N-{4-[4-amino-6-(fluoromethyl)-7-(morpholin-4-ylmethyl)-pyrrolo[2,1-f][1,2,4]triazin-5-yl]-2-fluorophenyl}-N'-[4-(trifluoromethyl)pyridin-2-yl]urea

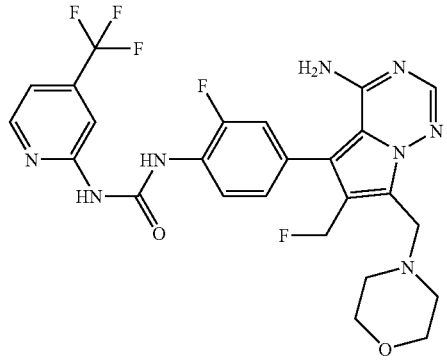

The title compound was prepared in a manner similar to the procedure described for the preparation of Example 87, using N-{4-[4-amino-6-(hydroxymethyl)-7-(morpholin-4-ylmethyl)pyrrolo[2,1-f]-[1,2,4]triazin-5-yl]-2-fluorophenyl}-N'-[4-(trifluoro-methyl)-pyridin-2-yl]urea (which can be prepared using the procedure used for the preparation of Example 62 substituting Intermediate AJ for Intermediate Y) in place of Example 85 (N-{4-[4-amino-6-formyl-7-(morpholin-4-ylmethyl)pyrrolo[2,1-f]-[1,2,4]triazin-5-yl]phenyl}-N'-[4-(trifluoro-methyl)pyridin-2-yl]urea), 45 mg (23%) of the desired product was isolated. $^1$H-NMR (DMSO-d$_6$) δ 10.16-10.10 (m, 2H), 8.54 (d, J=5.1 Hz, 1H), 8.31 (t, J=8.4 Hz, 1H), 8.01 (s, 1H), 7.95 (s, 1H), 7.39-7.19 (m, 3H), 5.35 (d, J=49.8 Hz, 2H), 3.92 (s, 2H), 3.53-3.52 (m, 4H), 2.48-2.43 (m, 4H); MS [M+H]$^+$=562.7; LCMS RT=2.50.

Example 116

N-{4-[4-amino-6-(difluoromethyl)-7-(morpholin-4-ylmethyl)-pyrrolo[2,1-f][1,2,4]triazin-5-yl]-2-fluorophenyl}-N'-[4-(trifluoromethyl)pyridin-2-yl]urea

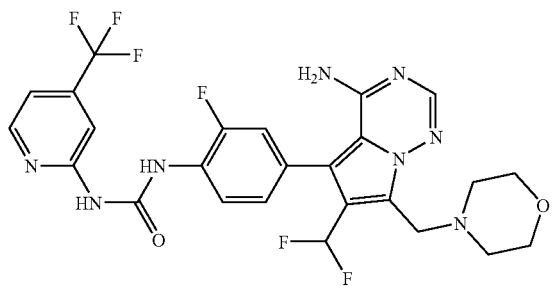

The title compound was prepared in a manner similar to the procedure described for the preparation of Example 87, using Intermediate AK Step 1 (N-[4-(4-amino-6-formylpyrrolo[2,1-f][1,2,4]triazin-5-yl)-2-fluorophenyl]-N'-[4-(trifluoromethyl)pyridin-2-yl]urea) in place of Example 85 (N-{4-[4-amino-6-formyl-7-(morpholin-4-ylmethyl)pyrrolo[2,1-f]-[1,2,4]triazin-5-yl]phenyl}-N'-[4-(trifluoro-methyl)pyridin-2-yl]urea), 18 mg (17%) of the desired product was isolated. $^1$H-NMR (DMSO-d$_6$) δ 10.16-10.12 (m, 2H), 9.93 (s, 1H), 8.55 (d, J=5.4 Hz, 1H), 8.31 (t, J=8.4 Hz, 1H), 8.01 (s, 2H), 7.47-7.37 (m, 2H), 7.27-7.23 (m, 1H), 4.12 (s, 2H), 3.52-3.48 (m, 4H), 2.46-2.40 (m, 4H); MS [M+H]$^+$=581.0; LCMS RT=2.60.

Example 117

N-{4-[4-amino-6-methyl-7-(1,4-oxazepan-4-ylmethyl)pyrrolo[2,1-f][1,2,4]triazin-5-yl]phenyl}-N'-[2-fluoro-5-(trifluoromethyl)phenyl]urea

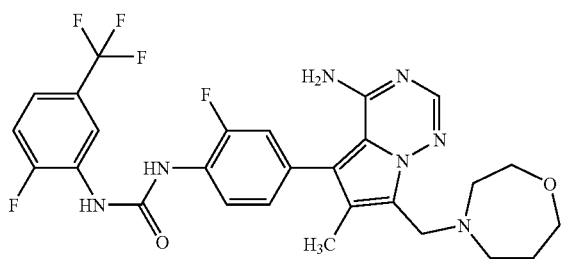

Step 1: Preparation of 6-methylpyrrolo[2,1-f][1,2,4]triazin-4-amine

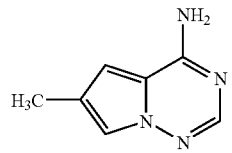

To a degassed solution of 6-bromopyrrolo[2,1-f][1,2,4]triazin-4-amine (Intermediate AAE) (316 mg, 1.48 mmol) and Bis(diphenylphosphino)ferrocenepalladium dichloride (30 mg, 0.037 mmol) in 1,4-dioxane (10 mL), was added dimethyl zinc (2.97 mL, 5.93 mmol, 2.0 M in toluene). The mixture was allowed to stir at 90° C. for 17 hr and then cooled to 0° C. The reaction was quenched with MeOH (1.0 mL) and partitioned between ethyl acetate (200 mL) and potassium phosphate dibasic pH 10 buffer (100 mL). The layers were separated and the organic phase was washed with brine, dried (Na$_2$SO$_4$), and concentrated to dryness. Trituration with Et$_2$O afforded 175 mg (79%) of the desired product. $^1$H-NMR (DMSO-d$_6$) δ 7.69 (s, 1H), 7.39 (s, 1H), 6.61 (s, 1H), 2.18 (s, 3H); MS [M+H]$^+$=148.9; LCMS RT=1.16.

Step 2: Preparation of 6-methyl-7-(1,4-oxazepan-4-ylmethyl)pyrrolo[2,1-f][1,2,4]triazin-4-amine

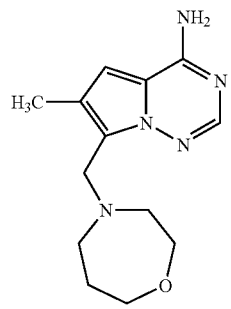

A solution of formaldehyde (0.61 mL, 8.10 mmol, 37% in H$_2$O) and homomorpholine hydrochloride (1.11 g, 8.10 mmol) in AcOH (5 mL) was added to a stirring solution of 6-methylpyrrolo[2,1-f][1,2,4]triazin-4-amine (1.00 g, 6.75 mmol) in AcOH (5 mL) at 60° C. The reaction was allowed to stir until all starting material had been consumed as shown by HPLC (1 hr). The reaction mixture was worked up by diluting with EtOAc and washing 3× with saturated sodium carbonate solution. The organic layer was dried over Na$_2$SO$_4$ and concentrated under reduced pressure. The crude product was triturated with Et$_2$O to obtain 1.37 g (78%) of a light brown powder. $^1$H-NMR (DMSO-d$_6$) δ 7.76 (s, 1H), 7.47 (br s, 2H), 6.65 (s, 1H), 3.85 (s, 2H), 3.62 (t, J=5.7 Hz, 2H), 3.55-3.51 (m, 2H), 2.61-2.55 (m, 4H), 2.21 (s, 3H), 1.77-1.74 (m, 2H); MS [M+H]$^+$=262.0; LCMS RT=1.02.

Step 3: Preparation of 5-bromo-6-methyl-7-(1,4-oxazepan-4-ylmethyl)pyrrolo[2,1-f][1,2,4]triazin-4-amine

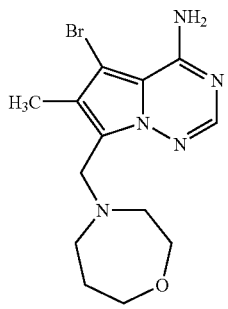

To a stirring solution of chloroform (20 mL) and 6-methyl-7-(1,4-oxazepan-4-ylmethyl)pyrrolo[2,1-f][1,2,4]triazin-4-amine (650 mg, 2.49 mmol), at −40° C., was added 1,3-dibromo-5,5-dimethylhydantoin (356 mg, 1.24 mmol). The mixture was allowed to stir for 10 minutes while warming to rt. The mixture was partitioned between ethyl acetate (200 mL) and saturated aqueous Na$_2$CO$_3$ solution (150 mL). The layers were separated and the organic phase was washed with brine, dried (Na$_2$SO$_4$), and concentrated to dryness. Trituration with acetonitrile afforded 500 mg (59%) of the desired product. $^1$H-NMR (DMSO-d$_6$) δ 7.82 (s, 1H), 3.91 (s, 2H), 3.62 (t, J=5.4 Hz, 2H), 3.55-3.53 (m, 2H), 2.61-2.56 (m, 4H), 2.15 (s, 3H), 1.77-1.72 (m, 2H); MS [M+H]$^+$=339.9, 341.9; LCMS RT=1.09.

Step 4: Preparation of the Title Compound

To a stirred solution of 5-bromo-6-methyl-7-(1,4-oxazepan-4-ylmethyl)pyrrolo[2,1-f][1,2,4]triazin-4-amine (100 mg, 0.29 mmol) and tetrakis(triphenylphosphine)-palladium(0) (101 mg, 0.088 mmol), in degassed 1,4 dioxane (4.0 mL), was added Intermediate AAN (1-[2-fluoro-5-(trifluoromethyl)phenyl]-3-[4-(4,4,5,5-tetramethyl-1,3,2-dioxaborolan-2-yl)phenyl]urea) (248 mg, 0.59 mmol), K$_2$CO$_3$ (162 mg, 1.18 mmol), and H$_2$O (0.4 mL). The mixture was degassed and heated (90° C.) for 17 h and then cooled to rt. The mixture was partitioned between ethyl acetate (25 mL) and saturated aqueous Na$_2$CO$_3$ solution (25 mL). The layers were separated and the organic phase was washed, dried (Na$_2$SO$_4$), and concentrated to dryness. The residue was purified by preparative HPLC using a gradient elution from 10% to 70% acetonitrile to obtain 24 mg (15%) of the desired product. $^1$H-NMR (DMSO-d$_6$) δ 9.36 (s, 1H), 8.98-8.97 (m, 1H), 8.63 (dd, J=2.4, 7.2 Hz, 1H), 7.85 (s, 1H), 7.60-7.47 (m, 3H), 7.41-7.33 (m, 1H), 7.33 (d, J=8.7 Hz, 2H), 3.95 (s, 2H), 3.66 (t, J=6.0 Hz, 2H), 3.59-3.56 (m, 2H), 3.31 (m, 2H), 2.68-2.62 (m, 4H), 2.10 (s, 3H), 1.83-1.75 (m, 2H); MS [M+H]$^+$=558.1; LCMS RT=2.94.

Example 118

N-{4-[4-amino-6-methyl-7-(1,4-oxazepan-4-ylmethyl)pyrrolo[2,1-f][1,2,4]triazin-5-yl]-2-fluorophenyl}-N'-[2-fluoro-5-(trifluoromethyl)-phenyl]urea

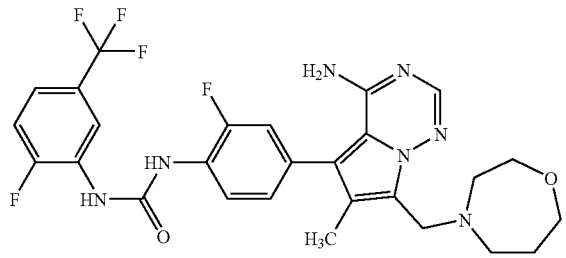

The title compound was prepared in a manner similar to the procedure described for the preparation of Example 117 Step 4, using Intermediate F (1-[2-fluoro-4-(4,4,5,5-tetramethyl-1,3,2-dioxaborolan-2-yl)phenyl]-3-[2-fluoro-5-(trifluoromethyl)phenyl]urea in place of Intermediate AAN (1-[2-fluoro-5-(trifluoromethyl)phenyl]-3-[4-(4,4,5,5-tetramethyl-1,3,2-dioxaborolan-2-yl)phenyl]urea) 49 mg (26%) of the desired product was isolated. $^1$H-NMR (DMSO-d$_6$) δ 9.43 (br s, 1H), 9.28 (br s, 1H), 8.66 (dd, J=2.4, 7.2 Hz, 1H), 8.29 (t, J=8.7 Hz, 1H), 7.86 (s, 1H), 7.55-7.48 (m, 1H), 7.43-7.40 (m, 1H), 7.29 (dd, J=2.1, 12.3 Hz, 1H), 7.15 (dd, J=1.5, 8.4 Hz, 1H), 4.00 (s, 2H), 3.65 (t, J=6.0 Hz, 2H), 3.58-3.56 (m, 2H), 2.68-2.62 (m, 4H), 2.12 (s, 3H), 1.81-1.77 (m, 2H); MS [M+H]$^+$=576.0; LCMS RT=2.66.

Example 119

N-{4-[4-amino-6-methyl-7-(morpholin-4-ylmethyl)pyrrolo[2,1-f][1,2,4]triazin-5-yl]-2-methylphenyl}-N'-[4-(trifluoromethyl)pyridin-2-yl]urea

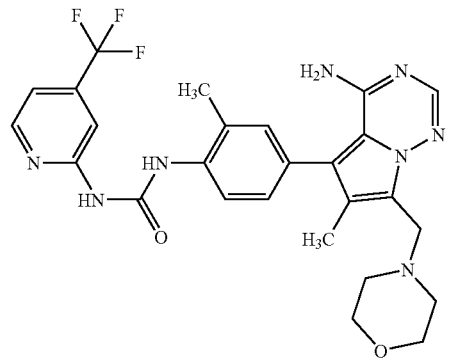

Step 1: Preparation of 5-bromo-6-methyl-7-(morpholin-4-ylmethyl)pyrrolo[2,1-f][1,2,4]triazin-4-amine

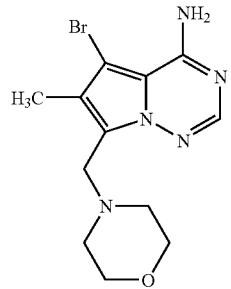

To a solution of 6-methylpyrrolo[2,1-f][1,2,4]triazin-4-amine (350 mg, 2.36 mmol) in DMF (5 mL), was added 4-methylenemorpholin-4-ium chloride (*Eur. J. Med. Chem.* 1989, 24, 379-384) (750 mg, 2.84 mmol) at rt. The reaction was stirred for 17 hr, cooled to −78° C., and treated with 1,3-dibromo-5,5-dimethylimidazolidone-2,4-dione (337 mg, 1.18 mmol). The reaction was allowed to stir for 30 minutes while warming to rt. The mixture was partitioned between ethyl acetate (200 mL) and saturated aqueous Na$_2$CO$_3$ solution (150 mL). The layers were separated and the organic phase was washed with brine, dried (Na$_2$SO$_4$), and concentrated to dryness. Trituration with acetonitrile afforded 300 mg (39%) of the desired product. ¹H-NMR (DMSO-d₆) δ 7.83 (s, 1H), 3.76 (s, 2H), 3.50-3.47 (m, 4H), 2.36-2.32 (m, 4H), 2.15 (s, 3H); MS [M+H]⁺=325.9, 327.9; LCMS RT=1.10.

Step 2: Preparation of the Title Compound

The title compound was prepared in a manner similar to the procedure described for the preparation of Example 117 Step 4, using 5-bromo-6-methyl-7-(morpholin-4-ylmethyl)pyrrolo[2,1-f][1,2,4]triazin-4-amine in place of 5-bromo-6-methyl-7-(1,4-oxazepan-4-ylmethyl)pyrrolo[2,1-f][1,2,4]triazin-4-amine and Intermediate AAI (1-[2-methyl-4-(4,4,5,5-tetramethyl-1,3,2-dioxaborolan-2-yl)phenyl]-3-[4-(trifluoromethyl)pyridin-2-yl]urea) in place of Intermediate AAN (1-[2-fluoro-5-(trifluoromethyl)phenyl]-3-[4-(4,4,5,5-tetramethyl-1,3,2-dioxaborolan-2-yl)phenyl]urea) 59 mg (36%) of the desired product was isolated. ¹H-NMR (DMSO-d₆) δ 10.19 (s, 1H), 9.52 (br s, 1H), 8.55 (d, J=5.1 Hz, 1H), 8.10 (d, J=8.4 Hz, 1H), 7.87 (s, 1H), 7.85 (s, 1H), 7.35 (d, J=4.8 Hz, 1H), 7.23 (s, 1H), 7.18 (dd, J=2.1, 8.7 Hz, 1H), 3.80 (s, 2H), 3.53-3.50 (m, 4H), 2.42-2.40 (m, 4H), 2.35 (s, 3H), 2.09 (s, 3H); MS [M+H]⁺=541.1; LCMS RT=2.49.

Example 120

N-{4-[4-amino-6-methyl-7-(morpholin-4-ylmethyl)pyrrolo[2,1-f][1,2,4]triazin-5-yl]-2-methylphenyl}-N'-[2-fluoro-5-(trifluoromethyl)-phenyl]urea

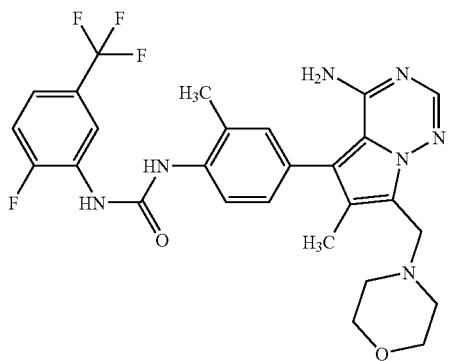

The title compound was prepared in a manner similar to the procedure described for the preparation of Example 117 Step 4, using the product of step 1, Example 119 (5-bromo-6-methyl-7-(morpholin-4-ylmethyl)pyrrolo[2,1-f][1,2,4]triazin-4-amine) in place of 5-bromo-6-methyl-7-(1,4-oxazepan-4-ylmethyl)pyrrolo[2,1-f][1,2,4]triazin-4-amine and Intermediate AAH (1-[2-fluoro-5-(trifluoromethyl)phenyl]-3-[2-methyl-4-(4,4,5,5-tetramethyl-1,3,2-dioxaborolan-2-yl)phenyl]urea) in place of Intermediate AAN (1-[2-fluoro-5-(trifluoromethyl)phenyl]-3-[4-(4,4,5,5-tetramethyl-1,3,2-dioxaborolan-2-yl)phenyl]-urea) 28 mg (16%) of the desired product was isolated. ¹H-NMR (DMSO-d₆) δ 9.41-9.40 (m, 1H), 8.67 (dd, J=2.1, 7.2 Hz, 1H), 8.58 (s, 1H), 8.01 (d, J=8.1 Hz, 1H), 7.85 (s, 1H), 7.53-7.46 (m, 1H), 7.39-7.35 (m, 1H), 7.22 (s, 1H), 7.18-7.15 (m, 1H), 3.80 (s, 2H), 3.53-3.50 (m, 4H), 2.41-2.39 (m, 4H), 2.31 (s, 3H), 2.09 (s, 3H); MS [M+H]⁺=558.1; LCMS RT=2.59.

Example 121

N-{4-[4-amino-6-methyl-7-(morpholin-4-ylmethyl)pyrrolo[2,1-f][1,2,4]triazin-5-yl]phenyl}-N'-[2-chloro-5-(trifluoromethyl)phenyl]urea

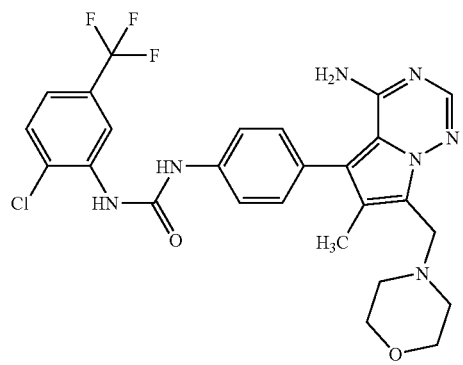

The title compound was prepared in a manner similar to the procedure described for the preparation of Example 117 Step 4, using the product of step 1, Example 119 (5-bromo-6-methyl-7-(morpholin-4-ylmethyl)pyrrolo[2,1-f][1,2,4]triazin-4-amine in place of 5-bromo-6-methyl-7-(1,4-oxazepan-4-ylmethyl)pyrrolo[2,1-f][1,2,4]triazin-4-amine and Intermediate AAL (1-[2-chloro-5-(trifluoromethyl)-phenyl]-3-[4-(4,4,5,5-tetramethyl-1,3,2-dioxaborolan-2-yl)phenyl]-urea) in place of Intermediate AAN (1-[2-fluoro-5-(trifluoromethyl)phenyl]-3-[4-(4,4,5,5-tetramethyl-1,3,2-dioxaborolan-2-yl)phenyl]-urea) 44 mg (26%) of the desired product was isolated. ¹H-NMR (DMSO-d₆) δ 9.72 (s, 1H), 8.67-8.63 (m, 2H), 7.85 (s, 1H), 7.72 (d, J=8.4 Hz, 1H), 7.60 (d, J=8.7 Hz, 2H), 7.39-7.30 (m, 3H), 3.80 (s, 2H), 3.53-3.50 (m, 4H), 2.42-2.39 (m, 4H), 2.09 (s, 3H); MS [M+H]⁺=560.2; LCMS RT=2.66.

Example 122

N-{4-[4-amino-6-methyl-7-(morpholin-4-ylmethyl)pyrrolo[2,1-f][1,2,4]triazin-5-yl]phenyl}-N'-[4-(trifluoromethyl)pyridin-2-yl]urea

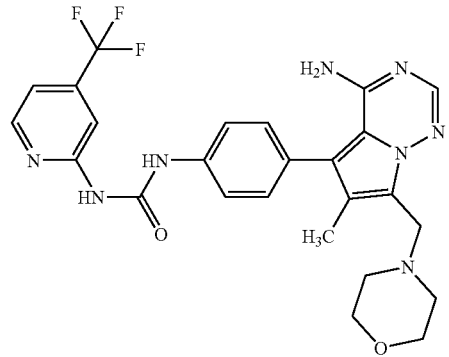

The title compound was prepared in a manner similar to the procedure described for the preparation of Example 117 Step 4, using the product of step 1, Example 119 (5-bromo-6-methyl-7-(morpholin-4-ylmethyl)pyrrolo[2,1-f][1,2,4]triazin-4-amine) in place of 5-bromo-6-methyl-7-(1,4-oxazepan-4-ylmethyl)pyrrolo[2,1-f][1,2,4]triazin-4-amine and Intermediate AAG (1-[4-(4,4,5,5-tetramethyl-1,3,2-dioxaborolan-2-yl)phenyl]-3-[4-(trifluoromethyl)pyridin-2-yl]urea) in place of Intermediate AAN (1-[2-fluoro-5-(trifluoromethyl)phenyl]-3-[4-(4,4,5,5-tetramethyl-1,3,2-dioxaborolan-2-yl)phenyl]urea), 53 mg (44%) of the desired product was isolated. $^1$H-NMR (DMSO-$d_6$) δ 9.88 (s, 1H), 9.75 (s, 1H), 8.54 (d, J=5.1 Hz, 1H), 8.06 (s, 1H), 7.85 (s, 1H), 7.63 (d, J=8.4 Hz, 3H), 7.36-7.31 (m, 3H), 3.80 (s, 2H), 3.55-3.50 (m, 4H), 2.42-2.39 (m, 4H), 2.09 (s, 3H); MS [M+H]$^+$=527.1; LCMS RT=2.34.

Example 123

N-{4-[4-amino-6-methyl-7-(morpholin-4-ylmethyl)pyrrolo[2,1-f][1,2,4]triazin-5-yl]-2,5-difluorophenyl}-N'-[2-fluoro-5-(trifluoromethyl)-phenyl]urea

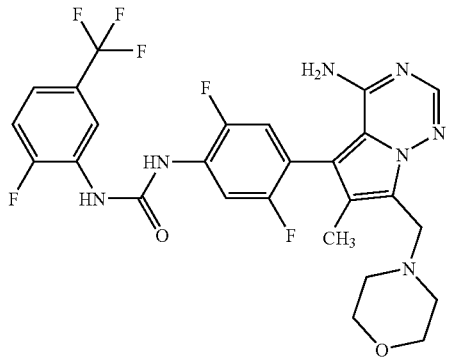

The title compound was prepared in a manner similar to the procedure described for the preparation of Example 117 Step 4, using the product of step 1, Example 119 (5-bromo-6-methyl-7-(morpholin-4-ylmethyl)pyrrolo[2,1-f][1,2,4]triazin-4-amine) in place of 5-bromo-6-methyl-7-(1,4-oxazepan-4-ylmethyl)pyrrolo[2,1-f][1,2,4]triazin-4-amine and Intermediate AAB (1-[2,5-difluoro-4-(4,4,5,5-tetramethyl-1,3,2-dioxaborolan-2-yl)phenyl]-3-[2-fluoro-5-(trifluoromethyl)-phenyl]urea) in place of Intermediate AAN (1-[2-fluoro-5-(trifluoromethyl)phenyl]-3-[4-(4,4,5,5-tetramethyl-1,3,2-dioxaborolan-2-yl)phenyl]urea) 25 mg (14%) of the desired product was isolated. $^1$H-NMR (DMSO-$d_6$) δ 9.51-9.45 (m, 2H), 8.63-8.61 (m, 1H), 8.20-8.13 (m, 1H), 7.87 (s, 1H), 7.55-7.48 (m, 1H), 7.45-7.39 (m, 1H), 7.33-7.27 (m, 1H), 3.80 (s, 2H), 3.53-3.50 (m, 4H), 2.41-2.39 (m, 4H), 2.03 (s, 3H); MS [M+H]$^+$=580.1; LCMS RT=2.65.

Example 124

N-{4-[4-amino-6-methyl-7-(1,4-oxazepan-4-ylmethyl)pyrrolo[2,1-f][1,2,4]triazin-5-yl]-2-methylphenyl}-N'-[4-(trifluoromethyl)pyridin-2-yl]urea

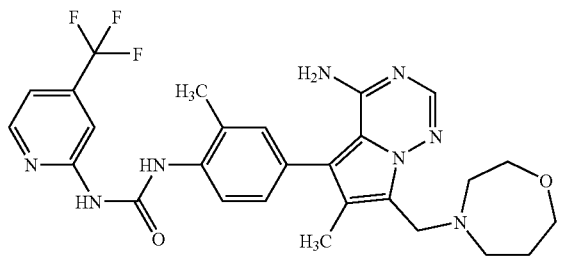

In a manner similar to the procedure described for the preparation of Example 117 Step 4, using Intermediate AAI (1-[2-methyl-4-(4,4,5,5-tetramethyl-1,3,2-dioxaborolan-2-yl)phenyl]-3-[4-(trifluoromethyl)pyridin-2-yl]urea) in place of Intermediate AAN (1-[2-fluoro-5-(trifluoromethyl)phenyl]-3-[4-(4,4,5,5-tetramethyl-1,3,2-dioxaborolan-2-yl)phenyl]-urea), 24 mg (15%) of the desired product was isolated. $^1$H-NMR (DMSO-$d_6$) δ 10.21 (s, 1H), 9.97 (br s, 1H), 8.55 (d, J=5.4 Hz, 1H), 8.12-8.08 (m, 1H), 7.88 (s, 1H), 7.84 (s, 1H), 7.36-7.17 (m, 3H), 3.65 (s, 2H), 3.65 (t, J=6.0 Hz, 2H), 3.58-3.55 (m, 2H), 2.67-2.62 (m, 4H), 2.35 (s, 3H), 2.10 (s, 3H), 1.80-1.76 (m, 2H); MS [M+H]$^+$=555.0; LCMS RT=2.48.

Example 125

1-{4-[4-amino-6-methyl-7-(1,4-oxazepan-4-ylmethyl)pyrrolo[2,1-f][1,2,4]triazin-5-yl]phenyl}-3-[4-(trifluoromethyl)pyridin-2-yl]urea

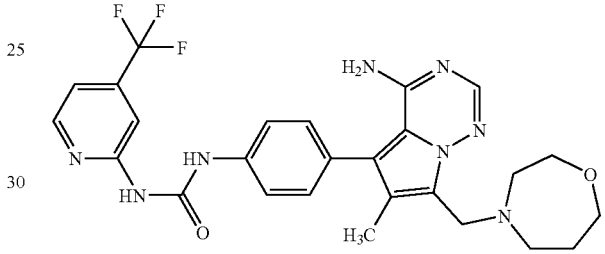

In a manner similar to the procedure described for the preparation of Example 117 Step 4, using Intermediate AAG (1-[4-(4,4,5,5-tetramethyl-1,3,2-dioxaborolan-2-yl)phenyl]-3-[4-(trifluoromethyl)pyridin-2-yl]urea) in place of Intermediate AAN (1-[2-fluoro-5-(trifluoromethyl)-phenyl]-3-[4-(4,4,5,5-tetramethyl-1,3,2-dioxaborolan-2-yl)phenyl]urea), 28 mg (15%) of the desired product was isolated. $^1$H-NMR (DMSO-$d_6$) δ 9.89 (s, 1H), 9.75 (s, 1H), 8.54 (d, J=5.4 Hz, 1H), 8.06 (s, 1H), 7.85 (s, 1H), 7.63 (d, J=8.4 Hz, 2H), 7.37-7.31 (m, 3H), 3.95 (s, 2H), 3.65 (t, J=6.0 Hz, 2H), 3.59-3.55 (m, 2H), 2.67-2.62 (m, 4H), 2.10 (s, 3H), 1.80-1.76 (m, 2H); MS [M+H]$^+$=540.6; LCMS RT=2.35.

Example 126

1-{4-[4-amino-6-methyl-7-(1,4-oxazepan-4-ylmethyl)pyrrolo[2,1-f][1,2,4]triazin-5-yl]-2-methylphenyl}-3-[2-fluoro-5-(trifluoromethyl)-phenyl]urea

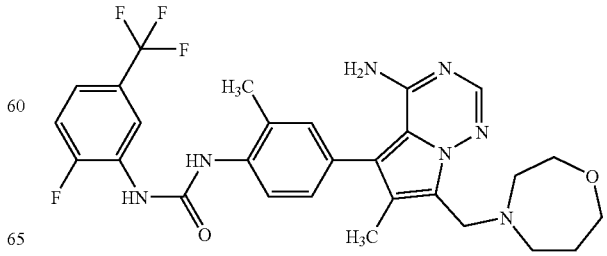

In a manner similar to the procedure described for the preparation of Example 117 Step 4, using Intermediate AAH (1-[2-fluoro-5-(trifluoromethyl)phenyl]-3-[2-methyl-4-(4,4,5,5-tetramethyl-1,3,2-dioxaborolan-2-yl)phenyl]urea) in place of Intermediate AAN (1-[2-fluoro-5-(trifluoromethyl)phenyl]-3-[4-(4,4,5,5-tetramethyl-1,3,2-dioxaborolan-2-yl)phenyl]urea), 31 mg (15%) of the desired product was isolated. $^1$H-NMR (DMSO-$d_6$) δ 9.42-9.41 (m, 1H), 8.67-8.66 (m, 1H), 8.58 (s, 1H), 8.01 (d, J=8.1 Hz, 1H), 7.84 (1H), 7.54-7.46 (m, 1H), 7.31-7.26 (m, 1H), 7.22-7.15 (2H), 3.95 (s, 2H), 3.65 (t, J=6.0 Hz, 2H), 3.58-3.54 (m, 2H), 2.67-2.63 (m, 4H), 2.31 (s, 3H), 2.10 (s, 3H), 1.80-1.76 (m, 2H); MS [M+H]$^+$=571.7; LCMS RT=2.50.

Example 127

1-{4-[4-amino-6-methyl-7-(1,4-oxazepan-4-ylmethyl)pyrrolo[2,1-f][1,2,4]triazin-5-yl]-2-fluorophenyl}-3-[4-(trifluoromethyl)pyridin-2-yl]urea

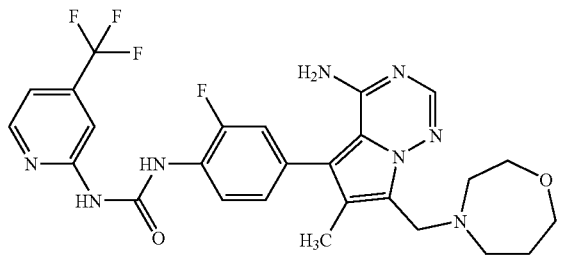

In a manner similar to the procedure described for the preparation of Example 117 Step 4, using Intermediate AAF (1-[2-fluoro-4-(4,4,5,5-tetramethyl-1,3,2-dioxaborolan-2-yl)phenyl]-3-[4-(trifluoromethyl)pyridin-2-yl]urea) in place of Intermediate AAN (1-[2-fluoro-5-(trifluoromethyl)phenyl]-3-[4-(4,4,5,5-tetramethyl-1,3,2-dioxaborolan-2-yl)phenyl]-urea), 25 mg (10%) of the desired product was isolated. $^1$H-NMR (DMSO-$d_6$) δ 10.23-10.12 (m, 1H), 8.63 (d, J=5.4 Hz, 1H), 8.38 (t, J=8.4 Hz, 1H), 8.10 (s, 1H), 7.95 (s, 1H), 7.47-7.46 (m, 1H), 7.39 (dd, J=1.8, 12 Hz, 1H), 7.26-7.23 (m, 1H), 4.03 (s, 2H), 3.74 (t, J=6.0 Hz, 2H), 3.67-3.64 (m, 2H), 2.79-2.72 (m, 4H), 2.20 (s, 3H), 1.89-1.85 (m, 2H); MS [M+H]$^+$=558.9; LCMS RT=2.52.

Example 128

1-{4-[4-amino-6-methyl-7-(1,4-oxazepan-4-ylmethyl)pyrrolo[2,1-f][1,2,4]triazin-5-yl]-2-fluorophenyl}-3-[4-(trifluoromethyl)pyridin-2-yl]urea

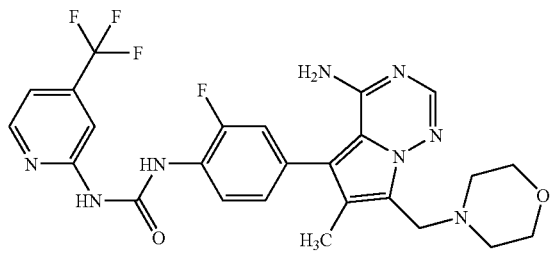

Step 1: Preparation of 1-[4-(4-amino-6-methylpyrrolo[2,1-f][1,2,4]triazin-5-yl)-2-fluorophenyl]-3-[4-(trifluoromethyl)pyridin-2-yl]urea

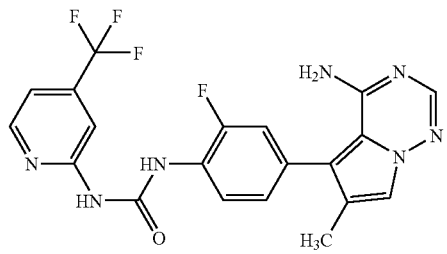

A suspension of Intermediate AJ (N-{4-[4-amino-6-(hydroxymethyl)-pyrrolo[2,1-f][1,2,4]triazin-5-yl]-2-fluorophenyl}-N'-[4-(trifluoromethyl)pyridin-2-yl]urea) (200 mg, 0.433 mmol) in CH$_2$Cl$_2$ (5 mL) was treated with thionyl chloride (129 mg, 1.08 mmol) and allowed to stir for 30 min at rt. The reaction mixture was diluted with dichloroethane (25 mL) and the volatiles removed under vacuum. The residue was suspended in dichloroethane (25 mL) and concentrated a second time. The residue was then placed under high vacuum for 1 h. All material was then suspended in THF (10 mL) and cooled to −78° C. L-Selectride (438 mg, 2.29 mmol) was added and the reaction moved to a rt water bath. After 1 h the reaction was quenched with MeOH (1 mL) and diluted with 1N NaOH (4 mL). 2 mL 30% H$_2$O$_2$ (2 mL) was added dropwise, and the reaction allowed to stir for 0.5 h. The mixture was diluted with EtOAc (50 mL) and washed well with sodium thiosulfate solution and brine. The organic layer was dried with sodium sulfate and the volatiles removed under vacuum to provide an amorphous solid. Trituration with CH$_2$Cl$_2$ provided the desired compound as a white solid (111 mg, 59%). $^1$H-NMR (DMSO-$d_6$) δ 10.10-10.30 (m, 2H), 8.54 (d, 1H, J=5 Hz), 8.28 (t, 1H, J=8 Hz), 8.02 (s, 1H), 7.81 (s, 1H), 7.60 (s, 1H), 7.36-7.40 (m, 1H), 7.28-7.32 (m, 1H), 7.14-7.18 (m, 1H), 2.10 (s, 3H); MS [M+H]$^+$=446.0; LCMS RT=2.97 min.

Step 2: Preparation of Title Compound

Morpholine (196 mg, 2.25 mmol) was added to Acetic acid (1 mL) and the mixture vigorously shaken for 5 min. The resulting mixture was treated with 37% aq formaldehyde (67 mg, 2.24 mmol) and stirred until homogeneous. The resulting solution was treated with a solution of 1-[4-(4-amino-6-methylpyrrolo[2,1-f][1,2,4]triazin-5-yl)-2-fluorophenyl]-3-[4-(trifluoromethyl)pyridin-2-yl]urea in 2 mL AcOH and the mixture heated at 80° C. for 14 h. The reaction was diluted with EtOAc (50 mL) and washed with sodium carbonate solution. The organic layer was dried with sodium sulfate and concentrated under vacuum. The resulting solid was taken up in 1 mL MeOH with the aid of TFA (50 uL). Purification by preparative RP-HPLC provided the desired product (41.1 mg, 34%) as a white solid. $^1$H-NMR (DMSO-$d_6$) δ 10.25 (s, 1H), 10.19 (bs, 1H), 9.98 (bs, 1H), 8.63 (d, 1H, J=5 Hz), 8.36-8.44 (m, 1H), 8.11 (s, 1H), 8.09 (s, 1H), 7.43-7.50 (m, 1H), 7.38 (dd, 1H, J=12, 2 Hz), 7.24 (dd, 1H, J=8, 1 Hz), 4.78 (s, 2H), 3.97-4.08 (m, 2H), 3.68-3.81 (m, 1H), 3.40-3.55 (m, 2H), 3.23-3.45 (m, 2H), 2.27 (s, 3H); MS [M+H]⁺=545.1; LCMS RT=2.56 min.

Example 129

N-(4-{4-amino-6-(cyanomethyl)-7-[(2,6-dimethyl-morpholin-4-yl)methyl]pyrrolo[2,1-f][1,2,4]triazin-5-yl}-2-fluorophenyl)-N'-[2-chloro-5-(trifluoromethyl)phenyl]urea

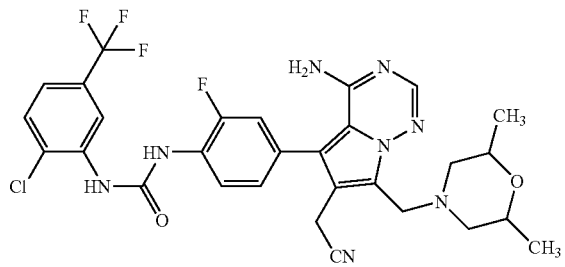

The procedure used for the preparation of Example 62 was used to prepare the title compound by substituting Intermediate AS for Intermediate Y and by substituting 2,6-dimethylmorpholine for morpholine. ¹H-NMR (CD₃OD-d₄) δ 9.53 (s, 1H), 8.93 (s, 1H), 8.66 (s, 1H), 8.42-8.37 (m, 1H), 8.05 (s, 1H), 7.64 (d, J=8.4 Hz, 1H), 7.37-7.23 (m, 3H), 4.85 (s, 2H), 3.91 (s, 2H), 3.94-3.88 (m, 2H), 3.52 (t, J=8.0 Hz, 2H), 2.93 (t, J=8.0 Hz, 2H), 1.24 (d, J=6.4 Hz, 6H); MS [M+H]⁺=631.1; LCMS RT=3.07.

Example 130

1-{4-[4-amino-6-(methoxymethyl)-7-(1,4-oxazepan-4-ylmethyl)-pyrrolo[2,1-f][1,2,4]triazin-5-yl]-2-fluorophenyl}-3-[2-fluoro-5-(trifluoromethyl)phenyl]urea

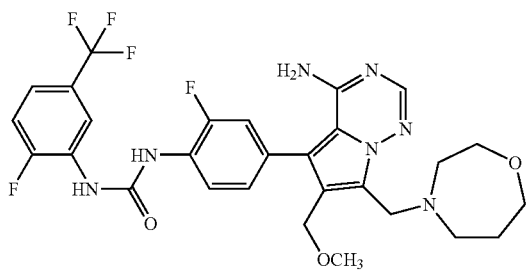

The procedure used to prepare Example 26 was used to prepare the title compound by substituting Intermediate AB (N-{4-[4-amino-6-(methoxymethyl)pyrrolo[2,1-f][1,2,4]triazin-5-yl]-2-fluorophenyl}-N'-[2-fluoro-5-(trifluoromethyl)-phenyl]urea) for Intermediate Q and homomorpholine for morpholine. ¹H-NMR (DMSO-d₆) δ 9.44 (d, J=2.6, 1H), 9.29 (d, J=2.3, 1H), 8.65 (dd, J=7.3, 2.3, 1H), 8.28 (t, J=8.7, 1H), 7.91 (s, 1H), 7.54 to 7.48 (m, 1H), 7.43 to 7.38 (m, 1H), 7.33 (dd, J=12.3, 1.8, 1H), 7.19 (dd, J=8.4, 1.7), 1H), 4.33 (s, 2H), 4.00 (s, 2H), 3.65 (t, J=6.2), 2H), 3.59 to 3.54 (m, 2H), 3.19 (s, 3H), 2.71 to 2.63 (m, 4H), 1.82 to 1.74 (m, 2H); MS [M+H]⁺=605.7; LCMS RT=2.61.

Example 131

N-{4-[4-amino-6-(methoxymethyl)-7-(morpholin-4-ylmethyl)-pyrrolo[2,1-f][1,2,4]triazin-5-yl]-2-fluorophenyl}-N'-(2-fluoro-5-methyl-phenyl)urea

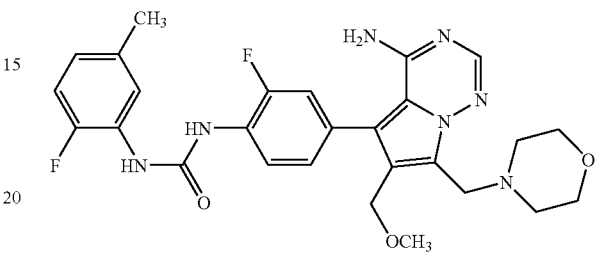

The procedure used to prepare Example 26 was used to prepare the title compound by substituting 1-{4-[4-amino-6-(methoxymethyl)pyrrolo[2,1-f][1,2,4]-triazin-5-yl]-2-fluorophenyl}-3-(2-fluoro-5-methylphenyl)urea for Intermediate Q. ¹H-NMR (DMSO-d₆) δ 9.15 (d, J=2.8, 1H), 9.04 (d, J=2.4, 1H), 8.29 (t, J=8.8, 1H), 8.02 (dd, J=8.0, 2.0, 1H), 7.91 (s, 1H), 7.31 (dd, J=12.4, 2.0, 1H), 7.17 (dd, J=8.4, 2.0, 1H), 7.11 (dd, J=11.6, 8.4, 1H), 6.83 to 6.79 (m, 1H), 4.31 (s, 2H), 3.86 (s, 2H), 3.52 (t, J=4.4, 4H), 3.19 (s, 3H), 2.43 (t, J=4.0, 4H), 2.26 (s, 3H); MS [M+H]⁺=538.0; LCMS RT=2.42.

Example 132

N-{4-[4-amino-6-(methoxymethyl)-7-(morpholin-4-ylmethyl)-pyrrolo[2,1-f][1,2,4]triazin-5-yl]-2-fluorophenyl}-N'-(3-methylphenyl)urea

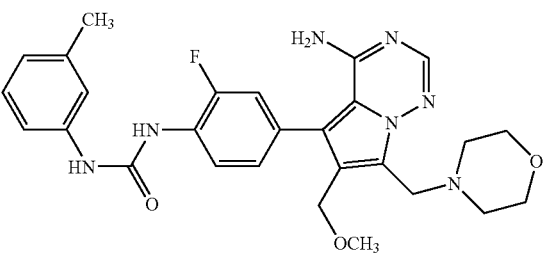

The procedure used to prepare Example 26 was used to prepare the title compound by substituting 1-{4-[4-amino-6-(methoxymethyl)pyrrolo[2,1-f][1,2,4]triazin-5-yl]-2-fluorophenyl}-3-(3-methylphenyl)urea for Intermediate Q. ¹H-NMR (DMSO-d₆) δ 9.05 (s, 1H), 8.66 (d, J=2.4, 1H), 8.27 (t, J=8.4, 1H), 7.91 (s, 1H), 7.32 to 7.28 (m, 2H), 7.23 (d, J=8.8, 1H), 7.18 to 7.14 (m, 2H), 6.80 (d, J=6.8, 1H), 4.30 (s, 2H), 3.86 (s, 2H), 3.51 (t, J=4.4, 4H), 3.19 (s, 3H), 2.43 (t, J=4.0, 4H), 2.27 (s, 3H); MS [M+H]⁺=520.0; LCMS RT=2.35.

Example 133

N-{4-[4-amino-6-(methoxymethyl)-7-(morpholin-4-ylmethyl)-pyrrolo[2,1-f][1,2,4]triazin-5-yl]-2-fluorophenyl}-N'-[3-(trifluoro-methyl)-phenyl]urea

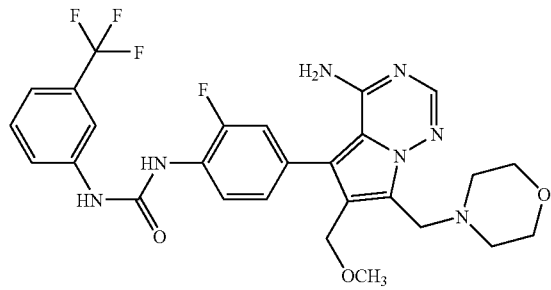

The procedure used to prepare Example 26 was used to prepare the title compound by substituting 1-{4-[4-amino-6-(methoxymethyl)pyrrolo[2,1-f][1,2,4]triazin-5-yl]-2-fluorophenyl}-3-[3-(trifluoromethyl)phenyl]urea for Intermediate Q. ¹H-NMR (DMSO-d₆) δ 9.49 (s, 1H), 8.78 (d, J=2.4, 1H), 8.23 (t, J=8.4, 1H), 8.05 (s, 1H), 7.92 (s, 1H), 7.56 to 7.50 (m, 2H), 7.34 to 7.30 (m, 2H), 7.18 (dd, J=8.4, 1.6, 1H), 4.31 (s, 2H), 3.86 (s, 2H), 3.52 (t, J=4.4, 4H), 3.19 (s, 3H), 2.43 (t, J=4.0, 4H); MS [M+H]⁺=574.0; LCMS RT=2.53.

Example 134

N-{4-[4-amino-6-(methoxymethyl)-7-(morpholin-4-ylmethyl)-pyrrolo[2,1-f][1,2,4]triazin-5-yl]-2-fluorophenyl}-N'-(4-methylpyridin-2-yl)urea

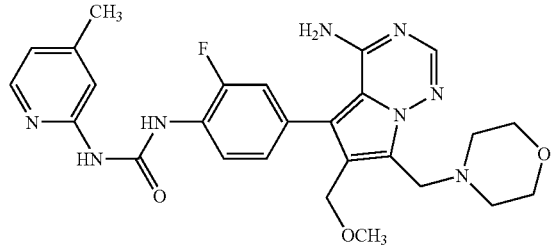

The procedure used to prepare Example 26 was used to prepare the title compound by substituting 1-{4-[4-amino-6-(methoxymethyl)pyrrolo[2,1-f][1,2,4]triazin-5-yl]-2-fluorophenyl}-3-(4-methylpyridin-2-yl)urea for Intermediate Q. ¹H-NMR (DMSO-d₆) δ 9.85 (s, 1H), 8.33 (t, J=8.4, 1H), 8.12 (d, J=5.2, 1H), 7.91 (s, 1H), 7.33 (dd, J=12.4, 2.0, 1H), 7.19 (dd, J=8.8, 2.0, 1H), 7.17 to 7.14 (m, 1H), 6.88 (dd, J=5.2, 1.6, 1H), 4.30 (s, 2H), 3.86 (s, 2H), 3.52 (t, J=4.4, 4H), 3.19 (s, 3H), 2.43 (t, J=4.0, 4H), 2.29 (s, 3H); MS [M+H]⁺=521.0; LCMS RT=1.98.

Example 135

N-{4-[4-amino-6-(methoxymethyl)-7-(morpholin-4-ylmethyl)-pyrrolo[2,1-f][1,2,4]triazin-5-yl]-2-fluorophenyl}-N'-(4-tert-butylpyridin-2-yl)urea

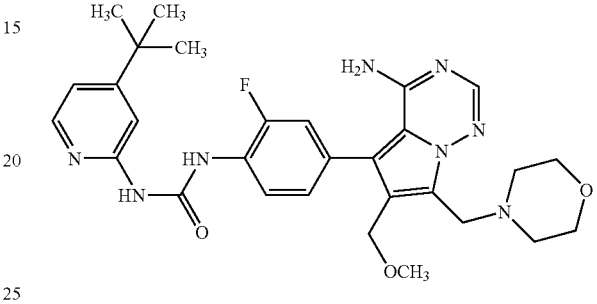

The procedure used to prepare Example 26 was used to prepare the title compound by substituting 1-{4-[4-amino-6-(methoxymethyl)pyrrolo[2,1-f][1,2,4]triazin-5-yl]-2-fluorophenyl}-3-(4-tert-butylpyridin-2-yl)urea for Intermediate Q. ¹H-NMR (DMSO-d₆) δ 9.82 (s, 1H), 8.33 (t, J=8.8, 1H), 8.17 (d, J=5.2, 1H), 7.92 (s, 1H), 7.40 to 7.36 (m, 1H), 7.33 (dd, J=12.0, 2.0, 1H), 7.19 (dd, J=8.8, 1.6, 1H), 7.08 (dd, J=5.6, 1.6, 1H), 4.30 (s, 2H), 3.86 (s, 2H), 3.52 (t, J=4.4, 4H), 3.19 (s, 3H), 2.43 (t, J=4.0, 4H), 1.25 (s, 9H); MS [M+H]⁺=563.2; LCMS RT=2.87.

Example 136

N-{4-[4-amino-6-(methoxymethyl)-7-(morpholin-4-ylmethyl)-pyrrolo[2,1-f][1,2,4]triazin-5-yl]-2-fluorophenyl}-N'-[4-(trifluoromethyl)pyridin-2-yl]urea

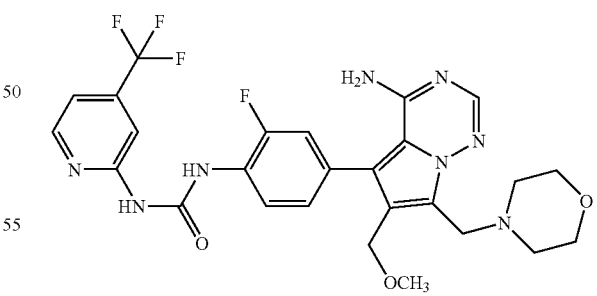

The procedure used to prepare Example 26 was used to prepare the title compound by substituting Intermediate AL (1-{4-[4-amino-6-(methoxymethyl)pyrrolo[2,1-f][1,2,4]triazin-5-yl]-2-fluorophenyl}-3-[4-(trifluoro-methyl)pyridin-2-yl]urea for Intermediate Q. ¹H-NMR (DMSO-d₆) δ 10.16 (s, 1H), 10.10 (s, 1H), 8.54 (d, J=5.2, 1H), 8.29 (t, J=8.4, 1H), 8.00 (s, 1H), 7.92 (s, 1H), 7.38 (dd, J=5.2, 1.2, 1H), 7.37 (dd, J=12.0, 2.0, 1H), 7.20 (dd, J=8.4, 1.2, 1H), 4.31 (s, 2H), 3.86

(s, 2H), 3.52 (t, J=4.4, 4H), 3.19 (s, 3H), 2.43 (t, J=4.0, 4H); MS [M+H]⁺=575.3; LCMS RT=3.02.

Example 137

N-{4-[4-amino-6-(methoxymethyl)-7-(1,4-oxazepan-4-ylmethyl)-pyrrolo[2,1-f][1,2,4]triazin-5-yl]-2-fluorophenyl}-N'-(3-tert-butylphenyl)urea

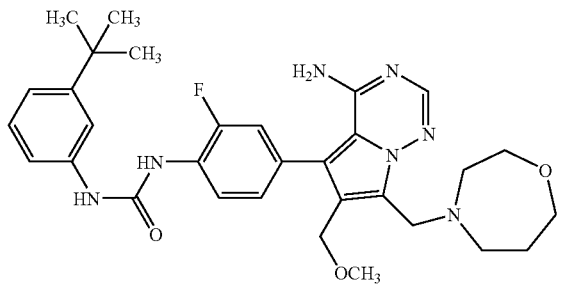

The procedure used to prepare Example 26 was used to prepare the title compound by substituting 1-{4-[4-amino-6-(methoxymethyl)pyrrolo[2,1-f][1,2,4]triazin-5-yl]-2-fluorophenyl}-3-(3-tert-butylphenyl)urea for Intermediate Q and homomorpholine for morpholine. ¹H-NMR (DMSO-d₆) δ 9.45 (s, 1H), 8.81 (s, 1H), 8.25 (t, J=9.2, 1H), 7.90 (s, 1H), 7.48 (t, J=2.4, 1H), 7.32 to 7.27 (m, 2H), 7.22 to 7.14 (m, 2H), 7.02 (d, J=8.0, 1H), 4.32 (s, 2H), 4.00 (s, 2H), 3.65 (t, J=6.0, 2H), 3.57 (br t, J=4.4, 2H), 3.19 (s, 3H), 2.69 to 2.65 (m, 4H), 1.81 to 1.75 (m, 2H), 1.26 (s, 9H); MS [M+H]⁺=576.2; LCMS RT=2.92.

Example 138

N-{4-[4-amino-6-(methoxymethyl)-7-(morpholin-4-ylmethyl)-pyrrolo[2,1-f][1,2,4]triazin-5-yl]-2-fluorophenyl}-N'-(3-tert-butylphenyl)urea

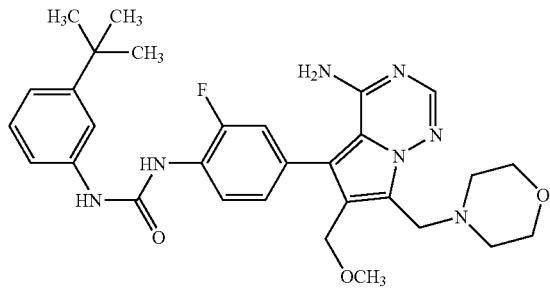

The procedure used to prepare Example 26 was used to prepare the title compound by substituting 1-{4-[4-amino-6-(methoxymethyl)pyrrolo[2,1-f][1,2,4]triazin-5-yl]-2-fluorophenyl}-3-(3-tert-butylphenyl)urea for Intermediate Q. ¹H-NMR (DMSO-d₆) δ 9.11 (s, 1H), 8.62 (d, J=2.4, 1H), 8.27 (t, J=8.4, 1H), 7.91 (s, 1H), 7.45 (t, J=2.0, 1H), 7.32 to 7.28 (m, 2H), 7.23 to 7.15 (m, 2H), 7.02 (d, J=8.0, 1H), 4.30 (s, 2H), 3.86 (s, 2H), 3.52 (t, J=4.4, 4H), 3.19 (s, 3H), 2.43 (t, J=4.0, 4H), 1.27 (s, 9H); MS [M+H]⁺=562.2; LCMS RT=3.05.

Example 139

N-{4-[4-amino-6-(methoxymethyl)-7-(1,4-oxazepan-4-ylmethyl)-pyrrolo[2,1-f][1,2,4]triazin-5-yl]-2-fluorophenyl}-N'-[3-(trifluoromethyl)phenyl]urea

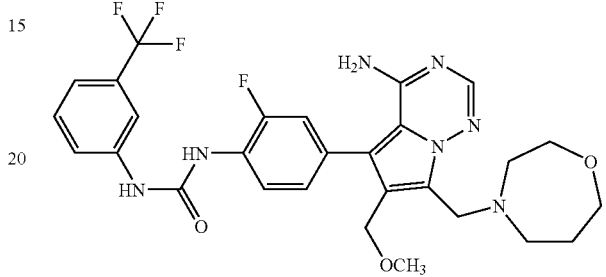

The procedure used to prepare Example 26 was used to prepare the title compound by substituting 1-{4-[4-amino-6-(methoxymethyl)pyrrolo[2,1-f][1,2,4]triazin-5-yl]-2-fluorophenyl}-3-[3-(trifluoromethyl)phenyl]urea for Intermediate Q and homomorpholine for morpholine. ¹H-NMR (DMSO-d₆) δ 9.64 (s, 1H), 8.93 (s, 1H), 8.21 (t, J=9.2, 1H), 8.06 (s, 1H), 7.91 (s, 1H), 7.58 to 7.50 (m, 2H), 7.30 to 7.35 (m, 2H), 7.18 (dd, J=8.4, 2.0, 1H), 4.33 (s, 2H), 4.00 (s, 2H), 3.65 (t, J=6.0, 2H), 3.57 (br t, J=4.4, 2H), 3.19 (s, 3H), 2.69 to 2.65 (m, 4H), 1.80 to 1.75 (m, 2H); MS [M+H]⁺=588.0; LCMS RT=2.57.

Example 140

N-{4-[4-amino-6-(methoxymethyl)-7-(1,4-oxazepan-4-ylmethyl)-pyrrolo[2,1-f][1,2,4]triazin-5-yl]-2-fluorophenyl}-N'-(2-fluoro-5-methylphenyl)urea

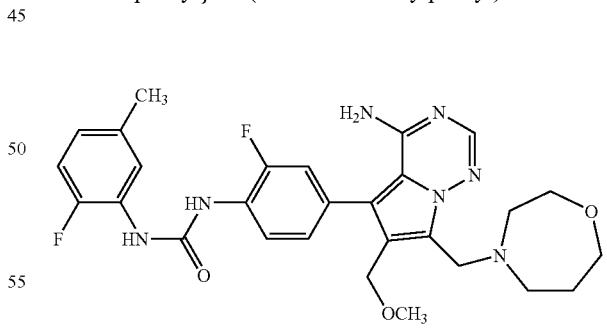

The procedure used to prepare Example 26 was used to prepare the title compound by substituting 1-{4-[4-amino-6-(methoxymethyl)pyrrolo[2,1-f][1,2,4]-triazin-5-yl]-2-fluorophenyl}-3-(2-fluoro-5-methylphenyl)-urea for Intermediate Q and homomorpholine for morpholine. ¹H-NMR (DMSO-d₆) δ 9.16 (d, J=2.8, 1H), 9.04 (d, J=2.8, 1H), 8.28 (t, J=8.8, 1H), 8.02 (dd, J=7.2, 1.6, 1H), 7.91 (s, 1H), 7.31 (dd, J=12.0, 2.0, 1H), 7.17 (dd, J=8.4, 1.6, 1H), 7.11 (dd, J=11.2, 8.0, 1H), 6.83 to 6.79 (m, 1H), 4.32 (s, 2H), 4.00 (s, 2H), 3.65

(t, J=6.0, 2H), 3.57 (br t, J=4.4, 2H), 3.19 (s, 3H), 2.69 to 2.64 (m, 4H), 2.26 (s, 3H), 1.80 to 1.74 (m, 2H); MS [M+H]⁺=552.1; LCMS RT=2.46.

Example 141

N-{4-[4-amino-6-(methoxymethyl)-7-(1,4-oxazepan-4-ylmethyl)-pyrrolo[2,1-f][1,2,4]triazin-5-yl]-2-fluorophenyl}-N'-[2-chloro-5-(trifluoromethyl)phenyl]urea

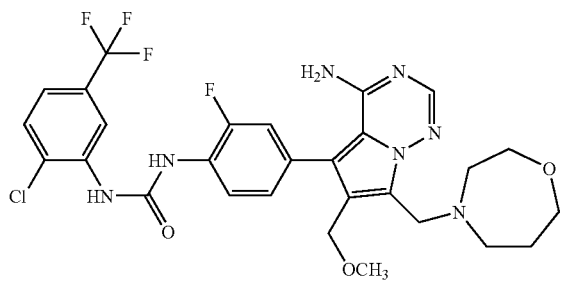

The procedure used to prepare Example 26 was used to prepare the title compound by substituting 1-{4-[4-amino-6-(methoxymethyl)pyrrolo[2,1-f][1,2,4]triazin-5-yl]-2-fluorophenyl}-3-[2-chloro-5-(trifluoromethyl)phenyl]urea for Intermediate Q and homomorpholine for morpholine. ¹H-NMR (DMSO-d₆) δ 9.67 (s, 1H), 9.17 (s, 1H), 8.63 (d, J=2.4, 1H), 8.27 (t, J=8.8, 1H), 7.91 (s, 1H), 7.73 (d, J=8.4, 1H), 7.39 (dd, J=8.8, 2.4, 1H), 7.33 (dd, J=12.0, 1.6, 1H), 7.19 (dd, J=8.4, 2.0, 1H), 4.33 (s, 2H), 4.00 (s, 2H), 3.65 (t, J=6.0, 2H), 3.57 (br t, J=4.4, 2H), 3.19 (s, 3H), 2.69 to 2.65 (m, 4H), 1.80 to 1.75 (m, 2H); MS [M+H]⁺=622.1; LCMS RT=2.69.

Example 142

N-{4-[4-amino-6-(methoxymethyl)-7-(morpholin-4-ylmethyl)-pyrrolo[2,1-f][1,2,4]triazin-5-yl]-2-fluorophenyl}-N'-[2-chloro-5-(trifluoromethyl)phenyl]urea

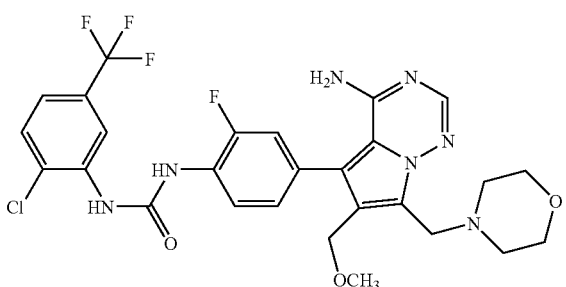

The procedure used to prepare Example 26 was used to prepare the title compound by substituting 1-{4-[4-amino-6-(methoxymethyl)pyrrolo[2,1-f][1,2,4]triazin-5-yl]-2-fluorophenyl}-3-[2-chloro-5-(trifluoromethyl)phenyl]urea for Intermediate Q. ¹H-NMR (DMSO-d₆) δ 9.65 (s, 1H), 9.16 (s, 1H), 8.63 (d, J=2.4, 1H), 8.28 (t, J=8.4, 1H), 7.92 (s, 1H), 7.73 (d, J=8.4, 1H), 7.39 (dd, J=8.8, 2.4, 1H), 7.33 (dd, J=12.0, 1.6, 1H), 7.19 (dd, J=8.4, 2.0, 1H), 4.31 (s, 2H), 3.86 (s, 2H), 3.52 (t, J=4.4, 4H), 3.19 (s, 3H), 2.43 (t, J=4.0, 4H); MS [M+H]⁺=609.0; LCMS RT=2.66.

Example 143

Preparation of N-4-[4-amino-6-(methoxymethyl)-7-(morpholin-4-ylmethyl)pyrrolo[2,1-f][1,2,4]triazin-5-yl]-2,5-difluorophenyl-N'-[2-fluoro-5-(trifluoromethyl)phenyl]urea

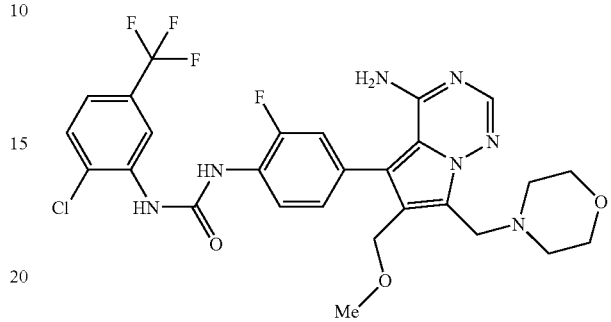

To a flask charged with N₂ was added 5-bromo-6-(methoxymethyl)-7-(morpholin-4-ylmethyl)pyrrolo[2,1-f][1,2,4]triazin-4-amine (1 eq) (Intermediate AAA) and 1-[2,5-difluoro-4-(4,4,5,5-tetramethyl-1,3,2-dioxaborolan-2-yl)phenyl]-3-[2-fluoro-5-(trifluoromethyl)-phenyl]urea (Intermediate AAB) (1 eq) followed by 1,4-dioxane (0.1M). Nitrogen was bubbled through the solution for 15 min and then dichlorobis(triphenylphosphine)palladium(II) (229 mg, 0.1 eq) was added followed by aq 1M Na₂CO₃ (2 eq). N₂ was bubbled through the solution for an additional 15 min and, then the reaction was heated to 80° C. for 17 h. The reaction material was allowed to cool to rt and was diluted with EtOAc and water. The solution was separated and the aqueous layer was back extracted with EtOAc. The organic fractions were combined, dried (MgSO₄), filtered, condensed, and purified by flash column chromatography (9:1 CH₂Cl₂/MeOH). The material was further purified by flash column chromatography (50:47:3 CH₂Cl₂/EtOAc/MeOH). The purified fractions were collected, evaporated, and left under vacuum overnight to yield the title compound. ¹H-NMR (DMSO-d₆) δ 9.51 (s, 1H), 9.47 (s, 1H), 8.64 (d, J=7.2 Hz, 1H), 8.18-8.13 (m, 1H), 7.92 (s, 1H), 7.55-7.50 (m, 1H), 7.45-7.41 (m, 1H), 7.36-7.31 (m, 1H), 4.43 (d, J=11.5 Hz, 1H), 4.22 (d, J=11.5 Hz, 1H), 3.86 (s, 2H), 3.54-3.51 (m, 4H), 3.09 (s, 3H), 2.43-2.39 (m, 4H); MS [M+H]⁺=610; LCMS RT=2.81.

Example 144

Preparation of N-4-[4-amino-6-(methoxymethyl)-7-(morpholin-4-ylmethyl)pyrrolo[2,1-f][1,2,4]triazin-5-yl]-2-methylphenyl-N'-[2-fluoro-5-(trifluoromethyl)phenyl]urea

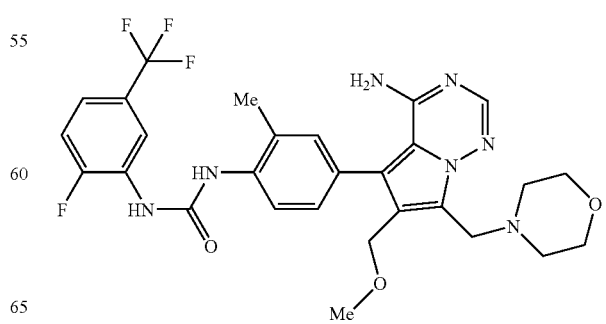

The procedure used for the preparation of Example 143 was used to prepare the title compound by substituting Intermediate AAH (1-[2-fluoro-5-(trifluoromethyl)phenyl]-3-[2-methyl-4-(4,4,5,5-tetramethyl-1,3,2-dioxaborolan-2-yl)phenyl]urea) for Intermediate AAB (1-[2,5-difluoro-4-(4,4,5,5-tetramethyl-1,3,2-dioxaborolan-2-yl)phenyl]-3-[2-fluoro-5-(trifluoromethyl)-phenyl]urea). $^1$H-NMR (DMSO-d$_6$) δ 9.42 (s, 1H), 8.67 (d, J=7.4 Hz, 1H), 8.58 (s, 1H), 8.02 (d, J=8.3 Hz, 1H), 7.90 (s, 1H), 7.53-7.48 (m, 1H), 7.40-7.36 (m, 1H), 7.27 (s, 1H), 7.22 (d, J=7.6 Hz, 1H), 4.30 (s, 2H), 3.86 (s, 2H), 3.53-3.51 (m, 4H), 3.18 (s, 3H), 2.44-2.41 (m, 4H), 2.31 (s, 3H); MS [M+H]$^+$=588; LCMS RT=2.61.

Example 145

Preparation of N-4-[4-amino-6-(methoxymethyl)-7-(morpholin-4-ylmethyl)pyrrolo[2,1-f][1,2,4]triazin-5-yl]-2-methylphenyl-N'-[4-(trifluoromethyl)pyridin-2-yl]urea

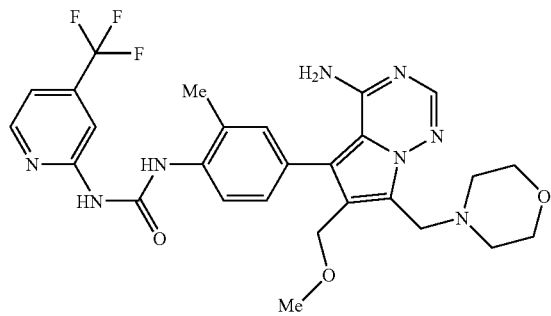

The procedure used for the preparation of Example 143 was used to prepare the title compound by substituting Intermediate AAI 1-[2-methyl-4-(4,4,5,5-tetramethyl-1,3,2-dioxaborolan-2-yl)phenyl]-3-[4-(trifluoromethyl)pyridin-2-yl]urea for Intermediate AAB (1-[2,5-difluoro-4-(4,4,5,5-tetramethyl-1,3,2-dioxaborolan-2-yl)phenyl]-3-[2-fluoro-5-(trifluoromethyl)phenyl]urea). $^1$H-NMR (DMSO-d$_6$) δ 10.19 (s, 1H), 10.00-9.94 (br s), 8.55 (d, J=5.4 Hz, 1H), 8.11 (d, J=8.5 Hz, 1H), 7.90 (s, 1H), 7.87 (s, 1H), 7.36 (d, J=5.3 Hz, 1H), 7.30 (s, 1H), 7.24 (d, J=8.3 Hz, 1H), 4.30 (s, 2H), 3.86 (s, 2H), 3.53-3.51 (m, 4H), 3.17 (s, 3H), 2.44-2.42 (m, 4H), 2.35 (s, 3H); MS [M+H]$^+$=571; LCMS RT=2.50.

Example 146

Preparation of 1-4-[4-amino-7-[(2-hydroxyethyl)amino]methyl-6-(methoxymethyl)pyrrolo[2,1-f][1,2,4]triazin-5-yl]-2-fluorophenyl-3-[2-fluoro-5-(trifluoromethyl)phenyl]urea

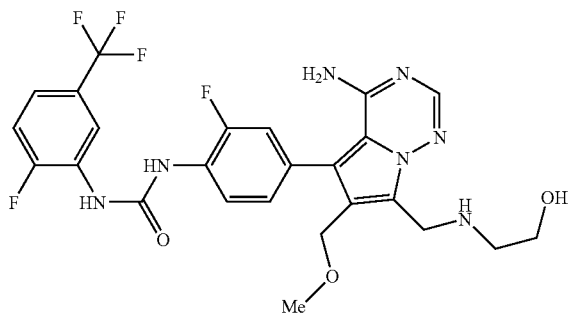

The procedure used for the preparation of Example 12 was used to prepare the title compound by substituting Intermediate AAC (1-{4-[4-amino-7-formyl-6-(methoxymethyl) pyrrolo[2,1-f][1,2,4]triazin-5-yl]-2-fluorophenyl}-3-[2-fluoro-5-(trifluoromethyl)phenyl]urea) for Intermediate AW (N-{4-[4-amino-7-formyl-6-(methoxymethyl)-pyrrolo[2,1-f][1,2,4]triazin-5-yl]phenyl}-N'-[2-fluoro-5-(trifluoromethyl)phenyl]urea) and 2-aminoethanol for morpholine. $^1$H-NMR (DMSO-d$_6$) δ 9.47 (s, 1H), 9.32 (s, 1H), 8.66 (d, J=7.3 Hz, 1H), 8.30 (t, J=8.5 Hz, 1H), 7.95 (s, 1H), 7.54-7.49 (m, 1H), 7.43-7.39 (m, 1H), 7.30 (d, J=12.1 Hz, 1H), 7.17 (d, J=8.9 Hz, 1H), 4.68-4.64 (br s, 1H), 4.31 (s, 2H), 4.28 (s, 2H), 3.50-3.46 (m, 2H), 3.20 (s, 3H), 2.70-2.66 (m, 2H); MS [M+H]$^+$=566; LCMS RT=2.54.

Example 147

Preparation of 1-{4-[4-amino-6-(methoxymethyl)-7-{[(3S)-3-methylmorpholin-4-yl]methyl}pyrrolo[2,1-f][1,2,4]triazin-5-yl]-2-fluorophenyl}-3-[2-fluoro-5-(trifluoromethyl)phenyl]urea

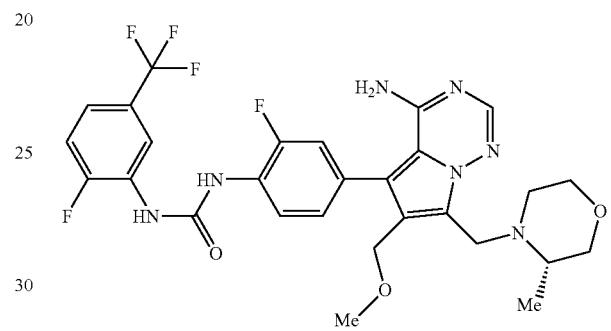

The procedure used for the preparation of Example 12 was used to prepare the title compound by substituting Intermediate AAC (1-{4-[4-amino-7-formyl-6-(methoxymethyl) pyrrolo[2,1-f][1,2,4]triazin-5-yl]-2-fluorophenyl}-3-[2-fluoro-5-(trifluoromethyl)phenyl]urea) for Intermediate AW (N-{4-[4-amino-7-formyl-6-(methoxymethyl)pyrrolo[2,1-f][1,2,4]triazin-5-yl]phenyl}-N'-[2-fluoro-5-(trifluoro-methyl)phenyl]urea) and 3-(S)-methylmorpholine for morpholine. $^1$H-NMR (DMSO-d$_6$) δ 9.45 (s, 1H), 9.29 (s, 1H), 8.66 (d, J=6.9 Hz, 1H), 8.29 (t, J=8.5 Hz, 1H), 7.92 (s, 1H), 7.54-7.50 (m, 1H), 7.43-7.39 (m, 1H), 7.33 (d, J=12.1 Hz, 1H), 7.19 (d, J=8.1 Hz, 1H), 4.40 (d, J=11.1 Hz, 1H), 4.26 (d, J=12.1 Hz, 2H), 3.67-3.57 (m, 3H), 3.20 (s, 3H), 3.10 (t, J=10.5 Hz, 1H), 2.45-2.41 (m, 1H), 2.21 (t, J=10.1 Hz, 1H), 1.09 (d, J=6.2 Hz, 3H); MS [M+H]$^+$=606; LCMS RT=2.70.

Example 148

N-{4-[4-amino-6-ethyl-7-(morpholin-4-ylmethyl)pyrrolo[2,1-f][1,2,4]triazin-5-yl]phenyl}-N'-[4-trifluoromethyl)pyridin-2-yl]urea

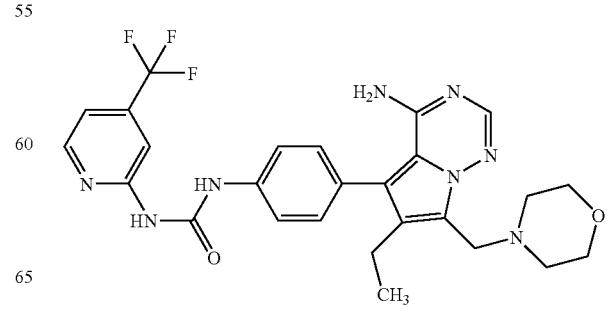

Step 1. Preparation of 1-[4-(4-amino-6-vinylpyrrolo [2,1-f][1,2,4]triazin-5-yl)phenyl]-3-[4-(trifluoromethyl)pyridin-2-yl]urea

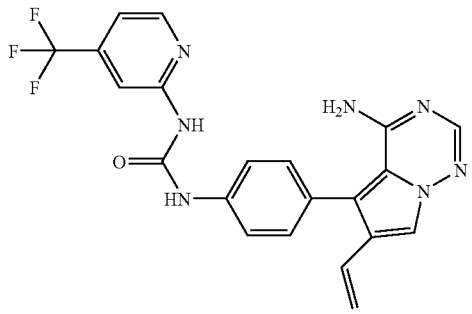

Potassium tert-butoxide (1.0 g, 9.06 mmol) was suspended in 1,4-dioxane (20 mL) and treated with methyltriphenylphosphonium bromide (3.2 g, 9.06 mmol). The mixture was allowed to stir at rt for 30 min. A yellow suspension formed then Intermediate AF (1-[4-(4-amino-6-formylpyrrolo[2,1-f][1,2,4]triazin-5-yl)phenyl]-3-[4-trifluoromethyl)-pyridin-2-yl]urea) (2.0 g, 4.53 mmol) in 1,4-dioxane (10 mL) was slowly added and the reaction was stirred at rt for 4 hr. The reaction was slowly poured into vigorously stirring water. The mixture was allowed to stir for 1 hr. The solid was filtered and rinsed with water and MeOH. A light brown solid was isolated (1.2 g, 60%). $^1$H-NMR (DMSO-$d_6$) δ 9.90 (s, 1H), 9.77 (s, 1H), 8.53 (d, J=5.2 Hz, 1H), 8.06-8.05 (m, 2H), 7.84 (s, 1H), 7.64 (d, J=8.5 Hz, 2H), 7.36 (d, J=5.4 Hz, 1H), 7.31 (d, J=8.5 Hz, 2H), 6.39 (dd, J=11.3, h=17.6 Hz, 1H), 5.63 (dd, J$_1$=1.7, J$_2$=17.5 Hz, 1H), 5.12 (dd, J$_1$=1.5, J$_2$=11.1 Hz, 2H). MS [M+H]$^+$=440.0; LCMS RT=2.88.

Step 2. Preparation of 1-[4-(4-amino-6-ethylpyrrolo [2,1-f][1,2,4]triazin-5-yl)phenyl]-3-[4-(trifluoromethyl)pyridin-2-yl]urea

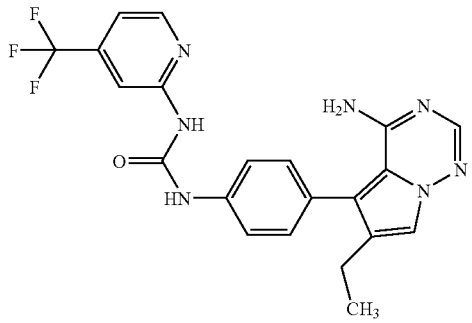

1-[4-(4-amino-6-vinylpyrrolo[2,1-f][1,2,4]triazin-5-yl)phenyl]-3-[4-(trifluoro-methyl)pyridin-2-yl]urea (150 mg, 0.341 mmol) was slowly dissolved in THF (100 mL) by adding acetic acid (10-20 mL). The solution was further diluted with EtOH (300 mL) and run through the H-Cube® apparatus at 20 bar, rt, 1 mL/min. The resulting solution was concentrated then washed with satd. NaHCO$_3$. A precipitate formed and the desired product was collected by vacuum filtration to yield a tan solid. (150 mg, 99%). $^1$H-NMR (DMSO-$d_6$) δ 11.89 (bs, 2H), 8.49 (d, J=5.0 Hz, 1H), 8.28 (s, 1H), 7.80 (s, 1H), 7.74 (d, J=8.8 Hz, 2H), 7.60 (s, 1H), 7.27 (m, 3H), 2.48 (q, J=7.8 Hz, 2H), 1.09 (t, J=7.5 Hz, 3H). MS [M+H]$^+$=442.0; LCMS RT=2.95.

Step 3. Preparation of Title Compound

A solution of 1-[4-(4-amino-6-ethylpyrrolo[2,1-f][1,2,4]triazin-5-yl)phenyl]-3-[4-(trifluoromethyl)pyridin-2-yl]urea (120 mg, 0.7 mmol) in acetic acid (2 mL) was treated with a mixture of morpholine (240 μL, 2.72 mmol) and formaldehyde (37%, 204 μL, 2.72 mmol) in acetic acid (1 mL). The reaction was heated to 60° C. overnight. The reaction was then diluted with EtOAc and washed with NaHCO$_3$. The organic layer was dried (MgSO$_4$) and concentrated. The pale orange solid was then triturated with ether. The desired product was collected by vacuum filtration (30 mg, 20%). $^1$H-NMR (DMSO-$d_6$) δ 9.95 (bs, 1H), 9.82 (bs, 1H), 8.55 (d, J=4.1 Hz, 1H), 8.07 (s, 1H), 7.86 (s, 1H), 7.64 (d, J=6.8 Hz, 2H), 7.38-7.32 (m, 3H), 3.82 (s, 2H), 3.53-3.50 (m, 4H), 2.54-2.49 (m, 2H), 2.44-2.41 (m, 4H), 0.97 (t, J=7.5 Hz, 3H). MS [M+H]$^+$=541.1; LCMS RT=2.86.

Example 149

1-{4-[4-amino-6-(methoxymethyl)-7-piperidin-4-ylpyrrolo[2,1-f][1,2,4]triazin-5-yl]-2-fluorophenyl}-3-[2-fluoro-5-(trifluoromethyl)phenyl]urea

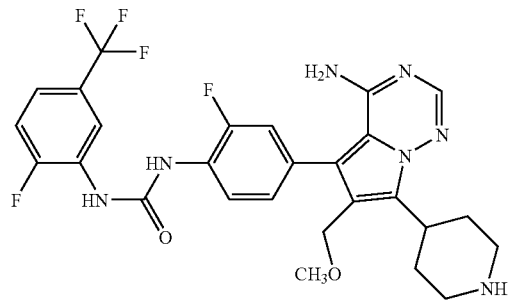

Step 1: Preparation of tert-butyl 4-{[(trifluoromethyl)sulfonyl]oxy}-3,6-dihydropyridine-1(2H)-carboxylate

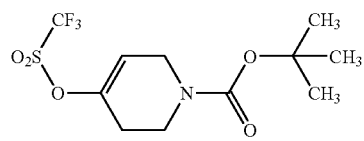

A 2 M solution of lithium diisopropylamide in heptane/tetrahydrofuran/ethylbenzene (20 mL; 0.04 Mol) was stirred under nitrogen atmosphere while cooling −78° C., and a solution of 1-BOC-4-piperidone (6.79 g; 0.033 Mol) in tetrahydrofuran (50 mL) added (internal temperature <−50° C.). After 10 min. a solution of N-phenyltrifluoromethanesulfonimide in tetrahydrofuran (50 mL) was added (internal temperature <−60° C.). After 1 hr. the cooling bath was removed, and the mixture allowed to warm to rt. After 3 h, the mixture was poured into stirred brine (300 mL) and extracted with hexanes (3×100 mL). The combined organic extracts had a lower, orange liquid phase, which was separated and discarded. The resulting organic phase was washed with brine, dried (anhydrous sodium sulfate), filtered and concentrated to afforded 16.45 g of orange brown oil, which was purified by silica gel chromatography (hexanes/dichloromethane gradient). There desired product (8.15 g, 74% yield) was obtained as an orange-yellow oil. $^1$H-NMR (CD$_2$Cl$_2$) δ 5.78 (d, 1H), 4.03 (q, 2H), 3.61 (t, 2H), 2.43 (d, 2H), 1.45 (s, 9H).

Step 2: Preparation of tert-butyl-4-(4,4,5,5-tetramethyl-1,3,2-dioxaborolan-2-yl)-3,6-dihydropyridine-1(2H)-carboxylate

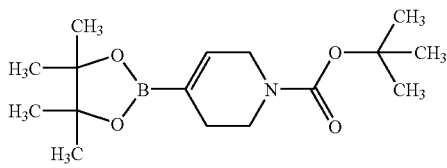

A stirred mixture of tert-butyl 4-{[(trifluoromethyl)sulfonyl]oxy}-3,6-dihydropyridine-1(2H)-carboxylate (61.4 g, 0.185 Mol), bis(pinacolato)diboron (51.77 g, 0.204 Mol) and potassium acetate (54.56 g, 0.556 Mol) in dioxane (2.0 L) was degassed with nitrogen for 20 minutes. Dichloro[bis(diphenylphosphino)ferrocene]palladium (II) dichloromethane adduct (4.07 g, 6.0 mMol) was then added, and the mixture was stirred at 80° C. under nitrogen atmosphere. After 1 hr, the mixture was cooled to rt, and filtered through Celite. The filtrate was concentrated in vacuo, and the residue purified by silica gel chromatography (hexanes/dichloromethane/ethyl acetate gradient) to afford 29.07 g (51% yield) of the desired product as a colorless, fluffy solid (38-3). $^1$H-NMR (CD$_2$Cl$_2$) δ 6.41 (d, 1H), 3.91 (q, 2H), 3.40 (t, 2H), 2.16 (m, 2H), 1.43 (s, 9H), 1.23 (s, 12H).

Step 3: Preparation of tert-butyl 4-{4-amino-5-[3-fluoro-4-({[2-fluoro-5-(trifluoromethyl)phenyl]carbamoyl}amino)phenyl]-6-(methoxymethyl)pyrrolo[2,1-f][1,2,4]triazin-7-yl}-3,6-dihydropyridine-1(2H)-carboxylate

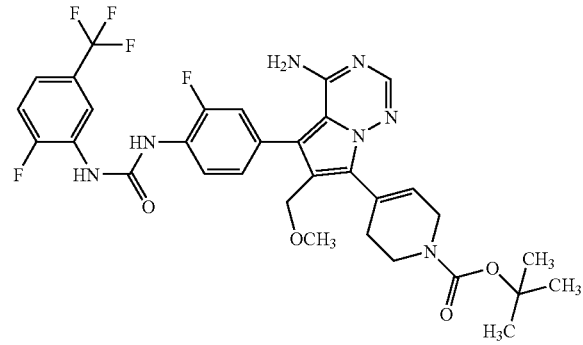

To a flask charged with N$_2$ was added 1-{4-[4-amino-7-bromo-6-(methoxymethyl)pyrrolo[2,1-f][1,2,4]triazin-5-yl]-2-fluorophenyl}-3-[2-fluoro-5-(trifluoromethyl)phenyl]urea (Intermediate AAC, Step 1) (500 mg, 0.875 mmol, 1.0 eq) and tert-butyl-4-(4,4,5,5-tetramethyl-1,3,2-dioxaborolan-2-yl)-3,6-dihydropyridine-1(2H)-carboxylate (677 mg, 2.19 mmol, 2.5 eq) followed by 1,4-dioxane (5 mL). Nitrogen was bubbled through the solution for 15 min and then 2M Na$_2$CO$_3$ (6 eq) was added. Nitrogen again bubbled through solution for 15 minutes and [1,1'-Bis(diphenylphosphino)ferrocene] (143 mg, 0.2 eq) was added. N$_2$ was bubbled through the solution for an additional 15 min and then the reaction was placed in a preheated 80° C. oil bath for 17 h. The reaction solution was allowed to cool to rt and was diluted with EtOAc and water. The organic layer was washed water and brine. The combined organic layers were dried (Na$_2$SO$_4$), filtered, condensed, and purified via flash column chromatography (1:1 tetrahydrofuran/hexanes). The purified fractions were collected, evaporated, and left under vacuum overnight to yield the title compound (520 mg, 88.2% yield). $^1$H-NMR (DMSO-d$_6$) MS [M+H]$^+$=674; LCMS RT=3.51 min.

Step 4: Preparation of tert-butyl 4-{4-amino-5-[3-fluoro-4-({[2-fluoro-5-(trifluoromethyl)phenyl]carbamoyl}amino)phenyl]-6-(methoxymethyl)pyrrolo[2,1-f][1,2,4]triazin-7-yl}piperidine-1-carboxylate

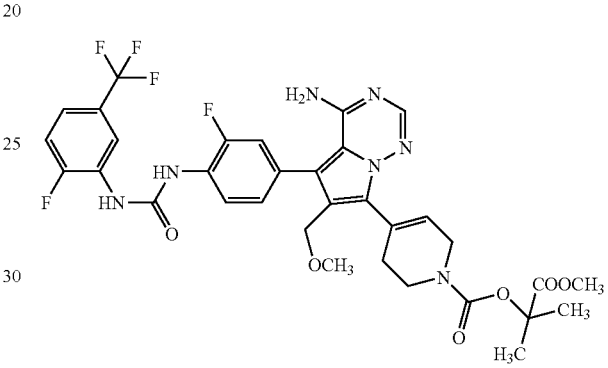

To a flask charged with N$_2$ was added tert-butyl 4-{4-amino-5-[3-fluoro-4-({[2-fluoro-5-(trifluoromethyl)phenyl]carbamoyl}amino)phenyl]-6-(methoxymethyl)-pyrrolo-[2,1-f][1,2,4]triazin-7-yl}-3,6-dihydropyridine-1(2H)-carboxylate (424 mg, 0.629 mmol, 1.0 eq) followed by glacial acetic acid (40 mL). To this solution was added platinum oxide (42 mg, 10% w/w). The reaction solution was evacuated via vacuum and replaced with nitrogen (5×). The reaction mixture was then evacuated again via vacuum and placed under 1 atm of hydrogen and was allowed to stir for 17 hours. The solution was filtered through a pad of celite, washed with acetic acid and concentrated. The crude concentrate was dissolved in EtOAc and washed with saturated sodium bicarbonate. The organic layer was dried (Na$_2$SO$_4$), filtered, condensed, and purified via flash chromatography (1:1 tetrahydrofuran/hexanes). The purified fractions were collected, evaporated, and left under vacuum overnight to yield the title compound (320 mg, 75.3% yield). $^1$H-NMR (DMSO-d$_6$) MS [M+H]$^+$=676; LCMS RT=3.52 min.

Step 5: Preparation of Title Compound

To a flask charged with tert-butyl 4-{4-amino-5-[3-fluoro-4-({[2-fluoro-5-(trifluoromethyl)phenyl]carbamoyl}amino)phenyl]-6-(methoxymethyl)pyrrolo[2,1-f][1,2,4]triazin-7-yl}piperidine-1-carboxylate was added methylene chloride (12.5 mL). To this suspension was added 12.5 mL of trifluoroacetic acid. The homogeneous solution was allowed to stir at rt under nitrogen for 17 hours. The reaction mixture was concentrated and the residue dissolved in EtOAc. The organic phase was washed with saturated sodium bicarbonate solution (2×), brine (1×), separated and the organic layer dried (Na$_2$SO$_4$). The organic layer was filtered, concentrated and left under vacuum overnight to yield the title compound (150 mg, 70.4% yield). $^1$H-NMR (DMSO-d$_6$) MS [M+H]$^+$=576; LCMS RT=2.51 min.

Example 150

4-{4-amino-5-[3-fluoro-4-({[2-fluoro-5-(trifluoromethyl)-phenyl]carbamoyl}amino)phenyl]-6-(methoxymethyl)-pyrrolo[2,1-f][1,2,4]-triazin-7-yl}-N,N-dimethylpiperidine-1-carboxamide

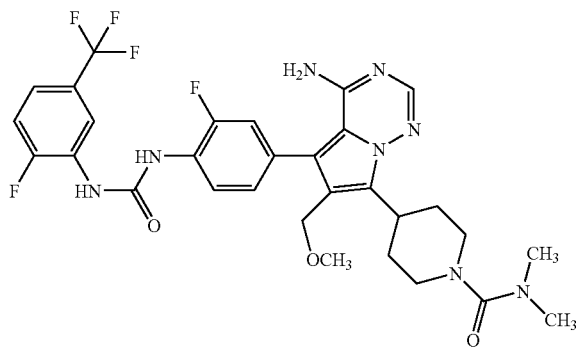

To a flask charged with N₂ was added 1-{4-[4-amino-6-(methoxymethyl)-7-piperidin-4-ylpyrrolo[2,1-f][1,2,4]triazin-5-yl]-2-fluorophenyl}-3-[2-fluoro-5-(trifluoro-methyl)phenyl]urea (Example 149) (30 mg, 0.052 mmol, 1.0 eq) and 1,2-dichloroethane (2 mL). Tetrahydrofuran was added dropwise until the reaction mixture was a complete solution. The solution was cooled to 0° C. and dimethylcarbamoyl chloride (4.7 µl, 1 eq) was added. The reaction mixture was allowed to gradually warm to rt over 17 hours. The reaction was concentrated and the residue dissolved in EtOAc. The organic phase was washed with saturated sodium bicarbonate solution (2×), brine (1×), separated and the organic layer dried (Na₂SO₄). The organic layer was filtered, concentrated and purified via flash column chromatography (6:4 tetrahydrofuran/hexanes). The purified fractions were collected, concentrated, stirred in hexanes and filtered. The filtrate was placed under vacuum overnight to yield the title compound (6 mg, 17.8% yield). ¹H-NMR (DMSO-d₆) δ 9.44 (s, 1H), 9.29 (s, 1H), 8.65 (d, J=6.5 Hz, 1H), 8.29 (t, J=8.5 Hz, 1H), 7.89 (s, 1H), 7.51 (t, J=9.9 Hz, 1H), 7.41 (m, 1H), 7.29 (dd, J=12.3, 1.7 Hz, 1H), 7.16 (d, J=8.3 Hz, 1H), 4.23 (s, 2H), 3.68 (m, 2H), 3.44 (m, 1H), 3.16 (s, 3H), 2.75 (s, 6H), 2.26 (m, 2H), 1.64 (m, 2H); MS [M+H]⁺=647; LCMS RT=3.03 min.

Example 151

4-{4-amino-5-[3-fluoro-4-({[2-fluoro-5-(trifluoromethyl)-phenyl]carbamoyl}amino)phenyl]-6-(methoxymethyl)pyrrolo[2,1-f][1,2,4]-triazin-7-yl}-N-methylpiperidine-1-carboxamide

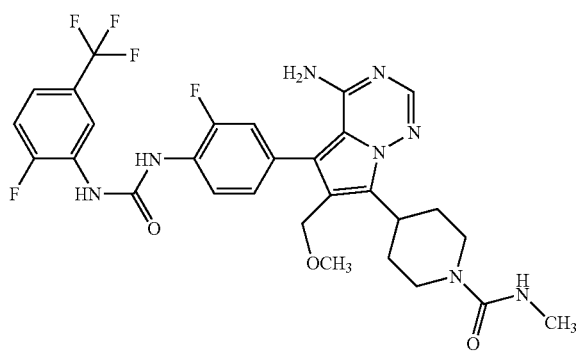

To a flask charged with N₂ was added 1-{4-[4-amino-6-(methoxymethyl)-7-piperidin-4-ylpyrrolo[2,1-f][1,2,4]triazin-5-yl]-2-fluorophenyl}-3-[2-fluoro-5-(trifluoro-methyl)phenyl]urea (Example 149) (30 mg, 0.052 mmol, 1.0 eq) and 1,2-dichloroethane (2 mL). Tetrahydrofuran was added dropwise until the reaction mixture was a complete solution. The solution was cooled to 0° C. and methyl isocyanate (5.2 µl, 1 eq) is added. The reaction mixture was allowed to gradually warm to rt over 17 hours. The reaction was concentrated and the residue dissolved in EtOAc. The organic phase was washed with saturated sodium bicarbonate solution (2×), brine (1×), separated and the organic layer dried (Na₂SO₄). The organic layer was filtered, concentrated and purified via flash column chromatography (tetrahydrofuran). The purified fractions were collected, concentrated, stirred in hexanes and filtered. The filtrate was placed under vacuum overnight to yield the title compound (18 mg, 32.8% yield). ¹H-NMR (DMSO-d₆) δ 9.44 (s, 1H), 9.29 (s, 1H), 8.65 (d, J=7.2 Hz, 1H), 8.29 (t, J=8.4 Hz, 1H), 7.88 (s, 1H), 7.51 (t, J=9.9 Hz, 1H), 7.41 (m, 1H), 7.2 (dd, J=12.1, 1.9 Hz, 1H), 7.1 (dd, J=8.5, 1.4 Hz, 1H), 4.22 (s, 2H), 4.06 (m, 2H), 3.42 (m, 1H), 3.15 (s, 3H), 2.73 (t, J=12.4 Hz, 2H), 2.57 (d, J=4.3 Hz, 3H) 2.17 (m, 2H), 1.59 (m, 2H); MS [M+H]⁺=633; LCMS RT=2.97 min.

Example 152

N-{4-[4-amino-6-chloro-7-(morpholin-4-ylmethyl)pyrrolo[2,1-f][1,2,4]triazin-5-yl]-2-fluorophenyl}-N'-[2-fluoro-5-(trifluoromethyl)-phenyl]urea

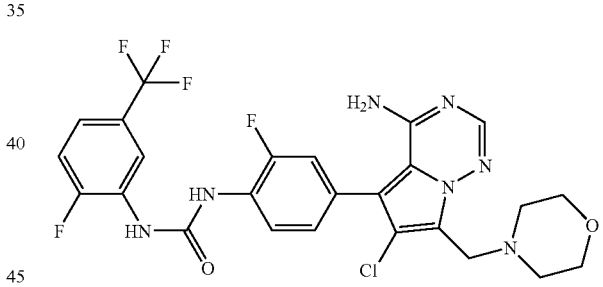

To a solution of Intermediate AAD (5-bromo-6-chloro-7-(morpholin-4-ylmethyl)pyrrolo[2,1-f][1,2,4]triazin-4-amine) (0.04 g, 0.12 mmol) in DMF (2 mL) was added Intermediate F (N-[2-fluoro-4-(4,4,5,5-tetramethyl-1,3,2-dioxaborolan-2-yl)phenyl]-N'-[2-fluoro-5-(trifluoromethyl)phenyl]urea) (0.06 g, 0.14 mmol) and tetrakis(triphenylphosphine) palladium (0.013 g, 0.012 mmol) under nitrogen atmosphere. The reaction mixture was degassed 3× and then microwaved for 10 minutes at 120° C. Upon cooling to rt, the mixture was filtered through a celite pad and DMF was removed under reduced pressure. The crude material was then purified by HPLC (0-70 acetonitrile/water) to yield 40 mg of the above compound (0.07 mmol, yield 60%). ¹H-NMR (CD₃OD-d₄) δ 8.65 (d, J=7.6 Hz, 1H), 8.40-8.35 (m, 1H), 8.06 (s, 1H), 7.37-7.25 (m, 4H), 4.82 (s, 2H), 4.15-3.72 (m, 4H), 3.60-3.41 (m, 4H); MS [M+H]⁺=581.9; LCMS RT=2.66 min.

Example 153

N-{4-[4-amino-6-chloro-7-(morpholin-4-ylmethyl)pyrrolo[2,1-f][1,2,4]triazin-5-yl]phenyl}-N'-[2-chloro-5-(trifluoromethyl)phenyl]urea

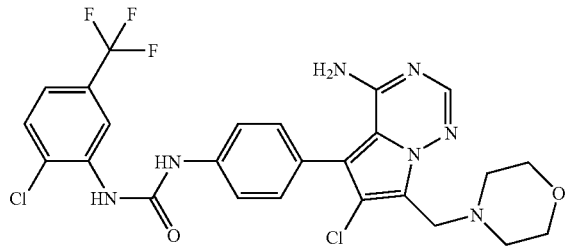

The title compound was prepared using the procedure to make Example 152 by substituting Intermediate AAL (1-[2-chloro-5-(trifluoromethyl)phenyl]-3-[4-(4,4,5,5-tetramethyl-1,3,2-dioxaborolan-2-yl)phenyl]urea) for Intermediate F. $^1$H-NMR (CD$_3$OD-d$_4$) δ 8.66 (d, J=2.4 Hz, 1H), 8.05 (s, 1H), 7.68 (d, J=8.8 Hz, 2H), 7.64 (d, J=8.0 Hz, 1H), 7.45 (d, J=8.8 Hz, 2H), 7.36-7.32 (m, 1H), 4.83 (s, 2H), 3.92-3.72 (m, 4H), 3.60-3.38 (m, 4H); MS [M+H]$^+$=580.0; LCMS RT=3.04 min.

Example 154

N-{4-[4-amino-6-chloro-7-(morpholin-4-ylmethyl)pyrrolo[2,1-f][1,2,4]triazin-5-yl]phenyl}-N'-[2-fluoro-5-(trifluoromethyl)phenyl]urea

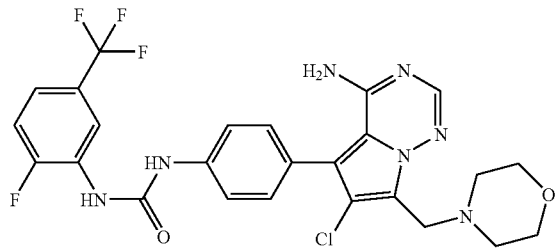

The title compound was prepared using the procedure to make Example 152 by substituting Intermediate AAN (1-[2-fluoro-5-(trifluoromethyl)phenyl]-3-[4-(4,4,5,5-tetramethyl-1,3,2-dioxaborolan-2-yl)phenyl]urea) for Intermediate F. $^1$H-NMR (CD$_3$OD-d$_4$) δ 8.62 (d, J=8 Hz, 1H), 8.06 (s, 1H), 7.69-7.66 (m, 2H), 7.46-7.43 (m, 2H), 7.36-7.34 (m, 2H), 4.02 (s, 2H), 4.15-3.72 (m, 4H), 3.58-3.42 (m, 4H); MS [M+H]$^+$=564.0; LCMS RT=2.72 min.

Example 155

N-{4-[4-amino-6-chloro-7-(morpholin-4-ylmethyl)pyrrolo[2,1-f][1,2,4]triazin-5-yl]-2-methylphenyl}-N'-[2-fluoro-5-(trifluoromethyl)-phenyl]urea

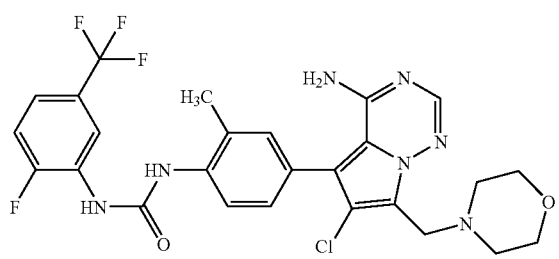

The title compound was prepared using the procedure to make Example 152 by substituting Intermediate AAH (1-[2-fluoro-5-(trifluoromethyl)phenyl]-3-[2-methyl-4-(4,4,5,5-tetramethyl-1,3,2-dioxaborolan-2-yl)phenyl]urea) for Intermediate F. $^1$H-NMR (CD$_3$OD-d$_4$) δ 8.63 (d, J=8 Hz, 1H), 8.06 (s, 1H), 7.94 (d, J=8.4 Hz, 1H), 7.36-7.30 (m, 4H), 4.82 (s, 2H), 4.15-3.72 (m, 4H), 3.60-3.38 (m, 4H), 2.40 (s, 3H); MS [M+H]$^+$=578.0; LCMS RT=3.05 min.

Example 156

N-{4-[4-amino-6-chloro-7-(morpholin-4-ylmethyl)pyrrolo[2,1-f][1,2,4]triazin-5-yl]-2,5-difluorophenyl}-N'-[2-fluoro-5-(trifluoromethyl)-phenyl]urea

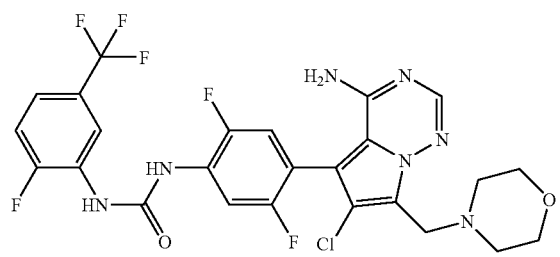

The title compound was prepared using the procedure to make Example 152 by substituting Intermediate AAB for Intermediate F. $^1$H-NMR (CD$_3$OD-d$_4$) δ 8.66 (d, J=8.0 Hz, 1H), 8.30 (dd, J=11.6, 7.2 Hz, 1H), 8.06 (s, 1H), 7.38-7.35 (m, 2H), 7.27 (dd, J=11.2, 6.8 Hz, 1H), 4.82 (s, 2H), 4.15-3.72 (m, 4H), 3.60-3.40 (m, 4H); MS [M+H]$^+$=600.0; LCMS RT=2.75 min.

Example 157

N-{4-[4-amino-6-chloro-7-(morpholin-4-ylmethyl)pyrrolo[2,1-f][1,2,4]triazin-5-yl]-2-fluorophenyl}-N'-[3-(trifluoromethyl)phenyl]urea

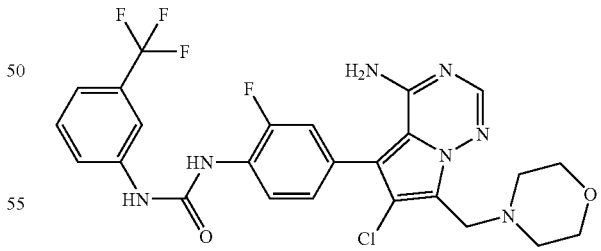

The title compound was prepared using the procedure to make Example 152 by substituting Intermediate AAO (1-[2-fluoro-4-(4,4,5,5-tetramethyl-1,3,2-dioxaborolan-2-yl)phenyl]-3-[3-(trifluoromethyl)phenyl]urea) for Intermediate F. $^1$H-NMR (CD$_3$OD-d$_4$) δ 8.29 (t, J=8.4 Hz, 1H), 8.05 (s, 1H), 7.97 (s, 1H), 7.60 (dd, J=8.4, 1.6 Hz, 1H), 7.49 (t, J=7.6 Hz, 1H), 7.34-7.30 (m, 2H), 7.25-7.24 (m, 1H), 4.82 (s, 2H), 4.15-3.72 (m, 4H), 3.60-3.40 (m, 4H); MS [M+H]$^+$=563.9; LCMS RT=2.64 min.

Example 158

N-{4-[4-amino-6-chloro-7-(morpholin-4-ylmethyl)pyrrolo[2,1-f][1,2,4]triazin-5-yl]-2-fluorophenyl}-N'-[4-(trifluoromethyl)pyridin-2-yl]urea

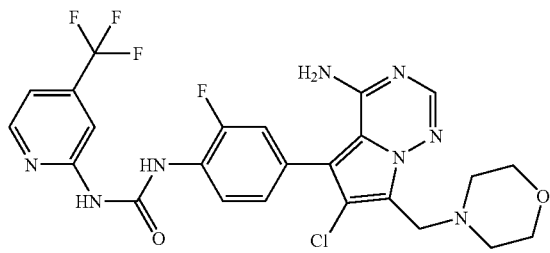

The title compound was prepared using the procedure to make Example 152 by substituting Intermediate AAF (1-[2-fluoro-4-(4,4,5,5-tetramethyl-1,3,2-dioxaborolan-2-yl)phenyl]-3-[4-(trifluoromethyl)pyridin-2-yl]urea) for Intermediate F. $^1$H-NMR (CD$_3$OD-d$_4$) δ 8.51 (d, J=5.2 Hz, 1H), 8.40 (t, J=8.4 Hz, 1H), 8.06 (s, 1H), 7.67 (s, 1H), 7.36 (dd, J=11.6, 2.0 Hz, 1H), 7.32-7.25 (m, 2H), 4.82 (s, 2H), 4.18-3.72 (m, 4H), 3.60-3.40 (m, 4H); MS [M+H]$^+$=564.9; LCMS RT=3.01 min.

Example 159

N-{4-[4-amino-6-chloro-7-(morpholin-4-ylmethyl)pyrrolo[2,1-f][1,2,4]triazin-5-yl]-2-fluorophenyl}-N'-[2-chloro-5-(trifluoromethyl)-phenyl]urea

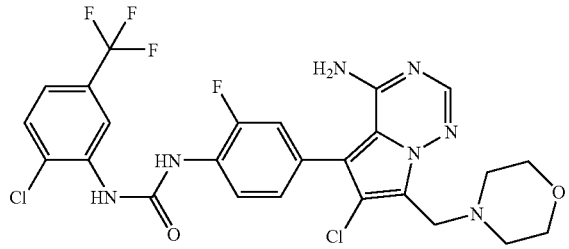

The title compound was prepared using the procedure to make Example 152 by substituting Intermediate AAK (1-[2-chloro-5-(trifluoromethyl)phenyl]-3-[2-fluoro-4-(4,4,5,5-tetramethyl-1,3,2-dioxaborolan-2-yl)phenyl]urea) for Intermediate F. $^1$H-NMR (CD$_3$OD-d$_4$) δ 9.49 (s, 1H), 8.94 (d, J=4.4 Hz, 1H), 8.66 (s, 1H), 8.39-8.33 (m, 1H), 8.06 (s, 1H), 7.64 (d, J=8.4 Hz, 1H), 7.36-7.26 (m, 3H), 4.82 (s, 2H), 4.18-3.72 (m, 4H), 3.60-3.40 (m, 4H); MS [M+H]$^+$=597.9; LCMS RT=2.76 min.

Example 160

N-{4-[4-amino-6-chloro-7-(morpholin-4-ylmethyl)pyrrolo[2,1-f][1,2,4]triazin-5-yl]-2-chlorophenyl}-N'-[3-(trifluoromethyl)phenyl]urea

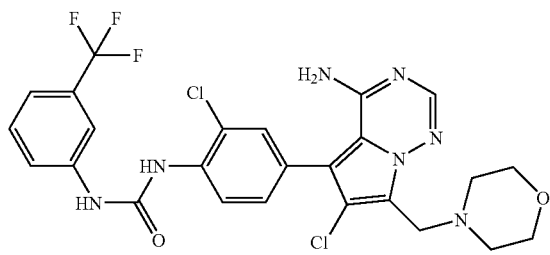

The title compound was prepared using the procedure to make Example 152 by substituting Intermediate AAP (1-[2-chloro-4-(4,4,5,5-tetramethyl-1,3,2-dioxaborolan-2-yl)phenyl]-3-[3-(trifluoromethyl)phenyl]urea) for Intermediate F. $^1$H-NMR (CD$_3$OD-d$_4$) δ 8.35 (d, J=8.4 Hz, 1H), 8.06 (s, 1H), 7.99 (s, 1H), 7.64-7.61 (m, 1H), 7.58 (d, J=1.6 Hz, 1H), 7.50 (t, J=7.6 Hz, 1H), 7.41 (dd, J=8.4, 2.0 Hz, 1H), 7.33 (d, J=8.0 Hz, 1H), 4.82 (s, 2H), 4.18-3.72 (m, 4H), 3.60-3.40 (m, 4H); MS [M+H]$^+$=579.9; LCMS RT=2.71 min.

Example 161

N-{4-[4-amino-6-chloro-7-(morpholin-4-ylmethyl)pyrrolo[2,1-f][1,2,4]triazin-5-yl]-2-fluorophenyl}-N'-(2-fluoro-5-methylphenyl)urea

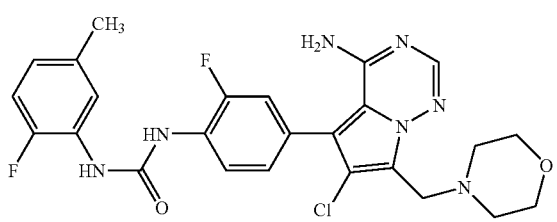

The title compound was prepared using the procedure to make Example 152 by substituting Intermediate AAJ (1-(2-fluoro-5-methylphenyl)-3-[2-fluoro-4-(4,4,5,5-tetramethyl-1,3,2-dioxaborolan-2-yl)phenyl]urea) for Intermediate F. $^1$H-NMR (CD$_3$OD-d$_4$) δ 8.35 (t, J=8.4 Hz, 1H), 8.09 (s, 1H), 7.94 (dd, J=7.6, 2.4 Hz, 1H), 7.32 (dd, J=11.6, 2.0 Hz, 1H), 7.27-7.23 (m, 1H), 7.00 (dd, J=11.2, 8.4 Hz, 1H), 6.86-6.82 (m, 1H); 4.82 (s, 2H), 4.18-3.72 (m, 4H), 3.60-3.40 (m, 4H), 2.31 (s, 3H); MS [M+H]$^+$=528.0; LCMS RT=2.66 min.

Example 162

1-{4-[4-amino-6-(methoxymethyl)-7-(4-methylmorpholin-3-yl)pyrrolo[2,1-f][1,2,4]triazin-5-yl]phenyl}-3-[2-fluoro-5-(trifluoromethyl)-phenyl]urea hydrochloride

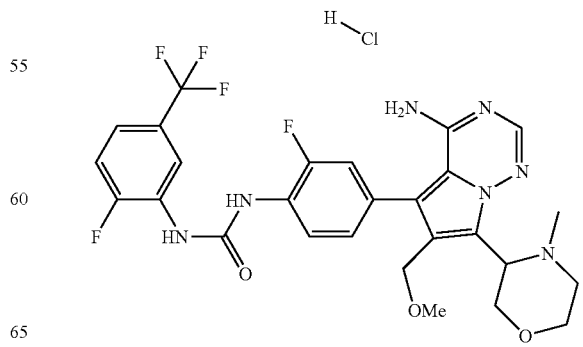

A solution of Intermediate AB (N-{4-[4-amino-6-(methoxymethyl)pyrrolo[2,1-f][1,2,4]triazin-5-yl]-2-fluorophenyl}-N'-[2-fluoro-5-(trifluoromethyl)-phenyl]urea (200 mg, 0.42 mmol) and 4-methyl-3,6-dihydro-2H-1,4-oxazin-4-ium chloride (69 mg, 0.51 mmol) in DMF (5 mL) is allowed to stir for 1 h at rt. Volatiles are removed in vacuo, and the residue triturated with $CH_2Cl_2$, providing the desired compound.

Biological Evaluation

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11 (6), 528-35), taxotere (Bissery et al. *Anti Cancer Drugs* 1995, 6 (3), 339), and topoisomerase inhibitors (Edelman et al. *Cancer Chemother. Pharmacol.* 1996, 37 (5), 385-93) were demonstrated with the use of in vitro tumor proliferation assays.

Demonstration of the activity of the compounds of the present invention may be accomplished through in vitro, ex vivo, and in vivo assays that are well known in the art. For example, to demonstrate the activity of the compounds of the present invention, the following assays may be used.

FGFR-1 TR-FRET Biochemical Assay

The FGFR-1 Assay was performed on half well 96-well opaque plates (Costar 3915) in a LANCE format. LANCE is a homogenous time resolved fluorometry based application available through Perkin Elmer. For this assay, 50 µL reactions were set up using: 0.6 uM ATP (Sigma), 25 nM poly GT-biotin (CIS BIO International), 2 nM Eu-labelled phospho-Tyr Ab (PY20 PerkinElmer), 10 nM Streptavidin-APC (Perkin Elmer), 5 nM FGFR1-GST (generated by DRT, Bayer Healthcare), 1% DMSO, 50 mM HEPES pH 7.5, 10 mM MgCl2, 0.1 mM EDTA, 0.015% Brij, 0.1 mg/ml BSA, 0.1% B-mercaptoethanol. All reactions were initiated with the addition of enzyme and were left to incubate for one hour at room temperature. Time-resolved fluorescence was then read on a Perkin Elmer VictorV Multilabel counter. The reading protocol uses an excitation wavelength at 340 nm and emission reads at both 615 and 665 nm. Signal was calculated as a ratio: (Flourescence at 665 nm/Flourescence at 615 nM)*10000 for each well. The background control used for this assay is the signal produced with all assay components excluding ATP. For $IC_{50}$ generation, compounds were added prior to the enzyme initiation. A 50-fold stock plate was made with compounds serially diluted 1:5 in a 50% DMSO/50% dH2O solution. A 1 µL addition of the stock to the assay wells gave final compound concentrations ranging from 10 µM –0.128 nM in 1% DMSO. The data were expressed as percent inhibition: % inhibition=100−((Signal with inhibitor−background)/(Signal without inhibitor−background))*100.

Tumor Cell Proliferation

Human tumor cells (e.g., HCT116 or MDA-MB-231 cells), were seeded in a Costar 96-well plate at $3.0 \times 10^3$ cells/well and grown in 150 µl of RPMI complete media (Invitrogen Corporation, Grand Island, N.Y.) containing 10% fetal bovine serum (Hyclone, Logan, Utah) at 37° C. for 16 h in an incubator with 5% $CO_2$. To each well, 50 µl of additional growth media containing 40 µM to 18 nM concentrations of compound with 0.4% DMSO was added. Cells were grown for another 72 h at 37° C. with 5% $CO_2$. 20 µl of Alamar Blue (Trek Diagnostic Systems, Inc., Cleveland, Ohio) reagent was added to each well and incubated for 3 h at 37° C. Plates were read in a SpectraMax Gemini (Molecular Devices, CA) with 544 nm excitation and 590 nm emission wavelength. $IC_{50}$ values were determined by linear regression analysis of log drug concentration versus percent inhibition.

p-Histone3

Compounds were assayed for the inhibition of histone 3 phosphorylation in colon carcinoma (HCT116). Briefly, 20,000 cells/well were seeded in a 96-well black-walled, poly-d-lysine plates in RPMI+ 10% FBS and incubated at 37° C. in 5% $CO_2$ overnight. The following day, the cells were treated with compounds for 24 hours at 37° C. Following compound treatment; plates were centrifuged at 1000 rpm for 2 minutes and washed twice with 100 µl of cold sterile TBS. Cells were then fixed with cold 3.7% formaldehyde in TBS (4° C. for 1 hour) and then permeabolized with 0.1% Triton-X-100 in TBS (room temperature for 30 minutes). Plates were then washed with of 0.25% BSA-TBS and blocked with BSA solution for 1 hour at room temperature while shaking. The supernatant was removed and replaced with diluted primary antibody (anti-phospho-histone 3, serine 10, Cell Signaling) at 1:250 in 0.25% BSA-TBS and incubated overnight at 4° C. The plates were washed and treated with diluted secondary antibody (anti-rabbit Eu-labeled) at 1:10000 in 0.25% BSA-TBS (room temperature for 1 hour). The antibody solution was removed from each well and washed eight times. The wash buffer was replaced with 50 µl pre-warmed enhancement solution and mixed on the orbital shaker for 10 minutes. Fluorescence was detected with a Victor V Fluorescence Detector. The data are expressed as percent inhibition: % inhibition=100−((Signal with inhibitor−background)/(Signal without inhibitor−background))×100.

In Vivo Efficacy Studies: Staged Human Xenograft Models

Staged human xenograft models grown in mice or rats were used to evaluate compound efficacy. To generate tumors, cells harvested from mid-log phase cultures or tumor fragments from in vivo passage were injected s.c. in the flank of athymic mice or rats. Treatment administered p.o. or i.v. was initiated when all mice in each experiment had established tumors. The general health of animals was monitored and mortality was recorded daily. Tumor dimensions and body weights were recorded two to three times a week starting with the first day of treatment. Tumor weights were calculated using the equation (l×w2)/2, where l and w refer to the larger and smaller dimensions collected at each measurement. Anti-tumor efficacy was measured as tumor growth inhibition (TGI). TGI is calculated by the equation [1−(T/C)*100], where T and C represent the mean tumor size of the treated (T) and untreated or vehicle control (C) groups, respectively, at the end of treatment.

In Vitro Soft Agar Assays Measuring Anchorage-Independent Growth:

One of the hallmarks of an oncogenically-transformed cell is its ability to survive and proliferate in an anchorage-independent manner. To measure this anchorage-independent growth, soft agar assays are performed. A mixture of 1000 cells in 100 µl of growth medium containing 0.36% agarose (supplemented with 10% (v/v) FBS) is plated onto 50 µl of solidified growth medium containing 0.6% (w/v) agarose in 96 well plates. Once the cell/medium/agarose mixture have solidified, 50 µl of growth medium is added to cover the wells and plates are incubated overnight at 37° C. in a 5% $CO_2$ incubator. The following day, compounds diluted in growth media with a final concentration of DMSO not to exceed 0.1% (v/v) are added to each well. Cells are further incubated for 5 days at 37° C. in a humidified incubator containing 5% $CO_2$. On day 5, 40 µl of MTS reagent (CellTiter 96 Aqueous One Solution, Promega, Madison, Wis.) is added to each well and the plates are incubated for an additional 2 hours at 37° C.

Plates are then read at 490 nm on a SpectraMax 250 plate reader (Molecular Devices, Sunnyvale, Calif.).

Percent inhibition is calculated using the following equation:

% inhibition=$1-(T_{5test}-T_0)/(T_{5control}-T_0)\times 100$.

$T_{5test}$=O.D. at 490 nm in the presence of test compound at day 5

$T_{5control}$=O.D. at 490 nm in the DMSO treated control cells at day 5

$T_0$=O.D. at 490 nm in the presence of compound at day 0

Apoptosis Assays: Cell Death Detection Assay to Measure DNA Fragmentation

The Cell Death Detection ELISAPlus kit (Roche, Mannheim, Germany) is used to measure DNA fragmentation as a marker for apoptosis. Cells are seeded in 96-well plates at 10,000 cells/well and after 24 hr, are dosed and grown for an additional 48 hr in media containing 10% FBS in 5% $CO_2$ at 37° C. Supernatants from control and treated cells are transferred into streptavidin-coated 96-well plates and incubated with biotinylated mouse anti-histone antibody and peroxidase-conjugated mouse anti-DNA antibody at room temperature for 2 hr. After the removal of unbound antibodies by washing, the amount of apoptosis-generated nucleosomes is quantified as the peroxidase retained in the immuno-complex using ABTS (2,2'-azino-di[3-ethylbenzthiazolin-sulfonate]) as the substrate. Absorbance is determined at 405-490 nm using a SpectraMax microplate reader (Molecular Devices, Sunnyvale, Calif.).

Apoptosis Assays: Caspase 3/7 Activation

Execution of cell death is dependent on caspase activity. Caspases 3/7 are central executioners for apoptosis. Cells ($10^4$ cells/well) are plated in 96-well microliter plates and incubated in media containing 10% FBS at 37° C. overnight in a humidified incubator containing 5% $CO_2$. On the following day, compounds are added to wells and cultures are incubated for an additional 24 hrs. Caspase 3/7 activity is measured by adding the profluorescent substrate, Z-DEVD-AFC (7-Amino-4-Trifluorocoumarin; 75 µM; Calbiochemicals, San Diego, Calif.), freezing the plate, and then thawing the cells for 3 hours at room temperature. Plates are read at 400 nm (excitation wavelength) and 505 nm (emission wavelength) on a SpectraMax Gemini microplate reader (Molecular Devices, Sunnyvale, Calif.).

Compounds of the invention were tested for activity using the FGFR1 biochemical, tumor cell proliferation and p-Histone3.

Compounds of examples 9, 10, 12, 19, 26, 27, 28, 29, 31, 32, 33 44, 45, 54, 58, 60, 63, 66, 68, 69, 70, 75, 79, 83, 102, 105, 111, 116, 117, 119, 124, 126, 128, 131, 135, 138, 145, 154, 158, and 161 demonstrate an $IC_{50}$ of less than 10 nM in the FGFR-1 biochemical, assay. Compounds of examples 1, 4, 5, 7, 13, 14, 15, 16, 20, 21, 23, 24, 34, 35, 37, 43, 47, 49, 55, 57, 59, 62, 67, 74, 88, 89, 90, 96, 99, 104, 106, 109, 114, 123, 140, 142, 148, 149, 152, 159, and 160 demonstrate an $IC_{50}$ greater than 10 nM but less than 100 nM in the FGFR-1 biochemical assay. Compounds of examples 6, 8, 11, 40, 50, 86, 92, 94, 97, 108, 110, 150, and 156 demonstrate an $IC_{50}$ greater than 100 nM but less than 1 µM in FGFR-1 biochemical assay.

Compounds of examples 7, 12, 13, 23 and 25 demonstrate an $IC_{50}$ greater than 500 nM but less than 4 µM in the HCT116 proliferation assay. Compounds of examples 7, 12, 13 and 23 demonstrate an $IC_{50}$ greater than 500 nM but less than 5 µM in the MDA-MB-231 proliferation assay.

Compound of examples 7, 9, 10, 13, 34, 53, 54, 69, and 111 demonstrate an $IC_{50}$ greater than 500 nM but less than 5 µM in the p-histone3 assay. Compounds of examples 12, 20, 33, and 62 demonstrate an $IC_{50}$ greater than 5 µM but less than 10 µM in the p-histone3 assay.

It is believed that one skilled in the art, using the preceeding information and information available in the art, can utilize the present invention to its fullest extent. Those skilled in the art will recognize that the invention may be practiced with variations on the disclosed structures, materials, compositions and methods without departing from the spirit or scope of the invention as it is set forth herein and such variations are regarded as within the ambit of the invention. The compounds described in the examples are intended to be representative of the invention, and it will be understood that the scope of the invention is not limited by the scope of the examples. The topic headings set forth above are meant as guidance where certain information can be found in the application, but are not intended to be the only source in the application where information on such topics can be found. All publications and patents cited above are incorporated herein by reference.

The invention claimed is:
1. A compound of formula (I)

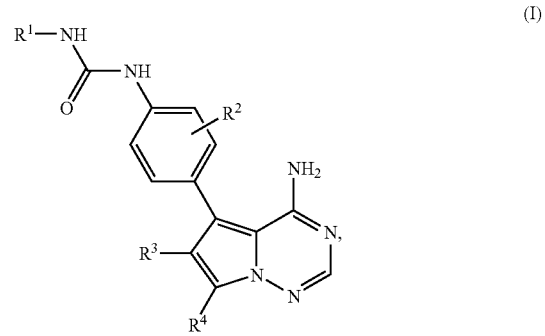

wherein
$R^1$ represents
1.1) phenyl or a bicyclic carbocycle of 9-10 ring members, in which at least one ring is aromatic, $R^1$ optionally bearing up to 4 substituents independently selected from the group consisting of
1.1.a) ($C_1$-$C_4$)alkyl, which may optionally bear up to 3 substituents independently selected from
1.1.a1) halogen;
1.1.a2) $OR^5$ wherein $R^5$ represents H or ($C_1$-$C_3$) alkyl which may optionally bear halogen or —($C_1$-$C_3$)mono- or di-alkylamino;
1.1.a3) —$NR^6R^7$ in which $R^6$ and $R^7$ are independently H or —($C_1$-$C_3$)alkyl which may optionally bear halogen or $OR^{7a}$ wherein $R^{7a}$ represents H or ($C_1$-$C_3$)alkyl, or $R^6$ and $R^7$ may be joined and taken together with the N atom to which they are attached form a 5-6 membered ring which may optionally contain a ring member selected from O, S, and $NR^8$ wherein $R^8$ represents H or ($C_1$-$C_3$)alkyl; and
1.1.a4) a 5-6 membered heteroaromatic containing up to two heteroatoms selected from O, S, and N;
1.1.b) —($C_3$-$C_6$)cycloalkyl which may optionally bear up to 2 substituents independently selected from
1.1.b1) halogen; and
1.1.b2) $OR^9$ wherein $R^9$ represents H or ($C_1$-$C_3$) alkyl which may optionally bear halogen or ($C_1$-$C_3$)mono- or di-alkylamino;

1.1.c) $OR^{10}$ wherein
- $R^{10}$ represents H; phenyl; benzyl; $(C_3-C_6)$cycloalkyl; or $(C_1-C_4)$alkyl which may optionally bear up to 3 substituents independently selected from
  - 1.1.c1) halogen;
  - 1.1.c2) $OR^{11}$ wherein $R^{11}$ represents H or $(C_1-C_3)$ alkyl which may optionally bear $(C_1-C_3)$mono- or di-alkylamino; and
  - 1.1.c3) $NR^{12}R^{13}$ in which $R^{12}$ and $R^{13}$ are independently H or $-(C_1-C_3)$alkyl which may optionally bear halogen, or $R^{12}$ and $R^{13}$ may be joined and taken together with the N atom to which they are attached form a 5-6 membered ring which may optionally contain a ring member selected from O, S, and $NR^{14}$ wherein $R^{14}$ represents H or $(C_1-C_3)$alkyl;
1.1.d) $-C(O)-OR^{15}$ wherein $R^{15}$ represents H or $-(C_1-C_4)$alkyl which may optionally bear up to 3 halogens;
1.1.e) $-C(O)-NR^{16}R^{17}$ wherein
- $R^{16}$ represents H or $(C_1-C_3)$alkyl which may optionally bear halogen; and
- $R^{17}$ represents H or $-(C_1-C_4)$alkyl which is optionally substituted with
  - 1.1.e1) halogen;
  - 1.1.e2) a 5-6 membered heteroaromatic containing up to two heteroatoms selected from O, S, and N;
  - 1.1.e3) phenyl;
  - 1.1.e4) $-SO_2CH_3$;
  - 1.1.e5) $-OR^{18}$ wherein $R^{18}$ represents H or $(C_1-C_3)$alkyl which may optionally bear halogen; or
  - 1.1.e6) $-NR^{19}R^{20}$ in which $R^{19}$ and $R^{20}$ are independently H or $-(C_1-C_3)$alkyl which may optionally bear halogen, or $R^{19}$ and $R^{20}$ may be joined and taken together with the N atom to which they are attached form a 5-6 membered ring which may optionally contain a ring member selected from O, S, and $NR^{21}$ wherein $R^{21}$ represents H or $(C_1-C_3)$alkyl;
1.1.f) $-N(R^{22})-C(O)-R^{23}$ wherein
- $R^{22}$ represents H or $(C_1-C_3)$alkyl; and
- $R^{23}$ represents optionally substituted phenyl, or $(C_1-C_4)$alkyl which is optionally substituted with
  - 1.1.f1) optionally substituted phenyl,
  - 1.1.f2) $OR^{24}$ wherein $R^{24}$ represents H or $(C_1-C_3)$ alkyl, or
  - 1.1.f3) $NR^{25}R^{26}$ wherein $R^{25}$ and $R^{26}$ are independently H or $-(C_1-C_3)$alkyl which may optionally bear halogen, or $R^{25}$ and $R^{26}$ may be joined and taken together with the N atom to which they are attached form a 5-6 membered ring which may optionally contain a ring member selected from O, S, and $NR^{27}$ wherein $R^{27}$ represents H or $(C_1-C_3)$alkyl;
1.1.g) $-SO_2NR^{28}R^{29}$ wherein
- $R^{28}$ represents H or $(C_1-C_3)$alkyl which may optionally bear halogen; and
- $R^{29}$ represents H or $-(C_1-C_4)$alkyl which is optionally substituted with:
  - 1.1.g1) halogen;
  - 1.1.g2) a 5-6 membered heteroaromatic containing up to two heteroatoms selected from O, S, and N;
  - 1.1.g3) phenyl;
  - 1.1.g4) $-SO_2CH_3$;
  - 1.1.g5) $-OR^{30}$ wherein $R^{30}$ represents H or $(C_1-C_3)$alkyl which may optionally bear halogen; or
  - 1.1.g6) $-NR^{31}R^{32}$ in which $R^{31}$ and $R^{32}$ are independently H or $-(C_1-C_3)$alkyl which may optionally bear halogen, or $R^{31}$ and $R^{32}$ may be joined and taken together with the N atom to which they are attached form a 5-6 membered ring which may optionally contain a ring member selected from O, S, and $NR^{33}$ wherein $R^{33}$ represents H or $(C_1-C_3)$alkyl;
1.1.h) $-N(R^{34})-SO_2-R^{35}$ wherein
- $R^{34}$ represents H or $(C_1-C_3)$alkyl, and
- $R^{35}$ represents optionally substituted phenyl, or $(C_1-C_4)$alkyl which is optionally substituted with
  - 1.1.h1) halogen;
  - 1.1.h2) optionally substituted phenyl,
  - 1.1.h3) $OR^{36}$ wherein $R^{36}$ represents H or $(C_1-C_3)$ alkyl, or
  - 1.1.h4) $NR^{37}R^{38}$ wherein $R^{37}$ and $R^{38}$ are independently H or $-(C_1-C_3)$alkyl which may optionally bear halogen, or $R^{37}$ and $R^{38}$ may be joined and taken together with the N atom to which they are attached form a 5-6 membered ring which may optionally contain a ring member selected from O, S, and $NR^{39}$ wherein $R^{39}$ represents H or $(C_1-C_3)$alkyl;
1.1.i) $-NR^{40}R^{41}$ in which $R^{40}$ and $R^{41}$ are independently H or $-(C_1-C_3)$alkyl which may optionally bear halogen or $OR^{42}$ in which $R^{42}$ represents H or $(C_1-C_3)$alkyl, or $R^{40}$ and $R^{41}$ may be joined and taken together with the N atom to which they are attached form a 5-6 membered ring which may optionally contain a ring member selected from O, S, and $NR^{43}$ wherein $R^{43}$ represents H or $(C_1-C_3)$ alkyl;
1.1.j) halogen;
1.1.k) optionally substituted phenyl;
1.1.l) $NO_2$;
1.1.m) CN; and
1.1.n) a 5-6 membered heteroaromatic containing up to two heteroatoms selected from O, S, and N;

or $R^1$ represents 1.2) a 5-6 membered aromatic heterocycle containing up to 3 heteroatoms independently selected from the group consisting of N, O, and S; or a bicyclic heterocycle of 8-10 ring members in which at least one ring is aromatic and contains up to 3 moieties independently selected from the group consisting of N, N→O, O, and S, and any non-aromatic ring of said bicyclic heterocycle optionally contains up to three moieties independently selected from the group consisting of O, S, S(O), S(O)$_2$, and $NR^{44}$ wherein $R^{44}$ represents H or $-(C_1-C_3)$alkyl; said $R^1$ heterocycle optionally bearing up to 4 substituents independently selected from the group consisting of 1.2.a) $(C_1-C_4)$alkyl, which may optionally bear up to 3 substituents independently selected from
- 1.2.a1) halogen;
- 1.2.a2) $OR^{45}$ wherein $R^{45}$ represents H or $(C_1-C_3)$ alkyl which may optionally bear halogen or $-(C_1-C_3)$mono- or di-alkylamino;
- 1.2.a3) $-NR^{46}R^{47}$ in which $R^{46}$ and $R^{47}$ are independently H or $-(C_1-C_3)$alkyl which may optionally bear halogen or $OR^{47a}$ wherein $R^{47a}$ represents H or $(C_1-C_3)$alkyl, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or $(C_1$-$C_3)$alkyl; and 1.2.a4) a 5-6 membered heteroaromatic containing up to two heteroatoms selected from O, S, and N;

1.2.b) —$(C_3$-$C_6)$cycloalkyl which may optionally bear up to 2 substituents independently selected from 1.2.b1) halogen; and 1.2.b2) $OR^{49}$ wherein $R^{49}$ represents H or $(C_1$-$C_3)$ alkyl which may optionally bear halogen or —$(C_1$-$C_3)$mono- or di-alkylamino;

1.2.c) $OR^{50}$ wherein $R^{50}$ represents H; phenyl; benzyl; —$(C_3$-$C_6)$cycloalkyl; or —$(C_1$-$C_4)$alkyl which may optionally bear up to 3 substituents independently selected from 1.2.c1) halogen;

1.2.c2) $OR^{51}$ wherein $R^{51}$ represents H or $(C_1$-$C_3)$ alkyl which may optionally bear —$(C_1$-$C_3)$ mono- or di-alkylamino; and 1.2.c3) —$NR^{52}R^{53}$ in which $R^{52}$ and $R^{53}$ are independently H or —$(C_1$-$C_3)$alkyl which may optionally bear halogen, or $R^{52}$ and $R^{53}$ may be joined and taken together with the N atom to which they are attached form a 5-6 membered ring which may optionally contain a ring member selected from O, S, and $NR^{54}$ wherein $R^{54}$ represents H or $(C_1$-$C_3)$alkyl;

1.2.d) —C(O)—$OR^{55}$ wherein $R^{55}$ represents H or —$(C_1$-$C_4)$alkyl which may optionally bear up to 3 halogens;

1.2.e) —C(O)—$NR^{56}R^{57}$ wherein $R^{56}$ represents H or $(C_1$-$C_3)$alkyl which may optionally bear halogen; and $R^{57}$ represents H or —$(C_1$-$C_4)$alkyl which is optionally substituted with 1.2.e1) halogen;

1.2.e2) a 5-6 membered heteroaromatic containing up to two heteroatoms selected from O, S, and N;

1.2.e3) phenyl;

1.2.e4) —$SO_2CH_3$;

1.2.e5) —$OR^{58}$ wherein $R^{58}$ represents H or $(C_1$-$C_3)$alkyl which may optionally bear halogen; or 1.2.e6) —$NR^{59}R^{60}$ in which $R^{59}$ and $R^{60}$ are independently H or —$(C_1$-$C_3)$alkyl which may optionally bear halogen, or $R^{59}$ and $R^{60}$ may be joined and taken together with the N atom to which they are attached form a 5-6 membered ring which may optionally contain a ring member selected from O, S, and $NR^{61}$ wherein $R^{61}$ represents H or $(C_1$-$C_3)$alkyl;

1.2.f) —$N(R^{62})$—C(O)—$R^{63}$ wherein $R^{62}$ represents H or $(C_1$-$C_3)$alkyl; and $R^{63}$ represents optionally substituted phenyl, or $(C_1$-$C_4)$alkyl which is optionally substituted with 1.2.f1) optionally substituted phenyl, 1.2.f2) $OR^{64}$ wherein $R^{64}$ represents H or $(C_1$-$C_3)$ alkyl, or 1.2.f3) $NR^{65}R^{66}$ wherein $R^{65}$ and $R^{66}$ are independently H or —$(C_1$-$C_3)$alkyl which may optionally bear halogen, or $R^{65}$ and $R^{66}$ may be joined and taken together with the N atom to which they are attached form a 5-6 membered ring which may optionally contain a ring member selected from O, S, and $NR^{67}$ wherein $R^{67}$ represents H or $(C_1$-$C_3)$alkyl;

1.2.g) —$SO_2NR^{68}R^{69}$ wherein $R^{68}$ represents H or $(C_1$-$C_3)$alkyl which may optionally bear halogen; and $R^{69}$ represents H or —$(C_1$-$C_4)$alkyl which is optionally substituted with 1.2.g1) halogen;

1.2.g2) a 5-6 membered heteroaromatic containing up to two heteroatoms selected from O, S, and N;

1.2.g3) phenyl;

1.2.g4) —$SO_2CH_3$;

1.2.g5) —$OR^{70}$ wherein $R^{70}$ represents H or $(C_1$-$C_3)$alkyl which may optionally bear halogen; or 1.2.g6 —$NR^{71}R^{72}$ in which $R^{71}$ and $R^{72}$ are independently H or —$(C_1$-$C_3)$alkyl which may optionally bear halogen, or $R^{71}$ and $R^{72}$ may be joined and taken together with the N atom to which they are attached form a 5-6 membered ring which may optionally contain a ring member selected from O, S, and $NR^{73}$ wherein $R^{73}$ represents H or $(C_1$-$C_3)$alkyl;

1.2.h) —$N(R^{74})$—$SO_2$—$R^{75}$ wherein $R^{74}$ represents H or $(C_1$-$C_3)$alkyl, and $R^{75}$ represents optionally substituted phenyl, or $(C_1$-$C_4)$alkyl which is optionally substituted with 1.2.h1) halogen;

1.2.h2) optionally substituted phenyl, 1.2.h3) $OR^{76}$ wherein $R^{76}$ represents H or $(C_1$-$C_3)$ alkyl, or 1.2.h4) $NR^{77}R^{78}$ wherein $R^{77}$ and $R^{78}$ are independently H or —$(C_1$-$C_3)$alkyl which may optionally bear halogen, or $R^{77}$ and $R^{78}$ may be joined and taken together with the N atom to which they are attached form a 5-6 membered ring which may optionally contain a ring member selected from O, S, and $NR^{79}$ wherein $R^{79}$ represents H or $(C_1$-$C_3)$alkyl;

1.2.i) —$NR^{80}R^{81}$ in which $R^{80}$ and $R^{81}$ are independently H or —$(C_1$-$C_3)$alkyl which may optionally bear halogen or $OR^{81a}$ wherein $R^{81a}$ represents H or $(C_1$-$C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1$-$C_3)$ alkyl;

1.2.j) halogen;

1.2.k) optionally substituted phenyl;

1.2.l) $NO_2$;

1.2.m) CN; and 1.2.n) a 5-6 membered heteroaromatic containing up to two heteroatoms selected from O, S, and N;

$R^2$ represents hydrogen; halogen; —$(C_1$-$C_5)$alkyl which may optionally bear halogen; or —$O(C_1$-$C_3)$alkyl which may optionally bear halogen;

$R^3$ represents 3.1) —$(C_1$-$C_5)$alkyl which is substituted with 3.1.a) -halogen;

3.1.b) phenyl optionally substituted with halogen, —$(C_1$-$C_3)$alkyl, or —$(C_1$-$C_3)$alkoxy, 3.1.c) a 5-6 membered heteroaromatic containing up to two heteroatoms selected from O, S, and N, optionally substituted with halogen or —$(C_1$-$C_3)$ alkyl, 3.1.d) —CN,
3.1.e) —OR$^{83}$ wherein R$^{83}$ represents H or —(C$_1$-C$_3$)alkyl which may optionally bear up to 3 substituents independently selected from
  3.1.e1) halogen;
  3.1.e2) optionally substituted phenyl;
  3.1.e3) —S(O)$_2$CH$_3$;
  3.1.e4) OR$^{84}$ wherein R$^{84}$ represents H or (C$_1$-C$_3$)alkyl which may optionally bear halogen or —(C$_1$-C$_3$)mono- or di-alkylamino; and
  3.1.e5) —NR$^{85}$R$^{86}$ in which R$^{85}$ and R$^{86}$ are independently H or —(C$_1$-C$_3$)alkyl which may optionally bear halogen, or R$^{85}$ and R$^{86}$ may be joined and taken together with the N atom to which they are attached form a 5-6 membered ring which may optionally contain a ring member selected from O, S, and NR$^{87}$ wherein R$^{87}$ represents H or (C$_1$-C$_3$)alkyl;
3.1.f) —(C$_3$-C$_5$)cycloalkyl which may optionally bear halogen or OR$^{88}$ wherein R$^{88}$ represents H or (C$_1$-C$_3$)alkyl; or
3.1.g) —NR$^{89}$R$^{90}$ wherein
  R$^{89}$ represents H or —(C$_1$-C$_3$)alkyl which may optionally bear halogen; and
  R$^{90}$ represents H or —(C$_1$-C$_4$)alkyl which is optionally substituted with
  3.1.g1) halogen;
  3.1.g2) a 5-6 membered heteroaromatic containing up to two heteroatoms selected from O, S, and N;
  3.1.g3) phenyl;
  3.1.g4) —SO$_2$CH$_3$;
  3.1.g5) —OR$^{91}$ wherein R$^{91}$ represents H or (C$_1$-C$_3$)alkyl which may optionally bear halogen; or
  3.1.g6) —NR$^{92}$R$^{93}$ in which R$^{92}$ and R$^{93}$ are independently H or —(C$_1$-C$_3$)alkyl which may optionally bear halogen, or R$^{92}$ and R$^{93}$ may be joined and taken together with the N atom to which they are attached form a 5-6 membered ring which may optionally contain a ring member selected from O, S, and NR$^{94}$ wherein R$^{94}$ represents H or (C$_1$-C$_3$)alkyl; or
  3.1.g7) R$^{89}$ and R$^{90}$ may be joined and taken together with the N to which they are attached form an aromatic or nonaromatic 5-6 membered ring which may optionally contain a ring member selected from O, S, and NR$^{95}$ wherein R$^{95}$ represents H or (C$_1$-C$_3$)alkyl;
3.2)

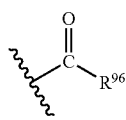

wherein
R$^{96}$ represents
3.2.a) H,
3.2.b) —(C$_3$-C$_5$)cycloalkyl which may optionally bear halogen or —(C$_1$-C$_3$)alkoxy; or
3.2.c) —(C$_1$-C$_5$)alkyl which may optionally bear up to 3 substituents independently selected from
  3.2.c1) halogen;
  3.2.c2) a 5-6 membered heteroaromatic containing up to two heteroatoms selected from O, S, and N;
  3.2.c3) phenyl;
  3.2.c4) —S(O)$_2$CH$_3$;
  3.2.c5) —OR$^{97}$ wherein R$^{97}$ represents H or (C$_1$-C$_3$)alkyl which may optionally bear halogen or —(C$_1$-C$_3$)mono- or di-alkylamino; and
  3.2.c6) —NR$^{98}$R$^{99}$ in which R$^{98}$ and R$^{99}$ are independently H or —(C$_1$-C$_3$)alkyl which may optionally bear halogen or OR$^{99a}$ wherein R$^{99a}$ represents H or (C$_1$-C$_3$)alkyl, or R$^{98}$ and R$^{99}$ may be joined and taken together with the N atom to which they are attached form a 5-6 membered ring which may optionally contain a ring member selected from O, S, and NR$^{100}$ wherein R$^{100}$ represents H or (C$_1$-C$_3$)alkyl;
3.3)

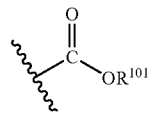

wherein R$^{101}$ represents H or —(C$_1$-C$_5$)alkyl which may optionally bear up to 3 substituents independently selected from
  3.3.a) halogen; and
  3.3.b) phenyl;
3.4)

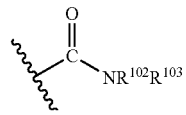

wherein
R$^{102}$ represents H or —(C$_1$-C$_3$)alkyl which may optionally bear halogen; and
R$^{103}$ represents H or —(C$_1$-C$_5$)alkyl which may optionally bear up to 3 substituents independently selected from
  3.4.a) halogen;
  3.4.b) a 5-6 membered heteroaromatic containing up to two heteroatoms selected from O, S, and N;
  3.4.c) phenyl;
  3.4.d) —S(O)$_2$CH$_3$;
  3.4.e) OR$^{104}$ wherein R$^{104}$ represents H or (C$_1$-C$_3$)alkyl which may optionally bear halogen; and
  3.4.f) —NR$^{105}$R$^{106}$ in which R$^{105}$ and R$^{106}$ are independently H or —(C$_1$-C$_3$)alkyl which may optionally bear halogen, or R$^{105}$ and R$^{106}$ may be joined and taken together with the N atom to which they are attached form a 5-6 membered ring which may optionally contain a ring member selected from O, S, and NR$^{107}$ wherein R$^{107}$ represents H or (C$_1$-C$_3$)alkyl;
3.5) optionally substituted phenyl;
3.6) a 5-6 membered heteroaromatic containing up to two heteroatoms selected from O, S, and N;
3.7) halogen;
3.8) —CN; or
3.9) —CH=N—OR$^{108}$ wherein R$^{108}$ represents H or —C(O)—(C$_1$-C$_3$)alkyl;

$R^4$ represents 4.1) $-(C_1-C_5)$alkyl which is substituted with 4.1.a) $-(C_3-C_5)$cycloalkyl which may optionally bear halogen or $OR^{109}$ wherein $R^{109}$ represents H or $(C_1-C_3)$alkyl;

4.1.b) -halogen;

4.1.c) $-OR^{110}$ wherein $R^{110}$ represents H or $-(C_1-C_3)$alkyl which may optionally bear up to 3 substituents independently selected from 4.1.c1) halogen;

4.1.c2) phenyl;

4.1.c3) $-S(O)_2CH_3$;

4.1.c4) $OR^{111}$ wherein $R^{111}$ represents H or $(C_1-C_3)$alkyl which may optionally bear halogen; and 4.1.c5) $-NR^{112}R^{113}$ in which $R^{112}$ and $R^{113}$ are independently H or $-(C_1-C_3)$alkyl which may optionally bear halogen, or $R^{112}$ and $R^{113}$ may be joined and taken together with the N atom to which they are attached form a 5-6 membered ring which may optionally contain a ring member selected from O, S, and $NR^{114}$ wherein $R^{114}$ represents H or $(C_1-C_3)$alkyl;

4.1.d) $-NR^{115}R^{116}$ wherein $R^{115}$ represents H or $-(C_1-C_3)$alkyl which may optionally bear halogen and $R^{116}$ represents H, optionally substituted phenyl, or $-(C_1-C_5)$alkyl which may optionally bear up to 3 substituents independently selected from 4.1.d1) halogen;

4.1.d2) $-S(O)_2CH_3$;

4.1.d3) $OR^{117}$ wherein $R^{117}$ represents H or $(C_1-C_3)$alkyl which may optionally bear halogen; and 4.1.d4) $-NR^{118}R^{119}$ in which $R^{118}$ and $R^{119}$ are independently H or $-(C_1-C_3)$alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or $(C_1-C_3)$alkyl;

4.1.e) optionally substituted phenyl; or 4.1.f) a 5-6 membered aromatic heterocycle containing up to two heteroatoms selected from O, S, and N;

4.2)

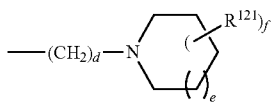

wherein $R^{121}$ represents $-(C_1-C_3)$alkyl which may optionally bear halogen or $-OR^{122}$ in which $R^{122}$ represents H or $-(C_1-C_3)$alkyl;

d represents 1, 2, or 3;

e represents 0 or 1;

f represents 0, 1, or 2;

4.3)

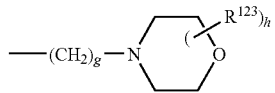

wherein $R^{123}$ represents $-(C_1-C_3)$alkyl which may optionally bear halogen or $-OR^{124}$ in which $R^{124}$ represents H or $-(C_1-C_3)$alkyl;

g represents 1, 2, or 3;

h represents 0, 1, or 2;

4.4)

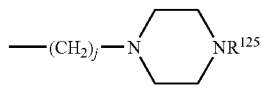

wherein $R^{125}$ represents 4.4.a) H;

4.4.b) $-(C_1-C_3)$alkyl which may optionally bear halogen or $-OR^{126}$ in which $R^{126}$ represents H or $-(C_1-C_3)$alkyl which in turn is optionally substituted with halogen;

4.4.c) $-SO_2R^{127}$ wherein $R^{127}$ represents optionally substituted phenyl, or $-(C_1-C_3)$alkyl which may optionally bear halogen or $OR^{128}$ wherein $R^{128}$ represents H or $(C_1-C_3)$alkyl;

4.4.d) $-C(O)R^{129}$ wherein $R^{129}$ represents 4.4.d1) optionally substituted phenyl, 4.4.d2) $-(C_1-C_3)$alkyl which may optionally bear up to 3 substituents independently selected from 4.4.d2.1) halogen;

4.4.d2.2) optionally substituted phenyl;

4.4.d2.3) $-S(O)_2CH_3$;

4.4.d2.4) $-OR^{130}$ wherein $R^{130}$ represents H or $(C_1-C_3)$alkyl which may optionally bear halogen; and 4.4.d2.5) $-NR^{131}R^{132}$ in which $R^{131}$ and $R^{132}$ are independently H or $-(C_1-C_3)$alkyl which may optionally bear halogen, or $R^{131}$ and $R^{132}$ may be joined and taken together with the N atom to which they are attached form a 5-6 membered ring which may optionally contain a ring member selected from O, S, and $NR^{133}$ wherein $R^{133}$ represents H or $(C_1-C_3)$alkyl;

4.4.d3) $-OR^{134}$ wherein $R^{134}$ represents H or $(C_1-C_3)$alkyl which may optionally bear halogen; or 4.4.d4) $NR^{135}R^{136}$ wherein $R^{135}$ and $R^{136}$ are independently H or $-(C_1-C_3)$alkyl which may optionally bear halogen, or $R^{135}$ and $R^{136}$ may be joined and taken together with the N atom to which they are attached form a 5-6 membered ring which may optionally contain a ring member selected from O, S, and $NR^{137}$ wherein $R^{137}$ represents H or $(C_1-C_3)$alkyl; and j represents 1, 2, or 3;

4.5)

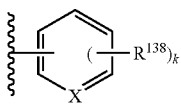

wherein

X represents C or N;

R$^{138}$ represents 4.5.a) (C$_1$-C$_4$)alkyl, which may optionally bear up to 3 substituents independently selected from
- 4.5.a1) halogen;
- 4.5.a2) OR$^{139}$ wherein R$^{139}$ represents H or (C$_1$-C$_3$)alkyl which may optionally bear halogen or —(C$_1$-C$_3$)mono- or di-alkylamino;
- 4.5.a3) —NR$^{140}$R$^{141}$ in which R$^{140}$ and R$^{141}$ are independently H or —(C$_1$-C$_3$)alkyl which may optionally bear halogen or OR$^{141a}$ wherein R$^{141a}$ represents H or (C$_1$-C$_3$)alkyl, or R$^{140}$ and R$^{141}$ may be joined and taken together with the N atom to which they are attached form a 5-6 membered ring which may optionally contain a ring member selected from O, S, and NR$^{142}$ wherein R$^{142}$ represents H or (C$_1$-C$_3$)alkyl; and
- 4.5.a4) a 5-6 membered heteroaromatic containing up to two heteroatoms selected from O, S, and N;

4.5.b) —(C$_3$-C$_6$)cycloalkyl which may optionally bear up to 2 substituents independently selected from
- 4.5.b1) halogen; and
- 4.5.b2) OR$^{143}$ wherein R$^{143}$ represents H or (C$_1$-C$_3$)alkyl which may optionally bear halogen;

4.5.c) OR$^{144}$ wherein
R$^{144}$ represents H; phenyl; benzyl; (C$_3$-C$_6$)cycloalkyl; or (C$_1$-C$_4$)alkyl which may optionally bear up to 3 substituents independently selected from
- 4.5.c1) halogen;
- 4.5.c2) OR$^{145}$ wherein R$^{145}$ represents H or (C$_1$-C$_3$)alkyl which may optionally bear (C$_1$-C$_3$) mono- or di-alkylamino; and
- 4.5.c3) NR$^{146}$R$^{147}$ in which R$^{146}$ and R$^{147}$ are independently H or —(C$_1$-C$_3$)alkyl which may optionally bear halogen, or R$^{146}$ and R$^{147}$ may be joined and taken together with the N atom to which they are attached form a 5-6 membered ring which may optionally contain a ring member selected from O, S, and NR$^{148}$ wherein R$^{148}$ represents H or (C$_1$-C$_3$)alkyl;

4.5.d) —C(O)—OR$^{149}$ wherein R$^{149}$ represents H or —(C$_1$-C$_4$)alkyl which may optionally bear up to 3 halogens;

4.5.e) —C(O)—NR$^{150}$R$^{151}$ wherein
R$^{150}$ represents H or (C$_1$-C$_3$)alkyl which may optionally bear halogen; and
R$^{151}$ represents H or —(C$_1$-C$_4$)alkyl which is optionally substituted with
- 4.5.e1) halogen;
- 4.5.e2) a 5-6 membered heteroaromatic containing up to two heteroatoms selected from O, S, and N;
- 4.5.e3) phenyl;
- 4.5.e4) —SO$_2$CH$_3$;
- 4.5.e5) —OR$^{152}$ wherein R$^{152}$ represents H or (C$_1$-C$_3$)alkyl which may optionally bear halogen; or
- 4.5.e6) —NR$^{153}$R$^{154}$ in which R$^{153}$ and R$^{154}$ are independently H or —(C$_1$-C$_3$)alkyl which may optionally bear halogen, or R$^{153}$ and R$^{154}$ may be joined and taken together with the N atom to which they are attached form a 5-6 membered ring which may optionally contain a ring member selected from O, S, and NR$^{155}$ wherein R$^{155}$ represents H or (C$_1$-C$_3$)alkyl;

4.5.f) —N(R$^{156}$)—C(O)—R$^{157}$ wherein
R$^{156}$ represents H or (C$_1$-C$_3$)alkyl; and
R$^{157}$ represents H, optionally substituted phenyl, or (C$_1$-C$_4$)alkyl which is optionally substituted with
- 4.5.f1) optionally substituted phenyl,
- 4.5.f2) OR$^{158}$ wherein R$^{158}$ represents H or (C$_1$-C$_3$) alkyl, or
- 4.5.f3) NR$^{159}$R$^{160}$ wherein R$^{159}$ and R$^{160}$ are independently H or —(C$_1$-C$_3$)alkyl which may optionally bear halogen, or R$^{159}$ and R$^{160}$ may be joined and taken together with the N atom to which they are attached form a 5-6 membered ring which may optionally contain a ring member selected from O, S, and NR$^{161}$ wherein R$^{161}$ represents H or (C$_1$-C$_3$)alkyl;

4.5.g) —SO$_2$NR$^{162}$R$^{163}$ wherein
R$^{162}$ represents H or (C$_1$-C$_3$)alkyl which may optionally bear halogen; and
R$^{163}$ represents H or —(C$_1$-C$_4$)alkyl which is optionally substituted with
- 4.5.g1) halogen;
- 4.5.g2) a 5-6 membered heteroaromatic containing up to two heteroatoms selected from O, S, and N;
- 4.5.g3) phenyl;
- 4.5.g4) —SO$_2$CH$_3$;
- 4.5.g5) —OR$^{164}$ wherein R$^{164}$ represents H or (C$_1$-C$_3$)alkyl which may optionally bear halogen; or
- 4.5.g6) —NR$^{165}$R$^{166}$ in which R$^{165}$ and R$^{166}$ are independently H or —(C$_1$-C$_3$)alkyl which may optionally bear halogen, or R$^{165}$ and R$^{166}$ may be joined and taken together with the N atom to which they are attached form a 5-6 membered ring which may optionally contain a ring member selected from O, S, and NR$^{167}$ wherein R$^{167}$ represents H or (C$_1$-C$_3$)alkyl;

4.5.h) —N(R$^{168}$)—SO$_2$—R$^{169}$ wherein
R$^{168}$ represents H or (C$_1$-C$_3$)alkyl, and
R$^{169}$ represents H, optionally substituted phenyl, or (C$_1$-C$_4$)alkyl which is optionally substituted with
- 4.5.h1) halogen,
- 4.5.h2) optionally substituted phenyl,
- 4.5.h3) OR$^{170}$ wherein R$^{170}$ represents H or (C$_1$-C$_3$)alkyl which may optionally bear halogen, or
- 4.5.h4) NR$^{171}$R$^{172}$ wherein R$^{171}$ and R$^{172}$ are independently H or —(C$_1$-C$_3$)alkyl which may optionally bear halogen, or R$^{171}$ and R$^{172}$ may be joined and taken together with the N atom to which they are attached form a 5-6 membered ring which may optionally contain a ring member selected from O, S, and NR$^{173}$ wherein R$^{173}$ represents H or (C$_1$-C$_3$)alkyl;

4.5.i) —NR$^{174}$R$^{175}$ in which R$^{174}$ and R$^{175}$ are independently H or —(C$_1$-C$_3$)alkyl which may optionally bear halogen or OR$^{175a}$ wherein R$^{175a}$ represents H or (C$_1$-C$_3$)alkyl, or R$^{174}$ and R$^{175}$ may be joined and taken together with the N atom to which they are attached form a 5-6 membered ring which may optionally contain a ring member selected from O, S, and $NR^{176}$ wherein $R^{176}$ represents H or $(C_1-C_3)$alkyl;

4.5.j) halogen;
4.5.k) optionally substituted phenyl;
4.5.l) $NO_2$;
4.5.m) CN; or
4.5.n) a 5-6 membered heteroaromatic containing up to two heteroatoms selected from O, S, and N; and k represents 0, 1, or 2;

4.6)

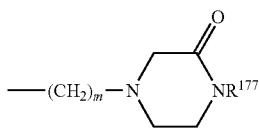

wherein $R^{177}$ represents H or $-(C_1-C_3)$alkyl; and
m represents 1, 2, or 3;

4.7)

 wherein n represents 1, 2, or 3; and
p represents 0, 1, or 2;

4.8)

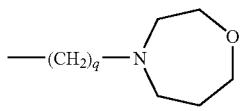

wherein
q represents 1, 2, or 3;

4.9)

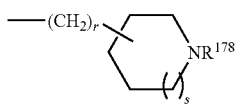

wherein
$R^{178}$ represents
  4.9.a) H;
  4.9.b) $-(C_1-C_3)$alkyl which may optionally bear halogen or $-OR^{179}$ in which $R^{179}$ represents H or $(C_1-C_3)$alkyl optionally substituted with halogen;
  4.9.c) $-SO_2R^{180}$ wherein $R^{180}$ represents optionally substituted phenyl or $-(C_1-C_3)$alkyl, which may be substituted with halogen or $-OR^{181}$ wherein $R^{181}$ represents H or $(C_1-C_3)$alkyl which may optionally bear halogen;
  4.9.d) $-C(O)R^{182}$ wherein $R^{182}$ represents optionally substituted phenyl or $-(C_1-C_3)$alkyl which may optionally bear up to 3 substituents independently selected from 4.9.d1) halogen;
    4.9.d2) optionally substituted phenyl;
    4.9.d3) $-S(O)_2CH_3$;
    4.9.d4) $OR^{183}$ wherein $R^{183}$ represents H or $(C_1-C_3)$alkyl which may optionally bear halogen; and
    4.9.d5) $-NR^{184}R^{185}$ in which $R^{184}$ and $R^{185}$ are independently H or $-(C_1-C_3)$alkyl which may optionally bear halogen or $OR^{185a}$ wherein $R^{185a}$ represents H or $(C_1-C_3)$alkyl, or $R^{184}$ and $R^{185}$ may be joined and taken together with the N atom to which they are attached form a 5-6 membered ring which may optionally contain a ring member selected from O, S, and $NR^{186}$ wherein $R^{186}$ represents H or $(C_1-C_3)$alkyl;
  4.9e) $-C(O)OR^{187}$ wherein $R^{187}$ represents $(C_1-C_3)$alkyl; or
  4.9.f) $-C(O)-NR^{188}R^{189}$ wherein $R^{188}$ and $R^{189}$ each independently represents H or $-(C_1-C_3)$alkyl which may optionally bear halogen, or $R^{188}$ and $R^{189}$ may be joined and taken together with the N atom to which they are attached form a 5-6 membered ring which may optionally contain a ring member selected from O, S, and $NR^{190}$ wherein $R^{190}$ represents H or $(C_1-C_3)$alkyl;

r represents 0, 1, or 2; and
s represents 0 or 1;

4.10)

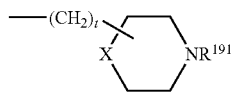

wherein
$R^{191}$ represents
  4.10.a) H;
  4.10.b) $-(C_1-C_3)$alkyl which may optionally bear halogen or $-OR^{192}$ in which $R^{192}$ represents H or $(C_1-C_3)$alkyl;
  4.10c) $-SO_2R^{193}$ wherein $R^{193}$ represents phenyl or $-(C_1-C_3)$alkyl, both of which may be substituted with halogen or $-(C_1-C_3)$alkyl;
  4.10.d) $-C(O)R^{194}$ wherein $R^{194}$ represents $(C_1-C_3)$alkyl which may optionally bear up to 3 substituents independently selected from
    4.10.d1) halogen;
    4.10.d2) phenyl;
    4.10.d3) $-S(O)_2CH_3$;
    4.10.d4) $OR^{195}$ wherein $R^{195}$ represents H or $(C_1-C_3)$alkyl which may optionally bear halogen; and
    4.10.d5) $-NR^{196}R^{197}$ in which $R^{196}$ and $R^{197}$ are independently H or $-(C_1-C_3)$alkyl which may optionally bear halogen or $OR^{197a}$ wherein $R^{197a}$ represents H or $(C_1-C_3)$alkyl, or $R^{196}$ and $R^{197}$ may be joined and taken together with the N atom to which they are attached form a 5-6 membered ring which may optionally contain a ring member selected from O, S, and $NR^{198}$ wherein $R^{198}$ represents H or $(C_1-C_3)$alkyl;
  4.10.e) $-C(O)OR^{199}$ wherein $R^{199}$ represents $(C_1-C_3)$alkyl; or
  4.10.f) $-C(O)-NR^{200}R^{201}$ wherein $R^{200}$ and $R^{201}$ each independently represents H or $-(C_1-C_3)$alkyl which may optionally bear halogen, or $R^{200}$ and $R^{201}$ may be joined and taken together with the N atom to which they are attached form a 5-6 membered ring which may optionally contain a ring member selected from O, S, and $NR^{202}$ wherein $R^{202}$ represents H or $(C_1$-$C_3)$alkyl; and X represents O, S, S(O), S(O)$_2$, or $NR^{203}$ wherein $R^{203}$ represents H or —$(C_1$-$C_3)$alkyl; and t represents 0, 1, or 2;

4.11) halogen; or 4.12) CN;

or a pharmaceutically acceptable salt thereof.

2. The compound of claim 1 wherein in formula (I)

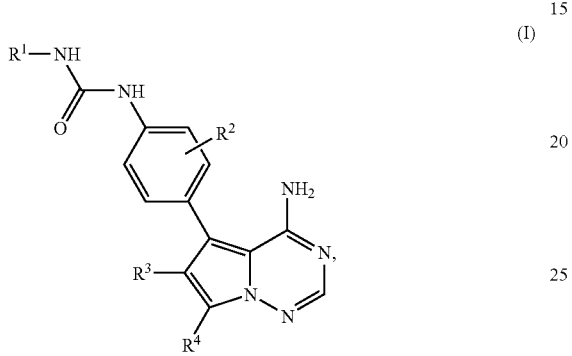

(I)

$R^1$ represents 1.1) phenyl which may optionally bear up to 4 substituents independently selected from the group consisting of
- 1.1.a) $(C_1$-$C_4)$alkyl, which may optionally bear up to 3 substituents independently selected from
  - 1.1.a1) halogen;
  - 1.1.a2) $OR^5$ wherein $R^5$ represents H or $(C_1$-$C_3)$ alkyl which may optionally bear halogen or —$(C_1$-$C_3)$mono- or di-alkylamino;
  - 1.1.a3) —$NR^6R^7$ in which $R^6$ and $R^7$ are independently H or —$(C_1$-$C_3)$alkyl which may optionally bear halogen or $OR^{7a}$ wherein $R^{7a}$ represents H or $(C_1$-$C_3)$alkyl, or $R^6$ and $R^7$ may be joined and taken together with the N atom to which they are attached form a 5-6 membered ring which may optionally contain a ring member selected from O, S, and $NR^8$ wherein $R^8$ represents H or $(C_1$-$C_3)$alkyl; and
  - 1.1.a4) a 5-6 membered heteroaromatic containing up to two heteroatoms selected from O, S, and N;
- 1.1.b) —$(C_3$-$C_6)$cycloalkyl which may optionally bear up to 2 substituents independently selected from
  - 1.1.b1) halogen;
- 1.1.c) $OR^{10}$ wherein
  $R^{10}$ represents H; phenyl; benzyl; $(C_3$-$C_6)$cycloalkyl; or $(C_1$-$C_4)$alkyl which may optionally bear up to 3 substituents independently selected from
  - 1.1.c1) halogen;
  - 1.1.c2) $OR^{11}$ wherein $R^{11}$ represents H or $(C_1$-$C_3)$ alkyl which may optionally bear $(C_1$-$C_3)$mono- or di-alkylamino; and
  - 1.1.c3) $NR^{12}R^{13}$ in which $R^{12}$ and $R^{13}$ are independently H or —$(C_1$-$C_3)$alkyl which may optionally bear halogen, or $R^{12}$ and $R^{13}$ may be joined and taken together with the N atom to which they are attached form a 5-6 membered ring which may optionally contain a ring member selected from O, S, and $NR^{14}$ wherein $R^{14}$ represents H or $(C_1$-$C_3)$alkyl;
- 1.1.e) —C(O)—$NR^{16}R^{17}$ wherein
  $R^{16}$ represents H or $(C_1$-$C_3)$alkyl which may optionally bear halogen; and
  $R^{17}$ represents H or —$(C_1$-$C_4)$alkyl which is optionally substituted with
  - 1.1.e1) halogen;
  - 1.1.e3) phenyl;
  - 1.1.e4) —$SO_2CH_3$;
  - 1.1.e5) —$OR^{18}$ wherein $R^{18}$ represents H or $(C_1$-$C_3)$alkyl which may optionally bear halogen; or
  - 1.1.e6) —$NR^{19}R^{20}$ in which $R^{19}$ and $R^{20}$ are independently H or —$(C_1$-$C_3)$alkyl which may optionally bear halogen, or $R^{19}$ and $R^{20}$ may be joined and taken together with the N atom to which they are attached form a 5-6 membered ring which may optionally contain a ring member selected from O, S, and $NR^{21}$ wherein $R^{21}$ represents H or $(C_1$-$C_3)$alkyl;
- 1.1.f) —$N(R^{22})$—C(O)—$R^{23}$ wherein
  $R^{22}$ represents H or $(C_1$-$C_3)$alkyl; and
  $R^{23}$ represents optionally substituted phenyl, or $(C_1$-$C_4)$alkyl which is optionally substituted with
  - 1.1.f1) optionally substituted phenyl,
  - 1.1.f2) $OR^{24}$ wherein $R^{24}$ represents H or $(C_1$-$C_3)$ alkyl, or
  - 1.1.f3) $NR^{25}R^{26}$ wherein $R^{25}$ and $R^{26}$ are independently H or —$(C_1$-$C_3)$alkyl which may optionally bear halogen, or $R^{25}$ and $R^{26}$ may be joined and taken together with the N atom to which they are attached form a 5-6 membered ring which may optionally contain a ring member selected from O, S, and $NR^{27}$ wherein $R^{27}$ represents H or $(C_1$-$C_3)$alkyl;
- 1.1.g) —$SO_2NR^{28}R^{29}$ wherein
  $R^{28}$ represents H or $(C_1$-$C_3)$alkyl which may optionally bear halogen; and
  $R^{29}$ represents H or —$(C_1$-$C_4)$alkyl which is optionally substituted with:
  - 1.1.g1) halogen;
  - 1.1.g3) phenyl;
  - 1.1.g4) —$SO_2CH_3$;
  - 1.1.g5) —$OR^{30}$ wherein $R^{30}$ represents H or $(C_1$-$C_3)$alkyl which may optionally bear halogen; or
  - 1.1.g6) —$NR^{31}R^{32}$ in which $R^{31}$ and $R^{32}$ are independently H or —$(C_1$-$C_3)$alkyl which may optionally bear halogen, or $R^{31}$ and $R^{32}$ may be joined and taken together with the N atom to which they are attached form a 5-6 membered ring which may optionally contain a ring member selected from O, S, and $NR^{33}$ wherein $R^{33}$ represents H or $(C_1$-$C_3)$alkyl;
- 1.1.h) —$N(R^{34})$—$SO_2$—$R^{35}$ wherein
  $R^{34}$ represents H or $(C_1$-$C_3)$alkyl, and
  $R^{35}$ represents optionally substituted phenyl, or $(C_1$-$C_4)$alkyl which is optionally substituted with
  - 1.1.h1) halogen;
  - 1.1.h2) optionally substituted phenyl,
  - 1.1.h3) $OR^{36}$ wherein $R^{36}$ represents H or $(C_1$-$C_3)$ alkyl, or
  - 1.1.h4) $NR^{37}R^{38}$ wherein $R^{37}$ and $R^{38}$ are independently H or —$(C_1$-$C_3)$alkyl which may optionally bear halogen, or $R^{37}$ and $R^{38}$ may be joined and taken together with the N atom to which they are attached form a 5-6 membered ring which may optionally contain a ring member selected from O, S, and $NR^{39}$ wherein $R^{39}$ represents H or $(C_1\text{-}C_3)$alkyl;

1.1.i) —$NR^{40}R^{41}$ in which $R^{40}$ and $R^{41}$ are independently H or —$(C_1\text{-}C_3)$alkyl which may optionally bear halogen or $OR^{42}$ in which $R^{42}$ represents H or $(C_1\text{-}C_3)$alkyl, or $R^{40}$ and $R^{41}$ may be joined and taken together with the N atom to which they are attached form a 5-6 membered ring which may optionally contain a ring member selected from O, S, and $NR^{43}$ wherein $R^{43}$ represents H or $(C_1\text{-}C_3)$alkyl;

1.1.j) halogen;

1.1.l) $NO_2$;

1.1.m) CN; and 1.1.n) a 5-6 membered heteroaromatic containing up to two heteroatoms selected from O, S, and N;

or $R^1$ represents 1.2) a 5-6 membered aromatic heterocycle containing up to 3 heteroatoms independently selected from the group consisting of N, O, and S; said $R^1$ heterocycle optionally bearing up to 4 substituents independently selected from the group consisting of 1.2.a) $(C_1\text{-}C_4)$alkyl, which may optionally bear up to 3 substituents independently selected from 1.2.a1) halogen;

1.2.a2) $OR^{45}$ wherein $R^{45}$ represents H or $(C_1\text{-}C_3)$ alkyl which may optionally bear halogen or —$(C_1\text{-}C_3)$mono- or di-alkylamino;

1.2.a3) —$NR^{46}R^{47}$ in which $R^{46}$ and $R^{47}$ are independently H or —$(C_1\text{-}C_3)$alkyl which may optionally bear halogen or $OR^{47a}$ wherein $R^{47a}$ represents H or $(C_1\text{-}C_3)$alkyl, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or $(C_1\text{-}C_3)$alkyl; and 1.2.a4) a 5-6 membered heteroaromatic containing up to two heteroatoms selected from O, S, and N;

1.2.b) —$(C_3\text{-}C_6)$cycloalkyl which may optionally bear up to 2 substituents independently selected from 1.2.b1) halogen;

1.2.c) $OR^{50}$ wherein $R^{50}$ represents H; phenyl; benzyl; —$(C_3\text{-}C_6)$cycloalkyl; or —$(C_1\text{-}C_4)$alkyl which may optionally bear up to 3 substituents independently selected from 1.2.c1) halogen;

1.2.c2) $OR^{51}$ wherein $R^{51}$ represents H or $(C_1\text{-}C_3)$ alkyl which may optionally bear —$(C_1\text{-}C_3)$ mono- or di-alkylamino; and 1.2.c3) —$NR^{52}R^{53}$ in which $R^{52}$ and $R^{53}$ are independently H or —$(C_1\text{-}C_3)$alkyl which may optionally bear halogen, or $R^{52}$ and $R^{53}$ may be joined and taken together with the N atom to which they are attached form a 5-6 membered ring which may optionally contain a ring member selected from O, S, and $NR^{54}$ wherein $R^{54}$ represents H or $(C_1\text{-}C_3)$alkyl;

1.2.e) —$C(O)$—$NR^{56}R^{57}$ wherein $R^{56}$ represents H or $(C_1\text{-}C_3)$alkyl which may optionally bear halogen; and $R^{57}$ represents H or —$(C_1\text{-}C_4)$alkyl which is optionally substituted with 1.2.e1) halogen;

1.2.e3) phenyl;

1.2.e4) —$SO_2CH_3$;

1.2.e5) —$OR^{58}$ wherein $R^{58}$ represents H or $(C_1\text{-}C_3)$alkyl which may optionally bear halogen; or 1.2.e6) —$NR^{59}R^{60}$ in which $R^{59}$ and $R^{60}$ are independently H or —$(C_1\text{-}C_3)$alkyl which may optionally bear halogen, or $R^{59}$ and $R^{60}$ may be joined and taken together with the N atom to which they are attached form a 5-6 membered ring which may optionally contain a ring member selected from O, S, and $NR^{61}$ wherein $R^{61}$ represents H or $(C_1\text{-}C_3)$alkyl;

1.2.f) —$N(R^{62})$—$C(O)$—$R^{63}$ wherein $R^{62}$ represents H or $(C_1\text{-}C_3)$alkyl; and $R^{63}$ represents optionally substituted phenyl, or $(C_1\text{-}C_4)$alkyl which is optionally substituted with 1.2.f1) optionally substituted phenyl, 1.2.f2) $OR^{64}$ wherein $R^{64}$ represents H or $(C_1\text{-}C_3)$ alkyl, or 1.2.f3) $NR^{65}R^{66}$ wherein $R^{65}$ and $R^{66}$ are independently H or —$(C_1\text{-}C_3)$alkyl which may optionally bear halogen, or $R^{65}$ and $R^{66}$ may be joined and taken together with the N atom to which they are attached form a 5-6 membered ring which may optionally contain a ring member selected from O, S, and $NR^{67}$ wherein $R^{67}$ represents H or $(C_1\text{-}C_3)$alkyl;

1.2.g) —$SO_2NR^{68}R^{69}$ wherein $R^{68}$ represents H or $(C_1\text{-}C_3)$alkyl which may optionally bear halogen; and $R^{69}$ represents H or —$(C_1\text{-}C_4)$alkyl which is optionally substituted with 1.2.g1) halogen;

1.2.g3) phenyl;

1.2.g4) —$SO_2CH_3$;

1.2.g5) —$OR^{70}$ wherein $R^{70}$ represents H or $(C_1\text{-}C_3)$alkyl which may optionally bear halogen; or 1.2.g6 —$NR^{71}R^{72}$ in which $R^{71}$ and $R^{72}$ are independently H or —$(C_1\text{-}C_3)$alkyl which may optionally bear halogen, or $R^{71}$ and $R^{72}$ may be joined and taken together with the N atom to which they are attached form a 5-6 membered ring which may optionally contain a ring member selected from O, S, and $NR^{73}$ wherein $R^{73}$ represents H or $(C_1\text{-}C_3)$alkyl;

1.2.h) —$N(R^{74})$—$SO_2$—$R^{75}$ wherein $R^{74}$ represents H or $(C_1\text{-}C_3)$alkyl, and $R^{75}$ represents optionally substituted phenyl, or $(C_1\text{-}C_4)$alkyl which is optionally substituted with 1.2.h1) halogen;

1.2.h2) optionally substituted phenyl, 1.2.h3) $OR^{76}$ wherein $R^{76}$ represents H or $(C_1\text{-}C_3)$ alkyl, or 1.2.h4) $NR^{77}R^{78}$ wherein $R^{77}$ and $R^{78}$ are independently H or —$(C_1\text{-}C_3)$alkyl which may optionally bear halogen, or $R^{77}$ and $R^{78}$ may be joined and taken together with the N atom to which they are attached form a 5-6 membered ring which may optionally contain a ring member selected from O, S, and $NR^{79}$ wherein $R^{79}$ represents H or $(C_1-C_3)$alkyl;

1.2.i) $-NR^{80}R^{81}$ in which $R^{80}$ and $R^{81}$ are independently H or $-(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$alkyl;

1.2.j) halogen;
1.2.k) optionally substituted phenyl;
1.2.l) $NO_2$;
1.2.m) CN; and
1.2.n) a 5-6 membered heteroaromatic containing up to two heteroatoms selected from O, S, and N;

$R^2$ represents hydrogen; halogen; $-(C_1-C_5)$alkyl which may optionally bear halogen; or $-(C_1-C_3)$alkyl which may optionally bear halogen;

$R^3$ represents 3.1) $-(C_1-C_5)$alkyl which is substituted with
  3.1.a) -halogen;
  3.1.b) phenyl optionally substituted with halogen, $-(C_1-C_3)$alkyl, or $-(C_1-C_3)$alkoxy,
  3.1.c) a 5-6 membered heteroaromatic containing up to two heteroatoms selected from O, S, and N, optionally substituted with halogen or $-(C_1-C_3)$alkyl,
  3.1.d) $-CN$,
  3.1.e) $-OR^{83}$ wherein $R^{83}$ represents H or $-(C_1-C_3)$alkyl which may optionally bear up to 3 substituents independently selected from
    3.1.e1) halogen;
    3.1.e2) optionally substituted phenyl;
    3.1.e3) $-S(O)_2CH_3$;
    3.1.e4) $OR^{84}$ wherein $R^{84}$ represents H or $(C_1-C_3)$alkyl which may optionally bear halogen or $-(C_1-C_3)$mono- or di-alkylamino; and
    3.1.e5) $-NR^{85}R^{86}$ in which $R^{85}$ and $R^{86}$ are independently H or $-(C_1-C_3)$alkyl which may optionally bear halogen, or $R^{85}$ and $R^{86}$ may be joined and taken together with the N atom to which they are attached form a 5-6 membered ring which may optionally contain a ring member selected from O, S, and $NR^{87}$ wherein $R^{87}$ represents H or $(C_1-C_3)$alkyl;
  3.1.f) $-(C_3-C_5)$cycloalkyl which may optionally bear halogen; or
  3.1.g) $-NR^{89}R^{90}$ wherein
    $R^{89}$ represents H or $-(C_1-C_3)$alkyl which may optionally bear halogen; and
    $R^{90}$ represents H or $-(C_1-C_4)$alkyl which is optionally substituted with
    3.1.g1) halogen;
    3.1.g2) a 5-6 membered heteroaromatic containing up to two heteroatoms selected from O, S, and N;
    3.1.g3) phenyl;
    3.1.g4) $-SO_2CH_3$;
    3.1.g5) $-OR^{91}$ wherein $R^{91}$ represents H or $(C_1-C_3)$alkyl which may optionally bear halogen; or
    3.1.g6) $-NR^{92}R^{93}$ in which $R^{92}$ and $R^{93}$ are independently H or $-(C_1-C_3)$alkyl which may optionally bear halogen, or $R^{92}$ and $R^{93}$ may be joined and taken together with the N atom to which they are attached form a 5-6 membered ring which may optionally contain a ring member selected from O, S, and $NR^{94}$ wherein $R^{94}$ represents H or $(C_1-C_3)$alkyl; or
    3.1.g7) $R^{89}$ and $R^{90}$ may be joined and taken together with the N to which they are attached form an aromatic or nonaromatic 5-6 membered ring which may optionally contain a ring member selected from O, S, and $NR^{95}$ wherein $R^{95}$ represents H or $(C_1-C_3)$alkyl;

3.2)

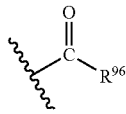

wherein
$R^{96}$ represents
3.2.a) H,
3.2.b) $-(C_3-C_5)$cycloalkyl which may optionally bear halogen; or
3.2.c) $-(C_1-C_5)$alkyl which may optionally bear up to 3 substituents independently selected from
  3.2.c1) halogen;
  3.2.c2) a 5-6 membered heteroaromatic containing up to two heteroatoms selected from O, S, and N;
  3.2.c3) phenyl;
  3.2.c5) $-OR^{97}$ wherein $R^{97}$ represents H or $(C_1-C_3)$alkyl which may optionally bear halogen or $-(C_1-C_3)$mono- or di-alkylamino; and
  3.2.c6) $-NR^{98}R^{99}$ in which $R^{98}$ and $R^{99}$ are independently H or $-(C_1-C_3)$alkyl which may optionally bear halogen or $OR^{99a}$ wherein $R^{99a}$ represents H or $(C_1-C_3)$alkyl, or $R^{98}$ and $R^{99}$ may be joined and taken together with the N atom to which they are attached form a 5-6 membered ring which may optionally contain a ring member selected from O, S, and $NR^{100}$ wherein $R^{100}$ represents H or $(C_1-C_3)$alkyl;

3.3)

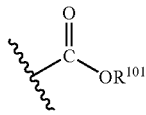

wherein $R^{101}$ represents H or $-(C_1-C_5)$alkyl which may optionally bear up to 3 substituents independently selected from
3.3.a) halogen; and
3.3.b) phenyl;

3.4)

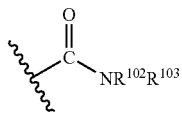

wherein
R$^{102}$ represents H or —(C$_1$-C$_3$)alkyl which may optionally bear halogen; and
R$^{103}$ represents H or —(C$_1$-C$_5$)alkyl which may optionally bear up to 3 substituents independently selected from
3.4.a) halogen;
3.4.b) a 5-6 membered heteroaromatic containing up to two heteroatoms selected from O, S, and N;
3.4.c) phenyl;
3.4.d) —S(O)$_2$CH$_3$;
3.4.e) OR$^{104}$ wherein R$^{104}$ represents H or (C$_1$-C$_3$)alkyl which may optionally bear halogen; and
3.4.f) —NR$^{105}$R$^{106}$ in which R$^{105}$ and R$^{106}$ are independently H or —(C$_1$-C$_3$)alkyl which may optionally bear halogen, or R$^{105}$ and R$^{106}$ may be joined and taken together with the N atom to which they are attached form a 5-6 membered ring which may optionally contain a ring member selected from O, S, and NR$^{107}$ wherein R$^{107}$ represents H or (C$_1$-C$_3$)alkyl;
3.6) a 5-6 membered heteroaromatic containing up to two heteroatoms selected from O, S, and N;
3.7) halogen; or
3.8) —CN;
R$^4$ represents
4.1) —(C$_1$-C$_5$)alkyl which is substituted with
4.1.a) —(C$_3$-C$_5$)cycloalkyl which may optionally bear halogen or OR$^{109}$ wherein R$^{109}$ represents H or (C$_1$-C$_3$)alkyl;
4.1.b) -halogen;
4.1.c) —OR$^{110}$ wherein R$^{110}$ represents H or —(C$_1$-C$_3$)alkyl which may optionally bear up to 3 substituents independently selected from
4.1.c1) halogen;
4.1.c2) phenyl;
4.1.c4) OR$^{111}$ wherein R$^{111}$ represents H or (C$_1$-C$_3$)alkyl which may optionally bear halogen; and
4.1.c5) —NR$^{112}$R$^{113}$ in which R$^{112}$ and R$^{113}$ are independently H or —(C$_1$-C$_3$)alkyl which may optionally bear halogen, or R$^{112}$ and R$^{113}$ may be joined and taken together with the N atom to which they are attached form a 5-6 membered ring which may optionally contain a ring member selected from O, S, and NR$^{114}$ wherein R$^{114}$ represents H or (C$_1$-C$_3$)alkyl;
4.1.d) —NR$^{115}$R$^{116}$ wherein
R$^{115}$ represents H or —(C$_1$-C$_3$)alkyl which may optionally bear halogen and
R$^{116}$ represents H, optionally substituted phenyl, or —(C$_1$-C$_5$)alkyl which may optionally bear up to 3 substituents independently selected from
4.1.d1) halogen;
4.1.d2) —S(O)$_2$CH$_3$;
4.1.d3) OR$^{117}$ wherein R$^{117}$ represents H or (C$_1$-C$_3$)alkyl which may optionally bear halogen; and
4.1.d4) —NR$^{118}$R$^{119}$ in which R$^{118}$ and R$^{119}$ are independently H or —(C$_1$-C$_3$)alkyl which may optionally bear halogen, or R$^{118}$ and R$^{119}$ may be joined and taken together with the N atom to which they are attached form a 5-6 membered ring which may optionally contain a ring member selected from O, S, and NR$^{120}$ wherein R$^{120}$ represents H or (C$_1$-C$_3$)alkyl; or 4.1.f) a 5-6 membered aromatic heterocycle containing up to two heteroatoms selected from O, S, and N;
4.2)

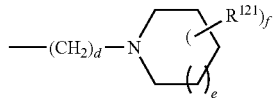

wherein R$^{121}$ represents —(C$_1$-C$_3$)alkyl which may optionally bear halogen or —OR$^{122}$ in which R$^{122}$ represents H or —(C$_1$-C$_3$)alkyl;
d represents 1, 2, or 3;
e represents 0 or 1;
f represents 0, 1, or 2;
4.3)

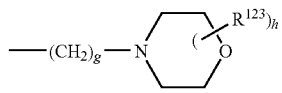

wherein R$^{123}$ represents —(C$_1$-C$_3$)alkyl which may optionally bear halogen or —OR$^{124}$ in which R$^{124}$ represents H or —(C$_1$-C$_3$)alkyl;
g represents 1, 2, or 3;
h represents 0, 1, or 2;
4.4)

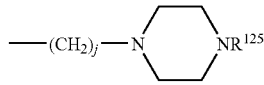

wherein
R$^{125}$ represents
4.4.a) H;
4.4.b) —(C$_1$-C$_3$)alkyl which may optionally bear halogen or —OR$^{126}$ in which R$^{126}$ represents H or —(C$_1$-C$_3$)alkyl which in turn is optionally substituted with halogen;
4.4.c) —SO$_2$R$^{127}$ wherein R$^{127}$ represents optionally substituted phenyl, or —(C$_1$-C$_3$)alkyl which may optionally bear halogen or OR$^{128}$ wherein R$^{128}$ represents H or (C$_1$-C$_3$)alkyl;
4.4.d) —C(O)R$^{129}$ wherein
R$^{129}$ represents
4.4.d1) optionally substituted phenyl,
4.4.d2) —(C$_1$-C$_3$)alkyl which may optionally bear up to 3 substituents independently selected from
4.4.d2.1) halogen;
4.4.d2.4) —OR$^{130}$ wherein R$^{130}$ represents H or (C$_1$-C$_3$)alkyl which may optionally bear halogen; and
4.4.d2.5) —NR$^{131}$R$^{132}$ in which R$^{131}$ and R$^{132}$ are independently H or —(C$_1$-C$_3$)alkyl which may optionally bear halogen, or R$^{131}$ and R$^{132}$ may be joined and taken together with the N atom to which they are attached form a 5-6 membered ring which may optionally contain a ring member selected from O, S, and NR$^{133}$ wherein R$^{133}$ represents H or (C$_1$-C$_3$)alkyl;

4.4.d3) —OR$^{134}$ wherein R$^{134}$ represents (C$_1$-C$_3$) alkyl which may optionally bear halogen; or 4.4.d4) NR$^{135}$R$^{136}$ wherein R$^{135}$ and R$^{136}$ are independently H or —(C$_1$-C$_3$)alkyl which may optionally bear halogen, or R$^{135}$ and R$^{136}$ may be joined and taken together with the N atom to which they are attached form a 5-6 membered ring which may optionally contain a ring member selected from O, S, and NR$^{137}$ wherein R$^{137}$ represents H or (C$_1$-C$_3$)alkyl; and j represents 1, 2, or 3;

4.5)

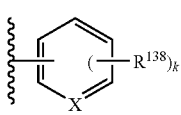

wherein

X represents C or N;

R$^{138}$ represents 4.5.a) (C$_1$-C$_4$)alkyl, which may optionally bear up to 3 substituents independently selected from 4.5.a1) halogen;

4.5.a2) OR$^{139}$ wherein R$^{139}$ represents H or (C$_1$-C$_3$)alkyl which may optionally bear halogen or —(C$_1$-C$_3$)mono- or di-alkylamino;

4.5.a3) —NR$^{140}$R$^{141}$ in which R$^{140}$ and R$^{141}$ are independently H or —(C$_1$-C$_3$)alkyl which may optionally bear halogen or OR$^{141a}$ wherein R$^{141a}$ represents H or (C$_1$-C$_3$)alkyl, or R$^{140}$ and R$^{141}$ may be joined and taken together with the N atom to which they are attached form a 5-6 membered ring which may optionally contain a ring member selected from O, S, and NR$^{142}$ wherein R$^{142}$ represents H or (C$_1$-C$_3$)alkyl; and 4.5.a4) a 5-6 membered heteroaromatic containing up to two heteroatoms selected from O, S, and N;

4.5.b) —(C$_3$-C$_6$)cycloalkyl which may optionally bear up to 2 substituents independently selected from 4.5.b1) halogen;

4.5.c) OR$^{144}$ wherein

R$^{144}$ represents H; phenyl; benzyl; (C$_3$-C$_6$)cycloalkyl; or (C$_1$-C$_4$)alkyl which may optionally bear up to 3 substituents independently selected from 4.5.c1) halogen;

4.5.c2) OR$^{145}$ wherein R$^{145}$ represents H or (C$_1$-C$_3$)alkyl which may optionally bear (C$_1$-C$_3$) mono- or di-alkylamino; and 4.5.c3) NR$^{146}$R$^{147}$ in which R$^{146}$ and R$^{1473}$ are independently H or —(C$_1$-C$_3$)alkyl which may optionally bear halogen, or R$^{146}$ and R$^{147}$ may be joined and taken together with the N atom to which they are attached form a 5-6 membered ring which may optionally contain a ring member selected from O, S, and NR$^{148}$ wherein R$^{148}$ represents H or (C$_1$-C$_3$)alkyl;

4.5.e) —C(O)—NR$^{150}$R$^{151}$ wherein

R$^{150}$ represents H or (C$_1$-C$_3$)alkyl which may optionally bear halogen; and R$^{151}$ represents H or —(C$_1$-C$_4$)alkyl which is optionally substituted with 4.5.e1) halogen;

4.5.e3) phenyl;

4.5.e4) —SO$_2$CH$_3$;

4.5.e5) —OR$^{152}$ wherein R$^{152}$ represents H or (C$_1$-C$_3$)alkyl which may optionally bear halogen; or 4.5.e6) —NR$^{153}$R$^{154}$ in which R$^{153}$ and R$^{154}$ are independently H or —(C$_1$-C$_3$)alkyl which may optionally bear halogen, or R$^{153}$ and R$^{154}$ may be joined and taken together with the N atom to which they are attached form a 5-6 membered ring which may optionally contain a ring member selected from O, S, and NR$^{155}$ wherein R$^{155}$ represents H or (C$_1$-C$_3$)alkyl;

4.5.f) —N(R$^{156}$)—C(O)—R$^{157}$ wherein

R$^{156}$ represents H or (C$_1$-C$_3$)alkyl; and

R$^{157}$ represents H, optionally substituted phenyl, or (C$_1$-C$_4$)alkyl which is optionally substituted with 4.5.f1) optionally substituted phenyl, 4.5.f2) OR$^{158}$ wherein R$^{158}$ represents H or (C$_1$-C$_3$) alkyl, or 4.5.f3) NR$^{159}$R$^{160}$ wherein R$^{159}$ and R$^{160}$ are independently H or —(C$_1$-C$_3$)alkyl which may optionally bear halogen, or R$^{159}$ and R$^{160}$ may be joined and taken together with the N atom to which they are attached form a 5-6 membered ring which may optionally contain a ring member selected from O, S, and NR$^{161}$ wherein R$^{161}$ represents H or (C$_1$-C$_3$)alkyl;

4.5.g) —SO$_2$NR$^{162}$R$^{163}$ wherein

R$^{162}$ represents H or (C$_1$-C$_3$)alkyl which may optionally bear halogen; and R$^{163}$ represents H or —(C$_1$-C$_4$)alkyl which is optionally substituted with 4.5.g1) halogen;

4.5.g3) phenyl;

4.5.g4) —SO$_2$CH$_3$;

4.5.g5) —OR$^{164}$ wherein R$^{164}$ represents H or (C$_1$-C$_3$)alkyl which may optionally bear halogen; or 4.5.g6) —NR$^{165}$R$^{166}$ in which R$^{165}$ and R$^{166}$ are independently H or —(C$_1$-C$_3$)alkyl which may optionally bear halogen, or R$^{165}$ and R$^{166}$ may be joined and taken together with the N atom to which they are attached form a 5-6 membered ring which may optionally contain a ring member selected from O, S, and NR$^{167}$ wherein R$^{167}$ represents H or (C$_1$-C$_3$)alkyl;

4.5.h) —N(R$^{168}$)—SO$_2$—R$^{169}$ wherein

R$^{168}$ represents H or (C$_1$-C$_3$)alkyl, and

R$^{169}$ represents H, optionally substituted phenyl, or (C$_1$-C$_4$)alkyl which is optionally substituted with 4.5.h1) halogen, 4.5.h2) optionally substituted phenyl, 4.5.h3) OR$^{170}$ wherein R$^{170}$ represents H or (C$_1$-C$_3$)alkyl which may optionally bear halogen, or 4.5.h4) NR$^{171}$R$^{172}$ wherein R$^{171}$ and R$^{172}$ are independently H or —(C$_1$-C$_3$)alkyl which may optionally bear halogen, or R$^{171}$ and R$^{172}$ may be joined and taken together with the N atom to which they are attached form a 5-6 membered ring which may optionally contain a ring member selected from O, S, and NR$^{173}$ wherein R$^{173}$ represents H or (C$_1$-C$_3$)alkyl;

4.5.i) —NR$^{174}$R$^{175}$ in which R$^{174}$ and R$^{175}$ are independently H or —(C$_1$-C$_3$)alkyl which may optionally bear halogen or OR$^{175a}$ wherein R$^{175a}$ represents H or (C$_1$-C$_3$)alkyl, or R$^{174}$ and R$^{175}$ may be joined and taken together with the N atom to which they are attached form a 5-6 membered ring which may optionally contain a ring member selected from O, S, and NR$^{176}$ wherein R$^{176}$ represents H or (C$_1$-C$_3$)alkyl;

4.5.j) halogen;

4.5.l) NO$_2$;

4.5.m) CN; or 4.5.n) a 5-6 membered heteroaromatic containing up to two heteroatoms selected from O, S, and N; and k represents 0, 1, or 2;

4.6)

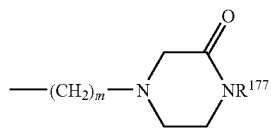

wherein R$^{177}$ represents H or —(C$_1$-C$_3$)alkyl; and
m represents 1, 2, or 3;

4.7)

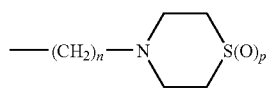

wherein
n represents 1, 2, or 3; and
p represents 0, 1, or 2;

4.8)

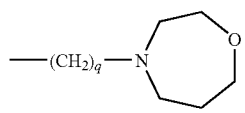

wherein
q represents 1, 2, or 3;

4.9)

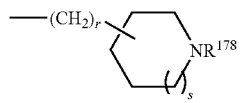

wherein
R$^{178}$ represents 4.9.a) H;

4.9.b) —(C$_1$-C$_3$)alkyl which may optionally bear halogen or —OR$^{179}$ in which R$^{179}$ represents H or (C$_1$-C$_3$)alkyl optionally substituted with halogen;

4.9.c) —SO$_2$R$^{180}$ wherein R$^{180}$ represents optionally substituted phenyl or —(C$_1$-C$_3$)alkyl, which may be substituted with halogen or —OR$^{181}$ wherein R$^{181}$ represents H or (C$_1$-C$_3$)alkyl which may optionally bear halogen;

4.9.d) —C(O)R$^{182}$ wherein R$^{182}$ represents optionally substituted phenyl or —(C$_1$-C$_3$)alkyl which may optionally bear up to 3 substituents independently selected from 4.9.d1) halogen;

4.9.d2) optionally substituted phenyl;

4.9.d4) OR$^{183}$ wherein R$^{183}$ represents H or (C$_1$-C$_3$)alkyl which may optionally bear halogen; and 4.9.d5) —NR$^{184}$R$^{185}$ in which R$^{184}$ and R$^{185}$ are independently H or —(C$_1$-C$_3$)alkyl which may optionally bear halogen or OR$^{185a}$ wherein R$^{185a}$ represents H or (C$_1$-C$_3$)alkyl, or R$^{184}$ and R$^{185}$ may be joined and taken together with the N atom to which they are attached form a 5-6 membered ring which may optionally contain a ring member selected from O, S, and NR$^{186}$ wherein R$^{186}$ represents H or (C$_1$-C$_3$)alkyl;

4.9e) —C(O)OR$^{187}$ wherein R$^{187}$ represents (C$_1$-C$_3$) alkyl; or 4.9.f) —C(O)—NR$^{188}$R$^{189}$ wherein R$^{188}$ and R$^{189}$ each independently represents H or —(C$_1$-C$_3$)alkyl which may optionally bear halogen, or R$^{188}$ and R$^{189}$ may be joined and taken together with the N atom to which they are attached form a 5-6 membered ring which may optionally contain a ring member selected from O, S, and NR$^{190}$ wherein R$^{190}$ represents H or (C$_1$-C$_3$)alkyl;

r represents 0, 1, or 2; and s represents 0 or 1;

4.10)

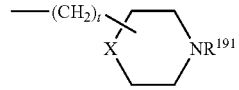

wherein
R$^{191}$ represents 4.10.a) H;

4.10.b) —(C$_1$-C$_3$)alkyl which may optionally bear halogen or —OR$^{192}$ in which R$^{192}$ represents H or (C$_1$-C$_3$)alkyl;

4.10c) —SO$_2$R$^{193}$ wherein R$^{193}$ represents phenyl or —(C$_1$-C$_3$)alkyl, both of which may be substituted with halogen or —(C$_1$-C$_3$)alkyl;

4.10.d) —C(O)R$^{194}$ wherein R$^{194}$ represents (C$_1$-C$_3$)alkyl which may optionally bear up to 3 substituents independently selected from 4.10.d1) halogen;

4.10.d2) phenyl;

4.10.d4) OR$^{195}$ wherein R$^{195}$ represents H or (C$_1$-C$_3$)alkyl which may optionally bear halogen; and 4.10.d5) —NR$^{196}$R$^{197}$ in which R$^{196}$ and R$^{197}$ are independently H or —(C$_1$-C$_3$)alkyl which may optionally bear halogen or OR$^{197a}$ wherein R$^{197a}$ represents H or (C$_1$-C$_3$)alkyl, or R$^{196}$ and R$^{197}$ may be joined and taken together with the N atom to which they are attached form a 5-6 membered ring which may optionally contain a ring member selected from O, S, and NR$^{198}$ wherein R$^{198}$ represents H or (C$_1$-C$_3$)alkyl;

4.10.e) —C(O)OR$^{199}$ wherein R$^{199}$ represents (C$_1$-C$_3$)alkyl; or 4.10.f) —C(O)—NR$^{200}$R$^{201}$ wherein R$^{200}$ and R$^{201}$ each independently represents H or —(C$_1$-C$_3$)alkyl which may optionally bear halogen, or R$^{200}$ and R$^{201}$ may be joined and taken together with the N atom to which they are attached form a 5-6 membered ring which may optionally contain a ring member selected from O, S, and NR$^{202}$ wherein R$^{202}$ represents H or (C$_1$-C$_3$)alkyl; and X represents O, S, S(O)$_2$, or NR$^{203}$ wherein R$^{203}$ represents H or —(C$_1$-C$_3$)alkyl; and t represents 0, 1, or 2;

4.11) halogen; or 4.12) —CN;

or a pharmaceutically acceptable salt thereof.

3. The compound of claim 1 wherein in formula (I)

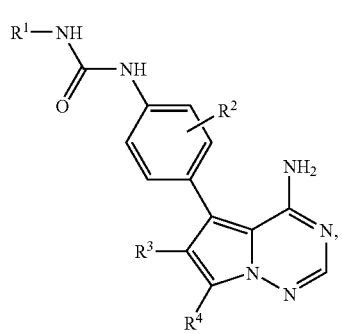

(I)

R$^1$ represents 1.1) phenyl which may optionally bear up to 4 substituents independently selected from the group consisting of 1.1.a) (C$_1$-C$_4$)alkyl, which may optionally bear up to 3 substituents independently selected from 1.1.a1) halogen;

1.1.a2) OR$^5$ wherein R$^5$ represents H or (C$_1$-C$_3$)alkyl which may optionally bear halogen;

1.1.a3) —NR$^6$R$^7$ in which R$^6$ and R$^7$ are independently H or —(C$_1$-C$_3$)alkyl which may optionally bear halogen or R$^6$ and R$^7$ may be joined and taken together with the N atom to which they are attached form a 5-6 membered ring which may optionally contain a ring member selected from O, S, and NR$^8$ wherein R$^8$ represents H or (C$_1$-C$_3$)alkyl; and 1.1.a4) an imidazole, thiazole, oxazole, pyridine, pyrazole, pyrimidine, isoxazole, isothiazole, thiophene, or furan;

1.1.b) —(C$_3$-C$_6$)cycloalkyl which may optionally bear up to 2 substituents independently selected from 1.1.b1) halogen;

1.1.c) OR$^{10}$ wherein

R$^{10}$ represents H; phenyl; benzyl; (C$_3$-C$_6$)cycloalkyl; or (C$_1$-C$_4$)alkyl which may optionally bear up to 3 substituents independently selected from 1.1.c1) halogen;

1.1.c2) OR$^{11}$ wherein R$^{11}$ represents H or (C$_1$-C$_3$)alkyl; and 1.1.c3) NR$^{12}$R$^{13}$ in which R$^{12}$ and R$^{13}$ are independently H or —(C$_1$-C$_3$)alkyl which may optionally bear halogen, or R$^{12}$ and R$^{13}$ may be joined and taken together with the N atom to which they are attached form a 5-6 membered ring which may optionally contain a ring member selected from O, S, and NR$^{14}$ wherein R$^{14}$ represents H or (C$_1$-C$_3$)alkyl;

1.1.e) —C(O)—NR$^{16}$R$^{17}$ wherein

R$^{16}$ represents H or (C$_1$-C$_3$)alkyl which may optionally bear halogen; and R$^{17}$ represents H or —(C$_1$-C$_4$)alkyl which is optionally substituted with 1.1.e1) halogen;

1.1.e5) —OR$^{18}$ wherein R$^{18}$ represents H or (C$_1$-C$_3$)alkyl which may optionally bear halogen; or 1.1.e6) —NR$^{19}$R$^{20}$ in which R$^{19}$ and R$^{20}$ are independently H or —(C$_1$-C$_3$)alkyl which may optionally bear halogen, or R$^{19}$ and R$^{20}$ may be joined and taken together with the N atom to which they are attached form a 5-6 membered ring which may optionally contain a ring member selected from O, S, and NR$^{21}$ wherein R$^{21}$ represents H or (C$_1$-C$_3$)alkyl;

1.1.f) —N(R$^{22}$)—C(O)—R$^{23}$ wherein

R$^{22}$ represents H or (C$_1$-C$_3$)alkyl; and

R$^{23}$ represents optionally substituted phenyl, or (C$_1$-C$_4$)alkyl;

1.1.g) —SO$_2$NR$^{28}$R$^{29}$ wherein

R$^{28}$ represents H or (C$_1$-C$_3$)alkyl which may optionally bear halogen; and R$^{29}$ represents H or —(C$_1$-C$_4$)alkyl which is optionally substituted with:

1.1.g1) halogen;

1.1.g4) —SO$_2$CH$_3$;

1.1.g5) —OR$^{30}$ wherein R$^{30}$ represents H or (C$_1$-C$_3$)alkyl which may optionally bear halogen; or 1.1.g6) —NR$^{31}$R$^{32}$ in which R$^{31}$ and R$^{32}$ are independently H or —(C$_1$-C$_3$)alkyl which may optionally bear halogen, or R$^{31}$ and R$^{32}$ may be joined and taken together with the N atom to which they are attached form a 5-6 membered ring which may optionally contain a ring member selected from O, S, and NR$^{33}$ wherein R$^{33}$ represents H or (C$_1$-C$_3$)alkyl;

1.1.h) —N(R$^{34}$)—SO$_2$—R$^{35}$ wherein

R$^{34}$ represents H or (C$_1$-C$_3$)alkyl, and

R$^{35}$ represents optionally substituted phenyl, or (C$_1$-C$_4$)alkyl which is optionally substituted with 1.1.h1) halogen;

1.1.i) —NR$^{40}$R$^{41}$ in which R$^{40}$ and R$^{41}$ are independently H or —(C$_1$-C$_3$)alkyl which may optionally bear halogen or OR$^{42}$ in which R$^{42}$ represents H or (C$_1$-C$_3$)alkyl, or R$^{40}$ and R$^{41}$ may be joined and taken together with the N atom to which they are attached form a 5-6 membered ring which may optionally contain a ring member selected from O, S, and NR$^{43}$ wherein R$^{43}$ represents H or (C$_1$-C$_3$)alkyl;

1.1.j) halogen;

1.1.l) NO$_2$;

1.1.m) CN; and 1.1.n) an imidazole, thiazole, oxazole, pyridine, pyrazole, pyrimidine, isoxazole, isothiazole, thiophene, or furan;

or $R^1$ represents

- 1.2) a 5-6 membered aromatic heterocycle selected from imidazole, thiazole, oxazole, pyridine, pyrazole, pyrimidine, isoxazole, isothiazole, thiophene, and furan; said $R^1$ heterocycle optionally bearing up to 4 substituents independently selected from the group consisting of
  - 1.2.a) $(C_1-C_4)$alkyl, which may optionally bear up to 3 substituents independently selected from
    - 1.2.a1) halogen;
    - 1.2.a2) $OR^{45}$ wherein $R^{45}$ represents H or $(C_1-C_3)$ alkyl which may optionally bear halogen;
    - 1.2.a3) —$NR^{46}R^{47}$ in which $R^{46}$ and $R^{47}$ are independently H or —$(C_1-C_3)$alkyl which may optionally bear halogen, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or $(C_1-C_3)$alkyl; and
    - 1.2.a4) an imidazole, thiazole, oxazole, pyridine, pyrazole, pyrimidine, isoxazole, isothiazole, thiophene, or furan;
  - 1.2.b) —$(C_3-C_6)$cycloalkyl which may optionally bear up to 2 substituents independently selected from
    - 1.2.b1) halogen;
  - 1.2.c) $OR^{50}$ wherein
    $R^{50}$ represents H; phenyl; benzyl; —$(C_3-C_6)$cycloalkyl; or —$(C_1-C_4)$alkyl which may optionally bear up to 3 substituents independently selected from
    - 1.2.c1) halogen;
  - 1.2.e) —$C(O)$—$NR^{56}R^{57}$ wherein
    $R^{56}$ represents H or $(C_1-C_3)$alkyl which may optionally bear halogen; and
    $R^{57}$ represents H or —$(C_1-C_4)$alkyl which is optionally substituted with
    - 1.2.e1) halogen; or
    - 1.2.e5) —$OR^{58}$ wherein $R^{58}$ represents H or $(C_1-C_3)$alkyl which may optionally bear halogen;
  - 1.2.f) —$N(R^{62})$—$C(O)$—$R^{63}$ wherein
    $R^{62}$ represents H or $(C_1-C_3)$alkyl; and
    $R^{63}$ represents optionally substituted phenyl, or $(C_1-C_4)$alkyl;
  - 1.2.g) —$SO_2NR^{68}R^{69}$ wherein
    $R^{68}$ represents H or $(C_1-C_3)$alkyl which may optionally bear halogen; and
    $R^{69}$ represents H or —$(C_1-C_4)$alkyl which is optionally substituted with
    - 1.2.g1) halogen; or
    - 1.2.g5) —$OR^{70}$ wherein $R^{70}$ represents H or $(C_1-C_3)$alkyl which may optionally bear halogen;
  - 1.2.h) —$N(R^{74})$—$SO_2$—$R^{75}$ wherein
    $R^{74}$ represents H or $(C_1-C_3)$alkyl, and
    $R^{75}$ represents optionally substituted phenyl, or $(C_1-C_4)$alkyl which is optionally substituted with
    - 1.2.h1) halogen;
  - 1.2.i) —$NR^{80}R^{81}$ in which $R^{80}$ and $R^{81}$ are independently H or —$(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$alkyl;
  - 1.2.j) halogen;
  - 1.2.k) optionally substituted phenyl;
  - 1.2.l) $NO_2$;
  - 1.2.m) CN; and
  - 1.2.n) an imidazole, thiazole, oxazole, pyridine, pyrazole, pyrimidine, isoxazole, isothiazole, thiophene, or furan;

$R^2$ represents hydrogen; halogen; —$(C_1-C_5)$alkyl which may optionally bear halogen; or —$O(C_1-C_3)$alkyl which may optionally bear halogen;

$R^3$ represents

- 3.1) —$(C_1-C_5)$alkyl which is substituted with
  - 3.1.a) -halogen;
  - 3.1.b) phenyl optionally substituted with halogen, —$(C_1-C_3)$alkyl, or —$(C_1-C_3)$alkoxy,
  - 3.1.c) a 5-6 membered heteroaromatic containing up to two heteroatoms selected from O, S, and N, optionally substituted with halogen or —$(C_1-C_3)$alkyl,
  - 3.1.d) —CN,
  - 3.1.e) —$OR^{83}$ wherein $R^{83}$ represents H or —$(C_1-C_3)$ alkyl which may optionally bear up to 3 substituents independently selected from
    - 3.1.e1) halogen;
    - 3.1.e2) optionally substituted phenyl;
    - 3.1.e3) —$S(O)_2CH_3$;
    - 3.1.e4) $OR^{84}$ wherein $R^{84}$ represents H or $(C_1-C_3)$ alkyl which may optionally bear halogen or —$(C_1-C_3)$mono- or di-alkylamino; and
    - 3.1.e5) —$NR^{85}R^{86}$ in which $R^{85}$ and $R^{86}$ are independently H or —$(C_1-C_3)$alkyl which may optionally bear halogen, or $R^{85}$ and $R^{86}$ may be joined and taken together with the N atom to which they are attached form a 5-6 membered ring which may optionally contain a ring member selected from O, S, and $NR^{87}$ wherein $R^{87}$ represents H or $(C_1-C_3)$alkyl;
  - 3.1.f) —$(C_3-C_5)$cycloalkyl which may optionally bear halogen; or
  - 3.1.g) —$NR^{89}R^{90}$ wherein
    $R^{89}$ represents H or —$(C_1-C_3)$alkyl which may optionally bear halogen; and
    $R^{90}$ represents H or —$(C_1-C_4)$alkyl which is optionally substituted with
    - 3.1.g1) halogen;
    - 3.1.g2) a 5-6 membered heteroaromatic containing up to two heteroatoms selected from O, S, and N;
    - 3.1.g3) phenyl;
    - 3.1.g4) —$SO_2CH_3$;
    - 3.1.g5) —$OR^{91}$ wherein $R^{91}$ represents H or $(C_1-C_3)$alkyl which may optionally bear halogen; or
    - 3.1.g6) —$NR^{92}R^{93}$ in which $R^{92}$ and $R^{93}$ are independently H or —$(C_1-C_3)$alkyl which may optionally bear halogen, or $R^{92}$ and $R^{93}$ may be joined and taken together with the N atom to which they are attached form a 5-6 membered ring which may optionally contain a ring member selected from O, S, and $NR^{94}$ wherein $R^{94}$ represents H or $(C_1-C_3)$alkyl; or
    - 3.1.g7) $R^{89}$ and $R^{90}$ may be joined and taken together with the N to which they are attached form an aromatic or nonaromatic 5-6 membered ring which may optionally contain a ring member selected from O, S, and $NR^{95}$ wherein $R^{95}$ represents H or $(C_1-C_3)$alkyl;

3.2)

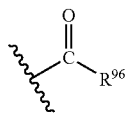

wherein
R$^{96}$ represents
3.2.a) H,
3.2.b) —(C$_3$-C$_5$)cycloalkyl which may optionally bear halogen; or
3.2.c) —(C$_1$-C$_5$)alkyl which may optionally bear up to 3 substituents independently selected from
3.2.c1) halogen;
3.2.c2) a 5-6 membered heteroaromatic containing up to two heteroatoms selected from O, S, and N;
3.2.c3) phenyl;
3.2.c5) —OR$^{97}$ wherein R$^{97}$ represents H or (C$_1$-C$_3$)alkyl which may optionally bear halogen or —(C$_1$-C$_3$)mono- or di-alkylamino; and
3.2.c6) —NR$^{98}$R$^{99}$ in which R$^{98}$ and R$^{99}$ are independently H or —(C$_1$-C$_3$)alkyl which may optionally bear halogen or OR$^{99a}$ wherein R$^{99a}$ represents H or (C$_1$-C$_3$)alkyl, or R$^{98}$ and R$^{99}$ may be joined and taken together with the N atom to which they are attached form a 5-6 membered ring which may optionally contain a ring member selected from O, S, and NR$^{100}$ wherein R$^{100}$ represents H or (C$_1$-C$_3$)alkyl;

3.3)

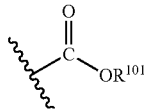

wherein R$^{101}$ represents H or —(C$_1$-C$_5$)alkyl which may optionally bear up to 3 substituents independently selected from
3.3.a) halogen; and
3.3.b) phenyl;

3.4)

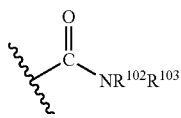

wherein
R$^{102}$ represents H or —(C$_1$-C$_3$)alkyl which may optionally bear halogen; and
R$^{103}$ represents H or —(C$_1$-C$_5$)alkyl which may optionally bear up to 3 substituents independently selected from
3.4.a) halogen;
3.4.b) a 5-6 membered heteroaromatic containing up to two heteroatoms selected from O, S, and N;
3.4.c) phenyl;
3.4.d) —S(O)$_2$CH$_3$;
3.4.e) OR$^{104}$ wherein R$^{104}$ represents H or (C$_1$-C$_3$) alkyl which may optionally bear halogen; and
3.4.f) —NR$^{105}$R$^{106}$ in which R$^{105}$ and R$^{106}$ are independently H or —(C$_1$-C$_3$)alkyl which may optionally bear halogen, or R$^{105}$ and R$^{106}$ may be joined and taken together with the N atom to which they are attached form a 5-6 membered ring which may optionally contain a ring member selected from O, S, and NR$^{107}$ wherein R$^{107}$ represents H or (C$_1$-C$_3$)alkyl;
3.6) a 5-6 membered heteroaromatic containing up to two heteroatoms selected from O, S, and N;
3.7) halogen; or
3.8) —CN;
R$^4$ represents
4.1) —(C$_1$-C$_5$)alkyl which is substituted with
4.1.a) —(C$_3$-C$_5$)cycloalkyl which may optionally bear halogen or OR$^{109}$ wherein R$^{109}$ represents H or (C$_1$-C$_3$)alkyl;
4.1.b) -halogen;
4.1.c) —OR$^{110}$ wherein R$^{110}$ represents H or —(C$_1$-C$_3$)alkyl which may optionally bear up to 3 substituents independently selected from
4.1.c1) halogen;
4.1.c2) phenyl;
4.1.c4) OR$^{111}$ wherein R$^{111}$ represents H or (C$_1$-C$_3$)alkyl which may optionally bear halogen; and
4.1.c5) —NR$^{112}$R$^{113}$ in which R$^{112}$ and R$^{113}$ are independently H or —(C$_1$-C$_3$)alkyl which may optionally bear halogen, or R$^{112}$ and R$^{113}$ may be joined and taken together with the N atom to which they are attached form a 5-6 membered ring which may optionally contain a ring member selected from O, S, and NR$^{114}$ wherein R$^{114}$ represents H or (C$_1$-C$_3$)alkyl;
4.1.d) —NR$^{115}$R$^{116}$ wherein
R$^{115}$ represents H or —(C$_1$-C$_3$)alkyl which may optionally bear halogen and
R$^{116}$ represents H, optionally substituted phenyl, or —(C$_1$-C$_5$)alkyl which may optionally bear up to 3 substituents independently selected from
4.1.d1) halogen;
4.1.d2) —S(O)$_2$CH$_3$;
4.1.d3) OR$^{117}$ wherein R$^{117}$ represents H or (C$_1$-C$_3$)alkyl which may optionally bear halogen; and
4.1.d4) —NR$^{118}$R$^{119}$ in which R$^{118}$ and R$^{119}$ are independently H or —(C$_1$-C$_3$)alkyl which may optionally bear halogen, or R$^{118}$ and R$^{119}$ may be joined and taken together with the N atom to which they are attached form a 5-6 membered ring which may optionally contain a ring member selected from O, S, and NR$^{120}$ wherein R$^{120}$ represents H or (C$_1$-C$_3$)alkyl; or
4.1.f) a 5-6 membered aromatic heterocycle containing up to two heteroatoms selected from O, S, and N;

4.2)

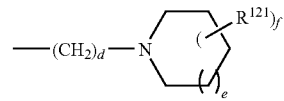

wherein $R^{121}$ represents —$(C_1-C_3)$alkyl which may optionally bear halogen or —$OR^{122}$ in which $R^{122}$ represents H or —$(C_1-C_3)$alkyl;
d represents 1, 2, or 3;
e represents 0 or 1;
f represents 0, 1, or 2;
4.3)

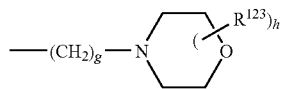

wherein $R^{123}$ represents —$(C_1-C_3)$alkyl which may optionally bear halogen or —$OR^{124}$ in which $R^{124}$ represents H or —$(C_1-C_3)$alkyl;
g represents 1, 2, or 3;
h represents 0, 1, or 2;
4.4)

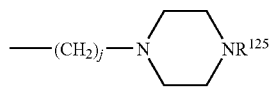

wherein
$R^{125}$ represents
  4.4.a) H;
  4.4.b) —$(C_1-C_3)$alkyl which may optionally bear halogen or —$OR^{126}$ in which $R^{126}$ represents H or —$(C_1-C_3)$alkyl which in turn is optionally substituted with halogen;
  4.4.c) —$SO_2R^{127}$ wherein $R^{127}$ represents optionally substituted phenyl, or —$(C_1-C_3)$alkyl which may optionally bear halogen or $OR^{128}$ wherein $R^{128}$ represents H or $(C_1-C_3)$alkyl;
  4.4.d) —$C(O)R^{129}$ wherein
$R^{129}$ represents
    4.4.d1) optionally substituted phenyl,
    4.4.d2) —$(C_1-C_3)$alkyl which may optionally bear up to 3 substituents independently selected from
      4.4.d2.1) halogen;
      4.4.d2.4) —$OR^{130}$ wherein $R^{130}$ represents H or $(C_1-C_3)$alkyl which may optionally bear halogen; and
      4.4.d2.5) —$NR^{131}R^{132}$ in which $R^{131}$ and $R^{132}$ are independently H or —$(C_1-C_3)$alkyl which may optionally bear halogen, or $R^{131}$ and $R^{132}$ may be joined and taken together with the N atom to which they are attached form a 5-6 membered ring which may optionally contain a ring member selected from O, S, and $NR^{133}$ wherein $R^{133}$ represents H or $(C_1-C_3)$alkyl;
    4.4.d3) —$OR^{134}$ wherein $R^{134}$ represents $(C_1-C_3)$alkyl which may optionally bear halogen; or
    4.4.d4) $NR^{135}R^{136}$ wherein $R^{135}$ and $R^{136}$ are independently H or —$(C_1-C_3)$alkyl which may optionally bear halogen, or $R^{135}$ and $R^{136}$ may be joined and taken together with the N atom to which they are attached form a 5-6 membered ring which may optionally contain a ring member selected from O, S, and $NR^{137}$ wherein $R^{137}$ represents H or $(C_1-C_3)$alkyl; and
j represents 1, 2, or 3;
4.5)

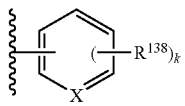

wherein
X represents C or N;
$R^{138}$ represents
  4.5.a) $(C_1-C_4)$alkyl, which may optionally bear up to 3 substituents independently selected from
    4.5.a1) halogen;
    4.5.a2) $OR^{139}$ wherein $R^{139}$ represents H or $(C_1-C_3)$alkyl which may optionally bear halogen or —$(C_1-C_3)$mono- or di-alkylamino;
    4.5.a3) —$NR^{140}R^{141}$ in which $R^{140}$ and $R^{141}$ are independently H or —$(C_1-C_3)$alkyl which may optionally bear halogen or $OR^{141a}$ wherein $R^{141a}$ represents H or $(C_1-C_3)$alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or $(C_1-C_3)$alkyl; and
    4.5.a4) a 5-6 membered heteroaromatic containing up to two heteroatoms selected from O, S, and N;
  4.5.b) —$(C_3-C_6)$cycloalkyl which may optionally bear up to 2 substituents independently selected from
    4.5.b1) halogen;
  4.5.c) $OR^{144}$ wherein
    $R^{144}$ represents H; phenyl; benzyl; $(C_3-C_6)$cycloalkyl; or $(C_1-C_4)$alkyl which may optionally bear up to 3 substituents independently selected from
    4.5.c1) halogen;
    4.5.c2) $OR^{145}$ wherein $R^{145}$ represents H or $(C_1-C_3)$alkyl which may optionally bear $(C_1-C_3)$ mono- or di-alkylamino; and
    4.5.c3) $NR^{146}R^{147}$ in which $R^{146}$ and $R^{1473}$ are independently H or —$(C_1-C_3)$alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or $(C_1-C_3)$alkyl;
  4.5.e) —$C(O)$—$NR^{150}R^{151}$ wherein
    $R^{150}$ represents H or $(C_1-C_3)$alkyl which may optionally bear halogen; and
    $R^{151}$ represents H or —$(C_1-C_4)$alkyl which is optionally substituted with
    4.5.e1) halogen;
    4.5.e3) phenyl;
    4.5.e4) —$SO_2CH_3$;
    4.5.e5) —$OR^{152}$ wherein $R^{152}$ represents H or $(C_1-C_3)$alkyl which may optionally bear halogen; or
    4.5.e6) —$NR^{153}R^{154}$ in which $R^{153}$ and $R^{154}$ are independently H or —$(C_1-C_3)$alkyl which may optionally bear halogen, or $R^{153}$ and $R^{154}$ may be joined and taken together with the N atom to which they are attached form a 5-6 membered ring which may optionally contain a ring member selected from O, S, and NR$^{155}$ wherein R$^{155}$ represents H or (C$_1$-C$_3$)alkyl;
4.5.f) —N(R$^{156}$)—C(O)—R$^{157}$ wherein
R$^{156}$ represents H or (C$_1$-C$_3$)alkyl; and
R$^{157}$ represents H, optionally substituted phenyl, or (C$_1$-C$_4$)alkyl which is optionally substituted with
4.5.f1) optionally substituted phenyl,
4.5.f2) OR$^{158}$ wherein R$^{158}$ represents H or (C$_1$-C$_3$)alkyl, or
4.5.f3) NR$^{159}$R$^{160}$ wherein R$^{159}$ and R$^{160}$ are independently H or —(C$_1$-C$_3$)alkyl which may optionally bear halogen, or R$^{159}$ and R$^{160}$ may be joined and taken together with the N atom to which they are attached form a 5-6 membered ring which may optionally contain a ring member selected from O, S, and NR$^{161}$ wherein R$^{161}$ represents H or (C$_1$ C$_3$)alkyl;
4.5.g) —SO$_2$NR$^{162}$R$^{163}$ wherein
R$^{162}$ represents H or (C$_1$-C$_3$)alkyl which may optionally bear halogen; and
R$^{163}$ represents H or —(C$_1$-C$_4$)alkyl which is optionally substituted with
4.5.g1) halogen;
4.5.g3) phenyl;
4.5.g4) —SO$_2$CH$_3$;
4.5.g5) —OR$^{164}$ wherein R$^{164}$ represents H or (C$_1$-C$_3$)alkyl which may optionally bear halogen; or
4.5.g6) —NR$^{165}$R$^{166}$ in which R$^{165}$ and R$^{166}$ are independently H or —(C$_1$-C$_3$)alkyl which may optionally bear halogen, or R$^{165}$ and R$^{166}$ may be joined and taken together with the N atom to which they are attached form a 5-6 membered ring which may optionally contain a ring member selected from O, S, and NR$^{167}$ wherein R$^{167}$ represents H or (C$_1$-C$_3$)alkyl;
4.5.h) —N(R$^{168}$)—SO$_2$—R$^{169}$ wherein
R$^{168}$ represents H or (C$_1$-C$_3$)alkyl, and
R$^{169}$ represents H, optionally substituted phenyl, or (C$_1$-C$_4$)alkyl which is optionally substituted with
4.5.h1) halogen,
4.5.h2) optionally substituted phenyl,
4.5.h3) OR$^{170}$ wherein R$^{170}$ represents H or (C$_1$-C$_3$)alkyl which may optionally bear halogen, or
4.5.h4) NR$^{171}$R$^{172}$ wherein R$^{171}$ and R$^{172}$ are independently H or —(C$_1$-C$_3$)alkyl which may optionally bear halogen, or R$^{171}$ and R$^{172}$ may be joined and taken together with the N atom to which they are attached form a 5-6 membered ring which may optionally contain a ring member selected from O, S, and NR$^{173}$ wherein R$^{173}$ represents H or (C$_1$ C$_3$)alkyl;
4.5.i) —NR$^{174}$R$^{175}$ in which R$^{174}$ and R$^{175}$ are independently H or —(C$_1$-C$_3$)alkyl which may optionally bear halogen or OR$^{175a}$ wherein R$^{175a}$ represents H or (C$_1$-C$_3$)alkyl, or R$^{174}$ and R$^{175}$ may be joined and taken together with the N atom to which they are attached form a 5-6 membered ring which may optionally contain a ring member selected from O, S, and NR$^{176}$ wherein R$^{176}$ represents H or (C$_1$-C$_3$) alkyl;
4.5.j) halogen;
4.5.l) NO$_2$;
4.5.m) CN; or
4.5.n) a 5-6 membered heteroaromatic containing up to two heteroatoms selected from O, S, and N; and
k represents 0, 1, or 2;

4.6)

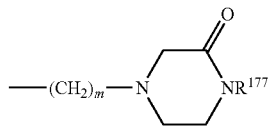

wherein R$^{177}$ represents H or —(C$_1$-C$_3$)alkyl; and
m represents 1, 2, or 3;

4.7)

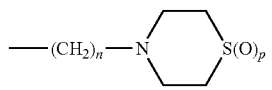

wherein
n represents 1, 2, or 3; and
p represents 0, 1, or 2;

4.8)

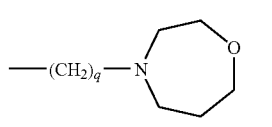

wherein
q represents 1, 2, or 3;

4.9)

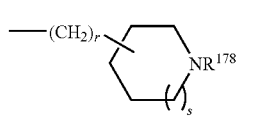

wherein
R$^{178}$ represents
  4.9.a) H;
  4.9.b) —(C$_1$-C$_3$)alkyl which may optionally bear halogen or —OR$^{179}$ in which R$^{179}$ represents H or (C$_1$-C$_3$)alkyl optionally substituted with halogen;
  4.9.c) —SO$_2$R$^{180}$ wherein R$^{180}$ represents optionally substituted phenyl or —(C$_1$-C$_3$)alkyl, which may be substituted with halogen or —OR$^{181}$ wherein R$^{181}$ represents H or (C$_1$-C$_3$)alkyl which may optionally bear halogen;
  4.9.d) —C(O)R$^{182}$ wherein R$^{182}$ represents optionally substituted phenyl or —(C$_1$-C$_3$)alkyl which may optionally bear up to 3 substituents independently selected from
    4.9.d1) halogen;
    4.9.d2) optionally substituted phenyl;
    4.9.d4) OR$^{183}$ wherein R$^{183}$ represents H or (C$_1$-C$_3$)alkyl which may optionally bear halogen; and
    4.9.d5) —NR$^{184}$R$^{185}$ in which R$^{184}$ and R$^{185}$ are independently H or —(C$_1$-C$_3$)alkyl which may optionally bear halogen or OR$^{185a}$ wherein R$^{185a}$ represents H or (C$_1$-C$_3$)alkyl, or R$^{184}$ and R$^{185}$ may be joined and taken together with the N atom to which they are attached form a 5-6 membered ring which may optionally contain a ring member selected from O, S, and $NR^{186}$ wherein $R^{186}$ represents H or $(C_1$-$C_3)$alkyl;
- 4.9e) —$C(O)OR^{187}$ wherein $R^{187}$ represents $(C_1$-$C_3)$alkyl; or
- 4.9.f) —$C(O)$—$NR^{188}R^{189}$ wherein $R^{188}$ and $R^{189}$ each independently represents H or —$(C_1$-$C_3)$alkyl which may optionally bear halogen, or $R^{188}$ and $R^{189}$ may be joined and taken together with the N atom to which they are attached form a 5-6 membered ring which may optionally contain a ring member selected from O, S, and $NR^{190}$ wherein $R^{190}$ represents H or $(C_1$-$C_3)$alkyl;

r represents 0, 1, or 2; and
s represents 0 or 1;
4.10)

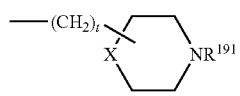

wherein
$R^{191}$ represents
- 4.10.a) H;
- 4.10.b) —$(C_1$-$C_3)$alkyl which may optionally bear halogen or —$OR^{192}$ in which $R^{192}$ represents H or $(C_1$-$C_3)$alkyl;
- 4.10c) —$SO_2R^{193}$ wherein $R^{193}$ represents phenyl or —$(C_1$-$C_3)$alkyl, both of which may be substituted with halogen or —$(C_1$-$C_3)$alkyl;
- 4.10.d) —$C(O)R^{194}$ wherein $R^{194}$ represents $(C_1$-$C_3)$alkyl which may optionally bear up to 3 substituents independently selected from
  - 4.10.d1) halogen;
  - 4.10.d2) phenyl;
  - 4.10.d4) $OR^{195}$ wherein $R^{195}$ represents H or $(C_1$-$C_3)$alkyl which may optionally bear halogen; and
  - 4.10.d5) —$NR^{196}R^{197}$ in which $R^{196}$ and $R^{197}$ are independently H or —$(C_1$-$C_3)$alkyl which may optionally bear halogen or $OR^{197a}$ wherein $R^{197a}$ represents H or $(C_1$-$C_3)$alkyl, or $R^{196}$ and $R^{197}$ may be joined and taken together with the N atom to which they are attached form a 5-6 membered ring which may optionally contain a ring member selected from O, S, and $NR^{198}$ wherein $R^{198}$ represents H or $(C_1$-$C_3)$alkyl;
- 4.10.e) —$C(O)OR^{199}$ wherein $R^{199}$ represents $(C_1$-$C_3)$alkyl; or
- 4.10.f) —$C(O)$—$NR^{200}R^{201}$ wherein $R^{200}$ and $R^{201}$ each independently represents H or —$(C_1$-$C_3)$alkyl which may optionally bear halogen, or $R^{200}$ and $R^{201}$ may be joined and taken together with the N atom to which they are attached form a 5-6 membered ring which may optionally contain a ring member selected from O, S, and $NR^{202}$ wherein $R^{202}$ represents H or $(C_1$-$C_3)$alkyl; and X represents O, S, $S(O)_2$, or $NR^{203}$ wherein $R^{203}$ represents H or —$(C_1$-$C_3)$alkyl; and
t represents 0, 1, or 2;
4.11) halogen; or
4.12) —CN;
or a pharmaceutically acceptable salt thereof.

4. The compound of claim 1 wherein in formula (I)

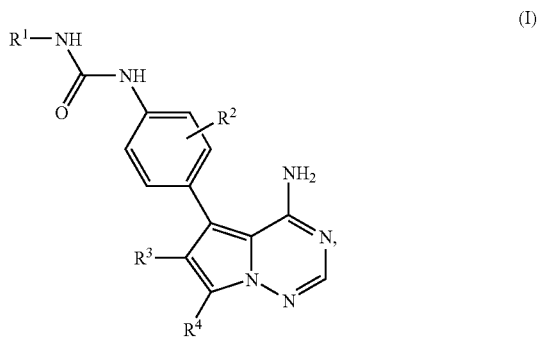

(I)

$R^1$ represents
- 1.1) phenyl which may optionally bear up to 4 substituents independently selected from the group consisting of
  - 1.1.a) $(C_1$-$C_4)$alkyl, which may optionally bear up to 3 substituents independently selected from
    - 1.1.a1) halogen;
    - 1.1.a2) $OR^5$ wherein $R^5$ represents H or $(C_1$-$C_3)$alkyl which may optionally bear halogen;
    - 1.1.a3) —$NR^6R^7$ in which $R^6$ and $R^7$ are independently H or —$(C_1$-$C_3)$alkyl which may optionally bear halogen or $R^6$ and $R^7$ may be joined and taken together with the N atom to which they are attached form a 5-6 membered ring which may optionally contain a ring member selected from O, S, and $NR^8$ wherein $R^8$ represents H or $(C_1$-$C_3)$alkyl; and
    - 1.1.a4) an imidazole, thiazole, oxazole, pyridine, pyrazole, pyrimidine, isoxazole, isothiazole, thiophene, or furan;
  - 1.1.b) —$(C_3$-$C_6)$cycloalkyl which may optionally bear up to 2 substituents independently selected from
    - 1.1.b1) halogen;
  - 1.1.c) $OR^{10}$ wherein
    $R^{10}$ represents H; phenyl; benzyl; $(C_3$-$C_6)$cycloalkyl; or $(C_1$-$C_4)$alkyl which may optionally bear up to 3 substituents independently selected from
    - 1.1.c1) halogen;
    - 1.1.c2) $OR^{11}$ wherein $R^{11}$ represents H or $(C_1$-$C_3)$alkyl; and
    - 1.1.c3) $NR^{12}R^{13}$ in which $R^{12}$ and $R^{13}$ are independently H or —$(C_1$-$C_3)$alkyl which may optionally bear halogen, or $R^{12}$ and $R^{13}$ may be joined and taken together with the N atom to which they are attached form a 5-6 membered ring which may optionally contain a ring member selected from O, S, and $NR^{14}$ wherein $R^{14}$ represents H or $(C_1$-$C_3)$alkyl;
  - 1.1.e) —$O(O)$—$NR^{16}R^{17}$ wherein
    $R^{16}$ represents H or $(C_1$-$C_3)$alkyl which may optionally bear halogen; and
    $R^{17}$ represents H or —$(C_1$-$C_4)$alkyl which is optionally substituted with
    - 1.1.e1) halogen;
    - 1.1.e5) —$OR^{18}$ wherein $R^{18}$ represents H or $(C_1$-$C_3)$alkyl which may optionally bear halogen; or 1.1.e6) —NR$^{19}$R$^{20}$ in which R$^{19}$ and R$^{20}$ are independently H or —(C$_1$-C$_3$)alkyl which may optionally bear halogen, or R$^{19}$ and R$^{20}$ may be joined and taken together with the N atom to which they are attached form a 5-6 membered ring which may optionally contain a ring member selected from O, S, and NR$^{21}$ wherein R$^{21}$ represents H or (C$_1$-C$_3$)alkyl;

1.1.f) —N(R$^{22}$)—C(O)—R$^{23}$ wherein
R$^{22}$ represents H or (C$_1$-C$_3$)alkyl; and
R$^{23}$ represents optionally substituted phenyl, or (C$_1$-C$_4$)alkyl;

1.1.g) —SO$_2$NR$^{28}$R$^{29}$ wherein
R$^{28}$ represents H or (C$_1$-C$_3$)alkyl which may optionally bear halogen; and
R$^{29}$ represents H or —(C$_1$-C$_4$)alkyl which is optionally substituted with:
1.1.g1) halogen;
1.1.g4) —SO$_2$CH$_3$;
1.1.g5) —OR$^{30}$ wherein R$^{30}$ represents H or (C$_1$-C$_3$)alkyl which may optionally bear halogen; or
1.1.g6) —NR$^{31}$R$^{32}$ in which R$^{31}$ and R$^{32}$ are independently H or —(C$_1$-C$_3$)alkyl which may optionally bear halogen, or R$^{31}$ and R$^{32}$ may be joined and taken together with the N atom to which they are attached form a 5-6 membered ring which may optionally contain a ring member selected from O, S, and NR$^{33}$ wherein R$^{33}$ represents H or (C$_1$-C$_3$)alkyl;

1.1.h) —N(R$^{34}$)—SO$_2$—R$^{35}$ wherein
R$^{34}$ represents H or (C$_1$-C$_3$)alkyl, and
R$^{35}$ represents optionally substituted phenyl, or (C$_1$-C$_4$)alkyl which is optionally substituted with
1.1.h1) halogen;

1.1.i) —NR$^{40}$R$^{41}$ in which R$^{40}$ and R$^{41}$ are independently H or —(C$_1$-C$_3$)alkyl which may optionally bear halogen or OR$^{42}$ in which R$^{42}$ represents H or (C$_1$-C$_3$)alkyl, or R$^{40}$ and R$^{41}$ may be joined and taken together with the N atom to which they are attached form a 5-6 membered ring which may optionally contain a ring member selected from O, S, and NR$^{43}$ wherein R$^{43}$ represents H or (C$_1$-C$_3$)alkyl;

1.1.j) halogen;
1.1.l) NO$_2$;
1.1.m) CN; and
1.1.n) an imidazole, thiazole, oxazole, pyridine, pyrazole, pyrimidine, isoxazole, isothiazole, thiophene, or furan;
or
R$^1$ represents
1.2) a 5-6 membered aromatic heterocycle selected from imidazole, thiazole, oxazole, pyridine, pyrazole, pyrimidine, isoxazole, isothiazole, thiophene, and furan; said R$^1$ heterocycle optionally bearing up to 4 substituents independently selected from the group consisting of
1.2.a) (C$_1$-C$_4$)alkyl, which may optionally bear up to 3 substituents independently selected from
1.2.a1) halogen;
1.2.a2) OR$^{45}$ wherein R$^{45}$ represents H or (C$_1$-C$_3$) alkyl which may optionally bear halogen;
1.2.a3) —NR$^{46}$R$^{47}$ in which R$^{46}$ and R$^{47}$ are independently H or —(C$_1$-C$_3$)alkyl which may optionally bear halogen, or R$^{46}$ and R$^{47}$ may be joined and taken together with the N atom to which they are attached form a 5-6 membered ring which may optionally contain a ring member selected from O, S, and NR$^{48}$ wherein R$^{48}$ represents H or (C$_1$-C$_3$)alkyl; and
1.2.a4) an imidazole, thiazole, oxazole, pyridine, pyrazole, pyrimidine, isoxazole, isothiazole, thiophene, or furan;

1.2.b) —(C$_3$-C$_6$)cycloalkyl which may optionally bear up to 2 substituents independently selected from
1.2.b1) halogen;

1.2.c) OR$^{50}$ wherein
R$^{50}$ represents H; phenyl; benzyl; —(C$_3$-C$_6$)cycloalkyl; or —(C$_1$-C$_4$)alkyl which may optionally bear up to 3 substituents independently selected from
1.2.c1) halogen;

1.2.e) —C(O)—NR$^{56}$R$^{57}$ wherein
R$^{56}$ represents H or (C$_1$-C$_3$)alkyl which may optionally bear halogen; and
R$^{57}$ represents H or —(C$_1$-C$_4$)alkyl which is optionally substituted with
1.2.e1) halogen; or
1.2.e5) —OR$^{58}$ wherein R$^{58}$ represents H or (C$_1$-C$_3$)alkyl which may optionally bear halogen;

1.2.f) —N(R$^{62}$)—C(O)—R$^{63}$ wherein
R$^{62}$ represents H or (C$_1$-C$_3$)alkyl; and
R$^{63}$ represents optionally substituted phenyl, or (C$_1$-C$_4$)alkyl;

1.2.g) —SO$_2$NR$^{68}$R$^{69}$ wherein
R$^{68}$ represents H or (C$_1$-C$_3$)alkyl which may optionally bear halogen; and
R$^{69}$ represents H or —(C$_1$-C$_4$)alkyl which is optionally substituted with
1.2.g1) halogen; or
1.2.g5) —OR$^{70}$ wherein R$^{70}$ represents H or (C$_1$-C$_3$)alkyl which may optionally bear halogen;

1.2.h) —N(R$^{74}$)—SO$_2$—R$^{75}$ wherein
R$^{74}$ represents H or (C$_1$-C$_3$)alkyl, and
R$^{75}$ represents optionally substituted phenyl, or (C$_1$-C$_4$)alkyl which is optionally substituted with
1.2.h1) halogen;

1.2.i) —NR$^{80}$R$^{81}$ in which R$^{80}$ and R$^{81}$ are independently H or —(C$_1$-C$_3$)alkyl which may optionally bear halogen or OR$^{81a}$ wherein R$^{81a}$ represents H or (C$_1$-C$_3$)alkyl, or R$^{80}$ and R$^{81}$ may be joined and taken together with the N atom to which they are attached form a 5-6 membered ring which may optionally contain a ring member selected from O, S, and NR$^{82}$ wherein R$^{82}$ represents H or (C$_1$-C$_3$) alkyl;

1.2.j) halogen;
1.2.k) optionally substituted phenyl;
1.2.l) NO$_2$;
1.2.m) CN; and
1.2.n) an imidazole, thiazole, oxazole, pyridine, pyrazole, pyrimidine, isoxazole, isothiazole, thiophene, or furan;

R$^2$ represents hydrogen; halogen; —(C$_1$-C$_5$)alkyl which may optionally bear halogen; or —O(C$_1$-C$_3$)alkyl which may optionally bear halogen;

$R^3$ represents 3.1) —$(C_1$-$C_5)$alkyl which is optionally substituted with 3.1.a) -halogen;

3.1.c) a 5-6 membered heteroaromatic containing up to two heteroatoms selected from O, S, and N, optionally substituted with halogen or —$(C_1$-$C_3)$alkyl;

3.1.d) —CN;

3.1.e) —$OR^{83}$ wherein $R^{83}$ represents H or —$(C_1$-$C_3)$alkyl which may optionally bear up to 3 substituents independently selected from 3.1.e1) halogen; or 3.1.e4) $OR^{84}$ wherein $R^{84}$ represents H or $(C_1$-$C_3)$alkyl which may optionally bear halogen;

3.1.f) —$(C_3$-$C_5)$cycloalkyl which may optionally bear halogen; or 3.1.g) —$NR^{89}R^{90}$ wherein $R^{89}$ represents H or —$(C_1$-$C_3)$alkyl which may optionally bear halogen; and $R^{90}$ represents H or —$(C_1$-$C_4)$alkyl which is optionally substituted with 3.1.g1) halogen;

3.1.g4) —$SO_2CH_3$;

3.1.g5) —$OR^{91}$ wherein $R^{91}$ represents H or $(C_1$-$C_3)$alkyl which may optionally bear halogen; or 3.1.g7) $R^{89}$ and $R^{90}$ may be joined and taken together with the N to which they are attached form an aromatic or nonaromatic 5-6 membered ring which may optionally contain a ring member selected from O, S, and $NR^{95}$ wherein $R^{95}$ represents H or $(C_1$-$C_3)$alkyl;

3.2)

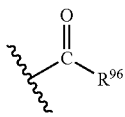

wherein $R^{96}$ represents 3.2.b) —$(C_3$-$C_5)$cycloalkyl which may optionally bear halogen; or 3.2.c) —$(C_1$-$C_5)$alkyl which may optionally bear up to 3 substituents independently selected from 3.2.c1) halogen; and 3.2.c5) —$OR^{97}$ wherein $R^{97}$ represents H or $(C_1$-$C_3)$alkyl which may optionally bear halogen;

3.3)

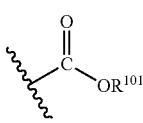

wherein $R^{101}$ represents H or —$(C_1$-$C_5)$alkyl;

3.4)

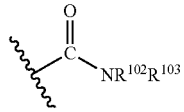

wherein $R^{102}$ represents H or —$(C_1$-$C_3)$alkyl which may optionally bear halogen; and $R^{103}$ represents H or —$(C_1$-$C_5)$alkyl which may optionally bear up to 3 substituents independently selected from 3.4.a) halogen;

3.4.d) —$S(O)_2CH_3$; and 3.4.e) $OR^{104}$ wherein $R^{104}$ represents H or $(C_1$-$C_3)$alkyl which may optionally bear halogen;

3.7) halogen; or 3.8) —CN;

$R^4$ represents 4.1) —$(C_1$-$C_5)$alkyl which is optionally substituted with 4.1.a) —$(C_3$-$C_5)$cycloalkyl which may optionally bear halogen or $OR^{109}$ wherein $R^{109}$ represents H or $(C_1$-$C_3)$alkyl;

4.1.b) -halogen;

4.1.c) —$OR^{110}$ wherein $R^{110}$ represents H or —$(C_1$-$C_3)$alkyl which may optionally bear up to 3 substituents independently selected from 4.1.c1) halogen;

4.1.c2) phenyl;

4.1.c4) $OR^{111}$ wherein $R^{111}$ represents H or $(C_1$-$C_3)$alkyl which may optionally bear halogen; and 4.1.c5) —$NR^{112}R^{113}$ in which $R^{112}$ and $R^{113}$ are independently H or —$(C_1$-$C_3)$alkyl which may optionally bear halogen, or $R^{112}$ and $R^{113}$ may be joined and taken together with the N atom to which they are attached form a 5-6 membered ring which may optionally contain a ring member selected from O, S, and $NR^{114}$ wherein $R^{114}$ represents H or $(C_1$-$C_3)$alkyl;

4.1.d) —$NR^{115}R^{116}$ wherein $R^{115}$ represents H or —$(C_1$-$C_3)$alkyl which may optionally bear halogen and $R^{116}$ represents H, optionally substituted phenyl, or —$(C_1$-$C_5)$alkyl which may optionally bear up to 3 substituents independently selected from 4.1.d1) halogen;

4.1.d2) —$S(O)_2CH_3$;

4.1.d3) $OR^{117}$ wherein $R^{117}$ represents H or $(C_1$-$C_3)$alkyl which may optionally bear halogen; and 4.1.d4) —$NR^{118}R^{119}$ in which $R^{118}$ and $R^{119}$ are independently H or —$(C_1$-$C_3)$alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or $(C_1$-$C_3)$alkyl; or 4.1.f) a 5-6 membered aromatic heterocycle containing up to two heteroatoms selected from O, S, and N;

4.2)

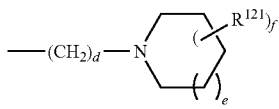

wherein R$^{121}$ represents —(C$_1$-C$_3$)alkyl which may optionally bear halogen or —OR$^{122}$ in which R$^{122}$ represents H or —(C$_1$-C$_3$)alkyl;
d represents 1, 2, or 3;
e represents 0 or 1;
f represents 0, 1, or 2;

4.3)

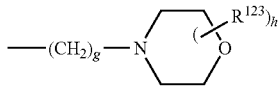

wherein R$^{123}$ represents —(C$_1$-C$_3$)alkyl which may optionally bear halogen or —OR$^{124}$ in which R$^{124}$ represents H or —(C$_1$-C$_3$)alkyl;
g represents 1, 2, or 3;
h represents 0, 1, or 2;

4.4)

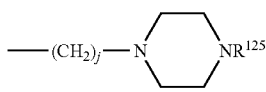

wherein
R$^{125}$ represents
- 4.4.a) H;
- 4.4.b) —(C$_1$-C$_3$)alkyl which may optionally bear halogen or —OR$^{126}$ in which R$^{126}$ represents H or —(C$_1$-C$_3$)alkyl which in turn is optionally substituted with halogen;
- 4.4.c) —SO$_2$R$^{127}$ wherein R$^{127}$ represents optionally substituted phenyl, or —(C$_1$-C$_3$)alkyl which may optionally bear halogen or OR$^{128}$ wherein R$^{128}$ represents H or (C$_1$-C$_3$)alkyl;
- 4.4.d) —C(O)R$^{129}$ wherein
R$^{129}$ represents
- 4.4.d1) optionally substituted phenyl,
- 4.4.d2) —(C$_1$-C$_3$)alkyl which may optionally bear up to 3 substituents independently selected from
- 4.4.d2.1) halogen;
- 4.4.d2.4) —OR$^{130}$ wherein R$^{130}$ represents H or (C$_1$-C$_3$)alkyl which may optionally bear halogen; and
- 4.4.d2.5) —NR$^{131}$R$^{132}$ in which R$^{131}$ and R$^{132}$ are independently H or —(C$_1$-C$_3$)alkyl which may optionally bear halogen, or R$^{131}$ and R$^{132}$ may be joined and taken together with the N atom to which they are attached form a 5-6 membered ring which may optionally contain a ring member selected from O, S, and NR$^{133}$ wherein R$^{133}$ represents H or (C$_1$-C$_3$)alkyl;
- 4.4.d3) —OR$^{134}$ wherein R$^{134}$ represents (C$_1$-C$_3$)alkyl which may optionally bear halogen; or
- 4.4.d4) NR$^{135}$R$^{136}$ wherein R$^{135}$ and R$^{136}$ are independently H or —(C$_1$-C$_3$)alkyl which may optionally bear halogen, or R$^{135}$ and R$^{136}$ may be joined and taken together with the N atom to which they are attached form a 5-6 membered ring which may optionally contain a ring member selected from O, S, and NR$^{137}$ wherein R$^{137}$ represents H or (C$_1$-C$_3$)alkyl; and j represents 1, 2, or 3;

4.5)

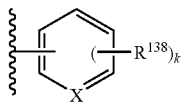

wherein
X represents C or N;
R$^{138}$ represents
- 4.5.a) (C$_1$-C$_4$)alkyl, which may optionally bear up to 3 substituents independently selected from
  - 4.5.a1) halogen;
  - 4.5.a2) OR$^{139}$ wherein R$^{139}$ represents H or (C$_1$-C$_3$)alkyl which may optionally bear halogen or —(C$_1$-C$_3$)mono- or di-alkylamino;
  - 4.5.a3) —NR$^{140}$R$^{141}$ in which R$^{140}$ and R$^{141}$ are independently H or —(C$_1$-C$_3$)alkyl which may optionally bear halogen or OR$^{141a}$ wherein R$^{141a}$ represents H or (C$_1$-C$_3$)alkyl, or R$^{140}$ and R$^{141}$ may be joined and taken together with the N atom to which they are attached form a 5-6 membered ring which may optionally contain a ring member selected from O, S, and NR$^{142}$ wherein R$^{142}$ represents H or (C$_1$-C$_3$)alkyl; and
  - 4.5.a4) a 5-6 membered heteroaromatic containing up to two heteroatoms selected from O, S, and N;
- 4.5.b) —(C$_3$-C$_6$)cycloalkyl which may optionally bear up to 2 substituents independently selected from
  - 4.5.b1) halogen;
- 4.5.c) OR$^{144}$ wherein
  R$^{144}$ represents H; phenyl; benzyl; (C$_3$-C$_6$)cycloalkyl; or (C$_1$-C$_4$)alkyl which may optionally bear up to 3 substituents independently selected from
  - 4.5.c1) halogen;
  - 4.5.c2) OR$^{145}$ wherein R$^{145}$ represents H or (C$_1$-C$_3$)alkyl which may optionally bear (C$_1$-C$_3$) mono- or di-alkylamino; and
  - 4.5.c3) NR$^{146}$R$^{147}$ in which R$^{146}$ and R$^{147}$ are independently H or —(C$_1$-C$_3$)alkyl which may optionally bear halogen, or R$^{146}$ and R$^{147}$ may be joined and taken together with the N atom to which they are attached form a 5-6 membered ring which may optionally contain a ring member selected from O, S, and NR$^{148}$ wherein R$^{148}$ represents H or (C$_1$-C$_3$)alkyl;
- 4.5.e) —C(O)—NR$^{150}$R$^{151}$ wherein
  R$^{150}$ represents H or (C$_1$-C$_3$)alkyl which may optionally bear halogen; and
  R$^{151}$ represents H or —(C$_1$-C$_4$)alkyl which is optionally substituted with
  - 4.5.e1) halogen;
  - 4.5.e3) phenyl;
  - 4.5.e4) —SO$_2$CH$_3$;
  - 4.5.e5) —OR$^{152}$ wherein R$^{152}$ represents H or (C$_1$-C$_3$)alkyl which may optionally bear halogen; or 4.5.e6) —NR$^{153}$R$^{154}$ in which R$^{153}$ and R$^{154}$ are independently H or —(C$_1$-C$_3$)alkyl which may optionally bear halogen, or R$^{153}$ and R$^{154}$ may be joined and taken together with the N atom to which they are attached form a 5-6 membered ring which may optionally contain a ring member selected from O, S, and NR$^{155}$ wherein R$^{155}$ represents H or (C$_1$ C$_3$)alkyl;

4.5.f) —N(R$^{156}$)—C(O)—R$^{157}$ wherein
R$^{156}$ represents H or (C$_1$-C$_3$)alkyl; and
R$^{157}$ represents H, optionally substituted phenyl, or (C$_1$-C$_4$)alkyl which is optionally substituted with 4.5.f1) optionally substituted phenyl,
4.5.f2) OR$^{158}$ wherein R$^{158}$ represents H or (C$_1$-C$_3$)alkyl, or
4.5.f3) NR$^{159}$R$^{160}$ wherein R$^{159}$ and R$^{160}$ are independently H or —(C$_1$-C$_3$)alkyl which may optionally bear halogen, or R$^{159}$ and R$^{160}$ may be joined and taken together with the N atom to which they are attached form a 5-6 membered ring which may optionally contain a ring member selected from O, S, and NR$^{161}$ wherein R$^{161}$ represents H or (C$_1$-C$_3$)alkyl;

4.5.g) —SO$_2$NR$^{162}$R$^{163}$ wherein
R$^{162}$ represents H or (C$_1$-C$_3$)alkyl which may optionally bear halogen; and
R$^{163}$ represents H or —(C$_1$-C$_4$)alkyl which is optionally substituted with 4.5.g1) halogen;
4.5.g3) phenyl;
4.5.g4) —SO$_2$CH$_3$;
4.5.g5) —OR$^{164}$ wherein R$^{164}$ represents H or (C$_1$-C$_3$)alkyl which may optionally bear halogen; or
4.5.g6) —NR$^{165}$R$^{166}$ in which R$^{165}$ and R$^{166}$ are independently H or —(C$_1$-C$_3$)alkyl which may optionally bear halogen, or R$^{165}$ and R$^{166}$ may be joined and taken together with the N atom to which they are attached form a 5-6 membered ring which may optionally contain a ring member selected from O, S, and NR$^{167}$ wherein R$^{167}$ represents H or (C$_1$-C$_3$)alkyl;

4.5.h) —N(R$^{168}$)—SO$_2$—R$^{169}$ wherein
R$^{168}$ represents H or (C$_1$-C$_3$)alkyl, and
R$^{169}$ represents H, optionally substituted phenyl, or (C$_1$-C$_4$)alkyl which is optionally substituted with 4.5.h1) halogen,
4.5.h2) optionally substituted phenyl,
4.5.h3) OR$^{170}$ wherein R$^{170}$ represents H or (C$_1$-C$_3$)alkyl which may optionally bear halogen, or
4.5.h4) —NR$^{171}$R$^{172}$ wherein R$^{171}$ and R$^{172}$ are independently H or —(C$_1$-C$_3$)alkyl which may optionally bear halogen, or R$^{171}$ and R$^{172}$ may be joined and taken together with the N atom to which they are attached form a 5-6 membered ring which may optionally contain a ring member selected from O, S, and NR$^{13}$ wherein R$^{173}$ represents H or (C$_1$-C$_3$)alkyl;

4.5.i) —NR$^{174}$R$^{175}$ in which R$^{174}$ and R$^{175}$ are independently H or —(C$_1$-C$_3$)alkyl which may optionally bear halogen or OR$^{175a}$ wherein R$^{175a}$ represents H or (C$_1$-C$_3$)alkyl, or R$^{174}$ and R$^{175}$ may be joined and taken together with the N atom to which they are attached form a 5-6 membered ring which may optionally contain a ring member selected from O, S, and NR$^{176}$ wherein R$^{176}$ represents H or (C$_1$-C$_3$)alkyl;

4.5.j) halogen;
4.5.l) NO$_2$;
4.5.m) CN; or
4.5.n) a 5-6 membered heteroaromatic containing up to two heteroatoms selected from O, S, and N; and
k represents 0, 1, or 2;

4.6)

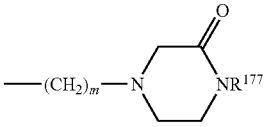

wherein R$^{177}$ represents H or —(C$_1$-C$_3$)alkyl; and
m represents 1, 2, or 3;

4.7)

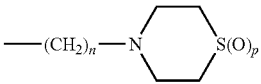

wherein
n represents 1, 2, or 3; and
p represents 0, 1, or 2;

4.8)

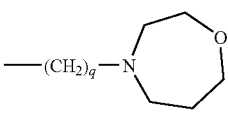

wherein
q represents 1, 2, or 3;

4.9)

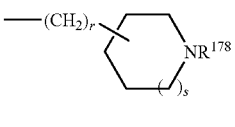

wherein
R$^{178}$ represents
  4.9.a) H;
  4.9.b) —(C$_1$-C$_3$)alkyl which may optionally bear halogen or —OR$^{179}$ in which R$^{179}$ represents H or (C$_1$-C$_3$)alkyl optionally substituted with halogen;
  4.9.c) —SO$_2$R$^{180}$ wherein R$^{180}$ represents optionally substituted phenyl or —(C$_1$-C$_3$)alkyl, which may be substituted with halogen or —OR$^{181}$ wherein R$^{181}$ represents H or (C$_1$-C$_3$)alkyl which may optionally bear halogen;
  4.9.d) —C(O)R$^{182}$ wherein R$^{182}$ represents optionally substituted phenyl or —(C$_1$-C$_3$)alkyl which may optionally bear up to 3 substituents independently selected from
    4.9.d1) halogen;
    4.9.d2) optionally substituted phenyl;

4.9.d4) OR¹⁸³ wherein R¹⁸³ represents H or (C₁-C₃)alkyl which may optionally bear halogen; and 4.9.d5) —NR¹⁸⁴R¹⁸⁵ in which R¹⁸⁴ and R¹⁸⁵ are independently H or —(C₁-C₃)alkyl which may optionally bear halogen or OR¹⁸⁵ᵃ wherein R¹⁸⁵ᵃ represents H or (C₁-C₃)alkyl, or R¹⁸⁴ and R¹⁸⁵ may be joined and taken together with the N atom to which they are attached form a 5-6 membered ring which may optionally contain a ring member selected from O, S, and NR¹⁸⁶ wherein R¹⁸⁶ represents H or (C₁-C₃)alkyl;

4.9e) —C(O)OR¹⁸⁷ wherein R¹⁸⁷ represents (C₁-C₃)alkyl; or 4.9.f) —C(O)—NR¹⁸⁸R¹⁸⁹ wherein R¹⁸⁸ and R¹⁸⁹ each independently represents H or —(C₁-C₃)alkyl which may optionally bear halogen, or R¹⁸⁸ and R¹⁸⁹ may be joined and taken together with the N atom to which they are attached form a 5-6 membered ring which may optionally contain a ring member selected from O, S, and NR¹⁹⁰ wherein R¹⁹⁰ represents H or (C₁-C₃)alkyl;

r represents 0, 1, or 2; and
s represents 0 or 1;

4.10)

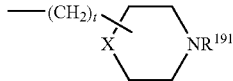

wherein
R¹⁹¹ represents
  4.10.a) H;
  4.10.b) —(C₁-C₃)alkyl which may optionally bear halogen or —OR¹⁹² in which R¹⁹² represents H or (C₁-C₃)alkyl;
  4.10c) —SO₂R¹⁹³ wherein R¹⁹³ represents phenyl or —(C₁-C₃)alkyl, both of which may be substituted with halogen or —(C₁-C₃)alkyl;
  4.10.d) —C(O)R¹⁹⁴ wherein R¹⁹⁴ represents (C₁-C₃)alkyl which may optionally bear up to 3 substituents independently selected from
    4.10.d1) halogen;
    4.10.d2) phenyl;
    4.10.d4) OR¹⁹⁵ wherein R¹⁹⁵ represents H or (C₁-C₃)alkyl which may optionally bear halogen; and
    4.10.d5) —NR¹⁹⁶R¹⁹⁷ in which R¹⁹⁶ and R¹⁹⁷ are independently H or —(C₁-C₃)alkyl which may optionally bear halogen or OR¹⁹⁷ᵃ wherein R¹⁹⁷ᵃ represents H or (C₁-C₃)alkyl, or R¹⁹⁶ and R¹⁹⁷ may be joined and taken together with the N atom to which they are attached form a 5-6 membered ring which may optionally contain a ring member selected from O, S, and NR¹⁹⁸ wherein R¹⁹⁸ represents H or (C₁-C₃)alkyl;
  4.10.e) —C(O)OR¹⁹⁹ wherein R¹⁹⁹ represents (C₁-C₃)alkyl; or
  4.10.f) —C(O)—NR²⁰⁰R²⁰¹ wherein R²⁰⁰ and R²⁰¹ each independently represents H or —(C₁-C₃)alkyl which may optionally bear halogen, or R²⁰⁰ and R²⁰¹ may be joined and taken together with the N atom to which they are attached form a 5-6 membered ring which may optionally contain a ring member selected from O, S, and NR²⁰² wherein R²⁰² represents H or (C₁-C₃)alkyl; and X represents O, S, S(O)₂, or NR²⁰³ wherein R²⁰³ represents H or —(C₁-C₃)alkyl; and
t represents 0, 1, or 2;
4.11) halogen; or
4.12) —CN;
or a pharmaceutically acceptable salt thereof.

5. The compound of claim 1 wherein in formula (I)

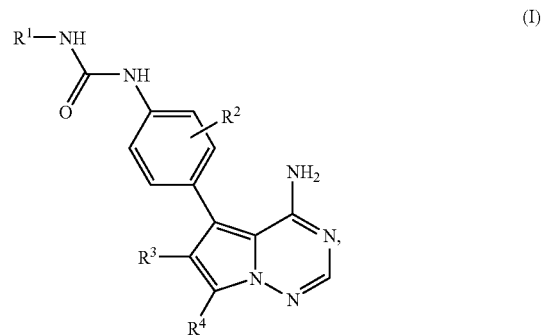

(I)

R¹ represents
  1.1) phenyl which may optionally bear up to 4 substituents independently selected from the group consisting of
    1.1.a) (C₁-C₄)alkyl, which may optionally bear up to 3 substituents independently selected from
      1.1.a1) halogen;
      1.1.a2) OR⁵ wherein R⁵ represents H or (C₁-C₃)alkyl which may optionally bear halogen;
      1.1.a3) —NR⁶R⁷ in which R⁶ and R⁷ are independently H or —(C₁-C₃)alkyl which may optionally bear halogen or R⁶ and R⁷ may be joined and taken together with the N atom to which they are attached form a 5-6 membered ring which may optionally contain a ring member selected from O, S, and NR⁸ wherein R⁸ represents H or (C₁-C₃)alkyl; and
      1.1.a4) an imidazole, thiazole, oxazole, pyridine, pyrazole, pyrimidine, isoxazole, isothiazole, thiophene, or furan;
    1.1.b) —(C₃-C₆)cycloalkyl which may optionally bear up to 2 substituents independently selected from
      1.1.b1) halogen;
    1.1.c) OR¹⁰ wherein
      R¹⁰ represents H; phenyl; benzyl; (C₃-C₆)cycloalkyl; or (C₁-C₄)alkyl which may optionally bear up to 3 substituents independently selected from
      1.1.c1) halogen;
      1.1.c2) OR¹¹ wherein R¹¹ represents H or (C₁-C₃)alkyl; and
      1.1.c3) NR¹²R¹³ in which R¹² and R¹³ are independently H or —(C₁-C₃)alkyl which may optionally bear halogen, or R¹² and R¹³ may be joined and taken together with the N atom to which they are attached form a 5-6 membered ring which may optionally contain a ring member selected from O, S, and NR¹⁴ wherein R¹⁴ represents H or (C₁-C₃)alkyl;

1.1.e) —O(O)—NR$^{16}$R$^{17}$ wherein
  R$^{16}$ represents H or (C$_1$-C$_3$)alkyl which may optionally bear halogen; and
  R$^{17}$ represents H or —(C$_1$-C$_4$)alkyl which is optionally substituted with
    1.1.e1) halogen;
  1.1.e5) —OR$^{18}$ wherein R$^{18}$ represents H or (C$_1$-C$_3$)alkyl which may optionally bear halogen; or
  1.1.e6) —NR$^{19}$R$^{20}$ in which R$^{19}$ and R$^{20}$ are independently H or —(C$_1$-C$_3$)alkyl which may optionally bear halogen, or R$^{19}$ and R$^{20}$ may be joined and taken together with the N atom to which they are attached form a 5-6 membered ring which may optionally contain a ring member selected from O, S, and NR$^{21}$ wherein R$^{21}$ represents H or (C$_1$-C$_3$)alkyl;
1.1.f) —N(R$^{22}$)—C(O)—R$^{23}$ wherein
  R$^{22}$ represents H or (C$_1$-C$_3$)alkyl; and
  R$^{23}$ represents optionally substituted phenyl, or (C$_1$-C$_4$)alkyl;
1.1.g) —SO$_2$NR$^{28}$R$^{29}$ wherein
  R$^{28}$ represents H or (C$_1$-C$_3$)alkyl which may optionally bear halogen; and
  R$^{29}$ represents H or —(C$_1$-C$_4$)alkyl which is optionally substituted with:
    1.1.g1) halogen;
    1.1.g4) —SO$_2$CH$_3$;
    1.1.g5) —OR$^{30}$ wherein R$^{30}$ represents H or (C$_1$-C$_3$)alkyl which may optionally bear halogen; or
    1.1.g6) —NR$^{31}$R$^{32}$ in which R$^{31}$ and R$^{32}$ are independently H or —(C$_1$-C$_3$)alkyl which may optionally bear halogen, or R$^{31}$ and R$^{32}$ may be joined and taken together with the N atom to which they are attached form a 5-6 membered ring which may optionally contain a ring member selected from O, S, and NR$^{33}$ wherein R$^{33}$ represents H or (C$_1$-C$_3$)alkyl;
1.1.h) —N(R$^{34}$)—SO$_2$—R$^{35}$ wherein
  R$^{34}$ represents H or (C$_1$-C$_3$)alkyl, and
  R$^{35}$ represents optionally substituted phenyl, or (C$_1$-C$_4$)alkyl which is optionally substituted with
    1.1.h1) halogen;
1.1.i) —NR$^{40}$R$^{41}$ in which R$^{40}$ and R$^{41}$ are independently H or —(C$_1$-C$_3$)alkyl which may optionally bear halogen or OR$^{42}$ in which R$^{42}$ represents H or (C$_1$-C$_3$)alkyl, or R$^{40}$ and R$^{41}$ may be joined and taken together with the N atom to which they are attached form a 5-6 membered ring which may optionally contain a ring member selected from O, S, and NR$^{43}$ wherein R$^{43}$ represents H or (C$_1$-C$_3$)alkyl;
1.1.j) halogen;
1.1.l) NO$_2$;
1.1.m) CN; and
1.1.n) an imidazole, thiazole, oxazole, pyridine, pyrazole, pyrimidine, isoxazole, isothiazole, thiophene, or furan;
or
R$^1$ represents
  1.2) a 5-6 membered aromatic heterocycle selected from imidazole, thiazole, oxazole, pyridine, pyrazole, pyrimidine, isoxazole, isothiazole, thiophene, and furan; said R$^1$ heterocycle optionally bearing up to 4 substituents independently selected from the group consisting of
    1.2.a) (C$_1$-C$_4$)alkyl, which may optionally bear up to 3 substituents independently selected from
      1.2.a1) halogen;
      1.2.a2) OR$^{45}$ wherein R$^{45}$ represents H or (C$_1$-C$_3$)alkyl which may optionally bear halogen;
      1.2.a3) —NR$^{46}$R$^{47}$ in which R$^{46}$ and R$^{47}$ are independently H or —(C$_1$-C$_3$)alkyl which may optionally bear halogen, or R$^{46}$ and R$^{47}$ may be joined and taken together with the N atom to which they are attached form a 5-6 membered ring which may optionally contain a ring member selected from O, S, and NR$^{48}$ wherein R$^{48}$ represents H or (C$_1$-C$_3$)alkyl; and
      1.2.a4) an imidazole, thiazole, oxazole, pyridine, pyrazole, pyrimidine, isoxazole, isothiazole, thiophene, or furan;
    1.2.b) —(C$_3$-C$_6$)cycloalkyl which may optionally bear up to 2 substituents independently selected from
      1.2.b1) halogen;
    1.2.c) OR$^{50}$ wherein
      R$^{50}$ represents H; phenyl; benzyl; —(C$_3$-C$_6$)cycloalkyl; or —(C$_1$-C$_4$)alkyl which may optionally bear up to 3 substituents independently selected from
        1.2.c1) halogen;
    1.2.e) —C(O)—NR$^{56}$R$^{57}$ wherein
      R$^{56}$ represents H or (C$_1$-C$_3$)alkyl which may optionally bear halogen; and
      R$^{57}$ represents H or —(C$_1$-C$_4$)alkyl which is optionally substituted with
        1.2.e1) halogen; or
        1.2.e5) —OR$^{58}$ wherein R$^{58}$ represents H or (C$_1$-C$_3$)alkyl which may optionally bear halogen;
    1.2.f) —N(R$^{62}$)—C(O)—R$^{63}$ wherein
      R$^{62}$ represents H or (C$_1$-C$_3$)alkyl; and
      R$^{63}$ represents optionally substituted phenyl, or (C$_1$-C$_4$)alkyl;
    1.2.g) —SO$_2$NR$^{68}$R$^{69}$ wherein
      R$^{68}$ represents H or (C$_1$-C$_3$)alkyl which may optionally bear halogen; and
      R$^{69}$ represents H or —(C$_1$-C$_4$)alkyl which is optionally substituted with
        1.2.g1) halogen; or
        1.2.g5) —OR$^{70}$ wherein R$^{70}$ represents H or (C$_1$-C$_3$)alkyl which may optionally bear halogen; or
    1.2.h) —N(R$^{74}$)—SO$_2$—R$^{75}$ wherein
      R$^{74}$ represents H or (C$_1$-C$_3$)alkyl, and
      R$^{75}$ represents optionally substituted phenyl, or (C$_1$-C$_4$)alkyl which is optionally substituted with
        1.2.h1) halogen;
    1.2.i) —NR$^{80}$R$^{81}$ in which R$^{80}$ and R$^{81}$ are independently H or —(C$_1$-C$_3$)alkyl which may optionally bear halogen or OR$^{81a}$ wherein R$^{81a}$ represents H or (C$_1$-C$_3$)alkyl, or R$^{80}$ and R$^{81}$ may be joined and taken together with the N atom to which they are attached form a 5-6 membered ring which may optionally contain a ring member selected from O, S, and NR$^{82}$ wherein R$^{82}$ represents H or (C$_1$-C$_3$)alkyl;
    1.2.j) halogen;
    1.2.k) optionally substituted phenyl;
    1.2.l) NO$_2$;
    1.2.m) CN; and
    1.2.n) an imidazole, thiazole, oxazole, pyridine, pyrazole, pyrimidine, isoxazole, isothiazole, thiophene, or furan;

$R^2$ represents hydrogen; halogen; —$(C_1-C_5)$alkyl which may optionally bear halogen; or —$O(C_1-C_3)$alkyl which may optionally bear halogen;
$R^3$ represents
3.1) —$(C_1-C_5)$alkyl which is substituted with
  3.1.a) -halogen;
  3.1.b) phenyl optionally substituted with halogen, —$(C_1-C_3)$alkyl, or —$(C_1-C_3)$alkoxy,
  3.1.c) a 5-6 membered heteroaromatic containing up to two heteroatoms selected from O, S, and N, optionally substituted with halogen or —$(C_1-C_3)$alkyl,
  3.1.d) —CN,
  3.1.e) —$OR^{83}$ wherein $R^{83}$ represents H or —$(C_1-C_3)$alkyl which may optionally bear up to 3 substituents independently selected from
    3.1.e1) halogen;
    3.1.e2) optionally substituted phenyl;
    3.1.e3) —$S(O)_2CH_3$;
    3.1.e4) $OR^{84}$ wherein $R^{84}$ represents H or $(C_1-C_3)$alkyl which may optionally bear halogen or —$(C_1-C_3)$mono- or di-alkylamino; and
    3.1.e5) —$NR^{85}R^{86}$ in which $R^{85}$ and $R^{86}$ are independently H or —$(C_1-C_3)$alkyl which may optionally bear halogen, or $R^{85}$ and $R^{86}$ may be joined and taken together with the N atom to which they are attached form a 5-6 membered ring which may optionally contain a ring member selected from O, S, and $NR^{87}$ wherein $R^{87}$ represents H or $(C_1-C_3)$alkyl;
  3.1.f) —$(C_3-C_5)$cycloalkyl which may optionally bear halogen; or
  3.1.g) —$NR^{89}R^{90}$ wherein
    $R^{89}$ represents H or —$(C_1-C_3)$alkyl which may optionally bear halogen; and
    $R^{90}$ represents H or —$(C_1-C_4)$alkyl which is optionally substituted with
    3.1.g1) halogen;
    3.1.g2) a 5-6 membered heteroaromatic containing up to two heteroatoms selected from O, S, and N;
    3.1.g3) phenyl;
    3.1.g4) —$SO_2CH_3$;
    3.1.g5) —$OR^{91}$ wherein $R^{91}$ represents H or $(C_1-C_3)$alkyl which may optionally bear halogen; or
    3.1.g6) —$NR^{92}R^{93}$ in which $R^{92}$ and $R^{93}$ are independently H or —$(C_1-C_3)$alkyl which may optionally bear halogen, or $R^{92}$ and $R^{93}$ may be joined and taken together with the N atom to which they are attached form a 5-6 membered ring which may optionally contain a ring member selected from O, S, and $NR^{94}$ wherein $R^{94}$ represents H or $(C_1-C_3)$alkyl; or
    3.1.g7) $R^{89}$ and $R^{90}$ may be joined and taken together with the N to which they are attached form an aromatic or nonaromatic 5-6 membered ring which may optionally contain a ring member selected from O, S, and $NR^{95}$ wherein $R^{95}$ represents H or $(C_1-C_3)$alkyl;
3.2)

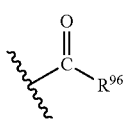

wherein
$R^{96}$ represents
3.2.a) H,
3.2.b) —$(C_3-C_5)$cycloalkyl which may optionally bear halogen; or
3.2.c) —$(C_1-C_5)$alkyl which may optionally bear up to 3 substituents independently selected from
  3.2.c1) halogen;
  3.2.c2) a 5-6 membered heteroaromatic containing up to two heteroatoms selected from O, S, and N;
  3.2.c3) phenyl;
  3.2.c5) —$OR^{97}$ wherein $R^{97}$ represents H or $(C_1-C_3)$alkyl which may optionally bear halogen or —$(C_1-C_3)$mono- or di-alkylamino; and
  3.2.c6) —$NR^{98}R^{99}$ in which $R^{98}$ and $R^{99}$ are independently H or —$(C_1-C_3)$alkyl which may optionally bear halogen or $OR^{99a}$ wherein $R^{99a}$ represents H or $(C_1-C_3)$alkyl, or $R^{98}$ and $R^{99}$ may be joined and taken together with the N atom to which they are attached form a 5-6 membered ring which may optionally contain a ring member selected from O, S, and $NR^{100}$ wherein $R^{100}$ represents H or $(C_1-C_3)$alkyl;
3.3)

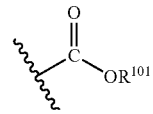

wherein $R^{101}$ represents H or —$(C_1-C_5)$alkyl which may optionally bear up to 3 substituents independently selected from
3.3.a) halogen; and
3.3.b) phenyl;
3.4)

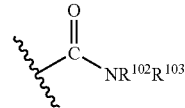

wherein
$R^{102}$ represents H or —$(C_1-C_3)$alkyl which may optionally bear halogen; and
$R^{103}$ represents H or —$(C_1-C_5)$alkyl which may optionally bear up to 3 substituents independently selected from
3.4.a) halogen;
3.4.b) a 5-6 membered heteroaromatic containing up to two heteroatoms selected from O, S, and N;
3.4.c) phenyl;
3.4.d) —$S(O)_2CH_3$;
3.4.e) $OR^{104}$ wherein $R^{104}$ represents H or $(C_1-C_3)$alkyl which may optionally bear halogen; and
3.4.f) —$NR^{105}R^{106}$ in which $R^{105}$ and $R^{106}$ are independently H or —$(C_1-C_3)$alkyl which may optionally bear halogen, or $R^{105}$ and $R^{106}$ may be joined and taken together with the N atom to which they are attached form a 5-6 membered ring which may optionally contain a ring member selected from O, S, and $NR^{107}$ wherein $R^{107}$ represents H or $(C_1-C_3)$alkyl;

3.6) a 5-6 membered heteroaromatic containing up to two heteroatoms selected from O, S, and N;
3.7) halogen; or
3.8) —CN;

$R^4$ represents
4.1) —($C_1$-$C_5$)alkyl which is optionally substituted with
  4.1.b) -halogen;
  4.1.c) —$OR^{110}$ wherein $R^{110}$ represents H or —($C_1$-$C_3$)alkyl which may optionally bear up to 3 substituents independently selected from
    4.1.c1) halogen; and
    4.1.c5) —$NR^{112}R^{113}$ in which $R^{112}$ and $R^{113}$ are independently H or —($C_1$-$C_3$)alkyl which may optionally bear halogen, or $R^{112}$ and $R^{113}$ may be joined and taken together with the N atom to which they are attached form a 5-6 membered ring which may optionally contain a ring member selected from O, S, and $NR^{114}$ wherein $R^{114}$ represents H or ($C_1$-$C_3$)alkyl; or
  4.1.d) —$NR^{115}R^{116}$ wherein
    $R^{115}$ represents H or —($C_1$-$C_3$)alkyl which may optionally bear halogen and
    $R^{116}$ represents H, optionally substituted phenyl, or —($C_1$-$C_5$)alkyl which may optionally bear up to 3 substituents independently selected from
    4.1.d1) halogen;
    4.1.d2) —$S(O)_2CH_3$;
    4.1.d3) $OR^{117}$ wherein $R^{117}$ represents H or ($C_1$-$C_3$)alkyl which may optionally bear halogen; and
    4.1.d4) —$NR^{118}R^{119}$ in which $R^{118}$ and $R^{119}$ are independently H or —($C_1$-$C_3$)alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or ($C_1$-$C_3$)alkyl;

4.2)

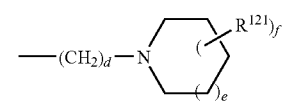

wherein $R^{121}$ represents —($C_1$-$C_3$)alkyl which may optionally bear halogen;
d represents 1, 2, or 3;
e represents 0 or 1;
f represents 0, 1, or 2;

4.3)

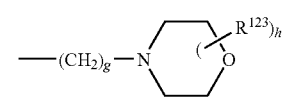

wherein $R^{123}$ represents —($C_1$-$C_3$)alkyl which may optionally bear halogen;
g represents 1, 2, or 3;
h represents 0, 1, or 2;

4.4)

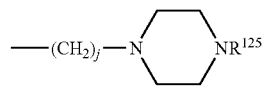

wherein
$R^{125}$ represents
  4.4.a) H;
  4.4.b) —($C_1$-$C_3$)alkyl which may optionally bear halogen;
  4.4.c) —$SO_2R^{127}$ wherein $R^{127}$ represents optionally substituted phenyl, or —($C_1$-$C_3$)alkyl which may optionally bear halogen;
  4.4.d) —$C(O)R^{129}$ wherein
  $R^{129}$ represents
    4.4.d1) optionally substituted phenyl,
    4.4.d2) —($C_1$-$C_3$)alkyl which may optionally bear up to 3 substituents independently selected from
      4.4.d2.1) halogen; and
      4.4.d2.4) —$OR^{130}$ wherein $R^{130}$ represents H or ($C_1$-$C_3$)alkyl which may optionally bear halogen;
    4.4.d3) —$OR^{134}$ wherein $R^{134}$ represents ($C_1$-$C_3$)alkyl; or
    4.4.d4) $NR^{135}R^{136}$ wherein $R^{135}$ and $R^{136}$ are independently H or —($C_1$-$C_3$)alkyl which may optionally bear halogen; and
j represents 1, 2, or 3;

4.5)

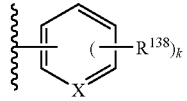

wherein
X represents C or N;
$R^{138}$ represents
  4.5.a) ($C_1$-$C_4$)alkyl, which may optionally bear up to 3 substituents independently selected from
    4.5.a1) halogen;
    4.5.a2) $OR^{139}$ wherein $R^{139}$ represents H or ($C_1$-$C_3$)alkyl which may optionally bear halogen; and
    4.5.a3) —$NR^{140}R^{141}$ in which $R^{140}$ and $R^{141}$ are independently H or —($C_1$-$C_3$)alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or ($C_1$-$C_3$)alkyl;
  4.5.b) —($C_3$-$C_6$)cycloalkyl which may optionally bear up to 2 substituents independently selected from
    4.5.b1) halogen;
  4.5.c) $OR^{144}$ wherein
    $R^{144}$ represents H; phenyl; benzyl; ($C_3$-$C_6$)cycloalkyl; or
    ($C_1$-$C_4$)alkyl which may optionally bear up to 3 substituents independently selected from
    4.5.c1) halogen;
    4.5.c2) $OR^{145}$ wherein $R^{145}$ represents H or ($C_1$-$C_3$)alkyl; and
    4.5.c3) $NR^{146}R^{147}$ in which $R^{146}$ and $R^{1473}$ are independently H or —($C_1$-$C_3$)alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or $(C_1C_3)$alkyl;

4.5.e) —C(O)—$NR^{150}R^{151}$ wherein
  $R^{150}$ represents H or $(C_1$-$C_3)$alkyl which may optionally bear halogen; and
  $R^{151}$ represents H or —$(C_1$-$C_4)$alkyl which is optionally substituted with
    4.5.e1) halogen; or
    4.5.e6) —$NR^{153}R^{154}$ in which $R^{153}$ and $R^{154}$ are independently H or —$(C_1$-$C_3)$alkyl which may optionally bear halogen, or $R^{153}$ and $R^{154}$ may be joined and taken together with the N atom to which they are attached form a 5-6 membered ring which may optionally contain a ring member selected from O, S, and $NR^{155}$ wherein $R^{155}$ represents H or $(C_1$-$C_3)$alkyl;

4.5.f) —$N(R^{156})$—C(O)—$R^{157}$ wherein
  $R^{156}$ represents H or $(C_1$-$C_3)$alkyl; and
  $R^{157}$ represents H, optionally substituted phenyl, or $(C_1$-$C_4)$alkyl;

4.5.g) —$SO_2NR^{162}R^{163}$ wherein
  $R^{162}$ represents H or $(C_1$-$C_3)$alkyl which may optionally bear halogen; and
  $R^{163}$ represents H or —$(C_1$-$C_4)$alkyl which is optionally substituted with
    4.5.g1) halogen; or
    4.5.g6) —$NR^{165}R^{166}$ in which $R^{165}$ and $R^{166}$ are independently H or —$(C_1$-$C_3)$alkyl which may optionally bear halogen, or $R^{165}$ and $R^{166}$ may be joined and taken together with the N atom to which they are attached form a 5-6 membered ring which may optionally contain a ring member selected from O, S, and $NR^{167}$ wherein $R^{167}$ represents H or $(C_1$-$C_3)$alkyl;

4.5.h) —$N(R^{168})$—$SO_2$—$R^{169}$ wherein
  $R^{168}$ represents H or $(C_1$-$C_3)$alkyl, and
  $R^{169}$ represents H, optionally substituted phenyl, or $(C_1$-$C_4)$alkyl which is optionally substituted with
    4.5.h1) halogen; or
    4.5.h4) $NR^{171}R^{172}$ wherein $R^{171}$ and $R^{172}$ are independently H or —$(C_1$-$C_3)$alkyl which may optionally bear halogen, or $R^{171}$ and $R^{172}$ may be joined and taken together with the N atom to which they are attached form a 5-6 membered ring which may optionally contain a ring member selected from O, S, and $NR^{13}$ wherein $R^{173}$ represents H or $(C_1$-$C_3)$alkyl;

4.5.i) —$NR^{174}R^{175}$ in which $R^{174}$ and $R^{175}$ are independently H or —$(C_1$-$C_3)$alkyl which may optionally bear halogen or $OR^{175a}$ wherein $R^{175a}$ represents H or $(C_1$-$C_3)$alkyl, or $R^{174}$ and $R^{175}$ may be joined and taken together with the N atom to which they are attached form a 5-6 membered ring which may optionally contain a ring member selected from O, S, and $NR^{176}$ wherein $R^{176}$ represents H or $(C_1$-$C_3)$alkyl;

4.5.j) halogen;
4.5.l) $NO_2$;
4.5.m) CN; or
4.5.n) an imidazole, thiazole, oxazole, pyridine, pyrazole, pyrimidine, isoxazole, isothiazole, thiophene, or furan; and
k represents 0, 1, or 2;

4.6)

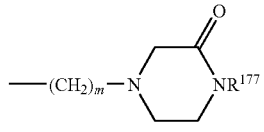

wherein $R^{177}$ represents H or —$(C_1$-$C_3)$alkyl; and
m represents 1, 2, or 3;

4.7)

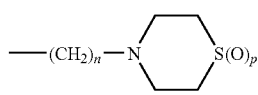

wherein
n represents 1, 2, or 3; and
p represents 0, 1, or 2;

4.8)

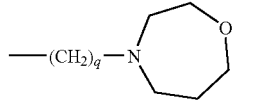

wherein
q represents 1, 2, or 3;

4.9)

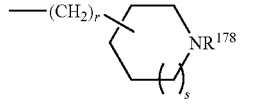

wherein
$R^{178}$ represents
  4.9.a) H;
  4.9.b) —$(C_1$-$C_3)$alkyl which may optionally bear halogen;
  4.9.c) —$SO_2R^{180}$ wherein $R^{180}$ represents optionally substituted phenyl or —$(C_1$-$C_3)$alkyl, which may be substituted with halogen;
  4.9.d) —$C(O)R^{182}$ wherein $R^{182}$ represents optionally substituted phenyl or —$(C_1$-$C_3)$alkyl which may optionally bear up to 3 substituents independently selected from
    4.9.d1) halogen; and
    4.9.d4) $OR^{183}$ wherein $R^{183}$ represents H or $(C_1$-$C_3)$alkyl which may optionally bear halogen;
  4.9e) —$C(O)OR^{187}$ wherein $R^{187}$ represents $(C_1$-$C_3)$alkyl; or
  4.9.f) —C(O)—$NR^{188}R^{189}$ wherein $R^{188}$ and $R^{189}$ each independently represents H or —$(C_1$-$C_3)$alkyl which may optionally bear halogen;
r represents 0, 1, or 2; and
s represents 0 or 1;

4.10)

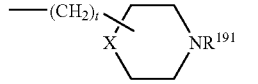

wherein
R$^{191}$ represents
4.10.a) H;
4.10.b) —(C$_1$-C$_3$)alkyl which may optionally bear halogen;
4.10c) —SO$_2$R$^{193}$ wherein R$^{193}$ represents phenyl or —(C$_1$-C$_3$)alkyl, both of which may be substituted with halogen;
4.10.d) —C(O)R$^{194}$ wherein R$^{194}$ represents (C$_1$-C$_3$)alkyl which may optionally bear up to 3 substituents independently selected from
4.10.d1) halogen;
4.10.d2) phenyl; and
4.10.d4) OR$^{195}$ wherein R$^{195}$ represents H or (C$_1$-C$_3$)alkyl which may optionally bear halogen;
4.10.e) —C(O)OR$^{199}$ wherein R$^{199}$ represents (C$_1$-C$_3$)alkyl; or
4.10.f) —C(O)—NR$^{200}$R$^{201}$ wherein R$^{200}$ and R$^{201}$ each independently represents H or —(C$_1$-C$_3$)alkyl which may optionally bear halogen;
X represents O, S, S(O)$_2$, or NR$^{203}$ wherein R$^{203}$ represents H or —(C$_1$-C$_3$)alkyl; and
t represents 0, 1, or 2;
4.11) halogen; or
4.12) —CN;
or a pharmaceutically acceptable salt thereof.

6. The compound of claim 1 wherein in formula (I)

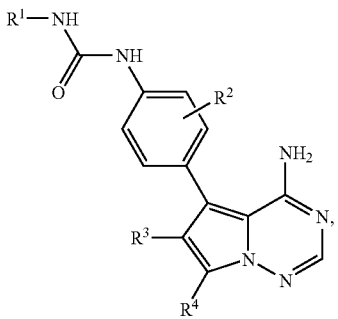

(I)

R$^1$ represents
1.1) phenyl which may optionally bear up to 4 substituents independently selected from the group consisting of
1.1.a) (C$_1$-C$_4$)alkyl, which may optionally bear up to 3 substituents independently selected from
1.1.a1) halogen;
1.1.a2) OR$^5$ wherein R$^5$ represents H or (C$_1$-C$_3$) alkyl which may optionally bear halogen;
1.1.a3) —NR$^6$R$^7$ in which R$^6$ and R$^7$ are independently H or —(C$_1$-C$_3$)alkyl which may optionally bear halogen or R$^6$ and R$^7$ may be joined and taken together with the N atom to which they are attached form a 5-6 membered ring which may optionally contain a ring member selected from O, S, and NR$^8$ wherein R$^8$ represents H or (C$_1$-C$_3$)alkyl; and
1.1.a4) an imidazole, thiazole, oxazole, pyridine, pyrazole, pyrimidine, isoxazole, isothiazole, thiophene, or furan;
1.1.b) —(C$_3$-C$_6$)cycloalkyl which may optionally bear up to 2 substituents independently selected from
1.1.b1) halogen;
1.1.c) OR$^{10}$ wherein
R$^{10}$ represents H; phenyl; benzyl; (C$_3$-C$_6$)cycloalkyl; or (C$_1$-C$_4$)alkyl which may optionally bear up to 3 substituents independently selected from
1.1.c1) halogen;
1.1.c2) OR$^{11}$ wherein R$^{11}$ represents H or (C$_1$-C$_3$) alkyl; and
1.1.c3) NR$^{12}$R$^{13}$ in which R$^{12}$ and R$^{13}$ are independently H or —(C$_1$-C$_3$)alkyl which may optionally bear halogen, or R$^{12}$ and R$^{13}$ may be joined and taken together with the N atom to which they are attached form a 5-6 membered ring which may optionally contain a ring member selected from O, S, and NR$^{14}$ wherein R$^{14}$ represents H or (C$_1$-C$_3$)alkyl;
1.1.e) —C(O)—NR$^{16}$R$^{17}$ wherein
R$^{16}$ represents H or (C$_1$-C$_3$)alkyl which may optionally bear halogen; and
R$^{17}$ represents H or —(C$_1$-C$_4$)alkyl which is optionally substituted with
1.1.e1) halogen;
1.1.e5) —OR$^{18}$ wherein R$^{18}$ represents H or (C$_1$-C$_3$)alkyl which may optionally bear halogen; or
1.1.e6) —NR$^{19}$R$^{20}$ in which R$^{19}$ and R$^{20}$ are independently H or —(C$_1$-C$_3$)alkyl which may optionally bear halogen, or R$^{19}$ and R$^{20}$ may be joined and taken together with the N atom to which they are attached form a 5-6 membered ring which may optionally contain a ring member selected from O, S, and NR$^{21}$ wherein R$^{21}$ represents H or (C$_1$-C$_3$)alkyl;
1.1.f) —N(R$^{22}$)—C(O)—R$^{23}$ wherein
R$^{22}$ represents H or (C$_1$-C$_3$)alkyl; and
R$^{23}$ represents optionally substituted phenyl, or (C$_1$-C$_4$)alkyl;
1.1.g) —SO$_2$NR$^{28}$R$^{29}$ wherein
R$^{28}$ represents H or (C$_1$-C$_3$)alkyl which may optionally bear halogen; and
R$^{29}$ represents H or —(C$_1$-C$_4$)alkyl which is optionally substituted with:
1.1.g1) halogen;
1.1.g4) —SO$_2$CH$_3$;
1.1.g5) —OR$^{30}$ wherein R$^{30}$ represents H or (C$_1$-C$_3$)alkyl which may optionally bear halogen; or
1.1.g6) —NR$^{31}$R$^{32}$ in which R$^{31}$ and R$^{32}$ are independently H or —(C$_1$-C$_3$)alkyl which may optionally bear halogen, or R$^{31}$ and R$^{32}$ may be joined and taken together with the N atom to which they are attached form a 5-6 membered ring which may optionally contain a ring member selected from O, S, and NR$^{33}$ wherein R$^{33}$ represents H or (C$_1$-C$_3$)alkyl;
1.1.h) —N(R$^{34}$)—SO$_2$—R$^{35}$ wherein
R$^{34}$ represents H or (C$_1$-C$_3$)alkyl, and
R$^{35}$ represents optionally substituted phenyl, or (C$_1$-C$_4$)alkyl which is optionally substituted with
1.1.h1) halogen;
1.1.i) —NR$^{40}$R$^{41}$ in which R$^{40}$ and R$^{41}$ are independently H or —(C$_1$-C$_3$)alkyl which may optionally bear halogen or OR$^{42}$ in which R$^{42}$ represents H or (C$_1$-C$_3$)alkyl, or R$^{40}$ and R$^{41}$ may be joined and taken together with the N atom to which they are attached form a 5-6 membered ring which may optionally contain a ring member selected from O, S, and $NR^{43}$ wherein $R^{43}$ represents H or $(C_1-C_3)$alkyl;
- 1.1.j) halogen;
- 1.1.l) $NO_2$;
- 1.1.m) CN; and
- 1.1.n) an imidazole, thiazole, oxazole, pyridine, pyrazole, pyrimidine, isoxazole, isothiazole, thiophene, or furan;

or $R^1$ represents
- 1.2) a 5-6 membered aromatic heterocycle selected from imidazole, thiazole, oxazole, pyridine, pyrazole, pyrimidine, isoxazole, isothiazole, thiophene, and furan; said $R^1$ heterocycle optionally bearing up to 4 substituents independently selected from the group consisting of
  - 1.2.a) $(C_1-C_4)$alkyl, which may optionally bear up to 3 substituents independently selected from
    - 1.2.a1) halogen;
    - 1.2.a2) $OR^{45}$ wherein $R^{45}$ represents H or $(C_1-C_3)$alkyl which may optionally bear halogen;
    - 1.2.a3) $-NR^{46}R^{47}$ in which $R^{46}$ and $R^{47}$ are independently H or $-(C_1-C_3)$alkyl which may optionally bear halogen, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or $(C_1-C_3)$alkyl; and
    - 1.2.a4) an imidazole, thiazole, oxazole, pyridine, pyrazole, pyrimidine, isoxazole, isothiazole, thiophene, or furan;
  - 1.2.b) $-(C_3-C_6)$cycloalkyl which may optionally bear up to 2 substituents independently selected from
    - 1.2.b1) halogen;
  - 1.2.c) $OR^{50}$ wherein
    $R^{50}$ represents H; phenyl; benzyl; $-(C_3-C_6)$cycloalkyl; or $-(C_1-C_4)$alkyl which may optionally bear up to 3 substituents independently selected from
    - 1.2.c1) halogen;
  - 1.2.e) $-C(O)-NR^{56}R^{57}$ wherein
    $R^{56}$ represents H or $(C_1-C_3)$alkyl which may optionally bear halogen; and
    $R^{57}$ represents H or $-(C_1-C_4)$alkyl which is optionally substituted with
    - 1.2.e1) halogen; or
    - 1.2.e5) $-OR^{58}$ wherein $R^{58}$ represents H or $(C_1-C_3)$alkyl which may optionally bear halogen;
  - 1.2.f) $-N(R^{62})-C(O)-R^{63}$ wherein
    $R^{62}$ represents H or $(C_1-C_3)$alkyl; and
    $R^{63}$ represents optionally substituted phenyl, or $(C_1-C_4)$alkyl;
  - 1.2.g) $-SO_2NR^{68}R^{69}$ wherein
    $R^{68}$ represents H or $(C_1-C_3)$alkyl which may optionally bear halogen; and
    $R^{69}$ represents H or $-(C_1-C_4)$alkyl which is optionally substituted with
    - 1.2.g1) halogen; or
    - 1.2.g5) $-OR^{70}$ wherein $R^{70}$ represents H or $(C_1-C_3)$alkyl which may optionally bear halogen;
  - 1.2.h) $-N(R^{74})-SO_2-R^{75}$ wherein
    $R^{74}$ represents H or $(C_1-C_3)$alkyl, and
    $R^{75}$ represents optionally substituted phenyl, or $(C_1-C_4)$alkyl which is optionally substituted with
    - 1.2.h1) halogen;
  - 1.2.i) $-NR^{80}R^{81}$ in which $R^{80}$ and $R^{81}$ are independently H or $-(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$alkyl;
  - 1.2.j) halogen;
  - 1.2.k) optionally substituted phenyl;
  - 1.2.l) $NO_2$;
  - 1.2.m) CN; and
  - 1.2.n) an imidazole, thiazole, oxazole, pyridine, pyrazole, pyrimidine, isoxazole, isothiazole, thiophene, or furan;

$R^2$ represents hydrogen; halogen; $-(C_1-C_5)$alkyl which may optionally bear halogen; or $-O(C_1-C_3)$alkyl which may optionally bear halogen;

$R^3$ represents
- 3.1) $-(C_1-C_5)$alkyl which is substituted with
  - 3.1.a) -halogen;
  - 3.1.c) a 5-6 membered heteroaromatic containing up to two heteroatoms selected from O, S, and N, optionally substituted with halogen or $-(C_1-C_3)$alkyl,
  - 3.1.d) $-CN$,
  - 3.1.e) $-OR^{83}$ wherein $R^{83}$ represents H or $-(C_1-C_3)$alkyl which may optionally bear up to 3 substituents independently selected from
    - 3.1.e1) halogen; and
    - 3.1.e4) $OR^{84}$ wherein $R^{84}$ represents H or $(C_1-C_3)$alkyl which may optionally bear halogen;
  - 3.1.f) $-(C_3-C_5)$cycloalkyl which may optionally bear halogen; or
  - 3.1.g) $-NR^{89}R^{90}$ wherein
    $R^{89}$ represents H or $-(C_1-C_3)$alkyl which may optionally bear halogen; and
    $R^{90}$ represents H or $-(C_1-C_4)$alkyl which is optionally substituted with
    - 3.1.g1) halogen;
    - 3.1.g4) $-SO_2CH_3$;
    - 3.1.g5) $-OR^{91}$ wherein $R^{91}$ represents H or $(C_1-C_3)$alkyl which may optionally bear halogen; or
    - 3.1.g7) $R^{89}$ and $R^{90}$ may be joined and taken together with the N to which they are attached form an aromatic or nonaromatic 5-6 membered ring which may optionally contain a ring member selected from O, S, and $NR^{95}$ wherein $R^{95}$ represents H or $(C_1-C_3)$alkyl;
- 3.2)

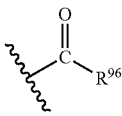

wherein
$R^{96}$ represents
- 3.2.b) $-(C_3-C_5)$cycloalkyl which may optionally bear halogen; or 3.2.c) —($C_1$-$C_5$)alkyl which may optionally bear up to 3 substituents independently selected from
3.2.c1) halogen; and
3.2.c5) —$OR^{97}$ wherein $R^{97}$ represents H or ($C_1$-$C_3$)alkyl which may optionally bear halogen;
3.3)

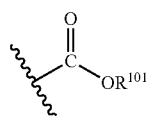

wherein $R^{101}$ represents H or —($C_1$-$C_5$)alkyl;
3.4)

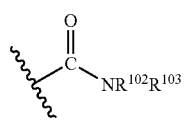

wherein
$R^{102}$ represents H or —($C_1$-$C_3$)alkyl which may optionally bear halogen; and
$R^{103}$ represents H or —($C_1$-$C_5$)alkyl which may optionally bear up to 3 substituents independently selected from
3.4.a) halogen;
3.4.d) —$S(O)_2CH_3$; and
3.4.e) $OR^{104}$ wherein $R^{104}$ represents H or ($C_1$-$C_3$)alkyl which may optionally bear halogen;
3.6) a 5-6 membered aromatic heterocycle selected from imidazole, thiazole, oxazole, pyridine, pyrazole, pyrimidine, isoxazole, isothiazole, thiophene, and furan;
3.7) halogen; or
3.8) —CN;
$R^4$ represents
4.1) —($C_1$-$C_5$)alkyl which is substituted with
4.1.b) -halogen;
4.1.c) —$OR^{110}$ wherein $R^{110}$ represents H or —($C_1$-$C_3$)alkyl which may optionally bear up to 3 substituents independently selected from
4.1.c1) halogen; and
4.1.c5) —$NR^{112}R^{113}$ in which $R^{112}$ and $R^{113}$ are independently H or —($C_1$-$C_3$)alkyl which may optionally bear halogen, or $R^{112}$ and $R^{113}$ may be joined and taken together with the N atom to which they are attached form a 5-6 membered ring which may optionally contain a ring member selected from O, S, and $NR^{114}$ wherein $R^{114}$ represents H or ($C_1$-$C_3$)alkyl; or
4.1.d) —$NR^{115}R^{116}$ wherein
$R^{115}$ represents H or —($C_1$-$C_3$)alkyl which may optionally bear halogen and
$R^{116}$ represents H, optionally substituted phenyl, or —($C_1$-$C_5$)alkyl which may optionally bear up to 3 substituents independently selected from
4.1.d1) halogen;
4.1.d2) —$S(O)_2CH_3$;
4.1.d3) $OR^{117}$ wherein $R^{117}$ represents H or ($C_1$-$C_3$)alkyl which may optionally bear halogen; and
4.1.d4) —$NR^{118}R^{119}$ in which $R^{118}$ and $R^{119}$ are independently H or —($C_1$-$C_3$)alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or ($C_1$-$C_3$)alkyl;
4.2)

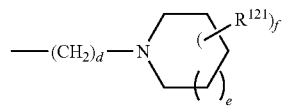

wherein $R^{121}$ represents —($C_1$-$C_3$)alkyl which may optionally bear halogen;
d represents 1, 2, or 3;
e represents 0 or 1;
f represents 0, 1, or 2;
4.3)

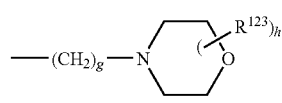

wherein $R^{123}$ represents —($C_1$-$C_3$)alkyl which may optionally bear halogen;
g represents 1, 2, or 3;
h represents 0, 1, or 2;
4.4)

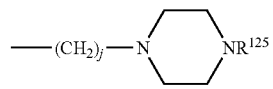

wherein
$R^{125}$ represents
4.4.a) H;
4.4.b) —($C_1$-$C_3$)alkyl which may optionally bear halogen;
4.4.c) —$SO_2R^{127}$ wherein $R^{127}$ represents optionally substituted phenyl, or —($C_1$-$C_3$)alkyl which may optionally bear halogen;
4.4.d) —$C(O)R^{129}$ wherein
$R^{129}$ represents
4.4.d1) optionally substituted phenyl,
4.4.d2) —($C_1$-$C_3$)alkyl which may optionally bear up to 3 substituents independently selected from
4.4.d2.1) halogen; and
4.4.d2.4) —$OR^{130}$ wherein $R^{130}$ represents H or ($C_1$-$C_3$)alkyl which may optionally bear halogen;
4.4.d3) —$OR^{134}$ wherein $R^{134}$ represents ($C_1$-$C_3$) alkyl; or
4.4.d4) $NR^{135}R^{136}$ wherein $R^{135}$ and $R^{136}$ are independently H or —($C_1$-$C_3$)alkyl which may optionally bear halogen; and
j represents 1, 2, or 3;

4.5)

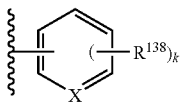

wherein

X represents C or N;

$R^{138}$ represents 4.5.a) $(C_1-C_4)$alkyl, which may optionally bear up to 3 substituents independently selected from
- 4.5.a1) halogen;
- 4.5.a2) $OR^{139}$ wherein $R^{139}$ represents H or $(C_1-C_3)$alkyl which may optionally bear halogen; and
- 4.5.a3) $-NR^{140}R^{141}$ in which $R^{140}$ and $R^{141}$ are independently H or $-(C_1-C_3)$alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or $(C_1-C_3)$alkyl;

4.5.b) $-(C_3-C_6)$cycloalkyl which may optionally bear up to 2 substituents independently selected from
- 4.5.b1) halogen;

4.5.c) $OR^{144}$ wherein
$R^{144}$ represents H; phenyl; benzyl; $(C_3-C_6)$cycloalkyl; or $(C_1-C_4)$alkyl which may optionally bear up to 3 substituents independently selected from
- 4.5.c1) halogen;
- 4.5.c2) $OR^{145}$ wherein $R^{145}$ represents H or $(C_1-C_3)$alkyl; and
- 4.5.c3) $NR^{146}R^{147}$ in which $R^{146}$ and $R^{1473}$ are independently H or $-(C_1-C_3)$alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or $(C_1-C_3)$alkyl;

4.5.e) $-C(O)-NR^{150}R^{151}$ wherein
$R^{150}$ represents H or $(C_1-C_3)$alkyl which may optionally bear halogen; and
$R^{151}$ represents H or $-(C_1-C_4)$alkyl which is optionally substituted with
- 4.5.e1) halogen; or
- 4.5.e6) $-NR^{153}R^{154}$ in which $R^{153}$ and $R^{154}$ are independently H or $-(C_1-C_3)$alkyl which may optionally bear halogen, or $R^{153}$ and $R^{154}$ may be joined and taken together with the N atom to which they are attached form a 5-6 membered ring which may optionally contain a ring member selected from O, S, and $NR^{155}$ wherein $R^{155}$ represents H or $(C_1-C_3)$alkyl;

4.5.f) $-N(R^{156})-C(O)-R^{157}$ wherein
$R^{156}$ represents H or $(C_1-C_3)$alkyl; and
$R^{157}$ represents H, optionally substituted phenyl, or $(C_1-C_4)$alkyl;

4.5.g) $-SO_2NR^{162}R^{163}$ wherein
$R^{162}$ represents H or $(C_1-C_3)$alkyl which may optionally bear halogen; and
$R^{163}$ represents H or $-(C_1-C_4)$alkyl which is optionally substituted with
- 4.5.g1) halogen; or
- 4.5.g6) $-NR^{165}R^{166}$ in which $R^{165}$ and $R^{166}$ are independently H or $-(C_1-C_3)$alkyl which may optionally bear halogen, or $R^{165}$ and $R^{166}$ may be joined and taken together with the N atom to which they are attached form a 5-6 membered ring which may optionally contain a ring member selected from O, S, and $NR^{167}$ wherein $R^{167}$ represents H or $(C_1-C_3)$alkyl;

4.5.h) $-N(R^{168})-SO_2-R^{169}$ wherein
$R^{168}$ represents H or $(C_1-C_3)$alkyl, and
$R^{169}$ represents H, optionally substituted phenyl, or $(C_1-C_4)$alkyl which is optionally substituted with
- 4.5.h1) halogen; or
- 4.5.h4) $NR^{171}R^{172}$ wherein $R^{171}$ and $R^{172}$ are independently H or $-(C_1-C_3)$alkyl which may optionally bear halogen, or $R^{171}$ and $R^{172}$ may be joined and taken together with the N atom to which they are attached form a 5-6 membered ring which may optionally contain a ring member selected from O, S, and $NR^{173}$ wherein $R^{173}$ represents H or $(C_1-C_3)$alkyl;

4.5.i) $-NR^{174}R^{175}$ in which $R^{174}$ and $R^{175}$ are independently H or $-(C_1-C_3)$alkyl which may optionally bear halogen or $OR^{175a}$ wherein $R^{175a}$ represents H or $(C_1-C_3)$alkyl, or $R^{174}$ and $R^{175}$ may be joined and taken together with the N atom to which they are attached form a 5-6 membered ring which may optionally contain a ring member selected from O, S, and $NR^{176}$ wherein $R^{176}$ represents H or $(C_1-C_3)$alkyl;

4.5.j) halogen;

4.5.l) $NO_2$;

4.5.m) CN; or 4.5.n) a 5-6 membered aromatic heterocycle selected from imidazole, thiazole, oxazole, pyridine, pyrazole, pyrimidine, isoxazole, isothiazole, thiophene, and furan; and k represents 0, 1, or 2;

4.6)

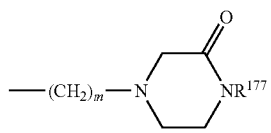

wherein $R^{177}$ represents H or $-(C_1-C_3)$alkyl; and
m represents 1, 2, or 3;

4.7)

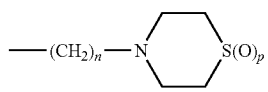

wherein
n represents 1, 2, or 3; and
p represents 0, 1, or 2;

4.8)

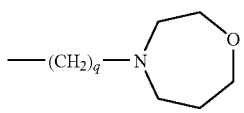

wherein
q represents 1, 2, or 3;

4.9)

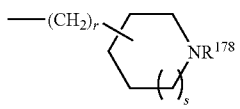

wherein
$R^{178}$ represents
- 4.9.a) H;
- 4.9.b) —$(C_1-C_3)$alkyl which may optionally bear halogen;
- 4.9.c) —$SO_2R^{180}$ wherein $R^{180}$ represents optionally substituted phenyl or —$(C_1-C_3)$alkyl, which may be substituted with halogen;
- 4.9.d) —$C(O)R^{182}$ wherein $R^{182}$ represents optionally substituted phenyl or —$(C_1-C_3)$alkyl which may optionally bear up to 3 substituents independently selected from
  - 4.9.d1) halogen; and
  - 4.9.d4) $OR^{183}$ wherein $R^{183}$ represents H or $(C_1-C_3)$alkyl which may optionally bear halogen;
- 4.9e) —$C(O)OR^{187}$ wherein $R^{187}$ represents $(C_1-C_3)$alkyl; or
- 4.9.f) —$C(O)$—$NR^{188}R^{189}$ wherein $R^{188}$ and $R^{189}$ each independently represents H or —$(C_1-C_3)$alkyl which may optionally bear halogen;

r represents 0, 1, or 2; and
s represents 0 or 1;

4.10)

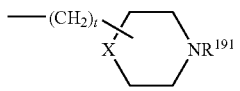

wherein
$R^{191}$ represents
- 4.10.a) H;
- 4.10.b) —$(C_1-C_3)$alkyl which may optionally bear halogen;
- 4.10c) —$SO_2R^{193}$ wherein $R^{193}$ represents phenyl or —$(C_1-C_3)$alkyl, both of which may be substituted with halogen;
- 4.10.d) —$C(O)R^{194}$ wherein $R^{194}$ represents $(C_1-C_3)$alkyl which may optionally bear up to 3 substituents independently selected from
  - 4.10.d1) halogen;
  - 4.10.d2) phenyl; and
  - 4.10.d4) $OR^{195}$ wherein $R^{195}$ represents H or $(C_1-C_3)$alkyl which may optionally bear halogen;
- 4.10.e) —$C(O)OR^{199}$ wherein $R^{199}$ represents $(C_1-C_3)$alkyl; or
- 4.10.f) —$C(O)$—$NR^{200}R^{201}$ wherein $R^{200}$ and $R^{201}$ each independently represents H or —$(C_1-C_3)$alkyl which may optionally bear halogen;

X represents O, S, $S(O)_2$, or $NR^{203}$ wherein $R^{203}$ represents H or —$(C_1-C_3)$alkyl; and
t represents 0, 1, or 2;
4.11) halogen; or
4.12) —CN;
or a pharmaceutically acceptable salt thereof.

7. The compound of claim 1 wherein in formula (I)

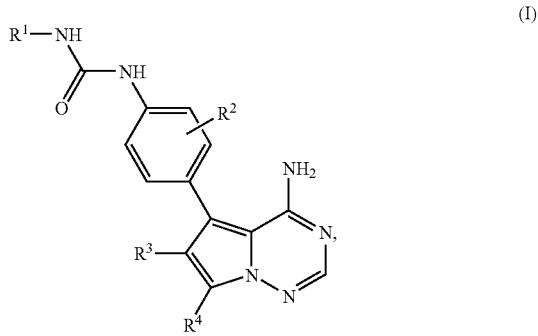

(I)

$R^1$ represents
1.1) phenyl which may optionally bear up to 4 substituents independently selected from the group consisting of
- 1.1.a) $(C_1-C_4)$alkyl, which may optionally bear up to 3 substituents independently selected from
  - 1.1.a1) halogen;
- 1.1.b) —$(C_3-C_6)$cycloalkyl which may optionally bear up to 2 substituents independently selected from
  - 1.1.b1) halogen;
- 1.1.c) $OR^{10}$ wherein
  $R^{10}$ represents H, or $(C_1-C_4)$alkyl which may optionally bear up to 3 substituents independently selected from
  - 1.1.c1) halogen;
- 1.1.i) —$NR^{40}R^{41}$ in which $R^{40}$ and $R^{41}$ are independently H or —$(C_1-C_3)$alkyl which may optionally bear halogen;
- 1.1.j) halogen;
- 1.1.l) $NO_2$; and
- 1.1.m) CN;

or
$R^1$ represents
1.2) a 5-6 membered aromatic heterocycle selected from thiazole, oxazole, pyridine, pyrazole, pyrimidine, isoxazole, isothiazole, and thiophene; said $R^1$ heterocycle optionally bearing up to 4 substituents independently selected from the group consisting of
- 1.2.a) $(C_1-C_4)$alkyl, which may optionally bear up to 3 substituents independently selected from
  - 1.2.a1) halogen; and
  - 1.2.a4) an imidazole, thiazole, oxazole, pyridine, pyrazole, pyrimidine, isoxazole, isothiazole, thiophene, or furan;
- 1.2.b) —$(C_3-C_6)$cycloalkyl which may optionally bear up to 2 substituents independently selected from
  - 1.2.b1) halogen;

1.2.c) OR$^{50}$ wherein
R$^{50}$ represents —(C$_1$-C$_4$)alkyl which may optionally bear up to 3 substituents independently selected from
1.2.c1) halogen;
1.2.i) —NR$^{80}$R$^{81}$ in which R$^{80}$ and R$^{81}$ are independently H or —(C$_1$-C$_3$)alkyl which may optionally bear halogen;
1.2.j) halogen;
1.2.k) optionally substituted phenyl;
1.2.l) NO$_2$; and
1.2.m) CN;

R$^2$ represents hydrogen; halogen or —(C$_1$-C$_5$)alkyl;
R$^3$ represents
3.1) —(C$_1$-C$_5$)alkyl which is substituted with
3.1.a) -halogen;
3.1.d) —CN; or
3.1.e) —OR$^{83}$ wherein R$^{83}$ represents H or —(C$_1$-C$_3$)alkyl which may optionally bear up to 3 substituents independently selected from
3.1.e1) halogen;
3.1.g) —NR$^{89}$R$^{90}$ wherein
R$^{89}$ represents H; and
R$^{90}$ represents —(C$_1$-C$_4$)alkyl which is optionally substituted with —OR$^{91}$ wherein R$^{91}$ represents H or (C$_1$-C$_3$)alkyl;
3.2)

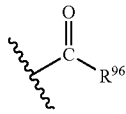

wherein
R$^{96}$ represents
3.2.b) —(C$_3$-C$_5$)cycloalkyl which may optionally bear halogen; or
3.2.c) —(C$_1$-C$_5$)alkyl;
3.3)

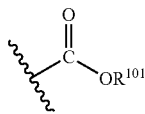

wherein R$^{101}$ represents H or —(C$_1$-C$_5$)alkyl;
3.4)

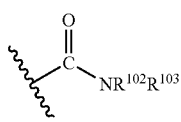

wherein
R$^{102}$ represents H or —(C$_1$-C$_3$)alkyl which may optionally bear halogen; and
R$^{103}$ represents H or —(C$_1$-C$_5$)alkyl which may optionally bear up to 3 substituents independently selected from
3.4.a) halogen;

3.6) a 5-6 membered aromatic heterocycle selected from imidazole, thiazole, oxazole, pyrazole, isoxazole, and isothiazole;
3.7) halogen; or
3.8) —CN;

R$^4$ represents
4.1) —(C$_1$-C$_5$)alkyl which is substituted with
4.1.b) -halogen;
4.1.c) —OR$^{110}$ wherein R$^{110}$ represents H or —(C$_1$-C$_3$)alkyl which may optionally bear up to 3 substituents independently selected from
4.1.c1) halogen; or
4.1.d) —NR$^{115}$R$^{116}$ wherein
R$^{115}$ represents H or —(C$_1$-C$_3$)alkyl which may optionally bear halogen, and
R$^{116}$ represents H, optionally substituted phenyl, or —(C$_1$-C$_5$)alkyl which may optionally bear up to 3 substituents independently selected from
4.1.d1) halogen;
4.1.d3) OR$^{117}$ wherein R$^{117}$ represents H or (C$_1$-C$_3$)alkyl which may optionally bear halogen; and
4.1.d4) —NR$^{118}$R$^{119}$ in which R$^{118}$ and R$^{119}$ are independently H or —(C$_1$-C$_3$)alkyl which may optionally bear halogen, or R$^{118}$ and R$^{119}$ may be joined and taken together with the N atom to which they are attached form a 5-6 membered ring which may optionally contain a ring member selected from O, S, and NR$^{120}$ wherein R$^{120}$ represents H or (C$_1$-C$_3$)alkyl;
4.2)

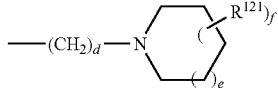

wherein R$^{121}$ represents —(C$_1$-C$_3$)alkyl which may optionally bear halogen;
d represents 1, 2, or 3;
e represents 0 or 1;
f represents 0, 1, or 2;
4.3)

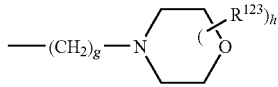

wherein R$^{123}$ represents —(C$_1$-C$_3$)alkyl which may optionally bear halogen;
g represents 1, 2, or 3;
h represents 0, 1, or 2;
4.4)

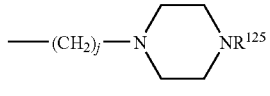

wherein
R$^{125}$ represents
4.4.a) H;
4.4.b) —(C$_1$-C$_3$)alkyl;

4.4.c) —$SO_2R^{127}$ wherein $R^{127}$ represents optionally substituted phenyl, or —$(C_1-C_3)$alkyl;
4.4.d) —$C(O)R^{129}$ wherein
   $R^{129}$ represents
   4.4.d2) —$(C_1-C_3)$alkyl which may optionally bear
   4.4.d2.4) —$OR^{130}$ wherein $R^{130}$ represents H or $(C_1-C_3)$alkyl;
   4.4.d3) —$OR^{134}$ wherein $R^{134}$ represents $(C_1-C_3)$alkyl; or
   4.4.d4) $NR^{135}R^{136}$ wherein $R^{135}$ and $R^{136}$ are independently H or —$(C_1-C_3)$; and
j represents 1, 2, or 3;
4.5)

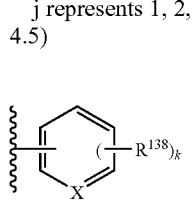

wherein
X represents C or N;
$R^{138}$ represents
   4.5.a) $(C_1-C_4)$alkyl, which may optionally bear up to 3 substituents independently selected from
      4.5.a1) halogen;
   4.5.b) —$(C_3-C_6)$cycloalkyl which may optionally bear up to 2 substituents independently selected from
      4.5.b1) halogen;
   4.5.c) $OR^{144}$ wherein
      $R^{144}$ represents H, or $(C_1-C_4)$alkyl which may optionally bear up to 3 substituents independently selected from
      4.5.c1) halogen;
   4.5.i) —$NR^{174}R^{175}$ in which $R^{174}$ and $R^{175}$ are independently H or —$(C_1-C_3)$alkyl which may optionally bear halogen;
   4.5.j) halogen;
   4.5.l) $NO_2$; or
   4.5.m) CN; and
k represents 0, 1, or 2;
4.6)

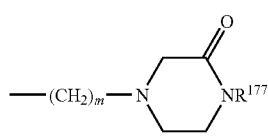

wherein
$R^{177}$ represents H or —$(C_1-C_3)$alkyl; and
m represents 1, 2, or 3;
4.7)

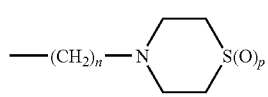

wherein
n represents 1, 2, or 3; and
p represents 0, 1, or 2;

4.8)

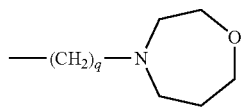

wherein
q represents 1, 2, or 3;
4.9)

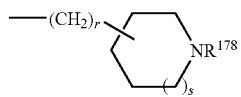

wherein
$R^{178}$ represents
   4.9.a) H;
   4.9.b) —$(C_1-C_3)$alkyl;
   4.9.c) —$SO_2R^{180}$ wherein $R^{180}$ represents —$(C_1-C_3)$alkyl;
   4.9.d) —$C(O)R^{182}$ wherein $R^{182}$ represents —$(C_1-C_3)$alkyl which may optionally bear up to 3 substituents independently selected from
   4.9.d4) $OR^{183}$ wherein $R^{183}$ represents H or $(C_1-C_3)$alkyl;
   4.9e) —$C(O)OR^{187}$ wherein $R^{187}$ represents $(C_1-C_3)$alkyl; or
   4.9.f) —$C(O)$—$NR^{188}R^{189}$ wherein $R^{188}$ and $R^{189}$ each independently represents H or —$(C_1-C_3)$alkyl;
r represents 0, 1, or 2; and
s represents 0 or 1;
4.10)

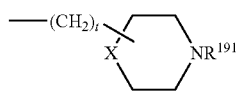

wherein
$R^{191}$ represents
   4.10.a) H;
   4.10.b) —$(C_1-C_3)$alkyl;
   4.10c) —$SO_2R^{193}$ wherein $R^{193}$ represents —$(C_1-C_3)$alkyl;
   4.10.d) —$C(O)R^{194}$ wherein $R^{194}$ represents $(C_1-C_3)$alkyl which may optionally bear up to 3 substituents independently selected from
   4.10.d4) $OR^{195}$ wherein $R^{195}$ represents H or $(C_1-C_3)$alkyl;
   4.10.e) —$C(O)OR^{199}$ wherein $R^{199}$ represents $(C_1-C_3)$alkyl; or
   4.10.f) —$C(O)$—$NR^{200}R^{201}$ wherein $R^{200}$ and $R^{201}$ each independently represents H or —$(C_1-C_3)$alkyl;
X represents O, S, $S(O)_2$, or $NR^{203}$ wherein $R^{203}$ represents H or —$(C_1-C_3)$alkyl; and
t represents 0, 1, or 2;
4.11) halogen; or
4.12) —CN;
or a pharmaceutically acceptable salt thereof.

8. A compound of formula (Q1)

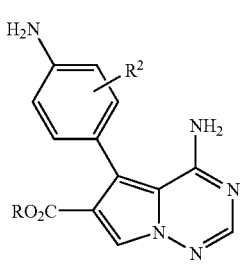

(Q1)

wherein
R represents H or $(C_1\text{-}C_5)$alkyl; and
$R^2$ represents halogen; —$(C_1\text{-}C_5)$alkyl which may optionally bear halogen; or —O$(C_1\text{-}C_3)$alkyl which may optionally bear halogen.

9. A compound of formula

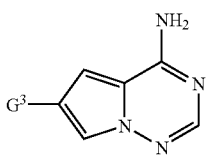

(Q2)

wherein
$G^3$ represents halogen, $(C_1\text{-}C_5)$alkyl, —CN, —C(O)O$(C_1\text{-}C_5)$alkyl, or —C(O)H.

10. A compound selected from the following list:
4-amino-5-{4-[({[2-fluoro-5-(trifluoromethyl)phenyl]amino}carbonyl)-amino]-phenyl}-7-(morpholin-4-ylmethyl)-N-(2,2,2-trifluoroethyl)-pyrrolo[2,1-f][1,2,4]-triazine-6-carboxamide;
4-amino-5-{4-[({[2-fluoro-5-(trifluoromethyl)phenyl]amino}carbonyl)-amino]phenyl}-7-[(4-methylpiperazin-1-yl)methyl]-N-(2,2,2-trifluoroethyl)-pyrrolo[2,1-f][1,2,4]triazine-6-carboxamide;
N-{4-[4-amino-6-(methoxymethyl)-7-(morpholin-4-ylmethyl)-pyrrolo[2,1-f][1,2,4]triazin-5-yl]phenyl}-N'-[2-fluoro-5-(trifluoromethyl)phenyl]urea;
N-(4-[4-amino-6-(methoxymethyl)-7-[(4-methylpiperazin-1-yl)methyl]-pyrrolo[2,1-f][1,2,4]triazin-5-yl]phenyl)-N'-[2-fluoro-5-(trifluoromethyl)-phenyl]urea;
N-{4-[4-amino-7-{[(2-methoxyethyl)amino]methyl}-6-(methoxymethyl)-pyrrolo[2,1-f][1,2,4]triazin-5-yl]phenyl}-N'-[2-fluoro-5-(trifluoromethyl)-phenyl]urea;
N-{4-[4-amino-7-[(2,6-dimethylmorpholin-4-yl)methyl]-6-(methoxymethyl)-pyrrolo[2,1-f][1,2,4]triazin-5-yl]phenyl}-N'-[2-fluoro-5-(trifluoromethyl)-phenyl]urea;
N-(4-[4-amino-6-(methoxymethyl)-7-[(3-oxopiperazin-1-yl)methyl]-pyrrolo[2,1-f][1,2,4]triazin-5-yl]phenyl)-N'-[2-fluoro-5-(trifluoromethyl)-phenyl]urea;
N-{4-[4-amino-7-{[(2-methoxyethyl)(methyl)amino]methyl}-6-(methoxymethyl)pyrrolo[2,1-f][1,2,4]triazin-5-yl]phenyl}-N'-[2-fluoro-5-(trifluoromethyl)phenyl]urea;
N-{4-[4-amino-7-(morpholin-4-ylmethyl)-6-(1,3-oxazol-5-yl)pyrrolo[2,1-f][1,2,4]triazin-5-yl]phenyl}-N'-[2-fluoro-5-(trifluoromethyl)phenyl]urea;
N-{4-[4-amino-7-(morpholin-4-ylmethyl)-6-(1,3-oxazol-5-yl)-pyrrolo[2,1-f][1,2,4]triazin-5-yl]phenyl}-N'-[4-(trifluoromethyl)pyridin-2-yl]urea;
N-{4-[4-amino-7-{[(2R,6S)-2,6-dimethylmorpholin-4-yl]methyl}-6-(1,3-oxazol-5-yl)pyrrolo[2,1-f][1,2,4]triazin-5-yl]phenyl}-N'-[2-fluoro-5-(trifluoromethyl)phenyl]urea;
N-{4-[4-amino-7-[(4-methylpiperazin-1-yl)methyl]-6-(1,3-oxazol-5-yl)-pyrrolo[2,1-f][1,2,4]triazin-5-yl]phenyl}-N'-[2-fluoro-5-(trifluoromethyl)-phenyl]urea;
N-{4-[4-amino-7-(morpholin-4-ylmethyl)-6-(1,3-oxazol-5-yl)-pyrrolo[2,1-f][1,2,4]triazin-5-yl]-2-fluorophenyl}-N'-[4-(trifluoromethyl)pyridin-2-yl]urea;
N-{4-[4-amino-6-(methoxymethyl)-7-(morpholin-4-ylmethyl)-pyrrolo[2,1-f][1,2,4]triazin-5-yl]phenyl}-N'-[4-(trifluoromethyl)pyridin-2-yl]urea;
N-(4-[4-amino-6-(methoxymethyl)-7-[(3-oxopiperazin-1-yl)methyl]-pyrrolo[2,1-f][1,2,4]triazin-5-yl]phenyl)-N'-[4-(trifluoromethyl)pyridin-2-yl]urea;
N-(4-[4-amino-6-(methoxymethyl)-7-[(3-oxopiperazin-1-yl)methyl]-pyrrolo[2,1-f][1,2,4]triazin-5-yl]-2-fluorophenyl)-N'-[2-fluoro-5-(trifluoromethyl)phenyl]urea;
N-{4-[4-amino-6-(methoxymethyl)-7-(morpholin-4-ylmethyl)pyrrolo[2,1-f][1,2,4]triazin-5-yl]-2-fluorophenyl}-N'-[2-fluoro-5-(trifluoromethyl)-phenyl]urea;
rel-N-{4-[4-amino-7-{[(2R,6S)-2,6-dimethylmorpholin-4-yl]methyl}-6-(methoxymethyl)pyrrolo[2,1-f][1,2,4]triazin-5-yl]-2-fluorophenyl}-N'-[2-fluoro-5-(trifluoromethyl)phenyl]urea;
N-{4-[4-amino-6-(methoxymethyl)-7-(morpholin-4-ylmethyl)-pyrrolo[2,1-f][1,2,4]triazin-5-yl]phenyl}-N'-[2-chloro-5-(trifluoromethyl)phenyl]urea;
N-{4-[4-amino-7-(morpholin-4-ylmethyl)-6-(1,3-oxazol-5-yl)-pyrrolo[2,1-f][1,2,4]triazin-5-yl]-2-fluorophenyl}-N'-[2-fluoro-5-(trifluoromethyl)-phenyl]urea;
N-{4-[6-acetyl-4-amino-7-(morpholin-4-ylmethyl)pyrrolo[2,1-f]-[1,2,4]-triazin-5-yl]-2-fluorophenyl}-N'-[2-fluoro-5-(trifluoromethyl)phenyl]urea;
N-{4-[6-acetyl-4-amino-7-(morpholin-4-ylmethyl)pyrrolo[2,1-f][1,2,4]-triazin-5-yl]-2-fluorophenyl}-N'-[3-(trifluoromethyl)phenyl]urea;
N-{4-[6-acetyl-4-amino-7-(morpholin-4-ylmethyl)pyrrolo[2,1-f][1,2,4]-triazin-5-yl]-2-fluorophenyl}-N'-[4-(trifluoromethyl)pyridin-2-yl]urea;
N-{4-[4-amino-6-(cyanomethyl)-7-(morpholin-4-ylmethyl)pyrrolo[2,1-f][1,2,4]triazin-5-yl]phenyl}-N'-[4-(trifluoromethyl)pyridin-2-yl]urea;
N-{4-[4-amino-6-(cyanomethyl)-7-(morpholin-4-ylmethyl)pyrrolo[2,1-f][1,2,4]triazin-5-yl]phenyl}-N'-[2-fluoro-5-(trifluoromethyl)phenyl]urea;
N-{4-[4-amino-6-(cyanomethyl)-7-(morpholin-4-ylmethyl)pyrrolo[2,1-f][1,2,4]triazin-5-yl]-2-fluorophenyl}-N'-[2-fluoro-5-(trifluoromethyl)-phenyl]urea;
N-{4-[4-amino-6-(difluoromethyl)-7-(morpholin-4-ylmethyl)pyrrolo[2,1-f][1,2,4]triazin-5-yl]phenyl}-N'-[4-(trifluoromethyl)pyridin-2-yl]urea;
N-{4-[4-amino-6-(cyclopropylcarbonyl)-7-(morpholin-4-ylmethyl)pyrrolo[2,1-f][1,2,4]triazin-5-yl]phenyl}-N'-[4-(trifluoromethyl)pyridin-2-yl]urea;
N-{4-[4-amino-6-(difluoromethyl)-7-(morpholin-4-ylmethyl)pyrrolo[2,1-f][1,2,4]triazin-5-yl]-2-fluorophenyl}-N'-[2-fluoro-5-(trifluoromethyl)-phenyl]urea;
N-{4-[6-acetyl-4-amino-7-(morpholin-4-ylmethyl)pyrrolo[2,1-f][1,2,4]-triazin-5-yl]phenyl}-N'-[2-fluoro-5-(trifluoromethyl)phenyl]urea;
N-{4-[4-amino-6-methyl-7-(morpholin-4-ylmethyl)pyrrolo[2,1-f][1,2,4]-triazin-5-yl]phenyl}-N'-[2-fluoro-5-(trifluoromethyl)phenyl]urea;

N-{4-[4-amino-6-methyl-7-(morpholin-4-ylmethyl)pyrrolo[2,1-f][1,2,4]-triazin-5-yl]-2-fluorophenyl}-N'-[2-fluoro-5-(trifluoromethyl)phenyl]urea;

N-{4-[4-amino-6-(difluoromethyl)-7-(morpholin-4-ylmethyl)pyrrolo[2,1-f][1,2,4]triazin-5-yl]-2-fluorophenyl}-N'-[4-(trifluoromethyl)pyridin-2-yl]urea;

N-{4-[4-amino-6-methyl-7-(1,4-oxazepan-4-ylmethyl)pyrrolo[2,1-f][1,2,4]triazin-5-yl]-2-fluorophenyl}-N'-[2-fluoro-5-(trifluoromethyl)-phenyl]urea;

N-{4-[4-amino-6-methyl-7-(morpholin-4-ylmethyl)pyrrolo[2,1-f][1,2,4]-triazin-5-yl]phenyl}-N'-[4-(trifluoromethyl)pyridin-2-yl]urea;

1-{4-[4-amino-6-methyl-7-(1,4-oxazepan-4-ylmethyl)pyrrolo[2,1-f][1,2,4]-triazin-5-yl]-2-fluorophenyl}-3-[4-(trifluoromethyl)pyridin-2-yl]urea;

N-{4-[4-amino-6-methyl-7-(morpholin-4-ylmethyl)pyrrolo[2,1-f][1,2,4]-triazin-5-yl]-2-fluorophenyl}-N'-[4-(trifluoromethyl)pyridin-2-yl]urea;

1-{4-[4-amino-6-(methoxymethyl)-7-(1,4-oxazepan-4-ylmethyl)pyrrolo[2,1-f][1,2,4]triazin-5-yl]-2-fluorophenyl}-3-[2-fluoro-5-(trifluoromethyl)-phenyl]urea;

N-{4-[4-amino-6-(methoxymethyl)-7-(morpholin-4-ylmethyl)pyrrolo[2,1-f][1,2,4]triazin-5-yl]-2-fluorophenyl}-N'-(2-fluoro-5-methylphenyl)urea;

N-{4-[4-amino-6-(methoxymethyl)-7-(morpholin-4-ylmethyl)pyrrolo[2,1-f][1,2,4]triazin-5-yl]-2-fluorophenyl}-N'-[3-(trifluoromethyl)phenyl]urea;

N-{4-[4-amino-6-(methoxymethyl)-7-(morpholin-4-ylmethyl)pyrrolo[2,1-f][1,2,4]triazin-5-yl]-2-fluorophenyl}-N'-(4-tert-butylpyridin-2-yl)urea;

N-{4-[4-amino-6-(methoxymethyl)-7-(morpholin-4-ylmethyl)pyrrolo[2,1-f][1,2,4]triazin-5-yl]-2-fluorophenyl}-N'-[4-(trifluoromethyl)pyridin-2-yl]urea;

N-{4-[4-amino-6-(methoxymethyl)-7-(morpholin-4-ylmethyl)pyrrolo[2,1-f][1,2,4]triazin-5-yl]-2-fluorophenyl}-N'-(3-tert-butylphenyl)urea;

N-{4-[4-amino-6-(methoxymethyl)-7-(1,4-oxazepan-4-ylmethyl)pyrrolo[2,1-f][1,2,4]triazin-5-yl]-2-fluorophenyl}-N'-[3-(trifluoromethyl)phenyl]urea;

N-{4-[4-amino-6-(methoxymethyl)-7-(morpholin-4-ylmethyl)pyrrolo[2,1-f][1,2,4]triazin-5-yl]-2,5-difluorophenyl}-N'-[2-fluoro-5-(trifluoromethyl)-phenyl]urea;

N-[4-[4-amino-6-(methoxymethyl)-7-(morpholin-4-ylmethyl)pyrrolo[2,1-f][1,2,4]triazin-5-yl]-2-methylphenyl]-N'-[2-fluoro-5-(trifluoromethyl)-phenyl]urea;

1-{4-[4-amino-7-{[(2-hydroxyethyl)amino]methyl}-6-(methoxymethyl)-pyrrolo[2,1-f][1,2,4]triazin-5-yl]-2-fluorophenyl)-3-[2-fluoro-5-(trifluoro-methyl)phenyl]urea;

1-(4-{4-amino-6-(methoxymethyl)-7-[(3-methylmorpholin-4-yl)methyl]-pyrrolo[2,1-f][1,2,4]triazin-5-yl}-2-fluorophenyl)-3-[2-fluoro-5-(trifluoro-methyl)phenyl]urea;

N-{4-[4-amino-6-chloro-7-(morpholin-4-ylmethyl)pyrrolo[2,1-f][1,2,4]-triazin-5-yl]-2-fluorophenyl}-N'-[2-fluoro-5-(trifluoromethyl)phenyl]urea;

N-{4-[4-amino-6-chloro-7-(morpholin-4-ylmethyl)pyrrolo[2,1-f][1,2,4]-triazin-5-yl]phenyl}-N'-[2-fluoro-5-(trifluoromethyl)phenyl]urea;

N-{4-[4-amino-6-chloro-7-(morpholin-4-ylmethyl)pyrrolo[2,1-f][1,2,4]-triazin-5-yl]-2-fluorophenyl}-N'-[3-(trifluoromethyl)phenyl]urea;

N-{4-[4-amino-6-chloro-7-(morpholin-4-ylmethyl)pyrrolo[2,1-f][1,2,4]-triazin-5-yl]-2-fluorophenyl}-N'-[4-(trifluoromethyl)pyridin-2-yl]urea;

N-{4-[4-amino-6-chloro-7-(morpholin-4-ylmethyl)pyrrolo[2,1-f][1,2,4]-triazin-5-yl]-2-fluorophenyl}-N'-(2-fluoro-5-methylphenyl)urea.

11. A pharmaceutical composition comprising a compound as defined in claim 1, plus a pharmaceutically acceptable carrier.

12. A method of treating breast cancer in a mammal, comprising
administering to said mammal an effective amount of a compound as defined in claim 1.

13. The method of claim 12 wherein said mammal is a human.

\* \* \* \* \*